United States Patent
Klein et al.

(10) Patent No.: US 11,547,748 B2
(45) Date of Patent: Jan. 10, 2023

(54) ADOPTIVE T-CELL THERAPY

(71) Applicants: Hoffmann-La Roche Inc., Little Falls, NJ (US); Ludwig-Maximilians-Universitat Munchen, Munich (DE)

(72) Inventors: Christian Klein, Bonstetten (CH); Claudio Sustmann, Munich (DE); Gerhard Niederfellner, Oberhausen (DE); Martina Geiger, Obfelden (CH); Stefan Endres, Munich (DE); Sebastian Kobold, Munich (DE)

( * ) Notice: Subject to any disclaimer, the term of this patent is extended or adjusted under 35 U.S.C. 154(b) by 373 days.

(21) Appl. No.: 16/314,117

(22) PCT Filed: Jun. 30, 2017

(86) PCT No.: PCT/EP2017/066375
§ 371 (c)(1),
(2) Date: Dec. 28, 2018

(87) PCT Pub. No.: WO2018/002358
PCT Pub. Date: Jan. 4, 2018

(65) Prior Publication Data
US 2019/0216908 A1 Jul. 18, 2019

(30) Foreign Application Priority Data
Jun. 30, 2016 (EP) .................................... 16177203

(51) Int. Cl.
| | |
|---|---|
| A61K 39/00 | (2006.01) |
| C07K 16/28 | (2006.01) |
| C07K 16/30 | (2006.01) |
| C07K 14/71 | (2006.01) |
| C12N 5/0783 | (2010.01) |
| A61P 35/00 | (2006.01) |
| A61K 39/395 | (2006.01) |

(52) U.S. Cl.
CPC .... *A61K 39/0011* (2013.01); *A61K 39/39558* (2013.01); *A61P 35/00* (2018.01); *C07K 14/71* (2013.01); *C07K 16/2863* (2013.01); *C07K 16/30* (2013.01); *C07K 16/3053* (2013.01); *C12N 5/0636* (2013.01); *A61K 2039/5156* (2013.01); *A61K 2039/5158* (2013.01); *A61K 2039/545* (2013.01); *C07K 2317/14* (2013.01); *C07K 2317/31* (2013.01); *C07K 2317/35* (2013.01); *C07K 2317/60* (2013.01); *C07K 2317/64* (2013.01); *C07K 2319/00* (2013.01); *C07K 2319/03* (2013.01); *C07K 2319/33* (2013.01)

(58) Field of Classification Search
CPC .......... A61K 39/0011; A61K 39/39558; A61K 2039/5156; A61K 2039/5158; A61K 2039/545; A61P 35/00; C07K 16/30; C07K 2317/14; C07K 2317/31; C07K 2317/35

See application file for complete search history.

(56) References Cited

U.S. PATENT DOCUMENTS

| | | | |
|---|---|---|---|
| 7,521,054 B2 * | 4/2009 | Pastan | C07K 16/28 |
| | | | 424/178.1 |
| 10,633,451 B2 * | 4/2020 | Bourquin | A61K 39/0011 |
| 11,192,935 B2 * | 12/2021 | Kobold | C12N 15/62 |

(Continued)

FOREIGN PATENT DOCUMENTS

| | | |
|---|---|---|
| WO | WO 2010/115589 | 10/2010 |
| WO | WO 2013/113615 | 8/2013 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*

(Continued)

*Primary Examiner* — Brad Duffy
*Assistant Examiner* — Cheom-Gil Cheong
(74) *Attorney, Agent, or Firm* — Grimes & Yvon LLP

(57) ABSTRACT

The present invention generally relates to T-cells, such as CD8+ T-cells, CD4+ T-cells, CD3+ T-cells, γδ T-cells or natural killer (NK) T-cells, transfected/transduced with a fusion protein which is recruited by the use of trivalent, bispecific antibody molecule which specifically binds to/interacts with the extracellular domain of the fusion protein. More precisely, the present invention relates to a kit comprising the nucleic acid molecules, vectors and/or the fusion proteins of the present invention and the trivalent, bispecific antibody molecules of the present invention. Further aspects of the inventions are expression vectors comprising nucleic acid molecules encoding the fusion proteins as well as the trivalent, bispecific antibody molecules. Further, a process for the production of the trivalent, bispecific antibody molecules of the invention and a medicament/pharmaceutical composition comprising said trivalent, bispecific antibody molecules are described. The invention also provides the use of said trivalent, bispecific antibody molecules in a method for the treatment of particular diseases as well as a pharmaceutical compositions/medicament comprising said trivalent, bispecific antibody molecules, wherein said trivalent, bispecific antibody molecule(s) is (are) to be administered in combination with transduced T-cells comprising the fusion protein of the invention. The invention also provides a method for the treatment of particular diseases.

24 Claims, 24 Drawing Sheets
Specification includes a Sequence Listing.

(56) References Cited

U.S. PATENT DOCUMENTS

| | | | | |
|---|---|---|---|---|
| 2005/0123546 A1* | 6/2005 | Umana | ............... | A61P 9/10 |
| | | | | 424/146.1 |
| 2012/0301447 A1* | 11/2012 | Jensen | ............... | C07K 14/71 |
| | | | | 424/93.21 |
| 2015/0010567 A1* | 1/2015 | Bourquin | ............... | C07K 16/32 |
| | | | | 424/136.1 |
| 2017/0096485 A1* | 4/2017 | Bacac | ............... | C07K 16/28 |
| 2019/0119383 A1* | 4/2019 | Bruenker | ............... | C07K 16/2809 |
| 2020/0317806 A1* | 10/2020 | Bourquin | ............... | C07K 16/32 |

FOREIGN PATENT DOCUMENTS

| | | |
|---|---|---|
| WO | WO 2014/131712 | 9/2014 |
| WO | WO 2016/090369 A1 | 6/2016 |

OTHER PUBLICATIONS

Klimka et al., British Journal of Cancer, 2000, 83:252-260. (Year: 2000).*

Ward et al., Nature, 1989, 341:544-546. (Year: 1989).*

Kobold S. et al., "P68. A new EGFR-EpCAM bispecific antibody enhances the efficacy of adoptive T-cell therapy . . . " J. Immunother. Cancer 2(Supp 2):P42 (2014).

Nakagawa T. et al., 2013; Development of next-generation adoptive immunotherapy . . . Drug Delivery System: vol. 28-1, 2013. Abstract only.

* cited by examiner

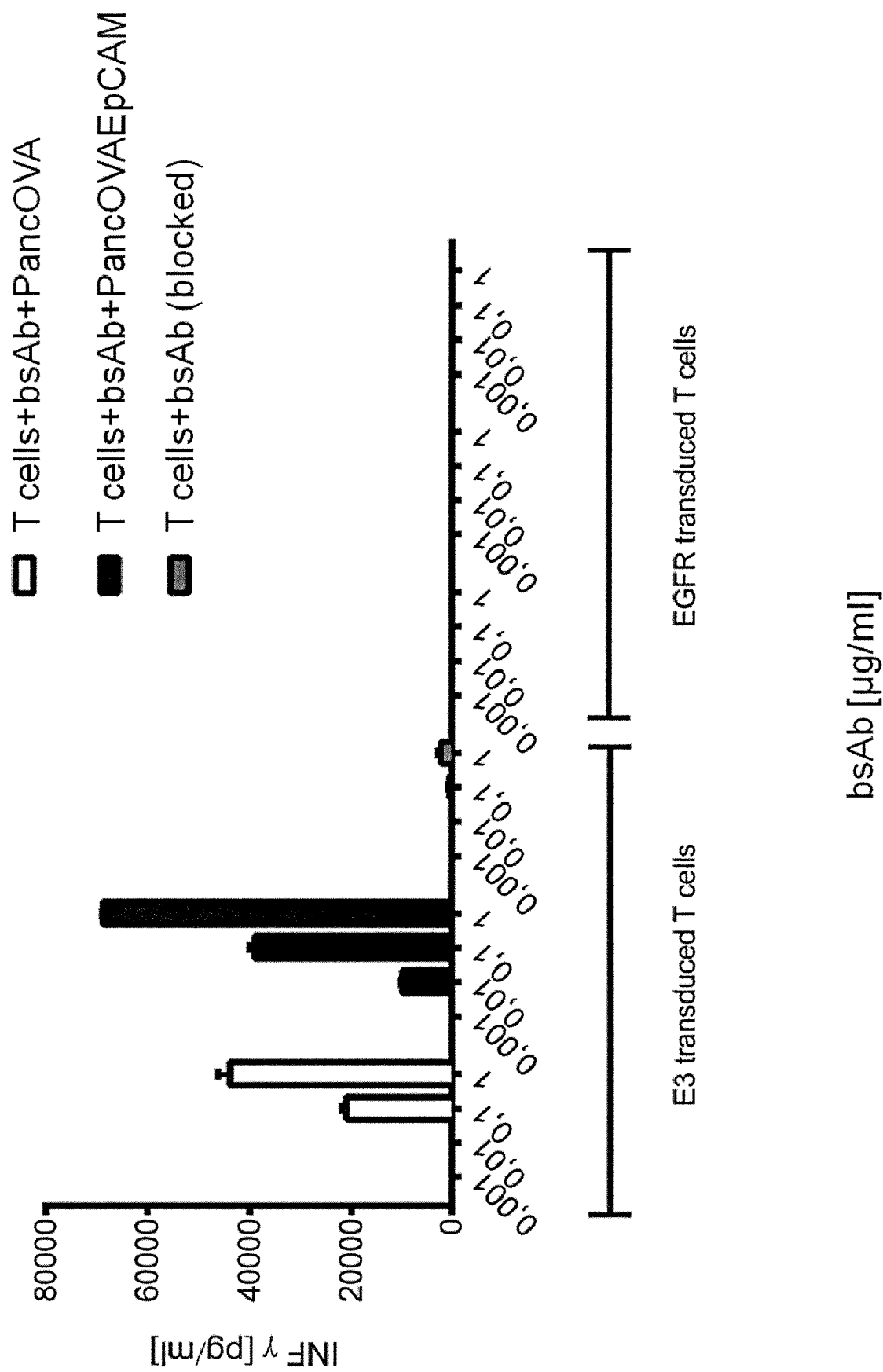

FIG. 15

Mesothelin Recomb. Protein (5μg/ml) inc. E3 + BsAb and UT + BsAb

IFN-gamma (pg/ml)

UT only*
UT BsAb (soluble)*
E3 only*
E3 BsAb (soluble)

ADOPTIVE T-CELL THERAPY

CROSS-REFERENCE TO RELATED APPLICATIONS

This application is the National Stage of International Application No. PCT/EP2017/066375, filed on Jun. 30, 2017, and claims the benefit of priority of EP Application No. 16177203.3, filed on Jun. 30, 2016.

FIELD OF THE INVENTION

The present invention generally relates to T-cells, such as CD8+ T-cells, CD4+ T-cells, CD3+ T-cells, γδ T-cells or natural killer (NK) T-cells, transfected/transduced with a fusion protein which is recruited by the use of a trivalent, bispecific antibody molecule which specifically binds to/interacts with the extracellular domain of the fusion protein. More precisely, the present invention relates to a kit comprising the nucleic acid molecules, vectors and/or the fusion proteins of the present invention and the trivalent, bispecific antibody molecules of the present invention. Further aspects of the inventions are expression vectors comprising nucleic acid molecules encoding the fusion proteins as well as the trivalent, bispecific antibody molecules. Further, a process for the production of the trivalent, bispecific antibody molecules of the invention and a medicament/pharmaceutical composition comprising said trivalent, bispecific antibody molecules are described. The invention also provides the use of said trivalent, bispecific antibody molecules in a method for the treatment of particular diseases as well as a pharmaceutical compositions/medicament comprising said trivalent, bispecific antibody molecules, wherein said trivalent, bispecific antibody molecule(s) is (are) to be administered in combination with transduced T-cells comprising the fusion protein of the invention. The invention also provides a method for the treatment of particular diseases.

BACKGROUND

Adoptive T-cell therapy (ACT) is a powerful treatment approach using cancer-specific T-cells (Rosenberg and Restifo, Science 348(6230) (2015), 62-68). ACT may use naturally occurring tumor-specific cells or T-cells rendered specific by genetic engineering using T-cell or chimeric antigen receptors (Rosenberg and Restifo, Science 348(6230) (2015), 62-68). ACT can successfully treat and induce remission in patients suffering even from advanced and otherwise treatment refractory diseases such as acute lymphatic leukemia, non-hodgkins lymphoma or melanoma (Dudley et al., J Clin Oncol 26(32) (2008), 5233-5239; Grupp et al., N Engl J Med 368 (16) (2013), 1509-1518; Kochenderfer et al., J Clin Oncol. (2015) 33(6):540-549, doi: 10.1200/JCO.2014.56.2025. Epub 2014 Aug. 25). However, long term benefits are restricted to a small subset of patients while most will relapse and succumb to their refractory disease.

Access of T-cells to tumor cells or tissue has been deemed essential for the success of ACT. Thus strategies enabling T-cell entry need to be developed and implemented (Gattinoni et al., Nat Rev Immunol 6(5) (2006), 383-393). The currently most effective method to achieve enhanced T-cell infiltration is total body irradiation, which permeabilizes tumor tissue, remodels the vasculature and depletes suppressive cells (Dudley et al., J Clin Oncol 23(10) (2005), 2346-2357). While this strategy has shown efficacy in clinical trials, its unspecific nature induces severe side effects, limiting its applicability and calling for more specific strategies (Dudley et al., J Clin Oncol 23(10) (2005), 2346-2357).

In addition, the approval of inhibitors such as anti-CTLA-4 or anti-PD1-antibodies for melanoma therapy has profoundly changed the treatment landscape and the outcome of patients with metastatic disease (Hodi et al., N Engl J Med 363(8) (2010), 711-723; Robert et al., N Engl J Med 372(4) (2015), 320-330). The combination of both of these modalities bears the promise of more profound responses as illustrated by the progression free survival rates and potentially prolonged overall survival (Larkin et al., N Engl J Med 373(1) (2015), 23-34). However, a substantial amount if not most patients will either not benefit or relapse, calling for additional treatment options.

The value of T-cells for melanoma therapy has been further demonstrated by the use of tumor infiltrating lymphocytes (TIL), which if combined with total body irradiation induce unparalleled response rates as high as in 77% of patients treated (Dudley et al., J Clin Oncol 26(32) (2008), 5233-5239; Rosenberg et al., Clin Cancer Res 17(13) (2011), 4550-4557). While a number of patients are considered cured, most will relapse and succumb to their disease, indicating the principal sensitivity of most melanomas to T-cell attack but calling for additional strategies to sustain anti-tumoral response and prevent relapse.

It was recently shown that the combination of antigen-specific T-cells transduced with a marker antigen and (a) tetravalent, bispecific antibody molecule(s) enhance(s) tumor-recognition and mediate(s) prolonged tumor control but fail(s) to eradicate the tumor, potentially due to local immune suppression and T-cell exhaustion (WO 2013/113615; Kobold et al., J Natl Cancer Inst 107(1) (2015), 364; Kobold et al., J Natl Cancer Inst 107(8) (2015) 1-10; Kobold et al., Journal for ImmunoTherapy of Cancer 2(Suppl. 2):P42 (2014)). However, the bispecific antibody molecules as described in Kobold et al., Journal for ImmunoTherapy of Cancer 2(Suppl. 2):P42 (2014) have neither been completely structurally characterized nor deposited. The strategy as described in WO 2013/113615; Kobold et al., J Natl Cancer Inst 107(1) (2015), 364; Kobold et al., J Natl Cancer Inst 107(8) (2015) 1-10; Kobold et al., Journal for ImmunoTherapy of Cancer 2(Suppl. 2):P42 (2014) also has the inconvenient, that T-cell therapy is dependent on MHC-restriction and does not allow for additional T-cell stimulation. Further, US 2010/0256340 discloses the construction of trivalent, bispecific antibody molecules. However, US 2010/0256340 nowhere describes the use of (a) trivalent, bispecific antibody molecule(s) as a tool for the specific recruitment of T-cells which were transduced with a fusion protein to a cancer cell. Further, the combination of bispecific antibody molecules with T-cells transduced with a fusion protein has been described (Urbanska et al., Journal of Translational Medicine 12(347) (2014), doi: 10.1186/12967-014-0347-2). However, the sole purpose of the experimental procedure described in the Urbanska et al. publication was to prove that antibody molecules, which were obtained by cross-linking of two monoclonal antibody molecules, targeting the folate receptor fused to CD8, CD28 and CD3z and a tumor associated antigen (CD20 and HER2) would re-direct T-cells against cancer cells. However, the data of Urbanska et al. cannot preclude further generalization of the concept because of the following reasons: 1) no data is provided that any antibody molecule targeting fusion proteins constituted of different extracellular domains fused to T-cell stimulatory domains would be able to activate T-cells; 2) no analysis of the impact of tetravalency on T-cell activation in the absence of tumor cells is provided; 3) no data is provided that trivalent, bispecific antibody molecules would be able to perform similarly or even with stronger capacity T-cell activation. Further, the data shown in the Urbanska et al. publication might be interpreted in such a way that the CD8 domain would be essential for T-cell activation.

Accordingly, the targeted tumor therapy, particularly the adoptive T-cell therapy needs to be improved in order to suffice the needs of the cancer patients. Thus, there is still a need to provide improved means having the potential to improve safety and efficacy of ACT and overcome the above disadvantages.

This need is addressed by the present invention by providing the embodiments as defined in the claims.

SUMMARY OF THE INVENTION

The present invention relates to a kit comprising (A) a fusion protein comprising an extracellular domain of a signaling receptor that does not naturally occur in or on T-cells obtained from a subject to be treated, an anchoring transmembrane domain, and a stimulatory signalling domain, and (B) a trivalent, bispecific antibody molecule which binds to the extracellular domain of the fusion protein (i.e. the extracellular domain of a signalling receptor that does not occur in or on T-cells) and to a tumor-specific antigen naturally occurring on the surface of a tumor cell. In a more preferred embodiment, the present invention relates to a kit comprising (A) a fusion protein comprising an extracellular domain of a signaling receptor that does not naturally occur in or on T-cells obtained from a subject to be treated, an anchoring transmembrane domain, at least one co-stimulatory signalling domain and a stimulatory signalling domain, and (B) a trivalent, bispecific antibody molecule which binds to the extracellular domain of the fusion protein (i.e. the extracellular domain of a signalling receptor that does not occur in or on T-cells) and to a tumor-specific antigen naturally occurring on the surface of a tumor cell.

The present invention relates to the transduction of T-cells, such as CD8+ T-cells, CD4+ T-cells, CD3+ T-cells, γδ T-cells or natural killer (NK) T-cells, preferably CD8+ T-cells, with a fusion protein as described herein and their targeted recruitment by a trivalent, bispecific antibody molecule to the tumor. In contrast to tetravalent, bispecific antibodies described in the Examples of WO 2013/113615 having two binding domains towards a marker antigen introduced into the T-cells and two binding domains towards a tumor-specific antigen that is naturally occurred on the surface of a tumor cell, the present invention is based on the use of trivalent, bispecific antibody molecules which has only one binding domain towards the extracellular domain of the fusion protein and two bindings towards a tumor-specific antigen naturally occurring on the surface of a tumor cell or, alternatively, two binding domains towards the extracellular domain of the fusion protein and only one binding domain towards the tumor-specific antigen naturally occurring on the surface of a tumor cell. As shown in the appended Examples, as a proof of the inventive concept, a trivalent, bispecific antibody "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953" (SEQ ID NO: 22 as encoded by the DNA sequence shown in SEQ ID NO: 21), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2), wherein the second binding domain, i.e. one binding domain, interacts with/binds to (human) EGFRvIII (representing the extracellular domain of a signalling receptor that does not naturally occur in or on said T-cells) and the first and third binding domains, i.e. two binding domains, interact with/bind to murine EpCAM (representing the tumor specific antigen that naturally occurs on the surface of a tumor cell) was constructed. Further, a trivalent, bispecific antibody "BsAB EGFRvIII-MSLN" (SEQ ID NO: 235 which comprises/consists of the plasmids/vectors "EGFR vIII MR1.1 VH Ck MSLN VH CH1 EE Fc knob PG LALA, pETR15655" (SEQ ID NO: 2 as encoded by the DNA sequence shown in SEQ ID NO: 1), "EGFR vIII MR1.1 VL CH1, pETR15656" (SEQ ID NOs: 4 (protein) and 3 (DNA), "VL MSLN Ck RK, pETR15443" (SEQ ID NOs: 6 (protein) and 5 (DNA) and "VH MSLN CH1 EE Fc hole PG LALA HRYF, pETR15667" (SEQ ID NOs: 8 (protein) and 7 (DNA); see also FIG. 10A and Tables 3 and 4), wherein the second binding domain, i.e. one binding domain interacts with/binds to human EGFRvIII (representing the extracellular domain of a signalling receptor that does not naturally occur in or on said T-cells) and the first and third binding domains, i.e. two binding domains, interact with/bind to human mesothelin (the UniProt Entry number of the human mesothelin is Q13421 (version number 132 with sequence number 2; SEQ ID NOs: 149 (DNA) and 150 (protein)) was constructed. Moreover, a trivalent, bispecific antibody "BsAB EGFRvIII-MCSP" (SEQ ID NO: 234 which comprises/consists of the plasmids/vectors "MR1.1 EGFRvIII VH-Ck-(G4S)2 MCSP M4-3 VH CH1 EE Fc knob PG LALA, pETR16621" (SEQ ID NOs: 208 (protein) and 207 (DNA), "EGFR vIII MR1.1 VL CH1, pETR15656" (SEQ ID NOs: 210 (protein) and 209 (DNA), "MCSP ML2 VL Ck RK, pETR16619" (SEQ ID NOs: 212 (protein) and 211 (DNA) and "MCSP M4-3 VH CH1 EE Fc hole PG LALA HYRF, pETR16618" (SEQ ID NOs: 214 (protein) and 213 (DNA); see also FIG. 11A and Tables 5 and 6), wherein the second binding domain, i.e. one binding domain interacts with/binds to human EGFRvIII (representing the extracellular domain of a signalling receptor that does not naturally occur in or on said T-cells) and the first and third binding domains, i.e. two binding domains, interact with/bind to human MCSP (melanoma chondroitin sulfate proteoglycan; the UniProt Entry number of the human MCSP is Q6UVK1 (version number 118; sequence version 2; SEQ ID NOs: 237 (protein) and 236 (DNA)). The treatment of tumors by the combination of the trivalent, bispecific antibody "BsAB EGFRvIII-EpCAM" (SEQ ID NO: 233) which comprises/consists of the plasmids/vectors "EGFR vIII MR1.1 VH Ck muEpCAM VH CH1 EE Fc knob PG LALA, pETR14953" (SEQ ID NO: 22 as encoded by the DNA sequence shown in SEQ ID NO: 21), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2) and transduced tumor specific T-cells (preferably CD8+ T-cells) expressing the EGFRvIII-CD28-CD3z fusion protein (SEQ ID NOs: 41 (DNA) and 42 (protein)) surprisingly abolishes the unspecific cell toxicity compared to experiments using the tetravalent, bispecific antibody "BsAb EpCAM-EGFRvIII, MR1.1" (SEQ ID NO: 229 (light chain (without leader sequence) and SEQ ID NO: 230 (heavy chain (without leader sequence)) having two binding domains that interact with/bind to human EGFRvIII (representing the extracellular domain of a signaling receptor that does not naturally occur in or on said T-cells) and two binding domains that interact with/bind to murine EpCAM (representing the extracellular domain of a signalling receptor that does not naturally occur in or on said T-cells); see FIGS. 6 and 7. Furthermore, the functionality of the trivalent, bispecific antibody "BsAB EGFRvIII-MSLN" (SEQ ID NO: 235; see also Tables 3 and 4) was also shown in a human tumor system; see, e.g., FIG. 17. Accordingly, it was surprisingly and unexpectedly found that T-cells, such as CD8+ T-cells, CD4+ T-cells, CD3+ T-cells, γδ T-cells or natural killer (NK) T-cells, preferably CD8+ T-cells, that were transduced with a fusion protein of the present invention can be specifically stimulated by the use of a trivalent, bispecific antibody molecule and recruited by said trivalent, bispecific antibody molecule to the tumor cell. Thus, it was surprisingly and unexpectedly shown in the present invention that pairing trivalent, bispecific antibody molecules with T-cells transduced with a fusion protein which comprise/consist of an extracellular domain of a signalling receptor that does not naturally occur in or on T-cells, an anchorching transmembrane domain, a T-cell stimulatory signalling domain (and optionally at least one co-stimulatory signalling domain) would result in a specific activation and MHC-independent lysis of the tumor cell. This approach also bears significant safety advantages over conventional T-cell based approaches, as the T-cell would be inert in the absence of the trivalent, bispecific antibody molecule and their availability may be controlled by the antibody molecule format chosen (i.e. smaller molecules for shorter half-life and vice-versa).

Accordingly, the present invention relates to a kit comprising (A) a nucleic acid molecule encoding a fusion protein for transducing T-cells, such as CD8+ T-cells, CD4+ T-cells, CD3+ T-cells, γδ T-cells or natural killer (NK) T-cells, preferably CD8+ T-cells, obtained from a subject to be treated which has the following domains: (1) an extracellular domain of a signalling receptor that does not naturally occur in or on said T-cells; (2) an anchoring transmembrane domain; (3) optionally at least one co-stimulatory signalling domain; and (4) a stimulatory signalling domain, and (B) a trivalent, bispecific antibody molecule which comprises: (i) a first binding domain binding the extracellular domain (1) of the fusion protein characterized in (A); (ii) a second binding domain binding a tumor-specific antigen naturally occurring on the surface of a tumor cell; and (iii) a third binding domain binding the extracellular domain (1) of the fusion protein characterized in (A), i.e. an extracellular domain of a signalling receptor that does not naturally occur in or on said T-cells, or binding said tumor-specific antigen naturally occurring on the surface of a tumor cell.

BRIEF DESCRIPTION OF THE DRAWINGS

FIG. 2 shows bispecific antibody titration in co-culture of transduced T-cells and PanOVA tumor cells.

FIG. 15 shows recombinant mesothelin (MSLN) stimulation of E3-transduced T-cells by BsAb EGFRvIII-MSLN.

DETAILED DESCRIPTION

Figure 1A:
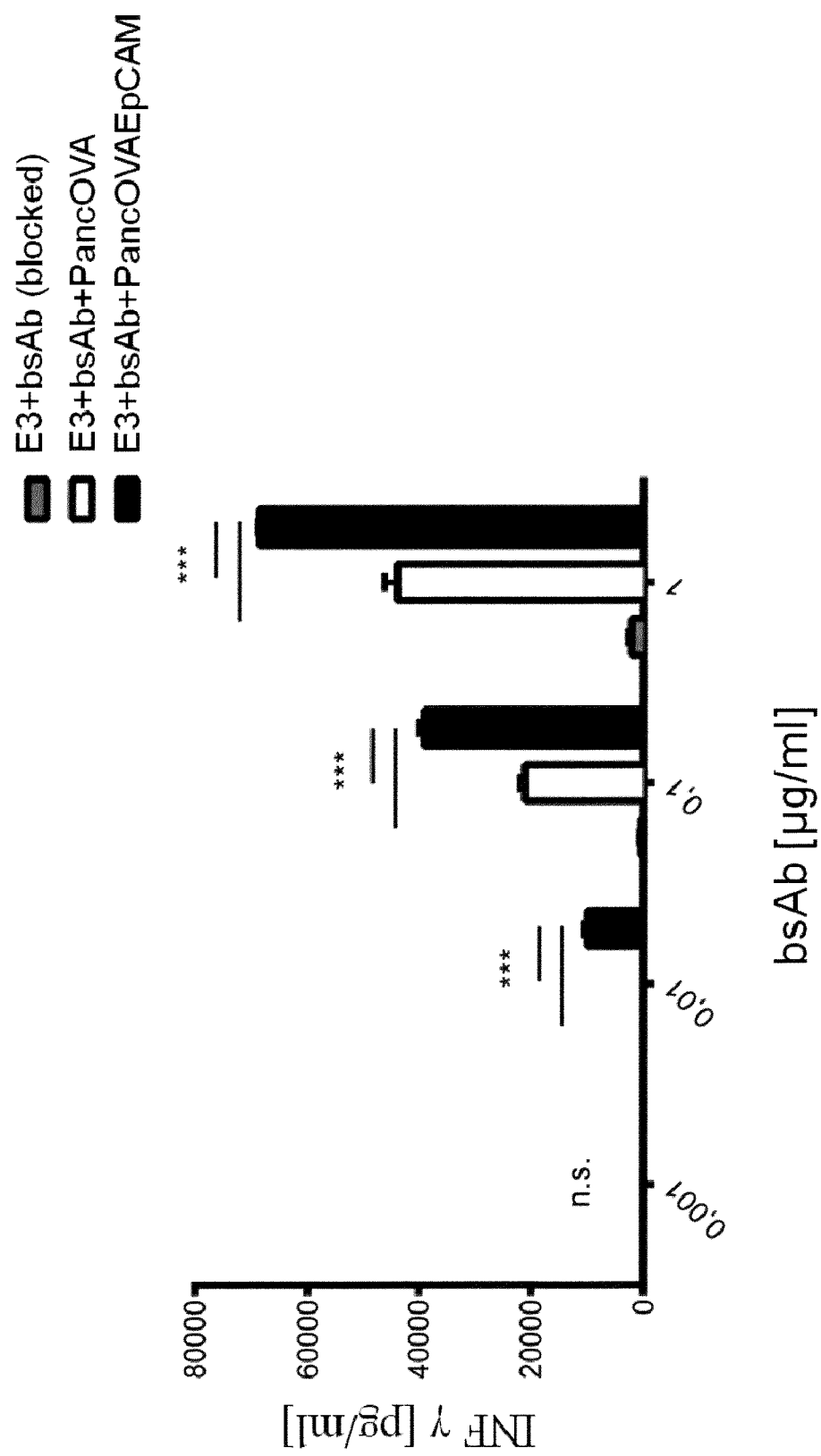
FIG. 1A shows INF-γ-secretion in E3 transduced T-cells incubated with or without tetravalent, bispecific antibody (bsAb) "BsAb EpCAM-EGFRvIII, MR1.1," co-cultured with murine pancreatic cancer tumor cells expressing the tumor antigen EpCAM (PanOVAEpCAM+) or not expressing the tumor antigen EpCAM (PanOVA).

In the context of the present invention the "fusion protein" relates to a protein which is made of polypeptide parts from different sources. Accordingly, it may be also understood as a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details to the production of the fusion protein of the present invention are described herein below.

In the context of the present invention, the terms "polypeptide", "peptide" and "protein" are used interchangeably to refer to a polymer of amino acid residues. The term also applies to amino acid polymers in which one or more amino acid residues is an artificial chemical mimetic or a corresponding naturally occurring amino acid, as well as to naturally occurring amino acid polymers. Accordingly, in the context of the present invention, the term "polypeptide" relates to a molecule which comprises or consists of chains of amino acid monomers linked by peptide (amide) bonds. Peptide bonds are covalent chemical bonds which are formed when the carboxyl group of one amino acid reacts with the amino group of another. Herein a "polypeptide" is not restricted to a molecule with a defined length. Thus, herein the term "polypeptide" relates to a peptide, an oligopeptide, a protein, or a polypeptide which encompasses amino acid chains, wherein the amino acid residues are linked by covalent peptide bonds. However, herein the term "polypeptide" also encompasses peptidomimetics of such proteins/polypeptides wherein amino acid(s) and/or peptide bond(s) have been replaced by functional analogs. The term polypeptide also refers to, and does not exclude, modifications of the polypeptide, e.g., glycosylation, acetylation, phosphorylation and the like. Such modifications are well described in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

In the context of the present invention, the fusion protein may comprise a fragment/polypeptide part of the extracellular domain of a signalling receptor that does not naturally occur in or on T-cells. Thus, the "extracellular domain of a signalling receptor that does not naturally occur in or on T-cells" which is comprised in the herein provided fusion protein is a fragment/polypeptide part of the full length extracellular domain of a signalling receptor that does not naturally occur in or on T-cells as defined herein. In the context of the present invention and as explained herein above, the trivalent, bispecific antibody molecules of the present invention bind to/interact with the extracellular domain of the fusion protein, i.e. the extracellular domain of a signalling receptor that does not naturally occur in or on T-cells.

In an illustrative embodiment of the present invention, as a proof of concept, a fusion protein is provided which comprise a fragment/polypeptide part of human EGFRvIII (the NCBI Reference Sequence of human EGFRvIII is NM_201283.1 (version: NM_201283.1; GI:41327733)) as shown herein as SEQ ID NOs: 151 (DNA) and 152 (protein) or comprise a fragment/polypeptide part of human Cripto (the Uniprot Entry number of the human Cripto is P13385 (with the version number 151 and version 1 of the sequence)) as shown herein as SEQ ID NOs: 153 (DNA) and 154 (protein). Accordingly, in the context of the present invention, the herein described fusion protein may comprise/consist of the amino acid sequence of human EGFRvIII as shown in SEQ ID NO: 152 (as encoded by the DNA sequence shown in SEQ ID NO: 151). Alternatively, in the context of the present invention, the fusion protein may comprise/consist of the amino acid sequence of human del-hEGFRvIII as shown in SEQ ID NO: 232 (as encoded by the DNA sequence shown in SEQ ID NO: 231). Moreover, in the context of the present invention, the herein described fusion protein may comprise/consist of the amino acid sequence of human Cripto as shown in SEQ ID NO: 154 (as encoded by the DNA sequence shown in SEQ ID NO: 153). Thus, more preferably, the extracellular domain of a signalling receptor that does not naturally occur in or on T-cells may comprise or consist of the amino acid sequence as shown in SEQ ID NO: 52 (human EGFRvIII) (as encoded by the DNA sequence shown in SEQ ID NO: 51 (human EGFRvIII)). In an alternative preferred embodiment of the present invention, the extracellular domain of a signalling receptor that does not naturally occur in or on T-cells may comprise or consist of the amino acid sequence as shown in SEQ ID NO: 232 (as encoded by the DNA sequence shown in SEQ ID NO: 231). Alternatively, in the context of the present invention, the extracellular domain of a signalling receptor that does not naturally occur in or on T-cells may comprise or consist of the amino acid sequence as shown in SEQ ID NO: 76 or 78 (as encoded by the DNA sequence shown in SEQ ID NO: 75 or 77). In the context of the present invention, the extracellular domain of a signalling receptor that does not naturally occur in or on T-cells may comprise or consist of the amino acid sequence as shown in SEQ ID NO: 62 (human Cripto) (as encoded by the DNA sequence shown in SEQ ID NO: 61). In the context of the present invention, also a smaller/shorter fragment of EGFRvIII or Cripto may be used. Accordingly, in the context of the present invention a smaller/shorter fragment of EGFRvIII as depicted in SEQ ID NOs: 52, 232, 76 or 78 or Cripto as depicted in SEQ ID NO: 62 may be used. In particular, any fraction of said extracellular domains (i.e. EGFRvIII or Cripto) may be used in the fusion proteins of the invention, provided that this fraction is bound by the bispecific antibody as defined herein. Such a fragment would be able to trigger T-cell activation, e.g. CD8+ T-cell activation, through the fusion proteins of the invention. Preferably, the extracellular domain of the fusion protein(s) of the invention is (are) derived from human EGFRvIII or human Cripto. An example for such an extracellular portion is an extracellular domain of EGFRvIII, for example, having the amino acid sequences as shown in SEQ ID NO: 52 (as encoded by the DNA as shown in SEQ ID NO: 51), SEQ ID NO: 232 (as encoded by the DNA sequence as shown in SEQ ID NO: 231) or SEQ ID NO: 76 (as encoded by the DNA as shown in SEQ ID NO: 75). Moreover, in the context of the present invention, the extracellular domain of Cripto may comprise/consist of the amino acid sequence as shown in SEQ ID NO: 62 (as encoded by the DNA sequence shown in SEQ ID NO: 61).

In the context of the present invention, the anchoring transmembrane domain of the fusion proteins of the present invention may be characterized by not having a cleavage site for mammalian proteases. In the context of the present invention, proteases refer to proteolytic enzymes that are able to hydrolyze the amino acid sequence of the anchoring transmembrane domain of the fusion protein of the present invention. The term proteases include both endopeptidases and exopeptidases. In the context of the present invention any extracellular portion of a transmembrane protein as laid down among others by the CD-nomenclature may be used to generate the fusion protein of the invention, which activates T-cells, such as CD8+ T-cells, CD4+ T-cells, CD3+ T-cells, γδ T-cells or natural killer (NK) T-cells, preferably CD8+ T-cells, upon binding to a trivalent, bispecific antibody as defined herein. An example for such an anchoring transmembrane domain is a transmembrane domain of CD28, for example, having the amino acid sequence as shown herein in SEQ ID NO: 54 (as encoded by the DNA sequence shown in SEQ ID NO: 53). However, because human sequences are most preferred in the context of the present invention, the anchoring transmembrane domain of the fusion protein may comprise or consist of an amino acid sequence as shown in SEQ ID NO: 66 (as encoded by the DNA sequence shown in SEQ ID NO: 65). In the context of the present invention, the transmembrane domain of the fusion protein of the present invention may comprise/consist of an amino acid sequence as shown in SEQ ID NO: 80 (as encoded by the DNA sequence shown in SEQ ID NO: 79). In case that the herein provided fusion protein comprises the transmembrane domain of EGFRvIII as shown in SEQ ID NO: 80, the fusion protein may comprise an anchoring domain as shown in SEQ ID NO: 82 (as encoded by the DNA sequence shown in SEQ ID NO: 81). In an illustrative embodiment of the present invention, as a proof of concept, a fusion protein is provided which comprises or consists of a fragment/polypeptide part of EGFRvIII as shown herein as SEQ ID NO: 52 (as encoded by the DNA sequence shown in SEQ ID NO: 51), SEQ ID NO: 232 (as encoded by the DNA sequence shown in SEQ ID NO: 231), SEQ ID NO: 76 (as encoded by the DNA sequence shown in SEQ ID NO: 75) or SEQ ID NO: 78 (as encoded by the DNA sequence shown in SEQ ID NO: 77) and comprise a fragment/polypeptide part of CD28 (the Uniprot Entry number of the human CD28 is P10747 (with the version number 173 and version 1 of the sequence)) as shown herein as SEQ ID NO: 156 (as encoded by the DNA sequence shown in SEQ ID NO: 155). In the context of the present invention any portion/fragment of CD28 may be used as an anchoring transmembrane domain. Alternatively, any protein having a transmembrane domain, as provided among others by the CD nomenclature, may be used as an anchoring domain of the fusion protein of the invention. According to the present invention such an anchoring transmembrane domain that does not have a cleavage site for mammalian proteases may be used to trigger T-cell (e.g. CD8+ T-cell) activation. In a further embodiment of the present invention, the anchoring transmembrane domain that does not have a cleavage site for mammalian protease of the fusion protein may comprise or consist of the amino acid sequence as shown in SEQ ID NO: 54 (as encoded by the DNA sequence shown in SEQ ID NO: 53 (mouse)). However, more preferably, the fusion protein of the present invention comprises polypeptides which are derived from a human origin. Thus, more preferably, the polypeptide which is comprised in the fusion protein of the present invention may comprise or consist of the amino acid sequence as shown in SEQ ID NO: 66 (as encoded by the DNA sequence shown in SEQ ID NO: 65 (human)).

As described above, the herein provided fusion protein may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO: 156 (as encoded by the cDNA shown in SEQ ID NO: 155). Accordingly, in the context of the present invention the anchoring transmembrane domain may comprise or consist of an amino acid sequence as shown in SEQ ID NO: 66.

As described above, the herein provided fusion protein optionally comprises at least one co-stimulatory domain which would provide additional activity to the T-cell (see below). The herein provided fusion protein may comprise a co-stimulatory signalling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)) or DAP10 (the UniProt Entry of the human DAP10 is Q9UBJ5 (version number 25 with sequence number 1); the UniProt entry of the murine/mouse DAP10 is Q9QUJ0 (primary citable accession number) or Q9R1E7 (secondary citable accession number) with the version number 101 and the sequence number 1)). In a further embodiment of the present invention the fusion protein of the present invention may comprise one or more, i.e. 1, 2, 3, 4, 5, 6 or 7 of the herein defined co-stimulatory signalling domains. Accordingly, in the context of the present invention, the fusion protein of the present invention may comprise a fragment/polypeptide part of a murine/mouse or preferably of a human CD28 as first co-stimulatory signalling domain and the second co-stimulatory signalling domain is selected from the group consisting of the murine/mouse or preferably of the human CD137, OX40, ICOS, CD27, 4-1-BB and DAP10. As illustrated in the appended Examples, the co-stimulatory signalling domain(s) comprised in the fusion protein of the present invention may comprise or consist of the amino acid sequence as shown in SEQ ID NO: 56 (as encoded by the DNA sequence shown in SEQ ID NO: 55 (mouse)) and/or the amino acid sequence as shown in SEQ ID NO: 60 (as encoded by the DNA sequence shown in SEQ ID NO: 59 (mouse)). However, more preferably, the fusion protein of the present invention comprises polypeptides which are derived from a human origin. Thus, more preferably, the fusion protein of the present invention comprises polypeptides which are derived from a human origin. Thus, more preferably, the co-stimulatory signalling domain(s) which is (are) comprised in the fusion protein of the present invention may comprise or consist of the amino acid sequence as shown in SEQ ID NO: 68 (as encoded by the DNA sequence shown in SEQ ID NO: 67 (human)) and/or the amino acid sequence as shown in SEQ ID NO: 72 (as encoded by the DNA sequence shown in SEQ ID NO: 71).

Thus, the co-stimulatory signalling domain which may be optionally comprised in the herein provided fusion protein is a fragment/polypeptide part of the full length CD28, CD137, OX40, ICOS, CD27, 4-1-BB or DAP10. The amino acid sequences of the murine/mouse full length CD28, CD137, OX40, ICOS, CD27, 4-1-BB or DAP10 are shown herein as SEQ ID NOs: 158 (CD28), 162 (CD137), 166 (OX40), 170 (ICOS), 174 (CD27), 203 (4-1-1B) or 178 (DAP10) (murine/mouse as encoded by the DNA sequences shown in SEQ ID NOs: 157 (CD28), 161 (CD137), 165 (OX40), 169 (ICOS), 173 (CD27), 227 (4-1-1B) or 177 (DAP10)). However, because human sequences are most preferred in the context of the present invention, the co-stimulatory signalling domain which may be optionally comprised in the herein provided fusion protein is a fragment/polypeptide part of the human full length CD29, CD137, OX40, ICOS, CD27, 4-1-BB or DAP10. The amino acid sequences of the human full length CD28, CD137, OX40, ICOS, CD27, 4-1-BB or DAP10 are shown herein as SEQ ID NOs: 156 (CD28), 160 (CD137), 164 (OX40), 168 (ICOS), 172 (CD27), 204 (4-1-BB1) or 176 (DAP10) (human as encoded by the DNA sequences shown in SEQ ID NOs: 155 (CD28), 159 (CD137), 163 (OX40), 167 (ICOS), 171 (CD27), 228 (4-1-nB) or 175 (DAP10)).

The herein provided fusion protein may comprise a fragment of CD28 as co-stimulatory domain, provided that at least one signaling domain of CD28 is comprised. In particular, any part/fragment of CD28 is suitable for the fusion protein of the invention as long as at least one of the signaling motives of CD28 is comprised. For example, the CD28 polypeptide which is comprised in the fusion protein of the present invention may comprise or consist of the amino acid sequence shown in SEQ ID NO: 56 (as encoded by the DNA sequence shown in SEQ ID NO: 55). In the present invention the intracellular domain of CD28, which functions as a co-stimulatory domain, may comprise a sequence derived from the intracellular domain of the CD28 polypeptide having the sequence(s) YMNM (SEQ ID NO: 122) and/or PYAP (SEQ ID NO: 121). However, more preferably, the fusion protein of the present invention comprises polypeptides which are derived from human origin. For example, the fragment/polypeptide part of the human CD28 which may be comprised in the fusion protein of the present invention may comprise or consist of the amino acid sequence shown in SEQ ID NO: 68 (as encoded by the DNA sequence shown in SEQ ID NO: 67). Accordingly, in the context of the present invention the fusion protein comprises the sequence as shown in SEQ ID NO: 68 or a sequence which has up to 1, 2, 3, 4, 5, 6, 7, 8, 9 or 10 substitutions, deletions or insertions in comparison to SEQ ID NO: 68 and which is characterized by having a co-stimulatory signalling activity. The co-stimulatory signalling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory domain of the fusion protein may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T-cell. CD28 activity can be measured by release of cytokines by ELISA or flow cytometry of cytokines such as interferon-gamma (IFN-γ) or interleukin 2 (IL-2), proliferation of T-cells measured e.g. by ki67-measurement, cell quantification by flow cytometry (as described below in the appended Examples), or lytic activity as assessed by real time impedance measurement of the target cell (by using e.g. an ICELLligence instrument as described e.g. in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Duwell et al., Cell Death Differ. 21(12) (2014), 1825-1837, Erratum in: Cell Death Differ. 21(12) (2014), 161). The co-stimulatory signalling domains PYAP (amino acids (AA) 208 to 211 of SEQ ID NO: 156 (as encoded by DNA sequence shown in SEQ ID NO: 155) and YMNM (AA 191 to 194 of SEQ ID NO: 156) are beneficial for the function of the CD28 polypeptide and the functional effects enumerated above. The amino acid sequence of the YMNM domain is shown in SEQ ID NO: 122; the amino acid sequence of the PYAP domain is shown in SEQ ID NO: 121. Accordingly, in the fusion protein of the present invention, the CD28 polypeptide preferably comprises a sequence derived from intracellular domain of a CD28 polypeptide having the sequences YMNM (SEQ ID NO: 122) and/or PYAP (SEQ ID NO: 121). In the context of the present invention an intracellular domain of a CD28 polypeptide having the sequences YMNM (SEQ ID NO: 122) and/or PYAP (SEQ ID NO: 121) characterized by a CD28 activity, defined as cytokine production, proliferation and lytic activity of a transduced cell described herein, like e.g. a transduced T-cell. Accordingly, in the context of the present invention the co-stimulatory signalling domain of the fusion proteins of the present invention has the amino acid sequence of SEQ ID NO: 68 (human) (as encoded by the DNA sequence shown in SEQ ID NO: 67) or SEQ ID NO: 56 (mouse/murine) (as encoded by the DNA sequence shown in SEQ ID NO: 55). However, in the fusion protein of the present invention, one or both of these domains may be mutated to FMNM (SEQ ID NO: 123) and/or AYAA (SEQ ID NO: 124), respectively. Either of these mutations reduces the ability of the fusion protein to release cytokines without affecting its ability to proliferate and can advantageously be used to prolong the viability and thus the therapeutic potential of the transduced cells. Or, in other words, such a non functional mutation preferably enhances the persistence of the cells which are transduced with the herein provided fusion protein in vivo. These signalling motives may, however, be present at any site within the intracellular domain of the herein provided fusion protein.

Accordingly, as mentioned above, the fusion protein of the present invention may comprise a fragment of CD28 as co-stimulatory domain, provided that at least one signaling domain of CD28 is comprised. In particular, any part/fragment of CD28 is suitable as co-stimulatory domain as long as at least one of the signaling motives, i.e. YMNM (SEQ ID NO: 122) and/or PYAP (SEQ ID NO: 121), of CD28 is comprised. For example, the CD28 polypeptide which is used as co-stimulatory domain may comprise or consist of the amino acid sequence shown in SEQ ID NO: 66 (as encoded by the DNA sequence shown in SEQ ID NO: 65). In the present invention the intracellular domain of CD28, which functions as a co-stimulatory domain, may comprise a sequence derived from the intracellular domain of the CD28 polypeptide having the sequence(s) YMNM (SEQ ID NO: 122) and/or PYAP (SEQ ID NO: 121). In the context of the present invention the co-stimulatory signalling domain of the CD28 polypeptide may be of any length provided that the co-stimulatory domain of the fusion protein of the present invention comprises the sequences YMNM (SEQ ID NO: 122) and/or PYAP (SEQ ID NO: 121). Accordingly, in the context of the present invention the co-stimulatory signalling domain of the CD28 of the fusion protein may comprise a sequence derived from the CD28 polypeptide having the sequences YMNM (SEQ ID NO: 122) and/or PYAP (SEQ ID NO: 121). For example, the CD28 polypeptide which is comprised in the fusion protein of the present invention may comprise or consist of the amino acid sequence as shown in SEQ ID NO: 56 (as encoded by the DNA sequence shown in SEQ ID NO: 55). As mentioned, the fusion protein preferably comprises polypeptides of human origin. For example, the CD28 polypeptide which is comprised in the fusion protein of the present invention may comprise or consist of the amino acid sequence as shown in SEQ ID NO: 66 (as encoded by the DNA sequence shown in SEQ ID NO: 65). In the context of the present invention the co-stimulatory signalling domain as derived from the CD28 polypeptide may be of any length provided that the co-stimulatory signalling domain of the fusion protein of the present invention comprises the sequences YMNM (SEQ ID NO: 122) and/or PYAP (SEQ ID NO: 121). Accordingly, in the context of the present invention the co-stimulatory domain of the CD28 of the fusion protein may comprise a sequence derived from the CD28 polypeptide having the sequences YMNM (SEQ ID NO: 122) and/or PYAP (SEQ ID NO: 121). For example, the CD28 polypeptide which is comprised in the fusion protein of the present invention may comprise or consist of the amino acid sequence as shown in SEQ ID NO: 56 (murine/mouse) or 66 (human). In the context of the present invention, the CD28 polypeptide of the fusion protein has the amino acid sequence of SEQ ID NO: 66 (human). In the context of the present invention, the fusion protein comprises an intracellular domain of a CD28 polypeptide having the sequences YMNM (SEQ ID NO: 122) and/or the PYAP (SEQ ID NO: 121). Accordingly, in the context of the present invention, the CD28 polypeptide has the amino acid sequence of SEQ ID NO: 66 (human).

As described above, the herein provided fusion protein comprises a stimulatory signalling domain, which provides T-cell activation, measured by the same means as T-cell activation. The herein provided fusion protein may comprise a stimulatory signalling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is O54709 (version number 132 with sequence number 2)).

Thus, the stimulatory signalling domain which is comprised in the herein provided fusion protein may be a fragment/polypeptide part of the full length of CD3z, FCGR3A or NKG2D. The amino acid sequences of the murine/mouse full length of CD3z, or NKG2D are shown herein as SEQ ID NOs: 180 (CD3z) or 182 (NKG2D) (murine/mouse as encoded by the DNA sequences shown in SEQ ID NOs: 179 (CD3z) or 181 (NKG2D). The amino acid sequences of the human full length CD3z, FCGR3A or NKG2D are shown herein as SEQ ID NOs: 184 (CD3z), 186 (FCGR3A) or 188 (NKG2D) (human as encoded by the DNA sequences shown in SEQ ID NOs: 183 (CD3z), 185 (FCGR3A) or 187 (NKG2D)). The fusion protein of the present invention may comprise fragment of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the fusion protein of the present invention comprises polypeptides which are derived from human origin. Thus, more preferably, the herein provided fusion protein comprises the amino acid sequences as shown herein as SEQ ID NOs: 184 (CD3z), 186 (FCGR3A) or 188 (NKG2D) (human as encoded by the DNA sequences shown in SEQ ID NOs: 183 (CD3z), 185 (FCGR3A) or 187 (NKG2D). For example, the fragment/polypeptide part of the human CD3z which may be comprised in the fusion protein of the present invention may comprise or consist of the amino acid sequence shown in SEQ ID NO: 70 (as encoded by the DNA sequence shown in SEQ ID NO: 69). Accordingly, in the context of the present invention the fusion protein comprises the sequence as shown in SEQ ID NO: 70 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO: 70 and which is characterized by having a stimulatory signalling activity. The stimulatory signalling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

Moreover, the herein provided fusion proteins may comprise a linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein provided fusion protein may comprise a linker between the extracellular domain of a signalling receptor that does not naturally occur in or on T-cells, the anchoring transmembrane domain that does not have a cleavage site for mammalian proteases, the co-stimulatory signalling domain and/or the stimulatory domain. Such linkers have the advantage that they can make it more likely that the different polypeptides of the fusion protein (i.e. the extracellular domain of a signalling receptor that does not naturally occur in or on T-cells, the anchoring transmembrane domain that does not have a cleavage site for mammalian proteases, the co-stimulatory signalling domain and/or the stimulatory domain) fold independently and behave as expected. Thus, in the context of the present invention, the extracellular domain of an extracellular domain of a signalling receptor that does not naturally occur in or on T-cells, the anchoring transmembrane domain that does not have a cleavage site for mammalian proteases, the co-stimulatory signalling domain and the stimulatory domain may be comprised in a single-chain multi-functional polypeptide. A single-chain fusion construct e.g. may consist of (a) polypeptide(s) comprising (an) extracellular domain(s) of a signalling receptor that does not naturally occur in or on T-cells, (an) anchoring transmembrane domain(s) that does not have a cleavage site for mammalian proteases, (a) co-stimulatory signalling domain(s) and/or (a) stimulatory domain(s).

Furthermore, the herein provided fusion protein may contain a hinge domain which acts as a spacer between the portion recognized by the antibody and the transmembrane domain. It may be of any length and may belong to the same or to a different extracellular portion of the antigen recognized by the trivalent, bispecific antibody molecule on the fusion protein. In the context of the present invention any extracellular part of an extracellular protein could be used as a hinge domain between the transmembrane domain and the antibody binding site. Candidates include any member of the CD nomenclature. Accordingly, in the context of the present invention any protein having an extracellular part of an extracellular domain, as provided among others by the CD nomenclature, may be used as a hinge domain in the fusion protein of the present invention. An example for such a hinge domain may be a extracellular portion of CD8, for example having the amino acid sequence as shown herein in SEQ ID NO: 64 (as encoded by the DNA sequence shown in SEQ ID NO: 63 (mouse)). However, because the human sequences are most preferred in the context of the present invention, the hinge domain of the fusion protein may comprise or consist of the amino acid sequence as shown in SEQ ID NO: 74 (as encoded by the DNA sequence shown in SEQ ID NO: 73). In case that the herein provided fusion protein comprises or consists of the hinge domain as depicted in SEQ ID NOs: 64 (mouse) or 74 (human), the fusion protein of the present invention does not have an anchoring transmembrane domain. Accordingly, in case that the herein provided fusion protein comprises or consists of the hinge domain as depicted in SEQ ID NOs: 64 or 74, the fusion protein of the following domains: (1) an extracellular domain of a signalling receptor that does not naturally occur in or on said T-cells, (2) a hinge domain as depicted in SEQ ID NOs: 64 or 74, (3) optionally at least one co-stimulatory signalling domain; and (4) a stimulatory signalling domain. Exemplarily, the fusion protein as depicted in SEQ ID NO: 46 (murine/mouse Cripto-CD28-CD3z as encoded by the DNA sequence shown in SEQ ID NO: 45) comprise the hinge domain as depicted in SEQ ID NO: 64. Moreover, the fusion protein as depicted or SEQ ID NO: 120 (human Cripto-CD28-CD3z as encoded by the DNA sequence shown in SEQ ID NO: 119) comprise the hinge domain as depicted in SEQ ID NO: 74. In another embodiment of the present invention, the fusion protein of the present invention is characterized by not having a hinge domain. Exemplarily, the fusion proteins as depicted in SEQ ID NO: 42 (murine/mouse EGFRvIII-CD28-CD3z as encoded by the DNA sequence shown in SEQ ID NO: 41), SEQ ID NO: 44 (murine/mouse EGFRvIII-CD28-4-1-BB-CD3z as encoded by the DNA sequence shown in SEQ ID NO: 43), SEQ ID NO: 48 (human EGFRvIII-CD28-CD3z as encoded by the DNA sequence shown in SEQ ID NO: 47), SEQ ID NO: 50 (human EGFRvIII-CD28-4-1-BB-CD3z (as encoded by the DNA sequence shown in SEQ ID NO: 49)) are characterized by not having a hinge domain.

The herein provided fusion proteins may comprise or consist of an amino acid sequence as shown in SEQ ID NO: 42 (murine/mouse EGFRvIII-CD28-CD3z (as encoded by the DNA sequence shown in SEQ ID NO: 41)), SEQ ID NO: 44 (murine/mouse EGFRvIII-CD28-4-1-BB-CD3z (as encoded by the DNA sequence shown in SEQ ID NO: 43)) or SEQ ID NO: 46 (murine/mouse Cripto-CD28-CD3z (as encoded by the DNA sequence shown in SEQ ID NO: 45)). Most preferably, the herein provided fusion protein comprises or consists of an amino acid sequence as shown in SEQ ID NO: 48 (human EGFRvIII-CD28-CD3z (as encoded by the DNA sequence shown in SEQ ID NO: 47)), SEQ ID NO: 50 (human EGFRvIII-CD28-4-1-BB-CD3z (as encoded by the DNA sequence shown in SEQ ID NO: 49)) or SEQ ID NO: 120 (human Cripto-CD28-CD3z (as encoded by the DNA sequence shown in SEQ ID NO: 119)). Accordingly, the present invention relates in a preferred embodiment to a fusion protein which may have the amino acid sequence of SEQ ID NO: 48, SEQ ID NO: 50 or SEQ ID NO: 120.

If the herein provided fusion protein comprises a fragment of Cripto, the fusion protein may comprise a leader sequence. Such a leader sequence will bring the protein to the surface of the T-cell membrane. For example, in the herein provided fusion protein the leader sequence may have the amino and amino acid sequence as shown in SEQ ID NO: 206 (as encoded by the DNA sequence shown in SEQ ID NO: 205).

Accordingly, in the context of the present invention the kit may comprise or consist of an amino acid sequence as shown in SEQ ID NO: 42 (murine/mouse EGFRvIII-CD28-CD3z (as encoded by the DNA sequence shown in SEQ ID NO: 41)) combined with the trivalent, bispecific antibody molecule as shown in SEQ ID NO: 235. Alternatively, the kit may comprise or consist of an amino acid sequence as shown in SEQ ID NO: 42 (murine/mouse EGFRvIII-CD28-CD3z (as encoded by the DNA sequence shown in SEQ ID NO: 41)) combined with the trivalent, bispecific antibody molecule as shown in SEQ ID NO: 233. Moreover, in the context of the present invention the kit may comprise or consist of an amino acid sequence as shown in SEQ ID NO: 42 combined with the trivalent, bispecific antibody molecule as shown in SEQ ID NO: 234. Moreover, in the context of the present invention the kit may comprise or consist of an amino acid sequence as shown in SEQ ID NO: 44 (murine/mouse EGFRvIII-CD28-4-1-BB-CD3z (as encoded by the DNA sequence shown in SEQ ID NO: 43)) combined with the trivalent, bispecific antibody molecule as shown in SEQ ID NO: 235. Alternatively, the kit may comprise or consist of an amino acid sequence as shown in SEQ ID NO: 44 (murine/mouse EGFRvIII-CD28-4-1-BB-CD3z (as encoded by the DNA sequence shown in SEQ ID NO: 43)) combined with the trivalent, bispecific antibody molecule as shown in SEQ ID NO: 233. Moreover, the kit may comprise or consist of an amino acid sequence as shown in SEQ ID NO: 44 combined the trivalent, bispecific antibody molecule as shown in SEQ ID NO: 234. However, because human sequences are most preferred in the context of the present invention, the kit of the present invention may comprise or consist of an amino acid sequence as shown in SEQ ID NO: 48 (human EGFRvIII-CD28-CD3z (as encoded by the DNA sequence shown in SEQ ID NO: 47)) combined with the trivalent, bispecific antibody molecule as shown in SEQ ID NO: 235.

Alternatively, in the context of the present invention the kit of the present invention may comprise or consist of an amino acid sequence as shown in SEQ ID NO: 50 (human EGFRvIII-CD28-4-1-BB-CD3z (as encoded by the DNA sequence shown in SEQ ID NO: 49)) combined with the trivalent, bispecific antibody molecule as shown in SEQ ID NO: 235. Further, the kit of the present invention may comprise or consist of an amino acid sequence as shown in SEQ ID NO: 48 (human EGFRvIII-CD28-CD3z (as encoded by the DNA sequence shown in SEQ ID NO: 47)) combined with the trivalent, bispecific antibody molecule as shown in SEQ ID NO: 233. Alternatively, the kit of the present invention may comprise or consist of an amino acid sequence as shown in SEQ ID NO: 50 (human EGFRvIII-CD28-4-1-BB-CD3z (as encoded by the DNA sequence shown in SEQ ID NO: 49)) combined with the trivalent, bispecific antibody molecule as shown in SEQ ID NO: 233. Moreover, the kit of the present invention may comprise or consist of an amino acid sequence as shown in SEQ ID NO: 50 (human EGFRvIII-CD28-4-1-BB-CD3z) combined with the trivalent, bispecific antibody molecule as shown in SEQ ID NO: 234. Moreover, the kit of the present invention may comprise or consist of an amino acid sequence as shown in SEQ ID NO: 48 (human EGFRvIII-CD28-CD3z (as encoded by the DNA sequence shown in SEQ ID NO: 47)) combined with the trivalent, bispecific antibody molecule as shown in SEQ ID NO: 234.

Furthermore, parts of the kit of the invention can be packaged individually in vials or bottles or in combination in containers or multicontainer units. Furthermore, the kit of the present invention comprises a (closed) bag cell incubation system where patient cells, preferably T-cells as described herein, can be transduced and incubated under GMP (good manufacturing practice, as described in the guidelines for good manufacturing practice published by the European Commission: EudraLex—Volume 4—Good Manufacturing Practice (GMP) guidelines; available on the ec.europa.eu website) conditions. Furthermore, the kit of the present invention comprises a (closed) bag cell incubation system where isolated/obtained patients T-cells can be transduced and incubated under GMP. Furthermore, in the context of the present invention, the kit may also comprise a vector encoding the fusion protein as described herein and/or a nucleic acid molecule encoding a T-cell receptor as described herein above. The kit of the present invention may be advantageously used, inter alia, for carrying out the method of the invention and could be employed in a variety of applications referred herein, e.g., as research tools or medical tools. The manufacture of the kits preferably follows standard procedures which are known to the person skilled in the art.

In this context, the term "trivalent, bispecific antibody molecule" as used herein relates to a bispecific antibody molecule capable of binding via one or two binding domains to an extracellular domain of the fusion protein described herein, i.e. an extracellular domain of a signalling receptor that does not naturally occur in or on said T-cells, and capable of inducing elimination/lysis of target cells via the remaining binding domain(s) to a tumor-specific antigen naturally occurring (that is endogeneously expressed) on the surface of a tumor cell. Binding of the extracellular domain of the fusion protein as described herein activates that T-cells and brings them through the trivalent, bispecific binding construct into physical contact with the tumor cell. Non-transduced or endogenous T-cells (e.g. CD8+ T-cells) remain unaffected by the trivalent, bispecific binding construct. Accordingly, the inventive, trivalent, bispecific antibody molecule has the ability to lyse target cells (tumor cells) in vivo and/or in vitro. Corresponding target cells comprise cells expressing a surface molecule, i.e. a tumor-specific antigen naturally occurring on the surface of a tumor cell, which is recognized by at least one, preferably two, binding domains of the inventive trivalent, bispecific antibody molecule. Such surface molecules are characterized in the context of the present invention. Accordingly, in the context of the present invention the trivalent, bispecific antibody molecule has only three binding domains. This means that in the context of the present invention the term "comprising" does not mean that bispecific antibody molecules are covered which has more than three binding domains.

Lysis of the target cell can be detected by methods known in the art. Accordingly, such methods comprise, inter alia, physiological in vitro assays. Such physiological assays may monitor cell death, for example by loss of cell membrane integrity (e.g. FACS based propidium Iodide assay, trypan Blue influx assay, photometric enzyme release assays (LDH), radiometric 51Cr release assay, fluorometric Europium release and CalceinAM release assays). Further assays comprise monitoring of cell viability, for example by photometric MTT, XTT, WST-1 and alamarBlue assays, radiometric 3H-Thd incorporation assay, clonogenic assay measuring cell division activity, and fluorometric Rhodamine123 assay measuring mitochondrial transmembrane gradient. In addition, apoptosis may be monitored for example by FACS-based phosphatidylserin exposure assay, ELISA-based TUNEL test, caspase activity assay (photometric, fluorometric or ELISA-based) or analyzing changed cell morphology (shrinking, membrane blebbing).

The term "binding to" as used in the context of the present invention defines a binding (interaction) of at least two "antigen-interaction-sites" with each other. The term "antigen-interaction-site" defines, in accordance with the present invention, a motif of a polypeptide which shows the capacity of specific interaction with a specific antigen or a specific group of antigens. Said binding/interaction is also understood to define a "specific recognition". The term "specifically recognizing" means in accordance with this invention that the antibody construct is capable of specifically interacting with and/or binding to at least two amino acids of each of the human target molecule as defined herein. Antibodies can recognize, interact and/or bind to different epitopes on the same target molecule. This term relates to the specificity of the antibody molecule, i.e., to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Thus, a specific motif in the amino acid sequence of the antigen-interaction-site and the antigen bind to each other as a result of their primary, secondary or tertiary structure as well as the result of secondary modifications of said structure.

The term "specific interaction" as used in accordance with the present invention means that the trivalent, bispecific binding construct (trivalent, bispecific antibody molecule) of the invention does not or does not essentially cross-react with (poly-) peptides of similar structures. Accordingly, the trivalent, bispecific antibody molecule of the invention specifically binds to/interacts with tumor markers, cell surface markers, antigens which do not naturally occur in and/or on T-cells and is capable to interact with specific, selected other compounds, antigens, cell-surface markers, tumor markers, etc. that do naturally occur on the surface of tumor cells. Specific examples of such trivalent, bispecific antibody molecules are given herein below.

Cross-reactivity of a panel of constructs under investigation may be tested, for example, by assessing binding of said panel of bispecific antibody constructs under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, (bispecific) scFvs and the like) that bind to the (poly) peptide/protein of interest but do not or do not essentially bind to any of the other (poly) peptides which are expressed by the same tissue as the (poly) peptide of interest, e.g. by the cells of the tumor tissue, are considered specific for the (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays. Furthermore, physiological assays, like cytotoxic assays and assays mentioned above may be performed. Accordingly, examples for the specific interaction of an antigen-interaction-site with a specific antigen may comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens such as antigens of the selectin family, integrins and of the family of growth factors like EGF. Another example for said interaction, which is also particularly comprised by said definition, is the interaction of an antigenic determinant (epitope) with the antigenic binding site of an antibody.

The term "binding to" does not only relate to a linear epitope but may also relate to a conformational epitope, a structural epitope or a discontinuous epitope consisting of two regions of the human target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with".

Accordingly, specificity can be determined experimentally by methods known in the art and methods as described herein. Such methods comprise, but are not limited to Western Blots, ELISA-, RIA-, ECL-, IRMA-tests and peptide scans.

The term (Ig-derived) "first binding domain", (Ig-derived) "second binding domain" or (Ig-derived) "third binding domain" relate to an "immunoglobulin-derived domain", specifically to an antibody molecule or fragments thereof, to single chain antibodies, to synthetic antibodies, to antibody fragments, such as Fab, a F(ab2)', Fv or scFv fragments etc, or a chemically modified derivative of any of these. These antibody molecules may be derived from different species or may be of chimeric origin. In the context of the present invention (as illustrated in the appended Examples), said (Ig-derived) first and third domain comprised in the bispecific antibody molecule of the invention can be a (monoclonal) antibody to which a third (Ig-derived) "binding domain" is fused.

"Antibodies" of the present invention have three binding domains and are bispecific. The antibodies can be full length from a single species, or be chimerized or humanized. For an antibody with more than two antigen binding domains, some binding domains may be identical, as long as the protein has binding domains for two different antigens.

The term "trivalent" as used within the current application denotes the presence of a specified number of binding domains in an antibody molecule. As such, the term "trivalent" denotes the presence of three binding domains in a bispecific antibody molecule. Trivalent, bispecific antibody molecules are described, for example, in Bacac et al., Clin. Cancer Res, 1-12 (DOI: 10.1158/1078-0432.CCR-15-1696), WO 2013/026833, WO 2014/131712 and WO 2016/020309. As illustrated in FIGS. 9, 10 and 11, the trivalent, bispecific antibody molecule of the present invention may comprise a full length antibody specifically binding to a first antigen and comprises/consists of a Fab fragment that specifically binds to the second antigen. The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE.) The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. A "Fab fragment" as used herein is comprised of one light chain and the $C_H1$ and variable regions of one heavy chain. The heavy chain of a Fab molecule cannot form a disulfide bond with another heavy chain molecule. Accordingly, trivalent, bispecific antibodies of the present invention include antibodies having the constant domain structure of a full length antibody to which a further antigen-binding domain, e.g., single chain Fv, a VH domain and or a VL domain or a Fab is linked via one or more peptide-linkers. In a preferred embodiment of the present invention the CH3 domains of said full length antibody molecule can be altered by the "knob-into-holes" technology which is described in detail with several examples in e.g. WO 96/027011, Ridgway et al., Protein Eng. 9 (1996), 617-621. In the "knob-into-holes" technology, the interaction surfaces of the two CH3 domains (of the two heavy chains of the full length antibody molecule) can be the "knob" while the other is the "hole". The introduction of a disulfide bridge further stabilizes the heterodimers (Merchant et al., Nature Biotech 16 (1998), 667-681, Atwell et al, J. Mol. Biol. 270 (1997), 26-35) and increases the yield.

Thus, in one aspect of the present invention the trivalent, bispecific antibody molecule as described herein may be further characterized in that the CH3 domain of one heavy chain of the full length antibody molecule and the CH3 domain of the other heavy chain of the full length antibody molecule each meet at an interface which comprises an original interface between the antibody CH3 domains; wherein the alteration is characterized in that (i) the CH3 domain of one heavy chain is substituted, so that within the original interface the CH3 domain of one heavy chain that meets the original interface of the CH3 domain of the other heavy chain within the trivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and (ii) the CH3 domain of the other heavy chain is substituted, so that within the original interface of the second CH3 domain that meets the original interface of the first CH3 domain within the trivalent, bispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of glycine (G), arginine (R), phenylalanine (F), tyrosine (Y), tryptophan (W). Preferably said amino acid residue having a smaller side chain volume is selected from the group consisting of alanine (A), proline (P), serine (S), threonine (T), valine (V). In one aspect of the invention both CH3 domains are further altered by the introduction of cysteine (C) as amino acid in the corresponding positions of each CH3 domain such that a disulfide bridge between both CH3 domains can be formed.

In a preferred embodiment of the present invention the trivalent, bispecific antibody molecule as described herein comprises a P329G mutation in the CH3 domain of the "knobs chain" and a P329G mutation in the CH3 domain of the "hole chain". An additional interchain disulfide bridge between the CH3 domains can also be used (Merchant et al., Nature Biotech 16 (1998), 667-681, Atwell et al, J. Mol. Biol. 270 (1997), 26-35) e.g. by introducing a Y349C mutation into the CH3 domain of the "knobs chain" and a "E356C" or "S354C" mutation into the CH3 domain of the "hole chain".

In an alternative embodiment of the present, the trivalent, bispecific antibody molecules as described herein associate through an electrostatic complementarity association in the CH3 domains. The electrostatic complementarity association technology is described e.g. in Klein et al., LandesBioscience 4(6) (2012), 653-663, Kitazawa et al., Nat Med. 18(10) (2012), 1570-1574 and Gunasekeran K. et al., J Biol Chem 285(25) (2010), 19637-19646.

The trivalent, bispecific antibody molecules, antibody fragments, antibody derivates (all being Ig-derived) to be employed in accordance can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the term "antibody" relates to full immunoglobulin molecules as well as to parts of such immunoglobulin molecules. Furthermore, the term relates, as discussed above, to modified and/or altered antibody molecules. The term also relates to recombinantly or synthetically generated/synthesized antibodies.

It is of note that the trivalent, bispecific antibody molecule of the invention may comprise, in addition to the herein defined first (Ig-derived) domain, second (Ig-derived) domain and the third (Ig-derived) domain (an) additional domain(s), e.g. for the isolation and/or preparation of recombinantly produced constructs.

It is of note that, in accordance with this invention, not only the above described domain(s) which specifically interact(s) with/bind(s) to the extracellular domain of the fusion protein as described herein, i.e. an extracellular domain of a signalling receptor that does not naturally occur in or on said T-cells may be modified. It is also envisaged that the (Ig-derived) first domain, the (Ig-derived) second domain, the (Ig-derived) third domain and/or (a) connecting linker-region(s) is (are) modified, for example a humanized antibody, a CDR grafted antibody or a fully human antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art, see e.g. LoBuglio, Proceedings of the American Society of Clinical Oncology Abstract (1997), 1562 and Khor, Proceedings of the American Society of Clinical Oncology Abstract (1997), 847.

Accordingly, in the context of this invention, in particular trivalent, bispecific antibody molecules are provided, which are humanized and can successfully be employed in pharmaceutical compositions. In the context of the invention, the herein described (humanized) trivalent, bispecific antibody molecules can be employed in a kit as defined herein.

In the context of the present invention, the trivalent, bispecific antibody molecule (Ig-derived) binding domain(s) comprise(s) an antigen-interaction-site with specificity for an extracellular domain of a signalling receptor that does not naturally occur in or on said T-cells.

The term "extracellular domain of a signalling receptor that does not naturally occur in or on said T-cells" as used herein, relates to molecules which are incorporated into the T-cells which are naturally not presented in and/or on the surface of T-cells and which are not (endogenously) expressed in or on normal (non-transduced) T-cells. Thus, the antigen/marker that does not naturally occur in and/or on T-cells is artificially introduced into T-cells. In the context of the present invention said T-cells, preferably CD8+ T-cells, are isolated/obtained from a subject to be treated as defined herein. Accordingly, these molecules which are artificially introduced and subsequently presented in and/or on the surface of said T-cells comprise domains or epitopes accessible (in vitro or in vivo) to (Ig-derived) binding domains, preferably antibodies, antibody fragments or derivatives that do not naturally occur in and/or on T-cells. In the context of the present invention, these artificially introduced molecules are presented in and/or on the surface of said T-cells after (retroviral) transduction as described herein below.

In the context of the present invention, the term "extracellular domain of a signalling receptor that does not naturally occur in or on said T-cells" refers to an extracellular domain of a signalling receptor which does not naturally occur/which is not endogenously expressed in and/or on T-cells with more than 500, 550, 600, 650, 700, 750, 800, 850, 900, 950 or 1000 antigen molecules/per T-cell. Thus, the extracellular domain of a signalling receptor that does not naturally occur/is not endogenously expressed in and/or on T-cells in more than 1.0, 1.1, 1.2, 1.3, 1.4, 1.5, 1.6, 1.7, 1.8, 1.9 or 2.0‰ (promille) of a population of normal (non-transduced) T-cells. The presence and amount of an extracellular domain of a signalling receptor that naturally occurs in and/or on T-cells, preferably CD8+ T-cells, can be monitored by methods known in the art, such as FACS analysis, ELISA, confocal microscopy, analytical HPLC and the like.

Examples for these molecules comprise non-immunogenic proteins, preferably of human origin. Alternatively, said molecules may be either per se a functionally inert protein molecule or will be made functionally inert by gene recombination techniques known in the art (examples would be mutated version of the human EGFR as e.g. the EGFRvIII as depicted in SEQ ID NOs: 152, 232, 52, 76 or 78 (as encoded by the SEQ ID NOs: 151, 231, 51, 75 or 77). EGFRvIII is a mutant of human epidermal growth factor receptor found in glioblastoma, and in carcinoma of the breast, ovary and lung. The mutant receptor has a deletion in its extracellular domain (Lorimer et al., Proc. Natl. Acad. Sci USA 93 (1996), 14815-14820). The non-mutated human EGFR version is depicted in SEQ ID NO: 198 (as encoded by the DNA sequence shown in SEQ ID NO: 197).

Examples of markers which fulfill these above mentioned criteria are given herein below and comprise, but are not limited to Cripto (cryptic family protein), members of the CD (cluster of differentiation)-family (non T-cell), EGFR, EGFRvIII, NGFR or TSH-R.

In the context of the present invention, (a) trivalent, bispecific antibody molecule(s) described herein binds to an extracellular domain of the fusion protein described herein, i.e. to an extracellular domain of a signalling receptor that does not naturally occur in and/or on T-cells. In the context of the present invention the extracellular domain of a signalling receptor that does not naturally occur in and/or on T-cells is selected from the group consisting of Cripto (cryptic family protein), members of the CD (cluster of differentiation)-family (non T-cell), EGFR, EGFRvIII, NGFR and TSH-R. Accordingly, the trivalent, bispecific antibody molecule(s) described herein interacts with/binds to members of the CD-family that (exclusively) do not naturally occur in and/or on T-cells (as it is addressed by the term "non T-cell"), Cripto, EGFR, EGFRvIII, NGFR or TSH-R. In the context of the present invention the trivalent, bispecific antibody molecule(s) described herein interacts with/binds to members of the CD-family that are not endogenously expressed in and/or on the surface of T-cells (as it is addressed by the term "non T-cell"), Cripto, EGFR, EGFRvIII, NGFR or TSH-R.

The sequence(s) of the (human) members of the Cripto (cryptic family protein), members of the CD (cluster of differentiation)-family (non T-cell), EGFR, EGFRvIII, NGFR or TSH-R are available in the UniProtKB/Swiss-Prot database. These (protein) sequences also relate to annotated modified sequences. The present invention also provides techniques and methods wherein homologous sequences, and also genetic allelic variants and the like of the concise sequences provided herein are used. Preferably such "variants" and the like of the concise sequences herein are used. Preferably, such "variants" are genetic variants. The skilled person may easily deduce the relevant coding region of these (protein) sequences in these databank entries, which may also comprise the entry of genomic DNA as well as mRNA/cDNA. Exemplarily, the murine/mouse sequence(s) of NGFR can be obtained from the UniProt database entry Q9Z0W1 (entry version 132, sequence version 1). The human sequence(s) of NGFR can be obtained from the UniProt database entry P08138 (entry version 182, sequence version 1).

The term "CD (cluster of differentiation)-family (non T-cell)" as used herein in connection with the "extracellular domain of a signalling receptor that does not naturally occur/that is not endogenously expressed in and/or on T-cells" refers to any one of the CD sequences selected from the group consisting of CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD43, CD46, CD48, CD49, CD50, CD51, CD54, CD55, CD56, CD57, CD59, CD61, CD63, CD64, CD66, CD67, CD68, CD70, CD72, CD74, CD75, CD76, CD77, CD79, CD81, CD82, CD83, CD84, CD87, CD88, CD89, CD90, CD91, CD92, CD93, CD94, CD95, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD121, CD123, CD124, CD125, CD126, CD130, CD131, CD133, CD134, CD135, CD136, CD137, CD138, CD140, CD141, CD142, CD143, CD144, CD146, CD147, CD148, CD151, CD153, CD155, CD156, CD157, CD158, CD159, CD160, CD161, CD162, CD163, CD164, CD166, CD167, CD168, CD169, CD170, CD171, CD172, CD177, CD178, CD179, CD180, CD181, CD182, CD183, CD184, CD185, CD186, CD191, CD192, CD193, CD200, CD201, CD204, CD206, CD207, CD208, CD209, CD217, CD218, CD220, CD221, CD222, CD223, CD224, CD225, CD226, CD227, CD228, CD230, CD231, CD232, CD233, CD234, CD236, CD238, CD239, CD241, CD242, CD243, CD244, CD246, CD248, CD249, CD252, CD253, CD254, CD256, CD257, CD258, CD261, CD262, CD263, CD264, CD265, CD266, CD267, CD268, CD269, CD270, CD271, CD276, CD277, CD280, CD281, CD282, CD283, CD284, CD286, CD288, CD289, CD290, CD292, CD294, CD295, CD296, CD297, CD298, CD299, CD300, CD301, CD302, CD303, CD304, CD305, CD306, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362 and CD363.

The sequence(s) of the (human) CD9 (CD9 antigen) can be obtained from the Swiss-Prot database entry P21926 (entry version 123, sequence version 4); the sequence(s) of the (human) CD10 (Neprilysin) can be obtained from the Swiss-Prot database entry P08473 (entry version 151, sequence version 2); the sequence(s) of the (human) CD11 (Integrin alpha-D) can be obtained from the Swiss-Prot database entry Q13349 (entry version 110, sequence version 2); the sequence(s) of the (human) CD13 (Aminopeptidase N) can be obtained from the Swiss-Prot database entry P15144 (entry version 145, sequence version 4); the sequence(s) of the (human) CD14 (Monocyte differentiation antigen CD14) can be obtained from the Swiss-Prot database entry P08571 (entry version 131, sequence version 2); the sequence(s) of the (human) CD16 (Fc-gamma receptor IIIb) can be obtained from the Swiss-Prot database entry Q9ULV2 (entry version 51, sequence version 1); the sequence(s) of the (human) CD18 (Integrin beta-2) can be obtained from the Swiss-Prot database entry P05107 (entry version 162, sequence version 2); the sequence(s) of the (human) CD19 (B-lymphocyte antigen CD19) can be obtained from the Swiss-Prot database entry P15391 (entry version 128, sequence version 6); the sequence(s) of the (human) CD20 (B-lymphocyte antigen CD20) can be obtained from the Swiss-Prot database entry P11836 (entry version 118, sequence version 1); the sequence(s) of the (human) CD21 (Complement receptor type 2) can be obtained from the Swiss-Prot database entry P20023 (entry version 128, sequence version 2); the sequence(s) of the (human) CD22 (B-cell receptor CD22) can be obtained from the Swiss-Prot database entry P20273 (entry version 136, sequence version 2); the sequence(s) of the (human) CD23 (Low affinity immunoglobulin epsilon Fc receptor) can be obtained from the Swiss-Prot database entry P06734 (entry version 133, sequence version 1); the sequence(s) of the (human) CD24 (Signal transducer CD24) can be obtained from the Swiss-Prot database entry P25063 (entry version 106, sequence version 2); the sequence(s) of the (human) CD26 (Dipeptidyl peptidase 4) can be obtained from the Swiss-Prot database entry P27487 (entry version 140, sequence version 2); the sequence(s) of the (human) CD27 (CD27 antigen) can be obtained from the Swiss-Prot database entry P26842 (entry version 119, sequence version 2); the sequence(s) of the (human) CD29 (Integrin beta-1) can be obtained from the Swiss-Prot database entry P05556 (entry version 154, sequence version 2); the sequence(s) of the (human) CD30 (Tumor necrosis factor receptor superfamily member 8) can be obtained from the Swiss-Prot database entry P28908 (entry version 129; sequence version 1); the sequence(s) of the (human) CD31 (Platelet endothelial cell adhesion molecule) can be obtained from the Swiss-Prot database entry P16284 (entry version 146, sequence version 1); the sequence(s) of the (human) CD32 (Low affinity immunoglobulin gamma Fc region receptor II-b) can be obtained from the Swiss-Prot database entry P31994 (entry version 138, sequence version 2); the sequence(s) of the (human) CD33 (Myeloid cell surface antigen CD33) can be obtained from the Swiss-Prot database entry P20138 (entry version 130, sequence version 2); the sequence(s) of the (human) CD34 (Hematopoietic progenitor cell antigen CD34) can be obtained from the Swiss-Prot database entry P28906 (entry version 108, sequence version 2); the sequence(s) of the (human) CD35 (Complement receptor type 1) can be obtained from the Swiss-Prot database entry P17927 (entry version 131, sequence version 3); the sequence(s) of the (human) CD36 (Platelet glycoprotein 4) can be obtained from the Swiss-Prot database entry P16671 (entry version 133, sequence version 2); the sequence(s) of the (human) CD38 (ADP-ribosyl cyclase 1) can be obtained from the Swiss-Prot database entry P28907 (entry version 126, sequence version 2); the sequence(s) of the (human) CD39 (Ectonucleoside triphosphate diphosphohydrolase 1) can be obtained from the Swiss-Prot database entry P49961 (entry version 114, sequence version 1); the sequence(s) of the (human) CD40 (Tumor necrosis factor receptor superfamily member 5) can be obtained from the Swiss-Prot database entry P25942 (entry version 147, sequence version 1); the sequence(s) of the (human) CD41 (Integrin alpha-IIb) can be obtained from the Swiss-Prot database entry P08514 (entry version 158, sequence version 3); the sequence(s) of the (human) CD43 (Leukosialin) can be obtained from the Swiss-Prot database entry P16150 (entry version 110, sequence version 1); the sequence(s) of the (human) CD46 (Membrane cofactor protein) can be obtained from the Swiss-Prot database entry P15529 (entry version 145, sequence version 3); the sequence(s) of the (human) CD48 (CD48 antigen) can be obtained from the Swiss-Prot database entry P09326 (entry version 137, sequence version 2); the sequence(s) of the (human) CD49

(Integrin alpha-4) can be obtained from the Swiss-Prot database entry P13612 (entry version 128, sequence version 3); the sequence(s) of the (human) CD50 (Intercellular adhesion molecule 3) can be obtained from the Swiss-Prot database entry P32942 (entry version 128, sequence version 2); the sequence(s) of the (human) CD51 (Integrin alpha-V) can be obtained from the Swiss-Prot database entry P06756 (entry version 149, sequence version 2); the sequence(s) of the (human) CD54 (Intercellular adhesion molecule 1) can be obtained from the Swiss-Prot database entry P05362 (entry version 160, sequence version 2); the sequence(s) of the (human) CD55 (Complement decay-accelerating factor) can be obtained from the Swiss-Prot database entry P08174 (entry version 143, sequence version 4); the sequence(s) of the (human) CD56 (Neural cell adhesion molecule 1) can be obtained from the Swiss-Prot database entry P13591 (entry version 132, sequence version 3); the sequence(s) of the (human) CD57 (Killer cell lectin-like receptor subfamily G member 1) can be obtained from the Swiss-Prot database entry Q96E93 (entry version 72, sequence version 1); the sequence(s) of the (human) CD59 (CD59 glycoprotein) can be obtained from the Swiss-Prot database entry P13987 (entry version 139, sequence information 1); the sequence(s) of the (human) CD61 (Integrin beta-3) can be obtained from the Swiss-Prot database entry P05106 (entry version 175, sequence version 2); the sequence(s) of the (human) CD63 (CD63 antigen) can be obtained from the Swiss-Prot database entry P08962 (entry version 122, sequence version 2); the sequence(s) of the (human) CD64 (High affinity immunoglobulin gamma Fc receptor I) can be obtained from the Swiss-Prot database entry P12314 (entry version 128, sequence version 2); the sequence(s) of the (human) CD66 (Carcinoembryonic antigen-related cell adhesion molecule 1) can be obtained from the Swiss-prot database entry P13688 (entry version 133, sequence version 2); the sequence(s) of the (human) CD67 (Carcinoembryonic antigen-related cell adhesion molecule 8) can be obtained from the Swiss-type prot database entry P31997 (entry version 115, sequence version 2); the sequence(s) of the (human) CD68 (Macrosialin) can be obtained from the Swiss-Prot database entry P34810 (entry version 106, sequence version 2); the sequence(s) of the (human) CD70 (CD70 antigen) can be obtained from the Swiss-Prot database entry P32970 (entry version 101, sequence version 2); the sequence(s) of the (human) CD72 (B-cell differentiation antigen CD72) can be obtained from the Swiss-Prot database entry P21854 (version entry 113, sequence version 1); the sequence(s) of the (human) CD74 (HLA class II histocompatibility antigen gamma chain) can be obtained from the Swiss-Prot database entry P04233 (entry version 141, sequence version 3); the sequence(s) of the (human) CD75 (Beta-galactoside alpha-2,6-sialyltransferase 1) can be obtained from the Swiss-Prot database entry P15907 (entry version 130, sequence version 1); the sequence(s) of the (human) CD77 (Lactosylceramide 4-alpha-galactosyltransferase) can be obtained from Swiss-Prot database entry Q9NPC4 (entry version 100, sequence version 1); the sequence(s) of the (human) CD79 (B-cell antigen receptor complex-associated protein alpha chain) can be obtained from Swiss-Prot database entry P11912 (entry version 120, sequence version 2); the sequence(s) of the (human) CD81 (CD81 antigen) can be obtained from Swiss-Prot database entry P60033 (entry version 82, sequence version 1); the sequence(s) of the (human) CD82 (CD82 antigen) can be obtained from Swiss-Prot database entry P27701 (entry version 98, sequence version 1); the sequence(s) of the (human) CD83 (CD83 antigen) can be obtained from Swiss-Prot database entry Q01151 (entry version 113, sequence version 1); the sequence(s) of the (human) CD84 (SLAM family member 5) can be obtained from Swiss-Prot database entry Q9UIB8 (entry version 87, sequence version 1); the sequence(s) of the (human) CD87 (Urokinase plasminogen activator surface receptor) can be obtained from Swiss-Prot database entry Q03405 (entry version 129, sequence version 1); the sequence(s) of the (human) CD88 (C5a anaphylatoxin chemotactic receptor) can be obtained from Swiss-Prot database entry P21730 (entry version 116, sequence version 2); the sequence(s) of the (human) CD89 (Immunoglobulin alpha Fc receptor) can be obtained from Swiss-Prot database entry P24071 (entry version 121, sequence version 1); the sequence(s) of the (human) CD90 (Thy-1 membrane glycoprotein) can be obtained from Swiss-Prot database entry P04216 (entry version 128, sequence version 2); the sequence(s) of the (human) CD91 (Prolow-density lipoprotein receptor-related protein 1) can be obtained from Swiss-Prot database entry Q07954 (entry version 133, sequence version 2); the sequence(s) of the (human) CD92 (Choline transporter-like protein 1) can be obtained from Swiss-Prot database entry Q8WWI5 (entry version 79, sequence version 1); the sequence(s) of the (human) CD93 (Complement component C1q receptor) can be obtained from Swiss-Prot database entry Q9NPY3 (entry version 115, sequence version 3); the sequence(s) of the (human) CD94 (Natural killer cells antigen CD94) can be obtained from Swiss-Prot database entry Q13241 (entry version 107, sequence version 2); the sequence(s) of the (human) CD95 (Tumor necrosis factor ligand superfamily member 6) can be obtained from Swiss-Prot database entry P48023 (entry version 134, sequence version 1); the sequence(s) of the (human) CD97 (CD97 antigen) can be obtained from Swiss-Prot database entry P48960 (entry version 125, sequence version 4); the sequence(s) of the (human) CD98 (4F2 cell-surface antigen heavy chain) can be obtained from Swiss-Prot database entry P08195 (entry version 140, sequence version 3); the sequence(s) of the (human) CD99 (CD99 antigen) can be obtained from Swiss-Prot database entry P14209 (entry version 117, sequence version 1); the sequence(s) of the (human) CD100 (Semaphorin-4D) can be obtained from Swiss-Prot database entry Q92854 (entry version 125, sequence version 1); the sequence(s) of the (human) CD101 (Immunoglobulin superfamily member 2) can be obtained from Swiss-Prot database entry Q93033 (entry version 89, sequence version 2); the sequence(s) of the (human) CD102 (Intercellular adhesion molecule 2) can be obtained from Swiss-Prot database entry P13598 (entry version 131, sequence version 2); the sequence(s) of the (human) CD103 (Integrin alpha-E) can be obtained from Swiss-Prot database entry P38570 (entry version 118, sequence version 3); the sequence(s) of the (human) CD104 (Integrin beta-4) can be obtained from Swiss-Prot database entry P16144 (entry version 160, sequence version 5); the sequence(s) of the (human) CD105 (Endoglin) can be obtained from Swiss-Prot database entry P17813 (entry version 133, sequence version 2); the sequence(s) of the (human) CD106 (Vascular cell adhesion protein 1) can be obtained from Swiss-Prot database entry P19320 (entry version 158, sequence version 1); the sequence(s) of the (human) CD107 (Lysosome-associated membrane glycoprotein 1) can be obtained from Swiss-Prot database entry P11279 (entry version 117, sequence version 3); the sequence(s) of the (human) CD108 (Semaphorin-7A) can be obtained from Swiss-Prot database entry O75326 (entry version 107, sequence version 1); the sequence(s) of the (human) CD109 (CD109 antigen) can be obtained from Swiss-Prot database entry Q6YHK3 (entry version 64, sequence version 2); the sequence(s) of the (human) CD110 (Thrombopoietin receptor) can be obtained from Swiss-Prot database entry P40238 (entry version 122, sequence version 1); the sequence(s) of the (human) CD111 (Poliovirus receptor-related protein 1) can be obtained from Swiss-Prot database entry Q15223 (entry version 114, sequence version 3); the sequence(s) of the (human) CD112 (Poliovirus receptor-related protein 2) can be obtained from Swiss-Prot database entry Q92692 (entry version 123, sequence version 1); the sequence(s) of the (human) CD113 (Poliovirus receptor-related protein 3) can be obtained from Swiss-Prot database entry Q9NQS3 (entry version 78, sequence version 1); the sequence(s) of the (human) CD114 (Granulocyte colony-stimulating factor receptor) can be obtained from Swiss-Prot database entry Q99062 (entry version 129, sequence version 1); the sequence(s) of the (human) CD115 (Macrophage colony-stimulating factor 1 receptor) can be obtained from Swiss-Prot database entry P07333 (entry version 145, sequence version 2); the sequence(s) of the (human) CD116 (Granulocyte-macrophage colony-stimulating factor receptor subunit alpha) can be obtained from Swiss-Prot database entry P15509 (entry version 128, sequence version 1); the sequence(s) of the (human) CD117 (Mast/stem cell growth factor receptor Kit) can be obtained from Swiss-Prot database entry P10721 (entry version 150, sequence version 1); the sequence(s) of the (human) CD118 (Leukemia inhibitory factor receptor) can be obtained from Swiss-Prot database entry P42702 (entry version 115, sequence version 1); the sequence(s) of the (human) CD 119 (Interferon gamma receptor 1) can be obtained from Swiss-Prot database entry P15260 (entry version 140, sequence version 1); the sequence(s) of the (human) CD121 (Interleukin-1 receptor type 1) can be obtained from Swiss-Prot database entry P14778 (entry version 151, sequence version 1); the sequence(s) of the (human) CD123 (Interleukin-3 receptor subunit alpha) can be obtained from Swiss-Prot database entry P26951 (entry version 110, sequence version 1); the sequence(s) of the (human) CD124 (Interleukin-4 receptor subunit alpha) can be obtained from Swiss-Prot database entry P24394 (entry version 144, sequence version 1); the sequence(s) of the (human) CD125 (Interleukin-5 receptor subunit alpha) can be obtained from Swiss-Prot database entry Q01344 (entry version 120, sequence version 2 the sequence(s) of the (human) CD126 (Interleukin-6 receptor subunit alpha) can be obtained from Swiss-Prot database entry P08887 (entry version 143, sequence version 1); the sequence(s) of the (human) CD130 (Interleukin-6 receptor subunit beta) can be obtained from Swiss-Prot database entry P40189 (entry version 142, sequence version 2); the sequence(s) of the (human) CD131 (Cytokine receptor common subunit beta) can be obtained from Swiss-Prot database entry P32927 (entry version 128, sequence version 2); the sequence(s) of the (human) CD133 (Prominin-1) can be obtained from Swiss-Prot database entry 043490 (entry version 110, sequence version 1); the sequence(s) of the (human) CD134 (Tumor necrosis factor receptor superfamily member 4) can be obtained from Swiss-Prot database entry P43489 (entry version 106, sequence version 1); the sequence(s) of the (human) CD135 (Receptor-type tyrosine-protein kinase FLT-3) can be obtained from Swiss-Prot database entry P36888 (entry version 119, sequence version 2); the sequence(s) of the (human) CD136 (Macrophage-stimulating protein receptor) can be obtained from Swiss-Prot database entry Q04912 (entry version 129, sequence version 2); the sequence(s) of the (human) CD137 (Tumor necrosis factor receptor superfamily member 9) can be obtained from Swiss-Prot database entry Q07011 (entry version 109, sequence version 1); the sequence(s) of the (human) CD138 (Syndecan-1) can be obtained from Swiss-Prot database entry P18827 (entry version 114, sequence version 3); the sequence(s) of the (human) CD140 (Platelet-derived growth factor receptor beta) can be obtained from Swiss-Prot database entry P09619 (entry version 154, sequence version 1); the sequence(s) of the (human) CD141 (Thrombomodulin) can be obtained from Swiss-Prot database entry P07204 (entry version 162, sequence version 2); the sequence(s) of the (human) CD142 (Tissue factor) can be obtained from Swiss-Prot database entry P13726 (entry version 137, sequence version 1); the sequence(s) of the (human) CD143 (Angiotensin-converting enzyme) can be obtained from Swiss-Prot database entry P12821 (entry version 157, sequence version 1); the sequence(s) of the (human) CD144 (Cadherin-5) can be obtained from Swiss-Prot database entry P33151 (entry version 108, sequence version 5); the sequence(s) of the (human) CD146 (Cell surface glycoprotein MUC18) can be obtained from Swiss-Prot database entry P43121 (entry version 109, sequence version 2); the sequence(s) of the (human) CD147 (Basigin) can be obtained from Swiss-Prot database entry P35613 (entry version 134, sequence version 2); the sequence(s) of the (human) CD148 (Receptor-type tyrosine-protein phosphatase eta) can be obtained from Swiss-Prot database entry Q12913 (entry version 124, sequence version 3); the sequence(s) of the (human) CD151 (CD151 antigen) can be obtained from Swiss-Prot database entry P48509 (entry version 108, sequence version 3); the sequence(s) of the (human) CD153 (Tumor necrosis factor ligand superfamily member 8) can be obtained from Swiss-Prot database entry P32971 (entry version 90, sequence version 1); the sequence(s) of the (human) CD155 (Poliovirus receptor) can be obtained from Swiss-Prot database entry P15151 (entry version 132, sequence version 2); the sequence(s) of the (human) CD156 (Disintegrin and metalloproteinase domain-containing protein 8) can be obtained from Swiss-Prot database entry P78325 (entry version 115, sequence version 1); the sequence(s) of the (human) CD157 (ADP-ribosyl cyclase 2) can be obtained from Swiss-Prot database entry Q10588 (entry version 116, sequence version 2); the sequence(s) of the (human) CD158 (Killer cell immunoglobulin-like receptor 3DL3) can be obtained from Swiss-Prot database entry Q8N743 (entry version 91, sequence version 2); the sequence(s) of the (human) CD159 (NKG2-A/NKG2-B type II integral membrane protein) can be obtained from Swiss-Prot database entry P26715 (entry version 116, sequence version 2); the sequence(s) of the (human) CD160 (CD160 antigen) can be obtained from Swiss-Prot database entry 095971 (entry version 98, sequence version 1); the sequence(s) of the (human) CD161 (Killer cell lectin-like receptor subfamily B member 1) can be obtained from Swiss-Prot database entry Q12918 (entry version 81, sequence version 1); the sequence(s) of the (human) CD162 (P-selectin glycoprotein ligand 1) can be obtained from Swiss-Prot database entry Q14242 (entry version 103, sequence version 1); the sequence(s) of the (human) CD163 (Scavenger receptor cysteine-rich type 1 protein M130) can be obtained from Swiss-Prot database entry Q86VB7 (entry version 77, sequence version 2); the sequence(s) of the (human) CD164 (Sialomucin core protein 24) can be obtained from Swiss-Prot database entry Q04900 (entry version 89), sequence version 2); the sequence(s) of the (human) CD166 (CD166 antigen) can be obtained from Swiss-Prot database entry Q13740 (entry version 111, sequence version 2); the sequence(s) of the (human) CD167

(Discoidin domain-containing receptor 2) can be obtained from Swiss-Prot database entry Q16832 (entry version 120, sequence version 2); the sequence(s) of the (human) CD168 (Hyaluronan mediated motility receptor) can be obtained from Swiss-Prot database entry O75330 (entry version 99, sequence version 2); the sequence(s) of the (human) CD169 (Sialoadhesin) can be obtained from Swiss-Prot database entry Q9BZZ2 (entry version 103, sequence version 2); the sequence(s) of the (human) CD170 (Sialic acid-binding Ig-like lectin 5) can be obtained from Swiss-Prot database entry O15389 (entry version 106, sequence version 1); the sequence(s) of the (human) CD171 (Neural cell adhesion molecule L1) can be obtained from Swiss-Prot database entry P32004 (entry version 139, sequence version 2); the sequence(s) of the (human) CD172 (Signal-regulatory protein beta-1) can be obtained from Swiss-Prot database entry O00241 (entry version 112, sequence version 5); the sequence(s) of the (human) CD177 (CD177 antigen) can be obtained from Swiss-Prot database entry Q8N6Q3 (entry version 65, sequence version 2); the sequence(s) of the (human) CD178 (Tumor necrosis factor ligand superfamily member 6) can be obtained from Swiss-Prot database entry P48023 (entry version 134, sequence version 1); the sequence(s) of the (human) CD179 (Immunoglobulin iota chain) can be obtained from Swiss-Prot database entry P12018 (entry version 115, sequence version 2); the sequence(s) of the (human) CD180 (CD180 antigen) can be obtained from Swiss-Prot database entry Q99467 (entry version 101, sequence version 2); the sequence(s) of the (human) CD181 (C-X-C chemokine receptor type 1) can be obtained from Swiss-Prot database entry P25024 (entry version 125, sequence version 2); the sequence(s) of the (human) CD182 (C-X-C chemokine receptor type 2) can be obtained from Swiss-Prot database entry P25025 (entry version 123, sequence version 2); the sequence(s) of the (human) CD183 (C-X-C chemokine receptor type 3) can be obtained from Swiss-Prot database entry P49682 (entry version 118, sequence version 2); the sequence(s) of the (human) CD184 (C-X-C chemokine receptor type 4) can be obtained from Swiss-Prot database entry P61073 (entry version 95, sequence version 1); the sequence(s) of the (human) CD185 (C-X-C chemokine receptor type 5) can be obtained from Swiss-Prot database entry P32302 (entry version 109, sequence version 1); the sequence(s) of the (human) CD186 (C-X-C chemokine receptor type 6) can be obtained from Swiss-Prot database entry O00574 (entry version 104, sequence version 1); the sequence(s) of the (human) CD191 (C-C chemokine receptor type 1) can be obtained from Swiss-Prot database entry P32246 (entry version 106, sequence version 1); the sequence(s) of the (human) CD192 (C-C chemokine receptor type 2) can be obtained from Swiss-Prot database entry P41597 (entry version 128, sequence version 1); the sequence(s) of the (human) CD193 (C-C chemokine receptor type 3) can be obtained from Swiss-Prot database entry P51677 (entry version 112, sequence version 1); the sequence(s) of the (human) CD200 (OX-2 membrane glycoprotein) can be obtained from Swiss-Prot database entry P41217 (entry version 110, sequence version 4); the sequence(s) of the (human) CD201 (Endothelial protein C receptor) can be obtained from Swiss-Prot database entry Q9UNN8 (entry version 110, sequence version 1); the sequence(s) of the (human) CD204 (Macrophage scavenger receptor types I and II) can be obtained from Swiss-Prot database entry P21757 (entry version 122, sequence version 1); the sequence(s) of the (human) CD206 (Macrophage mannose receptor 1) can be obtained from Swiss-Prot database entry P22897 (entry version 138, sequence version 1); the sequence(s) of the (human) CD207 (C-type lectin domain family 4 member K) can be obtained from Swiss-Prot database entry Q9UJ71 (entry version 85, sequence version 2); the sequence(s) of the (human) CD208 (Lysosome-associated membrane glycoprotein 3) can be obtained from Swiss-Prot database entry Q9UQV4 (entry version 69, sequence version 3); the sequence(s) of the (human) CD209 (CD209 antigen) can be obtained from Swiss-Prot database entry Q9NNX6 (entry version 103, sequence version 1); the sequence(s) of the (human) CD217 (Interleukin-17 receptor A) can be obtained from Swiss-Prot database entry Q96F46 (entry version 94, sequence version 2); the sequence(s) of the (human) CD218 (Interleukin-18 receptor 1) can be obtained from Swiss-Prot database entry Q13478 (entry version 104, sequence version 1); the sequence(s) of the (human) CD220 (Insulin receptor) can be obtained from Swiss-Prot database entry P06213 (entry version 175, sequence version 4); the sequence(s) of the (human) CD221 (Insulin-like growth factor 1 receptor) can be obtained from Swiss-Prot database entry P08069 (entry version 145, sequence version 1); the sequence(s) of the (human) CD222 (Cation-independent mannose-6-phosphate receptor) can be obtained from Swiss-Prot database entry P11717 (entry version 137, sequence version 3); the sequence(s) of the (human) CD223 (Lymphocyte activation gene 3 protein) can be obtained from Swiss-Prot database entry P18627 (entry version 108, sequence version 5); the sequence(s) of the (human) CD224 (Gamma-glutamyltranspeptidase 1) can be obtained from Swiss-Prot database entry P19440 (entry version 137, sequence version 2); the sequence(s) of the (human) CD225 (Interferon-induced transmembrane protein 1) can be obtained from Swiss-Prot database entry P13164 (entry version 101, sequence version 3); the sequence(s) of the (human) CD226 (CD226 antigen) can be obtained from Swiss-Prot database entry Q15762 (entry version 89, sequence version 2); the sequence(s) of the (human) CD227 (Mucin-1) can be obtained from Swiss-Prot database entry P15941 (entry version 136, sequence version 3); the sequence(s) of the (human) CD228 (Melanotransferrin) can be obtained from Swiss-Prot database entry P08582 (entry version 124, sequence version 2); the sequence(s) of the (human) CD230 (Major prion protein) can be obtained from Swiss-Prot database entry P04156 (entry version 161, sequence version 1); the sequence(s) of the (human) CD231 (Tetraspanin-7) can be obtained from Swiss-Prot database entry P41732 (entry version 115, sequence version 2); the sequence(s) of the (human) CD232 (Plexin-C1) can be obtained from Swiss-Prot database entry O60486 (entry version 80, sequence version 1); the sequence(s) of the (human) CD233 (Band 3 anion transport protein) can be obtained from Swiss-Prot database entry P02730 (entry version 167, sequence version 3); the sequence(s) of the (human) CD234 (Duffy antigen/chemokine receptor) can be obtained from Swiss-Prot database entry Q16570 (entry version 114, sequence version 3); the sequence(s) of the (human) CD236 (Glycophorin-C) can be obtained from Swiss-Prot database entry P04921 (entry version 116, sequence version 1); the sequence(s) of the (human) CD238 (Kell blood group glycoprotein) can be obtained from Swiss-Prot database entry P23276 (entry version 124, sequence version 2); the sequence(s) of the (human) CD239 (Basal cell adhesion molecule) can be obtained from Swiss-Prot database entry P50895 (entry version 117, sequence version 2); the sequence(s) of the (human) CD241 (Ammonium transporter Rh type A) can be obtained from Swiss-Prot database entry Q02094 (entry version 98, sequence version 2); the sequence(s) of the (human) CD242 (Intercellular adhesion molecule 4) can be obtained from Swiss-Prot database entry Q14773 (entry version 106, sequence version 1); the sequence(s) of the (human) CD243 (Multidrug resistance protein 1) can be obtained from Swiss-Prot database entry P08183 (entry version 146, sequence version 3; the sequence(s) of the (human) CD244 (Natural killer cell receptor 2B4) can be obtained from Swiss-Prot database entry Q9BZW8 (entry version 94, sequence version 2); the sequence(s) of the (human) CD246 (ALK tyrosine kinase receptor) can be obtained from Swiss-Prot database entry Q9UM73 (entry version 120, sequence version 3); the sequence(s) of the (human) CD248 (Endosialin) can be obtained from Swiss-Prot database entry Q9HCU0 (entry version 87, sequence version 1); the sequence(s) of the (human) CD249 (Glutamyl aminopeptidase) can be obtained from Swiss-Prot database entry Q07075 (entry version 121, sequence version 3); the sequence(s) of the (human) CD252 (Tumor necrosis factor ligand superfamily member 4) can be obtained from Swiss-Prot database entry P23510 (entry version 101, sequence version 1); the sequence(s) of the (human) CD253 (Tumor necrosis factor ligand superfamily member 10) can be obtained from Swiss-Prot database entry P50591 (entry version 118, sequence version 1); the sequence(s) of the (human) CD254 (Tumor necrosis factor ligand superfamily member 11) can be obtained from Swiss-Prot database entry 014788 (entry version 110, sequence version 1); the sequence(s) of the (human) CD256 (Tumor necrosis factor ligand superfamily member 13) can be obtained from Swiss-Prot database entry 075888 (entry version 111, sequence version 1); the sequence(s) of the (human) CD257 (Tumor necrosis factor ligand superfamily member 13B) can be obtained from Swiss-Prot database entry Q9Y275 (entry version 127, sequence version 1); the sequence(s) of the (human) CD258 (Tumor necrosis factor ligand superfamily member 14) can be obtained from Swiss-Prot database entry 043557 (entry version 117, sequence version 2); the sequence(s) of the (human) CD261 (Tumor necrosis factor receptor superfamily member 10A) can be obtained from Swiss-Prot database entry 000220 (entry version 112, sequence version 3); the sequence(s) of the (human) CD262 (Tumor necrosis factor receptor superfamily member 10B) can be obtained from Swiss-Prot database entry 014763 (entry version 133, sequence version 2); the sequence(s) of the (human) CD263 (Tumor necrosis factor receptor superfamily member 10C) can be obtained from Swiss-Prot database entry 014798 (entry version 99, sequence version 3); the sequence(s) of the (human) CD264 (Tumor necrosis factor receptor superfamily member 10D) can be obtained from Swiss-Prot database entry Q9UBN6 (entry version 109, sequence version 1); the sequence(s) of the (human) CD265 (Tumor necrosis factor receptor superfamily member 11A) can be obtained from Swiss-Prot database entry Q9Y6Q6 (entry version 100, sequence version 1); the sequence(s) of the (human) CD266 (Tumor necrosis factor receptor superfamily member 12A) can be obtained from Swiss-Prot database entry Q9NP84 (entry version 89, sequence version 1); the sequence(s) of the (human) CD267 (Tumor necrosis factor receptor superfamily member 13B) can be obtained from Swiss-Prot database entry 014836 (entry version 102, sequence version 1); the sequence(s) of the (human) CD268 (Tumor necrosis factor receptor superfamily member 13C) can be obtained from Swiss-Prot database entry Q96RJ3 (entry version 91, sequence version 1); the sequence(s) of the (human) CD269 (Tumor necrosis factor receptor superfamily member 17) can be obtained from Swiss-Prot database entry Q02223 (entry version 125, sequence version 2); the sequence(s) of the (human) CD270 (Tumor necrosis factor receptor superfamily member 14) can be obtained from Swiss-Prot database entry Q92956 (entry version 134, sequence version 3); the sequence(s) of the (human) CD271 (Tumor necrosis factor receptor superfamily member 16) can be obtained from Swiss-Prot database entry P08138 (entry version 135, sequence version 1); the sequence(s) of the (human) CD276 (CD276 antigen) can be obtained from Swiss-Prot database entry Q5ZPR3 (entry version 71, sequence version 1); the sequence(s) of the (human) CD277 (Butyrophilin subfamily 3 member A1) can be obtained from Swiss-Prot database entry 000481 (entry version 102, sequence version 3); the sequence(s) of the (human) CD280 (C-type mannose receptor 2) can be obtained from Swiss-Prot database entry Q9UBG0 (entry version 79, sequence version 2); the sequence(s) of the (human) CD281 (Toll-like receptor 1) can be obtained from Swiss-Prot database entry Q15399 (entry version 125, sequence version 3); the sequence(s) of the (human) CD282 (Toll-like receptor 2) can be obtained from Swiss-Prot database entry 060603 (entry version 129, sequence version 1); the sequence(s) of the (human) CD283 (Toll-like receptor 3) can be obtained from Swiss-Prot database entry 015455 (entry version 120, sequence version 1); the sequence(s) of the (human) CD284 (Toll-like receptor 4) can be obtained from Swiss-Prot database entry 000206 (entry version 125, sequence version 2); the sequence(s) of the (human) CD286 (Toll-like receptor 6) can be obtained from Swiss-Prot database entry Q9Y2C9 (entry version 108, sequence version 2); the sequence(s) of the (human) CD288 (Toll-like receptor 8) can be obtained from Swiss-Prot database entry Q9NR97 (entry version 103, sequence version 1); the sequence(s) of the (human) CD289 (Toll-like receptor 9) can be obtained from Swiss-Prot database entry Q9NR96 (entry version 107, sequence version 2); the sequence(s) of the (human) CD290 (Toll-like receptor 10) can be obtained from Swiss-Prot database entry Q9BXR5 (entry version 105, sequence version 2); the sequence(s) of the (human) CD292 (Bone morphogenetic protein receptor type-1A) can be obtained from Swiss-Prot database entry P36894 (entry version 146, sequence version 2); the sequence(s) of the (human) CD294 (Putative G-protein coupled receptor 44) can be obtained from Swiss-Prot database entry Q9Y5Y4 (entry version 91, sequence version 3); the sequence(s) of the (human) CD295 (Leptin receptor) can be obtained from Swiss-Prot database entry P48357 (entry version 132, sequence version 2); the sequence(s) of the (human) CD296 (GPI-linked NAD(P)(+)-arginine ADP-ribosyltransferase 1) can be obtained from Swiss-Prot database entry P52961 (entry version 96, sequence version 2); the sequence(s) of the (human) CD297 (Ecto-ADP-ribosyltransferase 4) can be obtained from Swiss-Prot database entry Q93070 (entry version 106, sequence version 2); the sequence(s) of the (human) CD298 (Sodium/potassium-transporting ATPase subunit beta-3) can be obtained from Swiss-Prot database entry P54709 (entry version 102, sequence version 1); the sequence(s) of the (human) CD299 (C-type lectin domain family 4 member M) can be obtained from Swiss-Prot database entry Q9H2X3 (entry version Q9H2X3 (entry version 108, sequence version 1); the sequence(s) of the (human) CD300 (CMRF35-like molecule 9) can be obtained from Swiss-Prot database entry Q6UXG3 (entry version 67, sequence version 2); the sequence(s) of the (human) CD301 (C-type lectin domain family 10 member A) can be obtained from Swiss-Prot database entry Q8IUN9 (entry version 80, sequence version 1); the sequence(s) of the (human) CD302 (CD302 antigen) can be obtained from Swiss-Prot database entry Q8IX05 (entry version 64, sequence version 1); the sequence(s) of the (human) CD303 (C-type lectin domain family 4 member C) can be obtained from Swiss-Prot database entry Q8WTT0 (entry version 82, sequence version 1); the sequence(s) of the (human) CD304 (Neuropilin-1) can be obtained from Swiss-Prot database entry 014786 (entry version 129, sequence version 3); the sequence(s) of the (human) CD305 (Leukocyte-associated immunoglobulin-like receptor 1) can be obtained from Swiss-Prot database entry Q6GTX8 (entry version 70, sequence version 1); the sequence(s) of the (human) CD306 (Leukocyte-associated immunoglobulin-like receptor 2) can be obtained from Swiss-Prot database entry Q6ISS4 (entry version 63, sequence version 1); the sequence(s) of the (human) CD309 (Vascular endothelial growth factor receptor 2) can be obtained from Swiss-Prot database entry P35968 (entry version 138, sequence version 2); the sequence(s) of the (human) CD312 (EGF-like module-containing mucin-like hormone receptor-like 2) can be obtained from Swiss-Prot database entry Q9UHX3 (entry version 113, sequence version 2); the sequence(s) of the (human) CD314 (NKG2-D type II integral membrane protein) can be obtained from Swiss-Prot database entry P26718 (entry version 117, sequence version 1); the sequence(s) of the (human) CD315 (Prostaglandin F2 receptor negative regulator) can be obtained from Swiss-Prot database entry Q9P2B2 (entry version 98, sequence version 2); the sequence(s) of the (human) CD316 (Immunoglobulin superfamily member 8) can be obtained from Swiss-Prot database entry Q969P0 (entry version 81, sequence version 1); the sequence(s) of the (human) CD317 (Bone marrow stromal antigen 2) can be obtained from Swiss-Prot database entry Q10589 (entry version 95, sequence version 1); the sequence(s) of the (human) CD318 (CUB domain-containing protein 1) can be obtained from Swiss-Prot database entry Q9H5V8 (entry version 78, sequence version 3; the sequence(s) of the (human) CD319 (SLAM family member 7) can be obtained from Swiss-Prot database entry Q9NQ25 (entry version 92, sequence version 1); the sequence(s) of the (human) CD320 (CD320 antigen) can be obtained from Swiss-Prot database entry Q9NPF0 (entry version 86, sequence version 1); the sequence(s) of the (human) CD321 (Junctional adhesion molecule A) can be obtained from Swiss-Prot database entry Q9Y624 (entry version 124, sequence version 1); the sequence(s) of the (human) CD322 (Junctional adhesion molecule B) can be obtained from Swiss-Prot database entry P57087 (entry version 107, sequence version 1); the sequence(s) of the (human) CD324 (Cadherin-1) can be obtained from Swiss-Prot database entry P12830 (entry version 157, sequence version 3); the sequence(s) of the (human) CD325 (Cadherin-2) can be obtained from Swiss-Prot database entry P19022 (entry version 118, sequence version 4), the sequence(s) of the (human) CD326 (Epithelial cell adhesion molecule) can be obtained from Swiss-Prot database entry P16422 (entry version 118, sequence version 2); the sequence(s) of the (human) CD327 (Sialic acid-binding Ig-like lectin 6) can be obtained from Swiss-Prot database entry 043699 (entry version 107, sequence version 2); the sequence(s) of the (human) CD328 (Sialic acid-binding Ig-like lectin 7) can be obtained from Swiss-Prot database entry Q9Y286 (entry version 111, sequence version 1); the sequence(s) of the (human) CD329 (Sialic acid-binding Ig-like lectin 8) can be obtained from Swiss-Prot database entry Q9NYZ4 (entry version 100, sequence version 2); the sequence(s) of the (human) CD331 (Fibroblast growth factor receptor 1) can be obtained from Swiss-Prot database entry P11362 (entry version 169, sequence version 3); the sequence(s) of the (human) CD332 (Fibroblast growth factor receptor 2) can be obtained from Swiss-Prot database entry P21802 (entry version 165, sequence version 1); the sequence(s) of the (human) CD333 (Fibroblast growth factor receptor 3) can be obtained from Swiss-Prot database entry P22607 (entry version 161, sequence version 1); the sequence(s) of the (human) CD334 (Fibroblast growth factor receptor 4) can be obtained from Swiss-Prot database entry P22455 (entry version 136, sequence version 2); the sequence(s) of the (human) CD335 (Natural cytotoxicity triggering receptor 1) can be obtained from Swiss-Prot database entry 076036 (entry version 98, sequence version 1); the sequence(s) of the (human) CD336 (Natural cytotoxicity triggering receptor 2) can be obtained from Swiss-Prot database entry 095944 (entry version 86, sequence version 2); the sequence(s) of the (human) CD337 (Natural cytotoxicity triggering receptor 3) can be obtained from Swiss-Prot database entry 014931 (entry version 103, sequence version 1); the sequence(s) of the (human) CD338 (ATP-binding cassette sub-family G member 2) can be obtained from Swiss-Prot database entry Q9UNQO (entry version 120, sequence version 3); the sequence(s) of the (human) CD339 (Protein jagged-1) can be obtained from Swiss-Prot database entry P78504 (entry version (entry version 129; sequence version 3); the sequence(s) of the (human) CD340 (Receptor tyrosine-protein kinase erbB-2) can be obtained from Swiss-Prot database entry P04626 (entry version 162, sequence version 1); the sequence(s) of the (human) CD344 (Frizzled-4) can be obtained from Swiss-Prot database entry Q9ULV1 (entry version 107, sequence version 2); the sequence(s) of the (human) CD349 (Frizzled-9) can be obtained from Swiss-Prot database entry 000144 (entry version 103, sequence version 1); the sequence(s) of the (human) CD350 (Frizzled-10) can be obtained from Swiss-Prot database entry Q9ULW2 (entry version 100, sequence version 1); the sequence(s) of the (human) CD351 (High affinity immunoglobulin alpha and immunoglobulin mu Fc receptor) can be obtained from Swiss-Prot database entry Q8WWV6 (entry version 65, sequence version 1); the sequence(s) of the (human) CD352 (SLAM family member 6) can be obtained from Swiss-Prot database entry Q96DU3 (entry version 93, sequence version 3); the sequence(s) of the (human) CD353 (SLAM family member 8) can be obtained from Swiss-Prot database entry Q9POV8 (entry version 80, sequence version 1); the sequence(s) of the (human) CD354 (Triggering receptor expressed on myeloid cells 1) can be obtained from Swiss-Prot database entry Q9NP99 (entry version 93, sequence version 1); the sequence(s) of the (human) CD355 (Cytotoxic and regulatory T-cell molecule) can be obtained from Swiss-Prot database entry 095727 (entry version 81, sequence version 2); the sequence(s) of the (human) CD357 (Tumor necrosis factor receptor superfamily member 18) can be obtained from Swiss-Prot database entry Q9Y5U5 (entry version 103, sequence version 1); the sequence(s) of the (human) CD358 (Tumor necrosis factor receptor superfamily member 21) can be obtained from Swiss-Prot database entry 075509 (entry version 110, sequence version 1); the sequence(s) of the (human) CD360 (Interleukin-21 receptor) can be obtained from Swiss-Prot database entry Q9HBE5 (entry version 104, sequence version 1); the sequence(s) of the (human) CD361 (Protein EVI2B) can be obtained from Swiss-Prot database entry P34910 (entry version 87, sequence version 2); the sequence(s) of the (human) CD362 (Syndecan-2) can be obtained from Swiss-Prot database entry P34741 (entry version 105, sequence version 2); the sequence(s) of the (human) CD363 (Sphingosine 1-phosphate receptor 1) can be obtained from Swiss-Prot database entry P21453 (entry version 116, sequence version 2); the sequence(s) of the (human) Criptic family protein (Criptic family protein 1-B) can be obtained from Swiss-Prot database entry POCG36 (entry version 12, sequence version 1); the sequence(s) of the (human) Thyrotropin receptor (TSH-R) can be obtained from Swiss-Prot database entry P16473 (entry version 152, sequence version 2); or the sequence(s) of the (human) Epidermal growth factor receptor (EGFR) can be obtained from Swiss-Prot database entry P00533 (entry version 178, sequence version 2; (SEQ ID NOs: 198 (protein) and 197 (DNA)).

As mentioned above, the (Ig-derived) domain(s) of the above-described trivalent, bispecific antibody molecule may comprise an antigen-interaction-site with specificity for a cell surface molecule, i.e. a tumor-specific antigen that naturally occurs on the surface of a tumor cell.

The term "cell surface molecule that naturally occurs on the surface of a tumor cell"/"tumor-specific antigen that naturally occurs on the surface of a tumor cell" as used herein, also denotes molecules which are presented on the surface of tumor cells. The term "naturally occurs" relates to molecules which are endogenously expressed on the surface of (a) tumor cell(s). The term "cell surface molecule", relates to molecules, which are (naturally/endogenously) expressed/presented on the surface of cells and comprise domains or epitopes accessible (in vitro or in vivo) to (a) domain(s) of the (Ig-derived) trivalent, bispecific antibody as described herein. Examples for said cell surface molecules are membrane and transmembrane proteins, molecules adapted to said proteins or the cell surface etc. Accordingly, in the context of the present invention said cell surface molecule is a tumor specific marker. In the context of the present invention said tumor specific marker relates to a marker which usually is endogenously expressed on the surface of the tumor cells.

In the context of this invention, the term "tumor specific marker" relate to molecules, which are naturally/endogenously presented and/or located on the surface of (a) tumor cell(s) or which are ubiquitously expressed but are only accessible for binding of trivalent, bispecific antibody molecules, antibody fragments or antibody derivatives on the surface of tumor cells. A "tumor specific marker" as referred herein describes a protein preferentially or exclusively expressed on a tumor cell. Preferentially means a relatively higher expression on a tumor than on a normal somatic cell while exclusively means an expression of a protein on a tumor cell which is not found on somatic cells by standard means of protein detection known to the expert. Proteins fulfilling these criteria can for instance be identified by subtractive or differential expression screens which are well known in the art. The degree to which tumor cell specific expression is required to be exploited by the method of therapy of the present invention can be assessed by a cellular assay in which cells expressing the antigen of interest and T-cells specific for this antigen are incubated together and specificity of induced killing is determined.

"Preferential expression" refers to proteins which are in comparison to normal cells highly expressed on tumor cells due to protein overexpression mediated by gene amplification, transcriptional upregulation or mRNA stabilization or mutations affecting the turnover of such proteins. Preferential also defines proteins which are expressed on tumor cells and also on normal cells, but in which normal cells are usually not accessible to T-cells or antibodies such as immune-privileged regions of the human body. Additionally, proteins which are expressed on tumor cells but are not expressed on normal cells within the scope of the treatment fall under this definition such as proteins which are exclusively expressed during embryonic development.

"Exclusive expression" refers to proteins which are solely found on tumor cells during the course of treatment. Preferably such proteins are displayed on the cell surface and carry point mutations or deletions in their extracellular part not found on normal cells. Similarly, neo-epitopes arising from tumor-specific activity of sheddases belong to this category. Exclusive expression also includes abnormal glycostructures exclusively found on tumor but not on normal cells.

Examples of tumor markers that naturally occur on the surface of tumor cells are given herein below and comprise, but are not limited to EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD20, CD22, CD33, CD52, FMS-like tyrosine kinase 3 (FLT-3), folate receptor 1 (FOLR1), human trophoblast cell-surface antigen 2 (Trop-2), cancer antigen 12-5 (CA-12-5), human leukocyte antigen—antigen D related (HLA-DR), MUC-1 (mucin-1), A33-antigen, PSMA (prostate specific membrane antigen), PSCA (prostate stem cell antigen), transferrin-receptor, tenascin or carbon anhydrase IX (CA-IX).

Accordingly, in the context of the present invention, the trivalent, bispecific antibody molecule(s) described herein binds to an antigen/marker that naturally occurs on the surface of tumor cells selected from the group consisting of EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD20, CD22, CD33, CD52, FMS-like tyrosine kinase 3 (FLT-3), folate receptor 1 (FOLR1), human trophoblast cell-surface antigen 2 (Trop-2), cancer antigen 12-5 (CA-12-5), human leukocyte antigen—antigen D related (HLA-DR), MUC-1 (mucin-1), A33-antigen, PSMA (prostate specific membrane antigen), PSCA (prostate stem cell antigen), transferrin-receptor, tenascin or CA-IX (carbon anhydrase IX).

The sequence(s) of the (human) members of the EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD20, CD22, CD33, CD52, FMS-like tyrosine kinase 3 (FLT-3), folate receptor 1 (FOLR1), human trophoblast cell-surface antigen 2 (Trop-2), cancer antigen 12-5 (CA-12-5), human leukocyte antigen—antigen D related (HLA-DR), MUC-1 (mucin-1), A33-antigen, PSMA (prostate specific membrane antigen), PSCA (prostate stem cell antigen), transferrin-receptor, tenascin or CA-IX (carbon anhydrase IX) are available in the UniProtKB/Swiss-Prot database. These (protein) sequences also relate to annotated modified sequences. The present invention also provides techniques and methods wherein homologous sequences, and also genetic allelic variants and the like of the concise sequences provided herein are used. Preferably such "variants" and the like of the concise sequences herein are used. Preferably, such "variants" are genetic variants. The skilled person may easily deduce the relevant coding region of these (protein) sequences in these databank entries, which may also comprise the entry of genomic DNA as well as mRNA/cDNA.

The sequence(s) of the of the (human) EpCAM (epithelial cell adhesion molecule) can be obtained from the Swiss-Prot database entry P16422 (entry version 117, sequence version 2); the sequence(s) of the (human) MSLN (mesothelin) can be obtained from the UniProt Entry number Q13421 (version number 132; sequence version 2); SEQ ID NOs: (149 (DNA) and 150 (protein); the sequence(s) of the (human) FMS-like tyrosine kinase 3 (FLT-3) can be obtained from the Swiss-Prot database entry P36888 (primary citable accession number) or Q13414 (secondary accession number) with the version number 165 and the sequence version 2; the sequences of (human) MCSP (melanoma chondroitin sulfate proteoglycan) can be obtained from the UniProt Entry number Q6UVK1 (version number 118; sequence version 2); the sequence(s) of the (human) folate receptor 1 (FOLR1) can be obtained from the UniProt Entry number P15328 (primary citable accession number) or Q53EW2 (secondary accession number) with the version number 153 and the sequence version 3; the sequence(s) of the (human) trophoblast cell-surface antigen 2 (Trop-2) can be obtained from the UniProt Entry number P09758 (primary citable accession number) or Q15658 (secondary accession number) with the version number 172 and the sequence version 3; the sequence(s) of the (human) PSCA (prostate stem cell antigen) can be obtained from the UniProt Entry number O43653 (primary citable accession number) or Q6UW92 (secondary accession number) with the version number 134 and the sequence version 1; the sequence(s) of the (human) HER-1 (epidermal growth factor receptor 1) can be obtained from the Swiss-Prot database entry P00533 (entry version 177, sequence version 2); the sequence(s) of the (human) HER-2 (epidermal growth factor 2) can be obtained from the Swiss-Prot database entry P04626 (entry version 161, sequence version 1); the sequence(s) of the (human) HER-3 (epidermal growth factor 3) can be obtained from the Swiss-Prot database entry P21860 (entry version 140, sequence version 1); the sequence(s) of the (human) CD20 (B-lymphocyte antigen CD20) can be obtained from the Swiss-Prot database entry P11836 (entry version 117, sequence version 1); the sequence(s) of the (human) CD22 (B-lymphocyte antigen CD22) can be obtained from the Swiss-Prot database entry P20273 (entry version 135, sequence version 2); the sequence(s) of the (human) CD33 (B-lymphocyte antigen CD33) can be obtained from the Swiss-Prot database entry P20138 (entry version 129, sequence version 2); the sequence(s) of the (human) CA-12-5 (Mucin 16) can be obtained from the Swiss-Prot database entry Q8WXI7 (entry version 66, sequence version 2); the sequence(s) of the (human) HLA-DR can be obtained from the Swiss-Prot database entry Q29900 (entry version 59, sequence version 1); the sequence(s) of the (human) MUC-1 (mucin-1) can be obtained from the Swiss-Prot database entry P15941 (entry version 135, sequence version 3); the sequence(s) of the (human) A33 (cell surface A33 antigen) can be obtained from the Swiss-Prot database entry Q99795 (entry version 104, sequence version 1); the sequence(s) of the (human) PSMA (prostate specific membrane antigen) can be obtained from the Swiss-Prot database entry Q04609 (entry version 133, sequence version 1), the sequence(s) of the (human) transferrin receptor can be obtained from the Swiss-Prot database entries Q9UP52 (entry version 99, sequence version 1) and P02786 (entry version 152, sequence version 2); the sequence of the (human) tenascin can be obtained from the Swiss-Prot database entry P24821 (entry version 141, sequence version 3); or the sequence(s) of the (human) CA-IX (carbonic anhydrase IX) can be obtained from the Swiss-Prot database entry Q16790 (entry version 115, sequence version 2).

The molecules or constructs (i.e., the trivalent, bispecific antibody molecules described herein) provided herein are particularly useful in medical settings. For examples malignant diseases may be treated with a trivalent, bispecific antibody molecule described herein. In the context of the present invention the malignant disease may be a cancer/carcinoma of epithelial, endothelial or mesothelial origin or a cancer of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitorurinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

The molecules or constructs (i.e., the bispecific antibody molecules described herein) provided herein are particularly useful in medical settings. For example, tumorous diseases and/or lymphomas may be treated with a bispecific construct directed against these medical indication(s). The indication for a trivalent, bispecific antibody/molecule is given by the expression of the tumor antigen. A tumor antigen expressed in an entity could be virtually combined with any of the above mentioned T-cell marker (representing the antigen that naturally occurs/that is endogenously expressed on the surface of a tumor cell). For example, gastrointestinal cancer, pancreatic cancer, cholangiocellular cancer, lung cancer, breast cancer, ovarian cancer, skin cancer and/or oral cancer may be treated with a trivalent, bispecific molecule or construct (i.e., the trivalent, bispecific antibody molecule described herein) directed against (human) EpCAM (as the tumor-specific antigen naturally occurring on the surface of a tumor cell) and comprises one or two binding domain(s) directed against/binding to/interacting with one of the herein defined extracellular domains of the fusion protein, i.e. an extracellular domain of a signalling receptor that does not naturally occur in and/or on T-cells. Accordingly, in the context of the present invention, a trivalent, bispecific antibody construct is directed against EpCAM, preferably human EpCAM, and further comprises one or two binding domain(s) directed against/binding to/interacting with Cripto may be used in the treatment of gastrointestinal cancer, for example adenocarcinoma of gastrointestinal origin. Thus, in the context of the present invention, a trivalent, bispecific antibody construct/molecule is directed against EpCAM, preferably human EpCAM, via one binding domain and comprising two binding domains directed against/binding to/interacting with one of the herein defined extracellular domains of the fusion protein, i.e. an extracellular domain of a signalling receptor that does not naturally occur in and/or on T-cells. In an alternative embodiment of the present invention, the trivalent, bispecific antibody molecule may be also designed in such a way that it is directed against EpCAM, preferably human EpCAM, via two binding domains and one binding domain directed against one of the herein defined extracellular domains of the fusion protein, i.e. an extracellular domain of a signalling receptor that does not naturally occur in and/or on T-cells.

Gastrointestinal cancer, pancreatic cancer, cholangiocellular cancer, lung cancer, breast cancer, ovarian cancer, skin cancer and/or oral cancer may be treated with a trivalent, bispecific molecule or construct (i.e., the trivalent, bispecific antibody molecule described herein) directed against HER1, preferably human HER1, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. This means that gastrointestinal cancer, pancreatic cancer, cholangiocellular cancer, lung cancer, breast cancer, ovarian cancer, skin cancer and/or oral cancer may be treated with a trivalent, bispecific molecule or construct (i.e., the trivalent, bispecific antibody molecule described herein) directed against HER1, preferably human HER1, (as the tumor-specific antigen naturally occurring on the surface of a tumor cell) via two binding domains and comprises one binding domains directed against/binding to/interacting with one of the herein defined extracellular domains of the fusion protein, i.e. an extracellular domain of a signalling receptor that does not naturally occur in and/or on T-cells. Alternatively, gastrointestinal cancer, pancreatic cancer, cholangiocellular cancer, lung cancer, breast cancer, ovarian cancer, skin cancer and/or oral cancer may be treated with a trivalent, bispecific molecule or construct (i.e., the trivalent, bispecific antibody molecule described herein) directed against HER1, preferably human HER1, (as the tumor-specific antigen naturally occurring on the surface of a tumor cell) via one binding domain and comprises two binding domains directed against/binding to/interacting with one of the herein defined extracellular domains of the fusion protein, i.e. an extracellular domain of a signalling receptor that does not naturally occur in and/or on T-cells. Furthermore, gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against MCSP, preferably human MCSP, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against FOLR1, preferably human FOLR1, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against Trop-2, preferably human Trop-2, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against PSCA, preferably human PSCA, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against EGFRvIII, preferably human EGFRvIII, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer, glioblastoma and/or oral cancer may be treated with a trivalent, bispecific molecule or construct (i.e. the trivalent, bispecific antibody molecule described herein) directed against MSLN, preferably human MSLN, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastric cancer, breast cancer and/or cervical cancer may be treated with a trivalent, bispecific molecule or construct (i.e., the trivalent, bispecific antibody molecule described herein) directed against HER2, preferably human HER2, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastric cancer and/or lung cancer may be treated with a trivalent, bispecific molecule or construct (i.e., the trivalent, bispecific antibody molecule described herein) directed against HER3, preferably human HER3, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. B-cell lymphoma and/or T-cell lymphoma may be treated with a trivalent, bispecific molecule or construct (i.e., the trivalent, bispecific antibody molecule described herein) directed against CD20, preferably human CD20, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. B-cell lymphoma and/or T-cell lymphoma may be treated with a trivalent, bispecific molecule or construct (i.e., the trivalent, bispecific antibody molecule described herein) directed against CD22, preferably human CD22, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Myeloid leukemia may be treated with a trivalent, bispecific construct directed against CD33, preferably human CD33, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Ovarian cancer, lung cancer, breast cancer and/or gastrointestinal cancer may be treated with a trivalent, bispecific molecule or construct (i.e., the trivalent, bispecific antibody molecule described herein) directed against CA12-5, preferably human CA12-5, (as the tumor-specific antigen naturally occurring on the surface of a tumor cell) via one or two binding domain(s) and comprises one or two binding domain(s) directed against/binding to/interacting with one of the herein defined extracellular domain of the fusion protein, i.e. an extracellular domains of a signalling receptor that does not naturally occur in and/or on T-cells. Gastrointestinal cancer, leukemia and/or nasopharyngeal carcinoma may be treated with a trivalent, bispecific molecule or construct (i.e., the trivalent, bispecific antibody molecule described herein) directed against HLA-DR, preferably human HLA-DR, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Colon cancer, breast cancer, ovarian cancer, lung cancer and/or pancreatic cancer may be treated with a trivalent, bispecific molecule or construct (i.e., the trivalent, bispecific antibody molecule described herein) directed against MUC-1, preferably human MUC-1, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Colon cancer may be treated with a trivalent, bispecific molecule or construct (i.e., the trivalent, bispecific antibody molecule described herein) directed against A33, preferably human A33, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Prostate cancer may be treated with a trivalent, bispecific molecule or construct (i.e., the trivalent, bispecific antibody molecule described herein) directed against PSMA, preferably human PSMA, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Gastrointestinal cancer, pancreatic cancer, cholangiocellular cancer, lung cancer, breast cancer, ovarian cancer, skin cancer and/or oral cancer may be treated with a trivalent, bispecific molecule or construct (i.e., the trivalent, bispecific antibody molecule described herein) directed against the transferrin receptor, preferably the human transferring receptor, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Pancreatic cancer, lunger cancer and/or breast cancer may be treated with a trivalent, bispecific molecule or construct (i.e., the trivalent, bispecific antibody molecule described herein) directed against the transferrin receptor, preferably the human transferring receptor, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells. Renal cancer may be treated with a trivalent, bispecific molecule or construct (i.e., the trivalent, bispecific antibody molecule described herein) directed against CA-IX, preferably human CA-IX, (as the tumor-specific antigen naturally occurring on the surface of a tumor cell) via one or two binding domain(s) and comprises one or two binding domain(s) directed against/binding to/interacting with one of the herein defined extracellular domains of the fusion protein, i.e. an extracellular domain of a signalling receptor that does not naturally occur in and/or on T-cells.

Figure 9A:
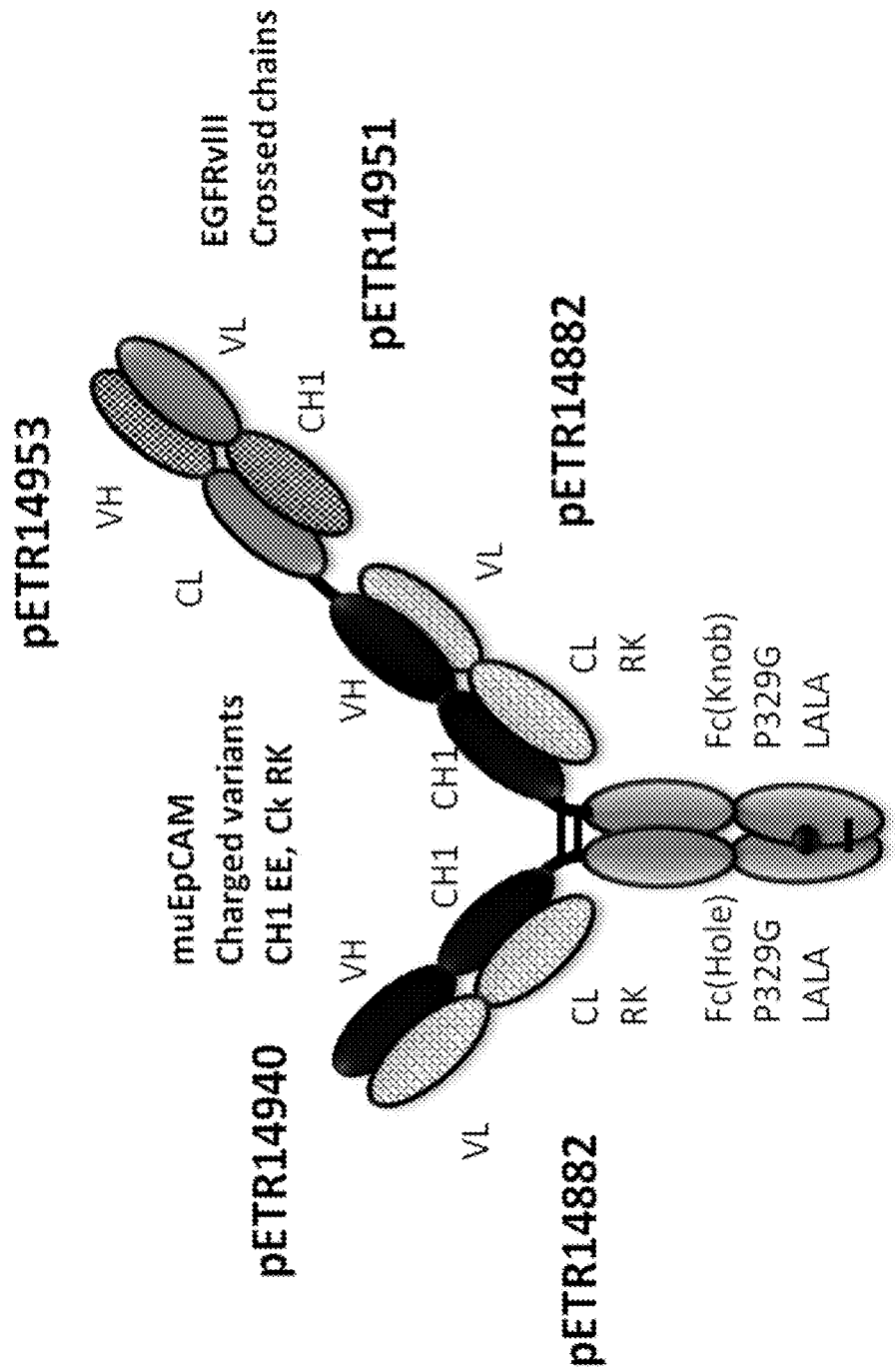
FIG. 9A shows a schematic structure of BsAb EGFRvIII-EpCAM.
Figure 10A:
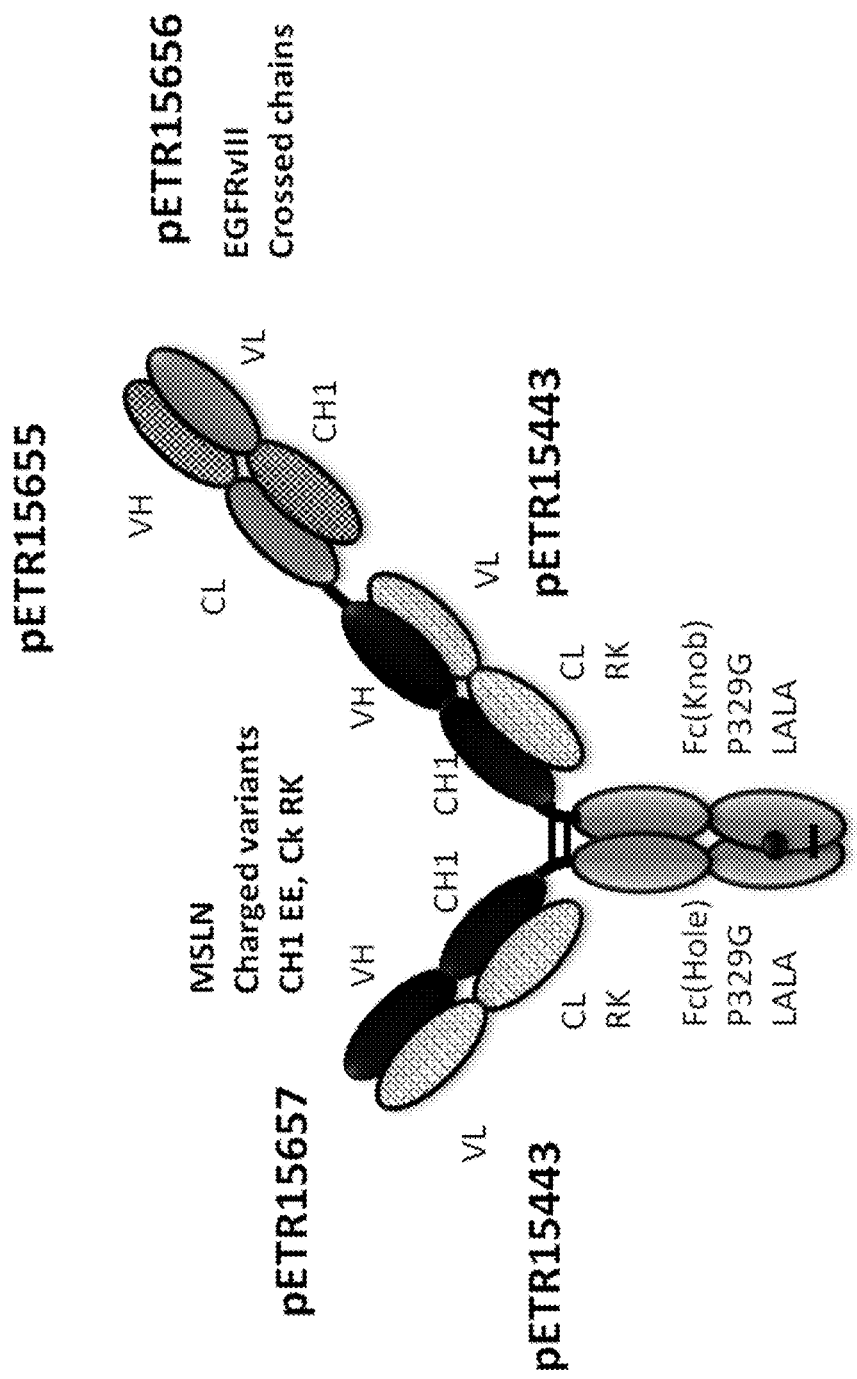
FIG. 10A shows a schematic structure of the trivalent, bispecific antibody (bsAb) molecule "BsAB EGFRvIII-MSLN.
Figure 11A:
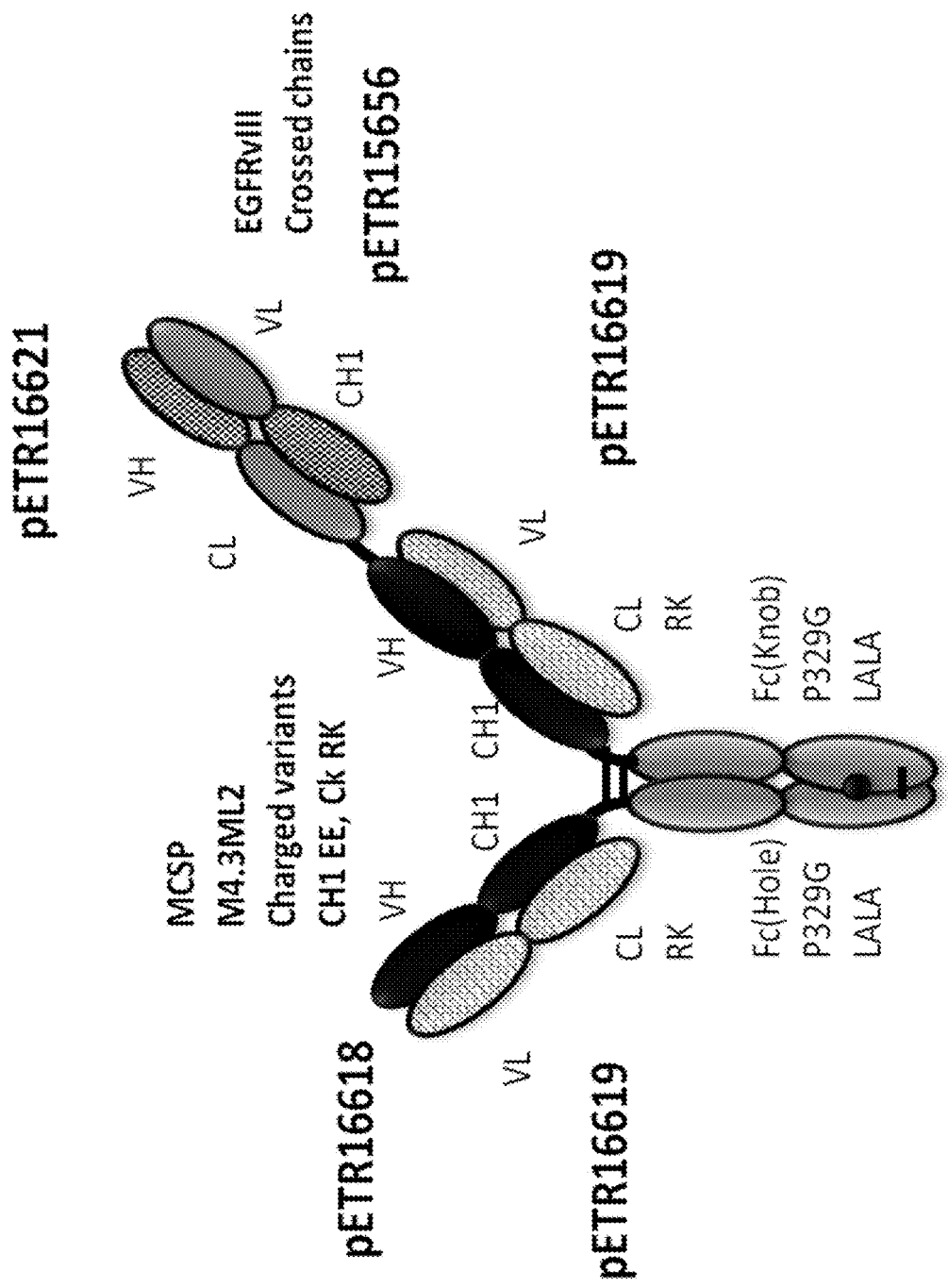
FIG. 11A shows a schematic structure of the trivalent, bispecific antibody (bsAb) molecule "BsAb EGFRvIII-MCSP.
Figure 11B:
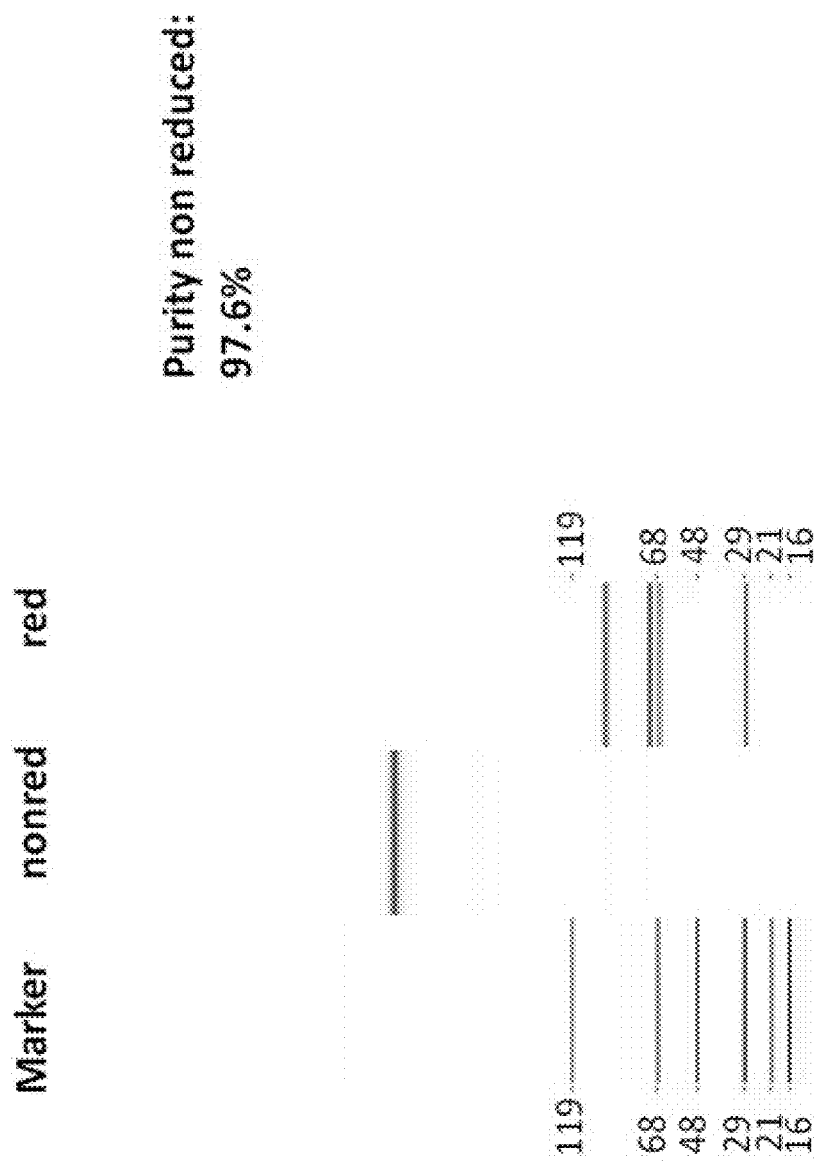
" FIG. 11B shows CE-SDS analysis of BsAB EGFRvIII-MCSP.

As also illustrated in the appended examples, as a proof of concept of the present invention, a specific trivalent, bispecific antibody molecule of the invention comprises the above defined first and second (Ig-derived) domain binding to/directed against/interacting with or on human EGFRvIII and a second (Ig-derived) domain binding to/directed against/interacting with or on murine EpCAM (see FIG. 9A). Further, FIG. 10A illustrates a specific trivalent, bispecific antibody molecule of the invention comprises the above defined first and second (Ig-derived) domain binding to/directed against/interacting with or on human EGFRvIII and a second (Ig-derived) domain binding to/directed against/interacting with or on human MSLN. Moreover, FIG. 11A illustrates a specific trivalent, bispecific antibody molecule of the invention comprises the above defined first and second (Ig-derived) domain binding to/directed against/interacting with or on human EGFRvIII and a second (Ig-derived) domain binding to/directed against/interacting with or on human MCSP. The diseases that may be treated by using a trivalent, bispecific antibody directed against EGFRvIII and EpCAM, by using a trivalent, bispecific antibody directed against EGFRvIII and MSLN, or by using a trivalent, bispecific antibody molecule directed against EGFRvIII and MCSP include gastrointestinal cancer, pancreatic cancer, cholangiocellular cancer, lung cancer, breast cancer, ovarian cancer, skin cancer, glioblastoma and/or oral cancer.

Epithelial cell adhesion molecule (EpCAM, also called 17-1A antigen, KSA, EGP40, GA733-2, ks1-4 or esa) is a 40-kDa membrane-integrated glycoprotein of 314 amino acids with specific expression in certain epithelia and on many human carcinomas (reviewed in Balzar, J. Mol. Med. (1999), 77, 699-712). EpCAM was discovered and subsequently cloned through its recognition by the murine monoclonal antibody 17-1A/edrecolomab (Goettlinger, Int J Cancer 38 (1986), 47-53 and Simon, Proc. Natl. Acad. Sci. USA 87 (1990), 2755-2759). EpCAM serves to adhere epithelial cells in an oriented and highly ordered fashion (Litvinov, J Cell Biol. 139 (1997), 1337-1348). Upon malignant transformation of epithelial cells the rapidly growing tumor cells are abandoning the high cellular order of epithelia. Consequently, the surface distribution of EpCAM becomes less restricted and the molecule better exposed on tumor cells and accessible for binding of antibodies, antibody fragments or antibody derivatives on the surface of tumor cells. Due to their epithelial cell origin, tumor cells from most carcinomas still express EpCAM on their surface.

In vivo, expression of EpCAM is related to increased epithelial proliferation and negatively correlates with cell differentiation (for review see Balzar, J. Mol. Med. 77 (1999), 699-712). Expression of EpCAM is essentially seen with all major carcinomas (reviewed in Balzar, J. Mol. Med. 77 (1999), 699-712 or documented, inter alia, in De Bree, Nucl Med Commun. 15 (1994), 613-27; Zhang, Clin Cancer Res. 4 (1998), 295-302). Because of its widespread expression, EpCAM is referred to as a "pan-carcinoma" antigen. In many cases, tumor cells were observed to express EpCAM to a much higher degree than their parental epithelium or less aggressive forms of said cancers. For example, increased EpCAM expression represents an early event in the development of prostate cancer (Poczatek, J. Urol. 162 (1999), 1462-1644). In addition, in the majority of both squamous and adenocarcinomas of the cervix a strong EpCAM expression correlates with an increased proliferation and the disappearance of markers for terminal differentiation (Litvinov, Am. J. Pathol. 148 (1996), 865-75). In breast cancer, overexpression of EpCAM on tumor cells is a predictor of survival (Gastl, Lancet 356 (2000), 1981-1982). EpCAM is a marker for the detection of disseminated tumor cells in patients suffering from squamous cell carcinoma of the head, neck and lung (Chaubal, Anticancer Res. 19 (1999), 2237-2242 and Piyathilake, Hum. Pathol. 31 (2000), 482-487). Normal squamous epithelium, as found in epidermis, oral cavity, epiglottis, pharynx, larynx and esophagus did not significantly express EpCAM (Quak, Hybridoma 9 (1990), 377-387). EpCAM has been shown to be expressed on the majority of primary, metastatic, and disseminated NSCLC (non small cell lung cancer cells (Passlick, Int J Cancer 87 (2000), 548-552)), on gastric and gastro-oesophageal junction adenocarcinomas (Martin, J. Clin. Pathol. 52 (1999), 701-4) and in cell lines derived from colorectal, pancreatic carcinomas and breast carcinomas (Szala, Proc. Natl. Acad. Sci. USA 87 (1990), 3542-6 and Packeisen, Hybridoma 18 (1999), 37-40).

As illustratively shown in the appended Examples, as a proof of concept of the present invention, the trivalent, bispecific antibody molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953", "EGFR vIII MR1.1 VH Ck muEpCAM VH CH1 EE Fc knob PG LALA, pETR14953", "EGFR vIII MR1.1 VL CH1, pETR14951", "VL EpCAM G.8.8 Ck RK, pETR14882" and "VH muEpCAM CH1 EE Fc hole PG LALA HRYF, pETR14940") was constructed which comprises one domain binding to/directed against/interacting with or on human EGFRvIII and two domains binding to/directed against, interacting with or on murine EpCAM. The sequences (amino acid and cDNA) of the trivalent, bispecific antibody molecule "BsAB EGFRvIII-EpCAM" are shown below in Tables 1 and 2.

TABLE 1

| CONSTRUCT | AMINO ACID SEQUENCE | SEQ ID NO |
|---|---|---|
| EGFR vIII MR1.1 VH Ck muEpCAM VH CH1 EE Fc knob PG LALA, pETR14953 | QVKLQQSGGGLVKPGASLKLSCVTSGFTFRK FGMSWVRQTSDKRLEWVASISTGGYNTYYSD NVKGRFTISRENAKNTLYLQMSSLKSEDTALY YCTRGYSPYSYAMDYWGQGTTVTVSSASVA APSVFIFPPSDEQLKSGTASVVCLLNNFYPREA KVQWKVDNALQSGNSQESVTEQDSKDSTYSL SSTLTLSKADYEKHKVYACEVTHQGLSSPVT KSFNRGECGGGGSGGGGSEVQLAESGGGLVQ PGRSMKLSCAASGFTFSNFPMAWVRQAPTKC LEWVATISTSGGSTYYRDSVKGRFTISRDNAK STLYLQMNSLRSEDTATYYCTRTLYILRVFYF DYWGQGVMVTVSSASTKGPSVFPLAPSSKST SGGTAALGCLVEDYFPEPVTVSWNSGALTSG VHTFPAVLQSSGLYSLSSVVTVPSSSLGTQTYI CNVNHKPSNTKVDEKVEPKSCDKTHTCPPCP APEAAGGPSVFLFPPKPKDTLMISRTPEVTCV VVDVSHEDPEVKFNWYVDGVEVHNAKTKPR EEQYNSTYRVVSVLTVLHQDWLNGKEYKCK VSNKALGAPIEKTISKAKGQPREPQVYTLPPC RDELTKNQVSLWCLVKGFYPSDIAVEWESNG QPENNYKTTPPVLDSDGSFFLYSKLTVDKSR WQQGNVFSCSVMHEALHNHYTQKSLSLSPG K | 22 |
| EGFR vIII MR1.1 VL CH1, pETR14951 | DIELTQSPASLSVATGEKVTIRCMTSTDIDDD MNAATYQQKPGEPPKFLISEGNTLRPGVPSRFSS SGTGTDFVFTIENTLSEDVGDYYCLQSWNVPL TFGDGTKLEIKSSASTKGPSVFPLAPSSKSTSG | 24 |

TABLE 1-continued

| CONSTRUCT | AMINO ACID SEQUENCE | SEQ ID NO |
|---|---|---|
| | GTAALGCLVKDYFPEPVTVSWNSGALTSGVH TFPAVLQSSGLYSLSSVVTVPSSSLGTQTYICN VNHKPSNTKVDKKVEPKSC | |
| VL EpCAM G8.8 Ck RK, pETR14882 | DIQMTQSPASLSASLGETVSIECLASEGISNDL AWYQQKSGKSPQLLIYATSRLQDGVPSRFSGS GSGTRYSLKISGMQPEDEADYFCQQSYKYPW TFGCGTKLELKRTVAAPSVFIFPPSDRKLKSGT ASVVCLLNNFYPREAKVQWKVDNALQSGNS QESVTEQDSKDSTYSLSSTLTLSKADYEKHKV YACEVTHQGLSSPVTKSFNRGEC | 26 |
| VH muEpCAM CH1 EE Fc hole PG LALA HRYF, pETR14940 | EVQLAESGGGLVQPGRSMKLSCAASGFTFSN FPMAWVRQAPTKCLEWVATISTSGGSTYYRD SVKGRFTISRDNAKSTLYLQMNSLRSEDTATY YCTRTLYILRVFYFDYWGQGVMVTVSSASTK GPSVFPLAPSSKSTSGGTAALGCLVEDYFPEP VTVSWNSGALTSGVHTFPAVLQSSGLYSLSSV VTVPSSSLGTQTYICNVNHKPSNTKVDEKVEP KSCDKTHTCPPCPAPEAAGGPSVFLFPPKPKD TLMISRTPEVTCVVVDVSHEDPEVKFNWYVD GVEVHNAKTKPREEQYNSTYRVVSVLTVLHQ DWLNGKEYKCKVSNKALGAPIEKTISKAKGQ PREPQVCTLPPSRDELTKNQVSLSCAVKGFYP SDIAVEWESNGQPENNYKTTPPVLDSDGSFFL VSKLTVDKSRWQQGNVFSCSVMHEALHNRF TQKSLSLSPGK | 28 |
| EGFRvIII MR1.1 CDR H1 Kabat | KFGMS | 29 |
| EGFRvIII MR1.1 CDR H2 Kabat | SISTGGYNTYYSDNVKG | 30 |
| EGFRvIII MR1.1 CDR H3 Kabat | GYSPYSYAMDY | 31 |
| EGFRvIII MR1.1 CDR1 L1 Kabat | MTSTDIDDDMN | 32 |
| EGFRvIII MR1.1 CDR L2 Kabat | EGNTLRP | 33 |
| EGFRvIII MR1.1 CDR L3 Kabat | LQSWNVPLT | 34 |
| muEpCAM CDR H1 Kabat | NFPMA | 35 |
| muEpCAM CDR H2 Kabat | TISTSGGSTYYRDSVKG | 36 |
| muEpCAM CDR H3 Kabat | TLYILRVFYFDY | 37 |
| muEpCAM CDR1 L1 Kabat | LASEGISNDLA | 38 |
| muEpCAM CDR L2 Kabat | ATSRLQDG | 39 |
| muEpCAM CDR L3 Kabat | QQSYKYPWT | 40 |
| Complete bsAb | QVKLQQSGGGLVKPGASLKLSCVTSGFTFRK FGMSWVRQTSDKRLEWVASISTGGYNTYYSD NVKGRFTISRENAKNTLYLQMSSLKSEDTALY YCTRGYSPYSYAMDYWGQGTTVTVSSASVA APSVFIFPPSDEQLKSGTASVVCLLNNFYPREA KVQWKVDNALQSGNSQESVTEQDSKDSTYSL SSTLTLSKADYEKHKVYACEVTHQGLSSPVT KSFNRGECGGGGSGGGGSEVQLAESGGGLVQ PGRSMKLSCAASGFTFSNFPMAWVRQAPTKC LEWVATISTSGGSTYYRDSVKGRFTISRDNAK STLYLQMNSLRSEDTATYYCTRTLYILRVFYF DYWGQGVMVTVSSASTKGPSVFPLAPSSKST SGGTAALGCLVEDYFPEPVTVSWNSGALTSG VHTFPAVLQSSGLYSLSSVVTVPSSSLGTQTYI | 233 |

TABLE 1-continued

| CONSTRUCT | AMINO ACID SEQUENCE | SEQ ID NO |
|---|---|---|
| | CNVNHKPSNTKVDEKVEPKSCDKTHTCPPCP APEAAGGPSVFLFPPKPKDTLMISRTPEVTCV VVDVSHEDPEVKFNWYVDGVEVHNAKTKPR EEQYNSTYRVVSVLTVLHQDWLNGKEYKCK VSNKALGAPIEKTISKAKGQPREPQVYTLPPC RDELTKNQVSLWCLVKGFYPSDIAVEWESNG QPENNYKTTPPVLDSDGSFFLYSKLTVDKSR WQQGNVFSCSVMHEALHNHYTQKSLSLSPG KDIELTQSPASLSVATGEKVTIRCMTSTDIDDD MNWYQQKPGEPPKFLISEGNTLRPGVPSRFSS SGTGTDFVFTIENTLSEDVGDYYCLQSWNVPL TFGDGTKLEIKSSASTKGPSVFPLAPSSKSTSG GTAALGCLVKDYFPEPVTVSVVNSGALTSGVH TFPAVLQSSGLYSLSSVVTVPSSSLGTQTYICN VNHKPSNTKVDKKVEPKSCDIQMTQSPASLS ASLGETVSIECLASEGISNDLAWYQQKSGKSP QLLIYATSRLQDGVPSRFSGSGSGTRYSLKISG MQPEDEADYFCQQSYKYPWTFGCGTKLELK RTVAAPSVFIFPPSDRKLKSGTASVVCLLNNF YPREAKVQWKVDNALQSGNSQESVTEQDSK DSTYSLSSTLTLSKADYEKHKVYACEVTHQG LSSPVTKSFNRGECDIQMTQSPASLSASLGETV SIECLASEGISNDLAWYQQKSGKSPQLLIYATS RLQDGVPSRFSGSGSGTRYSLKISGMQPEDEA DYFCQQSYKYPWTFGCGTKLELKRTVAAPSV FIFPPSDRKLKSGTASVVCLLNNFYPREAKVQ WKVDNALQSGNSQESVTEQDSKDSTYSLSST LTLSKADYEKHKVYACEVTHQGLSSPVTKSF NRGECEVQLAESGGGLVQPGRSMKLSCAASG FTFSNFPMAWVRQAPTKCLEWVATISTSGGST YYRDSVKGRFTISRDNAKSTLYLQMNSLRSE DTATYYCTRTLYILRVFYFDYWGQGVMVTVS SASTKGPSVFPLAPSSKSTSGGTAALGCLVED YFPEPVTVSWNSGALTSGVHTFPAVLQSSGLY SLSSVVTVPSSSLGTQTYICNVNHKPSNTKVD EKVEPKSCDKTHTCPPCPAPEAAGGPSVFLFP PKPKDTLMISRTPEVTCVVVDVSHEDPEVKFN WYVDGVEVHNAKTKPREEQYNSTYRVVSVL TVLHQDWLNGKEYKCKVSNKALGAPIEKTIS KAKGQPREPQVCTLPPSRDELTKNQVSLSCAV KGFYPSDIAVEWESNGQPENNYKTTPPVLDSD GSFFLVSKLTVDKSRWQQGNVFSCSVMHEAL HNRFTQKSLSLSPGK | |

TABLE 2

| CONSTRUCT | DNA SEQUENCE | SEQ ID NO |
|---|---|---|
| EGFR vIII MR1.1 VH Ck muEpCAM VH CH1 EE Fc knob PG LALA, pETR14953 | CAAGTGAAGCTGCAGCAGAGTGGGGGCGG ACTCGTGAAACCTGGCGCCTCTCTGAAGCT GAGCTGCGTGACCAGCGGCTTCACCTTCAG AAAGTTCGGCATGAGCTGGGTGCGCCAGAC CAGCGACAAGCGGCTGGAATGGGTGGCCAG CATCAGCACCGGCGGCTACAACACCTACTA CAGCGACAACGTGAAGGGCCGGTTCACCAT CAGCAGAGAGAACGCCAAGAACACCCTGTA CCTGCAGATGAGCAGCCTGAAGTCCGAGGA CACCGCCCTGTACTACTGCACCAGAGGCTA CAGCCCCTACAGCTACGCCATGGACTATTG GGGCCAGGGCACCACCGTGACCGTGTCATC TGCTAGCGTGGCCGCTCCCTCCGTGTTCATC TTCCCACCTTCCGACGAGCAGCTGAAGTCC GGCACCGCTTCTGTCGTGTGCCTGCTGAACA ACTTCTACCCCCGCGAGGCCAAGGTGCAGT GGAAGGTGGACAACGCCCTGCAGTCCGGCA ACAGCCAGGAATCCGTGACCGAGCAGGACT CCAAGGACAGCACCTACTCCCTGTCCTCCA CCCTGACCCTGTCCAAGGCCGACTACGAGA AGCACAAGGTGTACGCCTGCGAAGTGACCC ACCAGGGCCTGTCTAGCCCCGTGACCAAGT CTTTCAACCGGGGCGAGTGCGGTGGCGGAG GTTCCGGAGGCGGAGGATCCGAAGTGCAGC TGGCCGAGAGCGGCGGAGGCCTGGTGCAGC CTGGCAGATCCATGAAGCTGAGCTGCGCCG CCAGCGGCTTCACCTTCAGCAACTTCCCCAT | 21 |

TABLE 2-continued

| CONSTRUCT | DNA SEQUENCE | SEQ ID NO |
|---|---|---|
| | GGCCTGGGTCCGACAGGCCCCCACCAAGTG
CCTGGAATGGGTGGCCACCATCAGCACCAG
CGGCGGCAGCACCTACTACCGGGACAGCGT
GAAGGGCCGGTTCACCATCAGCCGGGACAA
CGCCAAGAGCACCCTGTACCTGCAGATGAA
CAGCCTGCGGAGCGAGGACACCGCCACCTA
CTACTGCACCCGGACCCTGTATATCCTGCGG
GTGTTCTACTTCGACTACTGGGGCCAGGGC
GTGATGGTCACCGTGTCTAGCGCTAGCACC
AAGGGCCCCTCCGTGTTTCCTCTGGCCCCTT
CCAGCAAGTCCACCTCTGGCGGAACTGCCG
CTCTGGGCTGCCTGGTGGAAGATTACTTCCC
CGAGCCCGTGACCGTGTCCTGGAATTCTGG
CGCTCTGACCTCCGGCGTGCACACCTTTCCA
GCTGTGCTGCAGTCCTCCGGCCTGTACTCCC
TGTCCTCCGTCGTGACAGTGCCCTCCAGCTC
TCTGGGCACCCAGACCTACATCTGCAACGT
GAACCACAAGCCCTCCAACACCAAGGTGGA
CGAGAAGGTGGAACCCAAGTCCTGCGACAA
GACCCACACCTGTCCCCCCTGCCCTGCTCCT
GAAGCTGCTGGTGGCCCTAGCGTGTTCCTGT
TCCCCCCAAAGCCCAAGGACACCCTGATGA
TCTCCCGGACCCCCGAAGTGACCTGCGTGG
TGGTGGATGTGTCCCACGAGGACCCTGAAG
TGAAGTTCAATTGGTACGTGGACGGCGTGG
AAGTGCACAACGCCAAGACCAAGCCTAGAG
AGGAACAGTACAACTCCACCTACCGGGTGG
TGTCCGTGCTGACAGTGCTGCACCAGGACT
GGCTGAACGGCAAAGAGTACAAGTGCAAG
GTGTCCAACAAGGCCCTGGGCGCTCCCATC
GAAAAGACCATCTCCAAGGCCAAGGGCCAG
CCCCGGGAACCCCAGGTGTACACCCTGCCC
CCATGCCGGGATGAGCTGACCAAGAACCAG
GTCAGCCTGTGGTGCCTGGTCAAAGGCTTCT
ATCCCAGCGACATCGCCGTGGAGTGGGAGA
GCAATGGGCAGCCGGAGAACAACTACAAG
ACCACGCCTCCCGTGCTGGACTCCGACGGC
TCCTTCTTCCTCTACAGCAAGCTCACCGTGG
ACAAGAGCAGGTGGCAGCAGGGGAACGTC
TTCTCATGCTCCGTGATGCATGAGGCTCTGC
ACAACCACTACACGCAGAAGAGCCTCTCCC
TGTCTCCGGGTAAATGA | |
| EGFR vIII MR1.1
VL CH1,
pETR14951 | GATATCGAGCTGACACAGAGCCCCGCCAGC
CTGTCTGTGGCCACCGGCGAGAAAGTGACC
ATCCGGTGCATGACCAGCACCGACATCGAC
GACGACATGAACTGGTATCAGCAGAAGCCC
GGCGAGCCCCCCAAGTTCCTGATCAGCGAG
GGCAACACACTGCGGCCTGGCGTGCCAAGC
AGATTCAGCAGCTCTGGCACCGGCACCGAC
TTCGTGTTTACCATCGAGAATACCCTGAGCG
AGGACGTGGGCGACTACTACTGCCTGCAGA
GCTGGAACGTGCCCCTGACCTTTGGCGACG
GCACCAAGCTGGAAATCAAGAGCAGCGCTA
GCACCAAAGGCCCTTCCGTGTTTCCTCTGGC
TCCTAGCTCCAAGTCCACCTCTGGAGGCAC
CGCTGCTCTCGGATGCCTCGTGAAGGATTAT
TTTCCTGAGCCTGTGACAGTGTCCTGGAATA
GCGGAGCACTGACCTCTGGAGTGCATACTT
TCCCCGCTGTGCTGCAGTCCTCTGGACTGTA
CAGCCTGAGCAGCGTGGTGACAGTGCCCAG
CAGCAGCCTGGGCACCCAGACCTACATCTG
CAACGTGAACCACAAGCCCAGCAACACCAA
GGTGGACAAGAAGGTGGAACCCAAGTCTTG
TTGA | 23 |
| VL EpCAM G8.8
Ck RK, pETR14882 | GACATCCAGATGACACAGAGCCCCGCCAGC
CTGAGCGCCTCTCTGGGCGAGACAGTGTCC
ATCGAGTGCCTGGCCAGCGAGGGCATCAGC
AACGACCTGGCCTGGTATCAGCAGAAGTCC
GGCAAGAGCCCCCAGCTGCTGATCTACGCC
ACCAGCAGACTGCAGGACGGCGTGCCCAGC
AGATTCAGCGGCAGCGGCTCCGGCACCCGG
TACAGCCTGAAGATCAGCGGCATGCAGCCC
GAGGACGAGGCCGACTACTTCTGCCAGCAG
AGCTACAAGTACCCCTGGACCTTCGGCTGC
GGCACCAAGCTGGAACTGAAGCGTACGGTG
GCTGCACCATCTGTCTTCATCTTCCCGCCA | 25 |

TABLE 2-continued

| CONSTRUCT | DNA SEQUENCE | SEQ ID NO |
|---|---|---|
| | TCTGATCGGAAGTTGAAATCTGGAACTGCC<br>TCTGTTGTGTGCCTGCTGAATAACTTCTATC<br>CCAGAGAGGCCAAAGTACAGTGGAAGGTG<br>GATAACGCCCTCCAATCGGGTAACTCCCAG<br>GAGAGTGTCACAGAGCAGGACAGCAAGGA<br>CAGCACCTACAGCCTCAGCAGCACCCTGAC<br>GCTGAGCAAAGCAGACTACGAGAAACACA<br>AAGTCTACGCCTGCGAAGTCACCCATCAGG<br>GCCTGAGCTCGCCCGTCACAAAGAGCTTCA<br>ACAGGGGAGAGTGTTAG | |
| VH muEpCAM<br>CH1 EE Fc hole<br>PG LALA HRYF,<br>pETR14940 | GAAGTGCAGCTGGCCGAGAGCGGCGGAGG<br>CCTGGTGCAGCCTGGCAGATCCATGAAGCT<br>GAGCTGCGCCGCCAGCGGCTTCACCTTCAG<br>CAACTTCCCCATGGCCTGGGTCCGACAGGC<br>CCCCACCAAGTGCCTGGAATGGGTGGCCAC<br>CATCAGCACCAGCGGCGGCAGCACCTACTA<br>CCGGGACAGCGTGAAGGGCCGGTTCACCAT<br>CAGCCGGGACAACGCCAAGAGCACCCTGTA<br>CCTGCAGATGAACAGCCTGCGGAGCGAGGA<br>CACCGCCACCTACTACTGCACCCGGACCCT<br>GTATATCCTGCGGGTGTTCTACTTCGACTAC<br>TGGGGCCAGGGCGTGATGGTCACCGTGTCT<br>AGCGCTAGCACCAAGGGCCCCTCCGTGTTC<br>CCCCTGGCCCCCAGCAGCAAGAGCACCAGC<br>GGCGGCACAGCCGCTCTGGGCTGCCTGGTC<br>GAGGACTACTTCCCCGAGCCCGTGACCGTG<br>TCCTGGAACAGCGGAGCCCTGACCTCCGGC<br>GTGCACACCTTCCCCGCCGTGCTGCAGAGTT<br>CTGGCCTGTATAGCCTGAGCAGCGTGGTCA<br>CCGTGCCTTCTAGCAGCCTGGGCACCCAGA<br>CCTACATCTGCAACGTGAACCACAAGCCCA<br>GCAACACCAAGGTGGACGAGAAGGTGGAG<br>CCCAAGAGCTGCGACAAAACTCACACATGC<br>CCACCGTGCCCAGCACCTGAAGCTGCAGGG<br>GGACCGTCAGTCTTCCTCTTCCCCCCAAAAC<br>CCAAGGACACCCTCATGATCTCCCGGACCC<br>CTGAGGTCACATGCGTGGTGGTGGACGTGA<br>GCCACGAAGACCCTGAGGTCAAGTTCAACT<br>GGTACGTGGACGGCGTGGAGGTGCATAATG<br>CCAAGACAAAGCCGCGGGAGGAGCAGTAC<br>AACAGCACGTACCGTGTGGTCAGCGTCCTC<br>ACCGTCCTGCACCAGGACTGGCTGAATGGC<br>AAGGAGTACAAGTGCAAGGTCTCCAACAAA<br>GCCCTCGGCGCCCCCATCGAGAAAACCATC<br>TCCAAAGCCAAAGGGCAGCCCCGAGAACCA<br>CAGGTGTGCACCCTGCCCCCATCCCGGGAT<br>GAGCTGACCAAGAACCAGGTCAGCCTCTCG<br>TGCGCAGTCAAAGGCTTCTATCCCAGCGAC<br>ATCGCCGTGGAGTGGGAGAGCAATGGGCAG<br>CCGGAGAACAACTACAAGACCACGCCTCCC<br>GTGCTGGACTCCGACGGCTCCTTCTTCCTCG<br>TGAGCAAGCTCACCGTGGACAAGAGCAGGT<br>GGCAGCAGGGGAACGTCTTCTCATGCTCCG<br>TGATGCATGAGGCTCTGCACAACCGCTTCA<br>CGCAGAAGAGCCTCTCCCTGTCTCCGGGTA<br>AATGA | 27 |

Furthermore, as illustrated in FIG. 10A, as a further proof of concept of the present invention, the trivalent, bispecific antibody "BsAB EGFRvIII-MSLN" (SEQ TD NO: 235 which comprises/consists of the plasmids/vectors "EGFRvIII MR1.1 VH Ck MSLN CH CH1 EE Fc knob PG LALA, pETR15655", "EGFR vIII MR1.1 VL CH1, pETR15656", "VL MSLN Ck K, pETR15443" and "V MSLN CH1 EE Fc hole PG LALA RYF, pETR15667") was constructed which comprises two domains binding to/directed against/interacting with or on human MSLN and one domain binding to/directed against/interacting with or on human EGFRvIII. The sequences (amino acid and DNA) of the trivalent, bispecific antibody molecule BsAB EGFRvIII-MSLN" are shown in Tables 3 and 4.

TABLE 3

| CONSTRUCT | AMINO ACID SEQUENCE | SEQ ID NO |
|---|---|---|
| EGFR vIII MR1.1<br>VH Ck MSLN VH<br>CH1 EE Fc knob PG<br>LALA, pETR15655 | QVKLQQSGGGLVKPGASLKLSCVTSGFTFRK<br>FGMSWVRQTSDKRLEWVASISTGGYNTYYSD<br>NVKGRFTISRENAKNTLYLQMSSLKSEDTALY<br>YCTRGYSPYSYAMDWGQGTTVTVSSASVA | 2 |

TABLE 3-continued

| CONSTRUCT | AMINO ACID SEQUENCE | SEQ ID NO |
|---|---|---|
| | APSVFIFPPSDEQLKSGTASVVCLLNNFYPREA KVQWKVDNALQSGNSQESVTEQDSKDSTYSL SSTLTLSKADYEKHKVYACEVTHQGLSSPVT KSFNRGECGGGGSGGGGSQVQLVQSGAEVK KPGASVKVSCKASGYSFTGYTMNWVRQAPG QGLEWMGLITPYNGASSYNQKFRGKATMTV DTSTSTVYMELSSLRSEDTAVYYCARGGYDG RGFDYWGQGTLVTVSSASTKGPSVFPLAPSSK STSGGTAALGCLVEDYFPEPVTVSWNSGALTS GVHTFPAVLQSSGLYSLSSVVTVPSSSLGTQT YICNVNHKPSNTKVDEKVEPKSCDKTHTCPPC PAPEAAGGPSVFLFPPKPKDTLMISRTPEVTCV VVDVSHEDPEVKFNWYVDGVEVHNAKTKPR EEQYNSTYRVVSVLTVLHQDWLNGKEYKCK VSNKALGAPIEKTISKAKGQPREPQVYTLPPC RDELTKNQVSLWCLVKGFYPSDIAVEWESNG QPENNYKTTPPVLDSDGSFFLYSKLTVDKSR WQQGNVFSCSVMHEALHNHYTQKSLSLSPG K | |
| EGFR vIII MR1.1 VL CH1, pETR15656 | DIELTQSPASLSVATGEKVTIRCMTSTDIDDD MNWYQQKPGEPPKFLISEGNTLRPGVPSRFSS SGTGTDFVFTIENTLSEDVGDYYCLQSWNVPL TFGDGTKLEIKSSASTKGPSVFPLAPSSKSTSG GTAALGCLVKDYFPEPVTVSWNSGALTSGVH TFPAVLQSSGLYSLSSVVTVPSSSLGTQTYICN VNHKPSNTKVDKKVEPKSC | 4 |
| VL MSLN Ck RK, pETR15443 | DIQMTQSPSSLSASVGDRVTITCSASSSVSYM HWYQQKSGKAPKLLIYDTSKLASGVPSRFSGS GSGTDFTLTISSLQPEDFATYYCQQWSKHPLT FGQGTKLEIKRTVAAPSVFIFPPSDRKLKSGTA SVVCLLNNFYPREAKVQWKVDNALQSGNSQ ESVTEQDSKDSTYSLSSTLTLSKADYEKHKVY ACEVTHQGLSSPVTKSFNRGEC | 6 |
| VH MSLN CH1 EE Fc hole PG LALA HRYF, pETR15657 | QVQLVQSGAEVKKPGASVKVSCKASGYSFTG YTMNWVRQAPGQGLEWMGLITPYNGASSYN QKFRGKATMTVDTSTSTVYMELSSLRSEDTA VYYCARGGYDGRGFDYWGQGTLVTVSSAST KGPSVFPLAPSSKSTSGGTAALGCLVEDYFPE PVTVSWNSGALTSGVHTFPAVLQSSGLYSLSS VVTVPSSSLGTQTYICNVNHKPSNTKVDKVE PKSCDKTHTCPPCPAPEAAGGPSVFLFPPKPK DTLMISRTPEVTCVVVDVSHEDPEVKFNWYV DGVEVHNAKTKPREEQYNSTYRVVSVLTVLH QDWLNGKEYKCKVSNKALGAPIEKTISKAKG QPREPQVCTLPPSRDELTKNQVSLSCAVKGFY PSDIAVEWESNGQPENNYKTTPPVLDSDGSFF LVSKLTVDKSRWQQGNVFSCSVMHEALHNH YTQKSLSLSPGK | 8 |
| EGFRvIII MR1.1 CDR H1 Kabat | KFGMS | 9 |
| EGFRvIII MR1.1 CDR H2 Kabat | SISTGGYNTYYSDNVKG | 10 |
| EGFRvIII MR1.1 CDR H3 Kabat | GYSPYSYAMDY | 11 |
| EGFRvIII MR1.1 CDR1 L1 Kabat | MTSTDIDDDMN | 12 |
| EGFRvIII MR1.1 CDR L2 Kabat | EGNTLRP | 13 |
| EGFRvIII MR1.1 CDR L3 Kabat | LQSWNVPLT | 14 |
| MSLN CDR H1 Kabat | GYTMN | 15 |
| MSLN CDR H2 Kabat | LITPYNGASSYNQKFRG | 16 |
| MSLN CDR H3 Kabat | GGYDGRGFDY | 17 |

TABLE 3-continued

| CONSTRUCT | AMINO ACID SEQUENCE | SEQ ID NO |
|---|---|---|
| MSLN CDR1 L1 Kabat | SASSSVSYMH | 18 |
| MSLN CDR L2 Kabat | DTSKLAS | 19 |
| MSLN CDR L3 Kabat | QQWSKHPLT | 20 |
| Complete bsAb | QVKLQQSGGGLVKPGASLKLSCVTSGFTFRKFGMSWVRQTSDKRLEWVASISTGGYNTYYSDNVKGRFTISRENAKNTLYLQMSSLKSEDTALYYCTRGYSPYSYAMDYWGQGTTVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSQVQLVQSGAEVKKPGASVKVSCKASGYSFTGYTMNWVRQAPGQGLEWMGLITPYNGASSYNQKFRGKATMTVDTSTSTVYMELSSLRSEDTAVYYCARGGYDGRGFDYVVGQGTLVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGKDIELTQSPASLSVATGEKVTIRCMTSTDIDDDMNWYQQKPGEPPKFLISEGNTLRPGVPSRFSSSGTGTDFVFTIENTLSEDVGDYYCLQSWNVPLTFGDGTKLEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDIQMTQSPSSLSASVGDRVTITCSASSSVSYMHWYQQKSGKAPKLLIYDTSKLASGVPSRFSGSGSGTDFTLTISSLQPEDFATYYCQQWSKHPLTFGQGTKLEIKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGECDIQMTQSPSSLSASVGDRVTITCSASSSVSYMHWYQQKSGKAPKLLIYDTSKLASGVPSRFSGSGSGTDFTLTISSLQPEDFATYYCQQWSKHPLTFGQGTKLETKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGASVKVSCKASGYSFTGYTMNWVRQAPGQGLEWMGLITPYNGASSYNQKFRGKATMTVDTSTSTVYMELSSLRSEDTAVYYCARGGYDGRGFDYWGQGTLVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 235 |

TABLE 4

| CONSTRUCT | DNA SEQUENCE | SEQ ID NO |
|---|---|---|
| EGFR vIII MR1.1 VH Ck MSLN VH CH1 EE Fc knob PG LALA, pETR15655 | CAAGTGAAGCTGCAGCAGAGTGGGGCGG ACTCGTGAAACCTGGCGCCTCTCTGAAGCT GAGCTGCGTGACCAGCGGCTTCACCTTCAG AAAGTTCGGCATGAGCTGGGTGCGCCAGAC CAGCGACAAGCGGCTGGAATGGGTGGCCAG CATCAGCACCGGCGGCTACAACACCTACTA CAGCGACAACGTGAAGGGCCGGTTCACCAT CAGCAGAGAGAACGCCAAGAACACCCTGTA CCTGCAGATGAGCAGCCTGAAGTCCGAGGA CACCGCCCTGTACTACTGCACCAGAGGCTA CAGCCCCTACAGCTACGCCATGGACTATTG GGGCCAGGGCACCACCGTGACCGTGTCATC TGCTAGCGTGGCCGCTCCCTCCGTGTTCATC TTCCCACCTTCCGACGAGCAGCTGAAGTCC GGCACCGCTTCTGTCGTGTGCCTGCTGAACA ACTTCTACCCCCGCGAGGCCAAGGTGCAGT GGAAGGTGGACAACGCCCTGCAGTCCGGCA ACAGCCAGGAATCCGTGACCGAGCAGGACT CCAAGGACAGCACCTACTCCCTGTCCTCCA CCCTGACCCTGTCCAAGGCCGACTACGAGA AGCACAAGGTGTACGCCTGCGAAGTGACCC ACCAGGGCCTGTCTAGCCCCGTGACCAAGT CTTTCAACCGGGGCGAGTGCGGTGGCGGAG GTTCCGGAGGCGGAGGATCCCAGGTGCAGC TGGTGCAGTCTGGCGCCGAAGTGAAGAAAC CAGGCGCCAGCGTGAAGGTGTCCTGCAAGG CCAGCGGCTACAGCTTCACCGGCTACACCA TGAACTGGGTGCGCCAGGCTCCTGGACAGG GCCTGGAATGGATGGGCCTGATCACCCCCT ACAACGGCGCCAGCAGCTACAACCAGAAGT TCCGGGGCAAGGCCACCATGACCGTGGACA CCAGCACCTCCACCGTGTATATGGAACTGA GCAGCCTGCGGAGCGAGGACACCGCCGTGT ACTATTGTGCCAGAGGCGGCTACGACGGCA GAGGCTTCGATTATTGGGGCCAGGGCACCC TCGTGACCGTGTCCAGCGCTAGCACCAAGG GCCCCTCCGTGTTCCCCCTGGCCCCCAGCAG CAAGAGCACCAGCGGCGGCACAGCCGCTCT GGGCTGCCTGGTCGAGGACTACTTCCCCGA GCCCGTGACCGTGTCCTGGAACAGCGGAGC CCTGACCTCCGGCGTGCACACCTTCCCCGCC GTGCTGCAGAGTTCTGGCCTGTATAGCCTG AGCAGCGTGGTCACCGTGCCTTCTAGCAGC CTGGGCACCCAGACCTACATCTGCAACGTG AACCACAAGCCCAGCAACACCAAGGTGGAC GAGAAGGTGGAGCCCAAGAGCTGCGACAA AACTCACACATGCCCACCGTGCCCAGCACC TGAAGCTGCAGGGGACCGTCAGTCTTCCT CTTCCCCCCAAAACCCAAGGACACCCTCAT GATCTCCCGGACCCCTGAGGTCACATGCGT GGTGGTGGACGTGAGCCACGAAGACCCTGA GGTCAAGTTCAACTGGTACGTGGACGGCGT GGAGGTGCATAATGCCAAGACAAAGCCGCG GGAGGAGCAGTACAACAGCACGTACCGTGT GGTCAGCGTCCTCACCGTCCTGCACCAGGA CTGGCTGAATGGCAAGGAGTACAAGTGCAA GGTCTCCAACAAAGCCCTCGGCGCCCCCAT CGAGAAAACCATCTCCAAAGCCAAGGGCA GCCCCGAGAACCACAGGTGTACACCCTGCC CCCATGCCGGGATGAGCTGACCAAGAACCA GGTCAGCCTGTGGTGCCTGGTCAAAGGCTT CTATCCCAGCGACATCGCCGTGGAGTGGGA GAGCAATGGGCAGCCGGAGAACAACTACA AGACCACGCCTCCCGTGCTGGACTCCGACG GCTCCTTCTTCCTCTACAGCAAGCTCACCGT GGACAAGAGCAGGTGGCAGCAGGGGAACG TCTTCTCATGCTCCGTGATGCATGAGGCTCT GCACAACCACTACACGCAGAAGAGCCTCTC CCTGTCTCCGGGTAAATGA | 1 |
| EGFR vIII MR1.1 VL CH1, pETR15656 | GATATCGAGCTGACACAGAGCCCCGCCAGC CTGTCTGTGGCCACCGGCGAGAAAGTGACC ATCCGGTGCATGACCAGCACCGACATCGAC GACGACATGAACTGGTATCAGCAGAAGCCC GGCGAGCCCCCCAAGTTCCTGATCAGCGAG GGCAACACACTGCGGCCTGGCGTGCCAAGC AGATTCAGCAGCTCTGGCACCGGCACCGAC TTCGTGTTTACCATCGAGAATACCCTGAGCG | 3 |

TABLE 4-continued

| CONSTRUCT | DNA SEQUENCE | SEQ ID NO |
|---|---|---|
| | AGGACGTGGGCGACTACTACTGCCTGCAGA<br>GCTGGAACGTGCCCCTGACCTTTGGCGACG<br>GCACCAAGCTGGAAATCAAGAGCAGCGCTA<br>GCACCAAAGGCCCTTCCGTGTTTCCTCTGGC<br>TCCTAGCTCCAAGTCCACCTCTGGAGGCAC<br>CGCTGCTCTCGGATGCCTCGTGAAGGATTAT<br>TTTCCTGAGCCTGTGACAGTGTCCTGGAATA<br>GCGGAGCACTGACCTCTGGAGTGCATACTT<br>TCCCCGCTGTGCTGCAGTCCTCTGGACTGTA<br>CAGCCTGAGCAGCGTGGTGACAGTGCCCAG<br>CAGCAGCCTGGGCACCCAGACCTACATCTG<br>CAACGTGAACCACAAGCCCAGCAACACCAA<br>GGTGGACAAGAAGGTGGAACCCAAGTCTTG<br>TTGA | |
| VL MSLN Ck RK,<br>pETR15443 | GACATCCAGATGACCCAGAGCCCCAGCAGC<br>CTGTCTGCCAGCGTGGGCGACAGAGTGACC<br>ATCACCTGTAGCGCCAGCAGCAGCGTGTCC<br>TACATGCACTGGTATCAGCAGAAGTCCGGC<br>AAGGCCCCCAAGCTGCTGATCTACGACACC<br>AGCAAGCTGGCCTCCGGCGTGCCCAGCAGA<br>TTTTCTGGCAGCGGCTCCGGCACCGACTTCA<br>CCCTGACAATCAGCTCCCTCCAGCCCGAGG<br>ACTTCGCCACCTACTACTGCCAGCAGTGGTC<br>CAAGCACCCCCTGACCTTTGGCCAGGGCAC<br>CAAGCTGGAAATCAAGCGTACGGTGGCTGC<br>ACCATCTGTCTTCATCTTCCCGCCATCTGAT<br>CGGAAGTTGAAATCTGGAACTGCCTCTGTT<br>GTGTGCCTGCTGAATAACTTCTATCCCAGAG<br>AGGCCAAAGTACAGTGGAAGGTGGATAAC<br>GCCCTCCAATCGGGTAACTCCCAGGAGAGT<br>GTCACAGAGCAGGACAGCAAGGACAGCAC<br>CTACAGCCTCAGCAGCACCCTGACGCTGAG<br>CAAAGCAGACTACGAGAAACACAAAGTCTA<br>CGCCTGCGAAGTCACCCATCAGGGCCTGAG<br>CTCGCCCGTCACAAAGAGCTTCAACAGGGG<br>AGAGTGTTAG | 5 |
| VH MSLN CH1 EE<br>Fc hole PG LALA<br>HRYF, pETR15657 | CAGGTGCAGCTGGTGCAGTCTGGCGCCGAA<br>GTGAAGAAACCAGGCGCCAGCGTGAAGGT<br>GTCCTGCAAGGCCAGCGGCTACAGCTTCAC<br>CGGCTACACCATGAACTGGGTGCGCCAGGC<br>TCCTGGACAGGGCCTGGAATGGATGGGCCT<br>GATCACCCCCTACAACGGCGCCAGCAGCTA<br>CAACCAGAAGTTCCGGGGCAAGGCCACCAT<br>GACCGTGGACACCAGCACCTCCACCGTGTA<br>TATGGAACTGAGCAGCCTGCGGAGCGAGGA<br>CACCGCCGTGTACTATTGTGCCAGAGGCGG<br>CTACGACGGCAGAGGCTTCGATTATTGGGG<br>CCAGGGCACCCTCGTGACCGTGTCCTCTGCT<br>AGCACCAAGGGCCCCTCCGTGTTCCCCCTG<br>GCCCCCAGCAGCAAGAGCACCAGCGGCGGC<br>ACAGCCGCTCTGGGCTGCCTGGTCGAGGAC<br>TACTTCCCCGAGCCCGTGACCGTGTCCTGGA<br>ACAGCGGAGCCCTGACCTCCGGCGTGCACA<br>CCTTCCCCGCCGTGCTGCAGAGTTCTGGCCT<br>GTATAGCCTGAGCAGCGTGGTCACCGTGCC<br>TTCTAGCAGCCTGGGCACCCAGACCTACAT<br>CTGCAACGTGAACCACAAGCCCAGCAACAC<br>CAAGGTGGACGAGAAGGTGGAGCCCAAGA<br>GCTGCGACAAAACTCACACATGCCCACCGT<br>GCCCAGCACCTGAAGCTGCAGGGGGACCGT<br>CAGTCTTCCTCTTCCCCCCAAAACCCAAGGA<br>CACCCTCATGATCTCCCGGACCCCTGAGGTC<br>ACATGCGTGGTGGTGGACGTGAGCCACGAA<br>GACCCTGAGGTCAAGTTCAACTGGTACGTG<br>GACGGCGTGGAGGTGCATAATGCCAAGACA<br>AAGCCGCGGGAGGAGCAGTACAACAGCAC<br>GTACCGTGTGGTCAGCGTCCTCACCGTCCTG<br>CACCAGGACTGGCTGAATGGCAAGGAGTAC<br>AAGTGCAAGGTCTCCAACAAAGCCCTCGGC<br>GCCCCCATCGAGAAAACCATCTCCAAAGCC<br>AAAGGGCAGCCCCGAGAACCACAGGTGTGC<br>ACCCTGCCCCCATCCCGGGATGAGCTGACC<br>AAGAACCAGGTCAGCCTCTCGTGCGCAGTC<br>AAAGGCTTCTATCCCAGCGACATCGCCGTG<br>GAGTGGGAGAGCAATGGGCAGCCGGAGAA<br>CAACTACAAGACCACGCCTCCCGTGCTGGA | 7 |

| CONSTRUCT | DNA SEQUENCE | SEQ ID NO |
|---|---|---|
| | CTCCGACGGCTCCTTCTTCCTCGTGAGCAAG<br>CTCACCGTGGACAAGAGCAGGTGGCAGCAG<br>GGGAACGTCTTCTCATGCTCCGTGATGCATG<br>AGGCTCTGCACAACCACTACACGCAGAAGA<br>GCCTCTCCCTGTCTCCGGGTAAATGA | |

Furthermore, as illustrated in FIG. 11A, as a further proof of concept of the present invention, the trivalent, bispecific antibody "BsAB EGFRvIII-MCSP" (SEQ TD NO: 234) which comprises/consists of the plasmids "MR1.1 EGFRvIII VH-Ck-(G4S)2 MCSP M4-3 VH CH1 EE Fc knob PG LALA, pETR16621", "EGFR vIII MR1.1 VL CH1, pETR15656", "MCSP ML2 VL Ck RK, pETR16619" and "MCSP M4-3 VH CH1 EE Fc hole PG LALA HYRF, pETR16618") was constructed which comprises two domains binding to/directed against/interacting with or on human MCSP and one domain binding to/directed against/interacting with or on human EGFRvIII. The sequences (amino acid and DNA) of the trivalent, bispecific antibody molecule "BsAB EGFRvIII-MCSP" are shown in Tables 5 and 6.

TABLE 5

| CONSTRUCT | AMINO ACID SEQUENCE | SEQ ID NO |
|---|---|---|
| MR1.1 EGFRvIII<br>VH-Ck-(G4S)2<br>MCSP M4-3 VH<br>CH1 EE Fc knob PG<br>LALA, pETR16621 | QVKLQQSGGGLVKPGASLKLSCVTSGFTFRK<br>FGMSWVRQTSDKRLEWVASISTGGYNTYYSD<br>NVKGRFTISRENAKNTLYLQMSSLKSEDTALY<br>YCTRGYSPYSYAMDYWGQGTTVTVSSASVA<br>APSVFIFPPSDEQLKSGTASVVCLLNNFYPREA<br>KVQWKVDNALQSGNSQESVTEQDSKDSTYSL<br>SSTLTLSKADYEKHKVYACEVTHQGLSSPVT<br>KSFNRGECGGGGSGGGGSGGGGSQVQLQESG<br>PGLVKPSQTLSLTCTVSGGSITSGYYWNWlRQ<br>HPGKGLEWIGYITFDGSNNYNPSLKSRVTISR<br>DTSKNQFSLKLSSVTAADTAVYYCADPDYW<br>GQGTLVTVSSASTKGPSVFPLAPSSKSTSGGT<br>AALGCLVEDYFPEPVTVSWNSGALTSGVHTF<br>PAVLQSSGLYSLSSVVTVPSSSLGTQTYICNVN<br>HKPSNTKVDEKVEPKSCDKTHTCPPCPAPEAA<br>GGPSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LGAPIEKTISKAKGQPREPQVYTLPPCRDELTK<br>NQVSLWCLVKGFYPSDIAVEWESNGQPENNY<br>KTIPPVLDSDGSFFLYSKLTVDKSRWQQGNV<br>FSCSVMHEALHNHYTQKSLSLSPGK | 208 |
| EGFR vIII MR1.1<br>VL CH1,<br>pETR15656 | DIELTQSPASLSVATGEKVTIRCMTSTDIDDD<br>MNWYQQKPGEPPKFLISEGNTLRPGVPSRFSS<br>SGTGTDFVFTIENTLSEDVGDYYCLQSWNVPL<br>TFGDGTKLEIKSSASTKGPSVFPLAPSSKSTSG<br>GTAALGCLVKDYFPEPVTVSWNSGALTSGVH<br>TFPAVLQSSGLYSLSSVVTVPSSSLGTQTYICN<br>VNHKPSNTKVDKKVEPKSC | 210 |
| MCSP ML2 VL Ck<br>RK, pETR16619 | DIQMTQSPSSLSASVGDRVTITCRASQGIRNYL<br>NWYQQKPGKAPKLLIYYTSSLHSGVPSRFSGS<br>GSGTDYTLTISSLQPEDFATYYCQQYSALPWT<br>FGQGTKVEIKRTVAAPSVFIFPPSDRKLKSGTA<br>SVVCLLNNFYPREAKVQWKVDNALQSGNSQ<br>ESVTEQDSKDSTYSLSSTLTLSKADYEKHKVY<br>ACEVTHQGLSSPVTKSFNRGEC | 212 |
| MCSP M4-3 VH<br>CH1 EE Fc hole PG<br>LALA HYRF,<br>pETR16618 | QVQLQESGPGLVKPSQTLSLTCTVSGGSITSG<br>YYWNWIRQHPGKGLEWIGYITFDGSNNYNPS<br>LKSRVTISRDTSKNQFSLKLSSVTAADTAVYY<br>CADFDWGQGTLVTVSSASTKGPSVFPLAPSS<br>KSTSGGTAALGCLVEDYFPEPVTVSWNSGAL<br>TSGVHTFPAVLQSSGLYSLSSVVTVPSSSLGTQ<br>TYICNVNHKPSNTKVDEKVEPKSCDKTHTCPP<br>CPAPEAAGGPSVFLFPPKPKDTLMISRTPEVTC<br>VVVDVSHEDPEVKFNWYVDGVEVHNAKTKP<br>REEQYNSTYRVVSVLTVLHQDWLNGKEYKC<br>KVSNKALGAPIEKTISKAKGQPREPQVCTLPPS<br>RDELTKNQVSLSCAVKGFYPSDIAVEWESNG<br>QPENNYKTTPPVLDSDGSFFLVSKLTVDKSR<br>WQQGNVFSCSVMHEALHNRFTQKSLSLSPGK | 214 |

TABLE 5-continued

| CONSTRUCT | AMINO ACID SEQUENCE | SEQ ID NO |
|---|---|---|
| EGFRvIII MR1.1 CDR H1 Kabat | KFGMS | 215 |
| EGFRvIII MR1.1 CDR H2 Kabat | SISTGGYNTYYSDNVKG | 216 |
| EGFRvIII MR1.1 CDR H3 Kabat | GYSPYSYAMDY | 217 |
| EGFRvIII MR1.1 CDR1 L1 Kabat | MTSTDIDDDMN | 218 |
| EGFRvIII MR1.1 CDR L2 Kabat | EGNTLRP | 219 |
| EGFRvIII MR1.1 CDR L3 Kabat | LQSWNVPLT | 220 |
| MCSP CDR H1 Kabat | SGYYWN | 221 |
| MCSP CDR H2 Kabat | YITFDGSNNYNPSLKS | 222 |
| MCSP CDR H3 Kabat | FDY | 223 |
| MCSP CDR1 L1 Kabat | RASQGIRNYLN | 224 |
| MCSP CDR L2 Kabat | YTSSLHS | 225 |
| MCSP CDR L3 Kabat | QQYSALPWT | 226 |
| Complete bsAb | QVKLQQSGGGLVKPGASLKLSCVTSGFTFRKFGMSWVRQTSDKRLEWVASISTGGYNTYYSDNVKGRFTISRENAKNTLYLQMSSLKSEDTALYYCTRGYSPYSYAMDYWGQGTTVTVSSASVAAPSVFIFPPSDEQLKSGTASVVCLLNNFYPREAKVQWKVDNALQSGNSQESVTEQDSKDSTYSLSSTLTLSICADYEKHICVYACEVTHQGLSSPVTKSFNRGECGGGGSGGGGSGGGGSQVQLQESGPGLVKPSQTLSLTCTVSGGSITSGYYWNWIRQHPGKGLEWIGYITFDGSNNYNPSLKSRVTISRDTSKNQFSLKLSSVTAADTAVYYCADFDYWGQGTLVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSICLTVDKSRWQQGNVFSCSVMHEALHNHYTQKSLSLSPGKDIQMTQSPSSLSASVGDRVTITCRASQGIRNYLNWYQQKPGKAPKLLIYYTSSLHSGVPSRFSGSGSGTDYTLTISSLQPEDFATYYCQQYSALPWTFGQGTKVEIKRTVAAPSVFIFPPSDRICLKSGTASVVCLLNNFYPREAKVQWKVDNALQSGNSQESVTEQDSKDSTYSLSSTLTLSKADYEKHKVYACEVTHQGLSSPVTKSFNRGECDIQMTQSPSSLSASVGDRVTITCRASQGIRNYLNWYQQKPGKAPKLLIYYTSSLHSGVPSRFSGSGSGTDYTLTISSLQPEDFATYYCQQYSALPWTFGQGTKVEIKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGECDIELTQSPASLSVATGEKVTIRCMTSTDIDDDMNWYQQKPGEPPKFLISEGNTLRPGVPSRFSSSGTGTDFVFTIENTLSEDVGDYYCLQSWNVPLTFGDGTKLEIKSSASTKGPSVFPLAPSSKSTSGGTAALGCLVKDYFPEPVTVSWNSGALTSGVHTFPAVLQSSGLYSLSSVVTVPS | 234 |

TABLE 5-continued

| CONSTRUCT | AMINO ACID SEQUENCE | SEQ ID NO |
|---|---|---|
| | SSLGTQTYICNVNHKPSNTKVDKKVEPKSCQ VQLQESGPGLVKPSQTLSLTCTVSGGSITSGY YWNWIRQHPGKGLEWIGYITFDGSNNYNPSL KSRVTISRDTSKNQFSLKLSSVTAADTAVYYC ADFDYWGQGTLVTVSSASTKGPSVFPLAPSSK STSGGTAALGCLVEDYFPEPVTVSWNSGALTS GVHTFPAVLQSSGLYSLSSVVTVPSSSLGTQT YICNVNHKPSNTKVDEKVEPKSCDKTHTCPPC PAPEAAGGPSVFLFPPKPKDTLMISRTPEVTCV VVDVSHEDPEVKFNWYVDGVEVHNAKTKPR EEQYNSTYRVVSVLTVLHQDWLNGKEYKCK VSNKALGAPIEKTISKAKGQPREPQVCTLPPSR DELTKNQVSLSCAVKGFYPSDIAVEWESNGQ PENNYKTTPPVLDSDGSFFLVSKLTVDKSRW QQGNVFSCSVMHEALHNRFTQKSLSLSPGK | |

TABLE 6

| CONSTRUCT | DNA SEQUENCE | SEQ ID NO |
|---|---|---|
| MR1.1 EGFRvIII VH-Ck-(G4S)2 MCSP M4-3 VH CH1 EE Fc knob PG LALA, pETR16621 | CAAGTGAAGCTGCAGCAGAGTGGGGCGG ACTCGTGAAACCTGGCGCCTCTCTGAAGCT GAGCTGCGTGACCAGCGGCTTCACCTTCAG AAAGTTCGGCATGAGCTGGGTGCGCCAGAC CAGCGACAAGCGGCTGGAATGGGTGGCCAG CATCAGCACCGGCGGCTACAACACCTACTA CAGCGACAACGTGAAGGGCCGGTTCACCAT CAGCAGAGAGAACGCCAAGAACACCCTGTA CCTGCAGATGAGCAGCCTGAAGTCCGAGGA CACCGCCCTGTACTACTGCACCAGAGGCTA CAGCCCCTACAGCTACGCCATGGACTATTG GGGCCAGGGCACCACCGTGACCGTGTCATC TGCTAGCGTGGCCGCTCCCTCCGTGTTCATC TTCCCACCTTCCGACGAGCAGCTGAAGTCC GGCACCGCTTCTGTCGTGTGCCTGCTGAACA ACTTCTACCCCGCGAGGCCAAGGTGCAGT GGAAGGTGGACAACGCCCTGCAGTCCGGCA ACAGCCAGGAATCCGTGACCGAGCAGGACT CCAAGGACAGCACCTACTCCCTGTCCTCCA CCCTGACCCTGTCCAAGGCCGACTACGAGA AGCACAAGGTGTACGCCTGCGAAGTGACCC ACCAGGGCCTGTCTAGCCCCGTGACCAAGT CTTTCAACCGGGGCGAGTGCGGTGGCGGAG GTTCCGGAGGCGGAGGATCCGGAGGAGGG GGATCTCAGGTGCAATTGCAGGAAAGCGGC CCTGGCCTGGTCAAGCCCAGCCAGACCCTG AGCCTGACCTGCACCGTGTCCGGCGGCAGC ATCACCAGCGGCTATTATTGGAACTGGATT CGGCAGCACCCCGGCAAGGGCCTGGAATGG ATCGGCTACATCACTTTCGACGGCTCTAACA ACTACAACCCCAGCCTGAAGTCCAGAGTGA CCATCAGCCGGGACACCAGCAAGAACCAGT TCAGCCTGAAGCTGTCCAGCGTGACAGCCG CCGACACCGCCGTGTACTACTGCGCCGACT TCGACTACTGGGGCCAGGGCACCCTGGTCA CCGTGTCCAGCGCTAGCACCAAGGGCCCCT CCGTGTTCCCCCTGGCCCCCAGCAGCAAGA GCACCAGCGGCGGCACAGCCGCTCTGGGCT GCCTGGTCGAGGACTACTTCCCCGAGCCCG TGACCGTGTCCTGGAACAGCGGAGCCCTGA CCTCCGGCGTGCACACCTTCCCCGCCGTGCT GCAGAGTTCTGGCCTGTATAGCCTGAGCAG CGTGGTCACCGTGCCTTCTAGCAGCCTGGG CACCCAGACCTACATCTGCAACGTGAACCA CAAGCCCAGCAACACCAAGGTGGACGAGA AGGTGGAGCCCAAGAGCTGCGACAAAACTC ACACATGCCCACCGTGCCCAGCACCTGAAG CTGCAGGGGGACCGTCAGTCTTCCTCTTCCC CCCAAAACCCAAGGACACCCTCATGATCTC CCGGACCCCTGAGGTCACATGCGTGGTGGT GGACGTGAGCCACGAAGACCCTGAGGTCAA GTTCAACTGGTACGTGGACGGCGTGGAGGT GCATAATGCCAAGACAAAGCCGCGGGAGG AGCAGTACAACAGCACGTACCGTGTGGTCA GCGTCCTCACCGTCCTGCACCAGGACTGGC | 207 |

TABLE 6-continued

| CONSTRUCT | DNA SEQUENCE | SEQ ID NO |
|---|---|---|
| | TGAATGGCAAGGAGTACAAGTGCAAGGTCT<br>CCAACAAAGCCCTCGGCGCCCCCATCGAGA<br>AAACCATCTCCAAAGCCAAAGGGCAGCCCC<br>GAGAACCACAGGTGTACACCCTGCCCCCAT<br>GCCGGGATGAGCTGACCAAGAACCAGGTCA<br>GCCTGTGGTGCCTGGTCAAAGGCTTCTATCC<br>CAGCGACATCGCCGTGGAGTGGGAGAGCAA<br>TGGGCAGCGGAGAACAACTACAAGACCAC<br>GCCTCCCGTGCTGGACTCCGACGGCTCCTTC<br>TTCCTCTACAGCAAGCTCACCGTGGACAAG<br>AGCAGGTGGCAGCAGGGGAACGTCTTCTCA<br>TGCTCCGTGATGCATGAGGCTCTGCACAAC<br>CACTACACGCAGAAGAGCCTCTCCCTGTCT<br>CCGGGTAAATGA | |
| EGFR vIII MR1.1<br>VL CH1,<br>pETR15656 | GATATCGAGCTGACACAGAGCCCCGCCAGC<br>CTGTCTGTGGCCACCGGCGAGAAAGTGACC<br>ATCCGGTGCATGACCAGCACCGACATCGAC<br>GACGACATGAACTGGTATCAGCAGAAGCCC<br>GGCGAGCCCCCCAAGTTCCTGATCAGCGAG<br>GGCAACACACTGCGGCCTGGCGTGCCAAGC<br>AGATTCAGCAGCTCTGGCACCGGCACCGAC<br>TTCGTGTTTACCATCGAGAATACCCTGAGCG<br>AGGACGTGGGCGACTACTACTGCCTGCAGA<br>GCTGGAACGTGCCCCTGACCTTTGGCGACG<br>GCACCAAGCTGGAAATCAAGAGCAGCGCTA<br>GCACCAAAGGCCCTTCCGTGTTTCCTCTGGC<br>TCCTAGCTCCAAGTCCACCTCTGGAGGCAC<br>CGCTGCTCTCGGATGCCTCGTGAAGGATTAT<br>TTTCCTGAGCCTGTGACAGTGTCCTGGAATA<br>GCGGAGCACTGACCTCTGGAGTGCATACTT<br>TCCCCGCTGTGCTGCAGTCCTCTGGACTGTA<br>CAGCCTGAGCAGCGTGGTGACAGTGCCCAG<br>CAGCAGCCTGGGCACCCAGACCTACATCTG<br>CAACGTGAACCACAAGCCCAGCAACACCAA<br>GGTGGACAAGAAGGTGGAACCCAAGTCTTG<br>TTGA | 209 |
| MCSP ML2 VL Ck<br>RK, pETR16619 | GACATCCAGATGACCCAGAGCCCCAGCAGC<br>CTGAGCGCCAGCGTGGGCGACAGAGTGACC<br>ATCACCTGCCGGGCCAGCCAGGGCATCCGG<br>AACTACCTGAACTGGTATCAGCAGAAGCCC<br>GGCAAGGCCCCCAAGCTGCTGATCTACTAC<br>ACCAGCAGCCTGCACAGCGGCGTGCCTAGC<br>CGGTTTAGCGGCAGCGGCTCCGGCACCGAC<br>TACACCCTGACCATTAGCTCCCTGCAGCCCG<br>AGGACTTCGCCACCTACTACTGCCAGCAGT<br>ACTCTGCTCTGCCGTGGACCTTCGGCCAGG<br>GAACAAAGGTGGAGATCAAGCGTACGGTG<br>GCTGCACCATCTGTCTTCATCTTCCCGCCAT<br>CTGATCGGAAGTTGAAATCTGGAACTGCCT<br>CTGTTGTGTGCCTGCTGAATAACTTCTATCC<br>CAGAGAGGCCAAAGTACAGTGGAAGGTGG<br>ATAACGCCCTCCAATCGGGTAACTCCCAGG<br>AGAGTGTCACAGAGCAGGACAGCAAGGAC<br>AGCACCTACAGCCTCAGCAGCACCCTGACG<br>CTGAGCAAAGCAGACTACGAGAAACACAA<br>AGTCTACGCCTGCGAAGTCACCCATCAGGG<br>CCTGAGCTCGCCCGTCACAAAGAGCTTCAA<br>CAGGGGAGAGTGTTAG | 211 |
| MCSP M4-3 VH<br>CH1 EE Fc hole PG<br>LALA HYRF,<br>pETR16618 | CAGGTGCAATTGCAGGAAAGCGGCCCTGGC<br>CTGGTCAAGCCCAGCCAGACCCTGAGCCTG<br>ACCTGCACCGTGTCCGGCGGCAGCATCACC<br>AGCGGCTATTATTGGAACTGGATTCGGCAG<br>CACCCCGGCAAGGGCCTGGAATGGATCGGC<br>TACATCACTTTCGACGGCTCTAACAACTACA<br>ACCCCAGCCTGAAGTCAGAGTGACCATCA<br>GCCGGGACACCAGCAAGAACCAGTTCAGCC<br>TGAAGCTGTCCAGCGTGACAGCCGCCGACA<br>CCGCCGTGTACTACTGCGCCGACTTCGACTA<br>CTGGGGCCAGGGCACCCTGGTCACCGTGTC<br>CAGCGCTAGCACCAAGGGCCCCTCCGTGTT<br>CCCCCTGGCCCCCAGCAGCAAGAGCACCAG<br>CGGCGGACAGCCGCTCTGGGCTGCCTGGT<br>CGAGGACTACTTCCCCGAGCCCGTGACCGT<br>GTCCTGGAACAGCGGAGCCCTGACCTCCGG<br>CGTGCACACCTTCCCCGCCGTGCTGCAGAG | 213 |

TABLE 6-continued

| CONSTRUCT | DNA SEQUENCE | SEQ ID NO |
|---|---|---|
| | TTCTGGCCTGTATAGCCTGAGCAGCGTGGTC | |
| | ACCGTGCCTTCTAGCAGCCTGGGCACCCAG | |
| | ACCTACATCTGCAACGTGAACCACAAGCCC | |
| | AGCAACACCAAGGTGGACGAGAAGGTGGA | |
| | GCCCAAGAGCTGCGACAAAACTCACACATG | |
| | CCCACCGTGCCCAGCACCTGAAGCTGCAGG | |
| | GGGACCGTCAGTCTTCCTCTTCCCCCCAAAA | |
| | CCCAAGGACACCCTCATGATCTCCCGGACC | |
| | CCTGAGGTCACATGCGTGGTGGTGGACGTG | |
| | AGCCACGAAGACCCTGAGGTCAAGTTCAAC | |
| | TGGTACGTGGACGGCGTGGAGGTGCATAAT | |
| | GCCAAGACAAAGCCGCGGGAGGAGCAGTA | |
| | CAACAGCACGTACCGTGTGGTCAGCGTCCT | |
| | CACCGTCCTGCACCAGGACTGGCTGAATGG | |
| | CAAGGAGTACAAGTGCAAGGTCTCCAACAA | |
| | AGCCCTCGGCGCCCCCATCGAGAAAACCAT | |
| | CTCCAAAGCCAAAGGGCAGCCCCGAGAACC | |
| | ACAGGTGTGCACCCTGCCCCCATCCCGGGA | |
| | TGAGCTGACCAAGAACCAGGTCAGCCTCTC | |
| | GTGCGCAGTCAAAGGCTTCTATCCCAGCGA | |
| | CATCGCCGTGGAGTGGGAGAGCAATGGGCA | |
| | GCCGGAGAACAACTACAAGACCACGCCTCC | |
| | CGTGCTGGACTCCGACGGCTCCTTCTTCCTC | |
| | GTGAGCAAGCTCACCGTGGACAAGAGCAGG | |
| | TGGCAGCAGGGGAACGTCTTCTCATGCTCC | |
| | GTGATGCATGAGGCTCTGCACAACCGCTTC | |
| | ACGCAGAAGAGCCTCTCCCTGTCTCCGGGT | |
| | AAATGA | |

The invention also provides (a) nucleic acid molecule(s) encoding a trivalent, bispecific antibody molecule of the invention. Also encompassed by the present invention are (a) nucleic acid molecule(s) encoding the fusion protein of the present invention.

The term "nucleic acid molecule" relates to the sequence of bases comprising purine- and pyrimidine bases which are comprised by polynucleotides, whereby said bases represent the primary structure of a nucleic acid molecule. Herein, the term "nucleic acid molecule" includes DNA, cDNA, genomic DNA, RNA, synthetic forms of DNA and mixed polymers comprising two or more of these molecules. In addition, the term "nucleic acid molecule" includes both, sense and antisense strands. Moreover, the herein described "nucleic acid molecule" may contain non-natural or derivatized nucleotide bases, as will be readily appreciated by those skilled in the art. Exemplary nucleic acid molecules encoding the fusion proteins of the present invention are shown in SEQ ID NO: 41, 43, 45, 47, 49 or 119. Further, exemplarily nucleic acid molecules encoding regions of the heavy and/or light chain of the trivalent, bispecific antibody molecules of the present invention are shown in SEQ ID NOs: 1, 3, 5, 7 (see Tables 1 and 2), SEQ ID NOs: 21, 23, 25, 27 (see Tables 3 and 4) and SEQ ID NOs: 207, 209, 211 and 213 (see Tables 5 and 6).

The nucleic acid molecules of the invention may be under the control of regulatory sequences. For example, promoters, transcriptional enhancers and/or sequences which allow for induced expression of the fusion protein of the invention may be employed. In the context of the present invention, the nucleic acid molecules are expressed under the control of constitutive or inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24).

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

Said nucleic acid molecule(s) may be a recombinantly produced chimeric nucleic acid molecule comprising any of the aforementioned nucleic acid molecules either alone or in combination. In the context of the present invention, the nucleic acid molecule(s) is (are) part of a vector.

The present invention therefore also relates to (a) vector(s) comprising the nucleic acid molecule(s) described in the present invention. Herein the term "vector" relates to a circular or linear nucleic acid molecule which can autonomously replicate in a host cell (i.e. in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

The invention also relates to (a) vector(s) comprising (a) nucleic acid molecule(s) which is (are) a regulatory sequence operably linked to said nucleic acid molecule(s) encoding a trivalent, bispecific antibody construct (molecule) defined herein. In the context of the present invention the vector can be polycistronic. As shown in the appended Examples, the trivalent, bispecific antibody molecules may be expressed on at least three different nucleic acid molecules, wherein each nucleic acid molecule is operably linked to a regulatory sequence.

Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells.

It is envisaged that said vector(s) is (are) an expression vector(s) comprising the nucleic acid molecule(s) encoding the trivalent, bispecific antibody constructs (molecules) defined herein.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An "expression vector" is a construct that can be used to transform a selected host and provides for expression of a coding sequence in the selected host. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), pEF-DHFR, pEF-ADA or pEF-neo (Raum et al. Cancer Immunol Immunother 50 (2001), 141-150) or pSPORT1 (GIBCO BRL).

In the context of the present invention, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended Examples.

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia* larvae. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia* larvae in which the protein of the invention is expressed (Smith, J. Virol. 46 (1983), 584; Engelhard, Proc. Nat. Acad. Sci. USA 91 (1994), 3224-3227).

Additional regulatory elements may include transcriptional as well as translational enhancers. Advantageously, the above-described vectors of the invention comprise a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or 8-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule(s) can be used alone or as part of (a) vector(s) to express the encoded trivalent, bispecific construct in cells, for, e.g., purification but also for gene therapy purposes, preferably in combination with the transduced T-cells. The nucleic acid molecules or vector(s) containing the DNA sequence(s) encoding any one of the above described trivalent, bispecific antibody molecules is introduced into the cells which in turn produced the polypeptide of interest. Gene therapy, which is based on introducing therapeutic genes into cells by ex-vivo or in-vivo techniques is one of the most important applications of gene transfer. Suitable vectors, methods or gene-delivery systems for in methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957; U.S. Pat. Nos. 5,580, 859; 5,589,466; or Schaper, Current Opinion in Biotechnology 7 (1996), 635-640. The recited nucleic acid molecule(s) and vector(s) may be designed for direct introduction or for introduction via liposomes, or viral vectors (e.g., adenoviral, retroviral) into the cell. In the context of the present invention, said cell is a germ line cell, embryonic cell, or egg cell or derived therefrom, most preferably said cell is a stem cell. An example for an embryonic stem cell can be, inter alia, a stem cell as described in, Nagy, Proc. Natl. Acad. Sci. USA 90 (1993), 8424-8428.

In accordance with the above, the present invention relates to methods to derive vectors, particularly plasmids, cosmids and bacteriophages used conventionally in genetic engineering that comprise a nucleic acid molecule encoding the polypeptide sequence of a bispecific antibody construct defined herein. In the context of the present invention, said vector is an expression vector and/or a gene transfer or targeting vector. Expression vectors derived from viruses such as retroviruses, vaccinia virus, adeno-associated virus, herpes virus, or bovine papilloma virus, may be used for delivery of the recited polynucleotides or vector into targeted cell populations.

Methods which are well known to those skilled in the art can be used to construct (a) recombinant vector(s); see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the present invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. The recited vector may, inter alia, be the pEF-DHFR, pEF-ADA or pEF-neo. The vectors pEF-DHFR, pEF-ADA and pEF-neo have been described in the art, e.g. in Mack et al. Proc. Natl. Acad. Sci. USA 92 (1995), 7021-7025 and Raum et al. Cancer Immunol Immunother 50 (2001), 141-150.

The present invention also provides a host transformed or transfected with a vector as described herein. Said host may be produced by introducing at least one of the above described vector or at least one of the above described nucleic acid molecules into the host. The presence of said at least one vector or at least one nucleic acid molecule in the host may mediate the expression of a gene encoding the above described trivalent, bispecific antibody molecules or constructs (i.e., the trivalent, bispecific antibody molecules described herein). The vector of the present invention can be polycistronic.

In the case of the expression of the trivalent, bispecific antibody molecule of the present invention, the duplication of the light chain may allow for improved assembly and/or expression of the complete trivalent, bispecific antibody molecule over the situation where the light chain coding regions are present in the host cell at a 1:1 ratio with the heavy chain coding region. Thus, the present invention provides constructs and methods wherein the coding region ratio of the light chain component to the heavy chain component is either 1:1 or greater than 1:1. For example, in an embodiment the ratio of the light chain component to heavy chain component is 2:1 or greater than 2:1, e.g. 3:1, 3:2, 4:1 or greater than 4:1. In case that the trivalent, bispecific antibody molecule of the present invention comprises an altered CH3 domain the cells can be transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)":"crossed light chain (VL-CH1)").

The described nucleic acid molecule(s) or vector(s) which is (are) introduced in the host may either integrate into the genome of the host or it may be maintained extrachromosomally.

The host can be any prokaryotic or eukaryotic cell.

The term "prokaryote" is meant to include all bacteria which can be transformed, transduced or transfected with DNA or DNA or RNA molecules for the expression of a protein of the present invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the present invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

In the context of the present invention, the host (cell) is a bacterium, an insect, fungal, plant or animal cell.

It is particularly envisaged that the recited host may be a mammalian cell, more preferably a human cell or human cell line.

Particularly preferred host cells comprise HEK293, CHO cells, COS cells, myeloma cells lines like SP2/0 or NS/0. As illustrated in the appended Examples, particularly preferred are HEK293 cells and CHO cells as hosts.

The present invention thus relates to a method for the production of (a) trivalent, bispecific antibody molecule(s) or construct(s) (i.e., the trivalent, bispecific antibody molecule(s) described herein) described above comprising culturing (cultivating) a cell and/or a host cell of the present invention under conditions allowing the expression of the trivalent, bispecific antibody molecule(s) or construct(s) (i.e., the trivalent, bispecific antibody molecule described herein) and recovering the molecule(s) or construct(s) (i.e., the trivalent, bispecific antibody molecule described herein) from the cell and/or culture medium.

The transformed hosts can be grown in fermentators and cultured according to techniques known in the art to achieve optimal cell growth. The polypeptide of the present invention can then be isolated from the growth medium. The isolation and purification of the, e.g., microbially expressed polypeptides of the invention may be by any conventional means such as, e.g., preparative chromotagraphie separations and immunological separations such as those involving the use of monoclonal or polyclonal antibodies directed, e.g., against a tag of the polypeptide of the invention or as described in the appended examples.

Furthermore, the invention provides a composition (medicament) comprising (a) trivalent, bispecific (monoclonal) antibody molecule(s) as defined herein or (a) (human) trivalent, bispecific antibody molecule(s) as produced by the method disclosed above, (a) nucleic acid molecule(s) encoding the trivalent, bispecific antibody molecule of the invention, (a) vector(s) or transduced T-cells comprising a fusion protein as described herein. In the context of the present invention, said composition is a pharmaceutical composition further comprising, optionally, suitable formulations of carrier, stabilizers and/or excipients.

Furthermore, the invention provides a trivalent, bispecific antibody molecule(s) as defined herein above for use as a medicament, wherein said trivalent, bispecific antibody molecule is to be administered before, simultaneously with or after administration of transduced T-cells comprising a fusion protein as described herein and wherein said T-cells were obtained from a subject to be treated.

In the context of the present invention a pharmaceutical composition/medicament is provided that comprises a trivalent, bispecific antibody molecule as defined herein above which is to be administered in combination with a transduced T-cells comprising a fusion protein as described herein, wherein said bispecific antibody molecule is to be administered before simultaneously with or after administration of transduced T-cells comprising an antigen which does not naturally occur in or on T-cells and wherein said T-cells were obtained from a subject to be treated.

In the context of the present invention T-cells are transduced with (a) nucleic acid molecules encoding the fusion protein as defined herein above and/or with (a) vector(s) comprising such (a) nucleic acid molecule. In the context of the T-cell transfection with the herein defined fusion protein, the term "vector" relates to a circular or linear nucleic acid molecule which can autonomously replicate in a host cell (i.e. in a transduced cell) into which it has been introduced. The "vector" as used herein particularly refers to a plasmid, a cosmid, a virus, a bacteriophage and other vectors commonly used in genetic engineering. In a preferred embodiment, the vector of the invention is suitable for the transformation of cells, preferably of T-cells, such as CD8+ T-cells, CD4+ T-cells, CD3+ T-cells, γδ T-cells or natural killer (NK) T-cells, most preferably CD8+ T-cells. Accordingly, in one aspect of the invention, the vector as provided herein is an expression vector. Expression vectors have been widely described in the literature. In particular, the herein provided vector preferably comprises a recombinant polynucleotide (i.e. a nucleic acid molecule encoding the fusion protein of the present invention) as well as expression control sequences operably linked to the nucleotide sequence to be expressed. The vector as provided herein preferably further comprises a promoter. The herein described vector for the transduction of the T-cells may also comprise a selection marker gene and a replication-origin ensuring replication in the host (i.e. the transduced cell). Moreover, the herein provided vector for the transduction of the T-cells may also comprise a termination signal for transcription. Between the promoter and the termination signal there is preferably at least one restriction site or a polylinker which enables the insertion of a nucleic acid molecule (e.g. a nucleic acid molecule encoding the fusion protein of the invention) desired to be expressed. The skilled person knows how such insertion can be put into practice. Examples of vectors suitable to comprise a nucleic acid molecule of the present invention to form the vector of the present invention for the transfection of the T-cells are known in the art. For example, in the context of the invention suitable vectors include cosmids, plasmids (e.g., naked or contained in liposomes) and viruses (e.g., lentiviruses, retroviruses, adenoviruses, and adeno-associated viruses) that incorporate the nucleic acid molecule of the invention (i.e. the nucleic acid molecule encoding the fusion protein of the present invention). Preferably, the vector of the present invention is a viral vector. More preferably, the vector of the present invention is a lentiviral vector, and even more preferably, the vector of the present invention is a retroviral vector (e.g. the pMP71 vector). Accordingly, in the context of the present invention, the vector is a lentiviral vector or a retroviral vector. The vector of the present invention allows for constitutive or conditional expression of the nucleic acid molecule encoding the fusion protein of the present invention. In this context, suitable retroviral vectors for the expression of the fusion protein of the present invention are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). Further, in the context of the present invention suitable lentiviral vectors for the expression of the fusion protein of the present invention are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The invention also relates to transduced T-cells, such as CD8+ T-cells, CD4+ T-cells, CD3+ T-cells, γδ T-cells or natural killer (NK) T-cells, preferably CD8+ T-cells, expressing a fusion protein encoded by (a) nucleic acid molecule(s) encoding the fusion protein of the present invention. Accordingly, in the context of the present, the transduced cell may comprise a nucleic acid molecule encoding the fusion protein of the present invention or a vector of the present invention which expresses a fusion protein of the present invention.

In the context of the present invention, the term "transduced cell" relates to a genetically modified cell (i.e. a cell wherein a nucleic acid molecule has been introduced deliberately). The herein provided transduced cell may comprise the vector of the present invention. Preferably, the herein provided transduced cell comprises the nucleic acid molecule encoding the fusion protein of the present invention and/or the vector of the present invention. The transduced cell of the invention may be a cell which transiently or stably expresses the foreign DNA (i.e. the nucleic acid molecule which has been introduced into the cell). In particular, the nucleic acid molecule encoding the fusion protein of the present invention can be stably integrated into the genome of the cell by using a retroviral or lentiviral transduction. By using mRNA transfection, the nucleic acid molecule encoding the fusion protein of the present invention may be expressed transiently. Preferably, the herein provided transduced cell has been genetically modified by introducing a nucleic acid molecule in the cell via a viral vector (e.g. a retroviral vector or a lentiviral vector). Accordingly, the expression of the fusion proteins may be constitutive and the extracellular domain of the fusion protein may be detectable on the cell surface. This extracellular domain of the fusion protein may comprise the complete extracellular domain of a signalling receptor that does not naturally occur in or on T-cells as defined herein but also parts thereof. The minimal size required being the epitope bound by the trivalent, bispecific antibody molecule on the side of the fusion protein.

The expression may also be conditional or inducible in the case that the fusion protein is introduced into T-cells, such as CD8+ T-cells, CD4+ T-cells, CD3+ T-cells, γδ T-cells or natural killer (NK) T-cells, preferably CD8+ T-cells, under the control of an inducible or repressible promoter. Examples for such inducible or repressible promoters can be a transcriptional system containing the alcohol dehydrogenase I (alcA) gene promoter and the transactivator protein AlcR. Different agricultural alcohol-based formulations are used to control the expression of a gene of interest linked to the alcA promoter. Furthermore, tetracycline-responsive promoter systems can function either to activate or repress gene expression system in the presence of tetracycline. Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence. Further, steroid-responsive promoters, metal-regulated or pathogenesis-related (PR) protein related promoters can be used.

The expression can be constitutive or constitutional, depending on the system used. The fusion proteins of the present invention can be expressed on the surface of the herein provided transduced cell. The extracellular proportion of the fusion protein (i.e. the extracellular domain of a signalling receptor that does not naturally occur in or on T-cells can be detected on the cell surface, while the intracellular (i.e. the anchoring transmembrane domain, the co-stimulatory signalling domain(s) and the stimulatory signalling domain of the fusion proteins) are bound to the membrane but are not detectable on cell surface. The detection of the extracellular domain of the fusion protein can be carried out by using an antibody which specifically binds to this extracellular domain. The extracellular domain can be detected using these antibodies by flow cytometry or microscopy. The transduced of the present invention may be any immune cell. These include but are not limited to B-cells, T-cells, natural killer (NK) cells, natural killer T- (NK) T-cells, γδ T-cells, innate lymphoid cells, macrophages, monocytes, dendritic cells, or neutrophils. Preferentially the said immune cell would be a lymphocyte, preferentially a NK or T-cells. The said T-cells include CD4 T-cells and CD8 T-cells, most preferably CD4+ T-cells and CD8+ T-cells. Triggering of the fusion protein of the present invention on the surface of the leukocyte will render the cell cytotoxic against its target cell irrespective of the lineage the cell originated from. Cytotoxicity will happen irrespective of the stimulatory signalling domain or co-stimulatory signalling domain chosen for the fusion protein and is not dependent on the exogenous supply of additional cytokines. Accordingly, the transduced cell of the present invention may be, e.g., a CD4+ T-cell, a CD8+-T-cell, a γδ T-cell, a natural killer (NK) T-cell, a natural killer (NK) cell, a tumor-infiltrating lymphocyte (TIL) cell, a myeloid cell, or a mesenchymal stem cell. Preferably, the herein provided transduced cell is a T-cell (e.g. an autologous T-cell), more preferably, the transduced cell is a CD8+ T-cell. Accordingly, in the context of the present invention, the transduced cell is a CD8+ T-cell. Further, in the context of the present invention, the transduced cell is an autologous T-cell. Accordingly, in the context of the present invention, the transduced cell is preferably an autologous CD8+ T-cell. In addition to the use of autologous cells (e.g. T-cells) isolated from the subject, the present invention also comprehends the use of allogeneic cells. Accordingly, in the context of the present invention the transduced cell may also be an allogeneic cell, such as an allogeneic CD8+ T-cell. The use of allogeneic cells is based on the fact that cells, preferably T-cells can recognize a specific antigen epitope presented by foreign antigen-presenting cells (APC), provided that the APC express the MHC molecule, class I or class II, to which the specific responding cell population, i.e. T-cell population is restricted, along with the antigen epitope recognized by the T-cells. Thus, the term allogeneic refers to cells from an unrelated coming from an unrelated donor individual/subject which is human leukocyte antigen (HLA) compatible to the individual/subject which will be treated by e.g. the herein described fusion protein expressing transduced cell. Autologous cells refer to cells which are isolated/obtained as described herein above from the subject to be treated with the transduced cell described herein.

As described above, the transduced cell(s) of the present invention is (are) transduced with a nucleic acid molecule expressing the herein provided fusion protein. In the case of cells bearing natural anti-tumoral specificity such as tumor-infiltrating lymphocyte cells (TIL, Dudley et al., J Clin Oncol. 31(17) (2013), 2152-2159 (doi: 10.1200/JCO.2012.46.6441)) or antigen-specific cells sorted from the peripheral blood of patients for their tumor-specificity by flow cytometry (Hunsucker et al., Cancer Immunol Res. 3(3) (2015), 228-235 (doi: 10.1158/2326-6066.CIR-14-0001)), the cells described herein would only be transduced with the fusion protein of the present invention. However, the transduced cell(s) of the invention may be co-transduced with further nucleic acid molecules, e.g. with a nucleic acid molecule encoding a T-cell receptor or a chimeric antigen receptor. Further, in the context of the present invention, the transduced cell(s) of the invention may be co-transduced with further nucleic acid molecules, e.g. with a nucleic acid molecule encoding a Fas ligand (FasL). It is known that FasL interacts with Fas (Nagata et al., Science 267(5203) (1995), 1449-1456; Walker et al., J Immunol. 158(10) (1997), 4521-4524). Fas and its ligand FasL are typeI and typeII transmembrane proteins and members of the tumor necrosis factor/nerve growth factor receptor and tumor necrosis factor family proteins, respectively (the human FAS is available under the UniProt entry no. P25445 (entry version 218, sequence version 1; SEQ ID NOs: 241 (protein) and 240 (DNA)); the human FasL has the UniProt entry no. P48023 (entry version 190, sequence version 1; SEQ ID NOs: 245 (protein) and 244 (DNA)); the murine FAS has the UniProt entry no. P41047 (entry version 169, sequence version 1; SEQ ID NO: 239 (protein) and 238 (DNA)); the murine FasL has the UniProt entry no. P41047 (entry version 169, sequence version 1; SEQ ID NO: 243 (protein) and 242 (DNA))). In the context of the present invention it has surprisingly and unexpectedly been found that the FasL is important for the mode of action. In particular it was shown that the killing capacity of T-cells, such as CD8+ T-cells, CD4+ T-cells, CD3+ T-cells, γδ T-cells or natural killer (NK) T-cells, transfected/transduced with a fusion protein as described herein can be impaired by blocking the FasL-Fas interactions (see FIG. 13). Accordingly, it was surprisingly found that transduced cell(s) (over-) expressing FasL can be used for the treatment of diseases characterized by having tumor cells having Fas (over-) expressing cells.

In accordance with this invention, the term "T-cell receptor" is commonly known in the art. In particular, herein the term "T-cell receptor" refers to any T-cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T-cell receptors which fulfill the above mentioned three criteria are known in the art such as receptors recognizing WT1 (Wilms tumor specific antigen 1; for sequence information(s) see, e.g., Sugiyama, Japanese Journal of Clinical Oncology 40 (2010), 377-87), MAGE (for sequence see, e.g., WO-A1 2007/032255 and PCT/US2011/57272), SSX (U.S. Provisional Application No. 61/388,983), NY-ESO-1 (for sequence information(s) see, e.g., PCT/GB2005/001924) and/or HER2neu (for sequence information(s) see WO-A1 2011/0280894).

The term "chimeric antigen receptor" or "chimeric receptor" is known in the art and refers to a receptor constituted of an extracellular portion of a single chain antibody domain fused by a spacer sequence to the signal domains of CD3z and CD28. Again, this chimeric antigen receptor should provide tumor specify and allow for the recognition of most tumor cells. Suitable chimeric receptors include: anti-EGFRvIII-CAR (for sequence see WO-A1 2012/138475), anti-CD22-CAR (see WO-A1 2013/059593), anti-BCMA-CAR (see WO-A1 2013/154760), anti-CD19-CAR (see WO-A1 2012/079000 or US-A1 2014/0271635), anti-CD123-CAR (see US-A1 2014/0271582), anti-CD30-CAR (see WO-A1 2015/028444) or anti-Mesothelin-CAR (see WO-A1 2013/142034).

The present invention also relates to a method for the production of a transduced cell expressing a fusion protein of the invention, comprising the steps of transducing a cell with a vector of the present invention, culturing the transduced cell under conditions allowing the expressing of the fusion protein in or on said transduced cell and recovering said transduced cell.

In the context of the present invention, the transduced cell of the present invention is preferably produced by the following process: cells (e.g., T-cells, preferably CD8+ T-cells) are isolated/obtained from a subject (preferably a human patient). Methods for isolating/obtaining cells (e.g. T-cells, preferably CD8+ T-cells) from patients or from donors are well known in the art and in the context of the present invention the cells (e.g. T-cells, preferably CD8+ T-cells) from patients or from donors may be isolated by blood draw or removal of bone marrow. After isolating/obtaining cells as a sample of the patient, the cells (e.g. T-cells) are separated from the other ingredients of the sample. Several methods for separating cells (e.g. T-cells) from the sample are known and include, without being limiting, e.g. leukapheresis for obtaining cells from the peripheral blood sample from a patient or from a donor, isolating/obtaining cells by using a FACSort apparatus, picking living of dead cells from fresh biopsy specimens harboring living cells by hand or by using a micromanipulator (see, e.g., Dudley, Immunother. 26 (2003), 332-342; Robbins, Clin. Oncol. 29 (201 1), 917-924 or Leisegang, J. Mol. Med. 86 (2008), 573-58). Herein the term "fresh patient biopsy" refers to tissue (preferably tumor tissue) removed from a subject by surgical or any other known means as well as tumor cell lines or (isolated) cells from a tumor tissue/tumor cell. The isolated/obtained cells T-cells, preferably CD8+ T-cells, are subsequently cultivated and expanded, e.g., by using an anti-CD3 antibody, by using anti-CD3 and anti-CD28 monoclonal antibodies and/or by using an anti-CD3 antibody, an anti-CD28 antibody and interleukin-2 (IL-2) (see, e.g., Dudley, Immunother. 26 (2003), 332-342 or Dudley, Clin. Oncol. 26 (2008), 5233-5239).

In a subsequent step the cells (e.g. T-cells) are artificially/genetically modified/transduced by methods known in the art (see, e.g., Lemoine, J Gene Med 6 (2004), 374-386). Methods for transducing cells (e.g. T-cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector In the context of the present invention, the methods for transducing cells (e.g. T-cells) include retroviral or lentiviral T-cell transduction as well as mRNA transfection. "mRNA transfection" refers to a method well known to those skilled in the art to transiently express a protein of interest, like in the present case the fusion protein of the present invention, in a cell to be transduced. In brief cells may be electroporated with the mRNA coding for the fusion protein of the present by using an electroporation system (such as e.g. Gene Pulser, Bio-Rad) and thereafter cultured by standard cell (e.g. T-cell) culture protocol as described above (see Zhao et al., Mol Ther. 13(1) (2006), 151-159.) The transduced cell of the invention is a T-cell, most preferably a CD8+ T-cell, and is generated by lentiviral, or most preferably retroviral T-cell transduction.

In this context, suitable retroviral vectors for transducing T-cells are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing cells (e.g. T-cells) are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.: 22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The transduced T-cell/T-cells of the present invention is/are preferably grown under controlled conditions, outside of their natural environment. In particular, the term "culturing" means that cells (e.g. the transduced cell(s) of the invention) which are derived from multi-cellular eukaryotes (preferably from a human patient) are grown in vitro. Culturing cells is a laboratory technique of keeping cells alive which are separated from their original tissue source. Herein, the transduced cell of the present invention is cultured under conditions allowing the expression of the fusion protein of the present invention in or on said transduced cells. Conditions which allow the expression or a transgene (i.e. of the fusion protein of the present invention) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the fusion protein of the present invention in the cultured transduced cell, the transduced cell is recovered (i.e. re-extracted) from the culture (i.e. from the culture medium).

Also encompassed by the invention is a transduced cell expressing a fusion protein encoded by a nucleic acid molecule of the invention obtainable by the method of the present invention.

Furthermore, the invention provides a pharmaceutical composition/medicament comprising a trivalent, bispecific antibody molecule of the present invention or a trivalent, bispecific antibody molecule as obtained by/produced by the method disclosed above. In the context of the present invention, said composition is a pharmaceutical composition further comprising, optionally, suitable formulations of carrier, stabilizers and/or excipients.

In accordance with this invention, the term "medicament" is used interchangeably with the term "pharmaceutical composition" and relates to a composition for administration to a patient, preferably a human patient. In the context of the present invention that medicament/pharmaceutical composition is to be administered to a patient from which the T-cells, most preferably the CD8+ T-cells, were isolated/ obtained. In the context of the present invention, the patient refers to human patient. Furthermore, in the context of the present invention that patient suffers from a disease, wherein said disease is a malignant disease, especially cancers/carcinomas of ephithelial, endothelial or mesothelial origin or a cancer of the blood. In the context of the present invention the cancers/carcinomas is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

In a preferred embodiment, the pharmaceutical composition/medicament comprises a trivalent, bispecific antibody molecule as defined herein for parenteral, transdermal, intraluminal, intra arterial, intrathecal administration or by direct injection into the tissue or tumor. In the context of the present invention the composition/medicament comprises a trivalent, bispecific antibody molecule as defined herein that is to be administered before, simultaneously with or after administration of transduced T-cells comprising a fusion protein as defined herein. In the context of the present invention the pharmaceutical composition/medicament comprising a trivalent, bispecific antibody molecule as defined herein is to be administered in combination with a transduced T-cells comprising a fusion protein as defined herein, wherein said T-cells were obtained from a subject to be treated.

The use of the term "in combination" does not restrict the order in which the components of the treatment regimen are to be administered to the subject. Accordingly, the pharmaceutical composition/medicament described herein encompass the administration of a trivalent, bispecific antibody molecule as defined herein before, simultaneously with or after administration of transduced T-cells comprising a fusion protein of the present invention. "In combination" as used herein also does not restrict the timing between the administration of a trivalent, bispecific antibody molecule as defined herein before and the transduced T-cells comprising a fusion protein as defined herein. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

In the context of the present invention the term "in combination" also encompasses the situation where the trivalent, bispecific antibody molecule as defined herein and the transduced T-cells comprising a fusion protein are pre-incubated together before administration to the subject. Thus, the two components may be pre-incubated before administration, for example, for 1 minute, 5 minutes, 10 minutes, 15 minutes, 30 minutes, 45 minutes or 1 hour or for any suitable time readily determined by one skilled in the art. The invention, in another preferred embodiment, relates to a treatment regimen, in which the trivalent, bispecific antibody molecule as defined herein and the transduced T-cells comprising a fusion protein as defined herein, are to be administered simultaneously with/concurrently. In the context of the present invention, the trivalent, bispecific antibody molecule as defined herein may be administered after the transduced T-cells comprising a fusion protein has been administered.

Further, "in combination" as used herein does not restrict the disclosed treatment regimens to the administration of a trivalent, bispecific antibody molecule as defined herein and transduced T-cells, preferably CD8+ T-cells, comprising a fusion protein in immediate sequence (i.e., the administration of one of the two components, followed (after a certain time interval) by the administration of the other without the administration and/or practice of any other treatment protocol in between. Therefore, the present treatment regimens also encompass the separate administration of a trivalent, bispecific antibody molecule as defined herein and transduced T-cells, preferably CD8+ T-cells, comprising a fusion protein, wherein the administrations are separated by one or more treatment protocols necessary and/or suitable for the treatment or prevention of the disease, or a symptom thereof. Examples of such intervening treatment protocols include but are not limited to, administration of pain medications; administration of chemotherapeutics, surgical handling of the disease or a symptom thereof. Accordingly, the treatment regimens as disclosed herein encompass the administration of a trivalent, bispecific antibody molecule as defined herein and transduced T-cells, preferably CD8+ T-cells, comprising a fusion protein as defined herein together with none, one, or more than one treatment protocol suitable for the treatment or prevention of a disease, or a symptom thereof, as described herein or as known in the art.

It is particular envisaged, that said pharmaceutical composition/medicament is to be administered to a patient via infusion or injection. In the context of the present invention the transduced T-cells comprising a fusion protein as defined is to be administered to a patient via infusion or injection. Administration of the suitable compositions/medicaments may be effected by different ways, intravenous, intraperitoneal, subcutaneous, intramuscular, topical or intradermal administration.

The pharmaceutical composition/medicament of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 µg to 5 g units per day. However, a more preferred dosage for continuous infusion might be in the range of 0.01 µg to 2 mg, preferably 0.01 µg to 1 mg, more preferably 0.01 µg to 100 µg, even more preferably 0.01 µg to 50 µg and most preferably 0.01 µg to 10 µg units per kilogram of body weight per hour. Particularly preferred dosages are recited herein. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous bispecific antibody constructs or nucleic acid molecules or vectors encoding the same (as described in this invention), further biologically active agents, depending on the intended use of the pharmaceutical composition. Such agents might be drugs acting on the gastro-intestinal system, drugs acting as cytostatica, drugs preventing hyperurikemia, drugs inhibiting immunereactions (e.g. corticosteroids), drugs acting on the circulatory system and/or agents such as T-cell co-stimulatory molecules or cytokines known in the art.

Possible indication for administration of the composition(s)/medicament(s) of the invention are malignant diseases especially epithelial cancers/carcinomas such as breast cancer, colon cancer, prostate cancer, head and neck cancer, skin cancer (melanoma), cancers of the genitorurinary tract, e.g., ovarial cancer, testis cancer, endothelial cancer, cervix cancer and kidney cancer, lung cancer, gastric cancer, cancer of the bile duct, esophagus cancer, cancer of the salivatory glands and cancer of the thyroid gland or other tumorous diseases like haematological tumors, gliomas, sarcomas or osteosarcomas.

The invention further envisages the co-administration protocols with other compounds, e.g., molecules capable of providing an activation signal for immune effector cells, for cell proliferation or for cell stimulation. Said molecule may be, e.g., a further primary activation signal for T-cells (e.g. a further costimulatory molecule: molecules of B7 family, Ox40L, 4.1 BBL, CD40L, anti-CTLA-4, anti-PD-1), or a further cytokine interleukin (e.g., IL-2).

The composition of the invention as described above may also be a diagnostic composition further comprising, optionally, means and methods for detection.

The trivalent, bispecific binding molecules or constructs (i.e., the trivalent, bispecific antibody molecules described herein) provided herein are also suited for use in immunoassays in which they can be utilized in liquid phase or bound to a solid phase carrier. Examples of immunoassays which can utilize the polypeptide of the invention are competitive or non-competitive immunoassays in either a direct or indirect format. Examples of such immunoassays are the enzyme linked immunosorbent assay (ELISA), enzyme immunoassay (EIA), radioimmunoassay (RIA), the sandwich (immunometric assay) and the Western blot assay.

The trivalent, bispecific binding molecules or constructs (i.e., the trivalent, bispecific antibody molecules described herein) of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble, e.g. as beads, for the purposes of the invention.

There are many different labels and methods of labeling known to those of ordinary skill in the art. Examples of the types of labels which can be used in the present invention include enzymes, radioisotypes, colloidal metals, fluorescent compounds, chemiluminescent compounds, and bioluminescent compounds.

In a most preferred embodiment of the present invention, the trivalent, bispecific antibody constructs/molecules of the invention for use as a medicament is envisaged. In the context of the present invention, the trivalent, bispecific antibody molecules for use as a medicament are described, wherein said trivalent, bispecific antibody molecule is to be administered before, simultaneously with or after administration of transduced T-cells, preferably CD8+ T-cells, comprising a fusion protein as defined herein and wherein said T-cells, preferably CD8+ T-cells, were obtained from a subject to be treated. Said medicament may be employed in a method of treatment of malignant diseases especially cancers/carcinomas of epithelial, endothelial or mesothelial origin or of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitorurinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in the context of the present invention a trivalent, bispecific antibody molecule as described herein which comprises (i) a first binding domain binding the extracellular domain of the fusion protein, i.e. to an extracellular domain of a signalling receptor that does not naturally occur in or on T-cells, (ii) a second binding domain binding a tumor-specific antigen naturally occurring on the surface of a tumor cell; and (iii) a third binding domain binding the extracellular domain of the fusion protein, i.e. to an extracellular domain of a signalling receptor that does not naturally occur in or on T-cells, or binding said tumor-specific antigen naturally occurring on the surface of a tumor cell for use in a method of treating a malignant disease is envisaged, wherein said bispecific antibody molecule is to be administered before, simultaneously with or after administration of transduced T-cells comprising a fusion protein as defined herein, wherein said T-cells, preferably CD8+ T-cells, were obtained from a subject to be treated.

Furthermore, in the context of the present invention a method of treatment of a malignant disease, the method comprising the administration of a trivalent, bispecific antibody molecule of the present invention to a subject in need thereof which comprises (i) a first binding domain binding the extracellular domain of the fusion protein, i.e. to an extracellular domain of a signalling receptor that does not naturally occur in or on T-cells, (ii) a second binding domain binding a tumor-specific antigen naturally occurring on the surface of a tumor cell; and (iii) a third binding domain binding the extracellular domain of the fusion protein, i.e. to an extracellular domain of a signalling receptor that does not naturally occur in or on T-cells, or binding said tumor-specific antigen naturally occurring on the surface of a tumor cell, wherein said trivalent, bispecific antibody molecule is to be administered before, simultaneously with or after administration of transduced T-cells, preferably CD8+ T-cells, from said subject comprising a fusion protein as defined herein. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitorurinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in accordance to the invention, a molecule or construct (i.e., the trivalent, bispecific antibody molecule described herein) comprising one or two binding domains directed to/binding to/interacting with EpCAM, preferably human EpCAM, (as the tumor-specific antigen naturally occurring on the surface of a tumor cell) and comprises one or two binding domains directed to/binding to/interacting with one of the herein defined extracellular domains of the fusion protein, i.e. an extracellular domain of a signalling receptor that does not naturally occur in and/or on T-cells can be used in a method for the treatment of gastrointestinal cancer, pancreatic cancer, cholangiocellular cancer, lung cancer, breast cancer, ovarian cancer, skin cancer and/or oral cancer. Thus, in the context of the present invention a trivalent, bispecific antibody molecule comprising two binding domains directed to/binding to/interacting with EpCAM, preferably human EpCAM, and comprise one binding domain directed to/binding to/interacting with one of the herein defined extracellular domains of the fusion protein, i.e. an extracellular domain of a signalling receptor that does not naturally occur in and/or on T-cells can be used in a method for the treatment of gastrointestinal cancer, pancreatic cancer, cholangiocellular cancer, lung cancer, breast cancer, ovarian cancer, skin cancer and/or oral cancer. In an alternative embodiment of the present invention a trivalent, bispecific antibody molecule comprising one binding domain directed to/binding to/interacting with EpCAM, preferably human EpCAM, and comprise two binding domains directed to/binding to/interacting with one of the herein defined extracellular domains of the fusion protein, i.e. an extracellular domain of a signalling receptor that does not naturally occur in and/or on T-cells can be used in a method for the treatment of gastrointestinal cancer, pancreatic cancer, cholangiocellular cancer, lung cancer, breast cancer, ovarian cancer, skin cancer and/or oral cancer. In the context of the present invention a trivalent, bispecific antibody molecule comprising one or two binding domain(s) against EpCAM, preferably human EpCAM, and comprises one or two binding domain(s) directed against/binding to/interacting with Cripto may be used in the treatment of gastrointestinal cancer, for example adenocarcinoma of gastrointestinal origin. A trivalent, bispecific antibody molecule described herein comprising one or two binding domain(s) against HER1, preferably human HER1 and one or two binding domains directed to/binding to/interacting with one of the herein defined extracellular domains of the fusion protein, i.e. an extracellular domain of a signalling receptor that does not naturally occur in and/or on T-cells can be used in a method for the treatment of gastrointestinal cancer, pancreatic cancer, cholangiocellular cancer, lung cancer, breast cancer, ovarian cancer, skin cancer and/or oral cancer. A molecule or construct (i.e., the trivalent, bispecific antibody molecule described herein) comprising one or two binding domain(s) directed to/binding to/interacting with HER2, preferably human HER2 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with HER3, preferably human HER3 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with CD20, preferably human CD20 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with CD22, preferably human CD22 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with CD33, preferably human CD33 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with CA12-5, preferably human CA12-5 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with HLA-DR, preferably human HLA-DR and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with MUC-1, preferably human MUC-1 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with A33, preferably human A33 and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with PSMA, preferably human PSMA and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with transferrin receptor, preferably human transferrin receptor and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer. A molecule or construct (i.e., the trivalent, bispecific antibody molecule described herein) comprising one or two binding domain(s) directed to/binding to/interacting with CA-IX, preferably human CA-IX and comprises one or two binding domain(s) directed to/binding to/interacting with one of the herein defined extracellular domains of the fusion protein, i.e. an extracellular domain of a signalling receptor that does not naturally occur in and/or on T-cells can be used in a method for the treatment of gastric cancer, breast cancer and/or cervical cancer.

The invention also relates to a method for the treatment of a disease, a malignant disease such as cancer of epithelial, endothelial or mesothelial origin and/or cancer of blood. Such diseases would be among others: cancer of esophagus, stomach, colon, small bowel, liver, pancreas, breast, lungs, brain, kidney, testis, skin cancer, leukemias and/or lymphonas comprising the administration the transduced T-cells to a subject. In the context of the present invention, said subject is a human.

In the context of the present invention a method for the treatment of a disease is described that comprises the steps of
(a) isolating T-cells, such as CD8+ T-cells, CD4+ T-cells, CD3+ T-cells, γδ T-cells or natural killer (NK) T-cells, preferably CD8+ T-cells, from a subject;
(b) transducing said isolated T-cells, such as CD8+ T-cells, CD4+ T-cells, CD3+ T-cells, γδ T-cells or natural killer (NK) T-cells, preferably CD8+ T-cells, with a fusion protein as described herein above; and
(c) administering the transduced T-cells, such as CD8+ T-cells, CD4+ T-cells, CD3+ T-cells, γδ T-cells or natural killer (NK) T-cells, preferably CD8+ T-cells, to said subject.

In the context of the present invention, said transduced T-cells, preferably CD8+ T-cells, are administered to said subject by intravenous infusion.

Moreover, the present invention provides a method for the treatment of a disease comprising the steps of
(a) isolating T-cells, such as CD8+ T-cells, CD4+ T-cells, CD3+ T-cells, γδ T-cells or natural killer (NK) T-cells, preferably CD8+ T-cells, from a subject;
(b) transducing said isolated T-cells, such as CD8+ T-cells, CD4+ T-cells, CD3+ T-cells, γδ T-cells or natural killer (NK) T-cells, preferably CD8+ T-cells, with a fusion protein as described herein above;
(c) co-transducing said isolated T-cells, such as CD8+ T-cells, CD4+ T-cells, CD3+ T-cells, γδ T-cells or natural killer (NK) T-cells, preferably CD8+ T-cells, with a T-cell receptor;
(d) expanding the T-cells, such as CD8+ T-cells, CD4+ T-cells, CD3+ T-cells, γδ T-cells or natural killer (NK) T-cells, preferably CD8+ T-cells, by anti-CD3 and anti-CD28 antibodies; and
(e) administering the transduced T-cells, such as CD8+ T-cells, CD4+ T-cells, CD3+ T-cells, γδ T-cells or natural killer (NK) T-cells, preferably CD8+ T-cells, to said subject.

The present invention relates to isolated T-cells that are analyzed by methods in order to make sure that the (tumor) antigen that naturally occurs on the isolated T-cells is identical to the tumor antigen to which the trivalent, bispecific antibody described herein bind via one or two binding domains. In the context of the present invention the isolated/obtained T-cells comprising a fusion protein as defined herein are artificially modified by introducing a fusion protein comprising an extracellular domain of signalling receptor that does not naturally occur/that is not naturally expressed in and/or on T-cells. In the context of the present invention, the artificial modification of the isolated/obtained T-cells relates to transduction methods described herein. Accordingly, in the context of the present invention, the subject to be treated, relates to a subject being characterized by suffering from a disease characterized by having a tumor-specific antigen naturally occurring on the surface of a tumor cell as described herein above. In the context of the present invention the administration of the transduced T-cells obtained/isolated from the subject to be treated will be performed by intravenous infusion.

In a further embodiment, the present invention relates to a method for the treatment of a disease comprising the steps of
(a) isolating tumor infiltrated lymphocytes (TIL) from a resected tumor from the patient;

(b) culturing and transduction of TIL with a fusion protein as described herein above;
(c) selecting TIL cultures on the basis of functional tumor recognition assays;
(d) expanding the TIL by anti-CD3 and/or anti-CD28 antibodies; and
(e) administering the transduced TIL to said subject.

The term "functional tumor recognition assays" means co-culture of TIL with either autologous, e.g. patient's, tumor cells or a cell line of identical HLA-type. The read out is the cytotoxic activity to the tumor cell (LDH, calcein-release). Further read outs could be cytokine secretion, flow cytometry of T-cells for the presence of intracellular cytokines, ELISPOT assays.

The above mentioned step (d) (referring to the expanding step of the T-cells such as TIL by anti-CD3 and/or anti-CD28 antibodies) may also be performed in the presence of (stimulating) cytokines such as interleukin-2 and/or interleukin-15 (TL-15). In the context of the present invention, the above mentioned step (d) (referring to the expanding step of the T-cells such as TIL by anti-CD3 and/or anti-CD28 antibodies) may also be performed in the presence of interleukin-12 (TL-12), interleukin-7 (TL-7) and/or interleukin-21 (TL-21).

The method for the treatment may also, in addition, comprise the administration of the trivalent, bispecific antibody of the present invention. Said trivalent, bispecific antibody may be administered before, simultaneously with or after the transduced T-cells are to be administered. In the context of the present invention the administration of the transduced T-cells will be performed by intravenous infusion. In the context of the present invention that transduced T-cells are isolated/obtained from the subject to be treated.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized. Further databases and resources, such as ncbi.nlm.nih.gov, infobiogen.fr, fmi.ch/biology/research_tools.html, andtigr.org, are known to the person skilled in the art.

The Figures show

Figure 1B:
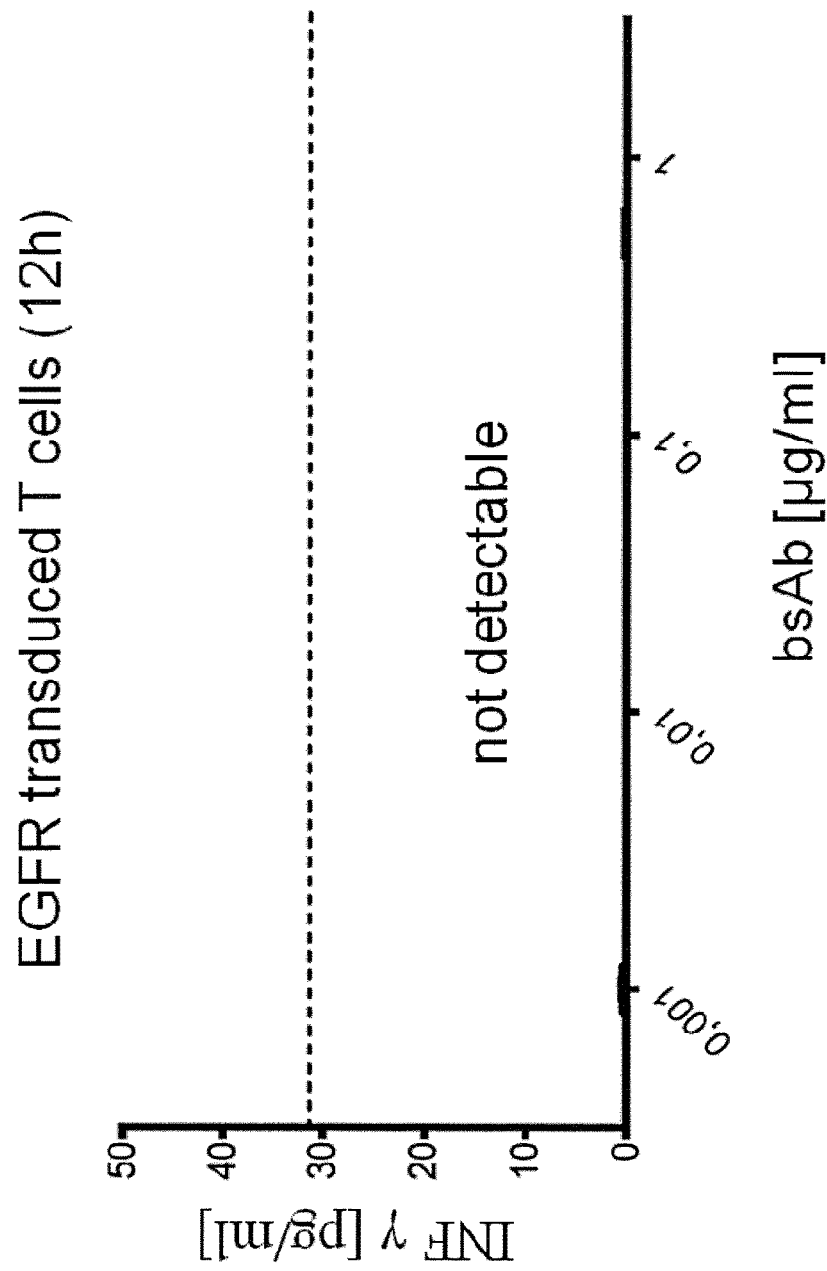
FIG. 1B shows INF-γ-secretion in EGFR transduced T-cells incubated with or without BsAb EpCAM-EGFRvIII, MR1.1.

FIG. 1A, 1B: Co-Culture of Transduced T-Cells and Murine Pancreatic Cancer Tumor Cells (Panc02-OVA) Expressing the Tumor Antigen EpCAM (EpCAM+) or not Expressing the Tumor Antigen EpCAM (EpCAM−)

In order to prove the activation of the transduced T-cells via the activating fusion protein EGFRvIII-CD28-CD3z (SEQ ID NOs: 42 (as encoded by the DNA shown in SEQ ID NO: 41)) T-cells were transduced with the EGFRvIII-CD28-CD3z fusion protein (named hereinafter "E3 T-cells"). The transduced T-cells were incubated with or without a tetravalent, bispecific antibody (bsAb) "BsAb EpCAM-EGFRvIII, MR1.1" (SEQ ID NO: 229 (light chain (without leader sequence) and SEQ ID NO: 230 (heavy chain (without leader sequence)) with pancreatic cancer (Panc02-OVA) cells expressing the tumor antigen EpCAM (EpCAM+) or pancreatic cancer (Panc02-OVA) cells that do not express the tumor antigen EpCAM (EpCAM−) at a 10:1 ratio for 12 hours. Additionally, a condition with E3 T-cells with the respective concentrations of the tetravalent, bispecific antibody "BsAb EpCAM-EGFRvIII, MR1.1" was pre-treated with 20% FCS (Gibco Products, Grand Island, USA) in PBS at 37° C. for 30 minutes to block unspecific binding. The concept of blocking is well known to those skilled in the art as a mean to prevent unspecific binding of a given protein, here an antibody, by addition of an excess of polyclonal proteins, here FCS. As a negative control T-cells were used which were transduced with the non-signalling marker antigen. The T-cell activation was measured as INF-γ-secretion using ELISA. The results show an enhanced tumor cell recognition for antigen-positive (EpCAM+) over antigen-negative tumor cells. The tetravalent, bispecific antibody (bsAb) "BsAb EpCAM-EGFRvIII, MR1.1" recruits E3 T-cells to the pancreatic cancer (Panc02-OVA) cells and induces specific redirected T-cell activation towards the EpCAM expressing tumor cell. In the EGFR-transduced T-cells no activation could be detected. These results indicate that the human EGFRvIII-CD28-CD3z fusion protein can be used to trigger T-cell activation through the tetravalent, bispecific antibody "BsAb EpCAM-EGFRvIII, MR1.1". However, T-cell activation in the presence of the tetravalent, bispecific antibody "BsAb EpCAM-EGFRvIII, MR1.1" also happens in the absence of the tumor target of the tetravalent, bispecific antibody molecule "BsAb EpCAM-EGFRvIII, MR1.1", indicating unspecific T-cell activation. The term "blocked" in FIG. 1A refers to a condition where transduced T-cells are co-incubated with the tetravalent, bispecific antibody on plates blocked with FCS in order to assess the extent of non-specific T-cell activation. In this condition, activation, if any, should result from undirected T-cell crosslinking. The term "PancO2-OVA" refers to a condition where transduced T-cells are co-incubated with the tetravalent, bispecific antibody and EpCAM⁻ tumor cells in order to assess the unspecific (non-tumor directed) activation and lysis. The term "Panc02-OVA-EpCAM" refers to a condition where transduced T-cells are co-incubated with the tetravalent, bispecific antibody and EpCAM+ tumor cells in order to assess the specific (on-tumor) activation and lysis.

FIG. 2: Bispecific Antibody Titration in the Co-Culture of Transduced T-Cells and Tumor Cells On the basis of the experimental setting described above with regard to FIGS. 1A and 1B, an experiment was performed in which the concentration of the tetravalent, bispecific antibody (bsAb) "BsAb EpCAM-EGFRvIII, MR1.1" (SEQ ID NO: 229 (light chain (without leader sequence) and SEQ ID NO: 230 (heavy chain (without leader sequence)) was varied. By titrating the bispecific antibody molecule (bsAb) from 1 ng/mL to 1 μg/mL an increase in the amount of secreted IFN-γ measured by ELISA could be seen. Both EpCAM-specific T-cell activation and unspecific T-cell activation were found to be dose dependent.

Figure 3:
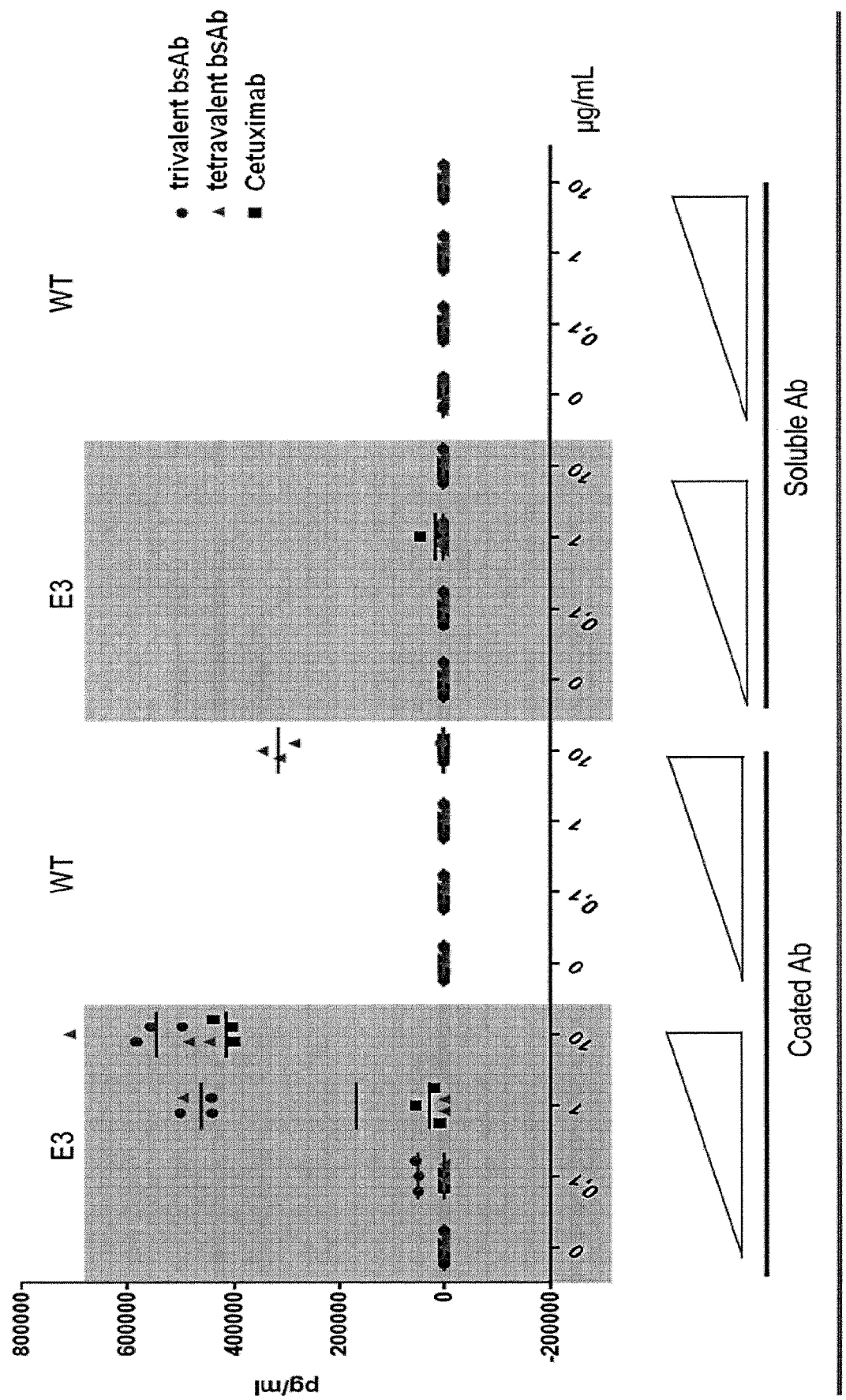
FIG. 3 shows a comparison of the activation of transduced T-cells by plate bound trivalent versus tetravalent bispecific antibodies.

FIG. 3: Comparison of T-Cell Activation Provided by Plate Bound Trivalent Versus Tetravalent Bispecific Antibodies T-cells transduced with the EGFRvIII-CD28-CD3z fusion protein (SEQ ID NOs: 42 (protein) and 41 (DNA); named hereinafter "E3 T-cells") or wild-type (WT) T-cells were stimulated for 48 hours with (i) the tetravalent, bispecific antibody "BsAb EpCAM-EGFRvIII, MR1.1" (SEQ ID NO: 229 (light chain (without leader sequence) and SEQ ID NO: 230 (heavy chain (without leader sequence)), (ii) the trivalent, bispecific antibody "BsAB EGFRvIII-EpCAM" (SEQ ID NO: 233 which comprises/consists of the plasmids/ vectors "EGFR vIII MR1.1 VH Ck muEpCAM VH CH1 EE Fc knob PG LALA, pETR14953" (SEQ ID NOs: 22 (protein) and 21 (DNA), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2) or (iii) as a positive control Cetuximab (Erbitux®, Merck Germany) at increasing concentrations, either coated on the plate or added to the T-cell culture. In the first condition, the assay plate was coated with the antibodies, in the second condition the antibodies were added soluble to the T-cells. The IFN-7 release was determined by ELISA. The results show a comparable E3-transduced T-cell activation by all antibodies in the coated condition. The term "blocked" in FIG. 3 refers to a condition where transduced T-cells are co-incubated with the tetravalent, bispecific antibody on plates blocked with FCS in order to assess the extent of non-specific T-cell activation. In this condition, activation, if any, should result from undirected T-cell crosslinking.

Figure 4:
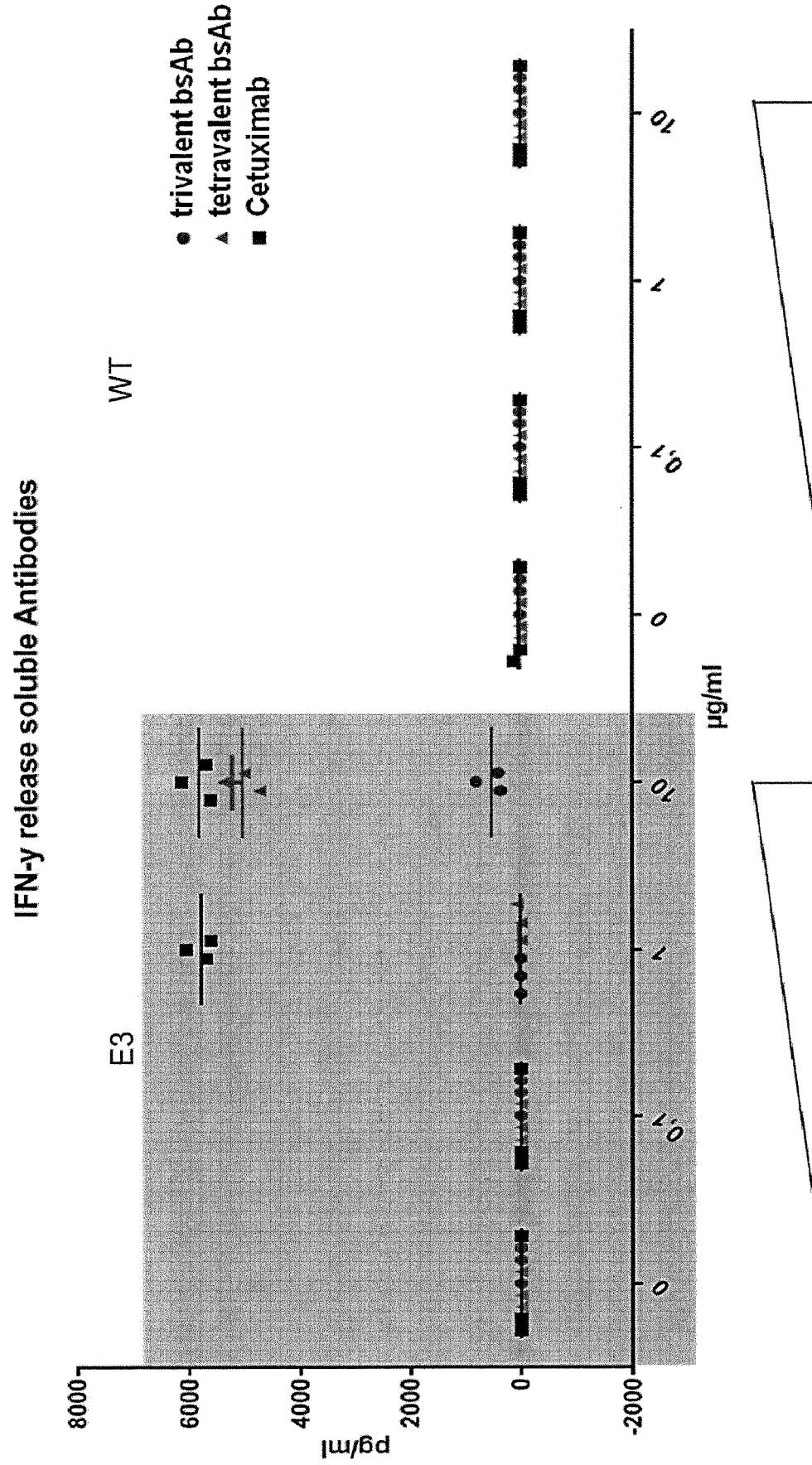
FIG. 4 shows a comparison of the activation of transduced T-cells incubated with soluble trivalent versus tetravalent, bispecific antibodies.

FIG. 4: Comparison of the Activation of Transduced T-Cells Incubated with Soluble Trivalent Versus Tetravalent, Bispecific Antibodies To investigate the unspecific activation of T-cells transduced with the EGFRvIII-CD28-CD3z fusion protein (SEQ ID NOs: 42 (protein) and 41 (DNA); hereinafter named "E3 T-cells") in the soluble condition, the samples as described in FIG. 3 were used undiluted in an IFN-7 ELISA. The tetravalent, bispecific antibody molecule "BsAb EpCAM-EGFRvIII, MR1.1" (SEQ ID NO: 229 (light chain (without leader sequence) and SEQ ID NO: 230 (heavy chain (without leader sequence)) shows an unspecific activation of the T-cells potentially due to the two binding sites for the T-cells. This can lead to a cross linkage between two T-cells and thereby to an IFN-7 secretion by the cells. To the contrary, with the trivalent, bispecific antibody (bsAb) molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953" (SEQ ID NOs: 22 (protein) and 21 (DNA), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2) this unspecific activation is abolished by the loss of one EGFR binding site.

Figure 5:
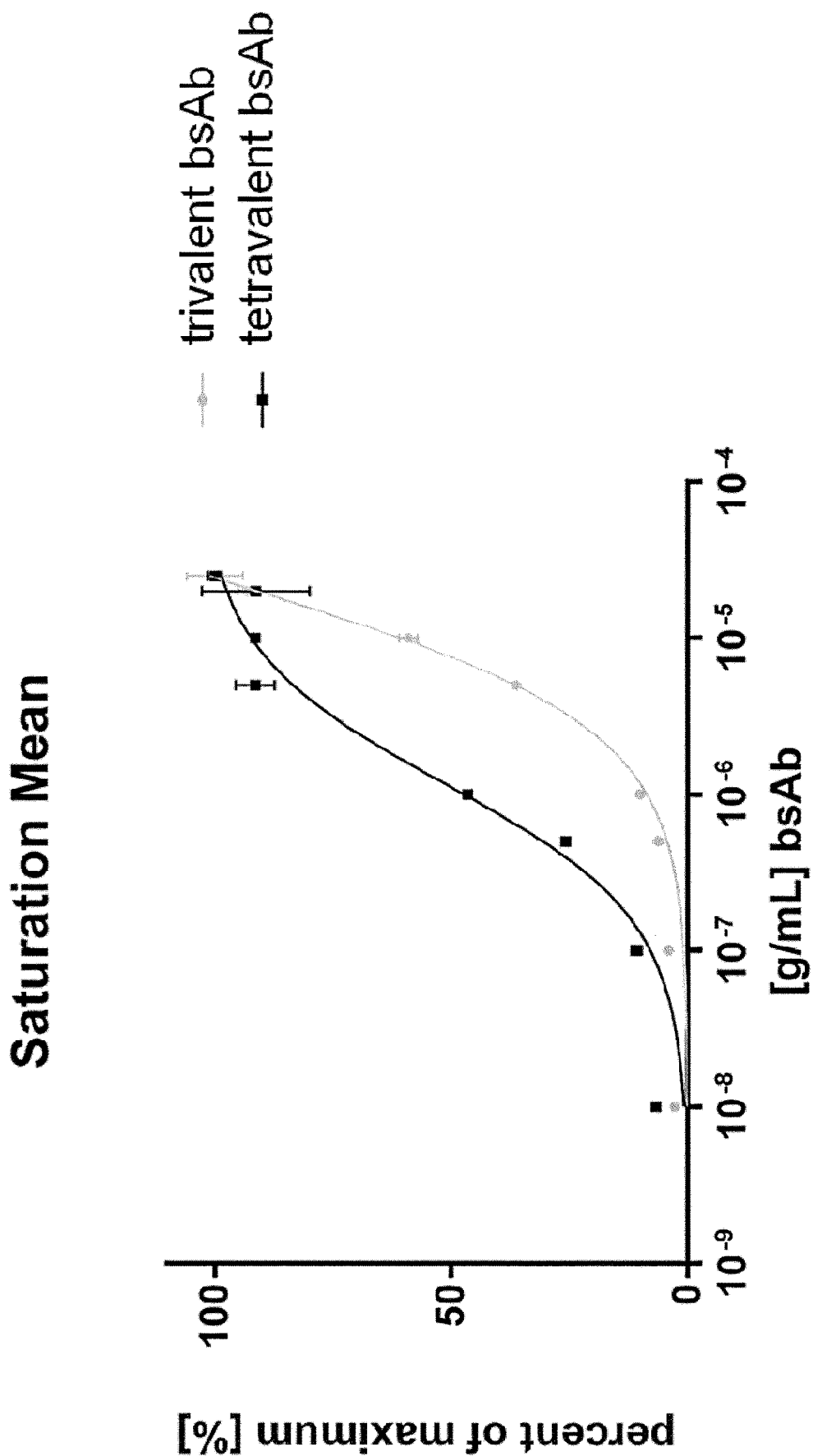
FIG. 5 shows an analysis of the dose dependency of surface antigen binding as function of antibody concentration.

FIG. 5: Analysis of the Dose Dependency of Surface Antigen Binding as Function of Antibody Concentration To address the impact of antibody valency on surface saturation of T-cells transduced with the EGFRvIII-CD28-CD3z fusion protein (SEQ ID NOs: 42 (protein) and 41 (DNA)) by the tetravalent, bispecific antibody molecule "BsAb EpCAM-EGFRvIII, MR1.1" (SEQ ID NO: 229 (light chain (without leader sequence) and SEQ ID NO: 230 (heavy chain (without leader sequence)) and the trivalent, bispecific antibody (bsAb) molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953" (SEQ ID NOs: 22 (protein) and 21 (DNA), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2) the cells were incubated with increasing concentrations of the tetravalent or trivalent/bsAb (10 ng/mL; 100 ng/mL; 500 ng/mL; 1 μg/mL; 5 μg/mL; 10 μg/mL; 20 μg/mL; 25 μg/mL) and determined the surface saturation by a secondary antibody (FITC AffiniPure F(ab')$_2$ Fragment Goat Anti-Human IgG, F(ab')$_2$ fragment specific: 109-096-097) staining by flow cytometry. The tetravalent, bispecific antibody (bsAb) shows a higher saturation at low concentrations favoured by the additional binding site for EGFR (left shift of the curve compared to the trivalent, bispecific antibody (bsAb)).

Figure 6:
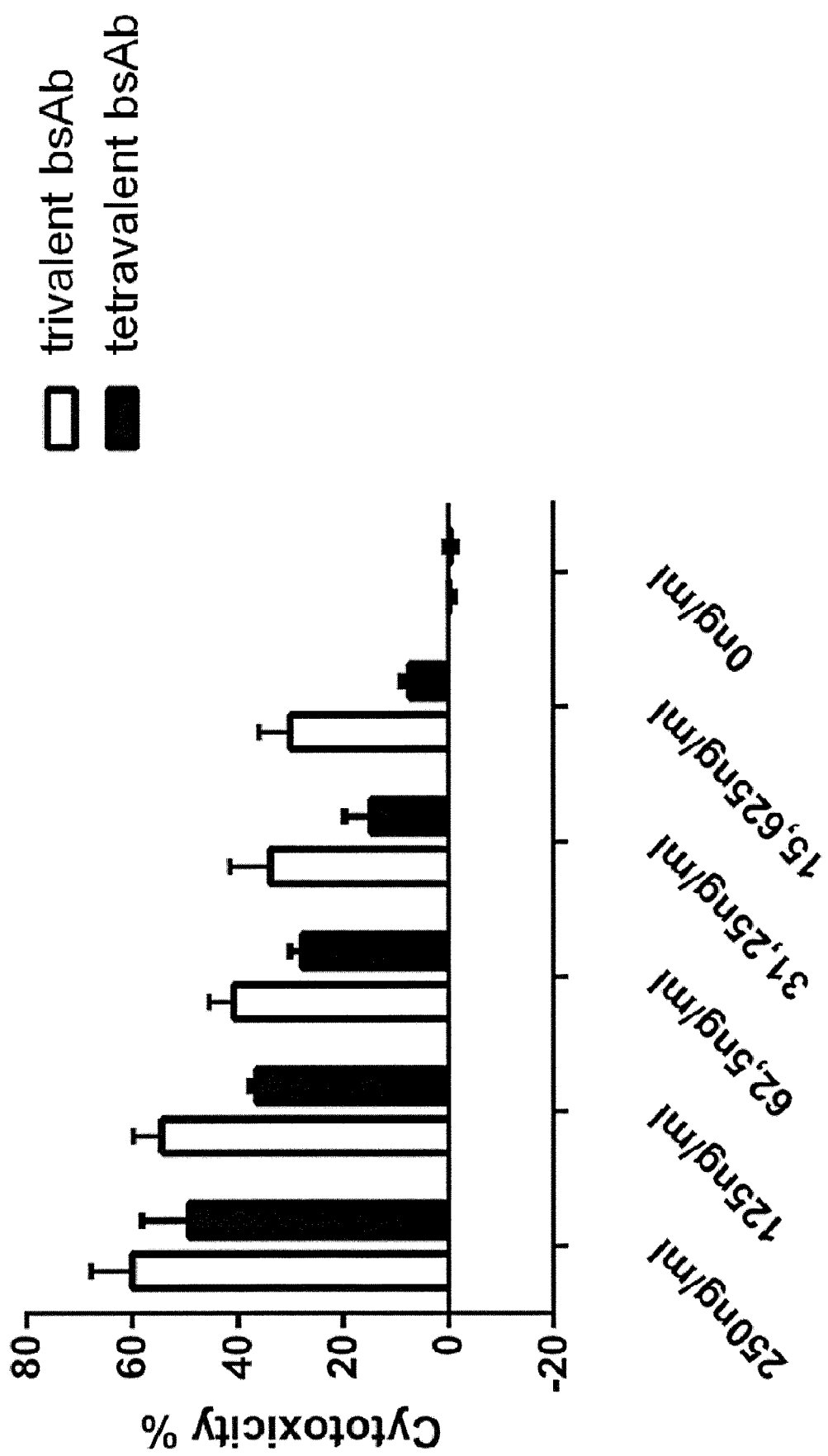
FIG. 6 shows a comparison of the redirect lysis capacity of transduced T-cells mediated by the trivalent, bispecific antibody (bsAb) molecule "BsAb EGFRvIII-EpCAM" versus the tetravalent, bispecific antibody (bsAb) "BsAb EpCAM-EGFRvIII, MR1.1" as a function of antibody concentration against EpCAM+ tumor cells.

FIG. 6: Comparison of the Redirect Lysis Capacity of Transduced T-Cell Mediated by the Trivalent Versus the Tetravalent, Bispecific Antibody (bsAb) as a Function of Antibody Concentration Against EpCAM+ Tumor Cells To compare the cytotoxic potential of both antibodies, bsAb preloaded T-cells transduced with the human EGFRvIII-CD28-CD3z fusion protein (SEQ ID NOs: 42 (protein) and 41 (DNA)); named hereinafter "E3 T-cells") (with the trivalent or tetravalent bispecific antibody (bsAb), respectively) were co-cultured with pancreatic cancer cells (Panc02-OVA) expressing the tumor antigen EpCAM for 9 hours. The killing efficacy was measured by LDH release of the tumor cells. The antibodies (at a concentration of 250 ng/ml, 125 ng/ml or 62.5 ng/ml) have a more or less identical lytic capacity towards EpCAM expressing (EpCAM+) pancreatic cancer cells. However, at lower concentrations (i.e. at concentrations of 31.25 ng/ml or 15.63 ng/ml) the trivalent bsAb is characterized by an increased cytotoxic effect towards the EpCAM+ cancer cells compared the tetravalent bispecific antibody molecule.

Figure 7:
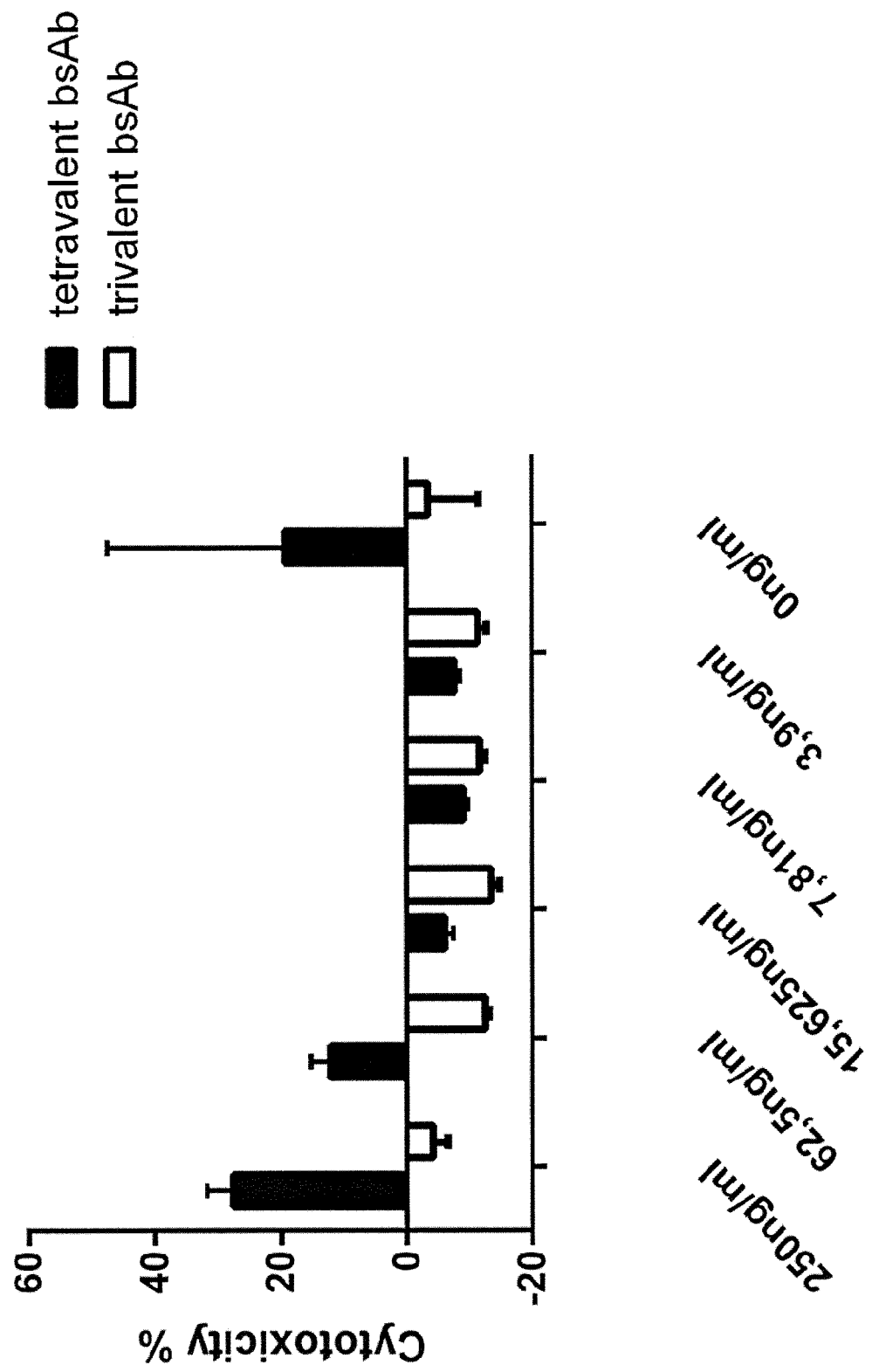
FIG. 7 shows a comparison of the unspecific lysis capacity of transduced T-cell mediated by BsAb EGFRvIII-EpCAM versus BsAb EpCAM-EGFRvIII, MR1.1 as a function of antibody concentration against EpCAM⁻ tumor cells.

FIG. 7: Comparison of the Unspecific Lysis Capacity of Transduced T-Cell Mediated by the Trivalent Versus the Tetravalent Bispecific Antibody as a Function of Antibody Concentration Against EpCAM⁻ Tumor Cells Pancreatic cancer cells (Panc02-OVA) not expressing EpCAM (EpCAM−) were co-cultured with bsAb preloaded T-cells (with either the trivalent or tetravalent bispecific antibody) for 9 hours. The lytic capacity was determinated by LDH release. At high antibody concentrations (i.e. at an antibody concentration of 250 ng/ml or 62.5 ng/ml) the tetravalent bispecific antibody molecule "BsAb EpCAM-EGFRvIII, MR1.1" shows an unspecific background lysis which decreases with lower antibody concentrations. To the contrary, the trivalent, bispecific antibody (bsAb) molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953" (SEQ ID NOs: 22 (protein) and 21 (DNA), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also FIG. 9A and Tables 1 and 2) at each tested concentration shows no unspecific background lysis. The unspecific target cell lysis as shown for the trivalent bsAb is abolished with the tetravalent bsAb. Thus, the combination of the trivalent, bispecific antibody (bsAb) molecule "BsAB EGFRvIII-EpCAM" (SEQ ID NO: 233) and T-cells transduced with the human EGFRvIII-CD28-CD3z fusion protein (SEQ ID NOs: 42 (protein) and 41 (DNA); named "E3 T-cells") specifically lyse EpCAM expressing (EpCAM+) pancreatic cancer cells.

Figure 8:
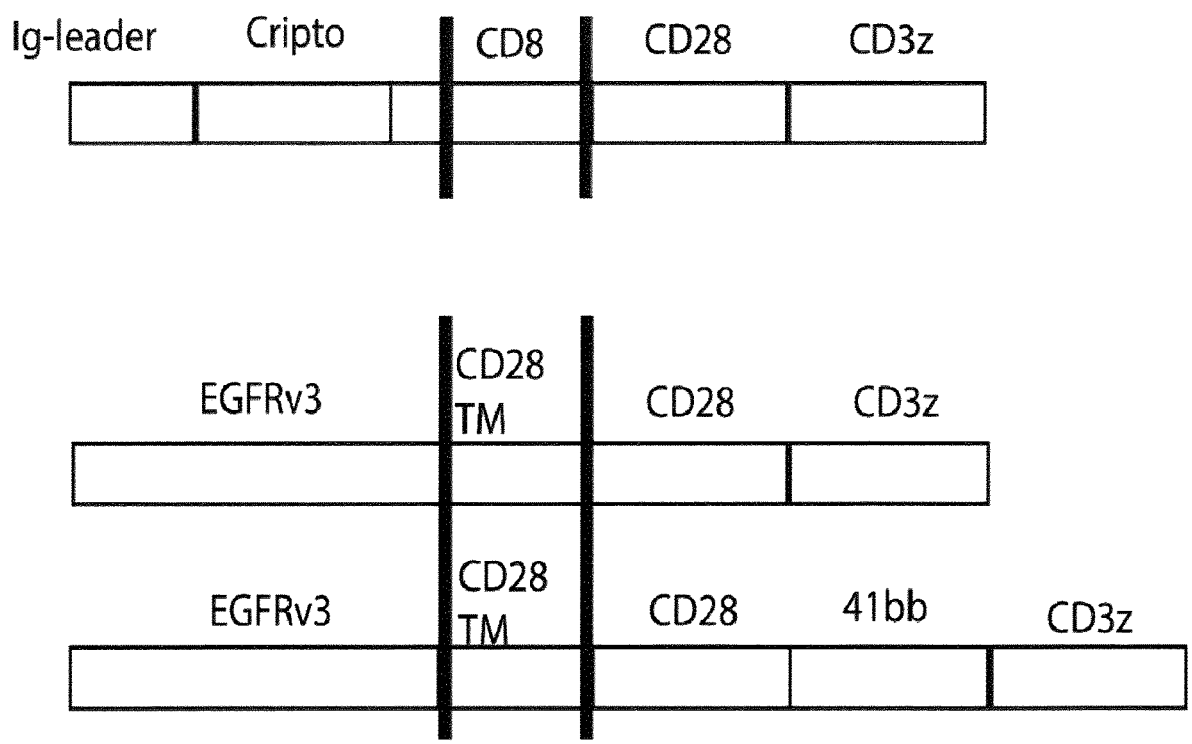
FIG. 8 shows a schematic overview of fusion proteins.

FIG. 8: Schematic Overview of the Fusion Proteins

The Cripto fusion protein (SEQ ID NOs: 46 (murine) and 120 (human)) constituted of the Ig leader sequence (SEQ ID NO: 206), the extracellular domain of Cripto (SEQ ID NO: 62), the hinge domain of CD8 (SEQ ID NOs: 64 (murine) and 74 (human)), and the co-stimulatory signaling domain of CD28 (SEQ ID NOs: 56 (murine) and 68 (human)) and CD3z (SEQ ID NOs: 58 (murine) and 70 (human)). The EGFRvIII fusion proteins (SEQ ID NOs: 42 (murine) and 48 (human)) constituted of the EGFRvIII extracellular domain (SEQ ID NO: 76), the anchoring transmembrane domain of CD28 (SEQ ID NOs: 54 (murine) and 66 (human)), the co-stimulatory signalling domain of CD28 (SEQ ID NOs: 56 (murine) and 68 (human)) and the signalling domain of CD3z (SEQ ID NOs: 58 (murine) and 70 (human)). Alternatively, the EGFRvIII fusion proteins (SEQ ID NOs: 44 (murine) and 50 (human)) constituted of the EGFRvIII extracellular domain (SEQ ID NO: 76) the anchoring transmembrane domain of CD28 (SEQ ID NOs: 54 (murine) and 66 (human)), the co-stimulatory signalling domains of CD28 (SEQ ID NOs: 56 (murine) or 66 (human)) and 4-1-BB (SEQ ID NOs: 60 (murine) or 72 (human)) and the stimulatory signalling domain CD3z (SEQ ID NOs: 58 (murine) or 70 (human)).

FIG. 9A: Schematic Structure of the Trivalent, Bispecific Antibody (bsAb) Molecule "BsAB EGFRvIII-EpCAM"

Figure 9B:
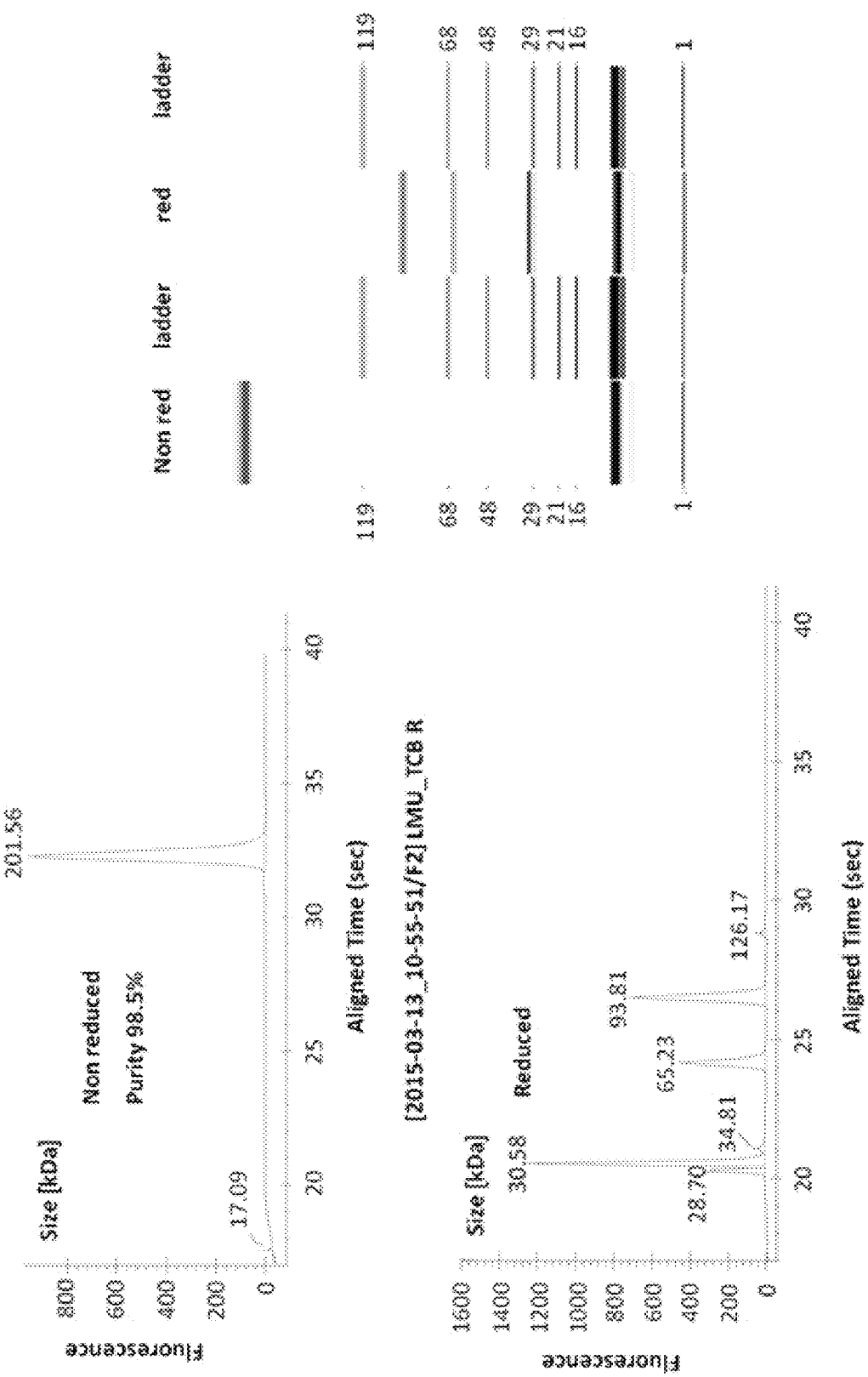
FIG. 9B and FIG. 9C show purity and molecular weight of the muEpCAM/EGFRvIII molecules.
Figure 9C:
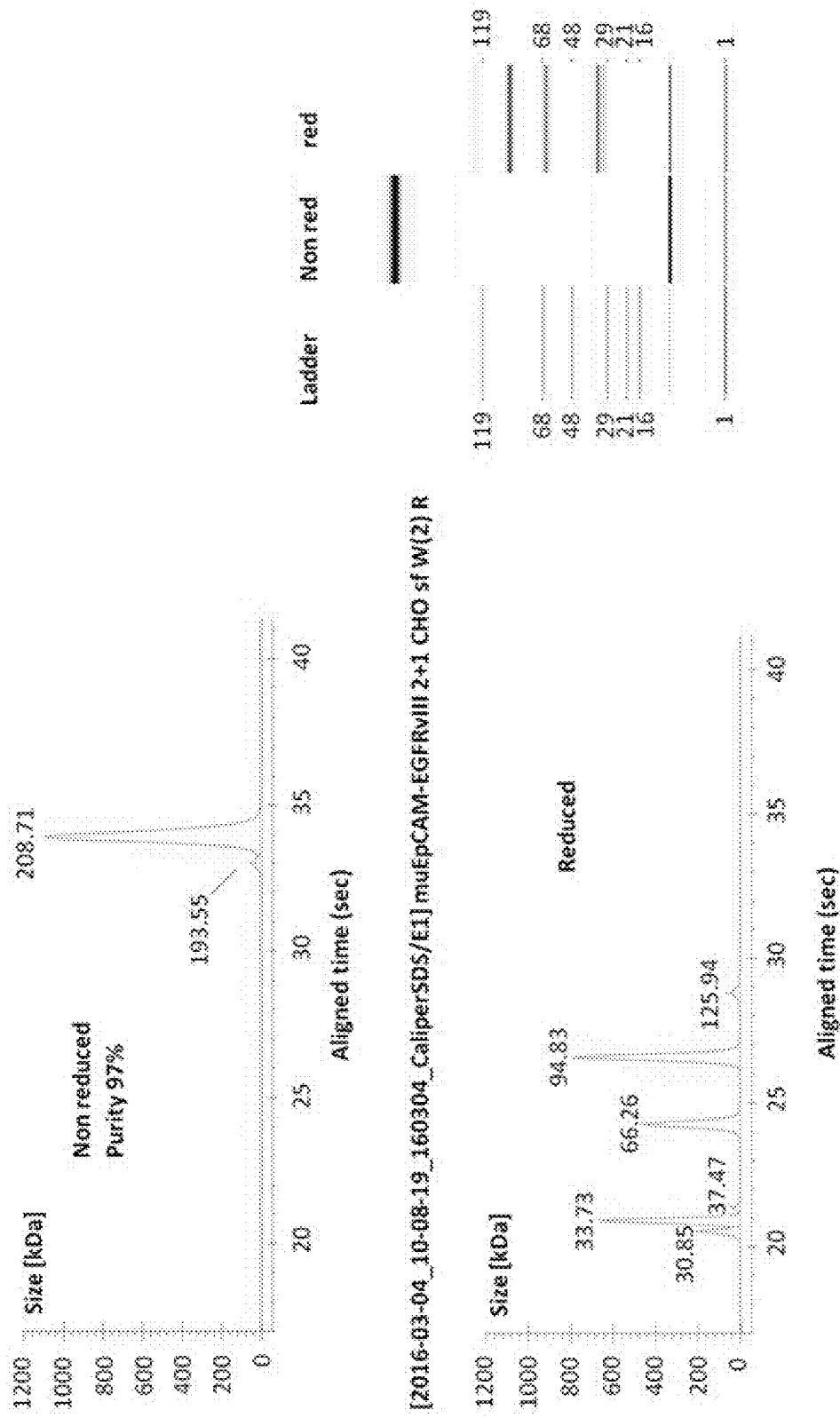

Schematic structure of the trivalent, bispecific antibody (bsAb) molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953", "EGFR vIII MR1.1 VL CH1, pETR14951", "VL EpCAM G.8.8 Ck RK, pETR14882" and "VH muEpCAM CH1 EE Fc hole PG LALA HRYF, pETR14940"; see also Tables 1 and 2). The variable domains of muEpCAM/EGFRvIII were subcloned in frame with the constant chains pre-inserted into the respective recipient mammalian expression vector. Protein expression is driven by a CMV promoter and a synthetic polyA signal sequence is present at the 3'-end of the coding sequence (CDS). In addition, each vector contains an EBV OriP sequence. The molecules were produced by co-transfecting CHO cells growing in suspension with the mammalian expression vectors. Transient transfection was done at Evitria AG (Switzerland). The cells were transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)":"crossed light chain (VL-CH1)"). The filtered supernatant was kept at 4° C. until purification. The secreted protein was purified from cell culture supernatants by affinity chromatography using ProteinA affinity chromatography, followed by one to two size exclusion chromatographic (SEC) steps. The protein concentration of purified protein samples was determined by measuring the optical density (OD) at 280 nm divided by the molar extinction coefficient calculated on the basis of the amino acid sequence. Purity and molecular weight of the molecules after the final purification step were analyzed by CE-SDS analyses in the presence and absence of a reducing agent (FIG. 9B, 9C, right). The Caliper LabChip GXII system (Caliper Lifescience) was used according to the manufacturer's instruction. The aggregate content of the molecules was analyzed using a TSKgel G3000 SW XL analytical size-exclusion column (Tosoh) in 25 mM K2HPO4, 125 mM NaCl, 200 mM L-arginine monohydrochloride, 0.02% (w/v) NaN3, pH 6.7 running buffer at 25° C. The final quality of all molecules was good, with ≥96% monomer content. Molecules 1 and 2 refer to the trivalent, bispecific antibody (bsAb) molecule "BsAB EGFRvIII-EpCAM" (SEQ ID NO: 233 which comprises/consists of the plasmids/vectors "EGFR vIII MR1.1 VH Ck muEpCAM VH CH1 EE Fc knob PG LALA, pETR14953" (SEQ ID NOs: 22 (protein) and 21 (DNA), "EGFR vIII MR1.1 VL CH1, pETR14951" (SEQ ID NOs: 24 (protein) and 23 (DNA), "VL EpCAM G.8.8 Ck RK, pETR14882" (SEQ ID NOs: 26 (protein) and 25 (DNA) and "VH muEpCAM CH1 EE Fc hole PG LALA HRYF, pETR14940" (SEQ ID NOs: 28 (protein) and 27 (DNA); see also Tables 1 and 2) as produced in an in vitro batch (Molecule 1) or as produced in an in vivo batch (Molecule 2). Summary of production and purification of the muEpCAM/EGFRvIII molecules:

| Molecule | Titer [mg/l] | Yield [mg/l] | Analytical SEC (HMW/Monomer/LMW) [%] |
|---|---|---|---|
| 1 (in vitro batch) | 18 | 6.98 | 0%/100%/0% |
| 2 (in vivo batch) | 18 | 11.6 | 3.68%/96.32%/0% |

HMW = High Molecular Weight
LMW = Low Molecular Weight

FIG. 10A: Schematic Structure of the Trivalent, Bispecific Antibody (bsAb) Molecule "BsAB EGFRvIII-MSLN"

Figure 10B:
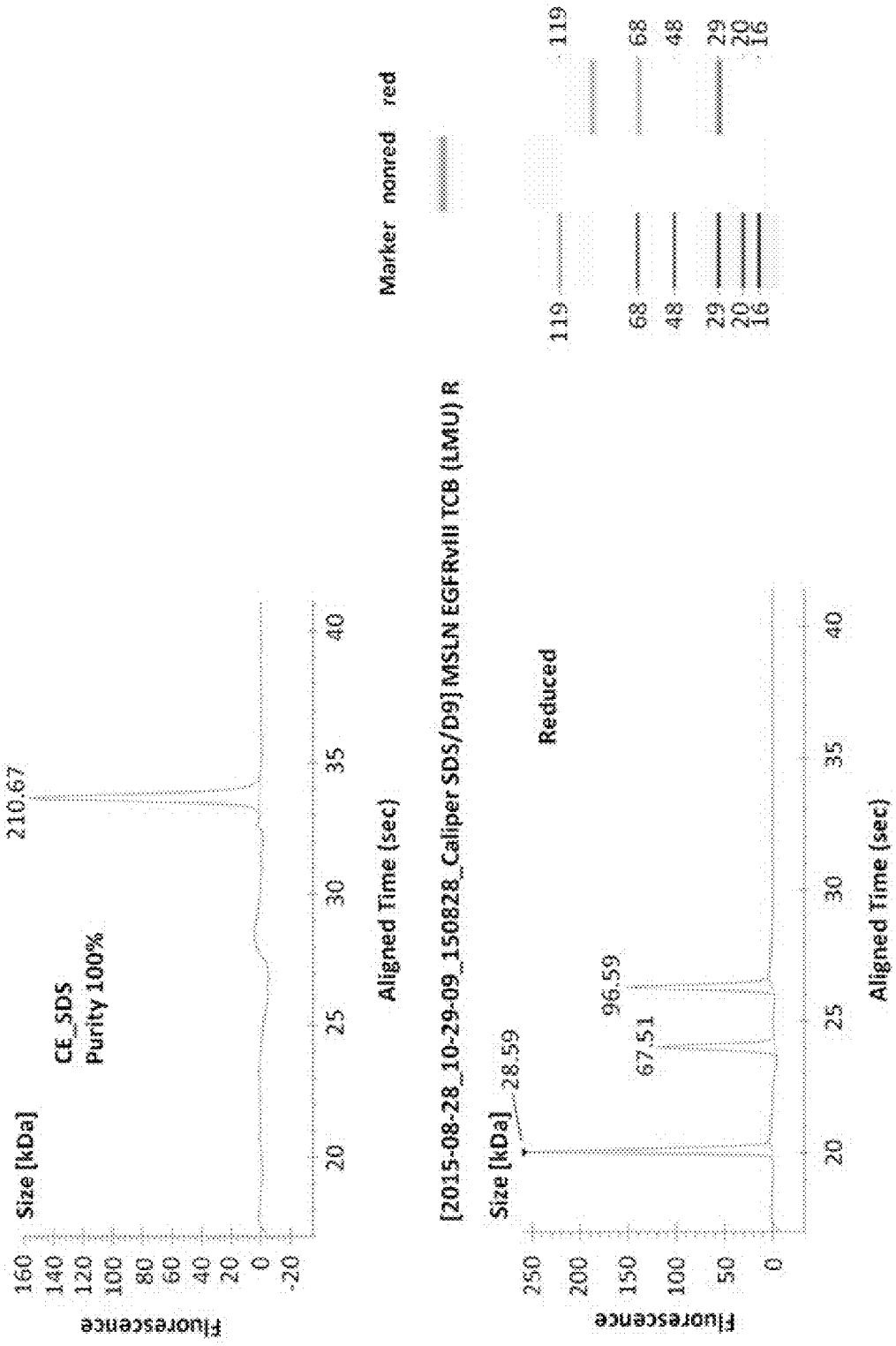
" FIG. 10B shows CE-SDS analysis of BsAB EGFRvIII-MSLN.

Schematic structure of the trivalent, bispecific antibody (bsAb) molecule "BsAB EGFRvIII-MSLN" (SEQ ID NO: 235 which comprises/consists of the plasmids/vectors "EGFR vIII MR1.1 VH Ck MSLN VH CH1 EE Fc knob PG LALA, pETR15655", "EGFR vIII MR1.1 VL CH1, pETR15656", "VL MSLN Ck RK, pETR15443" and "VH MSLN CH1 EE Fc hole PG LALA HRYF, pETR15667"; see also Tables 3 and 4). The variable domains of MSLN/EGFRvIII were subcloned in frame with the constant chains pre-inserted into the respective recipient mammalian expression vector. Protein expression is driven by an MPSV promoter and a synthetic polyA signal sequence is present at the 3' end of the CDS. In addition, each vector contains an EBV OriP sequence. The molecules were produced by co-transfecting HEK293-EBNA cells growing in suspension with the mammalian expression vectors using polyethylenimine (PEI). The cells were transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)":"crossed light chain (VL-CH1)"). The solution was sterile filtered (0.22 µm filter) and sodium azide in a final concentration of 0.01% w/v was added. The solution was kept at 4° C. until purification. The secreted protein was purified from cell culture supernatants by affinity chromatography using ProteinA affinity chromatography, followed by one to two size exclusion chromatographic (SEC) steps. Purity and molecular weight of the molecules after the final purification step were analyzed by CE-SDS analyses in the presence and absence of a reducing agent (FIG. 10B, right). The Caliper LabChip GXII system (Caliper Lifescience) was used according to the manufacturer's instruction. The aggregate content of the molecules was analyzed using a TSKgel G3000 SW XL analytical size-exclusion column (Tosoh) in 25 mM K2HPO4, 125 mM NaCl, 200 mM L-arginine monohydroclorine, 0.02% (w/v) NaN3, pH 6.7 running buffer at 25° C. (FIG. 10B). The final quality of all molecules was good, with ≥96% monomer content. Molecule 1 refers to the trivalent, bispecific antibody (bsAb) molecule "BsAB EGFRvIII-MSLN" (SEQ ID NO: 235 which comprises/consists of the plasmids/vectors "EGFR vIII MR1.1 VH Ck MSLN VH CH1 EE Fe knob PG LALA, pETR15655" (SEQ ID NOs: 2 (protein) and 1 (DNA), "EGFR vIII MR1.1 VL CH1, pETR15656" (SEQ ID NOs: 4 (protein) and 3 (DNA), "VL MSLN Ck RK, pETR15443" (SEQ ID NOs: 6 (protein) and 5 (DNA) and "VH MSLN CH1 EE Fe hole PG LALA HRYF, pETR15667" (SEQ ID NOs: 8 (protein) and 7 (DNA); see also FIG. 10A and Tables 3 and 4). Summary of production and purification of the MSLN/EGFRvIII molecules:

| Molecule | Titer [mg/l] | Yield [mg/l] | Analytical SEC (HMW/Monomer/LMW) [%] |
|---|---|---|---|
| 1 | 65 | 1.16 | 3.31/96.3/0.4 |

HMW = High Molecular Weight
LMW = Low Molecular Weight

FIG. 10B: CE-SDS analysis of the trivalent, bispecific antibody (bsAb) molecule "BsAB EGFRvIII-MSLN" (SEQ ID NO: 235 which comprises/consists of the plasmids/vectors "EGFR vIII MR1.1 VH Ck MSLN VH CH1 EE Fc knob PG LALA, pETR15655", "EGFR vIII MR1.1 VL CH1, pETR15656", "VL MSLN Ck RK, pETR15443" and "VH MSLN CH1 EE Fc hole PG LALA HRYF, pETR15667"; see also Tables 3 and 4): Protein standard, protein at non reduced conditions and protein at reduced conditions are shown for the electronic gel-electrophoresis. The graphs on the right show the fluorescence of the protein at non-reduced and reduced conditions. (FIG. 10C) Analytical size exclusion chromatography analysis of the trivalent, bispecific antibody (bsAb) molecule "BsAB EGFRvIII-MSLN" (SEQ ID NO: 235; see also Tables 3 and 4) for determination of purity.

FIG. 11A: Schematic Structure of the Trivalent, Bispecific Antibody (bsAb) Molecule "BsAB EGFRvIII-MCSP"

Figure 12A:
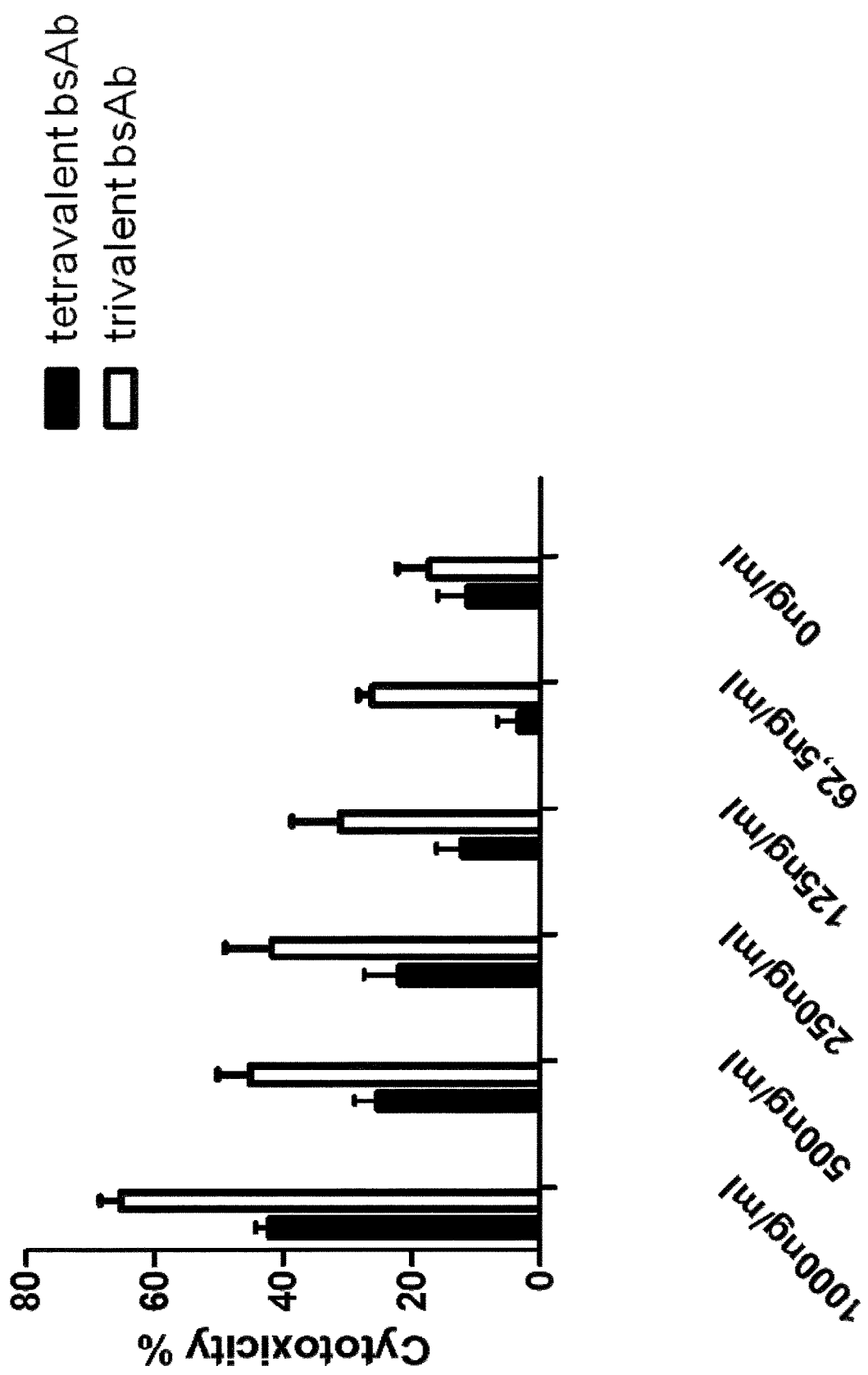
FIG. 12A and FIG. 12B show dose-response curves of BsAb EpCAM-EGFRvIII, MR1.1 and the BsAB EGFRvIII-EpCAM in the B16EpCAM tumor model (FIG. 12A) and 4T1 tumor model (FIG. 12B).

Schematic structure of the trivalent, bispecific antibody (bsAb) molecule "BsAB EGFRvIII-MCSP (SEQ ID NO: 234 which comprises/consists of the plasmids/vectors "MR1.1 EGFRvIII VH-Ck-(G4S)2 MCSP M4-3 VH CH1 EE Fc knob PG LALA, pETR16621 (SEQ ID NO: 208 as encoded by the DNA sequence shown in 207), "EGFR vIII MR1.1 VL CH1, pETR15656" (SEQ ID NOs: 210 (protein) and 209 (DNA), "MCSP ML2 VL Ck RK, pETR16619" (SEQ ID NOs: 212 (protein) and 211 (DNA) and "MCSP M4-3 VH CH1 EE Fc hole PG LALA HYRF, pETR16618" (SEQ ID NOs: 214 (protein) and 213 (DNA)); see also Tables 5 and 6) (FIG. 11B) CE-SDS analysis of the trivalent, bispecific antibody (bsAb) molecule "BsAB EGFRvIII-MCSP (SEQ ID NO: 234; see also Tables 5 and 6): Protein standard, protein at non reduced conditions and protein at reduced conditions are shown for the electronic gel-electrophoresis FIG. 12A: Co-Culture of Murine Cancer Tumor Cells (B16EpCAM and 4T1 Tumor Model) Expressing the Tumor Antigen EpCAM (EpCAM+) with the Tetravalent, Bispecific Antibody (bsAb) "BsAb EpCAM-EGFRvIII, MR1.1" (SEQ ID NO: 229 (Light Chain (without Leader Sequence) and SEQ ID NO: 230 (Heavy Chain (without Leader Sequence)) and the Trivalent, Bispecific Antibody "BsAB EGFRvIII-EpCAM" (SEQ ID NO: 233; See Also Tables 1 and 2)

Figure 12B:
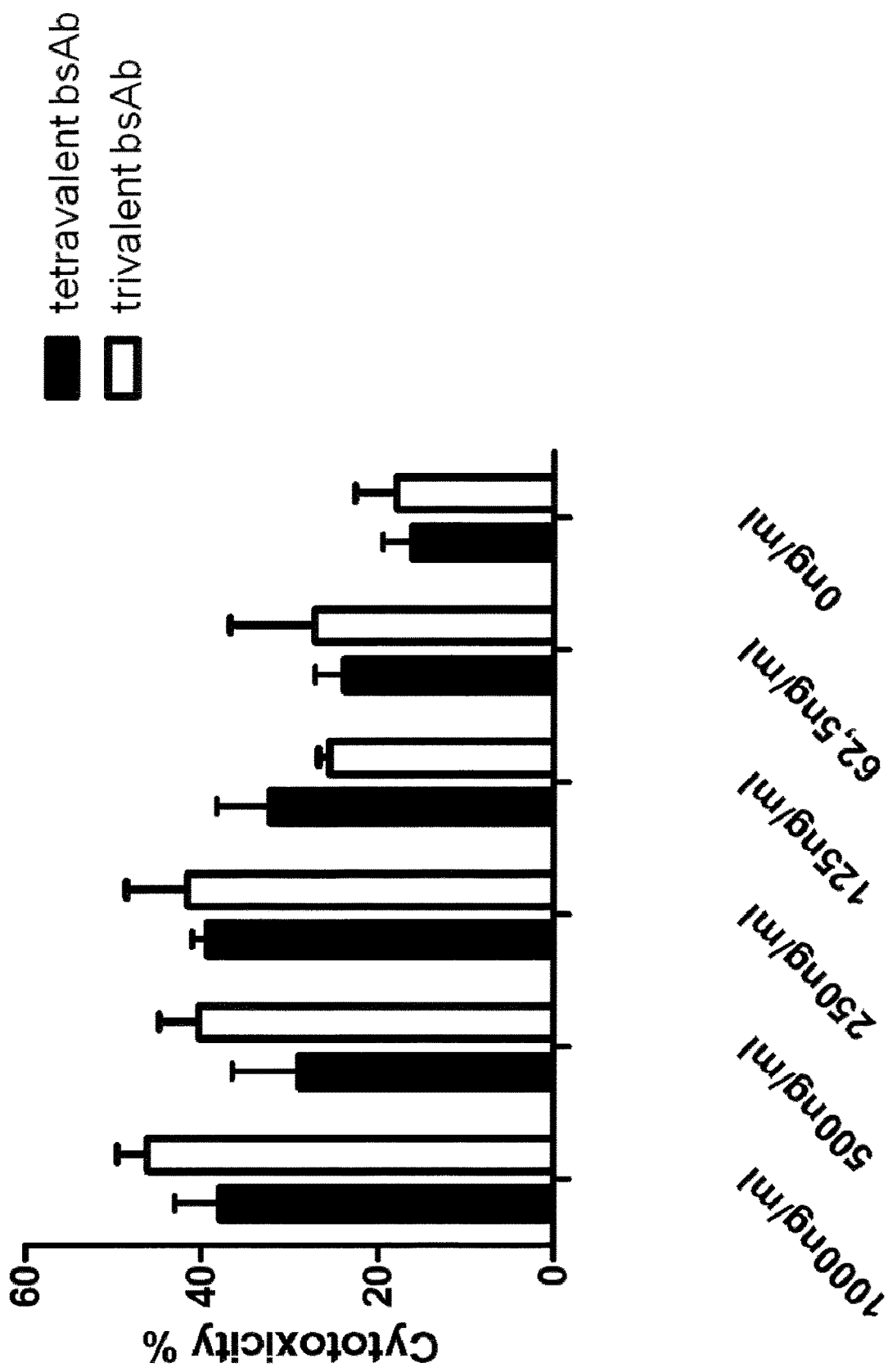

To determinate a dose-response curve of the bispecific antibody (bsAb), both the tetravalent, bispecific antibody (bsAb) "BsAb EpCAM-EGFRvIII, MR1.1" (SEQ ID NO: 229 (light chain (without leader sequence) and SEQ ID NO: 230 (heavy chain (without leader sequence)) and the trivalent, bispecific antibody "BsAB EGFRvIII-EpCAM" (SEQ ID NO: 233; see also Tables 1 and 2) were titrated down head-to-head and cytotoxicity was measured by lactate dehydrogenase (LDH) release. Therefore, in the B16EpCAM tumor model (FIG. 12B) as well as in the 4T1 tumor model (FIG. 12C), a decreasing cytotoxicity can be observed with lower doses of the antibody respectively. Furthermore, both antibody formats show a sufficient and comparable tumor cell killing.

Figure 13:
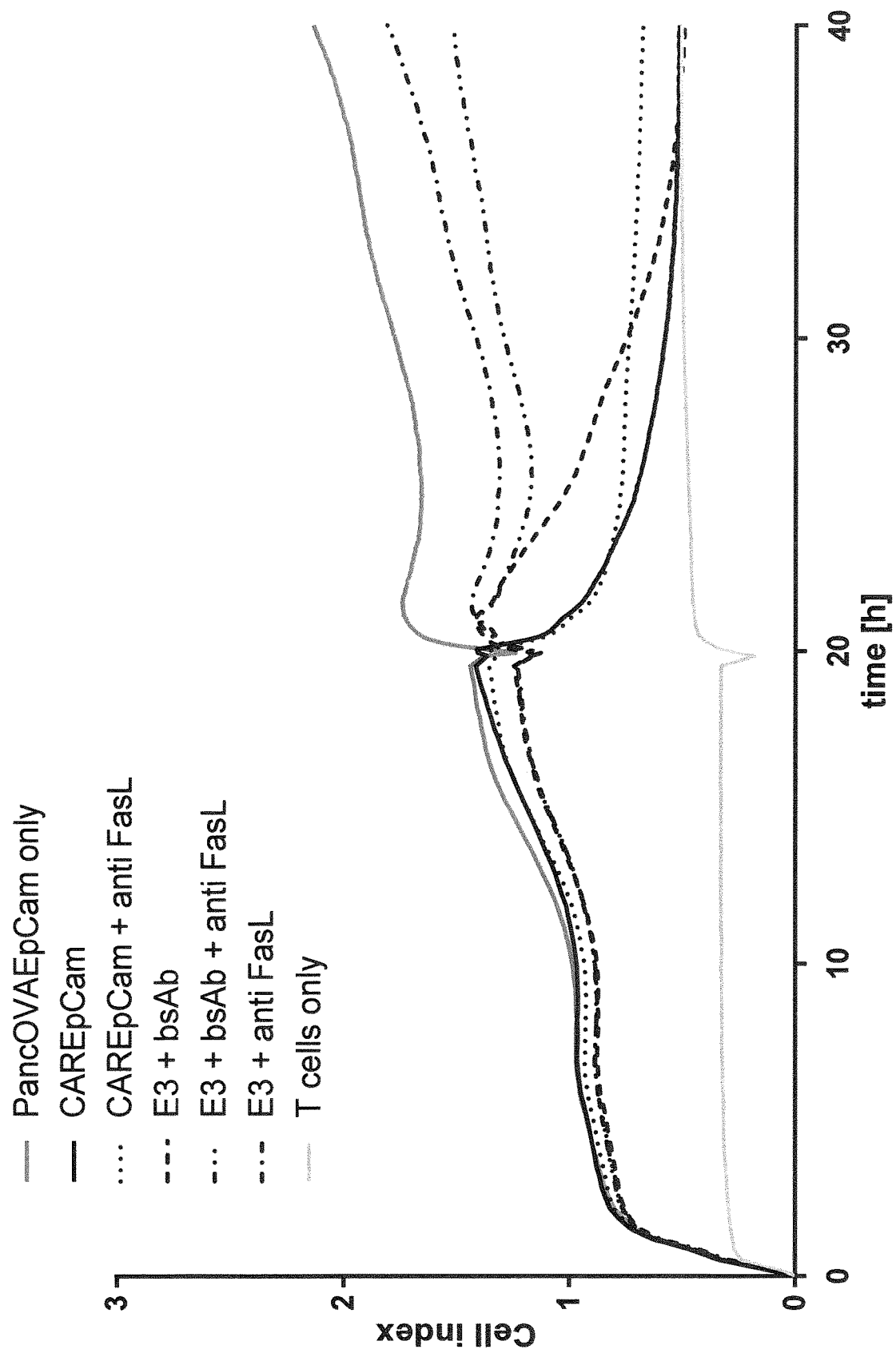
FIG. 13 shows results of a real-time cytotoxicity assay to determine the mechanism of killing by E3-transduced murine T-cells against Panc02-EpCAM tumor cells.

FIG. 13: Real Time Cytotoxicity Assay to Determine the Mechanism of Killing by E3-Transduced Murine T-Cells Against Panc02-EpCAM Tumor Cells The killing capacity of T-cells transduced with the EGFRvIII-CD28-CD3z fusion protein (SEQ ID NO: 42 (protein) and 41 (DNA)) (named as "E3") can be impaired by blocking the FasL-Fas interactions between the tumor cells and T-cells with a FasL blocking antibody (CD178 (Fas Ligand) monoclonal antibody, Clone MFL3 (Cat. No. 16-5911-85 (ThermoFisher Scientific™). This finding is shown in FIG. 13 by using the iCELLigence instrument from ACEA Bioscience. The device measures the changes in the magnitude of impedance over time which is dependent on the number of adherent cells. In contrast to the activating fusion protein EGFRvIII-CD28-CD3z (SEQ ID NO: 42 (protein) and 41 (DNA)), T-cells transduced with an EpCAM specific chimeric antigen receptor (CAREpcam; SEQ ID NOs: 249 (protein) and 248 (DNA)) are still capable to induce tumor cell lysis in the presence of FasL blocking antibody. The condition PancOVAEpCAM refers to the condition with tumor cells only. The condition T-cells refers to the condition with T-cells only. The condition with CAREpCAM refers to the co-culture of CAREpCAM (SEQ ID NOs: 249 (protein) and 248 (DNA)) transduced T-cells with PancOVA-EpCAM.

Figure 14:
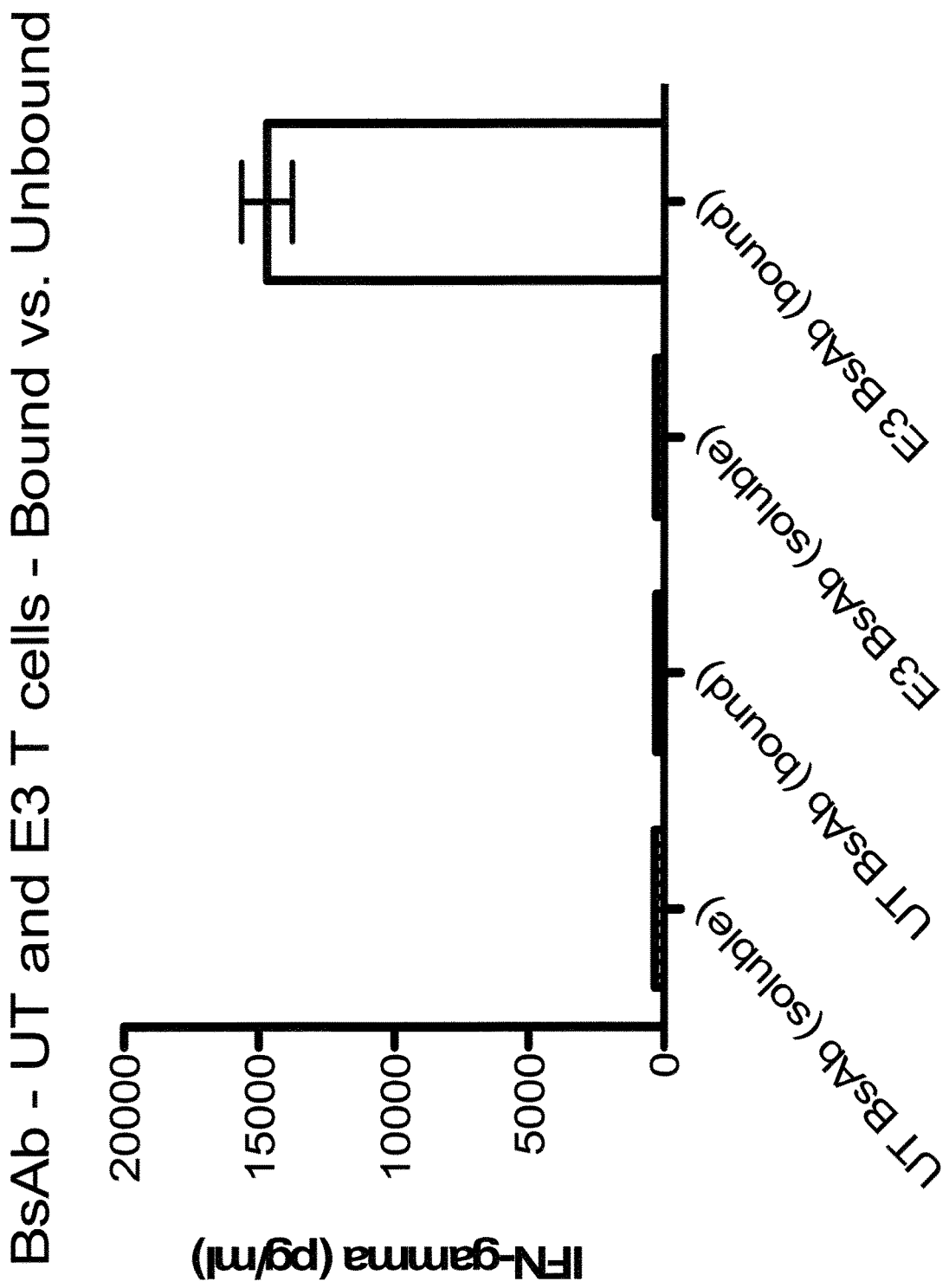
FIG. 14 shows results of an antibody binding assay using varying concentrations of BsAb EGFRvIII-MSLN.

FIG. 14: Antibody Binding Assay Using Varying Concentrations of the Trivalent, Bispecific Antibody Molecule "BsAb EGFRvIII-MSLN" (SEQ ID NO: 235; See Also Tables 3 and 4)

T-cells transduced with the human version of the EGFRvIII-CD28-CD3z fusion protein (SEQ ID NOs: 48 (protein) as encoded by SEQ ID NO: 47 (DNA)) (named hereinafter "E3 T-cells") were stimulated for 48 hours with the trivalent, bispecific antibody "EGFRvIII-MSLN" (SEQ ID NO: 235; see also Tables 3 and 4) at a bsAB concentration of 1.0 g/ml). The "EGFRvIII-MSLN" bsAb specifically stimulates E3 transduced T-cells while T-cells lacking the full E3 construct (E3del (SEQ ID NOs: 247 (protein) and 246 (DNA)) and UT) do not get stimulated in the presence of the "EGFRvIII-MSLN" bsAb. This T-cell stimulation is conditional to the E3-bsAb binding to the plate via its Fc-like part and so soluble E3-bsAb does not stimulate E3 transduced T-cells. E3del is a truncated version of E3, devoid of the intracellular domains while UT refers to untransduced T-cells.

FIG. 15: Recombinant Mesothelin (MSLN) Stimulation: Co-Culture of Transduced T-Cells and the Trivalent, Bispecific Antibody Molecule "BsAb EGFRvIII-MSLN" (SEQ ID NO: 235; See Also Tables 3 and 4) in the Presence of Recombinant Mesothelin T-cells transduced with the human version of the EGFRvIII-CD28-CD3z fusion protein (SEQ ID NOs: 48 (protein) as encoded by SEQ ID NO: 47 (DNA)) (named "E3 T-cells" or "E3") were stimulated for 48 hours with the trivalent, bispecific antibody (bsAb) "EGFRvIII-MSLN" (SEQ ID NO: 235; see also Tables 3 and 4) at an bsAb concentration of 1.0 µg/ml. "EGFRvIII-MSLN" bsAb specifically stimulates E3 T-cells while T-cells lacking the full E3 construct (E3del (SEQ ID NOs: 247 (protein) and 246 (DNA)) and UT) do not get stimulated in the presence of the "EGFRvIII-MSLN" bsAb (soluble) and recombinant mesothelin (coated to wells—concentration of 5 µg/ml). Controls were T-cells (E3 T-cells vs. non-transduced T-cells vs. E3del construct transduced T-cells). E3del is a truncated version of E3, devoid of the intracellular domains while UT refers to untransduced T-cells.

Figure 16:
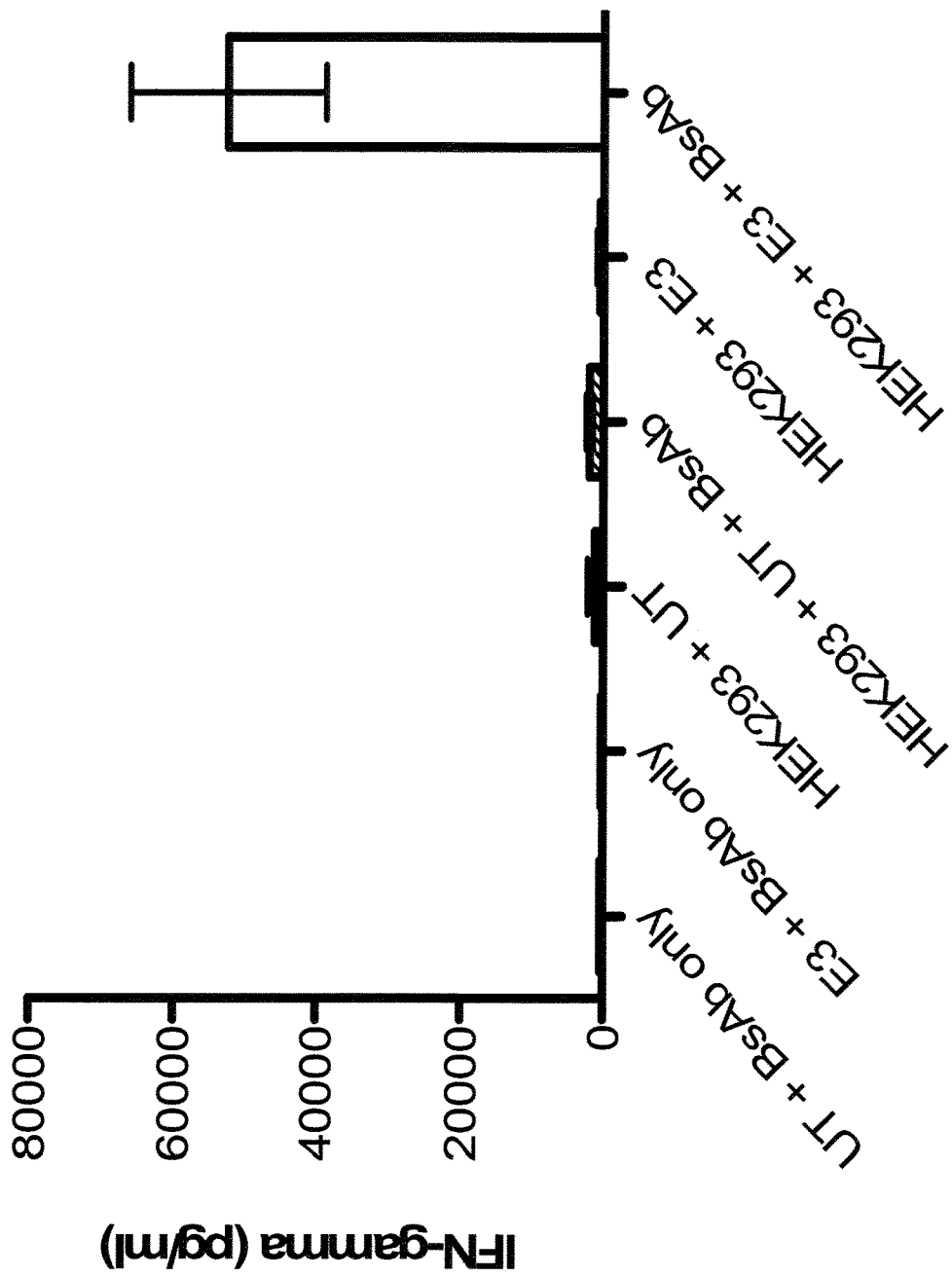
FIG. 16 shows INF-γ-secretion in HEK293-FLIPin-MSLN E3-transduced human T-cells stimulated with BsAb EGFRvIII-MSLN.

FIG. 16: Co-Culture of HEK293-FLIPin-MSLN E3-Transduced Human T-Cells

T-cells transduced with the human version of the EGFRvIII-CD38-CD3z fusion protein (SEQ ID NOs: 48 (protein) as encoded by SEQ ID NO: 47 (DNA)) (named hereinafter "E3 T-cells" or "E3") were stimulated for 48 hours with the trivalent, bispecific antibody "EGFRvIII-MSLN" (SEQ ID NO: 235; see also Tables 3 and 4) at an "EGFRvIII-MSLN" bsAB concentration of 1.0 µg/ml. "EGFRvIII-MSLN" bsAb specifically stimulates E3 T-cells while T-cells lacking full E3 construct (E3del (SEQ ID NOs: 247 (protein) and 246 (DNA)) and UT) do not get stimulated in the presence of "EGFRvIII-MSLN" bsAb (soluble) and HEK293-FLPin-MSLN cells (HEK293). This was observed when the assay was set-up with a single clone (C12) as well as with a polyclonal set-up. UT refers to untransduced T-cells. BsAB refers to the condition with bispecific antibodies (bsAb) only. The co-culture was run for 48 hours at an effector to target ratio of 10:1. The tumor cells were seeded 6 hours before co-culture; T-cells preloaded with bsAb 30 minutes before co-culture (bsAb concentration 1 µg/ml). E3del is a truncated version of E3, devoid of the intracellular domains while UT refers to untransduced T-cells.

Figure 17:
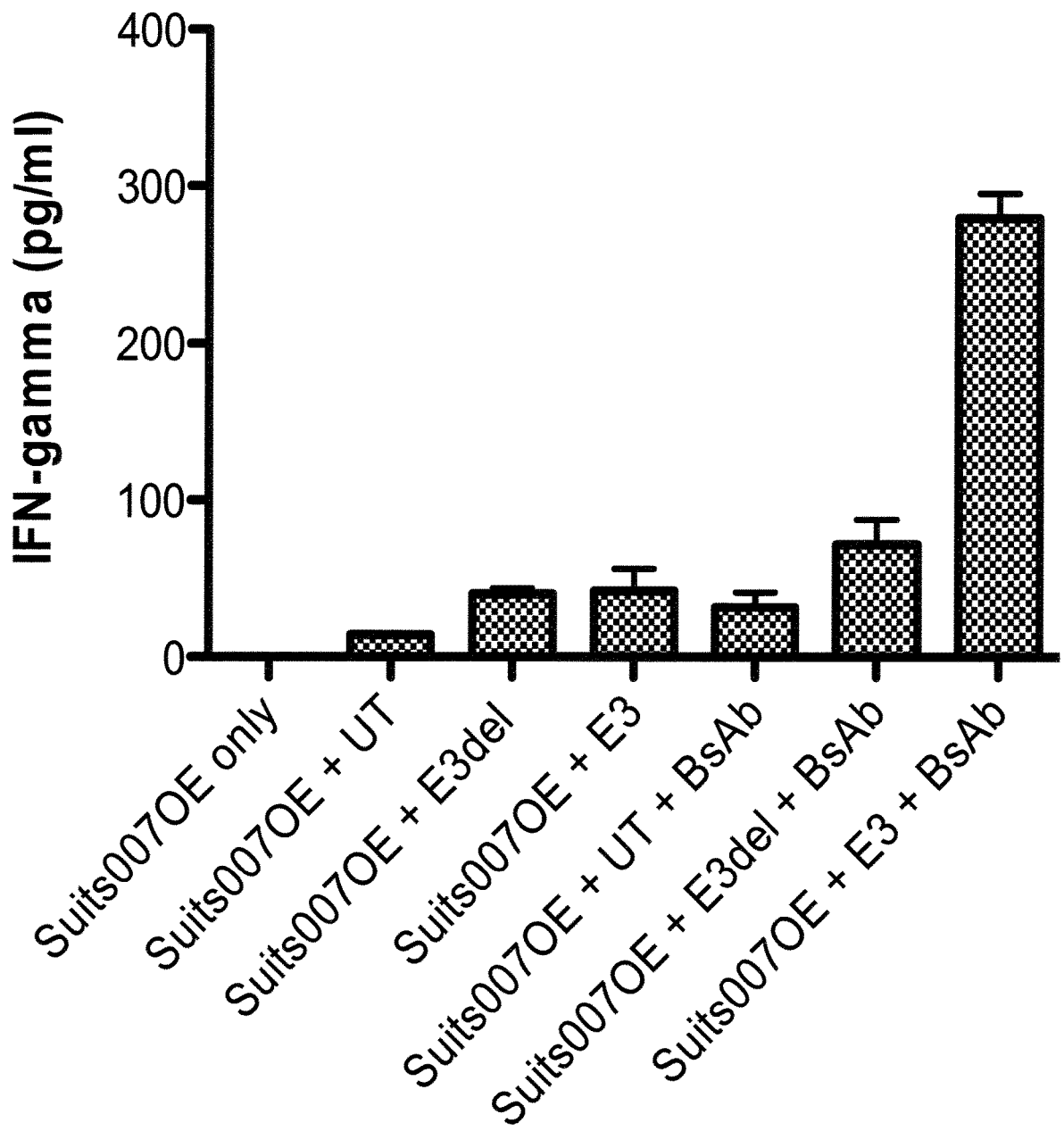
FIG. 17 shows INF-γ-secretion in T-cells of a mesothelin (MSLN) overexpressing pancreatic cell line ("Suits007OE") under various conditions.

FIG. 17: Suit-OE-MSLN Stimulation Assays: MSLN-Overexpressing Pancreatic Cells Lines Were Used to Test the Effectiveness of the Trivalent, Bispecific Antibody "EGFRvIII-MSLN" (SEQ ID NO: 235; See Also Tables 3 and 4) for the Conditional Stimulation of T-Cells in the Presence or Absence of Said Tumor Cells T-cells of a mesothelin (MSLN) overexpressing pancreatic cell line (named "Suits007OE" in the figure) were transduced with the human version of the EGFRvIII-CD38-CD3z fusion protein (SEQ ID NOs: 48 (protein) as encoded by SEQ ID NO: 47 (DNA)) (named hereinafter "E3 T-cells" or "E3") were stimulated for 48 hours with the trivalent, bispecific antibody (bsAb) "EGFRvIII-MSLN" (SEQ ID NO: 235; see also Tables 3 and 4) at an "EGFRvIII-MSLN" bsAB concentration of 1.0 µg/ml. The term "Suits007OE" refers to a pancreatic cell line. The "EGFRvIII-MSLN" bsAb specifically stimulates E3 T-cells while T-cells lacking full E3 construct (E3del (SEQ ID NOs: 247 (protein) and 246 (DNA)) and UT) do not get stimulated in the presence of the "EGFRvIII-MSLN" bsAb (soluble) and Suit007OE cells. The assay was performed at an effector to target ratio of 19:1 to tumour cells. Tumor cells were seeded 6 hours before co-culture; T-cells preloaded with the "EGFRvIII-MSLN" bsAb 30 minutes before co-culture (bsAb conc. 1 µg/ml). The results demonstrate the ability of the strategy to recognize and activate cancer cells. E3del is a truncated version of E3, devoid of the intracellular domains while UT refers to untransduced T-cells.

THE FOLLOWING EXAMPLES ILLUSTRATE THE INVENTION

Example 1: Preparation of the Tetravalent Bispecific Antibody "BsAb EpCAM-EGFRvIII, MR1.1" (SEQ ID NO: 229 (Light Chain (without Leader Sequence) and SEQ ID NO: 230 (Heavy Chain (without Leader Sequence))

The tetravalent, bispecific antibody molecule "BsAb EpCAM-EGFRvIII, MR1.1" (SEQ ID NO: 229 (light chain (without leader sequence) and SEQ ID NO: 230 (heavy chain (without leader sequence)) was prepared by the cloning strategy described in Examples 1, 2 and 4 of WO 2013/113615. Illustratively, as a proof of concept, in the following Example, the tetravalent, bispecific antibody molecule "BsAb EpCAM-EGFRvIII, MR1.1" (SEQ ID NOs: 229 and 230) with two antigen binding sites/binding domains for del-hEGFRvIII (SEQ ID NOs: 232 (protein) and 231 (nucleic acid (DNA)) on one arm and two antigen binding sites/binding domains for (murine) EpCAM (SEQ ID NO: 83 (nucleic acid (DNA)) and 84 (protein)) on the other arm was constructed in line with Example 4 of WO 2013/113615 (which is hereby incorporated by reference).

Example 2: Preparation of the Trivalent Bispecific Antibody 2.1 Preparation of the Trivalent, Bispecific Antibody (bsAb) Molecule "BsAB EGFRvIII-EpCAM" (SEQ ID NO: 233) which Comprises/Consists of the Plasmids/Vectors "EGFR vIII MR1.1 VH Ck muEpCAM VH CH1 EE Fc Knob PG LALA, pETR14953", "EGFR vIII MR1.1 VL CH1, pETR14951", "VL EpCAM G.8.8 Ck RK, pETR14882" and "VH muEpCAM CH1 EE Fc Hole PG LALA HRYF, pETR14940"; See Also Tables 1 and 2)

The trivalent, bispecific antibody molecule "BsAB EGFRvIII-EpCAM" (SEQ ID NO: 233) which comprises/consists of the plasmids/vectors "EGFR vIII MR1.1 VH Ck muEpCAM VH CH1 EE Fc knob PG LALA, pETR14953", "EGFR vIII MR1.1 VL CH1, pETR14951", "VL EpCAM G.8.8 Ck RK, pETR14882" and "VH muEpCAM CH1 EE Fc hole PG LALA HRYF, pETR14940"; see also Tables 1 and 2) was prepared in this example; schematic illustrations thereof is shown in FIG. 9A; muEpCAM/EGFRvIII 2+1 IgG, classic format (SEQ ID NO: 233; see also Tables 1 and 2). The variable domain of muEpCAM/ EGFRvIII was subcloned in frame with the constant chains pre-inserted into the respective recipient mammalian expression vector. Protein expression is driven by an CMV promoter and a synthetic polyA signal sequence is present at the 3' end of the CDS. In addition each vector contains an EBV OriP sequence. The molecules were produced by co-transfecting CHO cells growing in suspension with the mammalian expression vectors. Transient transfection was done at Evitria AG (Switzerland). The cells were transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)":"crossed light chain (VL-CH1)"). The filtered supernatant was kept at 4° C. until purification. The secreted protein was purified from cell culture supernatants by affinity chromatography using ProteinA affinity chromatography, followed by one to two size exclusion chromatographic steps. For affinity chromatography supernatant was loaded on a HiTrap Protein A FF column (CV=5 mL, GE Healthcare) equilibrated with 25 ml 20 mM sodium phosphate, 20 mM sodium citrate, 0.5 M sodium chloride, 0.01% Tween-20 pH 7.5. Unbound protein was removed by washing with at least 10 column volumes 20 mM sodium phosphate, 20 mM sodium citrate, 0.5 M sodium chloride, 0.01% Tween-20 pH 7.5 and target protein was eluted in 20 column volumes (gradient from 0%-100%) 20 mM sodium citrate, 0.5 M sodium chloride, 0.01% Tween-20 pH 2.5. Protein solution was neutralized by adding 1/10 of 2 M Tris pH 10.5. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM histidine, 140 mM sodium chloride, pH 6.0, 0.01% Tween20. For analytics after size exclusion chromatography the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% Bis-Tris, Invitrogen or 3-8% Tris-Acetate, Invitrogen) was used according to the manufacturer's instruction. The protein concentration of purified protein samples was determined by measuring the optical density (OD) at 280 nm divided by the molar extinction coefficient calculated on the basis of the amino acid sequence. Purity and molecular weight of the molecules after the final purification step were analyzed by CE-SDS analyses in the presence and absence of a reducing agent. The Caliper LabChip GXII system (Caliper Lifescience) was used according to the manufacturer's instruction (FIG. 9B, 9C). The aggregate content of the molecules was analyzed using a TSKgel G3000 SW XL analytical size-exclusion column (Tosoh) in 25 mM K2HPO4, 125 mM NaCl, 200 mM L-arginine monohydrocloride, 0.02% (w/v) NaN3, pH 6.7 running buffer at 25° C. (FIG. 9C). The final quality of all molecules was good, with ≥96% monomer content. The following Table 7 summarizes the production and purification of muEpCAM/EGFRvIII molecules. Molecules 1 and 2 in Table 7 refers to the trivalent, bispecific antibody molecule "BsAB EGFRvIII-EpCAM" (SEQ ID NO: 233) which comprises/consists of the plasmids/vectors "EGFR vIII MR1.1 VH Ck muEpCAM VH CH1 EE Fc knob PG LALA, pETR14953", "EGFR vIII MR1.1 VL CH1, pETR14951", "VL EpCAM G.8.8 Ck RK, pETR14882" and "VH muEpCAM CH1 EE Fe hole PG LALA HRYF, pETR14940"; see also Tables 1 and 2) as produced in an in vitro batch (Molecule 1) or as produced in an in vivo batch (Molecule 2).

TABLE 7

| Molecule | Titer [mg/l] | Yield [mg/l] | Analytical SEC (HMW/Monomer/LMW) [%] |
|---|---|---|---|
| 1 (in vitro batch) | 18 | 6.98 | 0%/100%/0% |
| 2 (in vivo batch) | 18 | 11.6 | 3.68%/96.32%/0% |

2.2 Preparation of the Trivalent, Bispecific Antibody (bsAb) Molecule "BsAB EGFRvIII-MSLN" (SEQ ID NO: 235 which Comprises/Consists of the Plasmids/Vectors "EGFRvIII MR1.1 VH Ck MSLN CH CH1 EE Fc Knob PG LALA, pETR15655", "EGFR VIII MR1.1 VL CH1, pETR15656", "VL MSLN Ck RK, pETR15443" and "VH MSLN CH1 EE Fc Hole PG LALA HRYF, pETR15667"; See Also Tables 3 and 4)

The trivalent, bispecific antibody molecule "BsAB EGFRvIII-MSLN" (SEQ ID NO: 235 which comprises/consists of the plasmids/vectors "EGFRvIII MR1.1 VH Ck MSLN CH CH1 EE Fc knob PG LALA, pETR15655", "EGFR vIII MR1.1 VL CH1, pETR15656", "VL MSLN Ck RK, pETR15443" and "VH MSLN CH1 EE Fc hole PG LALA HRYF, pETR15667"; see also Tables 3 and 4) was prepared in this example; schematic illustrations thereof is shown in FIG. 10A (MSLN/EGFRvIII 2+1 IgG, classic format (SEQ ID NO:235; see also Tables 3 and 4). The variable domain of MSLN/EGFRvIII was subcloned in frame with the constant chains pre-inserted into the respective recipient mammalian expression vector. Protein expression is driven by an MPSV promoter and a synthetic polyA signal sequence is present at the 3'-end of the CDS. In addition each vector contains an EBV OriP sequence. The molecules were produced by co-transfecting HEK293-EBNA cells growing in suspension with the mammalian expression vectors using polyethylenimine (PEI). The cells were transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)":"crossed light chain (VL-CH1)"). The filtered supernatant was kept at 4° C. until purification. For transfection HEK293 EBNA cells were cultivated in serum free ExCell culture medium containing 6 mM L-glutamine and 250 mg/l G418. For the production in 600 ml tube spin flasks (max. working volume 400 mL) 800 million HEK293 EBNA cells were seeded 24 hours before transfection without G418. For transfection 800 mio cells were centrifuged for 5 min at 210×g and supernatant was replaced by 40 ml pre-warmed CD-CHO medium containing 6 mM L-Glutamine. Expression vectors were mixed with 40 ml CD-CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tube spin flask and incubated for 3 hours at 37° C. in an incubator with a 5% $CO_2$ atmosphere. After incubation, 320 ml ExCell+6 mM L-glutamine+5 g/L Pepsoy+1.0 mM VPA+3 g/l glucose medium was added and cells were cultivated for 24 hours prior to feeding with 7% Feed 7. After 6-7 days, cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification. The secreted protein was purified from cell culture supernatants by affinity chromatography using ProteinA affinity chromatography, followed by one to two size exclusion chromatographic steps. For affinity chromatography supernatant was loaded on a HiTrap Protein A FF column (CV=5 mL, GE Healthcare) equilibrated with 25 ml 20 mM sodium phosphate, 20 mM sodium citrate, 0.5 M sodium chloride, 0.01% Tween-20 pH 7.5. Unbound protein was removed by washing with at least 10 column volumes 20 mM sodium phosphate, 20 mM sodium citrate, 0.5 M sodium chloride, 0.01% Tween-20 pH 7.5 and target protein was eluted in 20 column volumes (gradient from 0%-100%) 20 mM sodium citrate, 0.5 M sodium chloride, 0.01% Tween-20 pH 2.5. Protein solution was neutralized by adding 1/10 of 2 M Tris pH 10.5. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM histidine, 140 mM sodium chloride, pH 6.0, 0.01% Tween20.

Figure 10C:
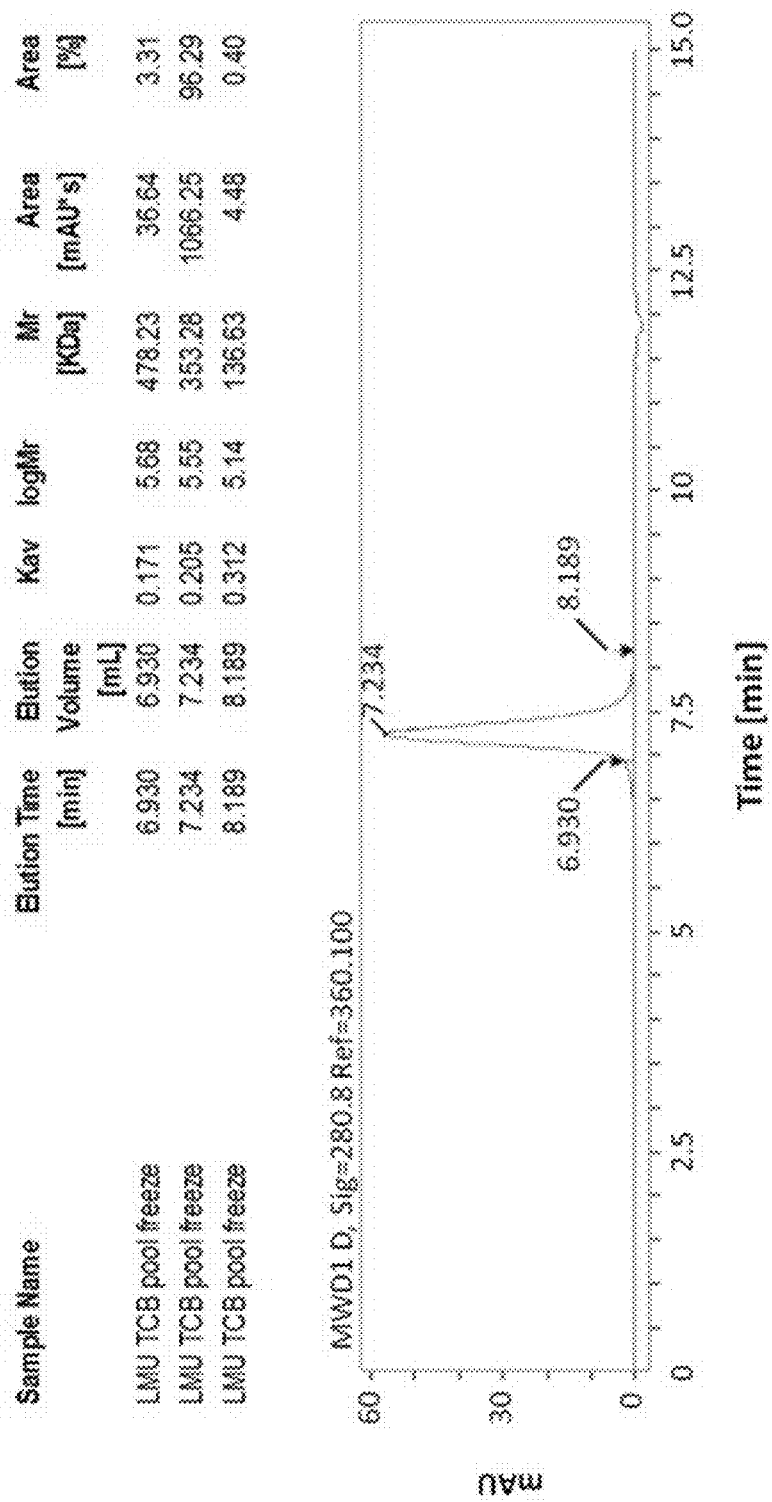
FIG. 10C shows analytical size exclusion chromatography analysis of BsAB EGFRvIII-MSLN.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction (FIG. 10C). The aggregate content (HMW) of the molecule was analyzed using a TSKgel G3000 SW XL analytical size-exclusion column (Tosoh) in 25 mM K2HPO4, 125 mM NaCl, 200 mM L-arginine monohydrocloride, 0.02% (w/v) NaN3, pH 6.7 running buffer at 25° C. (FIG. 10B). Molecule 1 in Table 8 refers to the trivalent, bispecific antibody molecule "BsAB EGFRvIII-MSLN" (SEQ ID NO: 235 which comprises/consists of the plasmids/vectors "EGFRvIII MR1.1 VH Ck MSLN CH CH1 EE Fc knob PG LALA, pETR15655", "EGFR vIII MR1.1 VL CH1, pETR15656", "VL MSLN Ck RK, pETR15443" and "VH MSLN CH1 EE Fc hole PG LALA HYRF, pETR15667"; see also Tables 3 and 4) as described above. The final quality of all molecules was good, with ≥96% monomer content. The following Table 8 summarizes the production and purification of MSLN/EGFRvIII molecules.

TABLE 8

| Molecule | Titer [mg/l] | Yield [mg/l] | Analytical SEC (HMW/Monomer/LMW) [%] |
|---|---|---|---|
| 1 | 65 | 1.16 | 3.31/96.3/0.4 |

2.3 Preparation of Trivalent, Bispecific Antibody (bsAb) Molecule "BsAB EGFRvIII-MCSP (SEQ ID NO: 234 which Comprises/Consists of the Plasmids/Vectors "MR1.1 EGFRvIII VH-Ck-(G4S)2 MCSP M4-3 VH CH1 EE Fc Knob PG LALA, pETR16621, "EGFR vIII MR1.1 VL CH1, pETR15656", "MCSP ML2 VL Ck RK, pETR16619" and "MCSP M4-3 VH CH1 EE Fc Hole PG LALA HYRF, pETR16618"; See Also Tables 5 and 6)

The trivalent, bispecific antibody molecule "BsAB EGFRvIII-MCSP (SEQ ID NO: 234 which comprises/consists of the plasmids/vectors "MR1.1 EGFRvIII VH-Ck-(G4S)2 MCSP M4-3 VH CH1 EE Fc knob PG LALA, pETR16621, "EGFR vIII MR1.1 VL CH1, pETR15656", "MCSP ML2 VL Ck RK, pETR16619" and "MCSP M4-3 VH CH1 EE Fc hole PG LALA HYRF, pETR16618"; see also Tables 5 and 6) was prepared in this example; schematic illustrations thereof is shown in FIG. 11A (MCSP/EGFRvIII 2+1 IgG, classic format (SEQ ID NO: 234; see also Tables 5 and 6). The variable domain of MCSP/EGFRvIII were subcloned in frame with the constant chains pre-inserted into the respective recipient mammalian expression vector. Protein expression is driven by an MPSV promoter and a synthetic polyA signal sequence is present at the 3'-end of the CDS. In addition each vector contains an EBV OriP sequence. The molecules were produced by co-transfecting HEK293-EBNA cells growing in suspension with the mammalian expression vectors using polyethylenimine (PEI). The cells were transfected with the corresponding expression vectors in a 1:2:1:1 ratio ("vector heavy chain hole (VH-CH1-CH2-CH3)":"light chain (LC)":"vector heavy chain knob (VH-CK-VH-CH1-CH2-CH3)": "crossed light chain (VL-CH1)"). The filtered supernatant was kept at 4° C. until purification. For transfection HEK293 EBNA cells were cultivated in serum free ExCell culture medium containing 6 mM L-glutamine and 250 mg/l G418. For the production in 600 ml tubespin flasks (max. working volume 400 mL) 800 million HEK293 EBNA cells were seeded 24 hours before transfection without G418. For transfection 800 mio cells were centrifuged for 5 min at 210×g and supernatant was replaced by 40 ml pre-warmed CD CHO medium containing 6 mM L-Glutamine. Expression vectors were mixed with 40 ml CD CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 320 ml ExCell+6 mM L-glutamine+5 g/L Pepsoy+1.25 mM VPA+3 g/l glucose medium was added and cells were cultivated for 24 hours prior to feeding with 12% Feed 7. After 6-7 days, cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification. The secreted protein was purified from cell culture supernatants by affinity chromatography followed by one to two size exclusion chromatographic steps. For affinity chromatography supernatant was loaded on a Protein A MabSelectSure GE Healthcare (CV=5 mL, GE Healthcare) equilibrated with 25 ml 20 mM Sodium Citrate, 20 mM Sodium Phosphate, pH 7.5. Unbound protein was removed by washing with at least 10 column volumes 20 mM Sodium Citrate, 20 mM Sodium Phosphate, pH 7.5 and target protein was eluted in 20 column volumes (gradient from 0%-100%) 20 mM Sodium Citrate, 100 mM Sodium Chloride, 100 mM Glycine, pH 3.0. Protein solution was neutralized by adding 0.5 M Na2HPO4 pH 8.0 (1:10). Target protein was concentrated with Amicon®Ultra-15 Ultracel 30K (Merck Millipore Ltd.) to a volume of 4 ml maximum prior loading on a HiLoad 16/600 S200, 120 ml column (GE Healthcare) equilibrated with 20 mM Histidine, 140 mM NaCl, 0.01% Tween pH 6.0. Purity and molecular weight of the molecules after the final purification step were analyzed by CE-SDS analyses in the presence and absence of a reducing agent. The Caliper LabChip GXII system (Caliper Lifescience) was used according to the manufacturer's instruction. The aggregate content of the molecules was analyzed using a TSKgel G3000 SW XL analytical size-exclusion column (Tosoh) in 25 mM K2HPO4, 125 mM NaCl, 200 mM L-arginine monohydrocloride, 0.02% (w/v) NaN3, pH 6.7 running buffer at 25° C. The final quality of all molecules was good, with ≥98% monomer content. The following Table 9 summarizes the production and purification of the trivalent bispecific antibody (bsAb) "BsAB EGFRvIII-MCSP (SEQ ID NO: 234) molecules.

TABLE 9

| Molecule | Titer [mg/l] | Yield [mg/l] | Analytical SEC (HMW/Monomer/LMW) [%] |
|---|---|---|---|
| 1 | 34 | 1.58 | 1.8/98.2/0 |

Example 3: Cloning and Expression of the Fusion Proteins 3.1 Cloning of the Fusion Proteins EGFRvIII-CD28-CD3z (SEQ ID NOs: 42 (Protein) and 41 (DNA)), EGFRvIII-CD28-4-1-BB-CD3z (SEQ ID NOs: 44 (Protein) and 43 (DNA)) and Cripto-CD28-4-CD3z (SEQ ID NOs: 46 (Protein) and 45 (DNA))

The EGFRvIII- and Cripto-fusion proteins were generated by overlap extension PCR and recombinant expression cloning into the retroviral pMP71 vector (Schambach et al., Mol Ther 2(5) (2000), 435-45; EP-B1 0 955 374). The construction of the EGFRvIII-CD28-CD3z fusion protein (SEQ ID NO: 42 (as encoded by the DNA shown in SEQ ID NO: 41)) was generated by PCR-amplification. Amplification was done in four steps: first, the human EGFRvIII-extracellular and transmembrane domain was amplified with a partial overlap for CD28 intracellular domain by using the following primers: 5'-AGCTTGCTCGCGGCCGCGCCAC-CATGCGACCCTCCG-3' (SEQ ID NO: 103; EGFRvIIINotIfwd) and 5'-TCTGTTCCTTCTACTAT-TCATGAAGAGGCCGATCCC-3' (SEQ ID NO: 104; EGFRtm CD28iz rev). At the same time, the intracellular domain of the murine CD28 was amplified with a partial overlap for the human EGFRvIII-transmembrane domain and murine CD3z domain by using the following primers: 5'-GGGATCGGCCTCTTCAT-GAATAGTAGAAGGAACAGA-3' (SEQ ID NO: 105; EGFRtm CD28iz fwd) and 5'-CTGCTGAAT-TTTGCTCTGGGGCGGTACGCTGCAA-3' (SEQ ID NO: 106; CD28in/CD3zeta rev). In the third reaction step, the murine CD3z was amplified with a partial overlap for the murine CD28 intracellular domain by using the following primers: 5'-TTGCAGCGTACCGCCCCAGAGCAAAAT-TCAGCAG-3' (SEQ ID NO: 107; CD3zeta/CD28fwd) and 5'-TAATGAATTCT-TAGCGAGGGGCCAGGGTC-3' (SEQ ID NO: 108; CD3zetaEcoRIrev). In the fourth and final step, all products were used as amplification templates using the EGFRvIII-primer (5'-AGCTTGCTCGCGGCCGCGC-CACCATGCGACCCTCCG; SEQ ID NO: 103; EGFRvIIINotIfwd) and the CD3z primer (5'-TAAT-GAATTCTTAGCGAGGGGCCAGGGTC-3'; CD3zetaEcoRIrev (SEQ ID NO: 108)).

For the Cripto-fusion proteins, cloning was done as follows in five steps: first the human was amplified with the following primers: 5'-ATTAGCGGCCGCGCCAC-CATGGAAACAGATACAC-3' (SEQ ID NO: 109; Leader_NotI_fwd) and 5'-AAATTCCT-GATGGCCCAGGCTTCTAGCAGGCTGGGC-3' (SEQ ID NO: 110; LeaderCriptoIsorev). The overlap of a IgK-leader sequence and human Cripto was done with the following primers: 5'-GCCCAGCCTGCTAGAAGCCTGGGCCATCAG-GAATTT-3' (SEQ ID NO: 111; LeaderCriptoIsofwd) and 5'-CAGCACTGGCTTGGTAGTAT-CACAGCCGGGTAGAAA-3' (SEQ ID NO: 112; Cripto CD8aex rev). Subsequently, the overlap of human Cripto and murine CD8 was done with the following primers: 5'-TTTCTACCCGGCTGTGA-TACTACCAAGCCAGTGCTG-3' (SEQ ID NO: 113; CriptoCD8aex fwd) and 5'-TCTGTTCCTTCTACTAT-TGATGAGAGTGATGATCAA-3' (SEQ ID NO: 114; CD8tm-CD28iz rev). Subsequently an overlap of murine CD8 and murine CD28 was done with the following primers: 5'-TTGATCATCACTCTCAT-CAATAGTAGAAGGAACAGA-3' (SEQ ID NO: 115; CD8tm-CD28izfwd) and 5'-CTGCTGAAT-TTTGCTCTGGGGCGGTACGCTGCAA-3' (SEQ ID NO: 116; CD28in/CD3zeta rev). The overlap of the murine CD28 and murine CD3z was done with the following primers: 5'-TTGCAGCGTACCGCCCCAGAGCAAAAT-TCAGCAG-3' (SEQ ID NO: 117; CD3zeta/CD28fwd) and 5'-TAATGAATTCT-TAGCGAGGGGCCAGGGTC-3' (SEQ ID NO: 118; CD3zetaEcoRIre). In the fifth and final reaction, all products were used as template, together with the following primers: 5'-ATTAGCGGCCGCGCCAC-CATGGAAACAGATACAC-3' (SEQ ID NO: 109; Leader_NotI_fwd) and 5'-TAATGAATTCT-TAGCGAGGGGCCAGGGTC-3' (SEQ ID NO: 118; CD3zetaEcoR1rev).

After amplification, the insert was ligated into the pMP71 vector using EcoRI and NotI restriction enzyme cutting and DNA-ligation.

3.2 Cloning of the Fusion Proteins EGFRvIII-CD28-CD3z (SEQ ID NOs: 48 (Protein) and 47 (DNA)) and EGFRvIII-CD28-4-1-BB-CD3z (SEQ ID NOs: 50 (Protein) and 49 (DNA))

3.2.1 EGFRvIII-CD28-CD3z (SEQ ID NOs: 48 (Protein) and 47 (DNA))

In a first reaction a 3'-overlap for CD28 was created by using the following primers: EGFRvIII fwd (5'-AGCTTGCTCGCGGCCGCGCCAC-CATGCGACCC-3' (SEQ ID NO: 125)) and the primer EGFRvIII (-human CD28) rev (5'-CCACCAGCACC-CAAAAGGACGGGATCTTAGGCCCA-3' (SEQ ID NO: 126)). In the second reaction a 5'-overlap for CD28 and 3'-overlap for CD3Z was done by using the primers: (EGFRvIII-) human CD28 fwd (5'-TGGGCCTAA-GATCCCGTCCTTTTGGGTGCTGGTGG-3' (SEQ ID NO: 127)) and human CD3z rev (5'-TAATGAAT-TCTTAGCGAGGGGGCAGG-3' (SEQ ID NO: 128)). The third reaction using the above products comprised the primers EGFRvIII fwd (5'-AGCTTGCTCGCGGCCGCGCCAC-CATGCGACCC-3' (SEQ ID NO: 129)) and human CD3z rev (5'-TAATGAATTCT-TAGCGAGGGGGCAGG-3' (SEQ ID NO: 130)).

After amplification, the insert was ligated into the pMP71 vector using EcoRI and NotI restriction enzyme cutting and DNA-ligation.

3.2.2 EGFRvIII-CD28-4-1-BB-CD3z (SEQ ID NOs: 50 (Protein) and 49 (DNA))

In a first reaction a 3'-overlap for CD28 was done by using the following primers: 5'-AGCTTGCTCGCGGCCGCGCCAC-CATGCGACCC-3' (SEQ ID NO: 131; EGFRvIII) and 5'-CCACCAGCACCCAAAAGGACGGGATCT-TAGGCCCA-3' (SEQ ID NO: 132; human CD28 rev). In the second reaction a 5'-overlap for EGFRv3 and a 3'-overlap for 4-1-BB was done by using the primer (EGFRvIII-) human CD28 fwd (5'-TGGGCCTAA-GATCCCGTCCTTTTGGGTGCTGGTGG-3' (SEQ ID NO: 133) and the primer human CD28 (-human 4-1-BB1) rev (5'-CTTTCTGCCCCGTTTGGAGCGA-TAGGCTGCGA-3' (SEQ ID NO: 134)). In the third reaction a 5'-overlap for CD28 and a 3'-overlap for CD3z was done with the following primers: (human CD28-) human 4-1-BB fwd (5'-TCGCAGCC-TATCGCTCCAAACGGGGCAGAAAG-3' (SEQ ID NO: 135)) and human 4-1-BB (-human CD3z) rev (5'-TGCTGAACTTCACTCTCAGTTCA-CATCCTCCT-3' (SEQ ID NO: 136)). In the fourth reaction a 5'-overlap for 41BB and 3'-overlap for CD3z was done by using the following primers: (human 4-1-BB-) human CD3z fwd (5'-GGAGGATGT-GAACTGAGAGTGAAGTTCAGCAGGA-3' (SEQ ID NO: 137)) and the primer human CD3z rev (5'-TAATGAATTCTTAGCGAGGGGGCAGG-3' (SEQ ID NO: 138)). In the fourth and final reaction, all products were used as template, together with the 5'-Leader primer EGFRvIII fwd (5'-AGCTTGCTCGCGGCCGCGCCAC-CATGCGACCC-3' (SEQ ID NO: 139)) and human CD3z rev (5'-TAATGAATTCT-TAGCGAGGGGGCAGG-3' (SEQ ID NO: 140)).

After amplification, the insert was ligated into the pMP71 vector using EcoRI and NotI restriction enzyme cutting and DNA-ligation.

3.2.3 CAR1 Human (Cripto-CD8aex/Tm-CD28iz-CD3z) (SEQ ID NOs: 120 (Protein) and 119 (DNA))

In the first reaction a 3'-overlap for CD8 was done by using the following primers: Cripto fwd (5'-ATT-AGCGGCCGCGCCACCATGGAAACAGATACAC-3' (SEQ ID NO: 141)) and Cripto (-human CD8a) rev (5'-ACACCCGGAACTGGCTAT-CACAGCCGGGTAGA-3' (SEQ ID NO: 142)). In the second reaction a 5'-overlap for Cripto and a 3'-overlap for CD28 was done by using the primers (Cripto-) human CD8a fwd (5'-TCTACCCGGCTGTGA-TAGCCAGTTCCGGGTG-3' (SEQ ID NO: 143)) and human CD8a (-human CD28) rev (5'-CTCCTCT-TACTCCTGGTGATAACCAGTGACAGG-3' (SEQ ID NO: 144)). In the third reaction a 5'-overlap for CD8 and a 3'-overlap for CD3z was amplified by using the following primers (human CD8a-) human CD28 fwd (5'-CCTGTCACTGGTTATCACCAGGAGTAAGAG-GAGCAGG-3' (SEQ ID NO: 145)) and human CD3z rev (5'-TAATGAATTCTTAGCGAGGGGGCAGG-3' (SEQ ID NO: 146)). In the fourth and final reaction, all products were used as template, together with the 5'-leader primer by using the following primers: Cripto fwd (5'-ATTAGCGGCCGCGCCACCATGGAAACA-GATACA-3' (SEQ ID NO: 147)) and human CD3z rev (5'-TAATGAATTCTTAGCGAGGGGGCAGG-3' (SEQ ID NO: 148)).

After amplification, the insert was ligated into the pMP71 vector using EcoRI and NotI restriction enzyme cutting and DNA-ligation.

3.2.4 The construct E3del (SEQ ID NOs: 247 (protein) and 246 (DNA)) were generated by overlap extension polymerase chain reaction (PCR) and cloned into the retroviral pMP71 vector. According to the EGFRvIII sequence, specific overlap primers were designed with the SnapGene Software Suite. The melting point of the annealing parts was calculated with the online Tm Calculator V 1.8.1 from New England BioLabs (NEB). All PCR reactions were solely executed with the Q5 polymerase from NEB. The construct E3del consist extracellular of the human EGFRvIII, the human EGFRvIII transmembrane domain and 10 intracellular amino acids to improve the anchoring of E3 del in the cell membrane.

Example 4: Transduction of T-Cells and Cytotoxic Killing Assay 4.1 Cell Culture 4.1.1 Murine Cancer Cell Line The murine pancreatic cancer cell line Panc02 and its ovalbumin-transfected counterpart Panc02-OVA have been previously described (Jacobs et al., Int J Cancer 128(4) (2011), 897-907). The Panc02-cell line was generated through injection of the carcinogen Methycholantren A into the pancreas of wild type C57Bl/6 mice to induce carcinogenesis. Panc02-OVA-EpCAM was generated by transduction with pMXs-puro (Kitamura et al., Exp. Hematol. 31 (2003), 1007-1014) containing full length murine EpCAM (SEQ ID NOs: 83 (nucleic acid (DNA)) and 84 (protein)) and selection with puromycin with a end concentration of 10 µg/ml. The packaging cell line Plat-E has been previously described by Morita et al., Gene Ther 7 (2000), 1063-6). All cells were cultured in DMEM with 10% fetal bovine serum (FBS, Life Technologies, USA), 1% penicillin and streptomycin (PS) and 1% L-glutamine (all from PAA, Germany). 10 µg/ml puromycin and 1 µg/ml blasticidin (Sigma, Germany) were added to the Plat-E medium. Primary murine T-cells (see section 2.5 below for the cultivation) were cultured in RPMI 1640 with 10% FBS, 1% PS and 1% L-glutamine. 1% sodium pyruvate, 1 mM HEPES and 50 µM β-mercaptoethanol were added to the T-cell medium.

4.1.2 Human Cancer Cell Line

The human pancreatic cancer cell line SUIT-2 has been previously described (Iwamora et al., Jpn J Cancer Res. 78(1) (1987), 54-62). The SUIT-2 cell line was derived from a metastatic liver tumor of human pancreatic carcinoma. SUIT-2-OE-MSLN was generated by transduction with pMP71-amp (Kitamura et al., Exp. Hematol. 31 (2003), 1007-1014) containing full length human MSLN (SEQ ID NOs: 83 (nucleic acid (DNA)) and 84 (protein)) and selection with ampicillin with an end concentration of 10 µg/ml. The Flp-HEK 293 human embryonic kidney epithelial cells have been previously described (Thankamony et al., The Journal of Biological Chemistry 281(45) (2006), 34601-34609). The cell line HEK293-FLPin-MSLN was generated by transduction with pMP71-amp (Kitamura et al., Exp. Hematol. 31 (2003), 1007-1014) containing full length human MSLN (SEQ ID NOs: 83 (nucleic acid (DNA)) and 84 (protein)) and selection with ampicillin with an end concentration of 10 µg/ml. The packaging cell line Plat-A has been previously described by Wu et al., J Biomed Biotechnol. 2009 (2009), 901079. All cells were cultured in DMEM with 10% fetal bovine serum (FBS, Life Technologies, USA), 1% penicillin and streptomycin (PS) and 1% L-glutamine (all from PAA, Germany). 10 µg/ml puromycin and 1 µg/ml blasticidin (Sigma, Germany) were added to the Plat-A medium. Primary human T-cells (see section 2.5 below for the cultivation) were cultured in VLE RPMI 1640 with 2.5% human serum, 1% PS, 1% L-glutamine, 1% sodium pyruvate, and 1% non-essential amino acids.

4.1.3 The human pancreatic cancer cell line SUIT-2 has been previously described (Iwamora et al., Jpn J Cancer Res. 78(1) (1987), 54-62). The cell line is available through different repositories such as the cell bank Australia (CODE: JCRB1094). The SUIT-2 cell line was derived from a metastatic liver tumour of human pancreatic carcinoma. SUIT-2-OE-MSLN was generated by transduction with pMXs-amp (Kitamura et al., Exp. Hematol. 31 (2003), 1007-1014) containing full length human MSLN/CAK1/MPF (HGNC ID: HGNC:7371 (Chang et al. PNAS. 93(1) (1996), 136-40). Human MSLN was derived from the cDNA of HeLa cells (Macville et al., Cancer Res. 59(1) (1999), 141-50). The MSLN gene encodes a 71-kDa precursor protein, further processed to a 40-kDa glycosyl-phosphatidylinositol-anchored cell-surface protein called mesothelin, and a N12-terminal 31-kDa fragment termed megakaryocyte-potentiating factor that is released from the cell (Ho et al., Clin Cancer Res. 13(5) (2007), 1571-75).

4.2 T-Cell Transduction 4.2.1 Murine T-Cell Tranduction

The retroviral vector pMP71 (Schambach et al., Mol Ther 2(5) (2000), 435-45; EP-B1 0 955 374) was used for transfection of the ecotrophic packaging cell line Plat-E. Transduction was performed according to the method described by Leisegang et al., J Mol Med 86 (2008), 573-83; Mueller et al., J Virol. 86 (2012), 10866-10869; Kobold et al., J Natl Cancer Inst (2014), in press. In brief, packaging cell line Plat E (as described by Morita et al., Gene Ther 7 (2000), 1063-6) was seeded in 6-well plates and grown over night to 70-80% confluence. On day one, 16 µg of DNA were mixed together with 100 mM CaCl2) (Merck, Germany) and 126.7 µM Chloroquin (Sigma, USA). Plat-E cells were starved for 30 min in low serum medium (3%) and then incubated for 6 h with the precipitated DNA. Medium was then removed and exchanged with culture medium. On day two, primary splenocytes were harvested from C57Bl/6 mice (Harlan Laboratories, The Netherlands). Single cell suspensions of splenocytes were stimulated with anti-CD3 (clone 145-2c11 BD Pharmingen, USA), anti-CD28 (clone 37.51, BD Pharmingen, USA) and recombinant murine IL-2 (Peprotech, Germany) in T-cell medium over night. On day 3, 24-well plates were coated with 12.5 µg/ml recombinant retronectin (Takara Biotech, Japan) for 2 h at room temperature, blocked with 2% bovine serum albumin (Roth, Germany) for 30 min at 37° C. and washed with PBS. Supernatant of Plat E was harvested and passed through a filter (40 µm, Milipore, USA). Fresh T-cell medium was then added to Plat E cells. 1 ml of filtered supernatant was distributed in each well and spinoculated for 2 h at 4° C. Supernatant was then removed from the 24-well plate. $10^6$ T-cells were seeded in one ml T-cell medium supplemented with 10U IL-2 and 400000 anti-CD3 and anti-CD28 beads (Invitrogen, Germany) per well and spinoculated at 800 g for 30 min at 32° C. On day four, Plat E supernatant was again harvested and filtered. 1 ml was added to each well of the 24-well plate and spinoculated at 800 g for 90 min at 32° C. Cells were subsequently incubated for 6 additional hours at 37° C. 1 ml supernatant was replaced by T-cell medium with IL-2. On day five, cells were harvested, counted and reseeded at $10^6$ cells/ml density in T-cell medium supplemented with 10 ng IL-15 per ml (Peprotech, Germany). T-cells were kept at this density until day 10 when cell analysis or functional assays were performed.

4.2.2 Human T-Cell Transduction

The retroviral vector pMP71 (Schambach et al., Mol Ther 2(5) (2000), 435-45; EP-B1 0 955 374) was used for transfection of the ecotrophic packaging cell line Plat-A. Transduction was performed according to the method described by Leisegang et al., J Mol Med 86 (2008), 573-83; Mueller et al., J Virol. 86 (2012), 10866-10869; Kobold et al., J Natl Cancer Inst (2014). In brief, packaging cell line Plat A (as described by Morita et al., Gene Ther 7 (2000), 1063-6) was seeded in 6-well plates and grown over night to 70-80% confluence. On day one, 18 µg of DNA was mixed together with 100 mM $CaCl_2$) (Merck, Germany). Plat-A cells were starved for 30 min in low serum medium (3%) and then incubated for 6 h with the precipitated DNA. Medium was then removed and exchanged with culture medium. Additionally 6-well plates are prepared for T-cells on day 2 by coating them with anti-human CD3 and CD28 antibodies (clones HIT3a and CD28.2, respectively) (eBiosciences, Germany). On day two, whole blood was taken from a healthy donor. PBMCs were then isolated using density-gradient centrifugation. Isolation of $CD3^+$ cells was carried out after incubation with human CD3 microbeads and following the MACS CD3 positive selection kit LS-column protocol (Miltenyi Biotec, Germany). CD3+ T-cells were then cultured as described in section 4.1 with the addition of IL-2, IL-15 and 0-mercaptoethanol (all Peprotech, Germany) and 8.25 µl/$10^6$ cells of human CD3/CD28 dynabeads in T-cell medium over night. On day 3, 24-well plates were coated with 12.5 μg/ml recombinant retronectin (Takara Biotech, Japan) and incubated at 4° C. overnight. On Day 4 plates are blocked with 2% bovine serum albumin (Roth, Germany) for 30 min at 37° C. and washed with 2.5% HEPES in PBS. Supernatant of Plat A was harvested and passed through a filter (40 μm, Milipore, USA). Fresh DMEM culture medium was then added to Plat A cells. 1 ml of filtered virus supernatant was added in each well and subsequently centrifuged for 1 h 30 minutes at 32° C. Supernatant was then removed from the 24-well plate. $10^6$ T-cells were seeded where the relevant virus supernatant was, in 1 ml T-cell medium supplemented with IL-2, IL-15 and β-mercaptoethanol. On day five, day four's protocol was repeated as the T-cells are given a second and final transduction hit. On day six, cells were harvested, counted and reseeded at $10^6$ cells/ml density in T-cell medium supplemented with IL-2, IL-15 and β-mercaptoethanol (Peprotech, Germany). T-cells are then checked for their transduction efficiency using FACS analysis. If transduction is successful T-cells are re-cultured and maintained at a concentration of $10^6$ cells/ml every second day.

4.3 Killing Assay 20.000 PancOVAEpCAM murine pancreatic cancer cells stably expressing ovalbumine (SEQ ID NOs: 200 (protein) and 199 (DNA)) and transduced with EpCAM (SEQ ID NOs: 202 (protein) and 201 (DNA)) were seeded on a 96-well flat bottom plate (Corning). 100.000 T-cells that were transduced with the EGFRvIII-CD28-CD3z fusion protein (SEQ ID NOs: 42 (protein) and 41 (DNA)) were preloaded with bsAb (either the trivalent, bispecific antibody molecule "EGFRvIII MR1.1 VH Ck MSLN CH CH1 EE Fc knob PG LALA, pETR15655" (SEQ ID NO: 2 (as encoded by the DNA sequence shown in SEQ ID NO: 1) or the tetravalent, bispecific antibody molecule "BsAb EpCAM-EGFRvIII, MR1.1" (SEQ ID NOs: 229 (light chain amino acid sequence) and 230 (heavy chain amino acid sequence)) for 30 min and co-cultured with the tumor cells (Panc02-OVA-EpCAM or Panc02-OVA) for 8-12 hours (E:T=5:1). Lactate dehydrogenase (LDH) levels in the supernatant was quantified according to the manufacturer's instructions (CytoTox 96® Non-Radioactive Cytotoxicity Assay, Promega). In brief, LDH catalyzes the reduction of $NAD^+$ to NADH and $H^+$ by oxidation of lactate to pyruvate. Next, diaphorase reacts with NADH and $H^+$ to catalyze the reduction of a tetrazolium salt (INT) to formazan which absorbs at 490 nm. Specific lysis (%) was calculated according to the following formula:

$$(LDH^{of\ interest} - LDH^{of\ background} - LDH^{effector\ only}) / (LDH^{total\ lysis} - LDH^{minimal\ lysis} - LDH^{of\ background}) \times 100\%.$$

4.4 Interferon-γ (IFN-γ) Release Assay

A 96-well flat bottom plate (Corning) was coated with the tetravalent bispecific antibody molecule "BsAb EpCAM-EGFRvIII, MR1.1", the trivalent bispecific antibody molecule "EGFRvIII MR1.1 VH Ck MSLN CH CH1 EE Fc knob PG LALA, pETR15655" (SEQ ID NOs: 2 (protein) and 1 (DNA)) or Cetuximab (Erbitux®, Merck) with increasing concentrations (0 μg/mL; 0.1 μg/mL; 1 μg/mL; 10 μg/mL) for 12 hours at 4° C. The wells were blocked with 20% fetal bovine serum (FBS, Life Technologies, USA) for 30 min at 37° C. and 0.25×$10^6$ T-cells with the EGFRvIII-CD28-CD3z fusion protein (SEQ ID NOs: 42 (protein) and 41 (DNA) (hereinafter referred to as E3 cells) or wild-type (WT) T-cells were added, respectively. After 48 hours the supernatants were collected and IFN-γ release was quantified by enzyme-linked immunosorbent assay (ELISA; BD). Absorbance was measured by Mithras LB 940 Multimode Microplate reader (Software MicroWin 2000).

4.5 Killing Assay with iCELLigence 50.000 PancOVAEpCAM tumor cells were seeded on an E-Plate L8 (OLS) and tumor cell proliferation was measured over the timeframe of 20 h every 20 min. 500.000 C57B16 wildtype T-cells transduced with the EGFRvIII-CD28-CD3z fusion protein (SEQ ID NOs: 42 (protein) and 41 (DNA) or an EpCam scVf-CD3z chimeric antigen receptor (CAREpCAM; SEQ ID NO: 249 (protein) and 248 (DNA)) were added to the tumor cells respectively. EGFRvIII-CD28-CD3z fusion protein (SEQ ID NOs: 42 (protein) and 41 (DNA) transduced T-cells were preloaded with 1 μg/mL bsAb as described previously. For the FasL blocking conditions 10 μg/mL CD178 (Fas Ligand) Monoclonal Antibody (clone: MFL3; Cat. No. 16-5911-85 (ThermoFisher Scientific™)), Functional Grade (eBioscience) were added immediately to the well. T-cell killing was measured for 24 h every 6 min.

4.6 Antibody Binding Assay 0.25×$10^6$/150 μL T-cells transduced with the EGFRvIII-CD28-CD3z fusion protein (SEQ ID NOs: 42 (protein) and 41 (DNA) were incubated with bsAb (tri- or tetraspecific in 50 μL PBS) in increasing concentrations (10 ng/mL; 100 ng/mL; 500 ng/mL; 1 μg/mL; 5 μg/mL; 10 μg/mL; 20 μg/mL; 25 μg/mL) for 30 min at 37° C. 1 μL of the secondary antibody FITC-conjugated AffiniPure F(ab')2 Fragment Goat Anti-Human IgG (Jackson Laboratories; FITC AffiniPure F(ab')$_2$ Fragment Goat Anti-Human IgG, F(ab')$_2$ fragment specific: 109-096-097) or Cy2-conjugated AffiniPure Goat Ant-Mouse IgG (Jackson Laboratories; Cy2 AffiniPure Goat Anti-Mouse IgG: 115-225-006) were added and incubated for 30 min at 4° C. FITC mean fluorescence intensity (FITC MFI) was quantified by flow cytometry. Staining was analysed using BD FACS Canto II (BD, Germany). Surface saturation was calculated as percentage of maximum (FITC MFIof interest/FITC MFIhighst concentration)×100%. Data analysis was performed with FlowJo 7.6.1.

4.7 Statistical Analysis

For statistics, GraphPad Prism software version 5.0b was used. All variables reported are continuous. Differences between experimental conditions were analyzed using the unpaired two-sided Student's t-test. For comparison of experimental conditions of individual mice, the Mann-Whitney test was used. p-values <0.05 were considered significant.

4.8 T-Cell Stimulation Assay

Suit-OE-MSLN tumor cells were seeded in T-cell medium for 6 hours in a 96-well flat bottom plate (Corning). After 5 and a half hours T-cells were co-incubated with the trivalent, bispecific antibody (bsAb) molecule "BsAb EGFRvIII-MSLN" (SEQ ID NO: 235; see also Tables 3 and 4) for 30 minutes. Following this the T-cell/bispecific antibody conjugate was added to the tumor cells, and incubated at 37° C., 5% $CO_2$ for 48 hours. Following this period the supernatants were collected and IFN-γ release was quantified by enzyme-linked immunosorbent assay (ELISA; BD). Absorbance was measured by Mithras LB 940 Multimode Microplate reader (Software MicroWin 2000).

4.9 Recombinant Mesothelin-T-Cell Stimulation Assay

Human recombinant mesothelin protein (5 μg/ml) (Sino Biological Inc., Germany) was coated and incubated at 4° C. overnight in a 96-well flat bottom plate (Corning). Plates were blocked with 10% FBS in PBS. T-cells were co-incubated with the trivalent, bispecific antibody (bsAb) molecule "BsAb EGFRvIII-MSLN" (SEQ ID NO: 235; see also Tables 3 and 4) for 30 minutes. Following this the T-cell/bispecific antibody conjugate was added to the recombinant mesothelin coated wells, and incubated at 37° C., 5% $CO_2$ for 48 hours. Following this period the supernatants were collected and IFN-γ release was quantified by enzyme-linked immunosorbent assay (ELISA; BD). Absorbance was measured by Mithras LB 940 Multimode Microplate reader (Software MicroWin 2000).

Example 5: Examples of Particular Embodiments

Examples of certain non-limiting embodiments of the disclosure are listed hereafter. In particular, the present invention relates to the following items:

1. A kit comprising
   (A) a nucleic acid molecule encoding a fusion protein for transducing T-cells obtained from a subject to be treated which has the following domains:
      (1) an extracellular domain of a signalling receptor that does not naturally occur in or on said T-cells;
      (2) an anchoring transmembrane domain; and
      (3) a stimulatory signalling domain, and
   (B) a trivalent, bispecific antibody molecule which comprises:
      (i) a first binding domain binding the extracellular domain (1) of the fusion protein characterized in (A);
      (ii) a second binding domain binding a tumor-specific antigen naturally occurring on the surface of a tumor cell; and
      (iii) a third binding domain binding the extracellular domain (1) of the fusion protein characterized in (A), or binding said tumor-specific antigen naturally occurring on the surface of a tumor cell.
2. The kit of item 1, wherein said fusion protein further comprises at least one co-stimulatory signalling domain.
3. The kit of item 1 or item 2, wherein said anchoring transmembrane domain does not have a cleavage site for mammalian proteases
4. The kit of any one of items 1 to 3, wherein said fusion protein further comprises a hinge domain.
5. A trivalent, bispecific antibody molecule which comprises:
   (i) a first binding domain binding the extracellular domain (1) of the fusion protein characterized in item 1(A);
   (ii) a second binding domain binding a tumor-specific antigen naturally occurring on the surface of a tumor cell; and
   (iii) a third binding domain binding the extracellular domain (1) of the fusion protein characterized in item 1(A), or binding said tumor-specific antigen naturally occurring on the surface of a tumor cell.
   for use as a medicament, wherein said bispecific antibody molecule is to be administered before, simultaneously with or after administration of transduced T-cells comprising a fusion protein characterized in item 1(A) and wherein said T-cells were obtained from the subject to be treated.
6. A pharmaceutical composition comprising a trivalent, bispecific antibody molecule which comprises:
   (i) a first binding domain binding the extracellular domain (1) of the fusion protein characterized in item 1(A);
   (ii) a second binding domain binding a tumor-specific antigen naturally occurring on the surface of a tumor cell; and
   (iii) a third binding domain binding the extracellular domain (1) of the fusion protein characterized in item 1(A), or binding said tumor-specific antigen naturally occurring on the surface of a tumor cell
   which is to be administered in combination with transduced T-cells comprising an a fusion protein characterized in item 1(A) and wherein said T-cells were obtained from the subject to be treated.
7. A trivalent, bispecific antibody molecule which comprises:
   (i) a first binding domain binding the extracellular domain (1) of the fusion protein characterized in item 1(A);
   (ii) a second binding domain binding a tumor-specific antigen naturally occurring on the surface of a tumor cell; and
   (iii) a third binding domain binding the extracellular domain (1) of the fusion protein characterized in item 1(A), or binding said tumor-specific antigen naturally occurring on the surface of a tumor cell
   for use in a method of treating a malignant disease, wherein said trivalent, bispecific antibody molecule is to be administered before, simultaneously with or after administration of transduced T-cells comprising a fusion protein characterized in item 1(A) and wherein said T-cells were obtained from the subject to be treated.
8. A method of treatment of a malignant disease, the method comprising the administration of a trivalent, bispecific antibody molecule to a subject in need thereof which comprises:
   (i) a first binding domain binding the extracellular domain (1) of the fusion protein characterized in item 1(A);
   (ii) a second binding domain binding a tumor-specific antigen naturally occurring on the surface of a tumor cell; and
   (iii) a third binding domain binding the extracellular domain (1) of the fusion protein characterized in item 1(A), or binding a tumor-specific antigen naturally occurring on the surface of a tumor cell,
   wherein said trivalent, bispecific antibody molecule is administered before, simultaneously with or after administration of transduced T-cells from said subject comprising a fusion protein characterized in item 1(A).
9. The trivalent, bispecific antibody molecule of item 7, or the method for treating a malignant disease according to item 8, wherein said malignant disease is selected from cancer of epithelial, endothelial or mesothelial origin and cancer of the blood.
10. The kit of any one of items 1 to 4, the pharmaceutical composition of item 6, the trivalent, bispecific antibody molecule of item 5 or 7, or the method of item 8 or 9, wherein said antigen that naturally occurs on the surface of tumor cells is selected from the group consisting of EpCAM, MSLN, MCSP, HER-1, HER-2, HER-3, CD20, CD22, CD33, CD52, FLT-3, FOLR1, Trop-2, CA-12-5, HLA-DR, MUC-1 (mucin), A33-antigen, PSMA PSCA, (prostate specific membrane antigen), transferrin-receptor, tenascin and CA-IX (carbonic anhydrase IX).
11. The kit of any one of items 1 to 4 or 10, the pharmaceutical composition of item 6 or item 10, the trivalent, bispecific antibody molecule of any one of items 5, 7 or 10, the method of any one of items 8, 9 or 10, wherein said extracellular domain of a signalling receptor that does not naturally occur in or on said T-cells is selected from the group consisting of consisting of Cripto (cryptic family protein), members of the CD (cluster of differentiation)-family (non T-cell), EGFR, EGFRvIII and TSH-R.
12. The kit of any one of items 1 to 4, 10 or 11, the pharmaceutical composition of any one of items 6, 10 or 11, the trivalent, bispecific antibody molecule of any one of items 5, 7, 10 or 11, or the method of any one of items 8 to 11, wherein said transduced T-cell further comprises a T-cell receptor that naturally occurs on said T-cell and/or a T-cell receptor that has been genetically introduced into said T-cell.
13. An expression vector comprising nucleic acid sequences encoding the trivalent, bispecific antibody as defined in any one of items 1(B) and 5 to 8.
14. The vector of item 13, which is polycistronic.
15. The vector of item 13 or item 14, wherein said vector further comprises a regulatory sequence which is operable linked to said nucleic acid sequence of item 13.
16. A host cell transformed with a vector as defined in any one of items 13 to 15.
17. A method for the production of a trivalent, bispecific antibody molecule as defined in any one of items 1(B) and 5 to 8, said method comprising
    (a) culturing a host cell as defined in item 16 under conditions allowing the expression of the trivalent, bispecific antibody molecule as defined in any one of items 1(B) and 5 to 8; and
    (b) recovering the produced trivalent, bispecific antibody molecule from the culture.
18. A trivalent, bispecific antibody molecule as defined in any one of items 1(B) and 5 to 8 which comprises
    (i) a first binding domain binding the extracellular domain (1) of the fusion protein characterized in item 1(A);
    (ii) a second binding domain binding a tumor-specific antigen naturally occurring on the surface of a tumor cell; and
    (iii) a third binding domain binding the extracellular domain (1) of the fusion protein characterized in item 1(A), or binding said tumor-specific antigen naturally occurring on the surface of a tumor cell,
    wherein said antibody molecule is obtainable by the method of item 17.
19. A method for treating a disease in a subject comprising the steps of:
    (a) isolating T-cells from a subject;
    (b) transducing said isolated T-cells with a fusion protein characterized in item 1(A); and
    (c) administering said transduced T-cells to said subject.
20. The method of item 19, wherein said transduced T-cells are administered to said subject by intravenous infusion.
21. The method of item 19 or item 20, wherein the transduced T-cells are co-transduced with a T-cell receptor.
22. The method of any one of items 19 to 21, wherein said transduced T-cells are expanded by anti-CD3 and anti-CD28 antibodies.
23. The method of any one of items 19 to 22, wherein the expansion of the transduced T-cells is performed in the presence of cytokines, preferably interleukin-2 (IL-2) and/or interleukin-15 (TL-15).
24. The method of any one of items 19 to 23, further comprising
    (d) administering the trivalent, bispecific antibody as defined in any one of items 1(B) and 5 to 8 or 18.
25. The method for treating a disease of any one of items 19 to 24, wherein said trivalent, bispecific antibody is to be administered before, simultaneously with or after administration of the transduced T-cells.
26. The method of any one of items 19 to 25, wherein said disease is a malignant disease.
27. The method of any one of items 19 to 26, wherein said malignant disease is selected from cancer of epithelial, endothelial or mesothelial origin and cancer of the blood.

The invention claimed is:

1. A trivalent, bispecific antibody molecule which comprises:
   (i) a first binding domain binding the extracellular domain of epithelial growth factor receptor variant III (EGFRvIII), wherein the first binding domain comprises a variable heavy chain complementarity determining region 1 (CDR-H1) comprising SEQ ID NO: 9, a variable heavy chain complementarity determining region (CDR-H2) comprising SEQ ID NO: 10, and a variable heavy chain complementarity determining region 3 (CDR-H3) comprising SEQ ID NO: 11; and wherein the first binding domain comprises a variable light chain complementarity determining region 1 (CDR-L1) comprising SEQ ID NO: 12, a variable light chain complementarity determining region 2 (CDR-L2) comprising SEQ ID NO: 13, and a variable light chain complementarity determining region 3 (CDR-L3) comprising SEQ ID NO: 14;
   (ii) a second binding domain binding a tumor-specific antigen naturally occurring on the surface of a tumor cell,
   wherein the tumor-specific antigen is mesothelin (MSLN), and wherein the second binding domain comprises a CDR-H1 comprising SEQ ID NO: 15, a CDR-H2 comprising SEQ ID NO: 16, a CDR-H3 comprising SEQ ID NO: 17, a CDR-L1 comprising SEQ ID NO: 18, a CDR-L2 comprising SEQ ID NO: 19, and a CDR-L3 comprising SEQ ID NO: 20; or
   wherein the tumor-specific antigen is melanoma chondroitin sulfate proteoglycan (MCSP), and wherein the second binding domain comprises a CDR-H1 comprising SEQ ID NO: 221, a CDR-H2 comprising SEQ ID NO: 222, a CDR-H3 comprising SEQ ID NO: 223, a CDR-L1 comprising SEQ ID NO: 224, a CDR-L2 comprising SEQ ID NO: 225, and a CDR-L3 comprising SEQ ID NO: 226; and
   (iii) a third binding domain, wherein the third binding domain is the same as the first binding domain or is the same as the second binding domain;
   wherein the trivalent, bispecific antibody molecule comprises at least one amino acid sequence selected from the group consisting of SEQ ID NO: 208, SEQ ID NO: 210, SEQ ID NO: 212, and SEQ ID NO: 214.

2. A trivalent, bispecific antibody molecule comprising amino acid sequences SEQ ID NO: 208, SEQ ID NO: 210, SEQ ID NO: 212, SEQ ID NO: 214, or amino acid sequences SEQ ID NO: 2, SEQ ID NO: 4, SEQ ID NO: 6, and SEQ ID NO: 8.

3. A pharmaceutical composition comprising the trivalent, bispecific antibody molecule according to claim 1.

4. An expression vector comprising nucleic acid sequences encoding the trivalent, bispecific antibody molecule according to claim 1.

5. The expression vector of claim 4, which is polycistronic.

6. The expression vector of claim 4, wherein said vector further comprises a regulatory sequence which is operably linked to said nucleic acid sequences.

7. A host cell transformed with the expression vector according to claim 4.

8. A method for the production of a trivalent, bispecific antibody, said method comprising: (a) culturing the host cell according to claim 7 under conditions allowing expression of the trivalent, bispecific antibody molecule; and (b) recovering the produced trivalent, bispecific antibody molecule from the host cell culture.

9. A kit comprising the trivalent, bispecific antibody molecule according to claim 1.

10. The kit according to claim 9, further comprising a nucleic acid molecule encoding a fusion protein comprising: (1) an extracellular domain of EGFRvIII comprising an amino acid sequence selected from the group consisting of: SEQ ID NO: 52, SEQ ID NO: 76, SEQ ID NO: 78, SEQ ID NO: 152, and SEQ ID NO: 232; (2) a transmembrane domain of CD28; and (3) a CD3zeta stimulatory domain.

11. The kit according to claim 10, wherein the fusion protein comprises an amino acid sequence selected from the group consisting of: SEQ ID NO: 42, SEQ ID NO: 44, SEQ ID NO: 48, and SEQ ID NO: 50.

12. The kit according to claim 10, wherein the nucleic acid molecule comprises a nucleotide sequence selected from the group consisting of: SEQ ID NO: 51, SEQ ID NO: 75, SEQ ID NO: 77, SEQ ID NO: 151, and SEQ ID NO: 231.

13. The kit according to claim 10, wherein the fusion protein comprises at least one co-stimulatory signalling domain comprising an amino acid sequence selected from the group consisting of SEQ ID NO: 56, SEQ ID NO: 60, SEQ ID NO: 66, SEQ ID NO: 68, SEQ ID NO: 69, SEQ ID NO: 72, SEQ ID NO: 121, and SEQ ID NO: 122.

14. A pharmaceutical composition comprising the trivalent, bispecific antibody molecule according to claim 2.

15. An expression vector comprising nucleic acid sequences encoding the trivalent, bispecific antibody molecule according to claim 2.

16. The expression vector of claim 15, which is polycistronic.

17. The expression vector of claim 15, wherein said vector further comprises a regulatory sequence which is operably linked to said nucleic acid sequences.

18. A host cell transformed with the expression vector according to claim 15.

19. A method for the production of a trivalent, bispecific antibody, said method comprising: (a) culturing the host cell according to claim 18 under conditions allowing expression of the trivalent, bispecific antibody molecule; and (b) recovering the produced trivalent, bispecific antibody molecule from the host cell culture.

20. A kit comprising the trivalent, bispecific antibody molecule according to claim 2.

21. The kit according to claim 20, further comprising a nucleic acid molecule encoding a fusion protein comprising: (1) an extracellular domain of EGFRvIII comprising an amino acid sequence selected from the group consisting of: SEQ ID NO: 52, SEQ ID NO: 76, SEQ ID NO: 78, SEQ ID NO: 152, and SEQ ID NO: 232; (2) a transmembrane domain of CD28; and (3) a CD3zeta stimulatory domain.

22. The kit according to claim 21, wherein the fusion protein comprises an amino acid sequence selected from the group consisting of: SEQ ID NO: 42, SEQ ID NO: 44, SEQ ID NO: 48, and SEQ ID NO: 50.

23. The kit according to claim 21, wherein the nucleic acid molecule comprises a nucleotide sequence selected from the group consisting of: SEQ ID NO: 51, SEQ ID NO: 75, SEQ ID NO: 77, SEQ ID NO: 151, and SEQ ID NO: 231.

24. The kit according to claim 21, wherein the fusion protein comprises at least one co-stimulatory signalling domain comprising an amino acid sequence selected from the group consisting of: SEQ ID NO: 56, SEQ ID NO: 60, SEQ ID NO: 66, SEQ ID NO: 68, SEQ ID NO: 69, SEQ ID NO: 72, SEQ ID NO: 121, and SEQ ID NO: 122.

\* \* \* \* \*

SEQUENCE LISTING

```
<160> NUMBER OF SEQ ID NOS: 249

<210> SEQ ID NO 1
<211> LENGTH: 2061
<212> TYPE: DNA
<213> ORGANISM: Artificial Sequence
<220> FEATURE:
<223> OTHER INFORMATION: EGFR vIII MR1.1 VH Ck MSLN VH CH1 EE Fc knob PG
      LALA, pETR15655
<220> FEATURE:
<221> NAME/KEY: CDS
<222> LOCATION: 1..2061
<223> OTHER INFORMATION: /transl_table=1

<400> SEQUENCE: 1 caa gtg aag ctg cag cag agt ggg ggc gga ctc gtg aaa cct ggc gcc       48
Gln Val Lys Leu Gln Gln Ser Gly Gly Gly Leu Val Lys Pro Gly Ala
1               5                   10                  15 tct ctg aag ctg agc tgc gtg acc agc ggc ttc acc ttc aga aag ttc       96
Ser Leu Lys Leu Ser Cys Val Thr Ser Gly Phe Thr Phe Arg Lys Phe
            20                  25                  30 ggc atg agc tgg gtg cgc cag acc agc gac aag cgg ctg gaa tgg gtg      144
Gly Met Ser Trp Val Arg Gln Thr Ser Asp Lys Arg Leu Glu Trp Val
        35                  40                  45 gcc agc atc agc acc ggc ggc tac aac acc tac tac agc gac aac gtg      192
Ala Ser Ile Ser Thr Gly Gly Tyr Asn Thr Tyr Tyr Ser Asp Asn Val
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 50  |     |     |     |     | 55  |     |     |     |     | 60  |     |     |     |     |

```
aag ggc cgg ttc acc atc agc aga gag aac gcc aag aac acc ctg tac         240
Lys Gly Arg Phe Thr Ile Ser Arg Glu Asn Ala Lys Asn Thr Leu Tyr
 65                  70                  75                  80 ctg cag atg agc agc ctg aag tcc gag gac acc gcc ctg tac tac tgc         288
Leu Gln Met Ser Ser Leu Lys Ser Glu Asp Thr Ala Leu Tyr Tyr Cys
                 85                  90                  95 acc aga ggc tac agc ccc tac agc tac gcc atg gac tat tgg ggc cag         336
Thr Arg Gly Tyr Ser Pro Tyr Ser Tyr Ala Met Asp Tyr Trp Gly Gln
            100                 105                 110 ggc acc acc gtg acc gtg tca tct gct agc gtg gcc gct ccc tcc gtg         384
Gly Thr Thr Val Thr Val Ser Ser Ala Ser Val Ala Ala Pro Ser Val
        115                 120                 125 ttc atc ttc cca cct tcc gac gag cag ctg aag tcc ggc acc gct tct         432
Phe Ile Phe Pro Pro Ser Asp Glu Gln Leu Lys Ser Gly Thr Ala Ser
130                 135                 140 gtc gtg tgc ctg ctg aac aac ttc tac ccc cgc gag gcc aag gtg cag         480
Val Val Cys Leu Leu Asn Asn Phe Tyr Pro Arg Glu Ala Lys Val Gln
145                 150                 155                 160 tgg aag gtg gac aac gcc ctg cag tcc ggc aac agc cag gaa tcc gtg         528
Trp Lys Val Asp Asn Ala Leu Gln Ser Gly Asn Ser Gln Glu Ser Val
                165                 170                 175 acc gag cag gac tcc aag gac agc acc tac tcc ctg tcc tcc acc ctg         576
Thr Glu Gln Asp Ser Lys Asp Ser Thr Tyr Ser Leu Ser Ser Thr Leu
            180                 185                 190 acc ctg tcc aag gcc gac tac gag aag cac aag gtg tac gcc tgc gaa         624
Thr Leu Ser Lys Ala Asp Tyr Glu Lys His Lys Val Tyr Ala Cys Glu
        195                 200                 205 gtg acc cac cag ggc ctg tct agc ccc gtg acc aag tct ttc aac cgg         672
Val Thr His Gln Gly Leu Ser Ser Pro Val Thr Lys Ser Phe Asn Arg
210                 215                 220 ggc gag tgc ggt ggc gga ggt tcc gga ggc gga gga tcc cag gtg cag         720
Gly Glu Cys Gly Gly Gly Gly Ser Gly Gly Gly Gly Ser Gln Val Gln
225                 230                 235                 240 ctg gtg cag tct ggc gcc gaa gtg aag aaa cca ggc gcc agc gtg aag         768
Leu Val Gln Ser Gly Ala Glu Val Lys Lys Pro Gly Ala Ser Val Lys
                245                 250                 255 gtg tcc tgc aag gcc agc ggc tac agc ttc acc ggc tac acc atg aac         816
Val Ser Cys Lys Ala Ser Gly Tyr Ser Phe Thr Gly Tyr Thr Met Asn
            260                 265                 270 tgg gtg cgc cag gct cct gga cag ggc ctg gaa tgg atg ggc ctg atc         864
Trp Val Arg Gln Ala Pro Gly Gln Gly Leu Glu Trp Met Gly Leu Ile
        275                 280                 285 acc ccc tac aac ggc gcc agc agc tac aac cag aag ttc cgg ggc aag         912
Thr Pro Tyr Asn Gly Ala Ser Ser Tyr Asn Gln Lys Phe Arg Gly Lys
290                 295                 300 gcc acc atg acc gtg gac acc agc acc tcc acc gtg tat atg gaa ctg         960
Ala Thr Met Thr Val Asp Thr Ser Thr Ser Thr Val Tyr Met Glu Leu
305                 310                 315                 320 agc agc ctg cgg agc gag gac acc gcc gtg tac tat tgt gcc aga ggc        1008
Ser Ser Leu Arg Ser Glu Asp Thr Ala Val Tyr Tyr Cys Ala Arg Gly
                325                 330                 335 ggc tac gac ggc aga ggc ttc gat tat tgg ggc cag ggc acc ctc gtg        1056
Gly Tyr Asp Gly Arg Gly Phe Asp Tyr Trp Gly Gln Gly Thr Leu Val
            340                 345                 350 acc gtg tcc agc gct agc acc aag ggc ccc tcc gtg ttc ccc ctg gcc        1104
Thr Val Ser Ser Ala Ser Thr Lys Gly Pro Ser Val Phe Pro Leu Ala
        355                 360                 365 ccc agc agc aag agc acc agc ggc ggc aca gcc gct ctg ggc tgc ctg        1152
```

```
                Pro Ser Ser Lys Ser Thr Ser Gly Gly Thr Ala Ala Leu Gly Cys Leu
                    370             375                 380 gtc gag gac tac ttc ccc gag ccc gtg acc gtg tcc tgg aac agc gga              1200
Val Glu Asp Tyr Phe Pro Glu Pro Val Thr Val Ser Trp Asn Ser Gly
385                 390                 395                 400 gcc ctg acc tcc ggc gtg cac acc ttc ccc gcc gtg ctg cag agt tct              1248
Ala Leu Thr Ser Gly Val His Thr Phe Pro Ala Val Leu Gln Ser Ser
                405                 410                 415 ggc ctg tat agc ctg agc agc gtg gtc acc gtg cct tct agc agc ctg              1296
Gly Leu Tyr Ser Leu Ser Ser Val Val Thr Val Pro Ser Ser Ser Leu
        420                 425                 430 ggc acc cag acc tac atc tgc aac gtg aac cac aag ccc agc aac acc              1344
Gly Thr Gln Thr Tyr Ile Cys Asn Val Asn His Lys Pro Ser Asn Thr
            435                 440                 445 aag gtg gac gag aag gtg gag ccc aag agc tgc gac aaa act cac aca              1392
Lys Val Asp Glu Lys Val Glu Pro Lys Ser Cys Asp Lys Thr His Thr
450                 455                 460 tgc cca ccg tgc cca gca cct gaa gct gca ggg gga ccg tca gtc ttc              1440
Cys Pro Pro Cys Pro Ala Pro Glu Ala Ala Gly Gly Pro Ser Val Phe
465                 470                 475                 480 ctc ttc ccc cca aaa ccc aag gac acc ctc atg atc tcc cgg acc cct              1488
Leu Phe Pro Pro Lys Pro Lys Asp Thr Leu Met Ile Ser Arg Thr Pro
                485                 490                 495 gag gtc aca tgc gtg gtg gtg gac gtg agc cac gaa gac cct gag gtc              1536
Glu Val Thr Cys Val Val Val Asp Val Ser His Glu Asp Pro Glu Val
                500                 505                 510 aag ttc aac tgg tac gtg gac ggc gtg gag gtg cat aat gcc aag aca              1584
Lys Phe Asn Trp Tyr Val Asp Gly Val Glu Val His Asn Ala Lys Thr
        515                 520                 525 aag ccg cgg gag gag cag tac aac agc acg tac cgt gtg gtc agc gtc              1632
Lys Pro Arg Glu Glu Gln Tyr Asn Ser Thr Tyr Arg Val Val Ser Val
530                 535                 540 ctc acc gtc ctg cac cag gac tgg ctg aat ggc aag gag tac aag tgc              1680
Leu Thr Val Leu His Gln Asp Trp Leu Asn Gly Lys Glu Tyr Lys Cys
545                 550                 555                 560 aag gtc tcc aac aaa gcc ctc ggc gcc ccc atc gag aaa acc atc tcc              1728
Lys Val Ser Asn Lys Ala Leu Gly Ala Pro Ile Glu Lys Thr Ile Ser
                565                 570                 575 aaa gcc aaa ggg cag ccc cga gaa cca cag gtg tac acc ctg ccc cca              1776
Lys Ala Lys Gly Gln Pro Arg Glu Pro Gln Val Tyr Thr Leu Pro Pro
                580                 585                 590 tgc cgg gat gag ctg acc aag aac cag gtc agc ctg tgg tgc ctg gtc              1824
Cys Arg Asp Glu Leu Thr Lys Asn Gln Val Ser Leu Trp Cys Leu Val
        595                 600                 605 aaa ggc ttc tat ccc agc gac atc gcc gtg gag tgg gag agc aat ggg              1872
Lys Gly Phe Tyr Pro Ser Asp Ile Ala Val Glu Trp Glu Ser Asn Gly
            610                 615                 620 cag ccg gag aac aac tac aag acc acg cct ccc gtg ctg gac tcc gac              1920
Gln Pro Glu Asn Asn Tyr Lys Thr Thr Pro Pro Val Leu Asp Ser Asp
625                 630                 635                 640 ggc tcc ttc ttc ctc tac agc aag ctc acc gtg gac aag agc agg tgg              1968
Gly Ser Phe Phe Leu Tyr Ser Lys Leu Thr Val Asp Lys Ser Arg Trp
                645                 650                 655 cag cag ggg aac gtc ttc tca tgc tcc gtg atg cat gag gct ctg cac              2016
Gln Gln Gly Asn Val Phe Ser Cys Ser Val Met His Glu Ala Leu His
                660                 665                 670 aac cac tac acg cag aag agc ctc tcc ctg tct ccg ggt aaa tga                  2061
Asn His Tyr Thr Gln Lys Ser Leu Ser Leu Ser Pro Gly Lys
        675                 680                 685
```

```
<210> SEQ ID NO 2
<211> LENGTH: 686
<212> TYPE: PRT
<213> ORGANISM: Artificial Sequence
<220> FEATURE:
<223> OTHER INFORMATION: [CDS]:1..2061 from SEQ ID NO 1

<400> SEQUENCE: 2

Gln Val Lys Leu Gln Gln Ser Gly Gly Leu Val Lys Pro Gly Ala
1               5                   10                  15

Ser Leu Lys Leu Ser Cys Val Thr Ser Gly Phe Thr Phe Arg Lys Phe
                20                  25                  30

Gly Met Ser Trp Val Arg Gln Thr Ser Asp Lys Arg Leu Glu Trp Val
            35                  40                  45

Ala Ser Ile Ser Thr Gly Gly Tyr Asn Thr Tyr Tyr Ser Asp Asn Val
        50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Gly Gly Gly Gly Ser Gly Gly Gly Gly Ser Gln Val Gln
225                 230                 235                 240

Leu Val Gln Ser Gly Ala Glu Val Lys Lys Pro Gly Ala Ser Val Lys
                245                 250                 255

Val Ser Cys Lys Ala Ser Gly Tyr Ser Phe Thr Gly Tyr Thr Met Asn
            260                 265                 270

Trp Val Arg Gln Ala Pro Gly Gln Gly Leu Glu Trp Met Gly Leu Ile
        275                 280                 285

Thr Pro Tyr Asn Gly Ala Ser Ser Tyr Asn Gln Lys Phe Arg Gly Lys
    290                 295                 300

Ala Thr Met Thr Val Asp Thr Ser Thr Ser Thr Val Tyr Met Glu Leu
305                 310                 315                 320

Ser Ser Leu Arg Ser Glu Asp Thr Ala Val Tyr Tyr Cys Ala Arg Gly
                325                 330                 335

Gly Tyr Asp Gly Arg Gly Phe Asp Tyr Trp Gly Gln Gly Thr Leu Val
            340                 345                 350

Thr Val Ser Ser Ala Ser Thr Lys Gly Pro Ser Val Phe Pro Leu Ala
        355                 360                 365
```

```
Pro Ser Ser Lys Ser Thr Ser Gly Gly Thr Ala Ala Leu Gly Cys Leu
    370                 375                 380

Val Glu Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Val Thr Val Pro Ser Ser Ser Leu
            420                 425                 430

Gly Thr Gln Thr Tyr Ile Cys Asn Val Asn His Lys Pro Ser Asn Thr
        435                 440                 445

Lys Val Asp Glu Lys Val Glu Pro Lys Ser Cys Asp Lys Thr His Thr
    450                 455                 460

Cys Pro Pro Cys Pro Ala Pro Glu Ala Ala Gly Gly Pro Ser Val Phe
465                 470                 475                 480

Leu Phe Pro Pro Lys Pro Lys Asp Thr Leu Met Ile Ser Arg Thr Pro
                485                 490                 495

Glu Val Thr Cys Val Val Val Asp Val Ser His Glu Asp Pro Glu Val
            500                 505                 510

Lys Phe Asn Trp Tyr Val Asp Gly Val Glu Val His Asn Ala Lys Thr
        515                 520                 525

Lys Pro Arg Glu Glu Gln Tyr Asn Ser Thr Tyr Arg Val Val Ser Val
    530                 535                 540

Leu Thr Val Leu His Gln Asp Trp Leu Asn Gly Lys Glu Tyr Lys Cys
545                 550                 555                 560

Lys Val Ser Asn Lys Ala Leu Gly Ala Pro Ile Glu Lys Thr Ile Ser
                565                 570                 575

Lys Ala Lys Gly Gln Pro Arg Glu Pro Gln Val Tyr Thr Leu Pro Pro
            580                 585                 590

Cys Arg Asp Glu Leu Thr Lys Asn Gln Val Ser Leu Trp Cys Leu Val
        595                 600                 605

Lys Gly Phe Tyr Pro Ser Asp Ile Ala Val Glu Trp Glu Ser Asn Gly
    610                 615                 620

Gln Pro Glu Asn Asn Tyr Lys Thr Thr Pro Pro Val Leu Asp Ser Asp
625                 630                 635                 640

Gly Ser Phe Phe Leu Tyr Ser Lys Leu Thr Val Asp Lys Ser Arg Trp
                645                 650                 655

Gln Gln Gly Asn Val Phe Ser Cys Ser Val Met His Glu Ala Leu His
            660                 665                 670

Asn His Tyr Thr Gln Lys Ser Leu Ser Leu Ser Pro Gly Lys
        675                 680                 685

<210> SEQ ID NO 3
<211> LENGTH: 639
<212> TYPE: DNA
<213> ORGANISM: Artificial Sequence
<220> FEATURE:
<223> OTHER INFORMATION: EGFR vIII MR1.1 VL CH1, pETR15656
<220> FEATURE:
<221> NAME/KEY: CDS
<222> LOCATION: 1..639
<223> OTHER INFORMATION: /transl_table=1

<400> SEQUENCE: 3 gat atc gag ctg aca cag agc ccc gcc agc ctg tct gtg gcc acc ggc      48
Asp Ile Glu Leu Thr Gln Ser Pro Ala Ser Leu Ser Val Ala Thr Gly
1               5                   10                  15 gag aaa gtg acc atc cgg tgc atg acc agc acc gac atc gac gac gac      96
```

```
                Glu Lys Val Thr Ile Arg Cys Met Thr Ser Thr Asp Ile Asp Asp Asp
                                20                  25                  30 atg aac tgg tat cag cag aag ccc ggc gag ccc ccc aag ttc ctg atc          144
Met Asn Trp Tyr Gln Gln Lys Pro Gly Glu Pro Pro Lys Phe Leu Ile
        35                  40                  45 agc gag ggc aac aca ctg cgg cct ggc gtg cca agc aga ttc agc agc          192
Ser Glu Gly Asn Thr Leu Arg Pro Gly Val Pro Ser Arg Phe Ser Ser
 50                  55                  60 tct ggc acc ggc acc gac ttc gtg ttt acc atc gag aat acc ctg agc          240
Ser Gly Thr Gly Thr Asp Phe Val Phe Thr Ile Glu Asn Thr Leu Ser
 65                  70                  75                  80 gag gac gtg ggc gac tac tac tgc ctg cag agc tgg aac gtg ccc ctg          288
Glu Asp Val Gly Asp Tyr Tyr Cys Leu Gln Ser Trp Asn Val Pro Leu
                85                  90                  95 acc ttt ggc gac ggc acc aag ctg gaa atc aag agc agc gct agc acc          336
Thr Phe Gly Asp Gly Thr Lys Leu Glu Ile Lys Ser Ser Ala Ser Thr
            100                 105                 110 aaa ggc cct tcc gtg ttt cct ctg gct cct agc tcc aag tcc acc tct          384
Lys Gly Pro Ser Val Phe Pro Leu Ala Pro Ser Ser Lys Ser Thr Ser
        115                 120                 125 gga ggc acc gct gct ctc gga tgc ctc gtg aag gat tat ttt cct gag          432
Gly Gly Thr Ala Ala Leu Gly Cys Leu Val Lys Asp Tyr Phe Pro Glu
130                 135                 140 cct gtg aca gtg tcc tgg aat agc gga gca ctg acc tct gga gtg cat          480
Pro Val Thr Val Ser Trp Asn Ser Gly Ala Leu Thr Ser Gly Val His
145                 150                 155                 160 act ttc ccc gct gtg ctg cag tcc tct gga ctg tac agc ctg agc agc          528
Thr Phe Pro Ala Val Leu Gln Ser Ser Gly Leu Tyr Ser Leu Ser Ser
                165                 170                 175 gtg gtg aca gtg ccc agc agc agc ctg ggc acc cag acc tac atc tgc          576
Val Val Thr Val Pro Ser Ser Ser Leu Gly Thr Gln Thr Tyr Ile Cys
            180                 185                 190 aac gtg aac cac aag ccc agc aac acc aag gtg gac aag aag gtg gaa          624
Asn Val Asn His Lys Pro Ser Asn Thr Lys Val Asp Lys Lys Val Glu
        195                 200                 205 ccc aag tct tgt tga                                                      639
Pro Lys Ser Cys
    210

<210> SEQ ID NO 4
<211> LENGTH: 212
<212> TYPE: PRT
<213> ORGANISM: Artificial Sequence
<220> FEATURE:
<223> OTHER INFORMATION: [CDS]:1..639 from SEQ ID NO 3

<400> SEQUENCE: 4

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
                20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95
```

```
Thr Phe Gly Asp Gly Thr Lys Leu Glu Ile Lys Ser Ser Ala Ser Thr
                100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
                195                 200                 205

Pro Lys Ser Cys
        210
```

<210> SEQ ID NO 5
<211> LENGTH: 642
<212> TYPE: DNA
<213> ORGANISM: Artificial Sequence
<220> FEATURE:
<223> OTHER INFORMATION: VL MSLN Ck RK, pETR15443
<220> FEATURE:
<221> NAME/KEY: CDS
<222> LOCATION: 1..642
<223> OTHER INFORMATION: /transl_table=1

<400> SEQUENCE: 5

```
gac atc cag atg acc cag agc ccc agc agc ctg tct gcc agc gtg ggc        48
Asp Ile Gln Met Thr Gln Ser Pro Ser Ser Leu Ser Ala Ser Val Gly
1               5                   10                  15 gac aga gtg acc atc acc tgt agc gcc agc agc agc gtg tcc tac atg        96
Asp Arg Val Thr Ile Thr Cys Ser Ala Ser Ser Ser Val Ser Tyr Met
                20                  25                  30 cac tgg tat cag cag aag tcc ggc aag gcc ccc aag ctg ctg atc tac       144
His Trp Tyr Gln Gln Lys Ser Gly Lys Ala Pro Lys Leu Leu Ile Tyr
            35                  40                  45 gac acc agc aag ctg gcc tcc ggc gtg ccc agc aga ttt tct ggc agc       192
Asp Thr Ser Lys Leu Ala Ser Gly Val Pro Ser Arg Phe Ser Gly Ser
        50                  55                  60 ggc tcc ggc acc gac ttc acc ctg aca atc agc tcc ctc cag ccc gag       240
Gly Ser Gly Thr Asp Phe Thr Leu Thr Ile Ser Ser Leu Gln Pro Glu
65                  70                  75                  80 gac ttc gcc acc tac tac tgc cag cag tgg tcc aag cac ccc ctg acc       288
Asp Phe Ala Thr Tyr Tyr Cys Gln Gln Trp Ser Lys His Pro Leu Thr
                85                  90                  95 ttt ggc cag ggc acc aag ctg gaa atc aag cgt acg gtg gct gca cca       336
Phe Gly Gln Gly Thr Lys Leu Glu Ile Lys Arg Thr Val Ala Ala Pro
            100                 105                 110 tct gtc ttc atc ttc ccg cca tct gat cgg aag ttg aaa tct gga act       384
Ser Val Phe Ile Phe Pro Pro Ser Asp Arg Lys Leu Lys Ser Gly Thr
        115                 120                 125 gcc tct gtt gtg tgc ctg ctg aat aac ttc tat ccc aga gag gcc aaa       432
Ala Ser Val Val Cys Leu Leu Asn Asn Phe Tyr Pro Arg Glu Ala Lys
130                 135                 140 gta cag tgg aag gtg gat aac gcc ctc caa tcg ggt aac tcc cag gag       480
Val Gln Trp Lys Val Asp Asn Ala Leu Gln Ser Gly Asn Ser Gln Glu
145                 150                 155                 160 agt gtc aca gag cag gac agc aag gac agc acc tac agc ctc agc agc       528
Ser Val Thr Glu Gln Asp Ser Lys Asp Ser Thr Tyr Ser Leu Ser Ser
```

```
                Ser Val Thr Glu Gln Asp Ser Lys Asp Ser Thr Tyr Ser Leu Ser Ser
                                165                 170                 175 acc ctg acg ctg agc aaa gca gac tac gag aaa cac aaa gtc tac gcc          576
Thr Leu Thr Leu Ser Lys Ala Asp Tyr Glu Lys His Lys Val Tyr Ala
            180                 185                 190 tgc gaa gtc acc cat cag ggc ctg agc tcg ccc gtc aca aag agc ttc          624
Cys Glu Val Thr His Gln Gly Leu Ser Ser Pro Val Thr Lys Ser Phe
    195                 200                 205 aac agg gga gag tgt tag                                                  642
Asn Arg Gly Glu Cys
    210
```

<210> SEQ ID NO 6
<211> LENGTH: 213
<212> TYPE: PRT
<213> ORGANISM: Artificial Sequence
<220> FEATURE:
<223> OTHER INFORMATION: [CDS]:1..642 from SEQ ID NO 5

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Ser Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 7
<211> LENGTH: 1350
<212> TYPE: DNA
<213> ORGANISM: Artificial Sequence
<220> FEATURE:
<223> OTHER INFORMATION: VH MSLN CH1 EE Fc hole PG LALA HRYF, pETR15657
<220> FEATURE:
<221> NAME/KEY: CDS
<222> LOCATION: 1..1350
<223> OTHER INFORMATION: /transl_table=1

<400> SEQUENCE: 7

```
cag gtg cag ctg gtg cag tct ggc gcc gaa gtg aag aaa cca ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac agc ttc acc ggc tac      96
Ser Val Lys Val Ser Cys Lys Ala Ser Gly Tyr Ser Phe Thr Gly Tyr
            20                  25                  30 acc atg aac tgg gtg cgc cag gct cct gga cag ggc ctg gaa tgg atg     144
Thr Met Asn Trp Val Arg Gln Ala Pro Gly Gln Gly Leu Glu Trp Met
        35                  40                  45 ggc ctg atc acc ccc tac aac ggc gcc agc agc tac aac cag aag ttc     192
Gly Leu Ile Thr Pro Tyr Asn Gly Ala Ser Ser Tyr Asn Gln Lys Phe
    50                  55                  60 cgg ggc aag gcc acc atg acc gtg gac acc agc acc tcc acc gtg tat     240
Arg Gly Lys Ala Thr Met Thr Val Asp Thr Ser Thr Ser Thr Val Tyr
65                  70                  75                  80 atg gaa ctg agc agc ctg cgg agc gag gac acc gcc gtg tac tat tgt     288
Met Glu Leu Ser Ser Leu Arg Ser Glu Asp Thr Ala Val Tyr Tyr Cys
                85                  90                  95 gcc aga ggc ggc tac gac ggc aga ggc ttc gat tat tgg ggc cag ggc     336
Ala Arg Gly Gly Tyr Asp Gly Arg Gly Phe Asp Tyr Trp Gly Gln Gly
            100                 105                 110 acc ctc gtg acc gtg tcc tct gct agc acc aag ggc ccc tcc gtg ttc     384
Thr Leu Val Thr Val Ser Ser Ala Ser Thr Lys Gly Pro Ser Val Phe
        115                 120                 125 ccc ctg gcc ccc agc agc aag agc acc agc ggc ggc aca gcc gct ctg     432
Pro Leu Ala Pro Ser Ser Lys Ser Thr Ser Gly Gly Thr Ala Ala Leu
    130                 135                 140 ggc tgc ctg gtc gag gac tac ttc ccc gag ccc gtg acc gtg tcc tgg     480
Gly Cys Leu Val Glu Asp Tyr Phe Pro Glu Pro Val Thr Val Ser Trp
145                 150                 155                 160 aac agc gga gcc ctg acc tcc ggc gtg cac acc ttc ccc gcc gtg ctg     528
Asn Ser Gly Ala Leu Thr Ser Gly Val His Thr Phe Pro Ala Val Leu
                165                 170                 175 cag agt tct ggc ctg tat agc ctg agc agc gtg gtc acc gtg cct tct     576
Gln Ser Ser Gly Leu Tyr Ser Leu Ser Ser Val Val Thr Val Pro Ser
            180                 185                 190 agc agc ctg ggc acc cag acc tac atc tgc aac gtg aac cac aag ccc     624
Ser Ser Leu Gly Thr Gln Thr Tyr Ile Cys Asn Val Asn His Lys Pro
        195                 200                 205 agc aac acc aag gtg gac gag aag gtg gag ccc aag agc tgc gac aaa     672
Ser Asn Thr Lys Val Asp Glu Lys Val Glu Pro Lys Ser Cys Asp Lys
    210                 215                 220 act cac aca tgc cca ccg tgc cca gca cct gaa gct gca ggg gga ccg     720
Thr His Thr Cys Pro Pro Cys Pro Ala Pro Glu Ala Ala Gly Gly Pro
225                 230                 235                 240 tca gtc ttc ctc ttc ccc cca aaa ccc aag gac acc ctc atg atc tcc     768
Ser Val Phe Leu Phe Pro Pro Lys Pro Lys Asp Thr Leu Met Ile Ser
                245                 250                 255 cgg acc cct gag gtc aca tgc gtg gtg gtg gac gtg agc cac gaa gac     816
Arg Thr Pro Glu Val Thr Cys Val Val Val Asp Val Ser His Glu Asp
            260                 265                 270 cct gag gtc aag ttc aac tgg tac gtg gac ggc gtg gag gtg cat aat     864
Pro Glu Val Lys Phe Asn Trp Tyr Val Asp Gly Val Glu Val His Asn
        275                 280                 285 gcc aag aca aag ccg cgg gag gag cag tac aac agc acg tac cgt gtg     912
Ala Lys Thr Lys Pro Arg Glu Glu Gln Tyr Asn Ser Thr Tyr Arg Val
    290                 295                 300 gtc agc gtc ctc acc gtc ctg cac cag gac tgg ctg aat ggc aag gag     960
Val Ser Val Leu Thr Val Leu His Gln Asp Trp Leu Asn Gly Lys Glu
```

```
Val Ser Val Leu Thr Val Leu His Gln Asp Trp Leu Asn Gly Lys Glu
305                 310                 315                 320 tac aag tgc aag gtc tcc aac aaa gcc ctc ggc gcc ccc atc gag aaa      1008
Tyr Lys Cys Lys Val Ser Asn Lys Ala Leu Gly Ala Pro Ile Glu Lys
                    325                 330                 335 acc atc tcc aaa gcc aaa ggg cag ccc cga gaa cca cag gtg tgc acc      1056
Thr Ile Ser Lys Ala Lys Gly Gln Pro Arg Glu Pro Gln Val Cys Thr
                340                 345                 350 ctg ccc cca tcc cgg gat gag ctg acc aag aac cag gtc agc ctc tcg      1104
Leu Pro Pro Ser Arg Asp Glu Leu Thr Lys Asn Gln Val Ser Leu Ser
            355                 360                 365 tgc gca gtc aaa ggc ttc tat ccc agc gac atc gcc gtg gag tgg gag      1152
Cys Ala Val Lys Gly Phe Tyr Pro Ser Asp Ile Ala Val Glu Trp Glu
        370                 375                 380 agc aat ggg cag ccg gag aac aac tac aag acc acg cct ccc gtg ctg      1200
Ser Asn Gly Gln Pro Glu Asn Asn Tyr Lys Thr Thr Pro Pro Val Leu
385                 390                 395                 400 gac tcc gac ggc tcc ttc ttc ctc gtg agc aag ctc acc gtg gac aag      1248
Asp Ser Asp Gly Ser Phe Phe Leu Val Ser Lys Leu Thr Val Asp Lys
                    405                 410                 415 agc agg tgg cag cag ggg aac gtc ttc tca tgc tcc gtg atg cat gag      1296
Ser Arg Trp Gln Gln Gly Asn Val Phe Ser Cys Ser Val Met His Glu
                420                 425                 430 gct ctg cac aac cac tac acg cag aag agc ctc tcc ctg tct ccg ggt      1344
Ala Leu His Asn His Tyr Thr Gln Lys Ser Leu Ser Leu Ser Pro Gly
            435                 440                 445 aaa tga                                                              1350
Lys

<210> SEQ ID NO 8
<211> LENGTH: 449
<212> TYPE: PRT
<213> ORGANISM: Artificial Sequence
<220> FEATURE:
<223> OTHER INFORMATION: [CDS]:1..1350 from SEQ ID NO 7

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Thr Pro Tyr Asn Gly Ala Ser Ser Tyr Asn Gln Lys Phe
    50                  55                  60

Arg Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Arg Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                 165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 9
<211> LENGTH: 5
<212> TYPE: PRT
<213> ORGANISM: Artificial Sequence
<220> FEATURE:
<223> OTHER INFORMATION: EGFRvIII MR1.1 CDR H1 Kabat

<400> SEQUENCE: 9

Lys Phe Gly Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: EGFRvIII MR1.1 CDR H2 Kabat

<400> SEQUENCE: 10

Ser Ile Ser Thr Gly Gly Tyr Asn Thr Tyr Tyr Ser Asp Asn Val Lys
```

```
1               5                   10                  15
Gly

<210> SEQ ID NO 11
<211> LENGTH: 11
<212> TYPE: PRT
<213> ORGANISM: Artificial Sequence
<220> FEATURE:
<223> OTHER INFORMATION: EGFRvIII MR1.1 CDR H3 Kabat

<400> SEQUENCE: 11

Gly Tyr Ser Pro Tyr Ser Tyr Ala Met Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: EGFRvIII MR1.1 CDR1 L1 Kabat

<400> SEQUENCE: 12

Met Thr Ser Thr Asp Ile Asp Asp Asp Met Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: EGFRvIII MR1.1 CDR L2 Kabat

<400> SEQUENCE: 13

Glu Gly Asn Thr Leu Arg Pro
1               5

<210> SEQ ID NO 14
<211> LENGTH: 9
<212> TYPE: PRT
<213> ORGANISM: Artificial Sequence
<220> FEATURE:
<223> OTHER INFORMATION: EGFRvIII MR1.1 CDR L3 Kabat

<400> SEQUENCE: 14

Leu Gln Ser Trp Asn Val Pro Leu Thr
1               5

<210> SEQ ID NO 15
<211> LENGTH: 5
<212> TYPE: PRT
<213> ORGANISM: Artificial Sequence
<220> FEATURE:
<223> OTHER INFORMATION: aMSLN CDR H1 Kabat

<400> SEQUENCE: 15

Gly Tyr Thr Met Asn
1               5

<210> SEQ ID NO 16
<211> LENGTH: 17
<212> TYPE: PRT
<213> ORGANISM: Artificial Sequence
<220> FEATURE:
<223> OTHER INFORMATION: aMSLN CDR H2 Kabat

<400> SEQUENCE: 16
```

-continued

```
Leu Ile Thr Pro Tyr Asn Gly Ala Ser Ser Tyr Asn Gln Lys Phe Arg
1               5                   10                  15

Gly
```

<210> SEQ ID NO 17
<211> LENGTH: 10
<212> TYPE: PRT
<213> ORGANISM: Artificial Sequence
<220> FEATURE:
<223> OTHER INFORMATION: aMSLN CDR H3 Kabat

<400> SEQUENCE: 17

```
Gly Gly Tyr Asp Gly Arg Gly Phe Asp Tyr
1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: aMSLN CDR1 L1 Kabat

<400> SEQUENCE: 18

```
Ser Ala Ser Ser Ser Val Ser Tyr Met His
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: aMSLN CDR L2 Kabat

<400> SEQUENCE: 19

```
Asp Thr Ser Lys Leu Ala Ser
1               5
```

<210> SEQ ID NO 20
<211> LENGTH: 9
<212> TYPE: PRT
<213> ORGANISM: Artificial Sequence
<220> FEATURE:
<223> OTHER INFORMATION: aMSLN CDR L3 Kabat

<400> SEQUENCE: 20

```
Gln Gln Trp Ser Lys His Pro Leu Thr
1               5
```

<210> SEQ ID NO 21
<211> LENGTH: 2067
<212> TYPE: DNA
<213> ORGANISM: Artificial Sequence
<220> FEATURE:
<223> OTHER INFORMATION: EGFR vIII MR1.1 VH Ck muEpCAM VH CH1 EE Fc knob
      PG LALA, pETR14953
<220> FEATURE:
<221> NAME/KEY: CDS
<222> LOCATION: 1..2067
<223> OTHER INFORMATION: /transl_table=1

<400> SEQUENCE: 21

```
caa gtg aag ctg cag cag agt ggg ggc gga ctc gtg aaa cct ggc gcc      48
Gln Val Lys Leu Gln Gln Ser Gly Gly Gly Leu Val Lys Pro Gly Ala
1               5                   10                  15 tct ctg aag ctg agc tgc gtg acc agc ggc ttc acc ttc aga aag ttc      96
Ser Leu Lys Leu Ser Cys Val Thr Ser Gly Phe Thr Phe Arg Lys Phe
            20                  25                  30
```

-continued

| | | |
|---|---|---|
| ggc atg agc tgg gtg cgc cag acc agc gac aag cgg ctg gaa tgg gtg<br>Gly Met Ser Trp Val Arg Gln Thr Ser Asp Lys Arg Leu Glu Trp Val<br>      35                          40                        45 | 144 |
| gcc agc atc agc acc ggc ggc tac aac acc tac tac agc gac aac gtg<br>Ala Ser Ile Ser Thr Gly Gly Tyr Asn Thr Tyr Tyr Ser Asp Asn Val<br>50                       55                        60 | 192 |
| aag ggc cgg ttc acc atc agc aga gag aac gcc aag aac acc ctg tac<br>Lys Gly Arg Phe Thr Ile Ser Arg Glu Asn Ala Lys Asn Thr Leu Tyr<br>65                     70                    75                      80 | 240 |
| ctg cag atg agc agc ctg aag tcc gag gac acc gcc ctg tac tac tgc<br>Leu Gln Met Ser Ser Leu Lys Ser Glu Asp Thr Ala Leu Tyr Tyr Cys<br>                 85                        90                    95 | 288 |
| acc aga ggc tac agc ccc tac agc tac gcc atg gac tat tgg ggc cag<br>Thr Arg Gly Tyr Ser Pro Tyr Ser Tyr Ala Met Asp Tyr Trp Gly Gln<br>                100                    105                    110 | 336 |
| ggc acc acc gtg acc gtg tca tct gct agc gtg gcc gct ccc tcc gtg<br>Gly Thr Thr Val Thr Val Ser Ser Ala Ser Val Ala Ala Pro Ser Val<br>          115                    120                    125 | 384 |
| ttc atc ttc cca cct tcc gac gag cag ctg aag tcc ggc acc gct tct<br>Phe Ile Phe Pro Pro Ser Asp Glu Gln Leu Lys Ser Gly Thr Ala Ser<br>130                       135                    140 | 432 |
| gtc gtg tgc ctg ctg aac aac ttc tac ccc cgc gag gcc aag gtg cag<br>Val Val Cys Leu Leu Asn Asn Phe Tyr Pro Arg Glu Ala Lys Val Gln<br>145                    150                  155                  160 | 480 |
| tgg aag gtg gac aac gcc ctg cag tcc ggc aac agc cag gaa tcc gtg<br>Trp Lys Val Asp Asn Ala Leu Gln Ser Gly Asn Ser Gln Glu Ser Val<br>                    165                    170                  175 | 528 |
| acc gag cag gac tcc aag gac agc acc tac tcc ctg tcc tcc acc ctg<br>Thr Glu Gln Asp Ser Lys Asp Ser Thr Tyr Ser Leu Ser Ser Thr Leu<br>                  180                    185                  190 | 576 |
| acc ctg tcc aag gcc gac tac gag aag cac aag gtg tac gcc tgc gaa<br>Thr Leu Ser Lys Ala Asp Tyr Glu Lys His Lys Val Tyr Ala Cys Glu<br>          195                    200                    205 | 624 |
| gtg acc cac cag ggc ctg tct agc ccc gtg acc aag tct ttc aac cgg<br>Val Thr His Gln Gly Leu Ser Ser Pro Val Thr Lys Ser Phe Asn Arg<br>210                       215                    220 | 672 |
| ggc gag tgc ggt ggc gga ggt tcc gga ggc gga gga tcc gaa gtg cag<br>Gly Glu Cys Gly Gly Gly Gly Ser Gly Gly Gly Gly Ser Glu Val Gln<br>225                       230                    235                  240 | 720 |
| ctg gcc gag agc ggc gga ggc ctg gtg cag cct ggc aga tcc atg aag<br>Leu Ala Glu Ser Gly Gly Gly Leu Val Gln Pro Gly Arg Ser Met Lys<br>                    245                    250                  255 | 768 |
| ctg agc tgc gcc gcc agc ggc ttc acc ttc agc aac ttc ccc atg gcc<br>Leu Ser Cys Ala Ala Ser Gly Phe Thr Phe Ser Asn Phe Pro Met Ala<br>                260                    265                  270 | 816 |
| tgg gtc cga cag gcc ccc acc aag tgc ctg gaa tgg gtg gcc acc atc<br>Trp Val Arg Gln Ala Pro Thr Lys Cys Leu Glu Trp Val Ala Thr Ile<br>          275                    280                    285 | 864 |
| agc acc agc ggc ggc agc acc tac tac cgg gac agc gtg aag ggc cgg<br>Ser Thr Ser Gly Gly Ser Thr Tyr Tyr Arg Asp Ser Val Lys Gly Arg<br>290                       295                    300 | 912 |
| ttc acc atc agc cgg gac aac gcc aag agc acc ctg tac ctg cag atg<br>Phe Thr Ile Ser Arg Asp Asn Ala Lys Ser Thr Leu Tyr Leu Gln Met<br>305                       310                    315                  320 | 960 |
| aac agc ctg cgg agc gag gac acc gcc acc tac tac tgc acc cgg acc<br>Asn Ser Leu Arg Ser Glu Asp Thr Ala Thr Tyr Tyr Cys Thr Arg Thr<br>                    325                    330                  335 | 1008 |
| ctg tat atc ctg cgg gtg ttc tac ttc gac tac tgg ggc cag ggc gtg<br>Leu Tyr Ile Leu Arg Val Phe Tyr Phe Asp Tyr Trp Gly Gln Gly Val | 1056 |

```
                340             345             350
atg gtc acc gtg tct agc gct agc acc aag ggc ccc tcc gtg ttt cct      1104
Met Val Thr Val Ser Ser Ala Ser Thr Lys Gly Pro Ser Val Phe Pro
            355             360             365 ctg gcc cct tcc agc aag tcc acc tct gga act gcc gct ctg ggc          1152
Leu Ala Pro Ser Ser Lys Ser Thr Ser Gly Gly Thr Ala Ala Leu Gly
370             375             380 tgc ctg gtg gaa gat tac ttc ccc gag ccc gtg acc gtg tcc tgg aat      1200
Cys Leu Val Glu Asp Tyr Phe Pro Glu Pro Val Thr Val Ser Trp Asn
385             390             395             400 tct ggc gct ctg acc tcc ggc gtg cac acc ttt cca gct gtg ctg cag      1248
Ser Gly Ala Leu Thr Ser Gly Val His Thr Phe Pro Ala Val Leu Gln
            405             410             415 tcc tcc ggc ctg tac tcc ctg tcc tcc gtc gtg aca gtg ccc tcc agc      1296
Ser Ser Gly Leu Tyr Ser Leu Ser Ser Val Val Thr Val Pro Ser Ser
            420             425             430 tct ctg ggc acc cag acc tac atc tgc aac gtg aac cac aag ccc tcc      1344
Ser Leu Gly Thr Gln Thr Tyr Ile Cys Asn Val Asn His Lys Pro Ser
            435             440             445 aac acc aag gtg gac gag aag gtg gaa ccc aag tcc tgc gac aag acc      1392
Asn Thr Lys Val Asp Glu Lys Val Glu Pro Lys Ser Cys Asp Lys Thr
450             455             460 cac acc tgt ccc ccc tgc cct gct cct gaa gct gct ggt ggc cct agc      1440
His Thr Cys Pro Pro Cys Pro Ala Pro Glu Ala Ala Gly Gly Pro Ser
465             470             475             480 gtg ttc ctg ttc ccc cca aag ccc aag gac acc ctg atg atc tcc cgg      1488
Val Phe Leu Phe Pro Pro Lys Pro Lys Asp Thr Leu Met Ile Ser Arg
            485             490             495 acc ccc gaa gtg acc tgc gtg gtg gtg gat gtg tcc cac gag gac cct      1536
Thr Pro Glu Val Thr Cys Val Val Val Asp Val Ser His Glu Asp Pro
            500             505             510 gaa gtg aag ttc aat tgg tac gtg gac ggc gtg gaa gtg cac aac gcc      1584
Glu Val Lys Phe Asn Trp Tyr Val Asp Gly Val Glu Val His Asn Ala
            515             520             525 aag acc aag cct aga gag gaa cag tac aac tcc acc tac cgg gtg gtg      1632
Lys Thr Lys Pro Arg Glu Glu Gln Tyr Asn Ser Thr Tyr Arg Val Val
530             535             540 tcc gtg ctg aca gtg ctg cac cag gac tgg ctg aac ggc aaa gag tac      1680
Ser Val Leu Thr Val Leu His Gln Asp Trp Leu Asn Gly Lys Glu Tyr
545             550             555             560 aag tgc aag gtg tcc aac aag gcc ctg ggc gct ccc atc gaa aag acc      1728
Lys Cys Lys Val Ser Asn Lys Ala Leu Gly Ala Pro Ile Glu Lys Thr
            565             570             575 atc tcc aag gcc aag ggc cag ccc cgg gaa ccc cag gtg tac acc ctg      1776
Ile Ser Lys Ala Lys Gly Gln Pro Arg Glu Pro Gln Val Tyr Thr Leu
            580             585             590 ccc cca tgc cgg gat gag ctg acc aag aac cag gtc agc ctg tgg tgc      1824
Pro Pro Cys Arg Asp Glu Leu Thr Lys Asn Gln Val Ser Leu Trp Cys
            595             600             605 ctg gtc aaa ggc ttc tat ccc agc gac atc gcc gtg gag tgg gag agc      1872
Leu Val Lys Gly Phe Tyr Pro Ser Asp Ile Ala Val Glu Trp Glu Ser
610             615             620 aat ggg cag ccg gag aac aac tac aag acc acg cct ccc gtg ctg gac      1920
Asn Gly Gln Pro Glu Asn Asn Tyr Lys Thr Thr Pro Pro Val Leu Asp
625             630             635             640 tcc gac ggc tcc ttc ttc ctc tac agc aag ctc acc gtg gac aag agc      1968
Ser Asp Gly Ser Phe Phe Leu Tyr Ser Lys Leu Thr Val Asp Lys Ser
            645             650             655 agg tgg cag cag ggg aac gtc ttc tca tgc tcc gtg atg cat gag gct      2016
```

```
Arg Trp Gln Gln Gly Asn Val Phe Ser Cys Ser Val Met His Glu Ala
                660                 665                 670 ctg cac aac cac tac acg cag aag agc ctc tcc ctg tct ccg ggt aaa    2064
Leu His Asn His Tyr Thr Gln Lys Ser Leu Ser Leu Ser Pro Gly Lys
        675                 680                 685 tga                                                                 2067
```

<210> SEQ ID NO 22
<211> LENGTH: 688
<212> TYPE: PRT
<213> ORGANISM: Artificial Sequence
<220> FEATURE:
<223> OTHER INFORMATION: [CDS]:1..2067 from SEQ ID NO 21

<400> SEQUENCE: 22

```
Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Gly Gly Gly Gly Ser Gly Gly Gly Gly Ser Glu Val Gln
225                 230                 235                 240

Leu Ala Glu Ser Gly Gly Gly Leu Val Gln Pro Gly Arg Ser Met Lys
                245                 250                 255

Leu Ser Cys Ala Ala Ser Gly Phe Thr Phe Ser Asn Phe Pro Met Ala
            260                 265                 270

Trp Val Arg Gln Ala Pro Thr Lys Cys Leu Glu Trp Val Ala Thr Ile
        275                 280                 285

Ser Thr Ser Gly Gly Ser Thr Tyr Tyr Arg Asp Ser Val Lys Gly Arg
    290                 295                 300

Phe Thr Ile Ser Arg Asp Asn Ala Lys Ser Thr Leu Tyr Leu Gln Met
305                 310                 315                 320
```

Asn Ser Leu Arg Ser Glu Asp Thr Ala Thr Tyr Tyr Cys Thr Arg Thr
              325                 330                 335

Leu Tyr Ile Leu Arg Val Phe Tyr Phe Asp Tyr Trp Gly Gln Gly Val
        340                 345                 350

Met Val Thr Val Ser Ser Ala Ser Thr Lys Gly Pro Ser Val Phe Pro
        355                 360                 365

Leu Ala Pro Ser Ser Lys Ser Thr Ser Gly Gly Thr Ala Ala Leu Gly
        370                 375                 380

Cys Leu Val Glu Asp Tyr Phe Pro Glu Pro Val Thr Val Ser Trp Asn
385                 390                 395                 400

Ser Gly Ala Leu Thr Ser Gly Val His Thr Phe Pro Ala Val Leu Gln
            405                 410                 415

Ser Ser Gly Leu Tyr Ser Leu Ser Ser Val Val Thr Val Pro Ser Ser
            420                 425                 430

Ser Leu Gly Thr Gln Thr Tyr Ile Cys Asn Val Asn His Lys Pro Ser
        435                 440                 445

Asn Thr Lys Val Asp Lys Val Glu Pro Lys Ser Cys Asp Lys Thr
        450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Asp Val Ser His Glu Asp Pro
            500                 505                 510

Glu Val Lys Phe Asn Trp Tyr Val Asp Gly Val Glu Val His Asn Ala
            515                 520                 525

Lys Thr Lys Pro Arg Glu Glu Gln Tyr Asn Ser Thr Tyr Arg Val Val
        530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Cys Arg Asp Glu Leu Thr Lys Asn Gln Val Ser Leu Trp Cys
            595                 600                 605

Leu Val Lys Gly Phe Tyr Pro Ser Asp Ile Ala Val Glu Trp Glu Ser
        610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 23
<211> LENGTH: 639
<212> TYPE: DNA
<213> ORGANISM: Artificial Sequence
<220> FEATURE:
<223> OTHER INFORMATION: EGFR vIII MR1.1 VL CH1, pETR14951
<220> FEATURE:
<221> NAME/KEY: CDS
<222> LOCATION: 1..639

<223> OTHER INFORMATION: /transl_table=1

<400> SEQUENCE: 23

```
gat atc gag ctg aca cag agc ccc gcc agc ctg tct gtg gcc acc ggc      48
Asp Ile Glu Leu Thr Gln Ser Pro Ala Ser Leu Ser Val Ala Thr Gly
1               5                   10                  15 gag aaa gtg acc atc cgg tgc atg acc agc acc gac atc gac gac gac      96
Glu Lys Val Thr Ile Arg Cys Met Thr Ser Thr Asp Ile Asp Asp Asp
            20                  25                  30 atg aac tgg tat cag cag aag ccc ggc gag ccc ccc aag ttc ctg atc     144
Met Asn Trp Tyr Gln Gln Lys Pro Gly Glu Pro Pro Lys Phe Leu Ile
        35                  40                  45 agc gag ggc aac aca ctg cgg cct ggc gtg cca agc aga ttc agc agc     192
Ser Glu Gly Asn Thr Leu Arg Pro Gly Val Pro Ser Arg Phe Ser Ser
    50                  55                  60 tct ggc acc ggc acc gac ttc gtg ttt acc atc gag aat acc ctg agc     240
Ser Gly Thr Gly Thr Asp Phe Val Phe Thr Ile Glu Asn Thr Leu Ser
65                  70                  75                  80 gag gac gtg ggc gac tac tac tgc ctg cag agc tgg aac gtg ccc ctg     288
Glu Asp Val Gly Asp Tyr Tyr Cys Leu Gln Ser Trp Asn Val Pro Leu
                85                  90                  95 acc ttt ggc gac ggc acc aag ctg gaa atc aag agc agc gct agc acc     336
Thr Phe Gly Asp Gly Thr Lys Leu Glu Ile Lys Ser Ser Ala Ser Thr
            100                 105                 110 aaa ggc cct tcc gtg ttt cct ctg gct cct agc tcc aag tcc acc tct     384
Lys Gly Pro Ser Val Phe Pro Leu Ala Pro Ser Ser Lys Ser Thr Ser
        115                 120                 125 gga ggc acc gct gct ctc gga tgc ctc gtg aag gat tat ttt cct gag     432
Gly Gly Thr Ala Ala Leu Gly Cys Leu Val Lys Asp Tyr Phe Pro Glu
    130                 135                 140 cct gtg aca gtg tcc tgg aat agc gga gca ctg acc tct gga gtg cat     480
Pro Val Thr Val Ser Trp Asn Ser Gly Ala Leu Thr Ser Gly Val His
145                 150                 155                 160 act ttc ccc gct gtg ctg cag tcc tct gga ctg tac agc ctg agc agc     528
Thr Phe Pro Ala Val Leu Gln Ser Ser Gly Leu Tyr Ser Leu Ser Ser
                165                 170                 175 gtg gtg aca gtg ccc agc agc agc ctg ggc acc cag acc tac atc tgc     576
Val Val Thr Val Pro Ser Ser Ser Leu Gly Thr Gln Thr Tyr Ile Cys
            180                 185                 190 aac gtg aac cac aag ccc agc aac acc aag gtg gac aag aag gtg gaa     624
Asn Val Asn His Lys Pro Ser Asn Thr Lys Val Asp Lys Lys Val Glu
        195                 200                 205 ccc aag tct tgt tga                                                  639
Pro Lys Ser Cys
    210
```

<210> SEQ ID NO 24
<211> LENGTH: 212
<212> TYPE: PRT
<213> ORGANISM: Artificial Sequence
<220> FEATURE:
<223> OTHER INFORMATION: [CDS]:1..639 from SEQ ID NO 23

<400> SEQUENCE: 24

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45
```

```
Ser Glu Gly Asn Thr Leu Arg Pro Gly Val Pro Ser Arg Phe Ser Ser
 50                  55                  60

Ser Gly Thr Gly Thr Asp Phe Val Phe Thr Ile Glu Asn Thr Leu Ser
 65                  70                  75                  80

Glu Asp Val Gly Asp Tyr Tyr Cys Leu Gln Ser Trp Asn Val Pro Leu
                 85                  90                  95

Thr Phe Gly Asp Gly Thr Lys Leu Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 25
<211> LENGTH: 645
<212> TYPE: DNA
<213> ORGANISM: Artificial Sequence
<220> FEATURE:
<223> OTHER INFORMATION: VL EpCAM G8.8 Ck RK, pETR14882
<220> FEATURE:
<221> NAME/KEY: CDS
<222> LOCATION: 1..645
<223> OTHER INFORMATION: /transl_table=1

<400> SEQUENCE: 25 gac atc cag atg aca cag agc ccc gcc agc ctg agc gcc tct ctg ggc    48
Asp Ile Gln Met Thr Gln Ser Pro Ala Ser Leu Ser Ala Ser Leu Gly
 1               5                  10                  15 gag aca gtg tcc atc gag tgc ctg gcc agc gag ggc atc agc aac gac    96
Glu Thr Val Ser Ile Glu Cys Leu Ala Ser Glu Gly Ile Ser Asn Asp
             20                  25                  30 ctg gcc tgg tat cag cag aag tcc ggc aag agc ccc cag ctg ctg atc   144
Leu Ala Trp Tyr Gln Gln Lys Ser Gly Lys Ser Pro Gln Leu Leu Ile
         35                  40                  45 tac gcc acc agc aga ctg cag gac ggc gtg ccc agc aga ttc agc ggc   192
Tyr Ala Thr Ser Arg Leu Gln Asp Gly Val Pro Ser Arg Phe Ser Gly
     50                  55                  60 agc ggc tcc ggc acc cgg tac agc ctg aag atc agc ggc atg cag ccc   240
Ser Gly Ser Gly Thr Arg Tyr Ser Leu Lys Ile Ser Gly Met Gln Pro
 65                  70                  75                  80 gag gac gag gcc gac tac ttc tgc cag cag agc tac aag tac ccc tgg   288
Glu Asp Glu Ala Asp Tyr Phe Cys Gln Gln Ser Tyr Lys Tyr Pro Trp
                 85                  90                  95 acc ttc ggc tgc ggc acc aag ctg gaa ctg aag cgt acg gtg gct gca   336
Thr Phe Gly Cys Gly Thr Lys Leu Glu Leu Lys Arg Thr Val Ala Ala
            100                 105                 110 cca tct gtc ttc atc ttc ccg cca tct gat cgg aag ttg aaa tct gga   384
Pro Ser Val Phe Ile Phe Pro Pro Ser Asp Arg Lys Leu Lys Ser Gly
        115                 120                 125
```

```
act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130             135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145             150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tgt tag                                        645
Phe Asn Arg Gly Glu Cys
    210

<210> SEQ ID NO 26
<211> LENGTH: 214
<212> TYPE: PRT
<213> ORGANISM: Artificial Sequence
<220> FEATURE:
<223> OTHER INFORMATION: [CDS]:1..645 from SEQ ID NO 25

<400> SEQUENCE: 26

Asp Ile Gln Met Thr Gln Ser Pro Ala Ser Leu Ser Ala Ser Leu Gly
1               5                   10                  15

Glu Thr Val Ser Ile Glu Cys Leu Ala Ser Gly Ile Ser Asn Asp
                20                  25                  30

Leu Ala Trp Tyr Gln Gln Lys Ser Gly Lys Ser Pro Gln Leu Leu Ile
            35                  40                  45

Tyr Ala Thr Ser Arg Leu Gln Asp Gly Val Pro Ser Arg Phe Ser Gly
        50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Cys Gly Thr Lys Leu Glu Leu Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130             135                 140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 1356
```

```
<212> TYPE: DNA
<213> ORGANISM: Artificial Sequence
<220> FEATURE:
<223> OTHER INFORMATION: VH muEpCAM CH1 EE Fc hole PG LALA HRYF,
      pETR14940
<220> FEATURE:
<221> NAME/KEY: CDS
<222> LOCATION: 1..1356
<223> OTHER INFORMATION: /transl_table=1

<400> SEQUENCE: 27
```

| | | | | | | | | | | | | | | | | |
|---|---|---|---|---|---|---|---|---|---|---|---|---|---|---|---|---|
| gaa | gtg | cag | ctg | gcc | gag | agc | ggc | gga | ggc | ctg | gtg | cag | cct | gga | aga | 48 |
| Glu | Val | Gln | Leu | Ala | Glu | Ser | Gly | Gly | Gly | Leu | Val | Gln | Pro | Gly | Arg | |
| 1 | | | | 5 | | | | | 10 | | | | | 15 | | |
| tcc | atg | aag | ctg | agc | tgc | gcc | gcc | agc | ggc | ttc | acc | ttc | agc | aac | ttc | 96 |
| Ser | Met | Lys | Leu | Ser | Cys | Ala | Ala | Ser | Gly | Phe | Thr | Phe | Ser | Asn | Phe | |
| | | | 20 | | | | | 25 | | | | | 30 | | | |
| ccc | atg | gcc | tgg | gtc | cga | cag | gcc | ccc | acc | aag | tgc | ctg | gaa | tgg | gtg | 144 |
| Pro | Met | Ala | Trp | Val | Arg | Gln | Ala | Pro | Thr | Lys | Cys | Leu | Glu | Trp | Val | |
| | | 35 | | | | | 40 | | | | | 45 | | | | |
| gcc | acc | atc | agc | acc | agc | ggc | ggc | agc | acc | tac | tac | cgg | gac | agc | gtg | 192 |
| Ala | Thr | Ile | Ser | Thr | Ser | Gly | Gly | Ser | Thr | Tyr | Tyr | Arg | Asp | Ser | Val | |
| | 50 | | | | | 55 | | | | | 60 | | | | | |
| aag | ggc | cgg | ttc | acc | atc | agc | cgg | gac | aac | gcc | aag | agc | acc | ctg | tac | 240 |
| Lys | Gly | Arg | Phe | Thr | Ile | Ser | Arg | Asp | Asn | Ala | Lys | Ser | Thr | Leu | Tyr | |
| 65 | | | | | 70 | | | | | 75 | | | | | 80 | |
| ctg | cag | atg | aac | agc | ctg | cgg | agc | gag | gac | acc | gcc | acc | tac | tac | tgc | 288 |
| Leu | Gln | Met | Asn | Ser | Leu | Arg | Ser | Glu | Asp | Thr | Ala | Thr | Tyr | Tyr | Cys | |
| | | | | 85 | | | | | 90 | | | | | 95 | | |
| acc | cgg | acc | ctg | tat | atc | ctg | cgg | gtg | ttc | tac | ttc | gac | tac | tgg | ggc | 336 |
| Thr | Arg | Thr | Leu | Tyr | Ile | Leu | Arg | Val | Phe | Tyr | Phe | Asp | Tyr | Trp | Gly | |
| | | | 100 | | | | | 105 | | | | | 110 | | | |
| cag | ggc | gtg | atg | gtc | acc | gtg | tct | agc | gct | agc | acc | aag | ggc | ccc | tcc | 384 |
| Gln | Gly | Val | Met | Val | Thr | Val | Ser | Ser | Ala | Ser | Thr | Lys | Gly | Pro | Ser | |
| | | 115 | | | | | 120 | | | | | 125 | | | | |
| gtg | ttc | ccc | ctg | gcc | ccc | agc | agc | aag | agc | acc | agc | ggc | ggc | aca | gcc | 432 |
| Val | Phe | Pro | Leu | Ala | Pro | Ser | Ser | Lys | Ser | Thr | Ser | Gly | Gly | Thr | Ala | |
| | 130 | | | | | 135 | | | | | 140 | | | | | |
| gct | ctg | ggc | tgc | ctg | gtc | gag | gac | tac | ttc | ccc | gag | ccc | gtg | acc | gtg | 480 |
| Ala | Leu | Gly | Cys | Leu | Val | Glu | Asp | Tyr | Phe | Pro | Glu | Pro | Val | Thr | Val | |
| 145 | | | | | 150 | | | | | 155 | | | | | 160 | |
| tcc | tgg | aac | agc | gga | gcc | ctg | acc | tcc | ggc | gtg | cac | acc | ttc | ccc | gcc | 528 |
| Ser | Trp | Asn | Ser | Gly | Ala | Leu | Thr | Ser | Gly | Val | His | Thr | Phe | Pro | Ala | |
| | | | | 165 | | | | | 170 | | | | | 175 | | |
| gtg | ctg | cag | agt | tct | ggc | ctg | tat | agc | ctg | agc | agc | gtg | gtc | acc | gtg | 576 |
| Val | Leu | Gln | Ser | Ser | Gly | Leu | Tyr | Ser | Leu | Ser | Ser | Val | Val | Thr | Val | |
| | | | 180 | | | | | 185 | | | | | 190 | | | |
| cct | tct | agc | agc | ctg | ggc | acc | cag | acc | tac | atc | tgc | aac | gtg | aac | cac | 624 |
| Pro | Ser | Ser | Ser | Leu | Gly | Thr | Gln | Thr | Tyr | Ile | Cys | Asn | Val | Asn | His | |
| | | 195 | | | | | 200 | | | | | 205 | | | | |
| aag | ccc | agc | aac | acc | aag | gtg | gac | gag | aag | gtg | gag | ccc | aag | agc | tgc | 672 |
| Lys | Pro | Ser | Asn | Thr | Lys | Val | Asp | Glu | Lys | Val | Glu | Pro | Lys | Ser | Cys | |
| | 210 | | | | | 215 | | | | | 220 | | | | | |
| gac | aaa | act | cac | aca | tgc | cca | ccg | tgc | cca | gca | cct | gaa | gct | gca | ggg | 720 |
| Asp | Lys | Thr | His | Thr | Cys | Pro | Pro | Cys | Pro | Ala | Pro | Glu | Ala | Ala | Gly | |
| 225 | | | | | 230 | | | | | 235 | | | | | 240 | |
| gga | ccg | tca | gtc | ttc | ctc | ttc | ccc | cca | aaa | ccc | aag | gac | acc | ctc | atg | 768 |
| Gly | Pro | Ser | Val | Phe | Leu | Phe | Pro | Pro | Lys | Pro | Lys | Asp | Thr | Leu | Met | |
| | | | | 245 | | | | | 250 | | | | | 255 | | |
| atc | tcc | cgg | acc | cct | gag | gtc | aca | tgc | gtg | gtg | gtg | gac | gtg | agc | cac | 816 |
| Ile | Ser | Arg | Thr | Pro | Glu | Val | Thr | Cys | Val | Val | Val | Asp | Val | Ser | His | |
| | | | 260 | | | | | 265 | | | | | 270 | | | |

```
gaa gac cct gag gtc aag ttc aac tgg tac gtg gac ggc gtg gag gtg    864
Glu Asp Pro Glu Val Lys Phe Asn Trp Tyr Val Asp Gly Val Glu Val
            275                 280                 285 cat aat gcc aag aca aag ccg cgg gag gag cag tac aac agc acg tac    912
His Asn Ala Lys Thr Lys Pro Arg Glu Glu Gln Tyr Asn Ser Thr Tyr
        290                 295                 300 cgt gtg gtc agc gtc ctc acc gtc ctg cac cag gac tgg ctg aat ggc    960
Arg Val Val Ser Val Leu Thr Val Leu His Gln Asp Trp Leu Asn Gly
305                 310                 315                 320 aag gag tac aag tgc aag gtc tcc aac aaa gcc ctc ggc gcc ccc atc   1008
Lys Glu Tyr Lys Cys Lys Val Ser Asn Lys Ala Leu Gly Ala Pro Ile
                325                 330                 335 gag aaa acc atc tcc aaa gcc aaa ggg cag ccc cga gaa cca cag gtg   1056
Glu Lys Thr Ile Ser Lys Ala Lys Gly Gln Pro Arg Glu Pro Gln Val
            340                 345                 350 tgc acc ctg ccc cca tcc cgg gat gag ctg acc aag aac cag gtc agc   1104
Cys Thr Leu Pro Pro Ser Arg Asp Glu Leu Thr Lys Asn Gln Val Ser
        355                 360                 365 ctc tcg tgc gca gtc aaa ggc ttc tat ccc agc gac atc gcc gtg gag   1152
Leu Ser Cys Ala Val Lys Gly Phe Tyr Pro Ser Asp Ile Ala Val Glu
370                 375                 380 tgg gag agc aat ggg cag ccg gag aac aac tac aag acc acg cct ccc   1200
Trp Glu Ser Asn Gly Gln Pro Glu Asn Asn Tyr Lys Thr Thr Pro Pro
385                 390                 395                 400 gtg ctg gac tcc gac ggc tcc ttc ttc ctc gtg agc aag ctc acc gtg   1248
Val Leu Asp Ser Asp Gly Ser Phe Phe Leu Val Ser Lys Leu Thr Val
                405                 410                 415 gac aag agc agg tgg cag cag ggg aac gtc ttc tca tgc tcc gtg atg   1296
Asp Lys Ser Arg Trp Gln Gln Gly Asn Val Phe Ser Cys Ser Val Met
            420                 425                 430 cat gag gct ctg cac aac cgc ttc acg cag aag agc ctc tcc ctg tct   1344
His Glu Ala Leu His Asn Arg Phe Thr Gln Lys Ser Leu Ser Leu Ser
        435                 440                 445 ccg ggt aaa tga                                                    1356
Pro Gly Lys
    450

<210> SEQ ID NO 28
<211> LENGTH: 451
<212> TYPE: PRT
<213> ORGANISM: Artificial Sequence
<220> FEATURE:
<223> OTHER INFORMATION: [CDS]:1..1356 from SEQ ID NO 27

<400> SEQUENCE: 28

Glu Val Gln Leu Ala Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Pro Met Ala Trp Val Arg Gln Ala Pro Thr Lys Cys Leu Glu Trp Val
        35                  40                  45

Ala Thr Ile Ser Thr Ser Gly Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Thr Leu Tyr Ile Leu Arg Val Phe Tyr Phe Asp Tyr Trp Gly
            100                 105                 110
```

```
Gln Gly Val Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
        165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
        245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
        325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
        405                 410                 415

Asp Lys Ser Arg Trp Gln Gln Gly Asn Val Phe Ser Cys Ser Val Met
        420                 425                 430

His Glu Ala Leu His Asn Arg Phe Thr Gln Lys Ser Leu Ser Leu Ser
        435                 440                 445

Pro Gly Lys
    450

<210> SEQ ID NO 29
<211> LENGTH: 5
<212> TYPE: PRT
<213> ORGANISM: Artificial Sequence
<220> FEATURE:
<223> OTHER INFORMATION: EGFRvIII MR1.1 CDR H1 Kabat

<400> SEQUENCE: 29

Lys Phe Gly Met Ser
1               5
```

```
<210> SEQ ID NO 30
<211> LENGTH: 17
<212> TYPE: PRT
<213> ORGANISM: Artificial Sequence
<220> FEATURE:
<223> OTHER INFORMATION: EGFRvIII MR1.1 CDR H2 Kabat

<400> SEQUENCE: 30

Ser Ile Ser Thr Gly Gly Tyr Asn Thr Tyr Tyr Ser Asp Asn Val Lys
1               5                   10                  15
Gly

<210> SEQ ID NO 31
<211> LENGTH: 11
<212> TYPE: PRT
<213> ORGANISM: Artificial Sequence
<220> FEATURE:
<223> OTHER INFORMATION: EGFRvIII MR1.1 CDR H3 Kabat

<400> SEQUENCE: 31

Gly Tyr Ser Pro Tyr Ser Tyr Ala Met Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: EGFRvIII MR1.1 CDR1 L1 Kabat

<400> SEQUENCE: 32

Met Thr Ser Thr Asp Ile Asp Asp Asp Met Asn
1               5                   10

<210> SEQ ID NO 33
<211> LENGTH: 7
<212> TYPE: PRT
<213> ORGANISM: Artificial Sequence
<220> FEATURE:
<223> OTHER INFORMATION: EGFRvIII MR1.1 CDR L2 Kabat

<400> SEQUENCE: 33

Glu Gly Asn Thr Leu Arg Pro
1               5

<210> SEQ ID NO 34
<211> LENGTH: 9
<212> TYPE: PRT
<213> ORGANISM: Artificial Sequence
<220> FEATURE:
<223> OTHER INFORMATION: EGFRvIII MR1.1 CDR L3 Kabat

<400> SEQUENCE: 34

Leu Gln Ser Trp Asn Val Pro Leu Thr
1               5

<210> SEQ ID NO 35
<211> LENGTH: 5
<212> TYPE: PRT
<213> ORGANISM: Artificial Sequence
<220> FEATURE:
<223> OTHER INFORMATION: muEpCAM CDR H1 Kabat

<400> SEQUENCE: 35

Asn Phe Pro Met Ala
```

```
<210> SEQ ID NO 36
<211> LENGTH: 17
<212> TYPE: PRT
<213> ORGANISM: Artificial Sequence
<220> FEATURE:
<223> OTHER INFORMATION: muEpCAM CDR H2 Kabat

<400> SEQUENCE: 36

Thr Ile Ser Thr Ser Gly Gly Ser Thr Tyr Tyr Arg Asp Ser Val Lys
 1               5                  10                  15
Gly

<210> SEQ ID NO 37
<211> LENGTH: 12
<212> TYPE: PRT
<213> ORGANISM: Artificial Sequence
<220> FEATURE:
<223> OTHER INFORMATION: muEpCAM CDR H3 Kabat

<400> SEQUENCE: 37

Thr Leu Tyr Ile Leu Arg Val Phe Tyr Phe Asp Tyr
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: muEpCAM CDR1 L1 Kabat

<400> SEQUENCE: 38

Leu Ala Ser Glu Gly Ile Ser Asn Asp Leu Ala
 1               5                  10

<210> SEQ ID NO 39
<211> LENGTH: 8
<212> TYPE: PRT
<213> ORGANISM: Artificial Sequence
<220> FEATURE:
<223> OTHER INFORMATION: muEpCAM CDR L2 Kabat

<400> SEQUENCE: 39

Ala Thr Ser Arg Leu Gln Asp Gly
 1               5

<210> SEQ ID NO 40
<211> LENGTH: 9
<212> TYPE: PRT
<213> ORGANISM: Artificial Sequence
<220> FEATURE:
<223> OTHER INFORMATION: muEpCAM CDR L3 Kabat

<400> SEQUENCE: 40

Gln Gln Ser Tyr Lys Tyr Pro Trp Thr
 1               5

<210> SEQ ID NO 41
<211> LENGTH: 1713
<212> TYPE: DNA
<213> ORGANISM: Artificial Sequence
<220> FEATURE:
<223> OTHER INFORMATION: E3 murin (EGFRex-CD28tm/iz-CD3z)

<400> SEQUENCE: 41
```

```
agcttgctcg cggccgcgcc accatgcgac cctccgggac ggccggggca gcgctcctgg   60
cgctgctggc tgcgctctgc ccggcgagtc gggctctgga ggaaaagaaa ggtaattatg  120
tggtgacaga tcacggctcg tgcgtccgag cctgtggggc cgacagctat gagatggagg  180
aagacggcgt ccgcaagtgt aagaagtgcg aagggccttg ccgcaaagtg tgtaacggaa  240
taggtattgg tgaatttaaa gactcactct ccataaatgc tacgaatatt aaacacttca  300
aaaactgcac ctccatcagt ggcgatctcc acatcctgcc ggtggcattt aggggtgact  360
ccttcacaca tactcctcct ctggatccac aggaactgga tattctgaaa accgtaaagg  420
aaatcacagg ttttttgctg attcaggctt ggcctgaaaa caggacggac ctccatgcct  480
ttgagaacct agaaatcata cgcggcagga ccaagcaaca tggtcagttt tctcttgcag  540
tcgtcagcct gaacataaca tccttgggat tacgctccct caaggagata agtgatggag  600
atgtgataat ttcaggaaac aaaaatttgt gctatgcaaa tacaataaac tggaaaaaac  660
tgtttgggac ctccggtcag aaaaccaaaa ttataagcaa cagaggtgaa aacagctgca  720
aggccacagg ccaggtctgc catgccttgt gctcccccga gggctgctgg ggcccggagc  780
ccagggactg cgtctcttgc cggaatgtca gccgaggcag ggaatgcgtg gacaagtgca  840
accttctgga gggtgagcca agggagtttg tggagaactc tgagtgcata cagtgccacc  900
cagagtgcct gcctcaggcc atgaacatca cctgcacagg acggggacca gacaactgta  960
tccagtgtgc ccactacatt gacggccccc actgcgtcaa gacctgcccg gcaggagtca 1020
tgggagaaaa caacaccctg gtctggaagt acgcagacgc cggccatgtg tgccacctgt 1080
gccatccaaa ctgcacctac ggatgcactg gccaggtct gaaggctgt caacgaatg  1140
ggcctaagat cccgtccttt tgggcactgg tcgtggttgc tggagtcctg ttttgttatg 1200
gcttgctagt gacagtggct cttttgtgtta tctggacaaa tagtagaagg aacagactcc 1260
ttcaaagtga ctacatgaac atgactcccc ggaggcctgg gctcactcga aagccttacc 1320
agccctacgc ccctgccaga gactttgcag cgtaccgccc cagagcaaaa ttcagcagga 1380
gtgcagagac tgctgccaac ctgcaggacc ccaaccagct ctacaatgag ctcaatctag 1440
ggcgaagaga ggaatatgac gtcttggaga gaagcgggc tcgggatcca gagatgggag 1500
gcaaacagca gaggaggagg aaccccccagg aaggcgtata caatgcactg cagaaagaca 1560
agatggcaga agcctacagt gagatcggca caaaaggcga gaggcggaga ggcaaggggc 1620
acgatggcct ttaccagggt ctcagcactg ccaccaagga cacctatgat gccctgcata 1680
tgcagaccct ggcccctcgc taagaattca tta                              1713
```

<210> SEQ ID NO 42
<211> LENGTH: 566
<212> TYPE: PRT
<213> ORGANISM: Artificial Sequence
<220> FEATURE:
<223> OTHER INFORMATION: E3 murin (EGFRex-CD28tm/iz-CD3z)

<400> SEQUENCE: 42

```
Leu Ala Arg Gly Arg Ala Thr Met Arg Pro Ser Gly Thr Ala Gly Ala
1               5                   10                  15

Ala Leu Leu Ala Leu Leu Ala Ala Leu Cys Pro Ala Ser Arg Ala Leu
            20                  25                  30

Glu Glu Lys Lys Gly Asn Tyr Val Val Thr Asp His Gly Ser Cys Val
        35                  40                  45

Arg Ala Cys Gly Ala Asp Ser Tyr Glu Met Glu Glu Asp Gly Val Arg
    50                  55                  60
```

```
Lys Cys Lys Lys Cys Glu Gly Pro Cys Arg Lys Val Cys Asn Gly Ile
 65                  70                  75                  80

Gly Ile Gly Glu Phe Lys Asp Ser Leu Ser Ile Asn Ala Thr Asn Ile
                 85                  90                  95

Lys His Phe Lys Asn Cys Thr Ser Ile Ser Gly Asp Leu His Ile Leu
            100                 105                 110

Pro Val Ala Phe Arg Gly Asp Ser Phe Thr His Thr Pro Pro Leu Asp
            115                 120                 125

Pro Gln Glu Leu Asp Ile Leu Lys Thr Val Lys Glu Ile Thr Gly Phe
            130                 135                 140

Leu Leu Ile Gln Ala Trp Pro Glu Asn Arg Thr Asp Leu His Ala Phe
145                 150                 155                 160

Glu Asn Leu Glu Ile Ile Arg Gly Arg Thr Lys Gln His Gly Gln Phe
                165                 170                 175

Ser Leu Ala Val Val Ser Leu Asn Ile Thr Ser Leu Gly Leu Arg Ser
            180                 185                 190

Leu Lys Glu Ile Ser Asp Gly Asp Val Ile Ile Ser Gly Asn Lys Asn
            195                 200                 205

Leu Cys Tyr Ala Asn Thr Ile Asn Trp Lys Lys Leu Phe Gly Thr Ser
210                 215                 220

Gly Gln Lys Thr Lys Ile Ile Ser Asn Arg Gly Glu Asn Ser Cys Lys
225                 230                 235                 240

Ala Thr Gly Gln Val Cys His Ala Leu Cys Ser Pro Glu Gly Cys Trp
                245                 250                 255

Gly Pro Glu Pro Arg Asp Cys Val Ser Cys Arg Asn Val Ser Arg Gly
            260                 265                 270

Arg Glu Cys Val Asp Lys Cys Asn Leu Leu Glu Gly Glu Pro Arg Glu
            275                 280                 285

Phe Val Glu Asn Ser Glu Cys Ile Gln Cys His Pro Glu Cys Leu Pro
            290                 295                 300

Gln Ala Met Asn Ile Thr Cys Thr Gly Arg Gly Pro Asp Asn Cys Ile
305                 310                 315                 320

Gln Cys Ala His Tyr Ile Asp Gly Pro His Cys Val Lys Thr Cys Pro
                325                 330                 335

Ala Gly Val Met Gly Glu Asn Asn Thr Leu Val Trp Lys Tyr Ala Asp
            340                 345                 350

Ala Gly His Val Cys His Leu Cys His Pro Asn Cys Thr Tyr Gly Cys
            355                 360                 365

Thr Gly Pro Gly Leu Glu Gly Cys Pro Thr Asn Gly Pro Lys Ile Pro
            370                 375                 380

Ser Phe Trp Ala Leu Val Val Ala Gly Val Leu Phe Cys Tyr Gly
385                 390                 395                 400

Leu Leu Val Thr Val Ala Leu Cys Val Ile Trp Thr Asn Ser Arg Arg
            405                 410                 415

Asn Arg Leu Leu Gln Ser Asp Tyr Met Asn Met Thr Pro Arg Arg Pro
            420                 425                 430

Gly Leu Thr Arg Lys Pro Tyr Gln Pro Tyr Ala Pro Ala Arg Asp Phe
            435                 440                 445

Ala Ala Tyr Arg Pro Arg Ala Lys Phe Ser Arg Ser Ala Glu Thr Ala
            450                 455                 460

Ala Asn Leu Gln Asp Pro Asn Gln Leu Tyr Asn Glu Leu Asn Leu Gly
465                 470                 475                 480
```

```
Arg Arg Glu Glu Tyr Asp Val Leu Glu Lys Lys Arg Ala Arg Asp Pro
                485                 490                 495
Glu Met Gly Gly Lys Gln Gln Arg Arg Arg Asn Pro Gln Glu Gly Val
            500                 505                 510
Tyr Asn Ala Leu Gln Lys Asp Lys Met Ala Glu Ala Tyr Ser Glu Ile
        515                 520                 525
Gly Thr Lys Gly Glu Arg Arg Arg Gly Lys Gly His Asp Gly Leu Tyr
    530                 535                 540
Gln Gly Leu Ser Thr Ala Thr Lys Asp Thr Tyr Asp Ala Leu His Met
545                 550                 555                 560
Gln Thr Leu Ala Pro Arg
                565

<210> SEQ ID NO 43
<211> LENGTH: 1857
<212> TYPE: DNA
<213> ORGANISM: Artificial Sequence
<220> FEATURE:
<223> OTHER INFORMATION: E4 murin (EGFRex-CD28tm/iz-4-1BB-CD3z)

<400> SEQUENCE: 43
agcttgctcg cggccgcgcc accatgcgac cctccgggac ggccggggca gcgctcctgg      60
cgctgctggc tgcgctctgc ccggcgagtc gggctctgga ggaaaagaaa ggtaattatg     120
tggtgacaga tcacggctcg tgcgtccgag cctgtggggc cgacagctat gagatggagg     180
aagacggcgt ccgcaagtgt aagaagtgcg aagggccttg ccgcaaagtg tgtaacggaa     240
taggtattgg tgaatttaaa gactcactct ccataaatgc tacgaatatt aaacacttca     300
aaaactgcac ctccatcagt ggcgatctcc acatcctgcc ggtggcattt aggggtgact     360
ccttcacaca tactcctcct ctggatccac aggaactgga tattctgaaa accgtaaagg     420
aaatcacagg gttttttgctg attcaggctt ggcctgaaaa caggacggac ctccatgcct     480
ttgagaacct agaaatcata cgcggcagga ccaagcaaca tggtcagttt tctcttgcag     540
tcgtcagcct gaacataaca tccttgggat tacgctccct caaggagata agtgatggag     600
atgtgataat tcaggaaaac aaaaatttgt gctatgcaaa tacaataaac tggaaaaaac     660
tgtttgggac ctccggtcag aaaaccaaaa ttataagcaa cagaggtgaa aacagctgca     720
aggccacagg ccaggtctgc catgccttgt gctccccccga gggctgctgg gcccggagc     780 ccagggactg cgtctcttgc cggaatgtca gccgaggcag ggaatgcgtg gacaagtgca     840
accttctgga gggtgagcca agggagtttg tggagaactc tgagtgcata cagtgccacc     900
cagagtgcct gcctcaggcc atgaacatca cctgcacagg acggggacca gacaactgta     960
tccagtgtgc ccactacatt gacggccccc actgcgtcaa gacctgcccg gcaggagtca    1020
tgggagaaaa caacaccctg gtctggaagt acgcagacgc cggccatgtg tgccacctgt    1080
gccatccaaa ctgcacctac ggatgcactg ggccaggtct tgaaggctgt ccaacgaatg    1140
ggcctaagat cccgtccttt tgggcactgg tcgtggttgc tggagtcctg tttttgttatg    1200 gcttgctagt gacagtggct ctttgtgtta tctggacaaa tagtagaagg aacagactcc    1260
ttcaaagtga ctacatgaac atgactcccc ggaggcctgg gctcactcga aagccttacc    1320
agccctacgc ccctgccaga gactttgcag cgtaccgccc ctctgtgctc aaatggatca    1380
ggaaaaaatt cccccacata ttcaagcaac catttaagaa gaccactgga gcagctcaag    1440
aggaagatgg ttgtagctgc cgatgtccac aggaagaaga aggaggagga ggaggctatg    1500
agctgagagc aaaattcagc aggagtgcag agactgctgc caacctgcag gacccccaacc    1560
```
agctctacaa tgagctcaat ctagggcgaa gagaggaata tgacgtcttg gagaagaagc 1620
gggctcggga tccagagatg ggaggcaaac agcagaggag gaggaacccc caggaaggcg 1680
tatacaatgc actgcagaaa gacaagatgg cagaagccta cagtgagatc ggcacaaaag 1740
gcgagaggcg gagaggcaag gggcacgatg gcctttacca gggtctcagc actgccacca 1800
aggacaccta tgatgccctg catatgcaga ccctggcccc tcgctaagaa ttcatta 1857

<210> SEQ ID NO 44
<211> LENGTH: 614
<212> TYPE: PRT
<213> ORGANISM: Artificial Sequence
<220> FEATURE:
<223> OTHER INFORMATION: E4 murin (EGFRex-CD28tm/iz-4-1BB-CD3z)

<400> SEQUENCE: 44

```
Leu Ala Arg Gly Arg Ala Thr Met Arg Pro Ser Gly Thr Ala Gly Ala
1               5                   10                  15
Ala Leu Leu Ala Leu Leu Ala Ala Leu Cys Pro Ala Ser Arg Ala Leu
                20                  25                  30
Glu Glu Lys Lys Gly Asn Tyr Val Val Thr Asp His Gly Ser Cys Val
            35                  40                  45
Arg Ala Cys Gly Ala Asp Ser Tyr Glu Met Glu Glu Asp Gly Val Arg
        50                  55                  60
Lys Cys Lys Lys Cys Glu Gly Pro Cys Arg Lys Val Cys Asn Gly Ile
65                  70                  75                  80
Gly Ile Gly Glu Phe Lys Asp Ser Leu Ser Ile Asn Ala Thr Asn Ile
                85                  90                  95
Lys His Phe Lys Asn Cys Thr Ser Ile Ser Gly Asp Leu His Ile Leu
            100                 105                 110
Pro Val Ala Phe Arg Gly Asp Ser Phe Thr His Thr Pro Pro Leu Asp
        115                 120                 125
Pro Gln Glu Leu Asp Ile Leu Lys Thr Val Lys Glu Ile Thr Gly Phe
    130                 135                 140
Leu Leu Ile Gln Ala Trp Pro Glu Asn Arg Thr Asp Leu His Ala Phe
145                 150                 155                 160
Glu Asn Leu Glu Ile Ile Arg Gly Arg Thr Lys Gln His Gly Gln Phe
                165                 170                 175
Ser Leu Ala Val Val Ser Leu Asn Ile Thr Ser Leu Gly Leu Arg Ser
            180                 185                 190
Leu Lys Glu Ile Ser Asp Gly Asp Val Ile Ile Ser Gly Asn Lys Asn
        195                 200                 205
Leu Cys Tyr Ala Asn Thr Ile Asn Trp Lys Lys Leu Phe Gly Thr Ser
    210                 215                 220
Gly Gln Lys Thr Lys Ile Ile Ser Asn Arg Gly Glu Asn Ser Cys Lys
225                 230                 235                 240
Ala Thr Gly Gln Val Cys His Ala Leu Cys Ser Pro Glu Gly Cys Trp
                245                 250                 255
Gly Pro Glu Pro Arg Asp Cys Val Ser Cys Arg Asn Val Ser Arg Gly
            260                 265                 270
Arg Glu Cys Val Asp Lys Cys Asn Leu Leu Glu Gly Glu Pro Arg Glu
        275                 280                 285
Phe Val Glu Asn Ser Glu Cys Ile Gln Cys His Pro Glu Cys Leu Pro
    290                 295                 300
Gln Ala Met Asn Ile Thr Cys Thr Gly Arg Gly Pro Asp Asn Cys Ile
```

```
                305                 310                 315                 320
        Gln Cys Ala His Tyr Ile Asp Gly Pro His Cys Val Lys Thr Cys Pro
                        325                 330                 335
        Ala Gly Val Met Gly Glu Asn Asn Thr Leu Val Trp Lys Tyr Ala Asp
                        340                 345                 350
        Ala Gly His Val Cys His Leu Cys His Pro Asn Cys Thr Tyr Gly Cys
                        355                 360                 365
        Thr Gly Pro Gly Leu Glu Gly Cys Pro Thr Asn Gly Pro Lys Ile Pro
                370                 375                 380
        Ser Phe Trp Ala Leu Val Val Ala Gly Val Leu Phe Cys Tyr Gly
        385                 390                 395                 400
        Leu Leu Val Thr Val Ala Leu Cys Val Ile Trp Thr Asn Ser Arg Arg
                        405                 410                 415
        Asn Arg Leu Leu Gln Ser Asp Tyr Met Asn Met Thr Pro Arg Arg Pro
                        420                 425                 430
        Gly Leu Thr Arg Lys Pro Tyr Gln Pro Tyr Ala Pro Ala Arg Asp Phe
                        435                 440                 445
        Ala Ala Tyr Arg Pro Ser Val Leu Lys Trp Ile Arg Lys Lys Phe Pro
                450                 455                 460
        His Ile Phe Lys Gln Pro Phe Lys Lys Thr Thr Gly Ala Ala Gln Glu
        465                 470                 475                 480
        Glu Asp Ala Cys Ser Cys Arg Cys Pro Gln Glu Glu Glu Gly Gly
                        485                 490                 495
        Gly Gly Tyr Glu Leu Arg Ala Lys Phe Ser Arg Ser Ala Glu Thr Ala
                        500                 505                 510
        Ala Asn Leu Gln Asp Pro Asn Gln Leu Tyr Asn Glu Leu Asn Leu Gly
                        515                 520                 525
        Arg Arg Glu Glu Tyr Asp Val Leu Glu Lys Lys Arg Ala Arg Asp Pro
                530                 535                 540
        Glu Met Gly Gly Lys Gln Gln Arg Arg Arg Asn Pro Gln Glu Gly Val
        545                 550                 555                 560
        Tyr Asn Ala Leu Gln Lys Asp Lys Met Ala Glu Ala Tyr Ser Glu Ile
                        565                 570                 575
        Gly Thr Lys Gly Glu Arg Arg Arg Gly Lys Gly His Asp Gly Leu Tyr
                        580                 585                 590
        Gln Gly Leu Ser Thr Ala Thr Lys Asp Thr Tyr Asp Ala Leu His Met
                595                 600                 605
        Gln Thr Leu Ala Pro Arg
            610

<210> SEQ ID NO 45
<211> LENGTH: 1132
<212> TYPE: DNA
<213> ORGANISM: Artificial Sequence
<220> FEATURE:
<223> OTHER INFORMATION: CAR1 murin (Cripto-CD8aex/tm-CD28iz-CD3z)

<400> SEQUENCE: 45
attagcggcc gcgccaccat ggaaacagat acactgctgc tgtgggtgct gctgctgtgg      60
gtgccaggat ctacagggga tggcgcccag cctgctagaa gcctgggcca tcaggaattt     120
gctcgtccat ctcggggata cctggccttc agagatgaca gcatttggcc caggaggag     180 cctgcaattc ggcctcggtc ttcccagcgt gtgccgccca tggggataca gcacagtaag     240
gagctaaaca gaacctgctg cctgaatggg ggaacctgca tgctggggtc cttttgtgcc     300
```

```
tgccctccct ccttctacgg acggaactgt gagcacgatg tgcgcaaaga gaactgtggg    360
tctgtgcccc atgacacctg gctgccaag aagtgttccc tgtgtaaatg ctggcacggt     420
cagctccgct gctttcctca ggcatttcta cccggctgtg atactaccaa gccagtgctg    480
cgaactccct cacctgtgca ccctaccggg acatctcagc cccagagacc agaagattgt    540
cggcccccgtg gctcagtgaa ggggaccgga ttggacttcg cctgtgatat ttacatctgg    600
gcacccttgg ccggaatctg cgtggcctt ctgctgtcct tgatcatcac tctcatcaat      660
agtagaagga acagactcct tcaaagtgac tacatgaaca tgactccccg gaggcctggg    720
ctcactcgaa agccttacca gccctacgcc cctgccagag actttgcagc gtaccgcccc    780
agagcaaaat tcagcaggag tgcagagact gctgccaacc tgcaggaccc caaccagctc    840
tacaatgagc tcaatctagg gcgaagagag gaatatgacg tcttggagaa gaagcgggct    900
cgggatccag agatgggagg caaacagcag aggaggagga accccaggaa aggcgtatac    960
aatgcactgc agaaagacaa gatggcagaa gcctacagtg agatcggcac aaaaggcgag   1020
aggcggagag gcaaggggca cgatggcctt taccagggtc tcagcactgc caccaaggac   1080
acctatgatg ccctgcatat gcagaccctg gcccctcgct aagaattcat ta            1132
```

<210> SEQ ID NO 46
<211> LENGTH: 373
<212> TYPE: PRT
<213> ORGANISM: Artificial Sequence
<220> FEATURE:
<223> OTHER INFORMATION: CAR1 murin (Cripto-CD8aex/tm-CD28iz-CD3z)

<400> SEQUENCE: 46

```
Ile Ser Gly Arg Ala Thr Met Glu Thr Asp Thr Leu Leu Leu Trp Val
1               5                   10                  15

Leu Leu Leu Trp Val Pro Gly Ser Thr Gly Asp Gly Ala Gln Pro Ala
            20                  25                  30

Arg Ser Leu Gly His Gln Glu Phe Ala Arg Pro Ser Arg Gly Tyr Leu
        35                  40                  45

Ala Phe Arg Asp Asp Ser Ile Trp Pro Gln Glu Pro Ala Ile Arg
    50                  55                  60

Pro Arg Ser Ser Gln Arg Val Pro Pro Met Gly Ile Gln His Ser Lys
65                  70                  75                  80

Glu Leu Asn Arg Thr Cys Cys Leu Asn Gly Thr Cys Met Leu Gly
                85                  90                  95

Ser Phe Cys Ala Cys Pro Pro Ser Phe Tyr Gly Arg Asn Cys Glu His
            100                 105                 110

Asp Val Arg Lys Glu Asn Cys Gly Ser Val Pro His Asp Thr Trp Leu
        115                 120                 125

Pro Lys Lys Cys Ser Leu Cys Lys Cys Trp His Gly Gln Leu Arg Cys
    130                 135                 140

Phe Pro Gln Ala Phe Leu Pro Gly Cys Asp Thr Thr Lys Pro Val Leu
145                 150                 155                 160

Arg Thr Pro Ser Pro Val His Pro Thr Gly Thr Ser Gln Pro Gln Arg
                165                 170                 175

Pro Glu Asp Cys Arg Pro Arg Gly Ser Val Lys Gly Thr Gly Leu Asp
            180                 185                 190

Phe Ala Cys Asp Ile Tyr Ile Trp Ala Pro Leu Ala Gly Ile Cys Val
        195                 200                 205

Ala Leu Leu Leu Ser Leu Ile Ile Thr Leu Ile Asn Ser Arg Arg Asn
    210                 215                 220
```

```
Arg Leu Leu Gln Ser Asp Tyr Met Asn Met Thr Pro Arg Arg Pro Gly
225                 230                 235                 240

Leu Thr Arg Lys Pro Tyr Gln Pro Tyr Ala Pro Ala Arg Asp Phe Ala
            245                 250                 255

Ala Tyr Arg Pro Arg Ala Lys Phe Ser Arg Ser Ala Glu Thr Ala Ala
        260                 265                 270

Asn Leu Gln Asp Pro Asn Gln Leu Tyr Asn Glu Leu Asn Leu Gly Arg
    275                 280                 285

Arg Glu Glu Tyr Asp Val Leu Glu Lys Lys Arg Ala Arg Asp Pro Glu
290                 295                 300

Met Gly Gly Lys Gln Arg Arg Arg Asn Pro Gln Glu Gly Val Tyr
305                 310                 315                 320

Asn Ala Leu Gln Lys Asp Lys Met Ala Glu Ala Tyr Ser Glu Ile Gly
                325                 330                 335

Thr Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Thr Leu Ala Pro Arg
    370

<210> SEQ ID NO 47
<211> LENGTH: 1700
<212> TYPE: DNA
<213> ORGANISM: Artificial Sequence
<220> FEATURE:
<223> OTHER INFORMATION: E3 human (EGFRex-CD28tm/iz-CD3z)

<400> SEQUENCE: 47
agcttgctcg cggccgcgcc accatgcgac cctccgggac ggccggggca gcgctcctgg      60
cgctgctggc tgcgctctgc ccggcgagtc gggctctgga ggaaaagaaa ggtaattatg     120
tggtgacaga tcacggctcg tgcgtccgag cctgtggggc cgacagctat gagatggagg     180
aagacggcgt ccgcaagtgt aagaagtgcg aagggccttg ccgcaaagtg tgtaacggaa     240
taggtattgg tgaatttaaa gactcactct ccataaatgc tacgaatatt aaacacttca     300
aaaactgcac ctccatcagt ggcgatctcc acatcctgcc ggtggcattt agggggtgact     360 ccttcacaca tactcctcct ctggatccac aggaactgga tattctgaaa accgtaaagg     420
aaatcacagg ttttttgctg attcaggctt ggcctgaaaa caggacggac ctccatgcct     480
ttgagaacct agaaatcata cgcggcagga ccaagcaaca tggtcagttt ctcttgcag     540 tcgtcagcct gaacataaca tccttgggat tacgctccct caaggagata agtgatggag     600
atgtgataat ttcaggaaac aaaaatttgt gctatgcaaa tacaataaac tggaaaaaac     660
tgtttgggac ctccggtcag aaaccaaaa ttataagcaa cagaggtgaa aacagctgca     720
aggccacagg ccaggtctgc catgccttgt gctccccga gggctgctgg ggcccggagc     780
ccagggactg cgtctcttgc cggaatgtca gccgaggcag ggaatgcgtg gacaagtgca     840
accttctgga gggtgagcca agggagtttg tggagaactc tgagtgcata cagtgccacc     900
cagagtgcct gcctcaggcc atgaacatca cctgcacagg acgggaccga gacaactgta     960
tccagtgtgc ccactacatt gacggccccc actgcgtcaa gacctgcccg gcaggagtca    1020
tgggagaaaa caacaccctg gtctggaagt acgcagacgc cggccatgtg tgccacctgt    1080
gccatccaaa ctgcacctac ggatgcactg ggccaggtct tgaaggctgt ccaacgaatg    1140
```

-continued

```
ggcctaagat cccgtcctttt tgggtgctgg tggtggttgg tggagtcctg gcttgctata    1200
gcttgctagt aacagtggcc tttattattt tctgggtgag gagtaagagg agcaggctcc    1260
tgcacagtga ctacatgaac atgactcccc gccgccccgg gcccacccgc aagcattacc    1320
agccctatgc cccaccacgc gacttcgcag cctatcgctc cagagtgaag ttcagcagga    1380
gcgcagacgc ccccgcgtac cagcagggcc agaaccagct ctataacgag ctcaatctag    1440
gacgaagaga ggagtacgat gttttggaca agagacgtgg ccgggaccct gagatggggg    1500
gaaagccgag aaggaagaac cctcaggaag gcctgtacaa tgaactgcag aaagataaga    1560
tggcggaggc ctacagtgag attgggatga aggcgagcg ccggaggggc aaggggcacg    1620
atggccttta ccagggtctc agtacagcca ccaaggacac ctacgacgcc cttcacatgc    1680
aggccctgcc ccctcgctaa                                                1700
```

<210> SEQ ID NO 48
<211> LENGTH: 565
<212> TYPE: PRT
<213> ORGANISM: Artificial Sequence
<220> FEATURE:
<223> OTHER INFORMATION: E3 human (EGFRex-CD28tm/iz-CD3z)

<400> SEQUENCE: 48

```
Leu Ala Arg Gly Arg Ala Thr Met Arg Pro Ser Gly Thr Ala Gly Ala
1               5                   10                  15

Ala Leu Leu Ala Leu Leu Ala Ala Leu Cys Pro Ala Ser Arg Ala Leu
            20                  25                  30

Glu Glu Lys Lys Gly Asn Tyr Val Val Thr Asp His Gly Ser Cys Val
        35                  40                  45

Arg Ala Cys Gly Ala Asp Ser Tyr Glu Met Glu Glu Asp Gly Val Arg
    50                  55                  60

Lys Cys Lys Lys Cys Glu Gly Pro Cys Arg Lys Val Cys Asn Gly Ile
65                  70                  75                  80

Gly Ile Gly Glu Phe Lys Asp Ser Leu Ser Ile Asn Ala Thr Asn Ile
                85                  90                  95

Lys His Phe Lys Asn Cys Thr Ser Ile Ser Gly Asp Leu His Ile Leu
            100                 105                 110

Pro Val Ala Phe Arg Gly Asp Ser Phe Thr His Thr Pro Pro Leu Asp
        115                 120                 125

Pro Gln Glu Leu Asp Ile Leu Lys Thr Val Lys Glu Ile Thr Gly Phe
    130                 135                 140

Leu Leu Ile Gln Ala Trp Pro Glu Asn Arg Thr Asp Leu His Ala Phe
145                 150                 155                 160

Glu Asn Leu Glu Ile Ile Arg Gly Arg Thr Lys Gln His Gly Gln Phe
                165                 170                 175

Ser Leu Ala Val Val Ser Leu Asn Ile Thr Ser Leu Gly Leu Arg Ser
            180                 185                 190

Leu Lys Glu Ile Ser Asp Gly Asp Val Ile Ile Ser Gly Asn Lys Asn
        195                 200                 205

Leu Cys Tyr Ala Asn Thr Ile Asn Trp Lys Lys Leu Phe Gly Thr Ser
    210                 215                 220

Gly Gln Lys Thr Lys Ile Ile Ser Asn Arg Gly Glu Asn Ser Cys Lys
225                 230                 235                 240

Ala Thr Gly Gln Val Cys His Ala Leu Cys Ser Pro Glu Gly Cys Trp
                245                 250                 255

Gly Pro Glu Pro Arg Asp Cys Val Ser Cys Arg Asn Val Ser Arg Gly
```

```
                260                 265                 270
Arg Glu Cys Val Asp Lys Cys Asn Leu Leu Glu Gly Glu Pro Arg Glu
            275                 280                 285

Phe Val Glu Asn Ser Glu Cys Ile Gln Cys His Pro Glu Cys Leu Pro
        290                 295                 300

Gln Ala Met Asn Ile Thr Cys Thr Gly Arg Gly Pro Asp Asn Cys Ile
305                 310                 315                 320

Gln Cys Ala His Tyr Ile Asp Gly Pro His Cys Val Lys Thr Cys Pro
                325                 330                 335

Ala Gly Val Met Gly Glu Asn Asn Thr Leu Val Trp Lys Tyr Ala Asp
            340                 345                 350

Ala Gly His Val Cys His Leu Cys His Pro Asn Cys Thr Tyr Gly Cys
        355                 360                 365

Thr Gly Pro Gly Leu Glu Gly Cys Pro Thr Asn Gly Pro Lys Ile Pro
    370                 375                 380

Ser Phe Trp Val Leu Val Val Val Gly Gly Val Leu Ala Cys Tyr Ser
385                 390                 395                 400

Leu Leu Val Thr Val Ala Phe Ile Ile Phe Trp Val Arg Ser Lys Arg
                405                 410                 415

Ser Arg Leu Leu His Ser Asp Tyr Met Asn Met Thr Pro Arg Arg Pro
            420                 425                 430

Gly Pro Thr Arg Lys His Tyr Gln Pro Tyr Ala Pro Pro Arg Asp Phe
        435                 440                 445

Ala Ala Tyr Arg Ser Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
                565

<210> SEQ ID NO 49
<211> LENGTH: 1826
<212> TYPE: DNA
<213> ORGANISM: Artificial Sequence
<220> FEATURE:
<223> OTHER INFORMATION: E4 human (EGFRex-CD28tm/iz-4-1BB-CD3z)

<400> SEQUENCE: 49
agcttgctcg cggccgcgcc accatgcgac cctccgggac ggccggggca gcgctcctgg      60
cgctgctggc tgcgctctgc ccggcgagtc gggctctgga ggaaaagaaa gtaattatg     120 tggtgacaga tcacggctcg tgcgtccgag cctgtgggc cgacagctat gagatggagg     180
aagacggcgt ccgcaagtgt aagaagtgcg aagggccttg ccgcaaagtg tgtaacggaa    240
taggtattgg tgaatttaaa gactcactct ccataaatgc tacgaatatt aaacacttca    300
```

```
aaaactgcac ctccatcagt ggcgatctcc acatcctgcc ggtggcattt agggtgact    360 ccttcacaca tactcctcct ctggatccac aggaactgga tattctgaaa accgtaaagg   420
aaatcacagg gttttgctg attcaggctt ggcctgaaaa caggacggac ctccatgcct    480
ttgagaacct agaaatcata cgcggcagga ccaagcaaca tggtcagttt tctcttgcag   540
tcgtcagcct gaacataaca tccttgggat tacgctccct caaggagata agtgatggag   600
atgtgataat ttcaggaaac aaaaatttgt gctatgcaaa tacaataaac tggaaaaaac   660
tgtttgggac ctccggtcag aaaaccaaaa ttataagcaa cagaggtgaa acagctgca    720 aggccacagg ccaggtctgc catgccttgt gctcccccga gggctgctgg ggcccggagc   780
ccagggactg cgtctcttgc cggaatgtca gccgaggcag ggaatgcgtg acaagtgca    840 accttctgga gggtgagcca agggagtttg tggagaactc tgagtgcata cagtgccacc   900
cagagtgcct gcctcaggcc atgaacatca cctgcacagg acgggaccca gacaactgta   960
tccagtgtgc ccactacatt gacggccccc actgcgtcaa gacctgcccg gcaggagtca   1020
tgggagaaaa caacaccctg gtctggaagt acgcagacgc cggccatgtg tgccacctgt   1080
gccatccaaa ctgcacctac ggatgcactg gccaggtct tgaaggctgt ccaacgaatg    1140
ggcctaagat cccgtccttt tgggtgctgg tgtggttgg tggagtcctg gcttgctata    1200
gcttgctagt aacagtggcc tttattattt tctgggtgag gagtaagagg agcaggctcc   1260
tgcacagtga ctacatgaac atgactcccc gccgccccgg gcccaccgc aagcattacc    1320 agccctatgc cccaccacgc gacttcgcag cctatcgctc caaacggggc agaaagaaac   1380
tcctgtatat attcaaacaa ccatttatga gaccagtaca aactactcaa gaggaagatg   1440
gctgtagctg ccgatttcca gaagaagaag aaggaggatg tgaactgaga gtgaagttca   1500
gcaggagcgc agacgccccc cgcgtaccagc agggccagaa ccagctctat aacgagctca   1560
atctaggacg aagagaggag tacgatgttt tggacaagag acgtggccgg accctgaga    1620 tgggggaaa gccgagaagg aagaaccctc aggaaggcct gtacaatgaa ctgcagaaag   1680
ataagatggc ggaggcctac agtgagattg ggatgaaagg cgagcgccgg aggggcaagg   1740
ggcacgatgg cctttaccag ggtctcagta cagccaccaa ggacacctac gacgcccttc   1800
acatgcaggc cctgcccct cgctaa                                         1826
```

<210> SEQ ID NO 50
<211> LENGTH: 607
<212> TYPE: PRT
<213> ORGANISM: Artificial Sequence
<220> FEATURE:
<223> OTHER INFORMATION: E4 human (EGFRex-CD28tm/iz-4-1BB-CD3z)

<400> SEQUENCE: 50

```
Leu Ala Arg Gly Arg Ala Thr Met Arg Pro Ser Gly Thr Ala Gly Ala
1               5                   10                  15

Ala Leu Leu Ala Leu Leu Ala Ala Leu Cys Pro Ala Ser Arg Ala Leu
            20                  25                  30

Glu Glu Lys Lys Gly Asn Tyr Val Val Thr Asp His Gly Ser Cys Val
        35                  40                  45

Arg Ala Cys Gly Ala Asp Ser Tyr Glu Met Glu Glu Asp Gly Val Arg
    50                  55                  60

Lys Cys Lys Lys Cys Glu Gly Pro Cys Arg Lys Val Cys Asn Gly Ile
65                  70                  75                  80

Gly Ile Gly Glu Phe Lys Asp Ser Leu Ser Ile Asn Ala Thr Asn Ile
                85                  90                  95
```

```
Lys His Phe Lys Asn Cys Thr Ser Ile Ser Gly Asp Leu His Ile Leu
                100                 105                 110

Pro Val Ala Phe Arg Gly Asp Ser Phe Thr His Thr Pro Leu Asp
        115                 120                 125

Pro Gln Glu Leu Asp Ile Leu Lys Thr Val Lys Glu Ile Thr Gly Phe
130                 135                 140

Leu Leu Ile Gln Ala Trp Pro Glu Asn Arg Thr Asp Leu His Ala Phe
145                 150                 155                 160

Glu Asn Leu Glu Ile Ile Arg Gly Arg Thr Lys Gln His Gly Gln Phe
                165                 170                 175

Ser Leu Ala Val Val Ser Leu Asn Ile Thr Ser Leu Gly Leu Arg Ser
                180                 185                 190

Leu Lys Glu Ile Ser Asp Gly Asp Val Ile Ile Ser Gly Asn Lys Asn
                195                 200                 205

Leu Cys Tyr Ala Asn Thr Ile Asn Trp Lys Lys Leu Phe Gly Thr Ser
        210                 215                 220

Gly Gln Lys Thr Lys Ile Ile Ser Asn Arg Gly Glu Asn Ser Cys Lys
225                 230                 235                 240

Ala Thr Gly Gln Val Cys His Ala Leu Cys Ser Pro Glu Gly Cys Trp
                245                 250                 255

Gly Pro Glu Pro Arg Asp Cys Val Ser Cys Arg Asn Val Ser Arg Gly
        260                 265                 270

Arg Glu Cys Val Asp Lys Cys Asn Leu Leu Glu Gly Glu Pro Arg Glu
        275                 280                 285

Phe Val Glu Asn Ser Glu Cys Ile Gln Cys His Pro Glu Cys Leu Pro
        290                 295                 300

Gln Ala Met Asn Ile Thr Cys Thr Gly Arg Gly Pro Asp Asn Cys Ile
305                 310                 315                 320

Gln Cys Ala His Tyr Ile Asp Gly Pro His Cys Val Lys Thr Cys Pro
                325                 330                 335

Ala Gly Val Met Gly Glu Asn Asn Thr Leu Val Trp Lys Tyr Ala Asp
                340                 345                 350

Ala Gly His Val Cys His Leu Cys His Pro Asn Cys Thr Tyr Gly Cys
                355                 360                 365

Thr Gly Pro Gly Leu Glu Gly Cys Pro Thr Asn Gly Pro Lys Ile Pro
        370                 375                 380

Ser Phe Trp Val Leu Val Val Gly Gly Val Leu Ala Cys Tyr Ser
385                 390                 395                 400

Leu Leu Val Thr Val Ala Phe Ile Ile Phe Trp Val Arg Ser Lys Arg
                405                 410                 415

Ser Arg Leu Leu His Ser Asp Tyr Met Asn Met Thr Pro Arg Arg Pro
        420                 425                 430

Gly Pro Thr Arg Lys His Tyr Gln Pro Tyr Ala Pro Pro Arg Asp Phe
        435                 440                 445

Ala Ala Tyr Arg Ser Lys Arg Gly Arg Lys Lys Leu Leu Tyr Ile Phe
        450                 455                 460

Lys Gln Pro Phe Met Arg Pro Val Gln Thr Thr Gln Glu Glu Asp Gly
465                 470                 475                 480

Cys Ser Cys Arg Phe Pro Glu Glu Glu Gly Gly Cys Glu Leu Arg
                485                 490                 495

Val Lys Phe Ser Arg Ser Ala Asp Ala Pro Ala Tyr Gln Gln Gly Gln
                500                 505                 510
```

```
Asn Gln Leu Tyr Asn Glu Leu Asn Leu Gly Arg Arg Glu Glu Tyr Asp
            515                 520                 525

Val Leu Asp Lys Arg Arg Gly Arg Asp Pro Glu Met Gly Gly Lys Pro
530                 535                 540

Arg Arg Lys Asn Pro Gln Glu Gly Leu Tyr Asn Glu Leu Gln Lys Asp
545                 550                 555                 560

Lys Met Ala Glu Ala Tyr Ser Glu Ile Gly Met Lys Gly Glu Arg Arg
                565                 570                 575

Arg Gly Lys Gly His Asp Gly Leu Tyr Gln Gly Leu Ser Thr Ala Thr
            580                 585                 590

Lys Asp Thr Tyr Asp Ala Leu His Met Gln Ala Leu Pro Pro Arg
            595                 600                 605

<210> SEQ ID NO 51
<211> LENGTH: 1134
<212> TYPE: DNA
<213> ORGANISM: Artificial Sequence
<220> FEATURE:
<223> OTHER INFORMATION: EGFRvIII ex
<220> FEATURE:
<221> NAME/KEY: CDS
<222> LOCATION: 1..1134
<223> OTHER INFORMATION: /transl_table=1

<400> SEQUENCE: 51 atg cga ccc tcc ggg acg gcc ggg gca gcg ctc ctg gcg ctg ctg gct      48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa ggt aat tat      96
Ala Leu Cys Pro Ala Ser Arg Ala Leu Glu Glu Lys Lys Gly Asn Tyr
                20                  25                  30 gtg gtg aca gat cac ggc tcg tgc gtc cga gcc tgt ggg gcc gac agc     144
Val Val Thr Asp His Gly Ser Cys Val Arg Ala Cys Gly Ala Asp Ser
            35                  40                  45 tat gag atg gag gaa gac ggc gtc cgc aag tgt aag aag tgc gaa ggg     192
Tyr Glu Met Glu Glu Asp Gly Val Arg Lys Cys Lys Lys Cys Glu Gly
        50                  55                  60 cct tgc cgc aaa gtg tgt aac gga ata ggt att ggt gaa ttt aaa gac     240
Pro Cys Arg Lys Val Cys Asn Gly Ile Gly Ile Gly Glu Phe Lys Asp
65                  70                  75                  80 tca ctc tcc ata aat gct acg aat att aaa cac ttc aaa aac tgc acc     288
Ser Leu Ser Ile Asn Ala Thr Asn Ile Lys His Phe Lys Asn Cys Thr
                85                  90                  95 tcc atc agt ggc gat ctc cac atc ctg ccg gtg gca ttt agg ggt gac     336
Ser Ile Ser Gly Asp Leu His Ile Leu Pro Val Ala Phe Arg Gly Asp
                100                 105                 110 tcc ttc aca cat act cct cct ctg gat cca cag gaa ctg gat att ctg     384
Ser Phe Thr His Thr Pro Pro Leu Asp Pro Gln Glu Leu Asp Ile Leu
        115                 120                 125 aaa acc gta aag gaa atc aca ggg ttt ttg ctg att cag gct tgg cct     432
Lys Thr Val Lys Glu Ile Thr Gly Phe Leu Leu Ile Gln Ala Trp Pro
    130                 135                 140 gaa aac agg acg gac ctc cat gcc ttt gag aac cta gaa atc ata cgc     480
Glu Asn Arg Thr Asp Leu His Ala Phe Glu Asn Leu Glu Ile Ile Arg
145                 150                 155                 160 ggc agg acc aag caa cat ggt cag ttt tct ctt gca gtc gtc agc ctg     528
Gly Arg Thr Lys Gln His Gly Gln Phe Ser Leu Ala Val Val Ser Leu
                165                 170                 175 aac ata aca tcc ttg gga tta cgc tcc ctc aag gag ata agt gat gga     576
Asn Ile Thr Ser Leu Gly Leu Arg Ser Leu Lys Glu Ile Ser Asp Gly
                180                 185                 190
```

```
gat gtg ata att tca gga aac aaa aat ttg tgc tat gca aat aca ata       624
Asp Val Ile Ile Ser Gly Asn Lys Asn Leu Cys Tyr Ala Asn Thr Ile
        195                 200                 205 aac tgg aaa aaa ctg ttt ggg acc tcc ggt cag aaa acc aaa att ata       672
Asn Trp Lys Lys Leu Phe Gly Thr Ser Gly Gln Lys Thr Lys Ile Ile
    210                 215                 220 agc aac aga ggt gaa aac agc tgc aag gcc aca ggc cag gtc tgc cat       720
Ser Asn Arg Gly Glu Asn Ser Cys Lys Ala Thr Gly Gln Val Cys His
225                 230                 235                 240 gcc ttg tgc tcc ccc gag ggc tgc tgg ggc ccg gag ccc agg gac tgc       768
Ala Leu Cys Ser Pro Glu Gly Cys Trp Gly Pro Glu Pro Arg Asp Cys
                245                 250                 255 gtc tct tgc cgg aat gtc agc cga ggc agg gaa tgc gtg gac aag tgc       816
Val Ser Cys Arg Asn Val Ser Arg Gly Arg Glu Cys Val Asp Lys Cys
            260                 265                 270 aac ctt ctg gag ggt gag cca agg gag ttt gtg gag aac tct gag tgc       864
Asn Leu Leu Glu Gly Glu Pro Arg Glu Phe Val Glu Asn Ser Glu Cys
        275                 280                 285 ata cag tgc cac cca gag tgc ctg cct cag gcc atg aac atc acc tgc       912
Ile Gln Cys His Pro Glu Cys Leu Pro Gln Ala Met Asn Ile Thr Cys
    290                 295                 300 aca gga cgg gga cca gac aac tgt atc cag tgt gcc cac tac att gac       960
Thr Gly Arg Gly Pro Asp Asn Cys Ile Gln Cys Ala His Tyr Ile Asp
305                 310                 315                 320 ggc ccc cac tgc gtc aag acc tgc ccg gca gga gtc atg gga gaa aac      1008
Gly Pro His Cys Val Lys Thr Cys Pro Ala Gly Val Met Gly Glu Asn
                325                 330                 335 aac acc ctg gtc tgg aag tac gca gac gcc ggc cat gtg tgc cac ctg      1056
Asn Thr Leu Val Trp Lys Tyr Ala Asp Ala Gly His Val Cys His Leu
            340                 345                 350 tgc cat cca aac tgc acc tac gga tgc act ggg cca ggt ctt gaa ggc      1104
Cys His Pro Asn Cys Thr Tyr Gly Cys Thr Gly Pro Gly Leu Glu Gly
        355                 360                 365 tgt cca acg aat ggg cct aag atc ccg tcc                              1134
Cys Pro Thr Asn Gly Pro Lys Ile Pro Ser
    370                 375
```

<210> SEQ ID NO 52
<211> LENGTH: 378
<212> TYPE: PRT
<213> ORGANISM: Artificial Sequence
<220> FEATURE:
<223> OTHER INFORMATION: [CDS]:1..1134 from SEQ ID NO 51

<400> SEQUENCE: 52

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
            35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
                100                 105                 110
```

```
Ser Phe Thr His Thr Pro Leu Asp Pro Gln Glu Leu Asp Ile Leu
            115                 120                 125
Lys Thr Val Lys Glu Ile Thr Gly Phe Leu Leu Ile Gln Ala Trp Pro
130                 135                 140
Glu Asn Arg Thr Asp Leu His Ala Phe Glu Asn Leu Glu Ile Ile Arg
145                 150                 155                 160
Gly Arg Thr Lys Gln His Gly Gln Phe Ser Leu Ala Val Val Ser Leu
                165                 170                 175
Asn Ile Thr Ser Leu Gly Leu Arg Ser Leu Lys Glu Ile Ser Asp Gly
            180                 185                 190
Asp Val Ile Ile Ser Gly Asn Lys Asn Leu Cys Tyr Ala Asn Thr Ile
        195                 200                 205
Asn Trp Lys Lys Leu Phe Gly Thr Ser Gly Gln Lys Thr Lys Ile Ile
    210                 215                 220
Ser Asn Arg Gly Glu Asn Ser Cys Lys Ala Thr Gly Gln Val Cys His
225                 230                 235                 240
Ala Leu Cys Ser Pro Glu Gly Cys Trp Gly Pro Glu Pro Arg Asp Cys
                245                 250                 255
Val Ser Cys Arg Asn Val Ser Arg Gly Arg Glu Cys Val Asp Lys Cys
            260                 265                 270
Asn Leu Leu Glu Gly Glu Pro Arg Glu Phe Val Glu Asn Ser Glu Cys
        275                 280                 285
Ile Gln Cys His Pro Glu Cys Leu Pro Gln Ala Met Asn Ile Thr Cys
    290                 295                 300
Thr Gly Arg Gly Pro Asp Asn Cys Ile Gln Cys Ala His Tyr Ile Asp
305                 310                 315                 320
Gly Pro His Cys Val Lys Thr Cys Pro Ala Gly Val Met Gly Glu Asn
                325                 330                 335
Asn Thr Leu Val Trp Lys Tyr Ala Asp Ala Gly His Val Cys His Leu
            340                 345                 350
Cys His Pro Asn Cys Thr Tyr Gly Cys Thr Gly Pro Gly Leu Glu Gly
        355                 360                 365
Cys Pro Thr Asn Gly Pro Lys Ile Pro Ser
    370                 375

<210> SEQ ID NO 53
<211> LENGTH: 81
<212> TYPE: DNA
<213> ORGANISM: Artificial Sequence
<220> FEATURE:
<223> OTHER INFORMATION: CD28TM (MOUSE)
<220> FEATURE:
<221> NAME/KEY: CDS
<222> LOCATION: 1..81
<223> OTHER INFORMATION: /transl_table=1

<400> SEQUENCE: 53 ttt tgg gca ctg gtc gtg gtt gct gga gtc ctg ttt tgt tat ggc ttg    48
Phe Trp Ala Leu Val Val Val Ala Gly Val Leu Phe Cys Tyr Gly Leu
1               5                   10                  15 cta gtg aca gtg gct ctt tgt gtt atc tgg aca                        81
Leu Val Thr Val Ala Leu Cys Val Ile Trp Thr
            20                  25

<210> SEQ ID NO 54
<211> LENGTH: 27
<212> TYPE: PRT
<213> ORGANISM: Artificial Sequence
```

```
<220> FEATURE:
<223> OTHER INFORMATION: [CDS]:1..81 from SEQ ID NO 53

<400> SEQUENCE: 54

Phe Trp Ala Leu Val Val Val Ala Gly Val Leu Phe Cys Tyr Gly Leu
1               5                   10                  15

Leu Val Thr Val Ala Leu Cys Val Ile Trp Thr
            20                  25

<210> SEQ ID NO 55
<211> LENGTH: 123
<212> TYPE: DNA
<213> ORGANISM: Artificial Sequence
<220> FEATURE:
<223> OTHER INFORMATION: CD28IC (MOUSE)
<220> FEATURE:
<221> NAME/KEY: CDS
<222> LOCATION: 1..123
<223> OTHER INFORMATION: /transl_table=1

<400> SEQUENCE: 55 aat agt aga agg aac aga ctc ctt caa agt gac tac atg aac atg act        48
Asn Ser Arg Arg Asn Arg Leu Leu Gln Ser Asp Tyr Met Asn Met Thr
1               5                   10                  15 ccc cgg agg cct ggg ctc act cga aag cct tac cag ccc tac gcc cct        96
Pro Arg Arg Pro Gly Leu Thr Arg Lys Pro Tyr Gln Pro Tyr Ala Pro
                20                  25                  30 gcc aga gac ttt gca gcg tac cgc ccc                                    123
Ala Arg Asp Phe Ala Ala Tyr Arg Pro
            35                  40

<210> SEQ ID NO 56
<211> LENGTH: 41
<212> TYPE: PRT
<213> ORGANISM: Artificial Sequence
<220> FEATURE:
<223> OTHER INFORMATION: [CDS]:1..123 from SEQ ID NO 55

<400> SEQUENCE: 56

Asn Ser Arg Arg Asn Arg Leu Leu Gln Ser Asp Tyr Met Asn Met Thr
1               5                   10                  15

Pro Arg Arg Pro Gly Leu Thr Arg Lys Pro Tyr Gln Pro Tyr Ala Pro
                20                  25                  30

Ala Arg Asp Phe Ala Ala Tyr Arg Pro
            35                  40

<210> SEQ ID NO 57
<211> LENGTH: 342
<212> TYPE: DNA
<213> ORGANISM: Artificial Sequence
<220> FEATURE:
<223> OTHER INFORMATION: CD3Z (MOUSE)
<220> FEATURE:
<221> NAME/KEY: CDS
<222> LOCATION: 1..342
<223> OTHER INFORMATION: /transl_table=1

<400> SEQUENCE: 57 aga gca aaa ttc agc agg agt gca gag act gct gcc aac ctg cag gac        48
Arg Ala Lys Phe Ser Arg Ser Ala Glu Thr Ala Ala Asn Leu Gln Asp
1               5                   10                  15 ccc aac cag ctc tac aat gag ctc aat cta ggg cga aga gag gaa tat        96
Pro Asn Gln Leu Tyr Asn Glu Leu Asn Leu Gly Arg Arg Glu Glu Tyr
                20                  25                  30 gac gtc ttg gag aag aag cgg gct cgg gat cca gag atg gga ggc aaa        144
```

```
Asp Val Leu Glu Lys Lys Arg Ala Arg Asp Pro Glu Met Gly Gly Lys
        35                  40                  45 cag cag agg agg agg aac ccc cag gaa ggc gta tac aat gca ctg cag     192
Gln Gln Arg Arg Arg Asn Pro Gln Glu Gly Val Tyr Asn Ala Leu Gln
 50                  55                  60 aaa gac aag atg gca gaa gcc tac agt gag atc ggc aca aaa ggc gag     240
Lys Asp Lys Met Ala Glu Ala Tyr Ser Glu Ile Gly Thr Lys Gly Glu
 65                  70                  75                  80 agg cgg aga ggc aag ggg cac gat ggc ctt tac cag ggt ctc agc act     288
Arg Arg Arg Gly Lys Gly His Asp Gly Leu Tyr Gln Gly Leu Ser Thr
                 85                  90                  95 gcc acc aag gac acc tat gat gcc ctg cat atg cag acc ctg gcc cct     336
Ala Thr Lys Asp Thr Tyr Asp Ala Leu His Met Gln Thr Leu Ala Pro
            100                 105                 110 cgc taa                                                             342
Arg

<210> SEQ ID NO 58
<211> LENGTH: 113
<212> TYPE: PRT
<213> ORGANISM: Artificial Sequence
<220> FEATURE:
<223> OTHER INFORMATION: [CDS]:1..342 from SEQ ID NO 57

<400> SEQUENCE: 58

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
 50                  55                  60

Lys Asp Lys Met Ala Glu Ala Tyr Ser Glu Ile Gly Thr Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Thr Leu Ala Pro
            100                 105                 110

Arg

<210> SEQ ID NO 59
<211> LENGTH: 144
<212> TYPE: DNA
<213> ORGANISM: Artificial Sequence
<220> FEATURE:
<223> OTHER INFORMATION: 41BB (MOUSE)
<220> FEATURE:
<221> NAME/KEY: CDS
<222> LOCATION: 1..144
<223> OTHER INFORMATION: /transl_table=1

<400> SEQUENCE: 59 tct gtg ctc aaa tgg atc agg aaa aaa ttc ccc cac ata ttc aag caa      48
Ser Val Leu Lys Trp Ile Arg Lys Lys Phe Pro His Ile Phe Lys Gln
1               5                   10                  15 cca ttt aag aag acc act gga gca gct caa gag gaa gat gct tgt agc      96
Pro Phe Lys Lys Thr Thr Gly Ala Ala Gln Glu Glu Asp Ala Cys Ser
            20                  25                  30 tgc cga tgt cca cag gaa gaa gaa gga gga gga gga ggc tat gag ctg     144
Cys Arg Cys Pro Gln Glu Glu Glu Gly Gly Gly Gly Gly Tyr Glu Leu
```

<210> SEQ ID NO 60
<211> LENGTH: 48
<212> TYPE: PRT
<213> ORGANISM: Artificial Sequence
<220> FEATURE:
<223> OTHER INFORMATION: [CDS]:1..144 from SEQ ID NO 59

<400> SEQUENCE: 60

```
Ser Val Leu Lys Trp Ile Arg Lys Lys Phe Pro His Ile Phe Lys Gln
1               5                   10                  15

Pro Phe Lys Lys Thr Thr Gly Ala Ala Gln Glu Glu Asp Ala Cys Ser
            20                  25                  30

Cys Arg Cys Pro Gln Glu Glu Gly Gly Gly Gly Gly Tyr Glu Leu
        35                  40                  45
```

<210> SEQ ID NO 61
<211> LENGTH: 360
<212> TYPE: DNA
<213> ORGANISM: Artificial Sequence
<220> FEATURE:
<223> OTHER INFORMATION: CRIPTO (HUMAN)
<220> FEATURE:
<221> NAME/KEY: CDS
<222> LOCATION: 1..360
<223> OTHER INFORMATION: /transl_table=1

<400> SEQUENCE: 61

```
ctg ggc cat cag gaa ttt gct cgt cca tct cgg gga tac ctg gcc ttc      48
Leu Gly His Gln Glu Phe Ala Arg Pro Ser Arg Gly Tyr Leu Ala Phe
1               5                   10                  15 aga gat gac agc att tgg ccc cag gag gag cct gca att cgg cct cgg      96
Arg Asp Asp Ser Ile Trp Pro Gln Glu Glu Pro Ala Ile Arg Pro Arg
            20                  25                  30 tct tcc cag cgt gtg ccg ccc atg ggg ata cag cac agt aag gag cta     144
Ser Ser Gln Arg Val Pro Pro Met Gly Ile Gln His Ser Lys Glu Leu
        35                  40                  45 aac aga acc tgc tgc ctg aat ggg gga acc tgc atg ctg ggg tcc ttt     192
Asn Arg Thr Cys Cys Leu Asn Gly Gly Thr Cys Met Leu Gly Ser Phe
    50                  55                  60 tgt gcc tgc cct ccc tcc ttc tac gga cgg aac tgt gag cac gat gtg     240
Cys Ala Cys Pro Pro Ser Phe Tyr Gly Arg Asn Cys Glu His Asp Val
65                  70                  75                  80 cgc aaa gag aac tgt ggg tct gtg ccc cat gac acc tgg ctg ccc aag     288
Arg Lys Glu Asn Cys Gly Ser Val Pro His Asp Thr Trp Leu Pro Lys
                85                  90                  95 aag tgt tcc ctg tgt aaa tgc tgg cac ggt cag ctc cgc tgc ttt cct     336
Lys Cys Ser Leu Cys Lys Cys Trp His Gly Gln Leu Arg Cys Phe Pro
            100                 105                 110 cag gca ttt cta ccc ggc tgt gat                                     360
Gln Ala Phe Leu Pro Gly Cys Asp
        115                 120
```

<210> SEQ ID NO 62
<211> LENGTH: 120
<212> TYPE: PRT
<213> ORGANISM: Artificial Sequence
<220> FEATURE:
<223> OTHER INFORMATION: [CDS]:1..360 from SEQ ID NO 61

<400> SEQUENCE: 62

```
Leu Gly His Gln Glu Phe Ala Arg Pro Ser Arg Gly Tyr Leu Ala Phe
1               5                   10                  15
```

```
Arg Asp Asp Ser Ile Trp Pro Gln Glu Glu Pro Ala Ile Arg Pro Arg
            20                  25                  30

Ser Ser Gln Arg Val Pro Pro Met Gly Ile Gln His Ser Lys Glu Leu
        35                  40                  45

Asn Arg Thr Cys Cys Leu Asn Gly Gly Thr Cys Met Leu Gly Ser Phe
    50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp
        115                 120

<210> SEQ ID NO 63
<211> LENGTH: 195
<212> TYPE: DNA
<213> ORGANISM: Artificial Sequence
<220> FEATURE:
<223> OTHER INFORMATION: CD8 (MURINE)
<220> FEATURE:
<221> NAME/KEY: CDS
<222> LOCATION: 1..195
<223> OTHER INFORMATION: /transl_table=1

<400> SEQUENCE: 63 act acc aag cca gtg ctg cga act ccc tca cct gtg cac cct acc ggg     48
Thr Thr Lys Pro Val Leu Arg Thr Pro Ser Pro Val His Pro Thr Gly
1               5                   10                  15 aca tct cag ccc cag aga cca gaa gat tgt cgg ccc cgt ggc tca gtg     96
Thr Ser Gln Pro Gln Arg Pro Glu Asp Cys Arg Pro Arg Gly Ser Val
            20                  25                  30 aag ggg acc gga ttg gac ttc gcc tgt gat att tac atc tgg gca ccc    144
Lys Gly Thr Gly Leu Asp Phe Ala Cys Asp Ile Tyr Ile Trp Ala Pro
        35                  40                  45 ttg gcc gga atc tgc gtg gcc ctt ctg ctg tcc ttg atc atc act ctc    192
Leu Ala Gly Ile Cys Val Ala Leu Leu Leu Ser Leu Ile Ile Thr Leu
    50                  55                  60 atc                                                                 195
Ile
65

<210> SEQ ID NO 64
<211> LENGTH: 65
<212> TYPE: PRT
<213> ORGANISM: Artificial Sequence
<220> FEATURE:
<223> OTHER INFORMATION: [CDS]:1..195 from SEQ ID NO 63

<400> SEQUENCE: 64

Thr Thr Lys Pro Val Leu Arg Thr Pro Ser Pro Val His Pro Thr Gly
1               5                   10                  15

Thr Ser Gln Pro Gln Arg Pro Glu Asp Cys Arg Pro Arg Gly Ser Val
            20                  25                  30

Lys Gly Thr Gly Leu Asp Phe Ala Cys Asp Ile Tyr Ile Trp Ala Pro
        35                  40                  45

Leu Ala Gly Ile Cys Val Ala Leu Leu Leu Ser Leu Ile Ile Thr Leu
    50                  55                  60

Ile
```

<210> SEQ ID NO 65
<211> LENGTH: 81
<212> TYPE: DNA
<213> ORGANISM: Artificial Sequence
<220> FEATURE:
<223> OTHER INFORMATION: CD28TM (HUMAN)
<220> FEATURE:
<221> NAME/KEY: CDS
<222> LOCATION: 1..81
<223> OTHER INFORMATION: /transl_table=1

<400> SEQUENCE: 65

```
ttt tgg gtg ctg gtg gtg gtt ggt gga gtc ctg gct tgc tat agc ttg      48
Phe Trp Val Leu Val Val Val Gly Gly Val Leu Ala Cys Tyr Ser Leu
1               5                   10                  15 cta gta aca gtg gcc ttt att att ttc tgg gtg                           81
Leu Val Thr Val Ala Phe Ile Ile Phe Trp Val
            20                  25
```

<210> SEQ ID NO 66
<211> LENGTH: 27
<212> TYPE: PRT
<213> ORGANISM: Artificial Sequence
<220> FEATURE:
<223> OTHER INFORMATION: [CDS]:1..81 from SEQ ID NO 65

<400> SEQUENCE: 66

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 67
<211> LENGTH: 123
<212> TYPE: DNA
<213> ORGANISM: Artificial Sequence
<220> FEATURE:
<223> OTHER INFORMATION: CD28IC (HUMAN)
<220> FEATURE:
<221> NAME/KEY: CDS
<222> LOCATION: 1..123
<223> OTHER INFORMATION: /transl_table=1

<400> SEQUENCE: 67

```
agg agt aag agg agc agg ctc ctg cac agt gac tac atg aac atg act      48
Arg Ser Lys Arg Ser Arg Leu Leu His Ser Asp Tyr Met Asn Met Thr
1               5                   10                  15 ccc cgc cgc ccc ggg ccc acc cgc aag cat tac cag ccc tat gcc cca      96
Pro Arg Arg Pro Gly Pro Thr Arg Lys His Tyr Gln Pro Tyr Ala Pro
            20                  25                  30 cca cgc gac ttc gca gcc tat cgc tcc                                  123
Pro Arg Asp Phe Ala Ala Tyr Arg Ser
        35                  40
```

<210> SEQ ID NO 68
<211> LENGTH: 41
<212> TYPE: PRT
<213> ORGANISM: Artificial Sequence
<220> FEATURE:
<223> OTHER INFORMATION: [CDS]:1..123 from SEQ ID NO 67

<400> SEQUENCE: 68

```
Arg Ser Lys Arg Ser Arg Leu Leu His Ser Asp Tyr Met Asn Met Thr
1               5                   10                  15
```

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 69
<211> LENGTH: 336
<212> TYPE: DNA
<213> ORGANISM: Artificial Sequence
<220> FEATURE:
<223> OTHER INFORMATION: CD3Z (HUMAN)
<220> FEATURE:
<221> NAME/KEY: CDS
<222> LOCATION: 1..336
<223> OTHER INFORMATION: /transl_table=1

<400> SEQUENCE: 69 aga gtg aag ttc agc agg agc gca gac gcc ccc gcg tac cag cag ggc        48
Arg Val Lys Phe Ser Arg Ser Ala Asp Ala Pro Ala Tyr Gln Gln Gly
1               5                   10                  15 cag aac cag ctc tat aac gag ctc aat cta gga cga aga gag gag tac        96
Gln Asn Gln Leu Tyr Asn Glu Leu Asn Leu Gly Arg Arg Glu Glu Tyr
            20                  25                  30 gat gtt ttg gac aag aga cgt ggc cgg gac cct gag atg ggg gga aag       144
Asp Val Leu Asp Lys Arg Arg Gly Arg Asp Pro Glu Met Gly Gly Lys
        35                  40                  45 ccg aga agg aag aac cct cag gaa ggc ctg tac aat gaa ctg cag aaa       192
Pro Arg Arg Lys Asn Pro Gln Glu Gly Leu Tyr Asn Glu Leu Gln Lys
    50                  55                  60 gat aag atg gcg gag gcc tac agt gag att ggg atg aaa ggc gag cgc       240
Asp Lys Met Ala Glu Ala Tyr Ser Glu Ile Gly Met Lys Gly Glu Arg
65                  70                  75                  80 cgg agg ggc aag ggg cac gat ggc ctt tac cag ggt ctc agt aca gcc       288
Arg Arg Gly Lys Gly His Asp Gly Leu Tyr Gln Gly Leu Ser Thr Ala
                85                  90                  95 acc aag gac acc tac gac gcc ctt cac atg cag gcc ctg ccc cct cgc       336
Thr Lys Asp Thr Tyr Asp Ala Leu His Met Gln Ala Leu Pro Pro Arg
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: [CDS]:1..336 from SEQ ID NO 69

<400> SEQUENCE: 70

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 71
<211> LENGTH: 126
<212> TYPE: DNA
<213> ORGANISM: Artificial Sequence
<220> FEATURE:
<223> OTHER INFORMATION: 41BB (HUMAN)
<220> FEATURE:
<221> NAME/KEY: CDS
<222> LOCATION: 1..126
<223> OTHER INFORMATION: /transl_table=1

<400> SEQUENCE: 71 aaa cgg ggc aga aag aaa ctc ctg tat ata ttc aaa caa cca ttt atg      48
Lys Arg Gly Arg Lys Lys Leu Leu Tyr Ile Phe Lys Gln Pro Phe Met
1               5                   10                  15 aga cca gta caa act act caa gag gaa gat ggc tgt agc tgc cga ttt      96
Arg Pro Val Gln Thr Thr Gln Glu Glu Asp Gly Cys Ser Cys Arg Phe
                20                  25                  30 cca gaa gaa gaa gaa gga gga tgt gaa ctg                             126
Pro Glu Glu Glu Glu Gly Gly Cys Glu Leu
            35                  40

<210> SEQ ID NO 72
<211> LENGTH: 42
<212> TYPE: PRT
<213> ORGANISM: Artificial Sequence
<220> FEATURE:
<223> OTHER INFORMATION: [CDS]:1..126 from SEQ ID NO 71

<400> SEQUENCE: 72

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 73
<211> LENGTH: 546
<212> TYPE: DNA
<213> ORGANISM: Artificial Sequence
<220> FEATURE:
<223> OTHER INFORMATION: CD8 (HUMAN)
<220> FEATURE:
<221> NAME/KEY: CDS
<222> LOCATION: 1..546
<223> OTHER INFORMATION: /transl_table=1

<400> SEQUENCE: 73 agc cag ttc cgg gtg tcg ccg ctg gat cgg acc tgg aac ctg ggc gag      48
Ser Gln Phe Arg Val Ser Pro Leu Asp Arg Thr Trp Asn Leu Gly Glu
1               5                   10                  15 aca gtg gag ctg aag tgc cag gtg ctg ctg tcc aac ccg acg tcg ggc      96
Thr Val Glu Leu Lys Cys Gln Val Leu Leu Ser Asn Pro Thr Ser Gly
                20                  25                  30 tgc tcg tgg ctc ttc cag ccg cgc ggc gcc gcc gcc agt ccc acc ttc     144
Cys Ser Trp Leu Phe Gln Pro Arg Gly Ala Ala Ala Ser Pro Thr Phe
            35                  40                  45 ctc cta tac ctc tcc caa aac aag ccc aag gcg gcc gag ggg ctg gac     192
Leu Leu Tyr Leu Ser Gln Asn Lys Pro Lys Ala Ala Glu Gly Leu Asp
        50                  55                  60 acc cag cgg ttc tcg ggc aag agg ttg ggg gac acc ttc gtc ctc acc     240
Thr Gln Arg Phe Ser Gly Lys Arg Leu Gly Asp Thr Phe Val Leu Thr
65                  70                  75                  80
```

```
ctg agc gac ttc cgc cga gag aac gag ggc tac tat ttc tgc tcg gcc        288
Leu Ser Asp Phe Arg Arg Glu Asn Glu Gly Tyr Tyr Phe Cys Ser Ala
            85                  90                  95 ctg agc aac tcc atc atg tac ttc agc cac ttc gtg ccg gtc ttc ctg        336
Leu Ser Asn Ser Ile Met Tyr Phe Ser His Phe Val Pro Val Phe Leu
        100                 105                 110 cca gcg aag ccc acc acg acg cca gcg ccg cga cca cca aca ccg gcg        384
Pro Ala Lys Pro Thr Thr Thr Pro Ala Pro Arg Pro Pro Thr Pro Ala
    115                 120                 125 ccc acc atc gcg tcg cag ccc ctg tcc ctg cgc cca gag gcg tgc cgg        432
Pro Thr Ile Ala Ser Gln Pro Leu Ser Leu Arg Pro Glu Ala Cys Arg
130                 135                 140 cca gcg gcg ggg ggc gca gtg cac acg agg ggg ctg gac ttc gcc tgt        480
Pro Ala Ala Gly Gly Ala Val His Thr Arg Gly Leu Asp Phe Ala Cys
145                 150                 155                 160 gat atc tac atc tgg gcg ccc ctg gcc ggg act tgt ggg gtc ctt ctc        528
Asp Ile Tyr Ile Trp Ala Pro Leu Ala Gly Thr Cys Gly Val Leu Leu
                165                 170                 175 ctg tca ctg gtt atc acc                                                 546
Leu Ser Leu Val Ile Thr
            180
```

<210> SEQ ID NO 74
<211> LENGTH: 182
<212> TYPE: PRT
<213> ORGANISM: Artificial Sequence
<220> FEATURE:
<223> OTHER INFORMATION: [CDS]:1..546 from SEQ ID NO 73

<400> SEQUENCE: 74

```
Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
            85                  90                  95

Leu Ser Asn Ser Ile Met Tyr Phe Ser His Phe Val Pro Val Phe Leu
        100                 105                 110

Pro Ala Lys Pro Thr Thr Thr Pro Ala Pro Arg Pro Pro Thr Pro Ala
    115                 120                 125

Pro Thr Ile Ala Ser Gln Pro Leu Ser Leu Arg Pro Glu Ala Cys Arg
130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr
            180
```

<210> SEQ ID NO 75
<211> LENGTH: 1260
<212> TYPE: DNA
<213> ORGANISM: Artificial Sequence
<220> FEATURE:
<223> OTHER INFORMATION: EGFRvIII (human)

<400> SEQUENCE: 75

```
agcttgctcg cggccgcgcc accatgcgac cctccgggac ggccggggca gcgctcctgg    60
cgctgctggc tgcgctctgc ccggcgagtc gggctctgga ggaaaagaaa ggtaattatg   120
tggtgacaga tcacggctcg tgcgtccgag cctgtggggc cgacagctat gagatggagg   180
aagacggcgt ccgcaagtgt aagaagtgcg aagggccttg ccgcaaagtg tgtaacggaa   240
taggtattgg tgaatttaaa gactcactct ccataaatgc tacgaatatt aaacacttca   300
aaaactgcac ctccatcagt ggcgatctcc acatcctgcc ggtggcattt agggggtgact   360
ccttcacaca tactcctcct ctggatccac aggaactgga tattctgaaa accgtaaagg   420
aaatcacagg ttttttgctg attcaggctt ggcctgaaaa caggacggac ctccatgcct   480
tgagaacct agaaatcata cgcggcagga ccaagcaaca tggtcagttt tctcttgcag   540
tcgtcagcct gaacataaca tcctgggat tacgctccct caaggagata agtgatggag   600
atgtgataat ttcaggaaac aaaaatttgt gctatgcaaa tacaataaac tggaaaaaac   660
tgtttgggac ctccggtcag aaaccaaaa ttataagcaa cagaggtgaa aacagctgca   720
aggccacagg ccaggtctgc catgccttgt gctcccccga gggctgctgg ggcccggagc   780
ccagggactg cgtctcttgc cggaatgtca gccgaggcag ggaatgcgtg gacaagtgca   840
accttctgga gggtgagcca agggagtttg tggagaactc tgagtgcata cagtgccacc   900
cagagtgcct gcctcaggcc atgaacatca cctgcacagg acgggaccca gacaactgta   960
tccagtgtgc ccactacatt gacggccccc actgcgtcaa gacctgcccg gcaggagtca  1020
tgggagaaaa caacaccctg gtctggaagt acgcagacgc cggccatgtg tgccacctgt  1080
gccatccaaa ctgcacctac ggatgcactg gccaggtct tgaaggctgt ccaacgaatg  1140
ggcctaagat cccgtccatc gccactggga tggtgggggc cctcctcttg ctgctggtgg  1200
tggccctggg gatcggcctc ttcatgcgaa ggcgccacat cgttcggaag cgctgagaat  1260
```

<210> SEQ ID NO 76
<211> LENGTH: 417
<212> TYPE: PRT
<213> ORGANISM: Artificial Sequence
<220> FEATURE:
<223> OTHER INFORMATION: EGFRvIII (human)

<400> SEQUENCE: 76

```
Leu Ala Arg Gly Arg Ala Thr Met Arg Pro Ser Gly Thr Ala Gly Ala
1               5                   10                  15

Ala Leu Leu Ala Leu Leu Ala Ala Leu Cys Pro Ala Ser Arg Ala Leu
            20                  25                  30

Glu Glu Lys Lys Gly Asn Tyr Val Val Thr Asp His Gly Ser Cys Val
        35                  40                  45

Arg Ala Cys Gly Ala Asp Ser Tyr Glu Met Glu Asp Gly Val Arg
    50                  55                  60

Lys Cys Lys Lys Cys Glu Gly Pro Cys Arg Lys Val Cys Asn Gly Ile
65                  70                  75                  80

Gly Ile Gly Glu Phe Lys Asp Ser Leu Ser Ile Asn Ala Thr Asn Ile
                85                  90                  95

Lys His Phe Lys Asn Cys Thr Ser Ile Ser Gly Asp Leu His Ile Leu
            100                 105                 110

Pro Val Ala Phe Arg Gly Asp Ser Phe Thr His Thr Pro Pro Leu Asp
```

```
            115                 120                 125
Pro Gln Glu Leu Asp Ile Leu Lys Thr Val Lys Glu Ile Thr Gly Phe
    130                 135                 140

Leu Leu Ile Gln Ala Trp Pro Glu Asn Arg Thr Asp Leu His Ala Phe
145                 150                 155                 160

Glu Asn Leu Glu Ile Ile Arg Gly Arg Thr Lys Gln His Gly Gln Phe
                165                 170                 175

Ser Leu Ala Val Val Ser Leu Asn Ile Thr Ser Leu Gly Leu Arg Ser
            180                 185                 190

Leu Lys Glu Ile Ser Asp Gly Asp Val Ile Ile Ser Gly Asn Lys Asn
        195                 200                 205

Leu Cys Tyr Ala Asn Thr Ile Asn Trp Lys Lys Leu Phe Gly Thr Ser
    210                 215                 220

Gly Gln Lys Thr Lys Ile Ile Ser Asn Arg Gly Glu Asn Ser Cys Lys
225                 230                 235                 240

Ala Thr Gly Gln Val Cys His Ala Leu Cys Ser Pro Glu Gly Cys Trp
                245                 250                 255

Gly Pro Glu Pro Arg Asp Cys Val Ser Cys Arg Asn Val Ser Arg Gly
            260                 265                 270

Arg Glu Cys Val Asp Lys Cys Asn Leu Leu Glu Gly Glu Pro Arg Glu
        275                 280                 285

Phe Val Glu Asn Ser Glu Cys Ile Gln Cys His Pro Glu Cys Leu Pro
    290                 295                 300

Gln Ala Met Asn Ile Thr Cys Thr Gly Arg Gly Pro Asp Asn Cys Ile
305                 310                 315                 320

Gln Cys Ala His Tyr Ile Asp Gly Pro His Cys Val Lys Thr Cys Pro
                325                 330                 335

Ala Gly Val Met Gly Glu Asn Asn Thr Leu Val Trp Lys Tyr Ala Asp
            340                 345                 350

Ala Gly His Val Cys His Leu Cys His Pro Asn Cys Thr Tyr Gly Cys
        355                 360                 365

Thr Gly Pro Gly Leu Glu Gly Cys Pro Thr Asn Gly Pro Lys Ile Pro
    370                 375                 380

Ser Ile Ala Thr Gly Met Val Gly Ala Leu Leu Leu Leu Leu Val Val
385                 390                 395                 400

Ala Leu Gly Ile Gly Leu Phe Met Arg Arg Arg His Ile Val Arg Lys
                405                 410                 415

Arg

<210> SEQ ID NO 77
<211> LENGTH: 1134
<212> TYPE: DNA
<213> ORGANISM: Artificial Sequence
<220> FEATURE:
<223> OTHER INFORMATION: EGFRvIII EXTRACELLULAR
<220> FEATURE:
<221> NAME/KEY: CDS
<222> LOCATION: 1..1134
<223> OTHER INFORMATION: /transl_table=1

<400> SEQUENCE: 77 atg cga ccc tcc ggg acg gcc ggg gca gcg ctc ctg gcg ctg ctg gct      48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa ggt aat tat      96
Ala Leu Cys Pro Ala Ser Arg Ala Leu Glu Glu Lys Lys Gly Asn Tyr
            20                  25                  30
```

-continued

| | | |
|---|---|---|
| gtg gtg aca gat cac ggc tcg tgc gtc cga gcc tgt ggg gcc gac agc<br>Val Val Thr Asp His Gly Ser Cys Val Arg Ala Cys Gly Ala Asp Ser<br>          35                  40                      45 | 144 |
| tat gag atg gag gaa gac ggc gtc cgc aag tgt aag aag tgc gaa ggg<br>Tyr Glu Met Glu Glu Asp Gly Val Arg Lys Cys Lys Lys Cys Glu Gly<br>50                     55                   60 | 192 |
| cct tgc cgc aaa gtg tgt aac gga ata ggt att ggt gaa ttt aaa gac<br>Pro Cys Arg Lys Val Cys Asn Gly Ile Gly Ile Gly Glu Phe Lys Asp<br>65                     70                  75                80 | 240 |
| tca ctc tcc ata aat gct acg aat att aaa cac ttc aaa aac tgc acc<br>Ser Leu Ser Ile Asn Ala Thr Asn Ile Lys His Phe Lys Asn Cys Thr<br>          85                  90                  95 | 288 |
| tcc atc agt ggc gat ctc cac atc ctg ccg gtg gca ttt agg ggt gac<br>Ser Ile Ser Gly Asp Leu His Ile Leu Pro Val Ala Phe Arg Gly Asp<br>          100                105               110 | 336 |
| tcc ttc aca cat act cct cct ctg gat cca cag gaa ctg gat att ctg<br>Ser Phe Thr His Thr Pro Pro Leu Asp Pro Gln Glu Leu Asp Ile Leu<br>          115                120               125 | 384 |
| aaa acc gta aag gaa atc aca ggg ttt ttg ctg att cag gct tgg cct<br>Lys Thr Val Lys Glu Ile Thr Gly Phe Leu Leu Ile Gln Ala Trp Pro<br>130                   135                140 | 432 |
| gaa aac agg acg gac ctc cat gcc ttt gag aac cta gaa atc ata cgc<br>Glu Asn Arg Thr Asp Leu His Ala Phe Glu Asn Leu Glu Ile Ile Arg<br>145                   150                155               160 | 480 |
| ggc agg acc aag caa cat ggt cag ttt tct ctt gca gtc gtc agc ctg<br>Gly Arg Thr Lys Gln His Gly Gln Phe Ser Leu Ala Val Val Ser Leu<br>                  165                170               175 | 528 |
| aac ata aca tcc ttg gga tta cgc tcc ctc aag gag ata agt gat gga<br>Asn Ile Thr Ser Leu Gly Leu Arg Ser Leu Lys Glu Ile Ser Asp Gly<br>          180                185               190 | 576 |
| gat gtg ata att tca gga aac aaa aat ttg tgc tat gca aat aca ata<br>Asp Val Ile Ile Ser Gly Asn Lys Asn Leu Cys Tyr Ala Asn Thr Ile<br>               195              200               205 | 624 |
| aac tgg aaa aaa ctg ttt ggg acc tcc ggt cag aaa acc aaa att ata<br>Asn Trp Lys Lys Leu Phe Gly Thr Ser Gly Gln Lys Thr Lys Ile Ile<br>210                   215                220 | 672 |
| agc aac aga ggt gaa aac agc tgc aag gcc aca ggc cag gtc tgc cat<br>Ser Asn Arg Gly Glu Asn Ser Cys Lys Ala Thr Gly Gln Val Cys His<br>225                   230                235               240 | 720 |
| gcc ttg tgc tcc ccc gag ggc tgc tgg ggc ccg gag ccc agg gac tgc<br>Ala Leu Cys Ser Pro Glu Gly Cys Trp Gly Pro Glu Pro Arg Asp Cys<br>                  245                250               255 | 768 |
| gtc tct tgc cgg aat gtc agc cga ggc agg gaa tgc gtg gac aag tgc<br>Val Ser Cys Arg Asn Val Ser Arg Gly Arg Glu Cys Val Asp Lys Cys<br>          260                265               270 | 816 |
| aac ctt ctg gag ggt gag cca agg gag ttt gtg gag aac tct gag tgc<br>Asn Leu Leu Glu Gly Glu Pro Arg Glu Phe Val Glu Asn Ser Glu Cys<br>          275                280               285 | 864 |
| ata cag tgc cac cca gag tgc ctg cct cag gcc atg aac atc acc tgc<br>Ile Gln Cys His Pro Glu Cys Leu Pro Gln Ala Met Asn Ile Thr Cys<br>290                   295                300 | 912 |
| aca gga cgg gga cca gac aac tgt atc cag tgt gcc cac tac att gac<br>Thr Gly Arg Gly Pro Asp Asn Cys Ile Gln Cys Ala His Tyr Ile Asp<br>305                   310                315               320 | 960 |
| ggc ccc cac tgc gtc aag acc tgc ccg gca gga gtc atg gga gaa aac<br>Gly Pro His Cys Val Lys Thr Cys Pro Ala Gly Val Met Gly Glu Asn<br>                  325                330               335 | 1008 |
| aac acc ctg gtc tgg aag tac gca gac gcc ggc cat gtg tgc cac ctg<br>Asn Thr Leu Val Trp Lys Tyr Ala Asp Ala Gly His Val Cys His Leu | 1056 |

```
                   340                 345                 350
tgc cat cca aac tgc acc tac gga tgc act ggg cca ggt ctt gaa ggc        1104
Cys His Pro Asn Cys Thr Tyr Gly Cys Thr Gly Pro Gly Leu Glu Gly
        355                 360                 365 tgt cca acg aat ggg cct aag atc ccg tcc                                 1134
Cys Pro Thr Asn Gly Pro Lys Ile Pro Ser
        370                 375
```

<210> SEQ ID NO 78
<211> LENGTH: 378
<212> TYPE: PRT
<213> ORGANISM: Artificial Sequence
<220> FEATURE:
<223> OTHER INFORMATION: [CDS]:1..1134 from SEQ ID NO 77

<400> SEQUENCE: 78

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320
```

Gly Pro His Cys Val Lys Thr Cys Pro Ala Gly Val Met Gly Glu Asn
            325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
            355                 360                 365

Cys Pro Thr Asn Gly Pro Lys Ile Pro Ser
    370                 375

<210> SEQ ID NO 79
<211> LENGTH: 69
<212> TYPE: DNA
<213> ORGANISM: Artificial Sequence
<220> FEATURE:
<223> OTHER INFORMATION: EGFRvIII TM
<220> FEATURE:
<221> NAME/KEY: CDS
<222> LOCATION: 1..69
<223> OTHER INFORMATION: /transl_table=1

<400> SEQUENCE: 79 atc gcc act ggg atg gtg ggg gcc ctc ctc ttg ctg ctg gtg gtg gcc      48
Ile Ala Thr Gly Met Val Gly Ala Leu Leu Leu Leu Leu Val Val Ala
1               5                   10                  15 ctg ggg atc ggc ctc ttc atg                                          69
Leu Gly Ile Gly Leu Phe Met
            20

<210> SEQ ID NO 80
<211> LENGTH: 23
<212> TYPE: PRT
<213> ORGANISM: Artificial Sequence
<220> FEATURE:
<223> OTHER INFORMATION: [CDS]:1..69 from SEQ ID NO 79

<400> SEQUENCE: 80

Ile Ala Thr Gly Met Val Gly Ala Leu Leu Leu Leu Leu Val Val Ala
1               5                   10                  15

Leu Gly Ile Gly Leu Phe Met
            20

<210> SEQ ID NO 81
<211> LENGTH: 27
<212> TYPE: DNA
<213> ORGANISM: Artificial Sequence
<220> FEATURE:
<223> OTHER INFORMATION: EGFRvIII IZ ANCHOR
<220> FEATURE:
<221> NAME/KEY: CDS
<222> LOCATION: 1..27
<223> OTHER INFORMATION: /transl_table=1

<400> SEQUENCE: 81 cga agg cgc cac atc gtt cgg aag cgc                                  27
Arg Arg Arg His Ile Val Arg Lys Arg
1               5

<210> SEQ ID NO 82
<211> LENGTH: 9
<212> TYPE: PRT
<213> ORGANISM: Artificial Sequence
<220> FEATURE:
<223> OTHER INFORMATION: [CDS]:1..27 from SEQ ID NO 81

<400> SEQUENCE: 82

Arg Arg Arg His Ile Val Arg Lys Arg
1               5

<210> SEQ ID NO 83
<211> LENGTH: 945
<212> TYPE: DNA
<213> ORGANISM: Artificial Sequence
<220> FEATURE:
<223> OTHER INFORMATION: Epcam (mouse)
<220> FEATURE:
<221> NAME/KEY: CDS
<222> LOCATION: 1..945
<223> OTHER INFORMATION: /transl_table=1

<400> SEQUENCE: 83

| | | | | | | | | | | | | | | | | |
|---|---|---|---|---|---|---|---|---|---|---|---|---|---|---|---|---|
| atg | gcg | ggc | ccg | cag | gcg | ctg | gcg | ttt | ggc | ctg | ctg | ctg | gcg | gtg | gtg | 48 |
| Met | Ala | Gly | Pro | Gln | Ala | Leu | Ala | Phe | Gly | Leu | Leu | Leu | Ala | Val | Val | |
| 1 | | | | 5 | | | | | 10 | | | | | 15 | | |

| acc | gcg | acc | ctg | gcg | gcg | gcg | cag | cgc | gat | tgc | gtg | tgc | gat | aac | tat | 96 |
|---|---|---|---|---|---|---|---|---|---|---|---|---|---|---|---|---|
| Thr | Ala | Thr | Leu | Ala | Ala | Ala | Gln | Arg | Asp | Cys | Val | Cys | Asp | Asn | Tyr | |
| | | | 20 | | | | | 25 | | | | | 30 | | | |

| aaa | ctg | gcg | acc | agc | tgc | agc | ctg | aac | gaa | tat | ggc | gaa | tgc | cag | tgc | 144 |
|---|---|---|---|---|---|---|---|---|---|---|---|---|---|---|---|---|
| Lys | Leu | Ala | Thr | Ser | Cys | Ser | Leu | Asn | Glu | Tyr | Gly | Glu | Cys | Gln | Cys | |
| | | 35 | | | | | 40 | | | | | 45 | | | | |

| acc | agc | tat | ggc | acc | cag | aac | acc | gtg | att | tgc | agc | aaa | ctg | gcg | agc | 192 |
|---|---|---|---|---|---|---|---|---|---|---|---|---|---|---|---|---|
| Thr | Ser | Tyr | Gly | Thr | Gln | Asn | Thr | Val | Ile | Cys | Ser | Lys | Leu | Ala | Ser | |
| | 50 | | | | | 55 | | | | | 60 | | | | | |

| aaa | tgc | ctg | gcg | atg | aaa | gcg | gaa | atg | acc | cat | agc | aaa | agc | ggc | cgc | 240 |
|---|---|---|---|---|---|---|---|---|---|---|---|---|---|---|---|---|
| Lys | Cys | Leu | Ala | Met | Lys | Ala | Glu | Met | Thr | His | Ser | Lys | Ser | Gly | Arg | |
| 65 | | | | 70 | | | | | 75 | | | | | 80 | | |

| cgc | att | aaa | ccg | gaa | ggc | gcg | att | cag | aac | aac | gat | ggc | ctg | tat | gat | 288 |
|---|---|---|---|---|---|---|---|---|---|---|---|---|---|---|---|---|
| Arg | Ile | Lys | Pro | Glu | Gly | Ala | Ile | Gln | Asn | Asn | Asp | Gly | Leu | Tyr | Asp | |
| | | | 85 | | | | | 90 | | | | | 95 | | | |

| ccg | gat | tgc | gat | gaa | cag | ggc | ctg | ttt | aaa | gcg | aaa | cag | tgc | aac | ggc | 336 |
|---|---|---|---|---|---|---|---|---|---|---|---|---|---|---|---|---|
| Pro | Asp | Cys | Asp | Glu | Gln | Gly | Leu | Phe | Lys | Ala | Lys | Gln | Cys | Asn | Gly | |
| | | 100 | | | | | 105 | | | | | 110 | | | | |

| acc | gcg | acc | tgc | tgg | tgc | gtg | aac | acc | gcg | ggc | gtg | cgc | cgc | acc | gat | 384 |
|---|---|---|---|---|---|---|---|---|---|---|---|---|---|---|---|---|
| Thr | Ala | Thr | Cys | Trp | Cys | Val | Asn | Thr | Ala | Gly | Val | Arg | Arg | Thr | Asp | |
| | 115 | | | | | 120 | | | | | 125 | | | | | |

| aaa | gat | acc | gaa | att | acc | tgc | agc | gaa | cgc | gtg | cgc | acc | tat | tgg | att | 432 |
|---|---|---|---|---|---|---|---|---|---|---|---|---|---|---|---|---|
| Lys | Asp | Thr | Glu | Ile | Thr | Cys | Ser | Glu | Arg | Val | Arg | Thr | Tyr | Trp | Ile | |
| 130 | | | | 135 | | | | | 140 | | | | | | | |

| att | att | gaa | ctg | aaa | cat | aaa | gaa | cgc | gaa | agc | ccg | tat | gat | cat | cag | 480 |
|---|---|---|---|---|---|---|---|---|---|---|---|---|---|---|---|---|
| Ile | Ile | Glu | Leu | Lys | His | Lys | Glu | Arg | Glu | Ser | Pro | Tyr | Asp | His | Gln | |
| 145 | | | | 150 | | | | | 155 | | | | | 160 | | |

| agc | ctg | cag | acc | gcg | ctg | cag | gaa | gcg | ttt | acc | agc | cgc | tat | aaa | ctg | 528 |
|---|---|---|---|---|---|---|---|---|---|---|---|---|---|---|---|---|
| Ser | Leu | Gln | Thr | Ala | Leu | Gln | Glu | Ala | Phe | Thr | Ser | Arg | Tyr | Lys | Leu | |
| | | | 165 | | | | | 170 | | | | | 175 | | | |

| aac | cag | aaa | ttt | att | aaa | aac | att | atg | tat | gaa | aac | aac | gtg | att | acc | 576 |
|---|---|---|---|---|---|---|---|---|---|---|---|---|---|---|---|---|
| Asn | Gln | Lys | Phe | Ile | Lys | Asn | Ile | Met | Tyr | Glu | Asn | Asn | Val | Ile | Thr | |
| | | 180 | | | | | 185 | | | | | 190 | | | | |

| att | gat | ctg | atg | cag | aac | agc | agc | cag | aaa | acc | cag | gat | gat | gtg | gat | 624 |
|---|---|---|---|---|---|---|---|---|---|---|---|---|---|---|---|---|
| Ile | Asp | Leu | Met | Gln | Asn | Ser | Ser | Gln | Lys | Thr | Gln | Asp | Asp | Val | Asp | |
| 195 | | | | | 200 | | | | | 205 | | | | | | |

| att | gcg | gat | gtg | gcg | tat | tat | ttt | gaa | aaa | gat | gtg | aaa | ggc | gaa | agc | 672 |
|---|---|---|---|---|---|---|---|---|---|---|---|---|---|---|---|---|
| Ile | Ala | Asp | Val | Ala | Tyr | Tyr | Phe | Glu | Lys | Asp | Val | Lys | Gly | Glu | Ser | |
| | 210 | | | | | 215 | | | | | 220 | | | | | |

| ctg | ttt | cat | agc | agc | aaa | agc | atg | gat | ctg | cgc | gtg | aac | ggc | gaa | ccg | 720 |
|---|---|---|---|---|---|---|---|---|---|---|---|---|---|---|---|---|
| Leu | Phe | His | Ser | Ser | Lys | Ser | Met | Asp | Leu | Arg | Val | Asn | Gly | Glu | Pro | |
| 225 | | | | 230 | | | | | 235 | | | | | 240 | | |

| ctg | gat | ctg | gat | ccg | ggc | cag | acc | ctg | att | tat | tat | gtg | gat | gaa | aaa | 768 |
|---|---|---|---|---|---|---|---|---|---|---|---|---|---|---|---|---|
| Leu | Asp | Leu | Asp | Pro | Gly | Gln | Thr | Leu | Ile | Tyr | Tyr | Val | Asp | Glu | Lys | |

```
                       245                 250                 255
gcg ccg gaa ttt agc atg cag ggc ctg acc gcg ggc att att gcg gtg       816
Ala Pro Glu Phe Ser Met Gln Gly Leu Thr Ala Gly Ile Ile Ala Val
        260                 265                 270 att gtg gtg gtg agc ctg gcg gtg att gcg ggc att gtg gtg ctg gtg       864
Ile Val Val Val Ser Leu Ala Val Ile Ala Gly Ile Val Val Leu Val
            275                 280                 285 att agc acc cgc aaa aaa agc gcg aaa tat gaa aaa gcg gaa att aaa       912
Ile Ser Thr Arg Lys Lys Ser Ala Lys Tyr Glu Lys Ala Glu Ile Lys
        290                 295                 300 gaa atg ggc gaa att cat cgc gaa ctg aac gcg                            945
Glu Met Gly Glu Ile His Arg Glu Leu Asn Ala
305                 310                 315

<210> SEQ ID NO 84
<211> LENGTH: 315
<212> TYPE: PRT
<213> ORGANISM: Artificial Sequence
<220> FEATURE:
<223> OTHER INFORMATION: [CDS]:1..945 from SEQ ID NO 83

<400> SEQUENCE: 84

Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
        195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Gly Ile Ile Ala Val
            260                 265                 270
```

```
Ile Val Val Val Ser Leu Ala Val Ile Ala Gly Ile Val Leu Val
            275                 280                 285

Ile Ser Thr Arg Lys Lys Ser Ala Lys Tyr Glu Lys Ala Glu Ile Lys
    290                 295                 300

Glu Met Gly Glu Ile His Arg Glu Leu Asn Ala
305                 310                 315
```

<210> SEQ ID NO 85
<211> LENGTH: 339
<212> TYPE: DNA
<213> ORGANISM: Artificial Sequence
<220> FEATURE:
<223> OTHER INFORMATION: CD3Z UniProtKB - P20963
<220> FEATURE:
<221> NAME/KEY: CDS
<222> LOCATION: 1..339
<223> OTHER INFORMATION: /transl_table=1

<400> SEQUENCE: 85

```
cgc gtg aaa ttt agc cgc agc gcg gat gcg ccg gcg tat cag cag ggc      48
Arg Val Lys Phe Ser Arg Ser Ala Asp Ala Pro Ala Tyr Gln Gln Gly
1               5                   10                  15 cag aac cag ctg tat aac gaa ctg aac ctg ggc cgc cgc gaa gaa tat      96
Gln Asn Gln Leu Tyr Asn Glu Leu Asn Leu Gly Arg Arg Glu Glu Tyr
            20                  25                  30 gat gtg ctg gat aaa cgc cgc ggc cgc gat ccg gaa atg ggc ggc aaa     144
Asp Val Leu Asp Lys Arg Arg Gly Arg Asp Pro Glu Met Gly Gly Lys
        35                  40                  45 ccg cag cgc cgc aaa aac ccg cag gaa ggc ctg tat aac gaa ctg cag     192
Pro Gln Arg Arg Lys Asn Pro Gln Glu Gly Leu Tyr Asn Glu Leu Gln
    50                  55                  60 aaa gat aaa atg gcg gaa gcg tat agc gaa att ggc atg aaa ggc gaa     240
Lys Asp Lys Met Ala Glu Ala Tyr Ser Glu Ile Gly Met Lys Gly Glu
65                  70                  75                  80 cgc cgc cgc ggc aaa ggc cat gat ggc ctg tat cag ggc ctg agc acc     288
Arg Arg Arg Gly Lys Gly His Asp Gly Leu Tyr Gln Gly Leu Ser Thr
                85                  90                  95 gcg acc aaa gat acc tat gat gcg ctg cat atg cag gcg ctg ccg ccg     336
Ala Thr Lys Asp Thr Tyr Asp Ala Leu His Met Gln Ala Leu Pro Pro
            100                 105                 110 cgc                                                                  339
Arg
```

<210> SEQ ID NO 86
<211> LENGTH: 113
<212> TYPE: PRT
<213> ORGANISM: Artificial Sequence
<220> FEATURE:
<223> OTHER INFORMATION: [CDS]:1..339 from SEQ ID NO 85

<400> SEQUENCE: 86

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80
```

-continued

```
Arg Arg Arg Gly Lys Gly His Asp Gly Leu Tyr Gln Gly Leu Ser Thr
            85                  90                  95
Ala Thr Lys Asp Thr Tyr Asp Ala Leu His Met Gln Ala Leu Pro Pro
        100                 105                 110
Arg

<210> SEQ ID NO 87
<211> LENGTH: 75
<212> TYPE: DNA
<213> ORGANISM: Artificial Sequence
<220> FEATURE:
<223> OTHER INFORMATION: Fcgr3a: UniProtKB - P08637
<220> FEATURE:
<221> NAME/KEY: CDS
<222> LOCATION: 1..75
<223> OTHER INFORMATION: /transl_table=1

<400> SEQUENCE: 87 aaa acc aac att cgc agc agc acc cgc gat tgg aaa gat cat aaa ttt    48
Lys Thr Asn Ile Arg Ser Ser Thr Arg Asp Trp Lys Asp His Lys Phe
1               5                   10                  15 aaa tgg cgc aaa gat ccg cag gat aaa                                75
Lys Trp Arg Lys Asp Pro Gln Asp Lys
            20                  25

<210> SEQ ID NO 88
<211> LENGTH: 25
<212> TYPE: PRT
<213> ORGANISM: Artificial Sequence
<220> FEATURE:
<223> OTHER INFORMATION: [CDS]:1..75 from SEQ ID NO 87

<400> SEQUENCE: 88

Lys Thr Asn Ile Arg Ser Ser Thr Arg Asp Trp Lys Asp His Lys Phe
1               5                   10                  15

Lys Trp Arg Lys Asp Pro Gln Asp Lys
            20                  25

<210> SEQ ID NO 89
<211> LENGTH: 153
<212> TYPE: DNA
<213> ORGANISM: Artificial Sequence
<220> FEATURE:
<223> OTHER INFORMATION: NKG2D UniProtKB - P26718
<220> FEATURE:
<221> NAME/KEY: CDS
<222> LOCATION: 1..153
<223> OTHER INFORMATION: /transl_table=1

<400> SEQUENCE: 89 atg ggc tgg att cgc ggc cgc cgc agc cgc cat agc tgg gaa atg agc    48
Met Gly Trp Ile Arg Gly Arg Arg Ser Arg His Ser Trp Glu Met Ser
1               5                   10                  15 gaa ttt cat aac tat aac ctg gat ctg aaa aaa agc gat ttt agc acc    96
Glu Phe His Asn Tyr Asn Leu Asp Leu Lys Lys Ser Asp Phe Ser Thr
            20                  25                  30 cgc tgg cag aaa cag cgc tgc ccg gtg gtg aaa agc aaa tgc cgc gaa   144
Arg Trp Gln Lys Gln Arg Cys Pro Val Val Lys Ser Lys Cys Arg Glu
        35                  40                  45 aac gcg agc                                                        153
Asn Ala Ser
    50

<210> SEQ ID NO 90
<211> LENGTH: 51
```

```
<212> TYPE: PRT
<213> ORGANISM: Artificial Sequence
<220> FEATURE:
<223> OTHER INFORMATION: [CDS]:1..153 from SEQ ID NO 89

<400> SEQUENCE: 90

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser
    50

<210> SEQ ID NO 91
<211> LENGTH: 123
<212> TYPE: DNA
<213> ORGANISM: Artificial Sequence
<220> FEATURE:
<223> OTHER INFORMATION: UniProtKB - P10747 CD28
<220> FEATURE:
<221> NAME/KEY: CDS
<222> LOCATION: 1..123
<223> OTHER INFORMATION: /transl_table=1

<400> SEQUENCE: 91 cgc agc aaa cgc agc cgc ctg ctg cat agc gat tat atg aac atg acc      48
Arg Ser Lys Arg Ser Arg Leu Leu His Ser Asp Tyr Met Asn Met Thr
1               5                   10                  15 ccg cgc cgc ccg ggc ccg acc cgc aaa cat tat cag ccg tat gcg ccg      96
Pro Arg Arg Pro Gly Pro Thr Arg Lys His Tyr Gln Pro Tyr Ala Pro
                20                  25                  30 ccg cgc gat ttt gcg gcg tat cgc agc                                 123
Pro Arg Asp Phe Ala Ala Tyr Arg Ser
            35                  40

<210> SEQ ID NO 92
<211> LENGTH: 41
<212> TYPE: PRT
<213> ORGANISM: Artificial Sequence
<220> FEATURE:
<223> OTHER INFORMATION: [CDS]:1..123 from SEQ ID NO 91

<400> SEQUENCE: 92

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 93
<211> LENGTH: 126
<212> TYPE: DNA
<213> ORGANISM: Artificial Sequence
<220> FEATURE:
<223> OTHER INFORMATION: UniProtKB - Q07011 CD137
<220> FEATURE:
<221> NAME/KEY: CDS
<222> LOCATION: 1..126
<223> OTHER INFORMATION: /transl_table=1

<400> SEQUENCE: 93 aaa cgc ggc cgc aaa aaa ctg ctg tat att ttt aaa cag ccg ttt atg      48
```

```
                    Lys Arg Gly Arg Lys Lys Leu Leu Tyr Ile Phe Lys Gln Pro Phe Met
                    1               5                   10                  15 cgc ccg gtg cag acc acc cag gaa gaa gat ggc tgc agc tgc cgc ttt              96
Arg Pro Val Gln Thr Thr Gln Glu Glu Asp Gly Cys Ser Cys Arg Phe
                20                  25                  30 ccg gaa gaa gaa gaa ggc ggc tgc gaa ctg                                      126
Pro Glu Glu Glu Glu Gly Gly Cys Glu Leu
            35                  40
```

<210> SEQ ID NO 94
<211> LENGTH: 42
<212> TYPE: PRT
<213> ORGANISM: Artificial Sequence
<220> FEATURE:
<223> OTHER INFORMATION: [CDS]:1..126 from SEQ ID NO 93

<400> SEQUENCE: 94

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 95
<211> LENGTH: 129
<212> TYPE: DNA
<213> ORGANISM: Artificial Sequence
<220> FEATURE:
<223> OTHER INFORMATION: UniProtKB - P23510 OX40
<220> FEATURE:
<221> NAME/KEY: CDS
<222> LOCATION: 1..129
<223> OTHER INFORMATION: /transl_table=1

<400> SEQUENCE: 95

```
cag gtg agc cat cgc tat ccg cgc att cag agc att aaa gtg cag ttt              48
Gln Val Ser His Arg Tyr Pro Arg Ile Gln Ser Ile Lys Val Gln Phe
1               5                   10                  15 acc gaa tat aaa atg gaa cgc gtg cag ccg ctg gaa gaa aac gtg ggc              96
Thr Glu Tyr Lys Met Glu Arg Val Gln Pro Leu Glu Glu Asn Val Gly
            20                  25                  30 aac gcg gcg cgc ccg cgc ttt gaa cgc aac aaa                                  129
Asn Ala Ala Arg Pro Arg Phe Glu Arg Asn Lys
        35                  40
```

<210> SEQ ID NO 96
<211> LENGTH: 43
<212> TYPE: PRT
<213> ORGANISM: Artificial Sequence
<220> FEATURE:
<223> OTHER INFORMATION: [CDS]:1..129 from SEQ ID NO 95

<400> SEQUENCE: 96

```
Gln Val Ser His Arg Tyr Pro Arg Ile Gln Ser Ile Lys Val Gln Phe
1               5                   10                  15

Thr Glu Tyr Lys Met Glu Arg Val Gln Pro Leu Glu Glu Asn Val Gly
            20                  25                  30

Asn Ala Ala Arg Pro Arg Phe Glu Arg Asn Lys
        35                  40
```

<210> SEQ ID NO 97
<211> LENGTH: 114
<212> TYPE: DNA

<213> ORGANISM: Artificial Sequence
<220> FEATURE:
<223> OTHER INFORMATION: UniProtKB - Q9Y6W8 ICOS
<220> FEATURE:
<221> NAME/KEY: CDS
<222> LOCATION: 1..114
<223> OTHER INFORMATION: /transl_table=1

<400> SEQUENCE: 97

```
tgc tgg ctg acc aaa aaa aaa tat agc agc agc gtg cat gat ccg aac      48
Cys Trp Leu Thr Lys Lys Lys Tyr Ser Ser Ser Val His Asp Pro Asn
1               5                  10                  15 ggc gaa tat atg ttt atg cgc gcg gtg aac acc gcg aaa aaa agc cgc      96
Gly Glu Tyr Met Phe Met Arg Ala Val Asn Thr Ala Lys Lys Ser Arg
            20                  25                  30 ctg acc gat gtg acc ctg                                             114
Leu Thr Asp Val Thr Leu
        35
```

<210> SEQ ID NO 98
<211> LENGTH: 38
<212> TYPE: PRT
<213> ORGANISM: Artificial Sequence
<220> FEATURE:
<223> OTHER INFORMATION: [CDS]:1..114 from SEQ ID NO 97

<400> SEQUENCE: 98

```
Cys Trp Leu Thr Lys Lys Lys Tyr Ser Ser Ser Val His Asp Pro Asn
1               5                  10                  15

Gly Glu Tyr Met Phe Met Arg Ala Val Asn Thr Ala Lys Lys Ser Arg
            20                  25                  30

Leu Thr Asp Val Thr Leu
        35
```

<210> SEQ ID NO 99
<211> LENGTH: 144
<212> TYPE: DNA
<213> ORGANISM: Artificial Sequence
<220> FEATURE:
<223> OTHER INFORMATION: UniProtKB - P26842 CD27
<220> FEATURE:
<221> NAME/KEY: CDS
<222> LOCATION: 1..144
<223> OTHER INFORMATION: /transl_table=1

<400> SEQUENCE: 99

```
cag cgc cgc aaa tat cgc agc aac aaa ggc gaa agc ccg gtg gaa ccg      48
Gln Arg Arg Lys Tyr Arg Ser Asn Lys Gly Glu Ser Pro Val Glu Pro
1               5                  10                  15 gcg gaa ccg tgc cat tat agc tgc ccg cgc gaa gaa gaa ggc agc acc      96
Ala Glu Pro Cys His Tyr Ser Cys Pro Arg Glu Glu Glu Gly Ser Thr
            20                  25                  30 att ccg att cag gaa gat tat cgc aaa ccg gaa ccg gcg tgc agc ccg     144
Ile Pro Ile Gln Glu Asp Tyr Arg Lys Pro Glu Pro Ala Cys Ser Pro
        35                  40                  45
```

<210> SEQ ID NO 100
<211> LENGTH: 48
<212> TYPE: PRT
<213> ORGANISM: Artificial Sequence
<220> FEATURE:
<223> OTHER INFORMATION: [CDS]:1..144 from SEQ ID NO 99

<400> SEQUENCE: 100

```
Gln Arg Arg Lys Tyr Arg Ser Asn Lys Gly Glu Ser Pro Val Glu Pro
1               5                  10                  15
```

```
Ala Glu Pro Cys His Tyr Ser Cys Pro Arg Glu Glu Gly Ser Thr
         20                  25                  30

Ile Pro Ile Gln Glu Asp Tyr Arg Lys Pro Glu Pro Ala Cys Ser Pro
         35                  40                  45
```

```
<210> SEQ ID NO 101
<211> LENGTH: 72
<212> TYPE: DNA
<213> ORGANISM: Artificial Sequence
<220> FEATURE:
<223> OTHER INFORMATION: UniProtKB - Q9UBK5 DAP10
<220> FEATURE:
<221> NAME/KEY: CDS
<222> LOCATION: 1..72
<223> OTHER INFORMATION: /transl_table=1

<400> SEQUENCE: 101
```

```
ctg tgc gcg cgc ccg cgc cgc agc ccg gcg cag gaa gat ggc aaa gtg    48
Leu Cys Ala Arg Pro Arg Arg Ser Pro Ala Gln Glu Asp Gly Lys Val
1               5                   10                  15 tat att aac atg ccg ggc cgc ggc                                    72
Tyr Ile Asn Met Pro Gly Arg Gly
            20
```

```
<210> SEQ ID NO 102
<211> LENGTH: 24
<212> TYPE: PRT
<213> ORGANISM: Artificial Sequence
<220> FEATURE:
<223> OTHER INFORMATION: [CDS]:1..72 from SEQ ID NO 101

<400> SEQUENCE: 102
```

```
Leu Cys Ala Arg Pro Arg Arg Ser Pro Ala Gln Glu Asp Gly Lys Val
1               5                   10                  15

Tyr Ile Asn Met Pro Gly Arg Gly
            20
```

```
<210> SEQ ID NO 103
<211> LENGTH: 36
<212> TYPE: DNA
<213> ORGANISM: Artificial Sequence
<220> FEATURE:
<223> OTHER INFORMATION: /note="EGFRvIIINot1fwd"
      /note="Primer"

<400> SEQUENCE: 103
agcttgctcg cggccgcgcc accatgcgac cctccg                            36
```

```
<210> SEQ ID NO 104
<211> LENGTH: 36
<212> TYPE: DNA
<213> ORGANISM: Artificial Sequence
<220> FEATURE:
<223> OTHER INFORMATION: /note="Primer"
      /note="EGFRtm CD28iz rev"

<400> SEQUENCE: 104
tctgttcctt ctactattca tgaagaggcc gatccc                            36
```

```
<210> SEQ ID NO 105
<211> LENGTH: 36
<212> TYPE: DNA
<213> ORGANISM: Artificial Sequence
<220> FEATURE:
<223> OTHER INFORMATION: /note="Primer"
      /note="EGFRtm CD28iz fwd"
```

<400> SEQUENCE: 105
gggatcggcc tcttcatgaa tagtagaagg aacaga                                    36

<210> SEQ ID NO 106
<211> LENGTH: 34
<212> TYPE: DNA
<213> ORGANISM: Artificial Sequence
<220> FEATURE:
<223> OTHER INFORMATION: /note="Primer"
     /note="CD28in/CD3zeta rev"

<400> SEQUENCE: 106
ctgctgaatt ttgctctggg gcggtacgct gcaa                                      34

<210> SEQ ID NO 107
<211> LENGTH: 34
<212> TYPE: DNA
<213> ORGANISM: Artificial Sequence
<220> FEATURE:
<223> OTHER INFORMATION: /note="Primer"
     /note="CD3zeta/CD28fwd"

<400> SEQUENCE: 107
ttgcagcgta ccgccccaga gcaaaattca gcag                                      34

<210> SEQ ID NO 108
<211> LENGTH: 29
<212> TYPE: DNA
<213> ORGANISM: Artificial Sequence
<220> FEATURE:
<223> OTHER INFORMATION: /note="CD3zetaEcoR1rev"
     /note="Primer"

<400> SEQUENCE: 108
taatgaattc ttagcgaggg gccagggtc                                            29

<210> SEQ ID NO 109
<211> LENGTH: 34
<212> TYPE: DNA
<213> ORGANISM: Artificial Sequence
<220> FEATURE:
<223> OTHER INFORMATION: /note="Primer"
     /note="Leader_Not1_fwd"

<400> SEQUENCE: 109
attagcggcc gcgccaccat ggaaacagat acac                                      34

<210> SEQ ID NO 110
<211> LENGTH: 36
<212> TYPE: DNA
<213> ORGANISM: Artificial Sequence
<220> FEATURE:
<223> OTHER INFORMATION: LeaderCriptoIsorev

<400> SEQUENCE: 110
aaattcctga tggcccaggc ttctagcagg ctgggc                                    36

<210> SEQ ID NO 111
<211> LENGTH: 36
<212> TYPE: DNA
<213> ORGANISM: Artificial Sequence
<220> FEATURE:
<223> OTHER INFORMATION: /note="Primer"
     /note="LeaderCriptoIsofwd"

<400> SEQUENCE: 111
gcccagcctg ctagaagcct gggccatcag gaattt                                    36

<210> SEQ ID NO 112
<211> LENGTH: 36
<212> TYPE: DNA
<213> ORGANISM: Artificial Sequence
<220> FEATURE:
<223> OTHER INFORMATION: /note="Cripto CD8aex rev"
      /note="Primer"

<400> SEQUENCE: 112
cagcactggc ttggtagtat cacagccggg tagaaa                                    36

<210> SEQ ID NO 113
<211> LENGTH: 36
<212> TYPE: DNA
<213> ORGANISM: Artificial Sequence
<220> FEATURE:
<223> OTHER INFORMATION: /note="CriptoCD8aex fwd"
      /note="Primer"

<400> SEQUENCE: 113
tttctacccg gctgtgatac taccaagcca gtgctg                                    36

<210> SEQ ID NO 114
<211> LENGTH: 36
<212> TYPE: DNA
<213> ORGANISM: Artificial Sequence
<220> FEATURE:
<223> OTHER INFORMATION: /note="Primer"
      /note="CD8tm-CD28iz rev"

<400> SEQUENCE: 114
tctgttcctt ctactattga tgagagtgat gatcaa                                    36

<210> SEQ ID NO 115
<211> LENGTH: 36
<212> TYPE: DNA
<213> ORGANISM: Artificial Sequence
<220> FEATURE:
<223> OTHER INFORMATION: /note="CD8tm-CD28izfwd"
      /note="Primer"

<400> SEQUENCE: 115
ttgatcatca ctctcatcaa tagtagaagg aacaga                                    36

<210> SEQ ID NO 116
<211> LENGTH: 34
<212> TYPE: DNA
<213> ORGANISM: Artificial Sequence
<220> FEATURE:
<223> OTHER INFORMATION: /note="Primer"
      /note="CD28in/CD3zeta rev"

<400> SEQUENCE: 116
ctgctgaatt ttgctctggg gcggtacgct gcaa                                      34

<210> SEQ ID NO 117
<211> LENGTH: 34
<212> TYPE: DNA
<213> ORGANISM: Artificial Sequence
<220> FEATURE:
<223> OTHER INFORMATION: /note="Primer"
      /note="CD3zeta/CD28fwd"

<400> SEQUENCE: 117
ttgcagcgta ccgccccaga gcaaaattca gcag					34

<210> SEQ ID NO 118
<211> LENGTH: 29
<212> TYPE: DNA
<213> ORGANISM: Artificial Sequence
<220> FEATURE:
<223> OTHER INFORMATION: /note="Primer"
		/note="CD3zetaEcoR1rev"

<400> SEQUENCE: 118
taatgaattc ttagcgaggg gccagggtc					29

<210> SEQ ID NO 119
<211> LENGTH: 1470
<212> TYPE: DNA
<213> ORGANISM: Artificial Sequence
<220> FEATURE:
<223> OTHER INFORMATION: CAR1 murin (Cripto-CD8aex/tm-CD28iz-CD3z

<400> SEQUENCE: 119
attagcggcc gcgccaccat ggaaacagat acactgctgc tgtgggtgct gctgctgtgg		60 gtgccaggat ctacagggga tggcgcccag cctgctagaa gcctgggcca tcaggaattt		120 gctcgtccat ctcggggata cctggccttc agagatgaca gcatttggcc ccaggaggag		180 cctgcaattc ggcctcggtc ttcccagcgt gtgccgccca tggggataca gcacagtaag		240 gagctaaaca gaacctgctg cctgaatggg ggaacctgca tgctggggtc cttttgtgcc		300 tgccctccct ccttctacgg acggaactgt gagcacgatg tgcgcaaaga gaactgtggg		360 tctgtgcccc atgacacctg gctgcccaag aagtgttccc tgtgtaaatg ctggcacggt		420 cagctccgct gctttcctca ggcatttcta cccggctgtg atagccagtt ccgggtgtcg		480 ccgctggatc ggacctggaa cctgggcgag acagtggagc tgaagtgcca ggtgctgctg		540 tccaacccga cgtcgggctg ctcgtggctc ttccagccgc gcggcgccgc cgccagtccc		600 accttcctcc tatacctctc ccaaaacaag cccaaggcgg ccgaggggct ggacacccag		660 cggttctcgg gcaagaggtt gggggacacc ttcgtcctca ccctgagcga cttccgccga		720 gagaacgagg gctactattt ctgctcggcc ctgagcaact ccatcatgta cttcagccac		780 ttcgtgccgg tcttcctgcc agcgaagccc accacgacgc cagcgccgcg accaccaaca		840 ccggcgccca catcgcgtc gcagcccctg tccctgcgcc cagaggcgtg ccggccagcg		900 gcggggggcg cagtgcacac gaggggggctg gacttcgcct gtgatatcta catctgggcg		960 cccctggccg ggacttgtgg ggtccttctc ctgtcactgg ttatcaccag gagtaagagg		1020 agcaggctcc tgcacagtga ctacatgaac atgactcccc gccgccccgg gcccacccgc		1080 aagcattacc agcccctatgc cccaccacgc gacttcgcag cctatcgctc cagagtgaag		1140 ttcagcagga gcgcagacgc ccccgcgtac cagcagggcc agaaccagct ctataacgag		1200 ctcaatctag gacgaagaga ggagtacgat gttttggaca gagacgtgg ccgggacccct		1260 gagatggggg gaaagccgag aaggaagaac cctcaggaag gcctgtacaa tgaactgcag		1320 aaagataaga tggcggaggc ctacagtgag attgggatga aggcgagcg ccggaggggc		1380 aaggggcacg atggccttta ccagggtctc agtacagcca ccaaggacac ctacgacgcc		1440 cttcacatgc aggccctgcc ccctcgctaa					1470

<210> SEQ ID NO 120
<211> LENGTH: 489
<212> TYPE: PRT

<213> ORGANISM: Artificial Sequence
<220> FEATURE:
<223> OTHER INFORMATION: CAR1 murin (Cripto-CD8aex/tm-CD28iz-CD3z

<400> SEQUENCE: 120

```
Ile Ser Gly Arg Ala Thr Met Glu Thr Asp Thr Leu Leu Leu Trp Val
1               5                   10                  15

Leu Leu Leu Trp Val Pro Gly Ser Thr Gly Asp Gly Ala Gln Pro Ala
            20                  25                  30

Arg Ser Leu Gly His Gln Glu Phe Ala Arg Pro Ser Arg Gly Tyr Leu
        35                  40                  45

Ala Phe Arg Asp Asp Ser Ile Trp Pro Gln Glu Pro Ala Ile Arg
50                  55                  60

Pro Arg Ser Ser Gln Arg Val Pro Pro Met Gly Ile Gln His Ser Lys
65                  70                  75                  80

Glu Leu Asn Arg Thr Cys Cys Leu Asn Gly Thr Cys Met Leu Gly
                85                  90                  95

Ser Phe Cys Ala Cys Pro Pro Ser Phe Tyr Gly Arg Asn Cys Glu His
            100                 105                 110

Asp Val Arg Lys Glu Asn Cys Gly Ser Val Pro His Asp Thr Trp Leu
        115                 120                 125

Pro Lys Lys Cys Ser Leu Cys Lys Cys Trp His Gly Gln Leu Arg Cys
130                 135                 140

Phe Pro Gln Ala Phe Leu Pro Gly Cys Asp Ser Gln Phe Arg Val Ser
145                 150                 155                 160

Pro Leu Asp Arg Thr Trp Asn Leu Gly Glu Thr Val Glu Leu Lys Cys
                165                 170                 175

Gln Val Leu Leu Ser Asn Pro Thr Ser Gly Cys Ser Trp Leu Phe Gln
            180                 185                 190

Pro Arg Gly Ala Ala Ala Ser Pro Thr Phe Leu Leu Tyr Leu Ser Gln
        195                 200                 205

Asn Lys Pro Lys Ala Ala Glu Gly Leu Asp Thr Gln Arg Phe Ser Gly
210                 215                 220

Lys Arg Leu Gly Asp Thr Phe Val Leu Thr Leu Ser Asp Phe Arg Arg
225                 230                 235                 240

Glu Asn Glu Gly Tyr Tyr Phe Cys Ser Ala Leu Ser Asn Ser Ile Met
                245                 250                 255

Tyr Phe Ser His Phe Val Pro Val Phe Leu Pro Ala Lys Pro Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
370                 375                 380

Ala Asp Ala Pro Ala Tyr Gln Gln Gly Gln Asn Gln Leu Tyr Asn Glu
```

```
                385                 390                 395                 400
Leu Asn Leu Gly Arg Arg Glu Glu Tyr Asp Val Leu Asp Lys Arg Arg
                    405                 410                 415
Gly Arg Asp Pro Glu Met Gly Gly Lys Pro Arg Arg Lys Asn Pro Gln
                420                 425                 430
Glu Gly Leu Tyr Asn Glu Leu Gln Lys Asp Lys Met Ala Glu Ala Tyr
                435                 440                 445
Ser Glu Ile Gly Met Lys Gly Glu Arg Arg Arg Gly Lys Gly His Asp
            450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485
```

```
<210> SEQ ID NO 121
<211> LENGTH: 4
<212> TYPE: PRT
<213> ORGANISM: Artificial Sequence
<220> FEATURE:
<223> OTHER INFORMATION: CD28 domain (not mutated)

<400> SEQUENCE: 121

Pro Tyr Ala Pro
1

<210> SEQ ID NO 122
<211> LENGTH: 4
<212> TYPE: PRT
<213> ORGANISM: Artificial Sequence
<220> FEATURE:
<223> OTHER INFORMATION: CD28 domain (not mutated)

<400> SEQUENCE: 122

Tyr Met Asn Met
1

<210> SEQ ID NO 123
<211> LENGTH: 4
<212> TYPE: PRT
<213> ORGANISM: Artificial Sequence
<220> FEATURE:
<223> OTHER INFORMATION: CD28 domain (mutated)

<400> SEQUENCE: 123

Phe Met Asn Met
1

<210> SEQ ID NO 124
<211> LENGTH: 4
<212> TYPE: PRT
<213> ORGANISM: Artificial Sequence
<220> FEATURE:
<223> OTHER INFORMATION: CD28 domain (mutated)

<400> SEQUENCE: 124

Ala Tyr Ala Ala
1

<210> SEQ ID NO 125
<211> LENGTH: 32
<212> TYPE: DNA
<213> ORGANISM: Artificial Sequence
<220> FEATURE:
<223> OTHER INFORMATION: /note="EGFRvIII fwd"
```

```
<210> SEQ ID NO 125
<211> LENGTH: 32
<212> TYPE: DNA
<213> ORGANISM: Artificial Sequence
<220> FEATURE:
<223> OTHER INFORMATION: /note="Primer"
```
    /note="Primer"

<400> SEQUENCE: 125
agcttgctcg cggccgcgcc accatgcgac cc                                32

```
<210> SEQ ID NO 126
<211> LENGTH: 35
<212> TYPE: DNA
<213> ORGANISM: Artificial Sequence
<220> FEATURE:
<223> OTHER INFORMATION: /note="Primer"
        /note="EGFRvIII (-human CD28) rev"
```

<400> SEQUENCE: 126
ccaccagcac ccaaaaggac gggatcttag gccca                             35

```
<210> SEQ ID NO 127
<211> LENGTH: 35
<212> TYPE: DNA
<213> ORGANISM: Artificial Sequence
<220> FEATURE:
<223> OTHER INFORMATION: /note="(EGFRvIII-) human CD28 fwd"
        /note="Primer"
```

<400> SEQUENCE: 127
tgggcctaag atcccgtcct tttgggtgct ggtgg                             35

```
<210> SEQ ID NO 128
<211> LENGTH: 26
<212> TYPE: DNA
<213> ORGANISM: Artificial Sequence
<220> FEATURE:
<223> OTHER INFORMATION: /note="Primer"
        /note="human CD3z rev"
```

<400> SEQUENCE: 128
taatgaattc ttagcgaggg ggcagg                                       26

```
<210> SEQ ID NO 129
<211> LENGTH: 32
<212> TYPE: DNA
<213> ORGANISM: Artificial Sequence
<220> FEATURE:
<223> OTHER INFORMATION: /note="Primer"
        /note="EGFRvIII fwd"
```

<400> SEQUENCE: 129
agcttgctcg cggccgcgcc accatgcgac cc                                32

```
<210> SEQ ID NO 130
<211> LENGTH: 26
<212> TYPE: DNA
<213> ORGANISM: Artificial Sequence
<220> FEATURE:
<223> OTHER INFORMATION: /note="human CD3z rev"
        /note="Primer"
```

<400> SEQUENCE: 130
taatgaattc ttagcgaggg ggcagg                                       26

```
<210> SEQ ID NO 131
<211> LENGTH: 32
<212> TYPE: DNA
<213> ORGANISM: Artificial Sequence
<220> FEATURE:
<223> OTHER INFORMATION: /note="EGFRvIII fwd"
        /note="Primer"
```

<400> SEQUENCE: 131
agcttgctcg cggccgcgcc accatgcgac cc                                    32

<210> SEQ ID NO 132
<211> LENGTH: 35
<212> TYPE: DNA
<213> ORGANISM: Artificial Sequence
<220> FEATURE:
<223> OTHER INFORMATION: /note="Primer"
      /note="EGFRvIII (-human CD28) rev"

<400> SEQUENCE: 132
ccaccagcac ccaaaaggac gggatcttag gccca                                 35

<210> SEQ ID NO 133
<211> LENGTH: 35
<212> TYPE: DNA
<213> ORGANISM: Artificial Sequence
<220> FEATURE:
<223> OTHER INFORMATION: /note="(EGFRvIII-) human CD28 fwd"
      /note="Primer"

<400> SEQUENCE: 133
tgggcctaag atcccgtcct tttgggtgct ggtgg                                 35

<210> SEQ ID NO 134
<211> LENGTH: 32
<212> TYPE: DNA
<213> ORGANISM: Artificial Sequence
<220> FEATURE:
<223> OTHER INFORMATION: /note="human CD28 (-human 41BB) rev"
      /note="Primer"

<400> SEQUENCE: 134
ctttctgccc cgtttggagc gataggctgc ga                                    32

<210> SEQ ID NO 135
<211> LENGTH: 32
<212> TYPE: DNA
<213> ORGANISM: Artificial Sequence
<220> FEATURE:
<223> OTHER INFORMATION: /note="(human CD28-) human 41BB fwd"
      /note="Primer"

<400> SEQUENCE: 135
tcgcagccta tcgctccaaa cggggcagaa ag                                    32

<210> SEQ ID NO 136
<211> LENGTH: 32
<212> TYPE: DNA
<213> ORGANISM: Artificial Sequence
<220> FEATURE:
<223> OTHER INFORMATION: /note="human 41BB (-human CD3z) rev"
      /note="Primer"

<400> SEQUENCE: 136
tgctgaactt cactctcagt tcacatcctc ct                                    32

<210> SEQ ID NO 137
<211> LENGTH: 34
<212> TYPE: DNA
<213> ORGANISM: Artificial Sequence
<220> FEATURE:
<223> OTHER INFORMATION: /note="(human 41BB-) human CD3z fwd"
      /note="Primer"

```
<400> SEQUENCE: 137
ggaggatgtg aactgagagt gaagttcagc agga                                34

<210> SEQ ID NO 138
<211> LENGTH: 26
<212> TYPE: DNA
<213> ORGANISM: Artificial Sequence
<220> FEATURE:
<223> OTHER INFORMATION: /note="Primer"
     /note="human CD3z rev"

<400> SEQUENCE: 138
taatgaattc ttagcgaggg ggcagg                                         26

<210> SEQ ID NO 139
<211> LENGTH: 32
<212> TYPE: DNA
<213> ORGANISM: Artificial Sequence
<220> FEATURE:
<223> OTHER INFORMATION: /note="Primer"
     /note="EGFRvIII fwd "

<400> SEQUENCE: 139
agcttgctcg cggccgcgcc accatgcgac cc                                  32

<210> SEQ ID NO 140
<211> LENGTH: 26
<212> TYPE: DNA
<213> ORGANISM: Artificial Sequence
<220> FEATURE:
<223> OTHER INFORMATION: /note="Primer"
     /note="human CD3z rev"

<400> SEQUENCE: 140
taatgaattc ttagcgaggg ggcagg                                         26

<210> SEQ ID NO 141
<211> LENGTH: 34
<212> TYPE: DNA
<213> ORGANISM: Artificial Sequence
<220> FEATURE:
<223> OTHER INFORMATION: /note="Primer"
     /note="Cripto fwd"

<400> SEQUENCE: 141
attagcggcc gcgccaccat ggaaacagat acac                                34

<210> SEQ ID NO 142
<211> LENGTH: 32
<212> TYPE: DNA
<213> ORGANISM: Artificial Sequence
<220> FEATURE:
<223> OTHER INFORMATION: /note="Cripto (-human CD8a) rev"
     /note="Primer"

<400> SEQUENCE: 142
acacccggaa ctggctatca cagccgggta ga                                  32

<210> SEQ ID NO 143
<211> LENGTH: 31
<212> TYPE: DNA
<213> ORGANISM: Artificial Sequence
<220> FEATURE:
<223> OTHER INFORMATION: /note="(Cripto-) human CD8a fwd"
     /note="Primer"

<400> SEQUENCE: 143
```

```
tctacccggc tgtgatagcc agttccgggt g                                          31
```

<210> SEQ ID NO 144
<211> LENGTH: 33
<212> TYPE: DNA
<213> ORGANISM: Artificial Sequence
<220> FEATURE:
<223> OTHER INFORMATION: /note="human CD8a (-human CD28) rev"
      /note="Primer"

<400> SEQUENCE: 144

```
ctcctcttac tcctggtgat aaccagtgac agg                                        33
```

<210> SEQ ID NO 145
<211> LENGTH: 37
<212> TYPE: DNA
<213> ORGANISM: Artificial Sequence
<220> FEATURE:
<223> OTHER INFORMATION: /note="Primer"
      /note="(human CD8a-) human CD28 fwd"

<400> SEQUENCE: 145

```
cctgtcactg gttatcacca ggagtaagag gagcagg                                    37
```

<210> SEQ ID NO 146
<211> LENGTH: 26
<212> TYPE: DNA
<213> ORGANISM: Artificial Sequence
<220> FEATURE:
<223> OTHER INFORMATION: /note="human CD3z rev"
      /note="Primer"

<400> SEQUENCE: 146

```
taatgaattc ttagcgaggg ggcagg                                                26
```

<210> SEQ ID NO 147
<211> LENGTH: 34
<212> TYPE: DNA
<213> ORGANISM: Artificial Sequence
<220> FEATURE:
<223> OTHER INFORMATION: /note="Cripto fwd "
      /note="Primer"

<400> SEQUENCE: 147

```
attagcggcc gcgccaccat ggaaacagat acac                                       34
```

<210> SEQ ID NO 148
<211> LENGTH: 26
<212> TYPE: DNA
<213> ORGANISM: Artificial Sequence
<220> FEATURE:
<223> OTHER INFORMATION: /note="Primer"
      /note="human CD3z rev"

<400> SEQUENCE: 148

```
taatgaattc ttagcgaggg ggcagg                                                26
```

<210> SEQ ID NO 149
<211> LENGTH: 1890
<212> TYPE: DNA
<213> ORGANISM: Artificial Sequence
<220> FEATURE:
<223> OTHER INFORMATION: human mesothelin
<220> FEATURE:
<221> NAME/KEY: CDS
<222> LOCATION: 1..1890
<223> OTHER INFORMATION: /transl_table=1

<400> SEQUENCE: 149

```
atg gcg ctg ccg acc gcg cgc ccg ctg ctg ggc agc tgc ggc acc ccg      48
Met Ala Leu Pro Thr Ala Arg Pro Leu Leu Gly Ser Cys Gly Thr Pro
1               5                   10                  15 gcg ctg ggc agc ctg ctg ttt ctg ctg ttt agc ctg ggc tgg gtg cag      96
Ala Leu Gly Ser Leu Leu Phe Leu Leu Phe Ser Leu Gly Trp Val Gln
            20                  25                  30 ccg agc cgc acc ctg gcg ggc gaa acc ggc cag gaa gcg gcg ccg ctg     144
Pro Ser Arg Thr Leu Ala Gly Glu Thr Gly Gln Glu Ala Ala Pro Leu
        35                  40                  45 gat ggc gtg ctg gcg aac ccg ccg aac att agc agc ctg agc ccg cgc     192
Asp Gly Val Leu Ala Asn Pro Pro Asn Ile Ser Ser Leu Ser Pro Arg
    50                  55                  60 cag ctg ctg ggc ttt ccg tgc gcg gaa gtg agc ggc ctg agc acc gaa     240
Gln Leu Leu Gly Phe Pro Cys Ala Glu Val Ser Gly Leu Ser Thr Glu
65                  70                  75                  80 cgc gtg cgc gaa ctg gcg gtg gcg ctg gcg cag aaa aac gtg aaa ctg     288
Arg Val Arg Glu Leu Ala Val Ala Leu Ala Gln Lys Asn Val Lys Leu
                85                  90                  95 agc acc gaa cag ctg cgc tgc ctg gcg cat cgc ctg agc gaa ccg ccg     336
Ser Thr Glu Gln Leu Arg Cys Leu Ala His Arg Leu Ser Glu Pro Pro
            100                 105                 110 gaa gat ctg gat gcg ctg ccg ctg gat ctg ctg ctg ttt ctg aac ccg     384
Glu Asp Leu Asp Ala Leu Pro Leu Asp Leu Leu Leu Phe Leu Asn Pro
        115                 120                 125 gat gcg ttt agc ggc ccg cag gcg tgc acc cgc ttt ttt agc cgc att     432
Asp Ala Phe Ser Gly Pro Gln Ala Cys Thr Arg Phe Phe Ser Arg Ile
    130                 135                 140 acc aaa gcg aac gtg gat ctg ctg ccg cgc ggc gcg ccg gaa cgc cag     480
Thr Lys Ala Asn Val Asp Leu Leu Pro Arg Gly Ala Pro Glu Arg Gln
145                 150                 155                 160 cgc ctg ctg ccg gcg gcg ctg gcg tgc tgg ggc gtg cgc ggc agc ctg     528
Arg Leu Leu Pro Ala Ala Leu Ala Cys Trp Gly Val Arg Gly Ser Leu
                165                 170                 175 ctg agc gaa gcg gat gtg cgc gcg ctg ggc ggc ctg gcg tgc gat ctg     576
Leu Ser Glu Ala Asp Val Arg Ala Leu Gly Gly Leu Ala Cys Asp Leu
            180                 185                 190 ccg ggc cgc ttt gtg gcg gaa agc gcg gaa gtg ctg ctg ccg cgc ctg     624
Pro Gly Arg Phe Val Ala Glu Ser Ala Glu Val Leu Leu Pro Arg Leu
        195                 200                 205 gtg agc tgc ccg ggc ccg ctg gat cag gat cag cag gaa gcg gcg cgc     672
Val Ser Cys Pro Gly Pro Leu Asp Gln Asp Gln Gln Glu Ala Ala Arg
    210                 215                 220 gcg gcg ctg cag ggc ggc ggc ccg ccg tat ggc ccg ccg agc acc tgg     720
Ala Ala Leu Gln Gly Gly Gly Pro Pro Tyr Gly Pro Pro Ser Thr Trp
225                 230                 235                 240 agc gtg agc acc atg gat gcg ctg cgc ggc ctg ctg ccg gtg ctg ggc     768
Ser Val Ser Thr Met Asp Ala Leu Arg Gly Leu Leu Pro Val Leu Gly
                245                 250                 255 cag ccg att att cgc agc att ccg cag ggc att gtg gcg gcg tgg cgc     816
Gln Pro Ile Ile Arg Ser Ile Pro Gln Gly Ile Val Ala Ala Trp Arg
            260                 265                 270 cag cgc agc agc cgc gat ccg agc tgg cgc cag ccg gaa cgc acc att     864
Gln Arg Ser Ser Arg Asp Pro Ser Trp Arg Gln Pro Glu Arg Thr Ile
        275                 280                 285 ctg cgc ccg cgc ttt cgc cgc gaa gtg gaa aaa acc gcg tgc ccg agc     912
Leu Arg Pro Arg Phe Arg Arg Glu Val Glu Lys Thr Ala Cys Pro Ser
    290                 295                 300
```

-continued

```
ggc aaa aaa gcg cgc gaa att gat gaa agc ctg att ttt tat aaa aaa    960
Gly Lys Lys Ala Arg Glu Ile Asp Glu Ser Leu Ile Phe Tyr Lys Lys
305                 310                 315                 320 tgg gaa ctg gaa gcg tgc gtg gat gcg gcg ctg ctg gcg acc cag atg   1008
Trp Glu Leu Glu Ala Cys Val Asp Ala Ala Leu Leu Ala Thr Gln Met
                325                 330                 335 gat cgc gtg aac gcg att ccg ttt acc tat gaa cag ctg gat gtg ctg   1056
Asp Arg Val Asn Ala Ile Pro Phe Thr Tyr Glu Gln Leu Asp Val Leu
            340                 345                 350 aaa cat aaa ctg gat gaa ctg tat ccg cag ggc tat ccg gaa agc gtg   1104
Lys His Lys Leu Asp Glu Leu Tyr Pro Gln Gly Tyr Pro Glu Ser Val
        355                 360                 365 att cag cat ctg ggc tat ctg ttt ctg aaa atg agc ccg gaa gat att   1152
Ile Gln His Leu Gly Tyr Leu Phe Leu Lys Met Ser Pro Glu Asp Ile
    370                 375                 380 cgc aaa tgg aac gtg acc agc ctg gaa acc ctg aaa gcg ctg ctg gaa   1200
Arg Lys Trp Asn Val Thr Ser Leu Glu Thr Leu Lys Ala Leu Leu Glu
385                 390                 395                 400 gtg aac aaa ggc cat gaa atg agc ccg cag gcg ccg cgc cgc ccg ctg   1248
Val Asn Lys Gly His Glu Met Ser Pro Gln Ala Pro Arg Arg Pro Leu
                405                 410                 415 ccg cag gtg gcg acc ctg att gat cgc ttt gtg aaa ggc cgc ggc cag   1296
Pro Gln Val Ala Thr Leu Ile Asp Arg Phe Val Lys Gly Arg Gly Gln
            420                 425                 430 ctg gat aaa gat acc ctg gat acc ctg acc gcg ttt tat ccg ggc tat   1344
Leu Asp Lys Asp Thr Leu Asp Thr Leu Thr Ala Phe Tyr Pro Gly Tyr
        435                 440                 445 ctg tgc agc ctg agc ccg gaa gaa ctg agc agc gtg ccg ccg agc agc   1392
Leu Cys Ser Leu Ser Pro Glu Glu Leu Ser Ser Val Pro Pro Ser Ser
    450                 455                 460 att tgg gcg gtg cgc ccg cag gat ctg gat acc tgc gat ccg cgc cag   1440
Ile Trp Ala Val Arg Pro Gln Asp Leu Asp Thr Cys Asp Pro Arg Gln
465                 470                 475                 480 ctg gat gtg ctg tat ccg aaa gcg cgc ctg gcg ttt cag aac atg aac   1488
Leu Asp Val Leu Tyr Pro Lys Ala Arg Leu Ala Phe Gln Asn Met Asn
                485                 490                 495 ggc agc gaa tat ttt gtg aaa att cag agc ttt ctg ggc ggc gcg ccg   1536
Gly Ser Glu Tyr Phe Val Lys Ile Gln Ser Phe Leu Gly Gly Ala Pro
            500                 505                 510 acc gaa gat ctg aaa gcg ctg agc cag cag aac gtg agc atg gat ctg   1584
Thr Glu Asp Leu Lys Ala Leu Ser Gln Gln Asn Val Ser Met Asp Leu
        515                 520                 525 gcg acc ttt atg aaa ctg cgc acc gat gcg gtg ctg ccg ctg acc gtg   1632
Ala Thr Phe Met Lys Leu Arg Thr Asp Ala Val Leu Pro Leu Thr Val
    530                 535                 540 gcg gaa gtg cag aaa ctg ctg ggc ccg cat gtg gaa ggc ctg aaa gcg   1680
Ala Glu Val Gln Lys Leu Leu Gly Pro His Val Glu Gly Leu Lys Ala
545                 550                 555                 560 gaa gaa cgc cat cgc ccg gtg cgc gat tgg att ctg cgc cag cgc cag   1728
Glu Glu Arg His Arg Pro Val Arg Asp Trp Ile Leu Arg Gln Arg Gln
                565                 570                 575 gat gat ctg gat acc ctg ggc ctg ggc ctg cag ggc ggc att ccg aac   1776
Asp Asp Leu Asp Thr Leu Gly Leu Gly Leu Gln Gly Gly Ile Pro Asn
            580                 585                 590 ggc tat ctg gtg ctg gat ctg agc atg cag gaa gcg ctg agc ggc acc   1824
Gly Tyr Leu Val Leu Asp Leu Ser Met Gln Glu Ala Leu Ser Gly Thr
        595                 600                 605 ccg tgc ctg ctg ggc ccg ggc ccg gtg ctg acc gtg ctg gcg ctg ctg   1872
Pro Cys Leu Leu Gly Pro Gly Pro Val Leu Thr Val Leu Ala Leu Leu
    610                 615                 620
```

```
ctg gcg agc acc ctg gcg                                              1890
Leu Ala Ser Thr Leu Ala
625             630
```

<210> SEQ ID NO 150
<211> LENGTH: 630
<212> TYPE: PRT
<213> ORGANISM: Artificial Sequence
<220> FEATURE:
<223> OTHER INFORMATION: [CDS]:1..1890 from SEQ ID NO 149

<400> SEQUENCE: 150

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu

```
            340                 345                 350
Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
            370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Glu Leu Ser Ser Val Pro Pro Ser Ser
            450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
            595                 600                 605

Pro Cys Leu Leu Gly Pro Gly Pro Val Leu Thr Val Leu Ala Leu Leu
            610                 615                 620

Leu Ala Ser Thr Leu Ala
625                 630

<210> SEQ ID NO 151
<211> LENGTH: 1595
<212> TYPE: DNA
<213> ORGANISM: Artificial Sequence
<220> FEATURE:
<223> OTHER INFORMATION: human EGFRvIII

<400> SEQUENCE: 151
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg cagcgctcc tggcgctgct ggctgcgctc      300
tgcccggcga gtcgggctct ggaggaaaag aaagtttgcc aaggcacgag taacaagctc     360
acgcagttgg gcacttttga agatcatttt ctcagcctcc agaggatgtt caataactgt     420
```

```
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa agtgtgatc aagctgtcc caatgggagc    840 tgctggggtg caggagagga gaactgccag aaactgacca aatcatctg tgcccagcag    900 tgctccgggc gctgccgtgg caagtccccc agtgactgct gccacaacca gtgtgctgca    960
ggctgcacag gccccgggga gcgactgcgc tggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca caggtttgag ctgaattatc acatgaatat aaatgggaaa tcagtgtttt   1500
agagagagaa cttttcgaca tatttcctgt tcccttggaa taaaaacatt tcttctgaaa   1560
ttttaccgtt aaaaaaaaaa aaaaaaaaaa aaaaa                             1595
```

<210> SEQ ID NO 152  
<211> LENGTH: 405  
<212> TYPE: PRT  
<213> ORGANISM: Artificial Sequence  
<220> FEATURE:  
<223> OTHER INFORMATION: human EGFRvIII
<400> SEQUENCE: 152

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
```

```
                     145                 150                 155                 160
      Ser Ile Gln Trp Arg Asp Ile Val Ser Ser Asp Phe Leu Ser Asn Met
                      165                 170                 175

Ser Met Asp Phe Gln Asn His Leu Gly Ser Cys Gln Lys Cys Asp Pro
                      180                 185                 190

Ser Cys Pro Asn Gly Ser Cys Trp Gly Ala Gly Glu Asn Cys Gln
                  195                 200                 205

Lys Leu Thr Lys Ile Ile Cys Ala Gln Gln Cys Ser Gly Arg Cys Arg
          210                 215                 220

Gly Lys Ser Pro Ser Asp Cys Cys His Asn Gln Cys Ala Ala Gly Cys
      225                 230                 235                 240

Thr Gly Pro Arg Glu Ser Asp Cys Leu Val Cys Arg Lys Phe Arg Asp
                      245                 250                 255

Glu Ala Thr Cys Lys Asp Thr Cys Pro Pro Leu Met Leu Tyr Asn Pro
                  260                 265                 270

Thr Thr Tyr Gln Met Asp Val Asn Pro Glu Gly Lys Tyr Ser Phe Gly
                  275                 280                 285

Ala Thr Cys Val Lys Lys Cys Pro Arg Asn Tyr Val Val Thr Asp His
          290                 295                 300

Gly Ser Cys Val Arg Ala Cys Gly Ala Asp Ser Tyr Glu Met Glu Glu
      305                 310                 315                 320

Asp Gly Val Arg Lys Cys Lys Lys Cys Glu Gly Pro Cys Arg Lys Val
                      325                 330                 335

Cys Asn Gly Ile Gly Ile Gly Glu Phe Lys Asp Ser Leu Ser Ile Asn
                  340                 345                 350

Ala Thr Asn Ile Lys His Phe Lys Asn Cys Thr Ser Ile Ser Gly Asp
              355                 360                 365

Leu His Ile Leu Pro Val Ala Phe Arg Gly Asp Ser Phe Thr His Thr
          370                 375                 380

Pro Pro Leu Asp Pro Gln Glu Leu Asp Ile Leu Lys Thr Val Lys Glu
      385                 390                 395                 400

Ile Thr Gly Leu Ser
                      405

<210> SEQ ID NO 153
<211> LENGTH: 564
<212> TYPE: DNA
<213> ORGANISM: Artificial Sequence
<220> FEATURE:
<223> OTHER INFORMATION: human Cripto
<220> FEATURE:
<221> NAME/KEY: CDS
<222> LOCATION: 1..564
<223> OTHER INFORMATION: /transl_table=1

<400> SEQUENCE: 153 atg gat tgc cgc aaa atg gcg cgc ttt agc tat agc gtg att tgg att       48
Met Asp Cys Arg Lys Met Ala Arg Phe Ser Tyr Ser Val Ile Trp Ile
1               5                   10                  15 atg gcg att agc aaa gtg ttt gaa ctg ggc ctg gtg gcg ggc ctg ggc       96
Met Ala Ile Ser Lys Val Phe Glu Leu Gly Leu Val Ala Gly Leu Gly
            20                  25                  30 cat cag gaa ttt gcg cgc ccg agc cgc ggc tat ctg gcg ttt cgc gat      144
His Gln Glu Phe Ala Arg Pro Ser Arg Gly Tyr Leu Ala Phe Arg Asp
        35                  40                  45 gat agc att tgg ccg cag gaa gaa ccg gcg att cgc ccg cgc agc agc      192
Asp Ser Ile Trp Pro Gln Glu Glu Pro Ala Ile Arg Pro Arg Ser Ser
    50                  55                  60
```

-continued

```
cag cgc gtg ccg ccg atg ggc att cag cat agc aaa gaa ctg aac cgc      240
Gln Arg Val Pro Pro Met Gly Ile Gln His Ser Lys Glu Leu Asn Arg
 65                  70                  75                  80 acc tgc tgc ctg aac ggc ggc acc tgc atg ctg ggc agc ttt tgc gcg      288
Thr Cys Cys Leu Asn Gly Gly Thr Cys Met Leu Gly Ser Phe Cys Ala
                 85                  90                  95 tgc ccg ccg agc ttt tat ggc cgc aac tgc gaa cat gat gtg cgc aaa      336
Cys Pro Pro Ser Phe Tyr Gly Arg Asn Cys Glu His Asp Val Arg Lys
            100                 105                 110 gaa aac tgc ggc agc gtg ccg cat gat acc tgg ctg ccg aaa aaa tgc      384
Glu Asn Cys Gly Ser Val Pro His Asp Thr Trp Leu Pro Lys Lys Cys
        115                 120                 125 agc ctg tgc aaa tgc tgg cat ggc cag ctg cgc tgc ttt ccg cag gcg      432
Ser Leu Cys Lys Cys Trp His Gly Gln Leu Arg Cys Phe Pro Gln Ala
    130                 135                 140 ttt ctg ccg ggc tgc gat ggc ctg gtg atg gat gaa cat ctg gtg gcg      480
Phe Leu Pro Gly Cys Asp Gly Leu Val Met Asp Glu His Leu Val Ala
145                 150                 155                 160 agc cgc acc ccg gaa ctg ccg ccg agc gcg cgc acc acc acc ttt atg      528
Ser Arg Thr Pro Glu Leu Pro Pro Ser Ala Arg Thr Thr Thr Phe Met
                165                 170                 175 ctg gtg ggc att tgc ctg agc att cag agc tat tat                      564
Leu Val Gly Ile Cys Leu Ser Ile Gln Ser Tyr Tyr
            180                 185
```

<210> SEQ ID NO 154
<211> LENGTH: 188
<212> TYPE: PRT
<213> ORGANISM: Artificial Sequence
<220> FEATURE:
<223> OTHER INFORMATION: [CDS]:1..564 from SEQ ID NO 153

<400> SEQUENCE: 154

```
Met Asp Cys Arg Lys Met Ala Arg Phe Ser Tyr Ser Val Ile Trp Ile
 1               5                  10                  15

Met Ala Ile Ser Lys Val Phe Glu Leu Gly Leu Val Ala Gly Leu Gly
                20                  25                  30

His Gln Glu Phe Ala Arg Pro Ser Arg Gly Tyr Leu Ala Phe Arg Asp
            35                  40                  45

Asp Ser Ile Trp Pro Gln Glu Pro Ala Ile Arg Pro Arg Ser Ser
        50                  55                  60

Gln Arg Val Pro Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                 85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185
```

<210> SEQ ID NO 155
<211> LENGTH: 660
<212> TYPE: DNA
<213> ORGANISM: Artificial Sequence
<220> FEATURE:
<223> OTHER INFORMATION: human CD28
<220> FEATURE:
<221> NAME/KEY: CDS
<222> LOCATION: 1..660
<223> OTHER INFORMATION: /transl_table=1

<400> SEQUENCE: 155

| atg | ctg | cgc | ctg | ctg | ctg | gcg | ctg | aac | ctg | ttt | ccg | agc | att | cag | gtg | 48 |
|---|---|---|---|---|---|---|---|---|---|---|---|---|---|---|---|---|
| Met | Leu | Arg | Leu | Leu | Leu | Ala | Leu | Asn | Leu | Phe | Pro | Ser | Ile | Gln | Val | |
| 1 | | | | 5 | | | | | 10 | | | | | 15 | | |

| acc | ggc | aac | aaa | att | ctg | gtg | aaa | cag | agc | ccg | atg | ctg | gtg | gcg | tat | 96 |
|---|---|---|---|---|---|---|---|---|---|---|---|---|---|---|---|---|
| Thr | Gly | Asn | Lys | Ile | Leu | Val | Lys | Gln | Ser | Pro | Met | Leu | Val | Ala | Tyr | |
| | | | 20 | | | | | 25 | | | | | 30 | | | |

| gat | aac | gcg | gtg | aac | ctg | agc | tgc | aaa | tat | agc | tat | aac | ctg | ttt | agc | 144 |
|---|---|---|---|---|---|---|---|---|---|---|---|---|---|---|---|---|
| Asp | Asn | Ala | Val | Asn | Leu | Ser | Cys | Lys | Tyr | Ser | Tyr | Asn | Leu | Phe | Ser | |
| | 35 | | | | | 40 | | | | | 45 | | | | | |

| cgc | gaa | ttt | cgc | gcg | agc | ctg | cat | aaa | ggc | ctg | gat | agc | gcg | gtg | gaa | 192 |
|---|---|---|---|---|---|---|---|---|---|---|---|---|---|---|---|---|
| Arg | Glu | Phe | Arg | Ala | Ser | Leu | His | Lys | Gly | Leu | Asp | Ser | Ala | Val | Glu | |
| 50 | | | | | 55 | | | | | 60 | | | | | | |

| gtg | tgc | gtg | gtg | tat | ggc | aac | tat | agc | cag | cag | ctg | cag | gtg | tat | agc | 240 |
|---|---|---|---|---|---|---|---|---|---|---|---|---|---|---|---|---|
| Val | Cys | Val | Val | Tyr | Gly | Asn | Tyr | Ser | Gln | Gln | Leu | Gln | Val | Tyr | Ser | |
| 65 | | | | | 70 | | | | | 75 | | | | | 80 | |

| aaa | acc | ggc | ttt | aac | tgc | gat | ggc | aaa | ctg | ggc | aac | gaa | agc | gtg | acc | 288 |
|---|---|---|---|---|---|---|---|---|---|---|---|---|---|---|---|---|
| Lys | Thr | Gly | Phe | Asn | Cys | Asp | Gly | Lys | Leu | Gly | Asn | Glu | Ser | Val | Thr | |
| | | | | 85 | | | | | 90 | | | | | 95 | | |

| ttt | tat | ctg | cag | aac | ctg | tat | gtg | aac | cag | acc | gat | att | tat | ttt | tgc | 336 |
|---|---|---|---|---|---|---|---|---|---|---|---|---|---|---|---|---|
| Phe | Tyr | Leu | Gln | Asn | Leu | Tyr | Val | Asn | Gln | Thr | Asp | Ile | Tyr | Phe | Cys | |
| | | | 100 | | | | | 105 | | | | | 110 | | | |

| aaa | att | gaa | gtg | atg | tat | ccg | ccg | ccg | tat | ctg | gat | aac | gaa | aaa | agc | 384 |
|---|---|---|---|---|---|---|---|---|---|---|---|---|---|---|---|---|
| Lys | Ile | Glu | Val | Met | Tyr | Pro | Pro | Pro | Tyr | Leu | Asp | Asn | Glu | Lys | Ser | |
| | | 115 | | | | | 120 | | | | | 125 | | | | |

| aac | ggc | acc | att | att | cat | gtg | aaa | ggc | aaa | cat | ctg | tgc | ccg | agc | ccg | 432 |
|---|---|---|---|---|---|---|---|---|---|---|---|---|---|---|---|---|
| Asn | Gly | Thr | Ile | Ile | His | Val | Lys | Gly | Lys | His | Leu | Cys | Pro | Ser | Pro | |
| | 130 | | | | | 135 | | | | | 140 | | | | | |

| ctg | ttt | ccg | ggc | ccg | agc | aaa | ccg | ttt | tgg | gtg | ctg | gtg | gtg | gtg | ggc | 480 |
|---|---|---|---|---|---|---|---|---|---|---|---|---|---|---|---|---|
| Leu | Phe | Pro | Gly | Pro | Ser | Lys | Pro | Phe | Trp | Val | Leu | Val | Val | Val | Gly | |
| 145 | | | | | 150 | | | | | 155 | | | | | 160 | |

| ggc | gtg | ctg | gcg | tgc | tat | agc | ctg | ctg | gtg | acc | gtg | gcg | ttt | att | att | 528 |
|---|---|---|---|---|---|---|---|---|---|---|---|---|---|---|---|---|
| Gly | Val | Leu | Ala | Cys | Tyr | Ser | Leu | Leu | Val | Thr | Val | Ala | Phe | Ile | Ile | |
| | | | | 165 | | | | | 170 | | | | | 175 | | |

| ttt | tgg | gtg | cgc | agc | aaa | cgc | agc | cgc | ctg | ctg | cat | agc | gat | tat | atg | 576 |
|---|---|---|---|---|---|---|---|---|---|---|---|---|---|---|---|---|
| Phe | Trp | Val | Arg | Ser | Lys | Arg | Ser | Arg | Leu | Leu | His | Ser | Asp | Tyr | Met | |
| | | | 180 | | | | | 185 | | | | | 190 | | | |

| aac | atg | acc | ccg | cgc | cgc | ccg | ggc | ccg | acc | cgc | aaa | cat | tat | cag | ccg | 624 |
|---|---|---|---|---|---|---|---|---|---|---|---|---|---|---|---|---|
| Asn | Met | Thr | Pro | Arg | Arg | Pro | Gly | Pro | Thr | Arg | Lys | His | Tyr | Gln | Pro | |
| | | 195 | | | | | 200 | | | | | 205 | | | | |

| tat | gcg | ccg | ccg | cgc | gat | ttt | gcg | gcg | tat | cgc | agc | | | | | 660 |
|---|---|---|---|---|---|---|---|---|---|---|---|---|---|---|---|---|
| Tyr | Ala | Pro | Pro | Arg | Asp | Phe | Ala | Ala | Tyr | Arg | Ser | | | | | |
| | 210 | | | | | 215 | | | | | 220 | | | | | |

<210> SEQ ID NO 156
<211> LENGTH: 220
<212> TYPE: PRT
<213> ORGANISM: Artificial Sequence
<220> FEATURE:
<223> OTHER INFORMATION: [CDS]:1..660 from SEQ ID NO 155

<400> SEQUENCE: 156

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 157
<211> LENGTH: 654
<212> TYPE: DNA
<213> ORGANISM: Artificial Sequence
<220> FEATURE:
<223> OTHER INFORMATION: murine CD28
<220> FEATURE:
<221> NAME/KEY: CDS
<222> LOCATION: 1..654
<223> OTHER INFORMATION: /transl_table=1

<400> SEQUENCE: 157 atg acc ctg cgc ctg ctg ttt ctg gcg ctg aac ttt ttt agc gtg cag      48
Met Thr Leu Arg Leu Leu Phe Leu Ala Leu Asn Phe Phe Ser Val Gln
1               5                   10                  15 gtg acc gaa aac aaa att ctg gtg aaa cag agc ccg ctg ctg gtg gtg      96
Val Thr Glu Asn Lys Ile Leu Val Lys Gln Ser Pro Leu Leu Val Val
            20                  25                  30 gat agc aac gaa gtg agc ctg agc tgc cgc tat agc tat aac ctg ctg     144
Asp Ser Asn Glu Val Ser Leu Ser Cys Arg Tyr Ser Tyr Asn Leu Leu
        35                  40                  45 gcg aaa gaa ttt cgc gcg agc ctg tat aaa ggc gtg aac agc gat gtg     192
Ala Lys Glu Phe Arg Ala Ser Leu Tyr Lys Gly Val Asn Ser Asp Val
    50                  55                  60 gaa gtg tgc gtg ggc aac ggc aac ttt acc tat cag ccg cag ttt cgc     240
Glu Val Cys Val Gly Asn Gly Asn Phe Thr Tyr Gln Pro Gln Phe Arg
65                  70                  75                  80 agc aac gcg gaa ttt aac tgc gat ggc gat ttt gat aac gaa acc gtg     288
Ser Asn Ala Glu Phe Asn Cys Asp Gly Asp Phe Asp Asn Glu Thr Val
```

```
acc ttt cgc ctg tgg aac ctg cat gtg aac cat acc gat att tat ttt    336
Thr Phe Arg Leu Trp Asn Leu His Val Asn His Thr Asp Ile Tyr Phe
            100                 105                 110 tgc aaa att gaa ttt atg tat ccg ccg ccg tat ctg gat aac gaa cgc    384
Cys Lys Ile Glu Phe Met Tyr Pro Pro Pro Tyr Leu Asp Asn Glu Arg
        115                 120                 125 agc aac ggc acc att att cat att aaa gaa aaa cat ctg tgc cat acc    432
Ser Asn Gly Thr Ile Ile His Ile Lys Glu Lys His Leu Cys His Thr
130                 135                 140 cag agc agc ccg aaa ctg ttt tgg gcg ctg gtg gtg gtg gcg ggc gtg    480
Gln Ser Ser Pro Lys Leu Phe Trp Ala Leu Val Val Val Ala Gly Val
145                 150                 155                 160 ctg ttt tgc tat ggc ctg ctg gtg acc gtg gcg ctg tgc gtg att tgg    528
Leu Phe Cys Tyr Gly Leu Leu Val Thr Val Ala Leu Cys Val Ile Trp
                165                 170                 175 acc aac agc cgc cgc aac cgc ctg ctg cag agc gat tat atg aac atg    576
Thr Asn Ser Arg Arg Asn Arg Leu Leu Gln Ser Asp Tyr Met Asn Met
            180                 185                 190 acc ccg cgc cgc ccg ggc ctg acc cgc aaa ccg tat cag ccg tat gcg    624
Thr Pro Arg Arg Pro Gly Leu Thr Arg Lys Pro Tyr Gln Pro Tyr Ala
        195                 200                 205 ccg gcg cgc gat ttt gcg gcg tat cgc ccg                            654
Pro Ala Arg Asp Phe Ala Ala Tyr Arg Pro
210                 215

<210> SEQ ID NO 158
<211> LENGTH: 218
<212> TYPE: PRT
<213> ORGANISM: Artificial Sequence
<220> FEATURE:
<223> OTHER INFORMATION: [CDS]:1..654 from SEQ ID NO 157

<400> SEQUENCE: 158

Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190
```

```
Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215

<210> SEQ ID NO 159
<211> LENGTH: 765
<212> TYPE: DNA
<213> ORGANISM: Artificial Sequence
<220> FEATURE:
<223> OTHER INFORMATION: human CD137
<220> FEATURE:
<221> NAME/KEY: CDS
<222> LOCATION: 1..765
<223> OTHER INFORMATION: /transl_table=1

<400> SEQUENCE: 159 atg ggc aac agc tgc tat aac att gtg gcg acc ctg ctg ctg gtg ctg        48
Met Gly Asn Ser Cys Tyr Asn Ile Val Ala Thr Leu Leu Leu Val Leu
1               5                   10                  15 aac ttt gaa cgc acc cgc agc ctg cag gat ccg tgc agc aac tgc ccg        96
Asn Phe Glu Arg Thr Arg Ser Leu Gln Asp Pro Cys Ser Asn Cys Pro
            20                  25                  30 gcg ggc acc ttt tgc gat aac aac cgc aac cag att tgc agc ccg tgc       144
Ala Gly Thr Phe Cys Asp Asn Asn Arg Asn Gln Ile Cys Ser Pro Cys
        35                  40                  45 ccg ccg aac agc ttt agc agc gcg ggc ggc cag cgc acc tgc gat att       192
Pro Pro Asn Ser Phe Ser Ser Ala Gly Gly Gln Arg Thr Cys Asp Ile
    50                  55                  60 tgc cgc cag tgc aaa ggc gtg ttt cgc acc cgc aaa gaa tgc agc agc       240
Cys Arg Gln Cys Lys Gly Val Phe Arg Thr Arg Lys Glu Cys Ser Ser
65                  70                  75                  80 acc agc aac gcg gaa tgc gat tgc acc ccg ggc ttt cat tgc ctg ggc       288
Thr Ser Asn Ala Glu Cys Asp Cys Thr Pro Gly Phe His Cys Leu Gly
                85                  90                  95 gcg ggc tgc agc atg tgc gaa cag gat tgc aaa cag ggc cag gaa ctg       336
Ala Gly Cys Ser Met Cys Glu Gln Asp Cys Lys Gln Gly Gln Glu Leu
            100                 105                 110 acc aaa aaa ggc tgc aaa gat tgc tgc ttt ggc acc ttt aac gat cag       384
Thr Lys Lys Gly Cys Lys Asp Cys Cys Phe Gly Thr Phe Asn Asp Gln
        115                 120                 125 aaa cgc ggc att tgc cgc ccg tgg acc aac tgc agc ctg gat ggc aaa       432
Lys Arg Gly Ile Cys Arg Pro Trp Thr Asn Cys Ser Leu Asp Gly Lys
    130                 135                 140 agc gtg ctg gtg aac ggc acc aaa gaa cgc gat gtg gtg tgc ggc ccg       480
Ser Val Leu Val Asn Gly Thr Lys Glu Arg Asp Val Val Cys Gly Pro
145                 150                 155                 160 agc ccg gcg gat ctg agc ccg ggc gcg agc agc gtg acc ccg ccg gcg       528
Ser Pro Ala Asp Leu Ser Pro Gly Ala Ser Ser Val Thr Pro Pro Ala
                165                 170                 175 ccg gcg cgc gaa ccg ggc cat agc ccg cag att att agc ttt ttt ctg       576
Pro Ala Arg Glu Pro Gly His Ser Pro Gln Ile Ile Ser Phe Phe Leu
            180                 185                 190 gcg ctg acc agc acc gcg ctg ctg ttt ctg ctg ttt ttt ctg acc ctg       624
Ala Leu Thr Ser Thr Ala Leu Leu Phe Leu Leu Phe Phe Leu Thr Leu
        195                 200                 205 cgc ttt agc gtg gtg aaa cgc ggc cgc aaa aaa ctg ctg tat att ttt       672
Arg Phe Ser Val Val Lys Arg Gly Arg Lys Lys Leu Leu Tyr Ile Phe
    210                 215                 220 aaa cag ccg ttt atg cgc ccg gtg cag acc acc cag gaa gaa gat ggc       720
Lys Gln Pro Phe Met Arg Pro Val Gln Thr Thr Gln Glu Glu Asp Gly
```

```
                225                 230                 235                 240
tgc agc tgc cgc ttt ccg gaa gaa gaa ggc ggc tgc gaa ctg                   765
Cys Ser Cys Arg Phe Pro Glu Glu Glu Gly Gly Cys Glu Leu
                245                 250                 255
```

<210> SEQ ID NO 160
<211> LENGTH: 255
<212> TYPE: PRT
<213> ORGANISM: Artificial Sequence
<220> FEATURE:
<223> OTHER INFORMATION: [CDS]:1..765 from SEQ ID NO 159

<400> SEQUENCE: 160

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255
```

<210> SEQ ID NO 161
<211> LENGTH: 768
<212> TYPE: DNA
<213> ORGANISM: Artificial Sequence
<220> FEATURE:
<223> OTHER INFORMATION: murine CD137
<220> FEATURE:
<221> NAME/KEY: CDS
<222> LOCATION: 1..768
<223> OTHER INFORMATION: /transl_table=1

<400> SEQUENCE: 161

```
atg ggc aac aac tgc tat aac gtg gtg gtg att gtg ctg ctg ctg gtg     48
```

```
Met Gly Asn Asn Cys Tyr Asn Val Val Ile Val Leu Leu Val
1               5                   10                  15 ggc tgc gaa aaa gtg ggc gcg gtg cag aac agc tgc gat aac tgc cag        96
Gly Cys Glu Lys Val Gly Ala Val Gln Asn Ser Cys Asp Asn Cys Gln
            20                  25                  30 ccg ggc acc ttt tgc cgc aaa tat aac ccg gtg tgc aaa agc tgc ccg       144
Pro Gly Thr Phe Cys Arg Lys Tyr Asn Pro Val Cys Lys Ser Cys Pro
        35                  40                  45 ccg agc acc ttt agc agc att ggc ggc cag ccg aac tgc aac att tgc       192
Pro Ser Thr Phe Ser Ser Ile Gly Gly Gln Pro Asn Cys Asn Ile Cys
    50                  55                  60 cgc gtg tgc gcg ggc tat ttt cgc ttt aaa aaa ttt tgc agc agc acc       240
Arg Val Cys Ala Gly Tyr Phe Arg Phe Lys Lys Phe Cys Ser Ser Thr
65                  70                  75                  80 cat aac gcg gaa tgc gaa tgc att gaa ggc ttt cat tgc ctg ggc ccg       288
His Asn Ala Glu Cys Glu Cys Ile Glu Gly Phe His Cys Leu Gly Pro
                85                  90                  95 cag tgc acc cgc tgc gaa aaa gat tgc cgc ccg ggc cag gaa ctg acc       336
Gln Cys Thr Arg Cys Glu Lys Asp Cys Arg Pro Gly Gln Glu Leu Thr
            100                 105                 110 aaa cag ggc tgc aaa acc tgc agc ctg ggc acc ttt aac gat cag aac       384
Lys Gln Gly Cys Lys Thr Cys Ser Leu Gly Thr Phe Asn Asp Gln Asn
        115                 120                 125 ggc acc ggc gtg tgc cgc ccg tgg acc aac tgc agc ctg gat ggc cgc       432
Gly Thr Gly Val Cys Arg Pro Trp Thr Asn Cys Ser Leu Asp Gly Arg
    130                 135                 140 agc gtg ctg aaa acc ggc acc acc gaa aaa gat gtg gtg tgc ggc ccg       480
Ser Val Leu Lys Thr Gly Thr Thr Glu Lys Asp Val Val Cys Gly Pro
145                 150                 155                 160 ccg gtg gtg agc ttt agc ccg agc acc acc att agc gtg acc ccg gaa       528
Pro Val Val Ser Phe Ser Pro Ser Thr Thr Ile Ser Val Thr Pro Glu
                165                 170                 175 ggc ggc ccg ggc ggc cat agc ctg cag gtg ctg acc ctg ttt ctg gcg       576
Gly Gly Pro Gly Gly His Ser Leu Gln Val Leu Thr Leu Phe Leu Ala
            180                 185                 190 ctg acc agc gcg ctg ctg ctg gcg ctg att ttt att acc ctg ctg ttt       624
Leu Thr Ser Ala Leu Leu Leu Ala Leu Ile Phe Ile Thr Leu Leu Phe
        195                 200                 205 agc gtg ctg aaa tgg att cgc aaa aaa ttt ccg cat att ttt aaa cag       672
Ser Val Leu Lys Trp Ile Arg Lys Lys Phe Pro His Ile Phe Lys Gln
    210                 215                 220 ccg ttt aaa aaa acc acc ggc gcg gcg cag gaa gaa gat gcg tgc agc       720
Pro Phe Lys Lys Thr Thr Gly Ala Ala Gln Glu Glu Asp Ala Cys Ser
225                 230                 235                 240 tgc cgc tgc ccg cag gaa gaa gaa ggc ggc ggc ggc ggc tat gaa ctg       768
Cys Arg Cys Pro Gln Glu Glu Glu Gly Gly Gly Gly Gly Tyr Glu Leu
                245                 250                 255

<210> SEQ ID NO 162
<211> LENGTH: 256
<212> TYPE: PRT
<213> ORGANISM: Artificial Sequence
<220> FEATURE:
<223> OTHER INFORMATION: [CDS]:1..768 from SEQ ID NO 161

<400> SEQUENCE: 162

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30
```

```
Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
 50                  55                  60

Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255
```

<210> SEQ ID NO 163
<211> LENGTH: 831
<212> TYPE: DNA
<213> ORGANISM: Artificial Sequence
<220> FEATURE:
<223> OTHER INFORMATION: human OX40
<220> FEATURE:
<221> NAME/KEY: CDS
<222> LOCATION: 1..831
<223> OTHER INFORMATION: /transl_table=1

<400> SEQUENCE: 163

```
atg tgc gtg ggc gcg cgc cgc ctg ggc cgc ggc ccg tgc gcg gcg ctg      48
Met Cys Val Gly Ala Arg Arg Leu Gly Arg Gly Pro Cys Ala Ala Leu
 1               5                  10                  15 ctg ctg ctg ggc ctg ggc ctg agc acc gtg acc ggc ctg cat tgc gtg      96
Leu Leu Leu Gly Leu Gly Leu Ser Thr Val Thr Gly Leu His Cys Val
             20                  25                  30 ggc gat acc tat ccg agc aac gat cgc tgc tgc cat gaa tgc cgc ccg     144
Gly Asp Thr Tyr Pro Ser Asn Asp Arg Cys Cys His Glu Cys Arg Pro
         35                  40                  45 ggc aac ggc atg gtg agc cgc tgc agc cgc agc cag aac acc gtg tgc     192
Gly Asn Gly Met Val Ser Arg Cys Ser Arg Ser Gln Asn Thr Val Cys
 50                  55                  60 cgc ccg tgc ggc ccg ggc ttt tat aac gat gtg gtg agc agc aaa ccg     240
Arg Pro Cys Gly Pro Gly Phe Tyr Asn Asp Val Val Ser Ser Lys Pro
 65                  70                  75                  80 tgc aaa ccg tgc acc tgg tgc aac ctg cgc agc ggc agc gaa cgc aaa     288
Cys Lys Pro Cys Thr Trp Cys Asn Leu Arg Ser Gly Ser Glu Arg Lys
                 85                  90                  95
```

```
cag ctg tgc acc gcg acc cag gat acc gtg tgc cgc tgc cgc gcg ggc    336
Gln Leu Cys Thr Ala Thr Gln Asp Thr Val Cys Arg Cys Arg Ala Gly
            100                 105                 110 acc cag ccg ctg gat agc tat aaa ccg ggc gtg gat tgc gcg ccg tgc    384
Thr Gln Pro Leu Asp Ser Tyr Lys Pro Gly Val Asp Cys Ala Pro Cys
        115                 120                 125 ccg ccg ggc cat ttt agc ccg ggc gat aac cag gcg tgc aaa ccg tgg    432
Pro Pro Gly His Phe Ser Pro Gly Asp Asn Gln Ala Cys Lys Pro Trp
130                 135                 140 acc aac tgc acc ctg gcg ggc aaa cat acc ctg cag ccg gcg agc aac    480
Thr Asn Cys Thr Leu Ala Gly Lys His Thr Leu Gln Pro Ala Ser Asn
145                 150                 155                 160 agc agc gat gcg att tgc gaa gat cgc gat ccg ccg gcg acc cag ccg    528
Ser Ser Asp Ala Ile Cys Glu Asp Arg Asp Pro Pro Ala Thr Gln Pro
                165                 170                 175 cag gaa acc cag ggc ccg ccg gcg cgc ccg att acc gtg cag ccg acc    576
Gln Glu Thr Gln Gly Pro Pro Ala Arg Pro Ile Thr Val Gln Pro Thr
            180                 185                 190 gaa gcg tgg ccg cgc acc agc cag ggc ccg agc acc cgc ccg gtg gaa    624
Glu Ala Trp Pro Arg Thr Ser Gln Gly Pro Ser Thr Arg Pro Val Glu
        195                 200                 205 gtg ccg ggc ggc cgc gcg gtg gcg gcg att ctg ggc ctg ggc ctg gtg    672
Val Pro Gly Gly Arg Ala Val Ala Ala Ile Leu Gly Leu Gly Leu Val
210                 215                 220 ctg ggc ctg ctg ggc ccg ctg gcg att ctg ctg gcg ctg tat ctg ctg    720
Leu Gly Leu Leu Gly Pro Leu Ala Ile Leu Leu Ala Leu Tyr Leu Leu
225                 230                 235                 240 cgc cgc gat cag cgc ctg ccg ccg gat gcg cat aaa ccg ccg ggc ggc    768
Arg Arg Asp Gln Arg Leu Pro Pro Asp Ala His Lys Pro Pro Gly Gly
                245                 250                 255 ggc agc ttt cgc acc ccg att cag gaa gaa cag gcg gat gcg cat agc    816
Gly Ser Phe Arg Thr Pro Ile Gln Glu Glu Gln Ala Asp Ala His Ser
            260                 265                 270 acc ctg gcg aaa att                                                831
Thr Leu Ala Lys Ile
        275

<210> SEQ ID NO 164
<211> LENGTH: 277
<212> TYPE: PRT
<213> ORGANISM: Artificial Sequence
<220> FEATURE:
<223> OTHER INFORMATION: [CDS]:1..831 from SEQ ID NO 163

<400> SEQUENCE: 164

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110
```

```
Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
            210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 165
<211> LENGTH: 816
<212> TYPE: DNA
<213> ORGANISM: Artificial Sequence
<220> FEATURE:
<223> OTHER INFORMATION: murine OX40
<220> FEATURE:
<221> NAME/KEY: CDS
<222> LOCATION: 1..816
<223> OTHER INFORMATION: /transl_table=1

<400> SEQUENCE: 165 atg tat gtg tgg gtg cag cag ccg acc gcg ctg ctg ctg ctg gcg ctg     48
Met Tyr Val Trp Val Gln Gln Pro Thr Ala Leu Leu Leu Leu Ala Leu
1               5                   10                  15 acc ctg ggc gtg acc gcg cgc cgc ctg aac tgc gtg aaa cat acc tat     96
Thr Leu Gly Val Thr Ala Arg Arg Leu Asn Cys Val Lys His Thr Tyr
            20                  25                  30 ccg agc ggc cat aaa tgc tgc cgc gaa tgc cag ccg ggc cat ggc atg    144
Pro Ser Gly His Lys Cys Cys Arg Glu Cys Gln Pro Gly His Gly Met
        35                  40                  45 gtg agc cgc tgc gat cat acc cgc gat acc ctg tgc cat ccg tgc gaa    192
Val Ser Arg Cys Asp His Thr Arg Asp Thr Leu Cys His Pro Cys Glu
    50                  55                  60 acc ggc ttt tat aac gaa gcg gtg aac tat gat acc tgc aaa cag tgc    240
Thr Gly Phe Tyr Asn Glu Ala Val Asn Tyr Asp Thr Cys Lys Gln Cys
65                  70                  75                  80 acc cag tgc aac cat cgc agc ggc agc gaa ctg aaa cag aac tgc acc    288
Thr Gln Cys Asn His Arg Ser Gly Ser Glu Leu Lys Gln Asn Cys Thr
                85                  90                  95 ccg acc cag gat acc gtg tgc cgc tgc cgc ccg ggc acc cag ccg cgc    336
Pro Thr Gln Asp Thr Val Cys Arg Cys Arg Pro Gly Thr Gln Pro Arg
            100                 105                 110 cag gat agc ggc tat aaa ctg ggc gtg gat tgc gtg ccg tgc ccg ccg    384
Gln Asp Ser Gly Tyr Lys Leu Gly Val Asp Cys Val Pro Cys Pro Pro
        115                 120                 125
```

```
ggc cat ttt agc ccg ggc aac aac cag gcg tgc aaa ccg tgg acc aac       432
Gly His Phe Ser Pro Gly Asn Asn Gln Ala Cys Lys Pro Trp Thr Asn
            130                 135                 140 tgc acc ctg agc ggc aaa cag acc cgc cat ccg gcg agc gat agc ctg       480
Cys Thr Leu Ser Gly Lys Gln Thr Arg His Pro Ala Ser Asp Ser Leu
145                 150                 155                 160 gat gcg gtg tgc gaa gat cgc agc ctg ctg gcg acc ctg ctg tgg gaa       528
Asp Ala Val Cys Glu Asp Arg Ser Leu Leu Ala Thr Leu Leu Trp Glu
                165                 170                 175 acc cag cgc ccg acc ttt cgc ccg acc acc gtg cag agc acc acc gtg       576
Thr Gln Arg Pro Thr Phe Arg Pro Thr Thr Val Gln Ser Thr Thr Val
            180                 185                 190 tgg ccg cgc acc agc gaa ctg ccg agc ccg acc ctg gtg acc ccg           624
Trp Pro Arg Thr Ser Glu Leu Pro Ser Pro Thr Leu Val Thr Pro
            195                 200                 205 gaa ggc ccg gcg ttt gcg gtg ctg ctg ggc ctg ggc ctg ggc ctg ctg       672
Glu Gly Pro Ala Phe Ala Val Leu Leu Gly Leu Gly Leu Gly Leu Leu
210                 215                 220 gcg ccg ctg acc gtg ctg ctg gcg ctg tat ctg ctg cgc aaa gcg tgg       720
Ala Pro Leu Thr Val Leu Leu Ala Leu Tyr Leu Leu Arg Lys Ala Trp
225                 230                 235                 240 cgc ctg ccg aac acc ccg aaa ccg tgc tgg ggc aac agc ttt cgc acc       768
Arg Leu Pro Asn Thr Pro Lys Pro Cys Trp Gly Asn Ser Phe Arg Thr
                245                 250                 255 ccg att cag gaa gaa cat acc gat gcg cat ttt acc ctg gcg aaa att       816
Pro Ile Gln Glu Glu His Thr Asp Ala His Phe Thr Leu Ala Lys Ile
            260                 265                 270

<210> SEQ ID NO 166
<211> LENGTH: 272
<212> TYPE: PRT
<213> ORGANISM: Artificial Sequence
<220> FEATURE:
<223> OTHER INFORMATION: [CDS]:1..816 from SEQ ID NO 165

<400> SEQUENCE: 166

Met Tyr Val Trp Val Gln Gln Pro Thr Ala Leu Leu Leu Ala Leu
1               5                   10                  15

Thr Leu Gly Val Thr Ala Arg Arg Leu Asn Cys Val Lys His Thr Tyr
                20                  25                  30

Pro Ser Gly His Lys Cys Cys Arg Glu Cys Gln Pro Gly His Gly Met
            35                  40                  45

Val Ser Arg Cys Asp His Thr Arg Asp Thr Leu Cys His Pro Cys Glu
        50                  55                  60

Thr Gly Phe Tyr Asn Glu Ala Val Asn Tyr Asp Thr Cys Lys Gln Cys
65              70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175
```

```
Thr Gln Arg Pro Thr Phe Arg Pro Thr Thr Val Gln Ser Thr Thr Val
            180                 185                 190

Trp Pro Arg Thr Ser Glu Leu Pro Ser Pro Thr Leu Val Thr Pro
        195                 200                 205

Glu Gly Pro Ala Phe Ala Val Leu Leu Gly Leu Gly Leu Gly Leu Leu
210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 167
<211> LENGTH: 597
<212> TYPE: DNA
<213> ORGANISM: Artificial Sequence
<220> FEATURE:
<223> OTHER INFORMATION: human ICOS
<220> FEATURE:
<221> NAME/KEY: CDS
<222> LOCATION: 1..597
<223> OTHER INFORMATION: /transl_table=1

<400> SEQUENCE: 167 atg aaa agc ggc ctg tgg tat ttt ttt ctg ttt tgc ctg cgc att aaa      48
Met Lys Ser Gly Leu Trp Tyr Phe Phe Leu Phe Cys Leu Arg Ile Lys
1               5                   10                  15 gtg ctg acc ggc gaa att aac ggc agc gcg aac tat gaa atg ttt att      96
Val Leu Thr Gly Glu Ile Asn Gly Ser Ala Asn Tyr Glu Met Phe Ile
            20                  25                  30 ttt cat aac ggc ggt gtg cag att ctg tgc aaa tat ccg gat att gtg     144
Phe His Asn Gly Gly Val Gln Ile Leu Cys Lys Tyr Pro Asp Ile Val
        35                  40                  45 cag cag ttt aaa atg cag ctg ctg aaa ggc ggc cag att ctg tgc gat     192
Gln Gln Phe Lys Met Gln Leu Leu Lys Gly Gly Gln Ile Leu Cys Asp
    50                  55                  60 ctg acc aaa acc aaa ggc agc ggc aac acc gtg agc att aaa agc ctg     240
Leu Thr Lys Thr Lys Gly Ser Gly Asn Thr Val Ser Ile Lys Ser Leu
65                  70                  75                  80 aaa ttt tgc cat agc cag ctg agc aac aac agc gtg agc ttt ttt ctg     288
Lys Phe Cys His Ser Gln Leu Ser Asn Asn Ser Val Ser Phe Phe Leu
                85                  90                  95 tat aac ctg gat cat agc cat gcg aac tat tat ttt tgc aac ctg agc     336
Tyr Asn Leu Asp His Ser His Ala Asn Tyr Tyr Phe Cys Asn Leu Ser
            100                 105                 110 att ttt gat ccg ccg ccg ttt aaa gtg acc ctg acc ggc ggt tat ctg     384
Ile Phe Asp Pro Pro Pro Phe Lys Val Thr Leu Thr Gly Gly Tyr Leu
        115                 120                 125 cat att tat gaa agc cag ctg tgc tgc cag ctg aaa ttt tgg ctg ccg     432
His Ile Tyr Glu Ser Gln Leu Cys Cys Gln Leu Lys Phe Trp Leu Pro
    130                 135                 140 att ggc tgc gcg gcg ttt gtg gtg gtg tgc att ctg ggc tgc att ctg     480
Ile Gly Cys Ala Ala Phe Val Val Val Cys Ile Leu Gly Cys Ile Leu
145                 150                 155                 160 att tgc tgg ctg acc aaa aaa aaa tat agc agc agc gtg cat gat ccg     528
Ile Cys Trp Leu Thr Lys Lys Lys Tyr Ser Ser Ser Val His Asp Pro
                165                 170                 175 aac ggc gaa tat atg ttt atg cgc gcg gtg aac acc gcg aaa aaa agc     576
Asn Gly Glu Tyr Met Phe Met Arg Ala Val Asn Thr Ala Lys Lys Ser
```

```
                    180                 185                 190
cgc ctg acc gat gtg acc ctg                                              597
Arg Leu Thr Asp Val Thr Leu
        195
```

<210> SEQ ID NO 168
<211> LENGTH: 199
<212> TYPE: PRT
<213> ORGANISM: Artificial Sequence
<220> FEATURE:
<223> OTHER INFORMATION: [CDS]:1..597 from SEQ ID NO 167

<400> SEQUENCE: 168

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195
```

<210> SEQ ID NO 169
<211> LENGTH: 600
<212> TYPE: DNA
<213> ORGANISM: Artificial Sequence
<220> FEATURE:
<223> OTHER INFORMATION: murine ICOS
<220> FEATURE:
<221> NAME/KEY: CDS
<222> LOCATION: 1..600
<223> OTHER INFORMATION: /transl_table=1

<400> SEQUENCE: 169

```
atg aaa ccg tat ttt tgc cgc gtg ttt gtg ttt tgc ttt ctg att cgc       48
Met Lys Pro Tyr Phe Cys Arg Val Phe Val Phe Cys Phe Leu Ile Arg
1               5                   10                  15 ctg ctg acc ggc gaa att aac ggc agc gcg gat cat cgc atg ttt agc       96
Leu Leu Thr Gly Glu Ile Asn Gly Ser Ala Asp His Arg Met Phe Ser
            20                  25                  30 ttt cat aac ggc ggc gtg cag att agc tgc aaa tat ccg gaa acc gtg      144
Phe His Asn Gly Gly Val Gln Ile Ser Cys Lys Tyr Pro Glu Thr Val
```

```
cag cag ctg aaa atg cgc ctg ttt cgc gaa cgc gaa gtg ctg tgc gaa    192
Gln Gln Leu Lys Met Arg Leu Phe Arg Glu Arg Glu Val Leu Cys Glu
        50                  55                  60 ctg acc aaa acc aaa ggc agc ggc aac gcg gtg agc att aaa aac ccg    240
Leu Thr Lys Thr Lys Gly Ser Gly Asn Ala Val Ser Ile Lys Asn Pro
 65                  70                  75                  80 atg ctg tgc ctg tat cat ctg agc aac aac agc gtg agc ttt ttt ctg    288
Met Leu Cys Leu Tyr His Leu Ser Asn Asn Ser Val Ser Phe Phe Leu
                 85                  90                  95 aac aac ccg gat agc agc cag ggc agc tat tat ttt tgc agc ctg agc    336
Asn Asn Pro Asp Ser Ser Gln Gly Ser Tyr Tyr Phe Cys Ser Leu Ser
            100                 105                 110 att ttt gat ccg ccg ccg ttt cag gaa cgc aac ctg agc ggc ggc tat    384
Ile Phe Asp Pro Pro Pro Phe Gln Glu Arg Asn Leu Ser Gly Gly Tyr
            115                 120                 125 ctg cat att tat gaa agc cag ctg tgc tgc cag ctg aaa ctg tgg ctg    432
Leu His Ile Tyr Glu Ser Gln Leu Cys Cys Gln Leu Lys Leu Trp Leu
    130                 135                 140 ccg gtg ggc tgc gcg gcg ttt gtg gtg gtg ctg ctg ttt ggc tgc att    480
Pro Val Gly Cys Ala Ala Phe Val Val Val Leu Leu Phe Gly Cys Ile
145                 150                 155                 160 ctg att att tgg ttt agc aaa aaa aaa tat ggc agc agc gtg cat gat    528
Leu Ile Ile Trp Phe Ser Lys Lys Lys Tyr Gly Ser Ser Val His Asp
                165                 170                 175 ccg aac agc gaa tat atg ttt atg gcg gcg gtg aac acc aac aaa aaa    576
Pro Asn Ser Glu Tyr Met Phe Met Ala Ala Val Asn Thr Asn Lys Lys
            180                 185                 190 agc cgc ctg gcg ggc gtg acc agc                                    600
Ser Arg Leu Ala Gly Val Thr Ser
        195                 200

<210> SEQ ID NO 170
<211> LENGTH: 200
<212> TYPE: PRT
<213> ORGANISM: Artificial Sequence
<220> FEATURE:
<223> OTHER INFORMATION: [CDS]:1..600 from SEQ ID NO 169

<400> SEQUENCE: 170

Met Lys Pro Tyr Phe Cys Arg Val Phe Val Phe Cys Phe Leu Ile Arg
 1               5                  10                  15

Leu Leu Thr Gly Glu Ile Asn Gly Ser Ala Asp His Arg Met Phe Ser
                20                  25                  30

Phe His Asn Gly Gly Val Gln Ile Ser Cys Lys Tyr Pro Glu Thr Val
            35                  40                  45

Gln Gln Leu Lys Met Arg Leu Phe Arg Glu Arg Glu Val Leu Cys Glu
        50                  55                  60

Leu Thr Lys Thr Lys Gly Ser Gly Asn Ala Val Ser Ile Lys Asn Pro
 65                  70                  75                  80

Met Leu Cys Leu Tyr His Leu Ser Asn Asn Ser Val Ser Phe Phe Leu
                 85                  90                  95

Asn Asn Pro Asp Ser Ser Gln Gly Ser Tyr Tyr Phe Cys Ser Leu Ser
            100                 105                 110

Ile Phe Asp Pro Pro Pro Phe Gln Glu Arg Asn Leu Ser Gly Gly Tyr
            115                 120                 125

Leu His Ile Tyr Glu Ser Gln Leu Cys Cys Gln Leu Lys Leu Trp Leu
    130                 135                 140
```

```
Pro Val Gly Cys Ala Ala Phe Val Val Leu Leu Phe Gly Cys Ile
145                 150                 155                 160

Leu Ile Ile Trp Phe Ser Lys Lys Tyr Gly Ser Ser Val His Asp
            165                 170                 175

Pro Asn Ser Glu Tyr Met Phe Met Ala Ala Val Asn Thr Asn Lys Lys
            180                     185                 190

Ser Arg Leu Ala Gly Val Thr Ser
        195                 200

<210> SEQ ID NO 171
<211> LENGTH: 780
<212> TYPE: DNA
<213> ORGANISM: Artificial Sequence
<220> FEATURE:
<223> OTHER INFORMATION: human CD27
<220> FEATURE:
<221> NAME/KEY: CDS
<222> LOCATION: 1..780
<223> OTHER INFORMATION: /transl_table=1

<400> SEQUENCE: 171 atg gcg cgc ccg cat ccg tgg tgg ctg tgc gtg ctg ggc acc ctg gtg      48
Met Ala Arg Pro His Pro Trp Trp Leu Cys Val Leu Gly Thr Leu Val
1               5                   10                  15 ggc ctg agc gcg acc ccg gcg ccg aaa agc tgc ccg gaa cgc cat tat      96
Gly Leu Ser Ala Thr Pro Ala Pro Lys Ser Cys Pro Glu Arg His Tyr
                20                  25                  30 tgg gcg cag ggc aaa ctg tgc tgc cag atg tgc gaa ccg ggc acc ttt     144
Trp Ala Gln Gly Lys Leu Cys Cys Gln Met Cys Glu Pro Gly Thr Phe
            35                  40                  45 ctg gtg aaa gat tgc gat cag cat cgc aaa gcg gcg cag tgc gat ccg     192
Leu Val Lys Asp Cys Asp Gln His Arg Lys Ala Ala Gln Cys Asp Pro
        50                  55                  60 tgc att ccg ggc gtg agc ttt agc ccg gat cat cat acc cgc ccg cat     240
Cys Ile Pro Gly Val Ser Phe Ser Pro Asp His His Thr Arg Pro His
65                  70                  75                  80 tgc gaa agc tgc cgc cat tgc aac agc ggc ctg ctg gtg cgc aac tgc     288
Cys Glu Ser Cys Arg His Cys Asn Ser Gly Leu Leu Val Arg Asn Cys
                85                  90                  95 acc att acc gcg aac gcg gaa tgc gcg tgc cgc aac ggc tgg cag tgc     336
Thr Ile Thr Ala Asn Ala Glu Cys Ala Cys Arg Asn Gly Trp Gln Cys
                100                 105                 110 cgc gat aaa gaa tgc acc gaa tgc gat ccg ctg ccg aac ccg agc ctg     384
Arg Asp Lys Glu Cys Thr Glu Cys Asp Pro Leu Pro Asn Pro Ser Leu
            115                 120                 125 acc gcg cgc agc agc cag gcg ctg agc ccg cat ccg cag ccg acc cat     432
Thr Ala Arg Ser Ser Gln Ala Leu Ser Pro His Pro Gln Pro Thr His
        130                 135                 140 ctg ccg tat gtg agc gaa atg ctg gaa gcg cgc acc gcg ggc cat atg     480
Leu Pro Tyr Val Ser Glu Met Leu Glu Ala Arg Thr Ala Gly His Met
145                 150                 155                 160 cag acc ctg gcg gat ttt cgc cag ctg ccg gcg cgc acc ctg agc acc     528
Gln Thr Leu Ala Asp Phe Arg Gln Leu Pro Ala Arg Thr Leu Ser Thr
                165                 170                 175 cat tgg ccg ccg cag cgc agc ctg tgc agc agc gat ttt att cgc att     576
His Trp Pro Pro Gln Arg Ser Leu Cys Ser Ser Asp Phe Ile Arg Ile
                180                 185                 190 ctg gtg att ttt agc ggc atg ttt ctg gtg ttt acc ctg gcg ggc gcg     624
Leu Val Ile Phe Ser Gly Met Phe Leu Val Phe Thr Leu Ala Gly Ala
            195                 200                 205 ctg ttt ctg cat cag cgc cgc aaa tat cgc agc aac aaa ggc gaa agc     672
Leu Phe Leu His Gln Arg Arg Lys Tyr Arg Ser Asn Lys Gly Glu Ser
```

```
Leu Phe Leu His Gln Arg Arg Lys Tyr Arg Ser Asn Lys Gly Glu Ser
    210                 215                 220 ccg gtg gaa ccg gcg gaa ccg tgc cat tat agc tgc ccg cgc gaa gaa       720
Pro Val Glu Pro Ala Glu Pro Cys His Tyr Ser Cys Pro Arg Glu Glu
225                 230                 235                 240 gaa ggc agc acc att ccg att cag gaa gat tat cgc aaa ccg gaa ccg       768
Glu Gly Ser Thr Ile Pro Ile Gln Glu Asp Tyr Arg Lys Pro Glu Pro
                    245                 250                 255 gcg tgc agc ccg                                                        780
Ala Cys Ser Pro
            260

<210> SEQ ID NO 172
<211> LENGTH: 260
<212> TYPE: PRT
<213> ORGANISM: Artificial Sequence
<220> FEATURE:
<223> OTHER INFORMATION: [CDS]:1..780 from SEQ ID NO 171

<400> SEQUENCE: 172

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 173
<211> LENGTH: 750
```

```
<212> TYPE: DNA
<213> ORGANISM: Artificial Sequence
<220> FEATURE:
<223> OTHER INFORMATION: murine CD27
<220> FEATURE:
<221> NAME/KEY: CDS
<222> LOCATION: 1..750
<223> OTHER INFORMATION: /transl_table=1

<400> SEQUENCE: 173 atg gcg tgg ccg ccg ccg tat tgg ctg tgc atg ctg ggc acc ctg gtg      48
Met Ala Trp Pro Pro Pro Tyr Trp Leu Cys Met Leu Gly Thr Leu Val
1               5                   10                  15 ggc ctg agc gcg acc ctg gcg ccg aac agc tgc ccg gat aaa cat tat      96
Gly Leu Ser Ala Thr Leu Ala Pro Asn Ser Cys Pro Asp Lys His Tyr
            20                  25                  30 tgg acc ggc ggc ggc ctg tgc tgc cgc atg tgc gaa ccg ggc acc ttt     144
Trp Thr Gly Gly Gly Leu Cys Cys Arg Met Cys Glu Pro Gly Thr Phe
        35                  40                  45 ttt gtg aaa gat tgc gaa cag gat cgc acc gcg gcg cag tgc gat ccg     192
Phe Val Lys Asp Cys Glu Gln Asp Arg Thr Ala Ala Gln Cys Asp Pro
50                  55                  60 tgc att ccg ggc acc agc ttt agc ccg gat tat cat acc cgc ccg cat     240
Cys Ile Pro Gly Thr Ser Phe Ser Pro Asp Tyr His Thr Arg Pro His
65                  70                  75                  80 tgc gaa agc tgc cgc cat tgc aac agc ggc ttt ctg att cgc aac tgc     288
Cys Glu Ser Cys Arg His Cys Asn Ser Gly Phe Leu Ile Arg Asn Cys
                85                  90                  95 acc gtg acc gcg aac gcg gaa tgc agc tgc agc aaa aac tgg cag tgc     336
Thr Val Thr Ala Asn Ala Glu Cys Ser Cys Ser Lys Asn Trp Gln Cys
            100                 105                 110 cgc gat cag gaa tgc acc gaa tgc gat ccg ccg ctg aac ccg gcg ctg     384
Arg Asp Gln Glu Cys Thr Glu Cys Asp Pro Pro Leu Asn Pro Ala Leu
        115                 120                 125 acc cgc cag ccg agc gaa acc ccg agc ccg cag ccg ccg acc cat         432
Thr Arg Gln Pro Ser Glu Thr Pro Ser Pro Gln Pro Pro Thr His
130                 135                 140 ctg ccg cat ggc acc gaa aaa ccg agc tgg ccg ctg cat cgc cag ctg     480
Leu Pro His Gly Thr Glu Lys Pro Ser Trp Pro Leu His Arg Gln Leu
145                 150                 155                 160 ccg aac agc acc gtg tat agc cag cgc agc agc cat cgc ccg ctg tgc     528
Pro Asn Ser Thr Val Tyr Ser Gln Arg Ser Ser His Arg Pro Leu Cys
                165                 170                 175 agc agc gat tgc att cgc att ttt gtg acc ttt agc agc atg ttt ctg     576
Ser Ser Asp Cys Ile Arg Ile Phe Val Thr Phe Ser Ser Met Phe Leu
            180                 185                 190 att ttt gtg ctg ggc gcg att ctg ttt ttt cat cag cgc cgc aac cat     624
Ile Phe Val Leu Gly Ala Ile Leu Phe Phe His Gln Arg Arg Asn His
        195                 200                 205 ggc ccg aac gaa gat cgc cag gcg gtg ccg gaa gaa ccg tgc ccg tat     672
Gly Pro Asn Glu Asp Arg Gln Ala Val Pro Glu Glu Pro Cys Pro Tyr
210                 215                 220 agc tgc ccg cgc gaa gaa gaa ggc agc gcg att ccg att cag gaa gat     720
Ser Cys Pro Arg Glu Glu Glu Gly Ser Ala Ile Pro Ile Gln Glu Asp
225                 230                 235                 240 tat cgc aaa ccg gaa ccg gcg ttt tat ccg                             750
Tyr Arg Lys Pro Glu Pro Ala Phe Tyr Pro
                245                 250

<210> SEQ ID NO 174
<211> LENGTH: 250
<212> TYPE: PRT
```

<213> ORGANISM: Artificial Sequence
<220> FEATURE:
<223> OTHER INFORMATION: [CDS]:1..750 from SEQ ID NO 173

<400> SEQUENCE: 174

```
Met Ala Trp Pro Pro Tyr Trp Leu Cys Met Leu Gly Thr Leu Val
1               5                   10                  15

Gly Leu Ser Ala Thr Leu Ala Pro Asn Ser Cys Pro Asp Lys His Tyr
            20                  25                  30

Trp Thr Gly Gly Gly Leu Cys Cys Arg Met Cys Glu Pro Gly Thr Phe
        35                  40                  45

Phe Val Lys Asp Cys Glu Gln Asp Arg Thr Ala Ala Gln Cys Asp Pro
    50                  55                  60

Cys Ile Pro Gly Thr Ser Phe Ser Pro Asp Tyr His Thr Arg Pro His
65                  70                  75                  80

Cys Glu Ser Cys Arg His Cys Asn Ser Gly Phe Leu Ile Arg Asn Cys
                85                  90                  95

Thr Val Thr Ala Asn Ala Glu Cys Ser Cys Ser Lys Asn Trp Gln Cys
            100                 105                 110

Arg Asp Gln Glu Cys Thr Glu Cys Asp Pro Pro Leu Asn Pro Ala Leu
        115                 120                 125

Thr Arg Gln Pro Ser Glu Thr Pro Ser Pro Gln Pro Pro Thr His
    130                 135                 140

Leu Pro His Gly Thr Glu Lys Pro Ser Trp Pro Leu His Arg Gln Leu
145                 150                 155                 160

Pro Asn Ser Thr Val Tyr Ser Gln Arg Ser Ser His Arg Pro Leu Cys
                165                 170                 175

Ser Ser Asp Cys Ile Arg Ile Phe Val Thr Phe Ser Ser Met Phe Leu
            180                 185                 190

Ile Phe Val Leu Gly Ala Ile Leu Phe Phe His Gln Arg Arg Asn His
        195                 200                 205

Gly Pro Asn Glu Asp Arg Gln Ala Val Pro Glu Pro Cys Pro Tyr
    210                 215                 220

Ser Cys Pro Arg Glu Glu Glu Gly Ser Ala Ile Pro Ile Gln Glu Asp
225                 230                 235                 240

Tyr Arg Lys Pro Glu Pro Ala Phe Tyr Pro
                245                 250
```

<210> SEQ ID NO 175
<211> LENGTH: 279
<212> TYPE: DNA
<213> ORGANISM: Artificial Sequence
<220> FEATURE:
<223> OTHER INFORMATION: human DAP10
<220> FEATURE:
<221> NAME/KEY: CDS
<222> LOCATION: 1..279
<223> OTHER INFORMATION: /transl_table=1

<400> SEQUENCE: 175

```
atg att cat ctg ggc cat att ctg ttt ctg ctg ctg ccg gtg gcg      48
Met Ile His Leu Gly His Ile Leu Phe Leu Leu Leu Pro Val Ala
1               5                   10                  15 gcg gcg cag acc acc ccg ggc gaa cgc agc agc ctg ccg gcg ttt tat  96
Ala Ala Gln Thr Thr Pro Gly Glu Arg Ser Ser Leu Pro Ala Phe Tyr
            20                  25                  30 ccg ggc acc agc ggc agc tgc agc ggc tgc ggc agc ctg agc ctg ccg  144
Pro Gly Thr Ser Gly Ser Cys Ser Gly Cys Gly Ser Leu Ser Leu Pro
        35                  40                  45
```

```
ctg ctg gcg ggc ctg gtg gcg gcg gat gcg gtg gcg agc ctg ctg att    192
Leu Leu Ala Gly Leu Val Ala Ala Asp Ala Val Ala Ser Leu Leu Ile
    50                  55                  60 gtg ggc gcg gtg ttt ctg tgc gcg cgc ccg cgc agc ccg gcg cag        240
Val Gly Ala Val Phe Leu Cys Ala Arg Pro Arg Arg Ser Pro Ala Gln
65                  70                  75                  80 gaa gat ggc aaa gtg tat att aac atg ccg ggc cgc ggc                279
Glu Asp Gly Lys Val Tyr Ile Asn Met Pro Gly Arg Gly
                85                  90
```

<210> SEQ ID NO 176
<211> LENGTH: 93
<212> TYPE: PRT
<213> ORGANISM: Artificial Sequence
<220> FEATURE:
<223> OTHER INFORMATION: [CDS]:1..279 from SEQ ID NO 175

<400> SEQUENCE: 176

```
Met Ile His Leu Gly His Ile Leu Phe Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Glu Asp Gly Lys Val Tyr Ile Asn Met Pro Gly Arg Gly
                85                  90
```

<210> SEQ ID NO 177
<211> LENGTH: 237
<212> TYPE: DNA
<213> ORGANISM: Artificial Sequence
<220> FEATURE:
<223> OTHER INFORMATION: murine DAP10
<220> FEATURE:
<221> NAME/KEY: CDS
<222> LOCATION: 1..237
<223> OTHER INFORMATION: /transl_table=1

<400> SEQUENCE: 177

```
atg gat ccg ccg ggc tat ctg ctg ttt ctg ctg ctg ccg gtg gcg        48
Met Asp Pro Pro Gly Tyr Leu Leu Phe Leu Leu Leu Pro Val Ala
1               5                   10                  15 gcg agc cag acc agc gcg ggc agc tgc agc ggc tgc ggc acc ctg agc    96
Ala Ser Gln Thr Ser Ala Gly Ser Cys Ser Gly Cys Gly Thr Leu Ser
            20                  25                  30 ctg ccg ctg ctg gcg ggc ctg gtg gcg gcg gat gcg gtg atg agc ctg    144
Leu Pro Leu Leu Ala Gly Leu Val Ala Ala Asp Ala Val Met Ser Leu
        35                  40                  45 ctg att gtg ggc gtg gtg ttt gtg tgc atg cgc ccg cat ggc cgc ccg    192
Leu Ile Val Gly Val Val Phe Val Cys Met Arg Pro His Gly Arg Pro
    50                  55                  60 gcg cag gaa gat ggc cgc gtg tat att aac atg ccg ggc cgc ggc        237
Ala Gln Glu Asp Gly Arg Val Tyr Ile Asn Met Pro Gly Arg Gly
65                  70                  75
```

<210> SEQ ID NO 178
<211> LENGTH: 79
<212> TYPE: PRT

<213> ORGANISM: Artificial Sequence
<220> FEATURE:
<223> OTHER INFORMATION: [CDS]:1..237 from SEQ ID NO 177

<400> SEQUENCE: 178

```
Met Asp Pro Pro Gly Tyr Leu Leu Phe Leu Leu Leu Pro Val Ala
1               5                   10                  15

Ala Ser Gln Thr Ser Ala Gly Ser Cys Ser Gly Cys Gly Thr Leu Ser
            20                  25                  30

Leu Pro Leu Leu Ala Gly Leu Val Ala Ala Asp Ala Val Met Ser Leu
        35                  40                  45

Leu Ile Val Gly Val Val Phe Val Cys Met Arg Pro His Gly Arg Pro
50                  55                  60

Ala Gln Glu Asp Gly Arg Val Tyr Ile Asn Met Pro Gly Arg Gly
65                  70                  75
```

<210> SEQ ID NO 179
<211> LENGTH: 492
<212> TYPE: DNA
<213> ORGANISM: Artificial Sequence
<220> FEATURE:
<223> OTHER INFORMATION: CD3z mouse
<220> FEATURE:
<221> NAME/KEY: CDS
<222> LOCATION: 1..492
<223> OTHER INFORMATION: /transl_table=1

<400> SEQUENCE: 179

```
atg aaa tgg aaa gtg agc gtg ctg gcg tgc att ctg cat gtg cgc ttt      48
Met Lys Trp Lys Val Ser Val Leu Ala Cys Ile Leu His Val Arg Phe
1               5                   10                  15 ccg ggc gcg gaa gcg cag agc ttt ggc ctg ctg gat ccg aaa ctg tgc      96
Pro Gly Ala Glu Ala Gln Ser Phe Gly Leu Leu Asp Pro Lys Leu Cys
            20                  25                  30 tat ctg ctg gat ggc att ctg ttt att tat ggc gtg att att acc gcg     144
Tyr Leu Leu Asp Gly Ile Leu Phe Ile Tyr Gly Val Ile Ile Thr Ala
        35                  40                  45 ctg tat ctg cgc gcg aaa ttt agc cgc agc gcg gaa acc gcg gcg aac     192
Leu Tyr Leu Arg Ala Lys Phe Ser Arg Ser Ala Glu Thr Ala Ala Asn
50                  55                  60 ctg cag gat ccg aac cag ctg tat aac gaa ctg aac ctg ggc cgc cgc     240
Leu Gln Asp Pro Asn Gln Leu Tyr Asn Glu Leu Asn Leu Gly Arg Arg
65                  70                  75                  80 gaa gaa tat gat gtg ctg gaa aaa aaa cgc gcg cgc gat ccg gaa atg     288
Glu Glu Tyr Asp Val Leu Glu Lys Lys Arg Ala Arg Asp Pro Glu Met
                85                  90                  95 ggc ggc aaa cag cag cgc cgc cgc aac ccg cag gaa ggc gtg tat aac     336
Gly Gly Lys Gln Gln Arg Arg Arg Asn Pro Gln Glu Gly Val Tyr Asn
            100                 105                 110 gcg ctg cag aaa gat aaa atg gcg gaa gcg tat agc gaa att ggc acc     384
Ala Leu Gln Lys Asp Lys Met Ala Glu Ala Tyr Ser Glu Ile Gly Thr
        115                 120                 125 aaa ggc gaa cgc cgc cgc ggc aaa ggc cat gat ggc ctg tat cag ggc     432
Lys Gly Glu Arg Arg Arg Gly Lys Gly His Asp Gly Leu Tyr Gln Gly
130                 135                 140 ctg agc acc gcg acc aaa gat acc tat gat gcg ctg cat atg cag acc     480
Leu Ser Thr Ala Thr Lys Asp Thr Tyr Asp Ala Leu His Met Gln Thr
145                 150                 155                 160 ctg gcg ccg cgc                                                     492
Leu Ala Pro Arg
```

```
<210> SEQ ID NO 180
<211> LENGTH: 164
<212> TYPE: PRT
<213> ORGANISM: Artificial Sequence
<220> FEATURE:
<223> OTHER INFORMATION: [CDS]:1..492 from SEQ ID NO 179

<400> SEQUENCE: 180

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Ile Thr Ala
            35                  40                  45

Leu Tyr Leu Arg Ala Lys Phe Ser Arg Ser Ala Glu Thr Ala Ala Asn
        50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Arg Asn Pro Gln Glu Gly Val Tyr Asn
                100                 105                 110

Ala Leu Gln Lys Asp Lys Met Ala Glu Ala Tyr Ser Glu Ile Gly Thr
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 181
<211> LENGTH: 696
<212> TYPE: DNA
<213> ORGANISM: Artificial Sequence
<220> FEATURE:
<223> OTHER INFORMATION: NKG2d mouse
<220> FEATURE:
<221> NAME/KEY: CDS
<222> LOCATION: 1..696
<223> OTHER INFORMATION: /transl_table=1

<400> SEQUENCE: 181 atg gcg ctg att cgc gat cgc aaa agc cat cat agc gaa atg agc aaa      48
Met Ala Leu Ile Arg Asp Arg Lys Ser His His Ser Glu Met Ser Lys
1               5                   10                  15 tgc cat aac tat gat ctg aaa ccg gcg aaa tgg gat acc agc cag gaa      96
Cys His Asn Tyr Asp Leu Lys Pro Ala Lys Trp Asp Thr Ser Gln Glu
                20                  25                  30 cag cag aaa cag cgc ctg gcg ctg acc acc agc cag ccg ggc gaa aac     144
Gln Gln Lys Gln Arg Leu Ala Leu Thr Thr Ser Gln Pro Gly Glu Asn
            35                  40                  45 ggc att att cgc ggc cgc tat ccg att gaa aaa ctg aaa att agc ccg     192
Gly Ile Ile Arg Gly Arg Tyr Pro Ile Glu Lys Leu Lys Ile Ser Pro
        50                  55                  60 atg ttt gtg gtg cgc gtg ctg gcg att gcg ctg gcg att cgc ttt acc     240
Met Phe Val Val Arg Val Leu Ala Ile Ala Leu Ala Ile Arg Phe Thr
65                  70                  75                  80 ctg aac acc ctg atg tgg ctg gcg att ttt aaa gaa acc ttt cag ccg     288
Leu Asn Thr Leu Met Trp Leu Ala Ile Phe Lys Glu Thr Phe Gln Pro
                85                  90                  95
```

| | | |
|---|---|---|
| gtg ctg tgc aac aaa gaa gtg ccg gtg agc agc cgc gaa ggc tat tgc<br>Val Leu Cys Asn Lys Glu Val Pro Val Ser Ser Arg Glu Gly Tyr Cys<br>100                     105                     110 | | 336 |
| ggc ccg tgc ccg aac aac tgg att tgc cat cgc aac aac tgc tat cag<br>Gly Pro Cys Pro Asn Asn Trp Ile Cys His Arg Asn Asn Cys Tyr Gln<br>    115                     120                     125 | | 384 |
| ttt ttt aac gaa gaa aaa acc tgg aac cag agc cag gcg agc tgc ctg<br>Phe Phe Asn Glu Glu Lys Thr Trp Asn Gln Ser Gln Ala Ser Cys Leu<br>130                     135                     140 | | 432 |
| agc cag aac agc agc ctg ctg aaa att tat agc aaa gaa gaa cag gat<br>Ser Gln Asn Ser Ser Leu Leu Lys Ile Tyr Ser Lys Glu Glu Gln Asp<br>145                 150                     155                 160 | | 480 |
| ttt ctg aaa ctg gtg aaa agc tat cat tgg atg ggc ctg gtg cag att<br>Phe Leu Lys Leu Val Lys Ser Tyr His Trp Met Gly Leu Val Gln Ile<br>                165                     170                     175 | | 528 |
| ccg gcg aac ggc agc tgg cag tgg gaa gat ggc agc agc ctg agc tat<br>Pro Ala Asn Gly Ser Trp Gln Trp Glu Asp Gly Ser Ser Leu Ser Tyr<br>            180                     185                     190 | | 576 |
| aac cag ctg acc ctg gtg gaa att ccg aaa ggc agc tgc gcg gtg tat<br>Asn Gln Leu Thr Leu Val Glu Ile Pro Lys Gly Ser Cys Ala Val Tyr<br>        195                     200                     205 | | 624 |
| ggc agc agc ttt aaa gcg tat acc gaa gat tgc gcg aac ctg aac acc<br>Gly Ser Ser Phe Lys Ala Tyr Thr Glu Asp Cys Ala Asn Leu Asn Thr<br>210                     215                     220 | | 672 |
| tat att tgc atg aaa cgc gcg gtg<br>Tyr Ile Cys Met Lys Arg Ala Val<br>225                 230 | | 696 |

<210> SEQ ID NO 182
<211> LENGTH: 232
<212> TYPE: PRT
<213> ORGANISM: Artificial Sequence
<220> FEATURE:
<223> OTHER INFORMATION: [CDS]:1..696 from SEQ ID NO 181

<400> SEQUENCE: 182

Met Ala Leu Ile Arg Asp Arg Lys Ser His His Ser Glu Met Ser Lys
1               5                   10                  15

Cys His Asn Tyr Asp Leu Lys Pro Ala Lys Trp Asp Thr Ser Gln Glu
            20                  25                  30

Gln Gln Lys Gln Arg Leu Ala Leu Thr Thr Ser Gln Pro Gly Glu Asn
        35                  40                  45

Gly Ile Ile Arg Gly Arg Tyr Pro Ile Glu Lys Leu Lys Ile Ser Pro
    50                  55                  60

Met Phe Val Val Arg Val Leu Ala Ile Ala Leu Ala Ile Arg Phe Thr
65                  70                  75                  80

Leu Asn Thr Leu Met Trp Leu Ala Ile Phe Lys Glu Thr Phe Gln Pro
                85                  90                  95

Val Leu Cys Asn Lys Glu Val Pro Val Ser Ser Arg Glu Gly Tyr Cys
            100                 105                 110

Gly Pro Cys Pro Asn Asn Trp Ile Cys His Arg Asn Asn Cys Tyr Gln
        115                 120                 125

Phe Phe Asn Glu Glu Lys Thr Trp Asn Gln Ser Gln Ala Ser Cys Leu
    130                 135                 140

Ser Gln Asn Ser Ser Leu Leu Lys Ile Tyr Ser Lys Glu Glu Gln Asp
145                 150                 155                 160

Phe Leu Lys Leu Val Lys Ser Tyr His Trp Met Gly Leu Val Gln Ile
                165                 170                 175

```
Pro Ala Asn Gly Ser Trp Gln Trp Glu Asp Gly Ser Ser Leu Ser Tyr
            180                 185                 190

Asn Gln Leu Thr Leu Val Glu Ile Pro Lys Gly Ser Cys Ala Val Tyr
        195                 200                 205

Gly Ser Ser Phe Lys Ala Tyr Thr Glu Asp Cys Ala Asn Leu Asn Thr
    210                 215                 220

Tyr Ile Cys Met Lys Arg Ala Val
225                 230

<210> SEQ ID NO 183
<211> LENGTH: 492
<212> TYPE: DNA
<213> ORGANISM: Artificial Sequence
<220> FEATURE:
<223> OTHER INFORMATION: human CD3z
<220> FEATURE:
<221> NAME/KEY: CDS
<222> LOCATION: 1..492
<223> OTHER INFORMATION: /transl_table=1

<400> SEQUENCE: 183 atg aaa tgg aaa gtg agc gtg ctg gcg tgc att ctg cat gtg cgc ttt      48
Met Lys Trp Lys Val Ser Val Leu Ala Cys Ile Leu His Val Arg Phe
1               5                   10                  15 ccg ggc gcg gaa gcg cag agc ttt ggc ctg ctg gat ccg aaa ctg tgc      96
Pro Gly Ala Glu Ala Gln Ser Phe Gly Leu Leu Asp Pro Lys Leu Cys
            20                  25                  30 tat ctg ctg gat ggc att ctg ttt att tat ggc gtg att att acc gcg     144
Tyr Leu Leu Asp Gly Ile Leu Phe Ile Tyr Gly Val Ile Ile Thr Ala
        35                  40                  45 ctg tat ctg cgc gcg aaa ttt agc cgc agc gcg gaa acc gcg gcg aac     192
Leu Tyr Leu Arg Ala Lys Phe Ser Arg Ser Ala Glu Thr Ala Ala Asn
    50                  55                  60 ctg cag gat ccg aac cag ctg tat aac gaa ctg aac ctg ggc cgc cgc     240
Leu Gln Asp Pro Asn Gln Leu Tyr Asn Glu Leu Asn Leu Gly Arg Arg
65                  70                  75                  80 gaa gaa tat gat gtg ctg gaa aaa aaa cgc gcg cgc gat ccg gaa atg     288
Glu Glu Tyr Asp Val Leu Glu Lys Lys Arg Ala Arg Asp Pro Glu Met
                85                  90                  95 ggc ggc aaa cag cag cgc cgc cgc aac ccg cag gaa ggc gtg tat aac     336
Gly Gly Lys Gln Gln Arg Arg Arg Asn Pro Gln Glu Gly Val Tyr Asn
            100                 105                 110 gcg ctg cag aaa gat aaa atg gcg gaa gcg tat agc gaa att ggc acc     384
Ala Leu Gln Lys Asp Lys Met Ala Glu Ala Tyr Ser Glu Ile Gly Thr
        115                 120                 125 aaa ggc gaa cgc cgc cgc ggc aaa ggc cat gat ggc ctg tat cag ggc     432
Lys Gly Glu Arg Arg Arg Gly Lys Gly His Asp Gly Leu Tyr Gln Gly
    130                 135                 140 ctg agc acc gcg acc aaa gat acc tat gat gcg ctg cat atg cag acc     480
Leu Ser Thr Ala Thr Lys Asp Thr Tyr Asp Ala Leu His Met Gln Thr
145                 150                 155                 160 ctg gcg ccg cgc                                                      492
Leu Ala Pro Arg <210> SEQ ID NO 184
<211> LENGTH: 164
<212> TYPE: PRT
<213> ORGANISM: Artificial Sequence
<220> FEATURE:
<223> OTHER INFORMATION: [CDS]:1..492 from SEQ ID NO 183

<400> SEQUENCE: 184
```

```
Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Ile Thr Ala
            35                  40                  45

Leu Tyr Leu Arg Ala Lys Phe Ser Arg Ser Ala Glu Thr Ala Ala Asn
        50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Arg Asn Pro Gln Glu Gly Val Tyr Asn
                100                 105                 110

Ala Leu Gln Lys Asp Lys Met Ala Glu Ala Tyr Ser Glu Ile Gly Thr
            115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 185
<211> LENGTH: 762
<212> TYPE: DNA
<213> ORGANISM: Artificial Sequence
<220> FEATURE:
<223> OTHER INFORMATION: human FCGR3a
<220> FEATURE:
<221> NAME/KEY: CDS
<222> LOCATION: 1..762
<223> OTHER INFORMATION: /transl_table=1

<400> SEQUENCE: 185 atg tgg cag ctg ctg ctg ccg acc gcg ctg ctg ctg ctg gtg agc gcg      48
Met Trp Gln Leu Leu Leu Pro Thr Ala Leu Leu Leu Leu Val Ser Ala
1               5                   10                  15 ggc atg cgc acc gaa gat ctg ccg aaa gcg gtg gtg ttt ctg gaa ccg      96
Gly Met Arg Thr Glu Asp Leu Pro Lys Ala Val Val Phe Leu Glu Pro
                20                  25                  30 cag tgg tat cgc gtg ctg gaa aaa gat agc gtg acc ctg aaa tgc cag     144
Gln Trp Tyr Arg Val Leu Glu Lys Asp Ser Val Thr Leu Lys Cys Gln
            35                  40                  45 ggc gcg tat agc ccg gaa gat aac agc acc cag tgg ttt cat aac gaa     192
Gly Ala Tyr Ser Pro Glu Asp Asn Ser Thr Gln Trp Phe His Asn Glu
        50                  55                  60 agc ctg att agc agc cag gcg agc agc tat ttt att gat gcg gcg acc     240
Ser Leu Ile Ser Ser Gln Ala Ser Ser Tyr Phe Ile Asp Ala Ala Thr
65                  70                  75                  80 gtg gat gat agc ggc gaa tat cgc tgc cag acc aac ctg agc acc ctg     288
Val Asp Asp Ser Gly Glu Tyr Arg Cys Gln Thr Asn Leu Ser Thr Leu
                85                  90                  95 agc gat ccg gtg cag ctg gaa gtg cat att ggc tgg ctg ctg cag         336
Ser Asp Pro Val Gln Leu Glu Val His Ile Gly Trp Leu Leu Leu Gln
                100                 105                 110 gcg ccg cgc tgg gtg ttt aaa gaa gaa gat ccg att cat ctg cgc tgc     384
Ala Pro Arg Trp Val Phe Lys Glu Glu Asp Pro Ile His Leu Arg Cys
            115                 120                 125 cat agc tgg aaa aac acc gcg ctg cat aaa gtg acc tat ctg cag aac     432
```

His Ser Trp Lys Asn Thr Ala Leu His Lys Val Thr Tyr Leu Gln Asn
            130                 135                 140 ggc aaa ggc cgc aaa tat ttt cat cat aac agc gat ttt tat att ccg    480
Gly Lys Gly Arg Lys Tyr Phe His His Asn Ser Asp Phe Tyr Ile Pro
145                 150                 155                 160 aaa gcg acc ctg aaa gat agc ggc agc tat ttt tgc cgc ggc ctg ttt    528
Lys Ala Thr Leu Lys Asp Ser Gly Ser Tyr Phe Cys Arg Gly Leu Phe
                165                 170                 175 ggc agc aaa aac gtg agc agc gaa acc gtg aac att acc att acc cag    576
Gly Ser Lys Asn Val Ser Ser Glu Thr Val Asn Ile Thr Ile Thr Gln
            180                 185                 190 ggc ctg gcg gtg agc acc att agc agc ttt ttt ccg ccg ggc tat cag    624
Gly Leu Ala Val Ser Thr Ile Ser Ser Phe Phe Pro Pro Gly Tyr Gln
        195                 200                 205 gtg agc ttt tgc ctg gtg atg gtg ctg ctg ttt gcg gtg gat acc ggc    672
Val Ser Phe Cys Leu Val Met Val Leu Leu Phe Ala Val Asp Thr Gly
210                 215                 220 ctg tat ttt agc gtg aaa acc aac att cgc agc agc acc cgc gat tgg    720
Leu Tyr Phe Ser Val Lys Thr Asn Ile Arg Ser Ser Thr Arg Asp Trp
225                 230                 235                 240 aaa gat cat aaa ttt aaa tgg cgc aaa gat ccg cag gat aaa            762
Lys Asp His Lys Phe Lys Trp Arg Lys Asp Pro Gln Asp Lys
                245                 250

<210> SEQ ID NO 186
<211> LENGTH: 254
<212> TYPE: PRT
<213> ORGANISM: Artificial Sequence
<220> FEATURE:
<223> OTHER INFORMATION: [CDS]:1..762 from SEQ ID NO 185

<400> SEQUENCE: 186

Met Trp Gln Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

```
Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 187
<211> LENGTH: 648
<212> TYPE: DNA
<213> ORGANISM: Artificial Sequence
<220> FEATURE:
<223> OTHER INFORMATION: human NKg2d
<220> FEATURE:
<221> NAME/KEY: CDS
<222> LOCATION: 1..648
<223> OTHER INFORMATION: /transl_table=1

<400> SEQUENCE: 187

```
atg ggc tgg att cgc ggc cgc cgc agc cgc cat agc tgg gaa atg agc      48
Met Gly Trp Ile Arg Gly Arg Arg Ser Arg His Ser Trp Glu Met Ser
1               5                   10                  15 gaa ttt cat aac tat aac ctg gat ctg aaa aaa agc gat ttt agc acc      96
Glu Phe His Asn Tyr Asn Leu Asp Leu Lys Lys Ser Asp Phe Ser Thr
                20                  25                  30 cgc tgg cag aaa cag cgc tgc ccg gtg gtg aaa agc aaa tgc cgc gaa     144
Arg Trp Gln Lys Gln Arg Cys Pro Val Val Lys Ser Lys Cys Arg Glu
            35                  40                  45 aac gcg agc ccg ttt ttt ttt tgc tgc ttt att gcg gtg gcg atg ggc     192
Asn Ala Ser Pro Phe Phe Phe Cys Cys Phe Ile Ala Val Ala Met Gly
        50                  55                  60 att cgc ttt att att atg gtg gcg att tgg agc gcg gtg ttt ctg aac     240
Ile Arg Phe Ile Ile Met Val Ala Ile Trp Ser Ala Val Phe Leu Asn
65                  70                  75                  80 agc ctg ttt aac cag gaa gtg cag att ccg ctg acc gaa agc tat tgc     288
Ser Leu Phe Asn Gln Glu Val Gln Ile Pro Leu Thr Glu Ser Tyr Cys
                85                  90                  95 ggc ccg tgc ccg aaa aac tgg att tgc tat aaa aac aac tgc tat cag     336
Gly Pro Cys Pro Lys Asn Trp Ile Cys Tyr Lys Asn Asn Cys Tyr Gln
            100                 105                 110 ttt ttt gat gaa agc aaa aac tgg tat gaa agc cag gcg agc tgc atg     384
Phe Phe Asp Glu Ser Lys Asn Trp Tyr Glu Ser Gln Ala Ser Cys Met
        115                 120                 125 agc cag aac gcg agc ctg ctg aaa gtg tat agc aaa gaa gat cag gat     432
Ser Gln Asn Ala Ser Leu Leu Lys Val Tyr Ser Lys Glu Asp Gln Asp
    130                 135                 140 ctg ctg aaa ctg gtg aaa agc tat cat tgg atg ggc ctg gtg cat att     480
Leu Leu Lys Leu Val Lys Ser Tyr His Trp Met Gly Leu Val His Ile
145                 150                 155                 160 ccg acc aac ggc agc tgg cag tgg gaa gat ggc agc att ctg agc ccg     528
Pro Thr Asn Gly Ser Trp Gln Trp Glu Asp Gly Ser Ile Leu Ser Pro
                165                 170                 175 aac ctg ctg acc att att gaa atg cag aaa ggc gat tgc gcg ctg tat     576
Asn Leu Leu Thr Ile Ile Glu Met Gln Lys Gly Asp Cys Ala Leu Tyr
            180                 185                 190 gcg agc agc ttt aaa ggc tat att gaa aac tgc agc acc ccg aac acc     624
Ala Ser Ser Phe Lys Gly Tyr Ile Glu Asn Cys Ser Thr Pro Asn Thr
        195                 200                 205 tat att tgc atg cag cgc acc gtg                                     648
Tyr Ile Cys Met Gln Arg Thr Val
    210                 215
```

```
<210> SEQ ID NO 188
<211> LENGTH: 216
<212> TYPE: PRT
<213> ORGANISM: Artificial Sequence
<220> FEATURE:
<223> OTHER INFORMATION: [CDS]:1..648 from SEQ ID NO 187

<400> SEQUENCE: 188

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215

<210> SEQ ID NO 189
<211> LENGTH: 2979
<212> TYPE: DNA
<213> ORGANISM: Artificial Sequence
<220> FEATURE:
<223> OTHER INFORMATION: human Flt3
<220> FEATURE:
<221> NAME/KEY: CDS
<222> LOCATION: 1..2979
<223> OTHER INFORMATION: /transl_table=1

<400> SEQUENCE: 189 atg ccg gcg ctg gcg cgc gat ggc ggc cag ctg ccg ctg ctg gtg gtg        48
Met Pro Ala Leu Ala Arg Asp Gly Gly Gln Leu Pro Leu Leu Val Val
1               5                   10                  15 ttt agc gcg atg att ttt ggc acc att acc aac cag gat ctg ccg gtg        96
Phe Ser Ala Met Ile Phe Gly Thr Ile Thr Asn Gln Asp Leu Pro Val
            20                  25                  30 att aaa tgc gtg ctg att aac cat aaa aac aac gat agc agc gtg ggc        144
Ile Lys Cys Val Leu Ile Asn His Lys Asn Asn Asp Ser Ser Val Gly
        35                  40                  45
```

| | | |
|---|---|---|
| aaa agc agc agc tat ccg atg gtg agc gaa agc ccg gaa gat ctg ggc<br>Lys Ser Ser Ser Tyr Pro Met Val Ser Glu Ser Pro Glu Asp Leu Gly<br>50                55                    60 | 192 |
| tgc gcg ctg cgc ccg cag agc agc ggc acc gtg tat gaa gcg gcg gcg<br>Cys Ala Leu Arg Pro Gln Ser Ser Gly Thr Val Tyr Glu Ala Ala Ala<br>65                   70                  75                 80 | 240 |
| gtg gaa gtg gat gtg agc gcg agc att acc ctg cag gtg ctg gtg gat<br>Val Glu Val Asp Val Ser Ala Ser Ile Thr Leu Gln Val Leu Val Asp<br>                   85                     90                   95 | 288 |
| gcg ccg ggc aac att agc tgc ctg tgg gtg ttt aaa cat agc agc ctg<br>Ala Pro Gly Asn Ile Ser Cys Leu Trp Val Phe Lys His Ser Ser Leu<br>100                    105                   110 | 336 |
| aac tgc cag ccg cat ttt gat ctg cag aac cgc ggc gtg gtg agc atg<br>Asn Cys Gln Pro His Phe Asp Leu Gln Asn Arg Gly Val Val Ser Met<br>               115                   120                 125 | 384 |
| gtg att ctg aaa atg acc gaa acc cag gcg ggc gaa tat ctg ctg ttt<br>Val Ile Leu Lys Met Thr Glu Thr Gln Ala Gly Glu Tyr Leu Leu Phe<br>130                    135                   140 | 432 |
| att cag agc gaa gcg acc aac tat acc att ctg ttt acc gtg agc att<br>Ile Gln Ser Glu Ala Thr Asn Tyr Thr Ile Leu Phe Thr Val Ser Ile<br>145                    150                   155                 160 | 480 |
| cgc aac acc ctg ctg tat acc ctg cgc cgc ccg tat ttt cgc aaa atg<br>Arg Asn Thr Leu Leu Tyr Thr Leu Arg Arg Pro Tyr Phe Arg Lys Met<br>               165                   170                 175 | 528 |
| gaa aac cag gat gcg ctg gtg tgc att agc gaa agc gtg ccg gaa ccg<br>Glu Asn Gln Asp Ala Leu Val Cys Ile Ser Glu Ser Val Pro Glu Pro<br>                   180                   185                 190 | 576 |
| att gtg gaa tgg gtg ctg tgc gat agc cag ggc gaa agc tgc aaa gaa<br>Ile Val Glu Trp Val Leu Cys Asp Ser Gln Gly Glu Ser Cys Lys Glu<br>195                    200                   205 | 624 |
| gaa agc ccg gcg gtg gtg aaa aaa gaa gaa aaa gtg ctg cat gaa ctg<br>Glu Ser Pro Ala Val Val Lys Lys Glu Glu Lys Val Leu His Glu Leu<br>210                    215                   220 | 672 |
| ttt ggc acc gat att cgc tgc tgc gcg cgc aac gaa ctg ggc cgc gaa<br>Phe Gly Thr Asp Ile Arg Cys Cys Ala Arg Asn Glu Leu Gly Arg Glu<br>225                    230                   235                 240 | 720 |
| tgc acc cgc ctg ttt acc att gat ctg aac cag acc ccg cag acc acc<br>Cys Thr Arg Leu Phe Thr Ile Asp Leu Asn Gln Thr Pro Gln Thr Thr<br>               245                   250                 255 | 768 |
| ctg ccg cag ctg ttt ctg aaa gtg ggc gaa ccg ctg tgg att cgc tgc<br>Leu Pro Gln Leu Phe Leu Lys Val Gly Glu Pro Leu Trp Ile Arg Cys<br>                   260                   265                 270 | 816 |
| aaa gcg gtg cat gtg aac cat ggc ttt ggc ctg acc tgg gaa ctg gaa<br>Lys Ala Val His Val Asn His Gly Phe Gly Leu Thr Trp Glu Leu Glu<br>275                    280                   285 | 864 |
| aac aaa gcg ctg gaa gaa ggc aac tat ttt gaa atg agc acc tat agc<br>Asn Lys Ala Leu Glu Glu Gly Asn Tyr Phe Glu Met Ser Thr Tyr Ser<br>290                    295                   300 | 912 |
| acc aac cgc acc atg att cgc att ctg ttt gcg ttt gtg agc agc gtg<br>Thr Asn Arg Thr Met Ile Arg Ile Leu Phe Ala Phe Val Ser Ser Val<br>305                    310                   315                 320 | 960 |
| gcg cgc aac gat acc ggc tat tat acc tgc agc agc agc aaa cat ccg<br>Ala Arg Asn Asp Thr Gly Tyr Tyr Thr Cys Ser Ser Ser Lys His Pro<br>                   325                   330                 335 | 1008 |
| agc cag agc gcg ctg gtg acc att gtg gaa aaa ggc ttt att aac gcg<br>Ser Gln Ser Ala Leu Val Thr Ile Val Glu Lys Gly Phe Ile Asn Ala<br>                   340                   345                 350 | 1056 |
| acc aac agc agc gaa gat tat gaa att gat cag tat gaa gaa ttt tgc<br>Thr Asn Ser Ser Glu Asp Tyr Glu Ile Asp Gln Tyr Glu Glu Phe Cys<br>               355                   360                 365 | 1104 |

| | | | | | | | | | | | | | | | |
|---|---|---|---|---|---|---|---|---|---|---|---|---|---|---|---|
| ttt | agc | gtg | cgc | ttt | aaa | gcg | tat | ccg | cag | att | cgc | tgc | acc | tgg | acc | 1152 |
| Phe | Ser | Val | Arg | Phe | Lys | Ala | Tyr | Pro | Gln | Ile | Arg | Cys | Thr | Trp | Thr | |
| | 370 | | | | 375 | | | | | 380 | | | | | | |

| ttt | agc | cgc | aaa | agc | ttt | ccg | tgc | gaa | cag | aaa | ggc | ctg | gat | aac | ggc | 1200 |
| Phe | Ser | Arg | Lys | Ser | Phe | Pro | Cys | Glu | Gln | Lys | Gly | Leu | Asp | Asn | Gly |
| 385 | | | | | 390 | | | | | 395 | | | | | 400 |

| tat | agc | att | agc | aaa | ttt | tgc | aac | cat | aaa | cat | cag | ccg | ggc | gaa | tat | 1248 |
| Tyr | Ser | Ile | Ser | Lys | Phe | Cys | Asn | His | Lys | His | Gln | Pro | Gly | Glu | Tyr |
| | | | | 405 | | | | | 410 | | | | | 415 | |

| att | ttt | cat | gcg | gaa | aac | gat | gat | gcg | cag | ttt | acc | aaa | atg | ttt | acc | 1296 |
| Ile | Phe | His | Ala | Glu | Asn | Asp | Asp | Ala | Gln | Phe | Thr | Lys | Met | Phe | Thr |
| | | 420 | | | | | 425 | | | | | 430 | | | |

| ctg | aac | att | cgc | cgc | aaa | ccg | cag | gtg | ctg | gcg | gaa | gcg | agc | gcg | agc | 1344 |
| Leu | Asn | Ile | Arg | Arg | Lys | Pro | Gln | Val | Leu | Ala | Glu | Ala | Ser | Ala | Ser |
| | | | 435 | | | | | 440 | | | | | 445 | | |

| cag | gcg | agc | tgc | ttt | agc | gat | ggc | tat | ccg | ctg | ccg | agc | tgg | acc | tgg | 1392 |
| Gln | Ala | Ser | Cys | Phe | Ser | Asp | Gly | Tyr | Pro | Leu | Pro | Ser | Trp | Thr | Trp |
| | 450 | | | | | 455 | | | | | 460 | | | | |

| aaa | aaa | tgc | agc | gat | aaa | agc | ccg | aac | tgc | acc | gaa | gaa | att | acc | gaa | 1440 |
| Lys | Lys | Cys | Ser | Asp | Lys | Ser | Pro | Asn | Cys | Thr | Glu | Glu | Ile | Thr | Glu |
| 465 | | | | | 470 | | | | | 475 | | | | | 480 |

| ggc | gtg | tgg | aac | cgc | aaa | gcg | aac | cgc | aaa | gtg | ttt | ggc | cag | tgg | gtg | 1488 |
| Gly | Val | Trp | Asn | Arg | Lys | Ala | Asn | Arg | Lys | Val | Phe | Gly | Gln | Trp | Val |
| | | | | 485 | | | | | 490 | | | | | 495 | |

| agc | agc | agc | acc | ctg | aac | atg | agc | gaa | gcg | att | aaa | ggc | ttt | ctg | gtg | 1536 |
| Ser | Ser | Ser | Thr | Leu | Asn | Met | Ser | Glu | Ala | Ile | Lys | Gly | Phe | Leu | Val |
| | | | 500 | | | | | 505 | | | | | 510 | | |

| aaa | tgc | tgc | gcg | tat | aac | agc | ctg | ggc | acc | agc | tgc | gaa | acc | att | ctg | 1584 |
| Lys | Cys | Cys | Ala | Tyr | Asn | Ser | Leu | Gly | Thr | Ser | Cys | Glu | Thr | Ile | Leu |
| | | 515 | | | | | 520 | | | | | 525 | | | |

| ctg | aac | agc | ccg | ggc | ccg | ttt | ccg | ttt | att | cag | gat | aac | att | agc | ttt | 1632 |
| Leu | Asn | Ser | Pro | Gly | Pro | Phe | Pro | Phe | Ile | Gln | Asp | Asn | Ile | Ser | Phe |
| | 530 | | | | | 535 | | | | | 540 | | | | |

| tat | gcg | acc | att | ggc | gtg | tgc | ctg | ctg | ttt | att | gtg | gtg | ctg | acc | ctg | 1680 |
| Tyr | Ala | Thr | Ile | Gly | Val | Cys | Leu | Leu | Phe | Ile | Val | Val | Leu | Thr | Leu |
| 545 | | | | | 550 | | | | | 555 | | | | | 560 |

| ctg | att | tgc | cat | aaa | tat | aaa | aaa | cag | ttt | cgc | tat | gaa | agc | cag | ctg | 1728 |
| Leu | Ile | Cys | His | Lys | Tyr | Lys | Lys | Gln | Phe | Arg | Tyr | Glu | Ser | Gln | Leu |
| | | | | 565 | | | | | 570 | | | | | 575 | |

| cag | atg | gtg | cag | gtg | acc | ggc | agc | agc | gat | aac | gaa | tat | ttt | tat | gtg | 1776 |
| Gln | Met | Val | Gln | Val | Thr | Gly | Ser | Ser | Asp | Asn | Glu | Tyr | Phe | Tyr | Val |
| | | | 580 | | | | | 585 | | | | | 590 | | |

| gat | ttt | cgc | gaa | tat | gaa | tat | gat | ctg | aaa | tgg | gaa | ttt | ccg | cgc | gaa | 1824 |
| Asp | Phe | Arg | Glu | Tyr | Glu | Tyr | Asp | Leu | Lys | Trp | Glu | Phe | Pro | Arg | Glu |
| | | 595 | | | | | 600 | | | | | 605 | | | |

| aac | ctg | gaa | ttt | ggc | aaa | gtg | ctg | ggc | agc | ggc | gcg | ttt | ggc | aaa | gtg | 1872 |
| Asn | Leu | Glu | Phe | Gly | Lys | Val | Leu | Gly | Ser | Gly | Ala | Phe | Gly | Lys | Val |
| | 610 | | | | | 615 | | | | | 620 | | | | |

| atg | aac | gcg | acc | gcg | tat | ggc | att | agc | aaa | acc | ggc | gtg | agc | att | cag | 1920 |
| Met | Asn | Ala | Thr | Ala | Tyr | Gly | Ile | Ser | Lys | Thr | Gly | Val | Ser | Ile | Gln |
| 625 | | | | | 630 | | | | | 635 | | | | | 640 |

| gtg | gcg | gtg | aaa | atg | ctg | aaa | gaa | aaa | gcg | gat | agc | agc | gaa | cgc | gaa | 1968 |
| Val | Ala | Val | Lys | Met | Leu | Lys | Glu | Lys | Ala | Asp | Ser | Ser | Glu | Arg | Glu |
| | | | | 645 | | | | | 650 | | | | | 655 | |

| gcg | ctg | atg | agc | gaa | ctg | aaa | atg | atg | acc | cag | ctg | ggc | agc | cat | gaa | 2016 |
| Ala | Leu | Met | Ser | Glu | Leu | Lys | Met | Met | Thr | Gln | Leu | Gly | Ser | His | Glu |
| | | | 660 | | | | | 665 | | | | | 670 | | |

| aac | att | gtg | aac | ctg | ctg | ggc | gcg | tgc | acc | ctg | agc | ggc | ccg | att | tat | 2064 |
| Asn | Ile | Val | Asn | Leu | Leu | Gly | Ala | Cys | Thr | Leu | Ser | Gly | Pro | Ile | Tyr |

-continued

```
             675                 680                 685
ctg att ttt gaa tat tgc tgc tat ggc gat ctg ctg aac tat ctg cgc      2112
Leu Ile Phe Glu Tyr Cys Cys Tyr Gly Asp Leu Leu Asn Tyr Leu Arg
    690                 695                 700 agc aaa cgc gaa aaa ttt cat cgc acc tgg acc gaa att ttt aaa gaa      2160
Ser Lys Arg Glu Lys Phe His Arg Thr Trp Thr Glu Ile Phe Lys Glu
705                 710                 715                 720 cat aac ttt agc ttt tat ccg acc ttt cag agc cat ccg aac agc agc      2208
His Asn Phe Ser Phe Tyr Pro Thr Phe Gln Ser His Pro Asn Ser Ser
                725                 730                 735 atg ccg ggc agc cgc gaa gtg cag att cat ccg gat agc gat cag att      2256
Met Pro Gly Ser Arg Glu Val Gln Ile His Pro Asp Ser Asp Gln Ile
            740                 745                 750 agc ggc ctg cat ggc aac agc ttt cat agc gaa gat gaa att gaa tat      2304
Ser Gly Leu His Gly Asn Ser Phe His Ser Glu Asp Glu Ile Glu Tyr
        755                 760                 765 gaa aac cag aaa cgc ctg gaa gaa gaa gaa gat ctg aac gtg ctg acc      2352
Glu Asn Gln Lys Arg Leu Glu Glu Glu Glu Asp Leu Asn Val Leu Thr
770                 775                 780 ttt gaa gat ctg ctg tgc ttt gcg tat cag gtg gcg aaa ggc atg gaa      2400
Phe Glu Asp Leu Leu Cys Phe Ala Tyr Gln Val Ala Lys Gly Met Glu
785                 790                 795                 800 ttt ctg gaa ttt aaa agc tgc gtg cat cgc gat ctg gcg gcg cgc aac      2448
Phe Leu Glu Phe Lys Ser Cys Val His Arg Asp Leu Ala Ala Arg Asn
                805                 810                 815 gtg ctg gtg acc cat ggc aaa gtg gtg aaa att tgc gat ttt ggc ctg      2496
Val Leu Val Thr His Gly Lys Val Val Lys Ile Cys Asp Phe Gly Leu
            820                 825                 830 gcg cgc gat att atg agc gat agc aac tat gtg gtg cgc ggc aac gcg      2544
Ala Arg Asp Ile Met Ser Asp Ser Asn Tyr Val Val Arg Gly Asn Ala
        835                 840                 845 cgc ctg ccg gtg aaa tgg atg gcg ccg gaa agc ctg ttt gaa ggc att      2592
Arg Leu Pro Val Lys Trp Met Ala Pro Glu Ser Leu Phe Glu Gly Ile
850                 855                 860 tat acc att aaa agc gat gtg tgg agc tat ggc att ctg ctg tgg gaa      2640
Tyr Thr Ile Lys Ser Asp Val Trp Ser Tyr Gly Ile Leu Leu Trp Glu
865                 870                 875                 880 att ttt agc ctg ggc gtg aac ccg tat ccg ggc att ccg gtg gat gcg      2688
Ile Phe Ser Leu Gly Val Asn Pro Tyr Pro Gly Ile Pro Val Asp Ala
                885                 890                 895 aac ttt tat aaa ctg att cag aac ggc ttt aaa atg gat cag ccg ttt      2736
Asn Phe Tyr Lys Leu Ile Gln Asn Gly Phe Lys Met Asp Gln Pro Phe
            900                 905                 910 tat gcg acc gaa gaa att tat att att atg cag agc tgc tgg gcg ttt      2784
Tyr Ala Thr Glu Glu Ile Tyr Ile Ile Met Gln Ser Cys Trp Ala Phe
        915                 920                 925 gat agc cgc aaa cgc ccg agc ttt ccg aac ctg acc agc ttt ctg ggc      2832
Asp Ser Arg Lys Arg Pro Ser Phe Pro Asn Leu Thr Ser Phe Leu Gly
930                 935                 940 tgc cag ctg gcg gat gcg gaa gaa gcg atg tat cag aac gtg gat ggc      2880
Cys Gln Leu Ala Asp Ala Glu Glu Ala Met Tyr Gln Asn Val Asp Gly
945                 950                 955                 960 cgc gtg agc gaa tgc ccg cat acc tat cag aac cgc cgc ccg ttt agc      2928
Arg Val Ser Glu Cys Pro His Thr Tyr Gln Asn Arg Arg Pro Phe Ser
                965                 970                 975 cgc gaa atg gat ctg ggc ctg ctg agc ccg cag gcg cag gtg gaa gat      2976
Arg Glu Met Asp Leu Gly Leu Leu Ser Pro Gln Ala Gln Val Glu Asp
            980                 985                 990 agc                                                                   2979
```

Ser

<210> SEQ ID NO 190
<211> LENGTH: 993
<212> TYPE: PRT
<213> ORGANISM: Artificial Sequence
<220> FEATURE:
<223> OTHER INFORMATION: [CDS]:1..2979 from SEQ ID NO 189

<400> SEQUENCE: 190

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
```

```
              355                 360                 365
Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
                420                 425                 430

Leu Asn Ile Arg Arg Lys Pro Gln Val Leu Ala Glu Ala Ser Ala Ser
                435                 440                 445

Gln Ala Ser Cys Phe Ser Asp Gly Tyr Pro Leu Pro Ser Trp Thr Trp
                450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
                500                 505                 510

Lys Cys Cys Ala Tyr Asn Ser Leu Gly Thr Ser Cys Glu Thr Ile Leu
                515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
                580                 585                 590

Asp Phe Arg Glu Tyr Glu Tyr Asp Leu Lys Trp Glu Phe Pro Arg Glu
                595                 600                 605

Asn Leu Glu Phe Gly Lys Val Leu Gly Ser Gly Ala Phe Gly Lys Val
                610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
                660                 665                 670

Asn Ile Val Asn Leu Leu Gly Ala Cys Thr Leu Ser Gly Pro Ile Tyr
                675                 680                 685

Leu Ile Phe Glu Tyr Cys Cys Tyr Gly Asp Leu Leu Asn Tyr Leu Arg
                690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
                740                 745                 750

Ser Gly Leu His Gly Asn Ser Phe His Ser Glu Asp Glu Ile Glu Tyr
                755                 760                 765

Glu Asn Gln Lys Arg Leu Glu Glu Glu Asp Leu Asn Val Leu Thr
770                 775                 780
```

```
Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
            805                 810                 815

Val Leu Val Thr His Gly Lys Val Lys Ile Cys Asp Phe Gly Leu
        820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 191
<211> LENGTH: 771
<212> TYPE: DNA
<213> ORGANISM: Artificial Sequence
<220> FEATURE:
<223> OTHER INFORMATION: human FOLR1
<220> FEATURE:
<221> NAME/KEY: CDS
<222> LOCATION: 1..771
<223> OTHER INFORMATION: /transl_table=1

<400> SEQUENCE: 191 atg gcg cag cgc atg acc acc cag ctg ctg ctg ctg gtg tgg gtg        48
Met Ala Gln Arg Met Thr Thr Gln Leu Leu Leu Leu Val Trp Val
1               5                   10                  15 gcg gtg gtg ggc gaa gcg cag acc cgc att gcg tgg gcg cgc acc gaa    96
Ala Val Val Gly Glu Ala Gln Thr Arg Ile Ala Trp Ala Arg Thr Glu
            20                  25                  30 ctg ctg aac gtg tgc atg aac gcg aaa cat cat aaa gaa aaa ccg ggc   144
Leu Leu Asn Val Cys Met Asn Ala Lys His His Lys Glu Lys Pro Gly
        35                  40                  45 ccg gaa gat aaa ctg cat gaa cag tgc cgc ccg tgg cgc aaa aac gcg  192
Pro Glu Asp Lys Leu His Glu Gln Cys Arg Pro Trp Arg Lys Asn Ala
    50                  55                  60 tgc tgc agc acc aac acc agc cag gaa gcg cat aaa gat gtg agc tat  240
Cys Cys Ser Thr Asn Thr Ser Gln Glu Ala His Lys Asp Val Ser Tyr
65                  70                  75                  80 ctg tat cgc ttt aac tgg aac cat tgc ggc gaa atg gcg ccg gcg tgc  288
Leu Tyr Arg Phe Asn Trp Asn His Cys Gly Glu Met Ala Pro Ala Cys
                85                  90                  95
```

```
aaa cgc cat ttt att cag gat acc tgc ctg tat gaa tgc agc ccg aac      336
Lys Arg His Phe Ile Gln Asp Thr Cys Leu Tyr Glu Cys Ser Pro Asn
            100                 105                 110 ctg ggc ccg tgg att cag cag gtg gat cag agc tgg cgc aaa gaa cgc      384
Leu Gly Pro Trp Ile Gln Gln Val Asp Gln Ser Trp Arg Lys Glu Arg
        115                 120                 125 gtg ctg aac gtg ccg ctg tgc aaa gaa gat tgc gaa cag tgg tgg gaa      432
Val Leu Asn Val Pro Leu Cys Lys Glu Asp Cys Glu Gln Trp Trp Glu
130                 135                 140 gat tgc cgc acc agc tat acc tgc aaa agc aac tgg cat aaa ggc tgg      480
Asp Cys Arg Thr Ser Tyr Thr Cys Lys Ser Asn Trp His Lys Gly Trp
145                 150                 155                 160 aac tgg acc agc ggc ttt aac aaa tgc gcg gtg ggc gcg gcg tgc cag      528
Asn Trp Thr Ser Gly Phe Asn Lys Cys Ala Val Gly Ala Ala Cys Gln
                165                 170                 175 ccg ttt cat ttt tat ttt ccg acc ccg acc gtg ctg tgc aac gaa att      576
Pro Phe His Phe Tyr Phe Pro Thr Pro Thr Val Leu Cys Asn Glu Ile
            180                 185                 190 tgg acc cat agc tat aaa gtg agc aac tat agc cgc ggc agc ggc cgc      624
Trp Thr His Ser Tyr Lys Val Ser Asn Tyr Ser Arg Gly Ser Gly Arg
        195                 200                 205 tgc att cag atg tgg ttt gat ccg gcg cag ggc aac ccg aac gaa gaa      672
Cys Ile Gln Met Trp Phe Asp Pro Ala Gln Gly Asn Pro Asn Glu Glu
210                 215                 220 gtg gcg cgc ttt tat gcg gcg gcg atg agc ggc gcg ggc ccg tgg gcg      720
Val Ala Arg Phe Tyr Ala Ala Ala Met Ser Gly Ala Gly Pro Trp Ala
225                 230                 235                 240 gcg tgg ccg ttt ctg ctg agc ctg gcg ctg atg ctg ctg tgg ctg ctg      768
Ala Trp Pro Phe Leu Leu Ser Leu Ala Leu Met Leu Leu Trp Leu Leu
                245                 250                 255 agc                                                                  771
Ser

<210> SEQ ID NO 192
<211> LENGTH: 257
<212> TYPE: PRT
<213> ORGANISM: Artificial Sequence
<220> FEATURE:
<223> OTHER INFORMATION: [CDS]:1..771 from SEQ ID NO 191

<400> SEQUENCE: 192

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
```

```
                    130                 135                 140
Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 193
<211> LENGTH: 969
<212> TYPE: DNA
<213> ORGANISM: Artificial Sequence
<220> FEATURE:
<223> OTHER INFORMATION: human Trop-2
<220> FEATURE:
<221> NAME/KEY: CDS
<222> LOCATION: 1..969
<223> OTHER INFORMATION: /transl_table=1

<400> SEQUENCE: 193 atg gcg cgc ggc ccg ggc ctg gcg ccg ccg ccg ctg cgc ctg ccg ctg      48
Met Ala Arg Gly Pro Gly Leu Ala Pro Pro Pro Leu Arg Leu Pro Leu
1               5                   10                  15 ctg ctg ctg gtg ctg gcg gcg gtg acc ggc cat acc gcg gcg cag gat      96
Leu Leu Leu Val Leu Ala Ala Val Thr Gly His Thr Ala Ala Gln Asp
                20                  25                  30 aac tgc acc tgc ccg acc aac aaa atg acc gtg tgc agc ccg gat ggc     144
Asn Cys Thr Cys Pro Thr Asn Lys Met Thr Val Cys Ser Pro Asp Gly
            35                  40                  45 ccg ggc ggc cgc tgc cag tgc cgc gcg ctg ggc agc ggc atg gcg gtg     192
Pro Gly Gly Arg Cys Gln Cys Arg Ala Leu Gly Ser Gly Met Ala Val
        50                  55                  60 gat tgc agc acc ctg acc agc aaa tgc ctg ctg ctg aaa gcg cgc atg     240
Asp Cys Ser Thr Leu Thr Ser Lys Cys Leu Leu Leu Lys Ala Arg Met
65                  70                  75                  80 agc gcg ccg aaa aac gcg cgc acc ctg gtg cgc ccg agc gaa cat gcg     288
Ser Ala Pro Lys Asn Ala Arg Thr Leu Val Arg Pro Ser Glu His Ala
                85                  90                  95 ctg gtg gat aac gat ggc ctg tat gat ccg gat tgc gat ccg gaa ggc     336
Leu Val Asp Asn Asp Gly Leu Tyr Asp Pro Asp Cys Asp Pro Glu Gly
            100                 105                 110 cgc ttt aaa gcg cgc cag tgc aac cag acc agc gtg tgc tgg tgc gtg     384
Arg Phe Lys Ala Arg Gln Cys Asn Gln Thr Ser Val Cys Trp Cys Val
        115                 120                 125 aac agc gtg ggc gtg cgc cgc acc gat aaa ggc gat ctg agc ctg cgc     432
Asn Ser Val Gly Val Arg Arg Thr Asp Lys Gly Asp Leu Ser Leu Arg
130                 135                 140 tgc gat gaa ctg gtg cgc acc cat cat att ctg att gat ctg cgc cat     480
Cys Asp Glu Leu Val Arg Thr His His Ile Leu Ile Asp Leu Arg His
145                 150                 155                 160
```

| | | |
|---|---|---|
| cgc ccg acc gcg ggc gcg ttt aac cat agc gat ctg gat gcg gaa ctg<br>Arg Pro Thr Ala Gly Ala Phe Asn His Ser Asp Leu Asp Ala Glu Leu<br>                165                      170                    175 | | 528 |
| cgc cgc ctg ttt cgc gaa cgc tat cgc ctg cat ccg aaa ttt gtg gcg<br>Arg Arg Leu Phe Arg Glu Arg Tyr Arg Leu His Pro Lys Phe Val Ala<br>                180                      185                    190 | | 576 |
| gcg gtg cat tat gaa cag ccg acc att cag att gaa ctg cgc cag aac<br>Ala Val His Tyr Glu Gln Pro Thr Ile Gln Ile Glu Leu Arg Gln Asn<br>            195                      200                    205 | | 624 |
| acc agc cag aaa gcg gcg ggc gat gtg gat att ggc gat gcg gcg tat<br>Thr Ser Gln Lys Ala Ala Gly Asp Val Asp Ile Gly Asp Ala Ala Tyr<br>210                      215                      220 | | 672 |
| tat ttt gaa cgc gat att aaa ggc gaa agc ctg ttt cag ggc cgc ggc<br>Tyr Phe Glu Arg Asp Ile Lys Gly Glu Ser Leu Phe Gln Gly Arg Gly<br>225                      230                      235                    240 | | 720 |
| ggc ctg gat ctg cgc gtg cgc ggc gaa ccg ctg cag gtg gaa cgc acc<br>Gly Leu Asp Leu Arg Val Arg Gly Glu Pro Leu Gln Val Glu Arg Thr<br>                245                      250                    255 | | 768 |
| ctg att tat tat ctg gat gaa att ccg ccg aaa ttt agc atg aaa cgc<br>Leu Ile Tyr Tyr Leu Asp Glu Ile Pro Pro Lys Phe Ser Met Lys Arg<br>            260                      265                    270 | | 816 |
| ctg acc gcg ggc ctg att gcg gtg att gtg gtg gtg gtg gtg gcg ctg<br>Leu Thr Ala Gly Leu Ile Ala Val Ile Val Val Val Val Val Ala Leu<br>275                      280                      285 | | 864 |
| gtg gcg ggc atg gcg gtg ctg gtg att acc aac cgc cgc aaa agc ggc<br>Val Ala Gly Met Ala Val Leu Val Ile Thr Asn Arg Arg Lys Ser Gly<br>            290                      295                    300 | | 912 |
| aaa tat aaa aaa gtg gaa att aaa gaa ctg ggc gaa ctg cgc aaa gaa<br>Lys Tyr Lys Lys Val Glu Ile Lys Glu Leu Gly Glu Leu Arg Lys Glu<br>305                      310                      315                    320 | | 960 |
| ccg agc ctg<br>Pro Ser Leu | | 969 |

<210> SEQ ID NO 194
<211> LENGTH: 323
<212> TYPE: PRT
<213> ORGANISM: Artificial Sequence
<220> FEATURE:
<223> OTHER INFORMATION: [CDS]:1..969 from SEQ ID NO 193

<400> SEQUENCE: 194

Met Ala Arg Gly Pro Gly Leu Ala Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

```
Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu
```

<210> SEQ ID NO 195
<211> LENGTH: 369
<212> TYPE: DNA
<213> ORGANISM: Artificial Sequence
<220> FEATURE:
<223> OTHER INFORMATION: human PSCA
<220> FEATURE:
<221> NAME/KEY: CDS
<222> LOCATION: 1..369
<223> OTHER INFORMATION: /transl_table=1

<400> SEQUENCE: 195

```
atg aaa gcg gtg ctg ctg gcg ctg ctg atg gcg ggc ctg gcg ctg cag      48
Met Lys Ala Val Leu Leu Ala Leu Leu Met Ala Gly Leu Ala Leu Gln
1               5                   10                  15 ccg ggc acc gcg ctg ctg tgc tat agc tgc aaa gcg cag gtg agc aac      96
Pro Gly Thr Ala Leu Leu Cys Tyr Ser Cys Lys Ala Gln Val Ser Asn
            20                  25                  30 gaa gat tgc ctg cag gtg gaa aac tgc acc cag ctg ggc gaa cag tgc     144
Glu Asp Cys Leu Gln Val Glu Asn Cys Thr Gln Leu Gly Glu Gln Cys
        35                  40                  45 tgg acc gcg cgc att cgc gcg gtg ggc ctg ctg acc gtg att agc aaa     192
Trp Thr Ala Arg Ile Arg Ala Val Gly Leu Leu Thr Val Ile Ser Lys
    50                  55                  60 ggc tgc agc ctg aac tgc gtg gat gat agc cag gat tat tat gtg ggc     240
Gly Cys Ser Leu Asn Cys Val Asp Asp Ser Gln Asp Tyr Tyr Val Gly
65                  70                  75                  80 aaa aaa aac att acc tgc tgc gat acc gat ctg tgc aac gcg agc ggc     288
Lys Lys Asn Ile Thr Cys Cys Asp Thr Asp Leu Cys Asn Ala Ser Gly
            85                  90                  95 gcg cat gcg ctg cag ccg gcg gcg gcg att ctg gcg ctg ctg ccg gcg     336
Ala His Ala Leu Gln Pro Ala Ala Ala Ile Leu Ala Leu Leu Pro Ala
        100                 105                 110 ctg ggc ctg ctg ctg tgg ggc ccg ggc cag ctg                         369
Leu Gly Leu Leu Leu Trp Gly Pro Gly Gln Leu
```

Leu Gly Leu Leu Leu Trp Gly Pro Gly Gln Leu
        115                 120

<210> SEQ ID NO 196
<211> LENGTH: 123
<212> TYPE: PRT
<213> ORGANISM: Artificial Sequence
<220> FEATURE:
<223> OTHER INFORMATION: [CDS]:1..369 from SEQ ID NO 195

<400> SEQUENCE: 196

Met Lys Ala Val Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120

<210> SEQ ID NO 197
<211> LENGTH: 1854
<212> TYPE: DNA
<213> ORGANISM: Artificial Sequence
<220> FEATURE:
<223> OTHER INFORMATION: EGFR
<220> FEATURE:
<221> NAME/KEY: CDS
<222> LOCATION: 1..1854
<223> OTHER INFORMATION: /transl_table=1

<400> SEQUENCE: 197 atg cgc ccg agc ggc acc gcg ggc gcg gcg ctg ctg gcg ctg ctg gcg      48
Met Arg Pro Ser Gly Thr Ala Gly Ala Ala Leu Leu Ala Leu Leu Ala
1               5                   10                  15 gcg ctg tgc ccg gcg agc cgc gcg ctg gaa gaa aaa aaa gtg tgc cag      96
Ala Leu Cys Pro Ala Ser Arg Ala Leu Glu Glu Lys Lys Val Cys Gln
            20                  25                  30 ggc acc agc aac aaa ctg acc cag ctg ggc acc ttt gaa gat cat ttt     144
Gly Thr Ser Asn Lys Leu Thr Gln Leu Gly Thr Phe Glu Asp His Phe
        35                  40                  45 ctg agc ctg cag cgc atg ttt aac aac tgc gaa gtg gtg ctg ggc aac     192
Leu Ser Leu Gln Arg Met Phe Asn Asn Cys Glu Val Val Leu Gly Asn
    50                  55                  60 ctg gaa att acc tat gtg cag cgc aac tat gat ctg agc ttt ctg aaa     240
Leu Glu Ile Thr Tyr Val Gln Arg Asn Tyr Asp Leu Ser Phe Leu Lys
65                  70                  75                  80 acc att cag gaa gtg gcg ggc tat gtg ctg att gcg ctg aac acc gtg     288
Thr Ile Gln Glu Val Ala Gly Tyr Val Leu Ile Ala Leu Asn Thr Val
                85                  90                  95 gaa cgc att ccg ctg gaa aac ctg cag att att cgc ggc aac atg tat     336
Glu Arg Ile Pro Leu Glu Asn Leu Gln Ile Ile Arg Gly Asn Met Tyr
            100                 105                 110

-continued

| | |
|---|---|
| tat gaa aac agc tat gcg ctg gcg gtg ctg agc aac tat gat gcg aac<br>Tyr Glu Asn Ser Tyr Ala Leu Ala Val Leu Ser Asn Tyr Asp Ala Asn<br>115                        120                     125 | 384 |
| aaa acc ggc ctg aaa gaa ctg ccg atg cgc aac ctg cag gaa att ctg<br>Lys Thr Gly Leu Lys Glu Leu Pro Met Arg Asn Leu Gln Glu Ile Leu<br>130                        135                     140 | 432 |
| cat ggc gcg gtg cgc ttt agc aac aac ccg gcg ctg tgc aac gtg gaa<br>His Gly Ala Val Arg Phe Ser Asn Asn Pro Ala Leu Cys Asn Val Glu<br>145                        150                     155                     160 | 480 |
| agc att cag tgg cgc gat att gtg agc agc gat ttt ctg agc aac atg<br>Ser Ile Gln Trp Arg Asp Ile Val Ser Ser Asp Phe Leu Ser Asn Met<br>                     165                     170                     175 | 528 |
| agc atg gat ttt cag aac cat ctg ggc agc tgc cag aaa tgc gat ccg<br>Ser Met Asp Phe Gln Asn His Leu Gly Ser Cys Gln Lys Cys Asp Pro<br>            180                     185                     190 | 576 |
| agc tgc ccg aac ggc agc tgc tgg ggc gcg ggc gaa gaa aac tgc cag<br>Ser Cys Pro Asn Gly Ser Cys Trp Gly Ala Gly Glu Glu Asn Cys Gln<br>         195                     200                     205 | 624 |
| aaa ctg acc aaa att att tgc gcg cag cag tgc agc ggc cgc tgc cgc<br>Lys Leu Thr Lys Ile Ile Cys Ala Gln Gln Cys Ser Gly Arg Cys Arg<br>210                        215                     220 | 672 |
| ggc aaa agc ccg agc gat tgc tgc cat aac cag tgc gcg gcg ggc tgc<br>Gly Lys Ser Pro Ser Asp Cys Cys His Asn Gln Cys Ala Ala Gly Cys<br>225                        230                     235                     240 | 720 |
| acc ggc ccg cgc gaa agc gat tgc ctg gtg tgc cgc aaa ttt cgc gat<br>Thr Gly Pro Arg Glu Ser Asp Cys Leu Val Cys Arg Lys Phe Arg Asp<br>                     245                     250                     255 | 768 |
| gaa gcg acc tgc aaa gat acc tgc ccg ccg ctg atg ctg tat aac ccg<br>Glu Ala Thr Cys Lys Asp Thr Cys Pro Pro Leu Met Leu Tyr Asn Pro<br>            260                     265                     270 | 816 |
| acc acc tat cag atg gat gtg aac ccg gaa ggc aaa tat agc ttt ggc<br>Thr Thr Tyr Gln Met Asp Val Asn Pro Glu Gly Lys Tyr Ser Phe Gly<br>         275                     280                     285 | 864 |
| gcg acc tgc gtg aaa aaa tgc ccg cgc aac tat gtg gtg acc gat cat<br>Ala Thr Cys Val Lys Lys Cys Pro Arg Asn Tyr Val Val Thr Asp His<br>290                        295                     300 | 912 |
| ggc agc tgc gtg cgc gcg tgc ggc gcg gat agc tat gaa atg gaa gaa<br>Gly Ser Cys Val Arg Ala Cys Gly Ala Asp Ser Tyr Glu Met Glu Glu<br>305                        310                     315                     320 | 960 |
| gat ggc gtg cgc aaa tgc aaa aaa tgc gaa ggc ccg tgc cgc aaa gtg<br>Asp Gly Val Arg Lys Cys Lys Lys Cys Glu Gly Pro Cys Arg Lys Val<br>                     325                     330                     335 | 1008 |
| tgc aac ggc att ggc att ggc gaa ttt aaa gat agc ctg agc att aac<br>Cys Asn Gly Ile Gly Ile Gly Glu Phe Lys Asp Ser Leu Ser Ile Asn<br>            340                     345                     350 | 1056 |
| gcg acc aac att aaa cat ttt aaa aac tgc acc agc att agc ggc gat<br>Ala Thr Asn Ile Lys His Phe Lys Asn Cys Thr Ser Ile Ser Gly Asp<br>         355                     360                     365 | 1104 |
| ctg cat att ctg ccg gtg gcg ttt cgc ggc gat agc ttt acc cat acc<br>Leu His Ile Leu Pro Val Ala Phe Arg Gly Asp Ser Phe Thr His Thr<br>370                        375                     380 | 1152 |
| ccg ccg ctg gat ccg cag gaa ctg gat att ctg aaa acc gtg aaa gaa<br>Pro Pro Leu Asp Pro Gln Glu Leu Asp Ile Leu Lys Thr Val Lys Glu<br>385                        390                     395                     400 | 1200 |
| att acc ggc ttt ctg ctg att cag gcg tgg ccg gaa aac cgc acc gat<br>Ile Thr Gly Phe Leu Leu Ile Gln Ala Trp Pro Glu Asn Arg Thr Asp<br>                     405                     410                     415 | 1248 |
| ctg cat gcg ttt gaa aac ctg gaa att att cgc ggc cgc acc aaa cag<br>Leu His Ala Phe Glu Asn Leu Glu Ile Ile Arg Gly Arg Thr Lys Gln<br>            420                     425                     430 | 1296 |

```
cat ggc cag ttt agc ctg gcg gtg gtg agc ctg aac att acc agc ctg    1344
His Gly Gln Phe Ser Leu Ala Val Val Ser Leu Asn Ile Thr Ser Leu
        435                 440                 445 ggc ctg cgc agc ctg aaa gaa att agc gat ggc gat gtg att att agc    1392
Gly Leu Arg Ser Leu Lys Glu Ile Ser Asp Gly Asp Val Ile Ile Ser
450                 455                 460 ggc aac aaa aac ctg tgc tat gcg aac acc att aac tgg aaa aaa ctg    1440
Gly Asn Lys Asn Leu Cys Tyr Ala Asn Thr Ile Asn Trp Lys Lys Leu
465                 470                 475                 480 ttt ggc acc agc ggc cag aaa acc aaa att att agc aac cgc ggc gaa    1488
Phe Gly Thr Ser Gly Gln Lys Thr Lys Ile Ile Ser Asn Arg Gly Glu
                485                 490                 495 aac agc tgc aaa gcg acc ggc cag gtg tgc cat gcg ctg tgc agc ccg    1536
Asn Ser Cys Lys Ala Thr Gly Gln Val Cys His Ala Leu Cys Ser Pro
            500                 505                 510 gaa ggc tgc tgg ggc ccg gaa ccg cgc gat tgc gtg agc tgc cgc aac    1584
Glu Gly Cys Trp Gly Pro Glu Pro Arg Asp Cys Val Ser Cys Arg Asn
        515                 520                 525 gtg agc cgc ggc cgc gaa tgc gtg gat aaa tgc aac ctg ctg gaa ggc    1632
Val Ser Arg Gly Arg Glu Cys Val Asp Lys Cys Asn Leu Leu Glu Gly
530                 535                 540 gaa ccg cgc gaa ttt gtg gaa aac agc gaa tgc att cag tgc cat ccg    1680
Glu Pro Arg Glu Phe Val Glu Asn Ser Glu Cys Ile Gln Cys His Pro
545                 550                 555                 560 gaa tgc ctg ccg cag gcg atg aac att acc tgc acc ggc cgc ggc ccg    1728
Glu Cys Leu Pro Gln Ala Met Asn Ile Thr Cys Thr Gly Arg Gly Pro
                565                 570                 575 gat aac tgc att cag tgc gcg cat tat att gat ggc ccg cat tgc gtg    1776
Asp Asn Cys Ile Gln Cys Ala His Tyr Ile Asp Gly Pro His Cys Val
            580                 585                 590 aaa acc tgc ccg gcg ggc gtg atg ggc gaa aac aac acc ctg gtg tgg    1824
Lys Thr Cys Pro Ala Gly Val Met Gly Glu Asn Asn Thr Leu Val Trp
        595                 600                 605 aaa tat gcg gat gcg ggc cat gtg tgc cat                            1854
Lys Tyr Ala Asp Ala Gly His Val Cys His
610                 615

<210> SEQ ID NO 198
<211> LENGTH: 618
<212> TYPE: PRT
<213> ORGANISM: Artificial Sequence
<220> FEATURE:
<223> OTHER INFORMATION: [CDS]:1..1854 from SEQ ID NO 197

<400> SEQUENCE: 198

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110
```

```
Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525
```

| | | | | | | | | | | | | |
|---|---|---|---|---|---|---|---|---|---|---|---|---|
| Val | Ser | Arg | Gly | Arg | Glu | Cys | Val | Asp | Lys | Cys | Asn | Leu Leu Glu Gly |
| | 530 | | | | 535 | | | | 540 | | | |
| Glu | Pro | Arg | Glu | Phe | Val | Glu | Asn | Ser | Glu | Cys | Ile | Gln Cys His Pro |
| 545 | | | | 550 | | | | 555 | | | | 560 |
| Glu | Cys | Leu | Pro | Gln | Ala | Met | Asn | Ile | Thr | Cys | Thr | Gly Arg Gly Pro |
| | | | 565 | | | | 570 | | | | 575 | |
| Asp | Asn | Cys | Ile | Gln | Cys | Ala | His | Tyr | Ile | Asp | Gly | Pro His Cys Val |
| | | 580 | | | | 585 | | | | 590 | | |
| Lys | Thr | Cys | Pro | Ala | Gly | Val | Met | Gly | Glu | Asn | Asn | Thr Leu Val Trp |
| | 595 | | | | 600 | | | | 605 | | | |
| Lys | Tyr | Ala | Asp | Ala | Gly | His | Val | Cys | His | | | |
| | 610 | | | | | 615 | | | | | | |

<210> SEQ ID NO 199
<211> LENGTH: 1158
<212> TYPE: DNA
<213> ORGANISM: Artificial Sequence
<220> FEATURE:
<223> OTHER INFORMATION: ovalbumine
<220> FEATURE:
<221> NAME/KEY: CDS
<222> LOCATION: 1..1158
<223> OTHER INFORMATION: /transl_table=1

<400> SEQUENCE: 199

```
atg ggc agc att ggc gcg gcg agc atg gaa ttt tgc ttt gat gtg ttt      48
Met Gly Ser Ile Gly Ala Ala Ser Met Glu Phe Cys Phe Asp Val Phe
1               5                   10                  15 aaa gaa ctg aaa gtg cat cat gcg aac gaa aac att ttt tat tgc ccg      96
Lys Glu Leu Lys Val His His Ala Asn Glu Asn Ile Phe Tyr Cys Pro
            20                  25                  30 att gcg att atg agc gcg ctg gcg atg gtg tat ctg ggc gcg aaa gat     144
Ile Ala Ile Met Ser Ala Leu Ala Met Val Tyr Leu Gly Ala Lys Asp
        35                  40                  45 agc acc cgc acc cag att aac aaa gtg gtg cgc ttt gat aaa ctg ccg     192
Ser Thr Arg Thr Gln Ile Asn Lys Val Val Arg Phe Asp Lys Leu Pro
    50                  55                  60 ggc ttt ggc gat agc att gaa gcg cag tgc ggc acc agc gtg aac gtg     240
Gly Phe Gly Asp Ser Ile Glu Ala Gln Cys Gly Thr Ser Val Asn Val
65                  70                  75                  80 cat agc agc ctg cgc gat att ctg aac cag att acc aaa ccg aac gat     288
His Ser Ser Leu Arg Asp Ile Leu Asn Gln Ile Thr Lys Pro Asn Asp
                85                  90                  95 gtg tat agc ttt agc ctg gcg agc cgc ctg tat gcg gaa gaa cgc tat     336
Val Tyr Ser Phe Ser Leu Ala Ser Arg Leu Tyr Ala Glu Glu Arg Tyr
            100                 105                 110 ccg att ctg ccg gaa tat ctg cag tgc gtg aaa gaa ctg tat cgc ggc     384
Pro Ile Leu Pro Glu Tyr Leu Gln Cys Val Lys Glu Leu Tyr Arg Gly
        115                 120                 125 ggc ctg gaa ccg att aac ttt cag acc gcg gcg gat cag gcg cgc gaa     432
Gly Leu Glu Pro Ile Asn Phe Gln Thr Ala Ala Asp Gln Ala Arg Glu
    130                 135                 140 ctg att aac agc tgg gtg gaa agc cag acc aac ggc att att cgc aac     480
Leu Ile Asn Ser Trp Val Glu Ser Gln Thr Asn Gly Ile Ile Arg Asn
145                 150                 155                 160 gtg ctg cag ccg agc agc gtg gat agc cag acc gcg atg gtg ctg gtg     528
Val Leu Gln Pro Ser Ser Val Asp Ser Gln Thr Ala Met Val Leu Val
                165                 170                 175 aac gcg att gtg ttt aaa ggc ctg tgg gaa aaa gcg ttt aaa gat gaa     576
Asn Ala Ile Val Phe Lys Gly Leu Trp Glu Lys Ala Phe Lys Asp Glu
            180                 185                 190
```

```
gat acc cag gcg atg ccg ttt cgc gtg acc gaa cag gaa agc aaa ccg      624
Asp Thr Gln Ala Met Pro Phe Arg Val Thr Glu Gln Glu Ser Lys Pro
        195                 200                 205 gtg cag atg atg tat cag att ggc ctg ttt cgc gtg gcg agc atg gcg      672
Val Gln Met Met Tyr Gln Ile Gly Leu Phe Arg Val Ala Ser Met Ala
    210                 215                 220 agc gaa aaa atg aaa att ctg gaa ctg ccg ttt gcg agc ggc acc atg      720
Ser Glu Lys Met Lys Ile Leu Glu Leu Pro Phe Ala Ser Gly Thr Met
225                 230                 235                 240 agc atg ctg gtg ctg ctg ccg gat gaa gtg agc ggc ctg gaa cag ctg      768
Ser Met Leu Val Leu Leu Pro Asp Glu Val Ser Gly Leu Glu Gln Leu
                245                 250                 255 gaa agc att att aac ttt gaa aaa ctg acc gaa tgg acc agc agc aac      816
Glu Ser Ile Ile Asn Phe Glu Lys Leu Thr Glu Trp Thr Ser Ser Asn
            260                 265                 270 gtg atg gaa gaa cgc aaa att aaa gtg tat ctg ccg cgc atg aaa atg      864
Val Met Glu Glu Arg Lys Ile Lys Val Tyr Leu Pro Arg Met Lys Met
        275                 280                 285 gaa gaa aaa tat aac ctg acc agc gtg ctg atg gcg atg ggc att acc      912
Glu Glu Lys Tyr Asn Leu Thr Ser Val Leu Met Ala Met Gly Ile Thr
    290                 295                 300 gat gtg ttt agc agc agc gcg aac ctg agc ggc att agc agc gcg gaa      960
Asp Val Phe Ser Ser Ser Ala Asn Leu Ser Gly Ile Ser Ser Ala Glu
305                 310                 315                 320 agc ctg aaa att agc cag gcg gtg cat gcg gcg cat gcg gaa att aac     1008
Ser Leu Lys Ile Ser Gln Ala Val His Ala Ala His Ala Glu Ile Asn
                325                 330                 335 gaa gcg ggc cgc gaa gtg gtg ggc agc gcg gaa gcg ggc gtg gat gcg     1056
Glu Ala Gly Arg Glu Val Val Gly Ser Ala Glu Ala Gly Val Asp Ala
            340                 345                 350 gcg agc gtg agc gaa gaa ttt cgc gcg gat cat ccg ttt ctg ttt tgc     1104
Ala Ser Val Ser Glu Glu Phe Arg Ala Asp His Pro Phe Leu Phe Cys
        355                 360                 365 att aaa cat att gcg acc aac gcg gtg ctg ttt ttt ggc cgc tgc gtg     1152
Ile Lys His Ile Ala Thr Asn Ala Val Leu Phe Phe Gly Arg Cys Val
    370                 375                 380 agc ccg                                                              1158
Ser Pro
385
```

<210> SEQ ID NO 200
<211> LENGTH: 386
<212> TYPE: PRT
<213> ORGANISM: Artificial Sequence
<220> FEATURE:
<223> OTHER INFORMATION: [CDS]:1..1158 from SEQ ID NO 199

<400> SEQUENCE: 200

```
Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
        50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
```

```
                    85                  90                  95
Val Tyr Ser Phe Ser Leu Ala Ser Arg Leu Tyr Ala Glu Arg Tyr
            100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
            195                 200                 205

Val Gln Met Met Tyr Gln Ile Gly Leu Phe Arg Val Ala Ser Met Ala
            210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
            275                 280                 285

Glu Glu Lys Tyr Asn Leu Thr Ser Val Leu Met Ala Met Gly Ile Thr
290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
            370                 375                 380

Ser Pro
385

<210> SEQ ID NO 201
<211> LENGTH: 945
<212> TYPE: DNA
<213> ORGANISM: Artificial Sequence
<220> FEATURE:
<223> OTHER INFORMATION: EpCAM
<220> FEATURE:
<221> NAME/KEY: CDS
<222> LOCATION: 1..945
<223> OTHER INFORMATION: /transl_table=1

<400> SEQUENCE: 201 atg gcg ggc ccg cag gcg ctg gcg ttt ggc ctg ctg ctg gcg gtg gtg      48
Met Ala Gly Pro Gln Ala Leu Ala Phe Gly Leu Leu Leu Ala Val Val
1               5                   10                  15 acc gcg acc ctg gcg gcg gcg cag cgc gat tgc gtg tgc gat aac tat      96
Thr Ala Thr Leu Ala Ala Ala Gln Arg Asp Cys Val Cys Asp Asn Tyr
```

```
                    20                  25                  30
aaa ctg gcg acc agc tgc agc ctg aac gaa tat ggc gaa tgc cag tgc       144
Lys Leu Ala Thr Ser Cys Ser Leu Asn Glu Tyr Gly Glu Cys Gln Cys
        35                  40                  45 acc agc tat ggc acc cag aac acc gtg att tgc agc aaa ctg gcg agc       192
Thr Ser Tyr Gly Thr Gln Asn Thr Val Ile Cys Ser Lys Leu Ala Ser
    50                  55                  60 aaa tgc ctg gcg atg aaa gcg gaa atg acc cat agc aaa agc ggc cgc       240
Lys Cys Leu Ala Met Lys Ala Glu Met Thr His Ser Lys Ser Gly Arg
65                  70                  75                  80 cgc att aaa ccg gaa ggc gcg att cag aac aac gat ggc ctg tat gat       288
Arg Ile Lys Pro Glu Gly Ala Ile Gln Asn Asn Asp Gly Leu Tyr Asp
                85                  90                  95 ccg gat tgc gat gaa cag ggc ctg ttt aaa gcg aaa cag tgc aac ggc       336
Pro Asp Cys Asp Glu Gln Gly Leu Phe Lys Ala Lys Gln Cys Asn Gly
            100                 105                 110 acc gcg acc tgc tgg tgc gtg aac acc gcg ggc gtg cgc cgc acc gat       384
Thr Ala Thr Cys Trp Cys Val Asn Thr Ala Gly Val Arg Arg Thr Asp
        115                 120                 125 aaa gat acc gaa att acc tgc agc gaa cgc gtg cgc acc tat tgg att       432
Lys Asp Thr Glu Ile Thr Cys Ser Glu Arg Val Arg Thr Tyr Trp Ile
130                 135                 140 att att gaa ctg aaa cat aaa gaa cgc gaa agc ccg tat gat cat cag       480
Ile Ile Glu Leu Lys His Lys Glu Arg Glu Ser Pro Tyr Asp His Gln
145                 150                 155                 160 agc ctg cag acc gcg ctg cag gaa gcg ttt acc agc cgc tat aaa ctg       528
Ser Leu Gln Thr Ala Leu Gln Glu Ala Phe Thr Ser Arg Tyr Lys Leu
                165                 170                 175 aac cag aaa ttt att aaa aac att atg tat gaa aac aac gtg att acc       576
Asn Gln Lys Phe Ile Lys Asn Ile Met Tyr Glu Asn Asn Val Ile Thr
            180                 185                 190 att gat ctg atg cag aac agc agc cag aaa acc cag gat gat gtg gat       624
Ile Asp Leu Met Gln Asn Ser Ser Gln Lys Thr Gln Asp Asp Val Asp
        195                 200                 205 att gcg gat gtg gcg tat tat ttt gaa aaa gat gtg aaa ggc gaa agc       672
Ile Ala Asp Val Ala Tyr Tyr Phe Glu Lys Asp Val Lys Gly Glu Ser
210                 215                 220 ctg ttt cat agc agc aaa agc atg gat ctg cgc gtg aac ggc gaa ccg       720
Leu Phe His Ser Ser Lys Ser Met Asp Leu Arg Val Asn Gly Glu Pro
225                 230                 235                 240 ctg gat ctg gat ccg ggc cag acc ctg att tat tat gtg gat gaa aaa       768
Leu Asp Leu Asp Pro Gly Gln Thr Leu Ile Tyr Tyr Val Asp Glu Lys
                245                 250                 255 gcg ccg gaa ttt agc atg cag ggc ctg acc gcg ggc att att gcg gtg       816
Ala Pro Glu Phe Ser Met Gln Gly Leu Thr Ala Gly Ile Ile Ala Val
            260                 265                 270 att gtg gtg gtg agc ctg gcg gtg att gcg ggc att gtg gtg ctg gtg       864
Ile Val Val Val Ser Leu Ala Val Ile Ala Gly Ile Val Val Leu Val
        275                 280                 285 att agc acc cgc aaa aaa agc gcg aaa tat gaa aaa gcg gaa att aaa       912
Ile Ser Thr Arg Lys Lys Ser Ala Lys Tyr Glu Lys Ala Glu Ile Lys
290                 295                 300 gaa atg ggc gaa att cat cgc gaa ctg aac gcg                           945
Glu Met Gly Glu Ile His Arg Glu Leu Asn Ala
305                 310                 315

<210> SEQ ID NO 202
<211> LENGTH: 315
<212> TYPE: PRT
<213> ORGANISM: Artificial Sequence
```

```
<220> FEATURE:
<223> OTHER INFORMATION: [CDS]:1..945 from SEQ ID NO 201

<400> SEQUENCE: 202

Met Ala Gly Pro Gln Ala Leu Ala Phe Gly Leu Leu Ala Val Val
1               5                   10                  15

Thr Ala Thr Leu Ala Ala Ala Gln Arg Asp Cys Val Cys Asp Asn Tyr
                20                  25                  30

Lys Leu Ala Thr Ser Cys Ser Leu Asn Glu Tyr Gly Glu Cys Gln Cys
                35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
                100                 105                 110

Thr Ala Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Val Ile Thr
                180                 185                 190

Ile Asp Leu Met Gln Asn Ser Ser Gln Lys Thr Gln Asp Val Asp
            195                 200                 205

Ile Ala Asp Val Ala Tyr Tyr Phe Glu Lys Asp Val Lys Gly Glu Ser
            210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Gly Ile Ile Ala Val
                260                 265                 270

Ile Val Val Val Ser Leu Ala Val Ile Ala Gly Ile Val Val Leu Val
            275                 280                 285

Ile Ser Thr Arg Lys Lys Ser Ala Lys Tyr Glu Lys Ala Glu Ile Lys
            290                 295                 300

Glu Met Gly Glu Ile His Arg Glu Leu Asn Ala
305                 310                 315

<210> SEQ ID NO 203
<211> LENGTH: 255
<212> TYPE: PRT
<213> ORGANISM: Homo sapiens
<220> FEATURE:
<223> OTHER INFORMATION: Tumor necrosis factor receptor superfamily
      member 9 (4-1-BB)

<400> SEQUENCE: 203

Met Gly Asn Ser Cys Tyr Asn Ile Val Ala Thr Leu Leu Leu Val Leu
1               5                   10                  15
```

```
Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 204
<211> LENGTH: 256
<212> TYPE: PRT
<213> ORGANISM: Mus musculus
<220> FEATURE:
<223> OTHER INFORMATION: Tumor necrosis factor receptor superfamily
      member 9 (4-1-BB)

<400> SEQUENCE: 204

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125
```

```
Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
                180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
    210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 205
<211> LENGTH: 84
<212> TYPE: DNA
<213> ORGANISM: Artificial Sequence
<220> FEATURE:
<223> OTHER INFORMATION: IgK leader sequence
<220> FEATURE:
<221> NAME/KEY: CDS
<222> LOCATION: 1..84
<223> OTHER INFORMATION: /transl_table=1

<400> SEQUENCE: 205 atg gaa aca gat aca ctg ctg ctg tgg gtg ctg ctg ctg tgg gtg cca      48
Met Glu Thr Asp Thr Leu Leu Leu Trp Val Leu Leu Leu Trp Val Pro
1               5                   10                  15 gga tct aca ggg gat ggc gcc cag cct gct aga agc                      84
Gly Ser Thr Gly Asp Gly Ala Gln Pro Ala Arg Ser
            20                  25

<210> SEQ ID NO 206
<211> LENGTH: 28
<212> TYPE: PRT
<213> ORGANISM: Artificial Sequence
<220> FEATURE:
<223> OTHER INFORMATION: [CDS]:1..84 from SEQ ID NO 205

<400> SEQUENCE: 206

Met Glu Thr Asp Thr Leu Leu Leu Trp Val Leu Leu Leu Trp Val Pro
1               5                   10                  15

Gly Ser Thr Gly Asp Gly Ala Gln Pro Ala Arg Ser
            20                  25

<210> SEQ ID NO 207
<211> LENGTH: 2055
<212> TYPE: DNA
<213> ORGANISM: Artificial Sequence
<220> FEATURE:
<223> OTHER INFORMATION: MR1.1 EGFRvIII VH-Ck-(G4S)2 MCSP M4-3 VH CH1 EE
     Fc knob PG LALA, pETR16621
<220> FEATURE:
<221> NAME/KEY: CDS
<222> LOCATION: 1..2055
<223> OTHER INFORMATION: /transl_table=1

<400> SEQUENCE: 207 caa gtg aag ctg cag cag agt ggg ggc gga ctc gtg aaa cct ggc gcc      48
```

```
                Gln Val Lys Leu Gln Gln Ser Gly Gly Gly Leu Val Lys Pro Gly Ala
                1               5                   10                  15 tct ctg aag ctg agc tgc gtg acc agc ggc ttc acc ttc aga aag ttc                 96
Ser Leu Lys Leu Ser Cys Val Thr Ser Gly Phe Thr Phe Arg Lys Phe
            20                  25                  30 ggc atg agc tgg gtg cgc cag acc agc gac aag cgg ctg gaa tgg gtg                144
Gly Met Ser Trp Val Arg Gln Thr Ser Asp Lys Arg Leu Glu Trp Val
        35                  40                  45 gcc agc atc agc acc ggc ggc tac aac acc tac tac agc gac aac gtg                192
Ala Ser Ile Ser Thr Gly Gly Tyr Asn Thr Tyr Tyr Ser Asp Asn Val
    50                  55                  60 aag ggc cgg ttc acc atc agc aga gag aac gcc aag aac acc ctg tac                240
Lys Gly Arg Phe Thr Ile Ser Arg Glu Asn Ala Lys Asn Thr Leu Tyr
65                  70                  75                  80 ctg cag atg agc agc ctg aag tcc gag gac acc gcc ctg tac tac tgc                288
Leu Gln Met Ser Ser Leu Lys Ser Glu Asp Thr Ala Leu Tyr Tyr Cys
                85                  90                  95 acc aga ggc tac agc ccc tac agc tac gcc atg gac tat tgg ggc cag                336
Thr Arg Gly Tyr Ser Pro Tyr Ser Tyr Ala Met Asp Tyr Trp Gly Gln
            100                 105                 110 ggc acc acc gtg acc gtg tca tct gct agc gtg gcc gct ccc tcc gtg                384
Gly Thr Thr Val Thr Val Ser Ser Ala Ser Val Ala Ala Pro Ser Val
        115                 120                 125 ttc atc ttc cca cct tcc gac gag cag ctg aag tcc ggc acc gct tct                432
Phe Ile Phe Pro Pro Ser Asp Glu Gln Leu Lys Ser Gly Thr Ala Ser
    130                 135                 140 gtc gtg tgc ctg ctg aac aac ttc tac ccc cgc gag gcc aag gtg cag                480
Val Val Cys Leu Leu Asn Asn Phe Tyr Pro Arg Glu Ala Lys Val Gln
145                 150                 155                 160 tgg aag gtg gac aac gcc ctg cag tcc ggc aac agc cag gaa tcc gtg                528
Trp Lys Val Asp Asn Ala Leu Gln Ser Gly Asn Ser Gln Glu Ser Val
                165                 170                 175 acc gag cag gac tcc aag gac agc acc tac tcc ctg tcc tcc acc ctg                576
Thr Glu Gln Asp Ser Lys Asp Ser Thr Tyr Ser Leu Ser Ser Thr Leu
            180                 185                 190 acc ctg tcc aag gcc gac tac gag aag cac aag gtg tac gcc tgc gaa                624
Thr Leu Ser Lys Ala Asp Tyr Glu Lys His Lys Val Tyr Ala Cys Glu
        195                 200                 205 gtg acc cac cag ggc ctg tct agc ccc gtg acc aag tct ttc aac cgg                672
Val Thr His Gln Gly Leu Ser Ser Pro Val Thr Lys Ser Phe Asn Arg
    210                 215                 220 ggc gag tgc ggt ggc gga ggt tcc gga ggc gga gga tcc gga gga ggg                720
Gly Glu Cys Gly Gly Gly Gly Ser Gly Gly Gly Gly Ser Gly Gly Gly
225                 230                 235                 240 gga tct cag gtg caa ttg cag gaa agc ggc cct ggc ctg gtc aag ccc                768
Gly Ser Gln Val Gln Leu Gln Glu Ser Gly Pro Gly Leu Val Lys Pro
                245                 250                 255 agc cag acc ctg agc ctg acc tgc acc gtg tcc ggc ggc agc atc acc                816
Ser Gln Thr Leu Ser Leu Thr Cys Thr Val Ser Gly Gly Ser Ile Thr
            260                 265                 270 agc ggc tat tat tgg aac tgg att cgg cag cac ccc ggc aag ggc ctg                864
Ser Gly Tyr Tyr Trp Asn Trp Ile Arg Gln His Pro Gly Lys Gly Leu
        275                 280                 285 gaa tgg atc ggc tac atc act ttc gac ggc tct aac aac tac aac ccc                912
Glu Trp Ile Gly Tyr Ile Thr Phe Asp Gly Ser Asn Asn Tyr Asn Pro
    290                 295                 300 agc ctg aag tcc aga gtg acc atc agc cgg gac acc agc aag aac cag                960
Ser Leu Lys Ser Arg Val Thr Ile Ser Arg Asp Thr Ser Lys Asn Gln
305                 310                 315                 320
```

```
ttc agc ctg aag ctg tcc agc gtg aca gcc gcc gac acc gcc gtg tac    1008
Phe Ser Leu Lys Leu Ser Ser Val Thr Ala Ala Asp Thr Ala Val Tyr
                325                 330                 335 tac tgc gcc gac ttc gac tac tgg ggc cag ggc acc ctg gtc acc gtg    1056
Tyr Cys Ala Asp Phe Asp Tyr Trp Gly Gln Gly Thr Leu Val Thr Val
                340                 345                 350 tcc agc gct agc acc aag ggc ccc tcc gtg ttc ccc ctg gcc ccc agc    1104
Ser Ser Ala Ser Thr Lys Gly Pro Ser Val Phe Pro Leu Ala Pro Ser
                355                 360                 365 agc aag agc acc agc ggc ggc aca gcc gct ctg ggc tgc ctg gtc gag    1152
Ser Lys Ser Thr Ser Gly Gly Thr Ala Ala Leu Gly Cys Leu Val Glu
                370                 375                 380 gac tac ttc ccc gag ccc gtg acc gtg tcc tgg aac agc gga gcc ctg    1200
Asp Tyr Phe Pro Glu Pro Val Thr Val Ser Trp Asn Ser Gly Ala Leu
385                 390                 395                 400 acc tcc ggc gtg cac acc ttc ccc gcc gtg ctg cag agt tct ggc ctg    1248
Thr Ser Gly Val His Thr Phe Pro Ala Val Leu Gln Ser Ser Gly Leu
                405                 410                 415 tat agc ctg agc agc gtg gtc acc gtg cct tct agc agc ctg ggc acc    1296
Tyr Ser Leu Ser Ser Val Val Thr Val Pro Ser Ser Ser Leu Gly Thr
                420                 425                 430 cag acc tac atc tgc aac gtg aac cac aag ccc agc aac acc aag gtg    1344
Gln Thr Tyr Ile Cys Asn Val Asn His Lys Pro Ser Asn Thr Lys Val
                435                 440                 445 gac gag aag gtg gag ccc aag agc tgc gac aaa act cac aca tgc cca    1392
Asp Glu Lys Val Glu Pro Lys Ser Cys Asp Lys Thr His Thr Cys Pro
                450                 455                 460 ccg tgc cca gca cct gaa gct gca ggg gga ccg tca gtc ttc ctc ttc    1440
Pro Cys Pro Ala Pro Glu Ala Ala Gly Gly Pro Ser Val Phe Leu Phe
465                 470                 475                 480 ccc cca aaa ccc aag gac acc ctc atg atc tcc cgg acc cct gag gtc    1488
Pro Pro Lys Pro Lys Asp Thr Leu Met Ile Ser Arg Thr Pro Glu Val
                485                 490                 495 aca tgc gtg gtg gtg gac gtg agc cac gaa gac cct gag gtc aag ttc    1536
Thr Cys Val Val Val Asp Val Ser His Glu Asp Pro Glu Val Lys Phe
                500                 505                 510 aac tgg tac gtg gac ggc gtg gag gtg cat aat gcc aag aca aag ccg    1584
Asn Trp Tyr Val Asp Gly Val Glu Val His Asn Ala Lys Thr Lys Pro
                515                 520                 525 cgg gag gag cag tac aac agc acg tac cgt gtg gtc agc gtc ctc acc    1632
Arg Glu Glu Gln Tyr Asn Ser Thr Tyr Arg Val Val Ser Val Leu Thr
530                 535                 540 gtc ctg cac cag gac tgg ctg aat ggc aag gag tac aag tgc aag gtc    1680
Val Leu His Gln Asp Trp Leu Asn Gly Lys Glu Tyr Lys Cys Lys Val
545                 550                 555                 560 tcc aac aaa gcc ctc ggc gcc ccc atc gag aaa acc atc tcc aaa gcc    1728
Ser Asn Lys Ala Leu Gly Ala Pro Ile Glu Lys Thr Ile Ser Lys Ala
                565                 570                 575 aaa ggg cag ccc cga gaa cca cag gtg tac acc ctg ccc cca tgc cgg    1776
Lys Gly Gln Pro Arg Glu Pro Gln Val Tyr Thr Leu Pro Pro Cys Arg
                580                 585                 590 gat gag ctg acc aag aac cag gtc agc ctg tgg tgc ctg gtc aaa ggc    1824
Asp Glu Leu Thr Lys Asn Gln Val Ser Leu Trp Cys Leu Val Lys Gly
                595                 600                 605 ttc tat ccc agc gac atc gcc gtg gag tgg gag agc aat ggg cag ccg    1872
Phe Tyr Pro Ser Asp Ile Ala Val Glu Trp Glu Ser Asn Gly Gln Pro
                610                 615                 620 gag aac aac tac aag acc acg cct ccc gtg ctg gac tcc gac ggc tcc    1920
Glu Asn Asn Tyr Lys Thr Thr Pro Pro Val Leu Asp Ser Asp Gly Ser
625                 630                 635                 640
```

```
ttc ttc ctc tac agc aag ctc acc gtg gac aag agc agg tgg cag cag     1968
Phe Phe Leu Tyr Ser Lys Leu Thr Val Asp Lys Ser Arg Trp Gln Gln
            645                 650                 655 ggg aac gtc ttc tca tgc tcc gtg atg cat gag gct ctg cac aac cac     2016
Gly Asn Val Phe Ser Cys Ser Val Met His Glu Ala Leu His Asn His
        660                 665                 670 tac acg cag aag agc ctc tcc ctg tct ccg ggt aaa tga                 2055
Tyr Thr Gln Lys Ser Leu Ser Leu Ser Pro Gly Lys
        675                 680
```

<210> SEQ ID NO 208
<211> LENGTH: 684
<212> TYPE: PRT
<213> ORGANISM: Artificial Sequence
<220> FEATURE:
<223> OTHER INFORMATION: [CDS]:1..2055 from SEQ ID NO 207

<400> SEQUENCE: 208

```
Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Gly Gly Gly Gly Ser Gly Gly Gly Gly Ser Gly Gly Gly
225                 230                 235                 240

Gly Ser Gln Val Gln Leu Gln Glu Ser Gly Pro Gly Leu Val Lys Pro
                245                 250                 255

Ser Gln Thr Leu Ser Leu Thr Cys Thr Val Ser Gly Gly Ser Ile Thr
            260                 265                 270

Ser Gly Tyr Tyr Trp Asn Trp Ile Arg Gln His Pro Gly Lys Gly Leu
        275                 280                 285

Glu Trp Ile Gly Tyr Ile Thr Phe Asp Gly Ser Asn Asn Tyr Asn Pro
    290                 295                 300
```

Ser Leu Lys Ser Arg Val Thr Ile Ser Arg Asp Thr Ser Lys Asn Gln
305                 310                 315                 320

Phe Ser Leu Lys Leu Ser Ser Val Thr Ala Ala Asp Thr Ala Val Tyr
            325                 330                 335

Tyr Cys Ala Asp Phe Asp Tyr Trp Gly Gln Gly Thr Leu Val Thr Val
        340                 345                 350

Ser Ser Ala Ser Thr Lys Gly Pro Ser Val Phe Pro Leu Ala Pro Ser
            355                 360                 365

Ser Lys Ser Thr Ser Gly Gly Thr Ala Ala Leu Gly Cys Leu Val Glu
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
            420                 425                 430

Gln Thr Tyr Ile Cys Asn Val Asn His Lys Pro Ser Asn Thr Lys Val
        435                 440                 445

Asp Glu Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
            485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
530                 535                 540

Val Leu His Gln Asp Trp Leu Asn Gly Lys Glu Tyr Lys Cys Lys Val
545                 550                 555                 560

Ser Asn Lys Ala Leu Gly Ala Pro Ile Glu Lys Thr Ile Ser Lys Ala
            565                 570                 575

Lys Gly Gln Pro Arg Glu Pro Gln Val Tyr Thr Leu Pro Pro Cys Arg
            580                 585                 590

Asp Glu Leu Thr Lys Asn Gln Val Ser Leu Trp Cys Leu Val Lys Gly
        595                 600                 605

Phe Tyr Pro Ser Asp Ile Ala Val Glu Trp Glu Ser Asn Gly Gln Pro
610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
            645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680

<210> SEQ ID NO 209
<211> LENGTH: 639
<212> TYPE: DNA
<213> ORGANISM: Artificial Sequence
<220> FEATURE:

<223> OTHER INFORMATION: EGFR vIII MR1.1 VL CH1, pETR15656
<220> FEATURE:
<221> NAME/KEY: CDS
<222> LOCATION: 1..639
<223> OTHER INFORMATION: /transl_table=1

<400> SEQUENCE: 209

```
gat atc gag ctg aca cag agc ccc gcc agc ctg tct gtg gcc acc ggc      48
Asp Ile Glu Leu Thr Gln Ser Pro Ala Ser Leu Ser Val Ala Thr Gly
1               5                   10                  15 gag aaa gtg acc atc cgg tgc atg acc agc acc gac atc gac gac gac      96
Glu Lys Val Thr Ile Arg Cys Met Thr Ser Thr Asp Ile Asp Asp Asp
                20                  25                  30 atg aac tgg tat cag cag aag ccc ggc gag ccc ccc aag ttc ctg atc     144
Met Asn Trp Tyr Gln Gln Lys Pro Gly Glu Pro Pro Lys Phe Leu Ile
            35                  40                  45 agc gag ggc aac aca ctg cgg cct ggc gtg cca agc aga ttc agc agc     192
Ser Glu Gly Asn Thr Leu Arg Pro Gly Val Pro Ser Arg Phe Ser Ser
        50                  55                  60 tct ggc acc ggc acc gac ttc gtg ttt acc atc gag aat acc ctg agc     240
Ser Gly Thr Gly Thr Asp Phe Val Phe Thr Ile Glu Asn Thr Leu Ser
65                  70                  75                  80 gag gac gtg ggc gac tac tac tgc ctg cag agc tgg aac gtg ccc ctg     288
Glu Asp Val Gly Asp Tyr Tyr Cys Leu Gln Ser Trp Asn Val Pro Leu
                85                  90                  95 acc ttt ggc gac ggc acc aag ctg gaa atc aag agc agc gct agc acc     336
Thr Phe Gly Asp Gly Thr Lys Leu Glu Ile Lys Ser Ser Ala Ser Thr
                100                 105                 110 aaa ggc cct tcc gtg ttt cct ctg gct cct agc tcc aag tcc acc tct     384
Lys Gly Pro Ser Val Phe Pro Leu Ala Pro Ser Ser Lys Ser Thr Ser
            115                 120                 125 gga ggc acc gct gct ctc gga tgc ctc gtg aag gat tat ttt cct gag     432
Gly Gly Thr Ala Ala Leu Gly Cys Leu Val Lys Asp Tyr Phe Pro Glu
        130                 135                 140 cct gtg aca gtg tcc tgg aat agc gga gca ctg acc tct gga gtg cat     480
Pro Val Thr Val Ser Trp Asn Ser Gly Ala Leu Thr Ser Gly Val His
145                 150                 155                 160 act ttc ccc gct gtg ctg cag tcc tct gga ctg tac agc ctg agc agc     528
Thr Phe Pro Ala Val Leu Gln Ser Ser Gly Leu Tyr Ser Leu Ser Ser
                165                 170                 175 gtg gtg aca gtg ccc agc agc agc ctg ggc acc cag acc tac atc tgc     576
Val Val Thr Val Pro Ser Ser Ser Leu Gly Thr Gln Thr Tyr Ile Cys
                180                 185                 190 aac gtg aac cac aag ccc agc aac acc aag gtg gac aag aag gtg gaa     624
Asn Val Asn His Lys Pro Ser Asn Thr Lys Val Asp Lys Lys Val Glu
            195                 200                 205 ccc aag tct tgt tga                                                  639
Pro Lys Ser Cys
    210
```

<210> SEQ ID NO 210
<211> LENGTH: 212
<212> TYPE: PRT
<213> ORGANISM: Artificial Sequence
<220> FEATURE:
<223> OTHER INFORMATION: [CDS]:1..639 from SEQ ID NO 209

<400> SEQUENCE: 210

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
                20                  25                  30
```

Met Asn Trp Tyr Gln Gln Lys Pro Gly Glu Pro Pro Lys Phe Leu Ile
                35                  40                  45

Ser Glu Gly Asn Thr Leu Arg Pro Gly Val Pro Ser Arg Phe Ser Ser
 50                  55                  60

Ser Gly Thr Gly Thr Asp Phe Val Phe Thr Ile Glu Asn Thr Leu Ser
 65                  70                  75                  80

Glu Asp Val Gly Asp Tyr Tyr Cys Leu Gln Ser Trp Asn Val Pro Leu
                 85                  90                  95

Thr Phe Gly Asp Gly Thr Lys Leu Glu Ile Lys Ser Ser Ala Ser Thr
                100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
        210

<210> SEQ ID NO 211
<211> LENGTH: 645
<212> TYPE: DNA
<213> ORGANISM: Artificial Sequence
<220> FEATURE:
<223> OTHER INFORMATION: MCSP ML2 VL Ck RK, pETR16619
<220> FEATURE:
<221> NAME/KEY: CDS
<222> LOCATION: 1..645
<223> OTHER INFORMATION: /transl_table=1

<400> SEQUENCE: 211 gac atc cag atg acc cag agc ccc agc agc ctg agc gcc agc gtg ggc    48
Asp Ile Gln Met Thr Gln Ser Pro Ser Ser Leu Ser Ala Ser Val Gly
 1               5                  10                  15 gac aga gtg acc atc acc tgc cgg gcc agc cag ggc atc cgg aac tac    96
Asp Arg Val Thr Ile Thr Cys Arg Ala Ser Gln Gly Ile Arg Asn Tyr
                20                  25                  30 ctg aac tgg tat cag cag aag ccc ggc aag gcc ccc aag ctg ctg atc   144
Leu Asn Trp Tyr Gln Gln Lys Pro Gly Lys Ala Pro Lys Leu Leu Ile
             35                  40                  45 tac tac acc agc agc ctg cac agc ggc gtg cct agc cgg ttt agc ggc   192
Tyr Tyr Thr Ser Ser Leu His Ser Gly Val Pro Ser Arg Phe Ser Gly
 50                  55                  60 agc ggc tcc ggc acc gac tac acc ctg acc att agc tcc ctg cag ccc   240
Ser Gly Ser Gly Thr Asp Tyr Thr Leu Thr Ile Ser Ser Leu Gln Pro
 65                  70                  75                  80 gag gac ttc gcc acc tac tac tgc cag cag tac tct gct ctg ccg tgg   288
Glu Asp Phe Ala Thr Tyr Tyr Cys Gln Gln Tyr Ser Ala Leu Pro Trp
                 85                  90                  95 acc ttc ggc cag gga aca aag gtg gag atc aag cgt acg gtg gct gca   336
Thr Phe Gly Gln Gly Thr Lys Val Glu Ile Lys Arg Thr Val Ala Ala
                100                 105                 110

-continued

| | | |
|---|---|---|
| cca tct gtc ttc atc ttc ccg cca tct gat cgg aag ttg aaa tct gga<br>Pro Ser Val Phe Ile Phe Pro Pro Ser Asp Arg Lys Leu Lys Ser Gly<br>     115                      120                      125 | 384 |
| act gcc tct gtt gtg tgc ctg ctg aat aac ttc tat ccc aga gag gcc<br>Thr Ala Ser Val Val Cys Leu Leu Asn Asn Phe Tyr Pro Arg Glu Ala<br>130                      135                      140 | 432 |
| aaa gta cag tgg aag gtg gat aac gcc ctc caa tcg ggt aac tcc cag<br>Lys Val Gln Trp Lys Val Asp Asn Ala Leu Gln Ser Gly Asn Ser Gln<br>145                      150                      155                      160 | 480 |
| gag agt gtc aca gag cag gac agc aag gac agc acc tac agc ctc agc<br>Glu Ser Val Thr Glu Gln Asp Ser Lys Asp Ser Thr Tyr Ser Leu Ser<br>                      165                      170                      175 | 528 |
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>            180                      185                      190 | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>     195                      200                      205 | 624 |
| ttc aac agg gga gag tgt tag<br>Phe Asn Arg Gly Glu Cys<br>    210 | 645 |

<210> SEQ ID NO 212
<211> LENGTH: 214
<212> TYPE: PRT
<213> ORGANISM: Artificial Sequence
<220> FEATURE:
<223> OTHER INFORMATION: [CDS]:1..645 from SEQ ID NO 211

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 213
<211> LENGTH: 1329
<212> TYPE: DNA
<213> ORGANISM: Artificial Sequence
<220> FEATURE:
<223> OTHER INFORMATION: MCSP M4-3 VH CH1 EE Fc hole PG LALA HYRF, pETR16618
<220> FEATURE:
<221> NAME/KEY: CDS
<222> LOCATION: 1..1329
<223> OTHER INFORMATION: /transl_table=1

<400> SEQUENCE: 213

```
cag gtg caa ttg cag gaa agc ggc cct ggc ctg gtc aag ccc agc cag      48
Gln Val Gln Leu Gln Glu Ser Gly Pro Gly Leu Val Lys Pro Ser Gln
1               5                   10                  15 acc ctg agc ctg acc tgc acc gtg tcc ggc ggc agc atc acc agc ggc      96
Thr Leu Ser Leu Thr Cys Thr Val Ser Gly Gly Ser Ile Thr Ser Gly
            20                  25                  30 tat tat tgg aac tgg att cgg cag cac ccc ggc aag ggc ctg gaa tgg    144
Tyr Tyr Trp Asn Trp Ile Arg Gln His Pro Gly Lys Gly Leu Glu Trp
        35                  40                  45 atc ggc tac atc act ttc gac ggc tct aac aac tac aac ccc agc ctg    192
Ile Gly Tyr Ile Thr Phe Asp Gly Ser Asn Asn Tyr Asn Pro Ser Leu
    50                  55                  60 aag tcc aga gtg acc atc agc cgg gac acc agc aag aac cag ttc agc    240
Lys Ser Arg Val Thr Ile Ser Arg Asp Thr Ser Lys Asn Gln Phe Ser
65                  70                  75                  80 ctg aag ctg tcc agc gtg aca gcc gcc gac acc gcc gtg tac tac tgc    288
Leu Lys Leu Ser Ser Val Thr Ala Ala Asp Thr Ala Val Tyr Tyr Cys
                85                  90                  95 gcc gac ttc gac tac tgg ggc cag ggc acc ctg gtc acc gtg tcc agc    336
Ala Asp Phe Asp Tyr Trp Gly Gln Gly Thr Leu Val Thr Val Ser Ser
            100                 105                 110 gct agc acc aag ggc ccc tcc gtg ttc ccc ctg gcc ccc agc agc aag    384
Ala Ser Thr Lys Gly Pro Ser Val Phe Pro Leu Ala Pro Ser Ser Lys
        115                 120                 125 agc acc agc ggc ggc aca gcc gct ctg ggc tgc ctg gtc gag gac tac    432
Ser Thr Ser Gly Gly Thr Ala Ala Leu Gly Cys Leu Val Glu Asp Tyr
    130                 135                 140 ttc ccc gag ccc gtg acc gtg tcc tgg aac agc gga gcc ctg acc tcc    480
Phe Pro Glu Pro Val Thr Val Ser Trp Asn Ser Gly Ala Leu Thr Ser
145                 150                 155                 160 ggc gtg cac acc ttc ccc gcc gtg ctg cag agt tct ggc ctg tat agc    528
Gly Val His Thr Phe Pro Ala Val Leu Gln Ser Ser Gly Leu Tyr Ser
                165                 170                 175 ctg agc agc gtg gtc acc gtg cct tct agc agc ctg ggc acc cag acc    576
Leu Ser Ser Val Val Thr Val Pro Ser Ser Ser Leu Gly Thr Gln Thr
            180                 185                 190 tac atc tgc aac gtg aac cac aag ccc agc aac acc aag gtg gac gag    624
Tyr Ile Cys Asn Val Asn His Lys Pro Ser Asn Thr Lys Val Asp Glu
        195                 200                 205 aag gtg gag ccc aag agc tgc gac aaa act cac aca tgc cca ccg tgc    672
Lys Val Glu Pro Lys Ser Cys Asp Lys Thr His Thr Cys Pro Pro Cys
    210                 215                 220 cca gca cct gaa gct gca ggg gga ccg tca gtc ttc ctc ttc ccc cca    720
Pro Ala Pro Glu Ala Ala Gly Gly Pro Ser Val Phe Leu Phe Pro Pro
225                 230                 235                 240 aaa ccc aag gac acc ctc atg atc tcc cgg acc cct gag gtc aca tgc    768
Lys Pro Lys Asp Thr Leu Met Ile Ser Arg Thr Pro Glu Val Thr Cys
                245                 250                 255
```

```
gtg gtg gtg gac gtg agc cac gaa gac cct gag gtc aag ttc aac tgg      816
Val Val Val Asp Val Ser His Glu Asp Pro Glu Val Lys Phe Asn Trp
            260                 265                 270 tac gtg gac ggc gtg gag gtg cat aat gcc aag aca aag ccg cgg gag      864
Tyr Val Asp Gly Val Glu Val His Asn Ala Lys Thr Lys Pro Arg Glu
        275                 280                 285 gag cag tac aac agc acg tac cgt gtg gtc agc gtc ctc acc gtc ctg      912
Glu Gln Tyr Asn Ser Thr Tyr Arg Val Val Ser Val Leu Thr Val Leu
    290                 295                 300 cac cag gac tgg ctg aat ggc aag gag tac aag tgc aag gtc tcc aac      960
His Gln Asp Trp Leu Asn Gly Lys Glu Tyr Lys Cys Lys Val Ser Asn
305                 310                 315                 320 aaa gcc ctc ggc gcc ccc atc gag aaa acc atc tcc aaa gcc aaa ggg     1008
Lys Ala Leu Gly Ala Pro Ile Glu Lys Thr Ile Ser Lys Ala Lys Gly
                325                 330                 335 cag ccc cga gaa cca cag gtg tgc acc ctg ccc cca tcc cgg gat gag     1056
Gln Pro Arg Glu Pro Gln Val Cys Thr Leu Pro Pro Ser Arg Asp Glu
            340                 345                 350 ctg acc aag aac cag gtc agc ctc tcg tgc gca gtc aaa ggc ttc tat     1104
Leu Thr Lys Asn Gln Val Ser Leu Ser Cys Ala Val Lys Gly Phe Tyr
        355                 360                 365 ccc agc gac atc gcc gtg gag tgg gag agc aat ggg cag ccg gag aac     1152
Pro Ser Asp Ile Ala Val Glu Trp Glu Ser Asn Gly Gln Pro Glu Asn
    370                 375                 380 aac tac aag acc acg cct ccc gtg ctg gac tcc gac ggc tcc ttc ttc     1200
Asn Tyr Lys Thr Thr Pro Pro Val Leu Asp Ser Asp Gly Ser Phe Phe
385                 390                 395                 400 ctc gtg agc aag ctc acc gtg gac aag agc agg tgg cag cag ggg aac     1248
Leu Val Ser Lys Leu Thr Val Asp Lys Ser Arg Trp Gln Gln Gly Asn
                405                 410                 415 gtc ttc tca tgc tcc gtg atg cat gag gct ctg cac aac cgc ttc acg     1296
Val Phe Ser Cys Ser Val Met His Glu Ala Leu His Asn Arg Phe Thr
            420                 425                 430 cag aag agc ctc tcc ctg tct ccg ggt aaa tga                         1329
Gln Lys Ser Leu Ser Leu Ser Pro Gly Lys
        435                 440

<210> SEQ ID NO 214
<211> LENGTH: 442
<212> TYPE: PRT
<213> ORGANISM: Artificial Sequence
<220> FEATURE:
<223> OTHER INFORMATION: [CDS]:1..1329 from SEQ ID NO 213

<400> SEQUENCE: 214

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Phe Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110
```

```
Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Glu Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Glu
        195                 200                 205

Lys Val Glu Pro Lys Ser Cys Asp Lys Thr His Thr Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Gly Ala Pro Ile Glu Lys Thr Ile Ser Lys Ala Lys Gly
                325                 330                 335

Gln Pro Arg Glu Pro Gln Val Cys Thr Leu Pro Pro Ser Arg Asp Glu
            340                 345                 350

Leu Thr Lys Asn Gln Val Ser Leu Ser Cys Ala Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Val Ser Lys Leu Thr Val Asp Lys Ser Arg Trp Gln Gln Gly Asn
                405                 410                 415

Val Phe Ser Cys Ser Val Met His Glu Ala Leu His Asn Arg Phe Thr
            420                 425                 430

Gln Lys Ser Leu Ser Leu Ser Pro Gly Lys
        435                 440

<210> SEQ ID NO 215
<211> LENGTH: 5
<212> TYPE: PRT
<213> ORGANISM: Artificial Sequence
<220> FEATURE:
<223> OTHER INFORMATION: EGFRvIII MR1.1 CDR H1 Kabat

<400> SEQUENCE: 215

Lys Phe Gly Met Ser
1               5

<210> SEQ ID NO 216
```

```
<211> LENGTH: 17
<212> TYPE: PRT
<213> ORGANISM: Artificial Sequence
<220> FEATURE:
<223> OTHER INFORMATION: EGFRvIII MR1.1 CDR H2 Kabat

<400> SEQUENCE: 216

Ser Ile Ser Thr Gly Gly Tyr Asn Thr Tyr Tyr Ser Asp Asn Val Lys
1               5                   10                  15
Gly

<210> SEQ ID NO 217
<211> LENGTH: 11
<212> TYPE: PRT
<213> ORGANISM: Artificial Sequence
<220> FEATURE:
<223> OTHER INFORMATION: EGFRvIII MR1.1 CDR H3 Kabat

<400> SEQUENCE: 217

Gly Tyr Ser Pro Tyr Ser Tyr Ala Met Asp Tyr
1               5                   10

<210> SEQ ID NO 218
<211> LENGTH: 11
<212> TYPE: PRT
<213> ORGANISM: Artificial Sequence
<220> FEATURE:
<223> OTHER INFORMATION: EGFRvIII MR1.1 CDR1 L1 Kabat

<400> SEQUENCE: 218

Met Thr Ser Thr Asp Ile Asp Asp Asp Met Asn
1               5                   10

<210> SEQ ID NO 219
<211> LENGTH: 7
<212> TYPE: PRT
<213> ORGANISM: Artificial Sequence
<220> FEATURE:
<223> OTHER INFORMATION: EGFRvIII MR1.1 CDR L2 Kabat

<400> SEQUENCE: 219

Glu Gly Asn Thr Leu Arg Pro
1               5

<210> SEQ ID NO 220
<211> LENGTH: 9
<212> TYPE: PRT
<213> ORGANISM: Artificial Sequence
<220> FEATURE:
<223> OTHER INFORMATION: EGFRvIII MR1.1 CDR L3 Kabat

<400> SEQUENCE: 220

Leu Gln Ser Trp Asn Val Pro Leu Thr
1               5

<210> SEQ ID NO 221
<211> LENGTH: 6
<212> TYPE: PRT
<213> ORGANISM: Artificial Sequence
<220> FEATURE:
<223> OTHER INFORMATION: MCSP CDR H1 Kabat

<400> SEQUENCE: 221

Ser Gly Tyr Tyr Trp Asn
1               5
```

```
<210> SEQ ID NO 222
<211> LENGTH: 16
<212> TYPE: PRT
<213> ORGANISM: Artificial Sequence
<220> FEATURE:
<223> OTHER INFORMATION: MCSP CDR H2 Kabat

<400> SEQUENCE: 222

Tyr Ile Thr Phe Asp Gly Ser Asn Asn Tyr Asn Pro Ser Leu Lys Ser
1               5                   10                  15

<210> SEQ ID NO 223
<211> LENGTH: 4
<212> TYPE: PRT
<213> ORGANISM: Artificial Sequence
<220> FEATURE:
<223> OTHER INFORMATION: MCSP CDR H3 Kabat

<400> SEQUENCE: 223

Phe Asp Tyr Tyr
1

<210> SEQ ID NO 224
<211> LENGTH: 11
<212> TYPE: PRT
<213> ORGANISM: Artificial Sequence
<220> FEATURE:
<223> OTHER INFORMATION: MCSP CDR1 L1 Kabat

<400> SEQUENCE: 224

Arg Ala Ser Gln Gly Ile Arg Asn Tyr Leu Asn
1               5                   10

<210> SEQ ID NO 225
<211> LENGTH: 7
<212> TYPE: PRT
<213> ORGANISM: Artificial Sequence
<220> FEATURE:
<223> OTHER INFORMATION: MCSP CDR L2 Kabat

<400> SEQUENCE: 225

Tyr Thr Ser Ser Leu His Ser
1               5

<210> SEQ ID NO 226
<211> LENGTH: 9
<212> TYPE: PRT
<213> ORGANISM: Artificial Sequence
<220> FEATURE:
<223> OTHER INFORMATION: MCSP CDR L3 Kabat

<400> SEQUENCE: 226

Gln Gln Tyr Ser Ala Leu Pro Trp Thr
1               5

<210> SEQ ID NO 227
<211> LENGTH: 768
<212> TYPE: DNA
<213> ORGANISM: Homo sapiens
<220> FEATURE:
<223> OTHER INFORMATION: Tumor necrosis factor receptor superfamily
      member 9 (4-1-BB)

<400> SEQUENCE: 227
atgggcaaca actgctataa cgtggtggtg attgtgctgc tgctggtggg ctgcgaaaaa      60
gtgggcgcgg tgcagaacag ctgcgataac tgccagccgg gcacctttg  ccgcaaatat    120
```

-continued

```
aacccggtgt gcaaaagctg cccgccgagc acctttagca gcattggcgg ccagccgaac      180
tgcaacattt gccgcgtgtg cgcgggctat tttcgcttta aaaattttg cagcagcacc       240 cataacgcgg aatgcgaatg cattgaaggc tttcattgcc tgggcccgca gtgcacccgc      300
tgcgaaaaag attgccgccc gggccaggaa ctgaccaaac agggctgcaa acctgcagc       360 ctgggcacct taacgatca gaacggcacc ggcgtgtgcc gcccgtggac caactgcagc      420
ctggatggcc gcagcgtgct gaaaaccggc accaccgaaa aagatgtggt gtgcggcccg      480
ccggtggtga gctttagccc gagcaccacc attagcgtga ccccggaagg cggcccgggc      540
ggccatagcc tgcaggtgct gaccctgttt ctggcgctga ccagcgcgct gctgctggcg      600
ctgattttta ttaccctgct gtttagcgtg ctgaaatgga ttcgcaaaaa atttccgcat      660
atttttaaac agccgtttaa aaaaccacc ggcgcggcgc aggaagaaga tgcgtgcagc      720
tgccgctgcc cgcaggaaga gaaggcggc ggcggcggct atgaactg                   768
```

<210> SEQ ID NO 228
<211> LENGTH: 765
<212> TYPE: DNA
<213> ORGANISM: Mus musculus
<220> FEATURE:
<223> OTHER INFORMATION: Tumor necrosis factor receptor superfamily member 9 (4-1-BB)

<400> SEQUENCE: 228

```
atgggcaaca gctgctataa cattgtggcg accctgctgc tggtgctgaa ctttgaacgc       60
acccgcagcc tgcaggatcc gtgcagcaac tgcccggcgg gcaccttttg cgataacaac      120
cgcaaccaga tttgcagccc gtgcccgccg aacagcttta gcgcgcgggg cggccagcgc      180
acctgcgata tttgccgcca gtgcaaaggc gtgtttcgca cccgcaaaga atgcagcagc      240
accagcaacg cggaatgcga ttgcacccccg ggctttcatt gcctgggcgc gggctgcagc      300
atgtgcgaac aggattgcaa acagggccag gaactgacca aaaaaggctg caaagattgc      360
tgctttggca cctttaacga tcagaaacgc ggcatttgcc gcccgtggac caactgcagc      420
ctggatggca aaagcgtgct ggtgaacggc accaaagaac gcgatgtggt gtgcggcccg      480
agcccggcgg atctgagccc gggcgcgagc agcgtgaccc gccggcgcc ggcgcgcgaa      540 ccgggccata gcccgcagat tattagctttt tttctggcgc tgaccagcac cgcgctgctg      600
tttctgctgt ttttttctgac cctgcgcttt agcgtggtga acgcggccg caaaaaactg      660 ctgtatattt ttaaacagcc gtttatgcgc ccggtgcaga ccacccagga gaagatggc      720 tgcagctgcc gctttccgga agaagaagaa ggcggctgcg aactg                     765
```

<210> SEQ ID NO 229
<211> LENGTH: 214
<212> TYPE: PRT
<213> ORGANISM: Artificial Sequence
<220> FEATURE:
<223> OTHER INFORMATION: Light chain without leader sequence

<400> SEQUENCE: 229

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
                20                  25                  30

Leu Ala Trp Tyr Gln Gln Lys Ser Gly Lys Ser Pro Gln Leu Leu Ile
            35                  40                  45

Tyr Ala Thr Ser Arg Leu Gln Asp Gly Val Pro Ser Arg Phe Ser Gly

```
            50                  55                  60
Ser Gly Ser Gly Thr Arg Tyr Ser Leu Lys Ile Ser Gly Met Gln Pro
 65                  70                  75                  80

Glu Asp Glu Ala Asp Tyr Phe Cys Gln Gln Ser Tyr Lys Tyr Pro Trp
                     85                  90                  95

Thr Phe Gly Gly Gly Thr Lys Leu Glu Leu Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
            210

<210> SEQ ID NO 230
<211> LENGTH: 703
<212> TYPE: PRT
<213> ORGANISM: Artificial Sequence
<220> FEATURE:
<223> OTHER INFORMATION: Heavy chain without leader sequence

<400> SEQUENCE: 230

Glu Val Gln Leu Ala Glu Ser Gly Gly Gly Leu Val Gln Pro Gly Arg
 1               5                  10                  15

Ser Met Lys Leu Ser Cys Ala Ala Ser Gly Phe Thr Phe Ser Asn Phe
                20                  25                  30

Pro Met Ala Trp Val Arg Gln Ala Pro Thr Lys Gly Leu Glu Trp Val
            35                  40                  45

Ala Thr Ile Ser Thr Ser Gly Gly Ser Thr Tyr Tyr Arg Asp Ser Val
 50                  55                  60

Lys Gly Arg Phe Thr Ile Ser Arg Asp Asn Ala Lys Ser Thr Leu Tyr
 65                  70                  75                  80

Leu Gln Met Asn Ser Leu Arg Ser Glu Asp Thr Ala Thr Tyr Tyr Cys
                85                  90                  95

Thr Arg Thr Leu Tyr Ile Leu Arg Val Phe Tyr Phe Asp Tyr Trp Gly
                100                 105                 110

Gln Gly Val Met Val Thr Val Ser Ser Ala Lys Thr Thr Ala Pro Ser
            115                 120                 125

Val Tyr Pro Leu Ala Pro Val Cys Gly Asp Thr Thr Gly Ser Ser Val
            130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
```

```
                195                 200                 205
Ala Ser Ser Thr Lys Val Asp Lys Lys Ile Glu Pro Arg Gly Pro Thr
210                 215                 220
Ile Lys Pro Cys Pro Pro Cys Lys Cys Pro Ala Pro Asn Leu Leu Gly
225                 230                 235                 240
Gly Pro Ser Val Phe Ile Phe Pro Pro Lys Ile Lys Asp Val Leu Met
                245                 250                 255
Ile Ser Leu Ser Pro Ile Val Thr Cys Val Val Asp Val Ser Glu
            260                 265                 270
Asp Asp Pro Asp Val Gln Ile Ser Trp Phe Val Asn Asn Val Glu Val
            275                 280                 285
His Thr Ala Gln Thr Gln Thr His Arg Glu Asp Tyr Asn Ser Thr Leu
        290                 295                 300
Arg Val Val Ser Ala Leu Pro Ile Gln His Gln Asp Trp Met Ser Gly
305                 310                 315                 320
Lys Glu Phe Lys Cys Lys Val Asn Asn Lys Asp Leu Pro Ala Pro Ile
                325                 330                 335
Glu Arg Thr Ile Ser Lys Pro Lys Gly Ser Val Arg Ala Pro Gln Val
            340                 345                 350
Tyr Val Leu Pro Pro Glu Glu Met Thr Lys Lys Gln Val Thr
            355                 360                 365
Leu Thr Cys Met Val Thr Asp Phe Met Pro Glu Asp Ile Tyr Val Glu
370                 375                 380
Trp Thr Asn Asn Gly Lys Thr Glu Leu Asn Tyr Lys Asn Thr Glu Pro
385                 390                 395                 400
Val Leu Asp Ser Asp Gly Ser Tyr Phe Met Tyr Ser Lys Leu Arg Val
                405                 410                 415
Glu Lys Lys Asn Trp Val Glu Arg Asn Ser Tyr Ser Cys Ser Val Val
            420                 425                 430
His Glu Gly Leu His Asn His His Thr Thr Lys Ser Phe Ser Arg Thr
        435                 440                 445
Pro Gly Lys Gly Gly Gly Ser Gly Gly Gly Gly Ser Gln Val Lys
450                 455                 460
Leu Gln Gln Ser Gly Gly Gly Leu Val Lys Pro Gly Ala Ser Leu Lys
465                 470                 475                 480
Leu Ser Cys Val Thr Ser Gly Phe Thr Phe Arg Lys Phe Gly Met Ser
                485                 490                 495
Trp Val Arg Gln Thr Ser Asp Lys Arg Leu Glu Trp Val Ala Ser Ile
            500                 505                 510
Ser Thr Gly Gly Tyr Asn Thr Tyr Tyr Ser Asp Asn Val Lys Gly Arg
        515                 520                 525
Phe Thr Ile Ser Arg Glu Asn Ala Lys Asn Thr Leu Tyr Leu Gln Met
        530                 535                 540
Ser Ser Leu Lys Ser Glu Asp Thr Ala Leu Tyr Tyr Cys Thr Arg Gly
545                 550                 555                 560
Tyr Ser Pro Tyr Ser Tyr Ala Met Asp Tyr Trp Gly Gln Gly Thr Thr
                565                 570                 575
Val Thr Val Ser Ser Gly Gly Gly Ser Gly Gly Gly Gly Ser Gly
            580                 585                 590
Gly Gly Gly Ser Asp Ile Glu Leu Thr Gln Ser Pro Ala Ser Leu Ser
        595                 600                 605
Val Ala Thr Gly Glu Lys Val Thr Ile Arg Cys Met Thr Ser Thr Asp
610                 615                 620
```

```
Ile Asp Asp Asp Met Asn Trp Tyr Gln Gln Lys Pro Gly Glu Pro
625                 630                 635                 640

Lys Phe Leu Ile Ser Glu Gly Asn Thr Leu Arg Pro Gly Val Pro Ser
                645                 650                 655

Arg Phe Ser Ser Ser Gly Thr Gly Thr Asp Phe Val Phe Thr Ile Glu
                660                 665                 670

Asn Thr Leu Ser Glu Asp Val Gly Asp Tyr Tyr Cys Leu Gln Ser Trp
                675                 680                 685

Asn Val Pro Leu Thr Phe Gly Asp Gly Thr Lys Leu Glu Ile Lys
                690                 695                 700
```

<210> SEQ ID NO 231
<211> LENGTH: 1253
<212> TYPE: DNA
<213> ORGANISM: Artificial Sequence
<220> FEATURE:
<223> OTHER INFORMATION: DNA sequence of del-hEGFRvIII

<400> SEQUENCE: 231

```
gcggccgcgc caccatgcga ccctccggga cggccggggc agcgctcctg gcgctgctgg      60
ctgcgctctg cccggcgagt cgggctctgg aggaaaagaa aggtaattat gtggtgacag     120
atcacggctc gtgcgtccga gcctgtgggg ccgacagcta tgagatggag gaagacggcg     180
tccgcaagtg taagaagtgc gaagggcctt gccgcaaagt gtgtaacgga ataggtattg     240
gtgaattta a agactcactc tccataaatg ctacgaatat aaacacttc a aaaaactgca    300
cctccatcag tggcgatctc cacatcctgc cggtggcatt taggggtgac tccttcacac     360
atactcctcc tctggatcca caggaactgg atattctgaa aaccgtaaag gaaatcacag     420
ggttttttgct gattcaggct tggcctgaaa acaggacgga cctccatgcc tttgagaacc     480
tagaaatcat acgcggcagg accaagcaac atggtcagtt ttctcttgca gtcgtcagcc     540
tgaacataac atccttggga ttacgctccc tcaaggagat aagtgatgga gatgtgataa     600
tttcaggaaa caaaaatttg tgctatgcaa atacaataaa ctggaaaaaa ctgtttggga     660
cctccggtca gaaaaccaaa attataagca acagaggtga aaacagctgc aaggccacag     720
gccaggtctg ccatgccttg tgctcccccg agggctgctg gggcccggag cccagggact     780
gcgtctcttg ccgaaatgtc agccgaggca gggaatgcgt ggacaagtgc aaccttctgg     840
agggtgagcc aagggagttt gtggagaact ctgagtgcat acagtgccac cagagtgcc     900
tgcctcaggc catgaacatc acctgcacag acgggaccc agacaactgt atccagtgtg     960
cccactacat tgacggcccc cactgcgtca agacctgcc ggcaggagtc atgggagaaa    1020
acaacaccct ggtctggaag tacgcagacg ccggccatgt gtgccacctg tgccatccaa    1080
actgcaccta cggatgcact gggccaggtc ttgaaggctg tccaacgaat gggcctaaga    1140
tcccgtccat cgccactggg atggtggggg ccctcctctt gctgctggtg gtggccctgg    1200
ggatcggcct cttcatgcga aggcgccaca tcgttcggaa gcgctgagaa ttc           1253
```

<210> SEQ ID NO 232
<211> LENGTH: 420
<212> TYPE: PRT
<213> ORGANISM: Artificial Sequence
<220> FEATURE:
<223> OTHER INFORMATION: Protein sequence of del-hEGFRvIII

<400> SEQUENCE: 232

Met Arg Pro Ser Gly Thr Ala Gly Ala Ala Leu Leu Ala Leu Leu Ala

-continued

```
1               5                   10                  15
Ala Leu Cys Pro Ala Ser Arg Ala Leu Glu Glu Lys Lys Gly Asn Tyr
                20                  25                  30
Val Val Thr Asp His Gly Ser Cys Val Arg Ala Cys Gly Ala Asp Ser
                35                  40                  45
Tyr Glu Met Glu Thr Glu Glu Asp Gly Val Arg Lys Cys Lys Lys Cys
 50                  55                  60
Glu Gly Pro Cys Arg Lys Val Cys Asn Gly Ile Gly Ile Gly Glu Phe
 65                  70                  75                  80
Lys Asp Ser Leu Ser Ile Asn Ala Thr Asn Ile Lys His Phe Lys Asn
                85                  90                  95
Cys Thr Ser Ile Ser Gly Asp Leu His Ile Leu Pro Val Ala Phe Arg
                100                 105                 110
Gly Asp Ser Phe Thr His Thr Pro Pro Leu Asp Pro Gln Glu Leu Asp
                115                 120                 125
Ile Leu Lys Thr Val Lys Glu Ile Thr Gly Phe Leu Leu Ile Gln Ala
 130                 135                 140
Trp Pro Glu Asn Arg Thr Asp Leu His Ala Phe Glu Asn Leu Glu Ile
 145                 150                 155                 160
Ile Arg Gly Arg Thr Lys Gln His Gly Gln Phe Ser Leu Ala Val Val
                165                 170                 175
Ser Leu Asn Ile Thr Ser Leu Gly Leu Arg Ser Leu Lys Glu Ile Ser
                180                 185                 190
Asp Gly Asp Val Ile Ile Ser Gly Asn Lys Asn Leu Cys Tyr Ala Asn
                195                 200                 205
Thr Ile Asn Trp Lys Lys Leu Phe Gly Thr Ser Gly Gln Lys Thr Lys
 210                 215                 220
Ile Ile Ser Asn Arg Gly Glu Asn Ser Cys Lys Ala Thr Gly Gln Val
 225                 230                 235                 240
Cys His Ala Leu Cys Ser Pro Glu Gly Cys Trp Gly Pro Glu Pro Arg
                245                 250                 255
Asp Cys Val Ser Cys Arg Asn Val Ser Arg Gly Arg Glu Cys Val Asp
                260                 265                 270
Lys Cys Asn Leu Leu Glu Gly Glu Pro Arg Glu Phe Val Glu Asn Ser
                275                 280                 285
Glu Cys Ile Gln Cys His Pro Glu Cys Leu Pro Gln Ala Met Glu Thr
                290                 295                 300
Asn Ile Thr Cys Thr Gly Arg Gly Pro Asp Asn Cys Ile Gln Cys Ala
 305                 310                 315                 320
His Tyr Ile Asp Gly Pro His Cys Val Lys Thr Cys Pro Ala Gly Val
                325                 330                 335
Met Glu Thr Gly Glu Asn Asn Thr Leu Val Trp Lys Tyr Ala Asp Ala
                340                 345                 350
Gly His Val Cys His Leu Cys His Pro Asn Cys Thr Tyr Gly Cys Thr
                355                 360                 365
Gly Pro Gly Leu Glu Gly Cys Pro Thr Asn Gly Pro Lys Ile Pro Ser
                370                 375                 380
Ile Ala Thr Gly Met Glu Thr Val Gly Ala Leu Leu Leu Leu Leu Val
 385                 390                 395                 400
Val Ala Leu Gly Ile Gly Leu Phe Met Glu Thr Arg Arg His Ile
                405                 410                 415
Val Arg Lys Arg
                420
```

-continued

<210> SEQ ID NO 233
<211> LENGTH: 1779
<212> TYPE: PRT
<213> ORGANISM: Artificial Sequence
<220> FEATURE:
<223> OTHER INFORMATION: BsAB EGFRvIII-EpCAM

<400> SEQUENCE: 233

```
Gln Val Lys Leu Gln Gln Ser Gly Gly Leu Val Lys Pro Gly Ala
1               5                   10                  15

Ser Leu Lys Leu Ser Cys Val Thr Ser Gly Phe Thr Phe Arg Lys Phe
                20                  25                  30

Gly Met Ser Trp Val Arg Gln Thr Ser Asp Lys Arg Leu Glu Trp Val
            35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Gly Gly Gly Ser Gly Gly Gly Gly Ser Glu Val Gln
225                 230                 235                 240

Leu Ala Glu Ser Gly Gly Gly Leu Val Gln Pro Gly Arg Ser Met Lys
                245                 250                 255

Leu Ser Cys Ala Ala Ser Gly Phe Thr Phe Ser Asn Phe Pro Met Ala
            260                 265                 270

Trp Val Arg Gln Ala Pro Thr Lys Cys Leu Glu Trp Val Ala Thr Ile
        275                 280                 285

Ser Thr Ser Gly Gly Ser Thr Tyr Tyr Arg Asp Ser Val Lys Gly Arg
    290                 295                 300

Phe Thr Ile Ser Arg Asp Asn Ala Lys Ser Thr Leu Tyr Leu Gln Met
305                 310                 315                 320

Asn Ser Leu Arg Ser Glu Asp Thr Ala Thr Tyr Tyr Cys Thr Arg Thr
                325                 330                 335

Leu Tyr Ile Leu Arg Val Phe Tyr Phe Asp Tyr Trp Gly Gln Gly Val
            340                 345                 350

Met Val Thr Val Ser Ser Ala Ser Thr Lys Gly Pro Ser Val Phe Pro
        355                 360                 365
```

```
Leu Ala Pro Ser Ser Lys Ser Thr Ser Gly Gly Thr Ala Ala Leu Gly
    370                 375                 380

Cys Leu Val Glu Asp Tyr Phe Pro Glu Pro Val Thr Val Ser Trp Asn
385                 390                 395                 400

Ser Gly Ala Leu Thr Ser Gly Val His Thr Phe Pro Ala Val Leu Gln
                405                 410                 415

Ser Ser Gly Leu Tyr Ser Leu Ser Ser Val Val Thr Val Pro Ser Ser
            420                 425                 430

Ser Leu Gly Thr Gln Thr Tyr Ile Cys Asn Val Asn His Lys Pro Ser
        435                 440                 445

Asn Thr Lys Val Asp Glu Lys Val Glu Pro Lys Ser Cys Asp Lys Thr
    450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Cys Arg Asp Glu Leu Thr Lys Asn Gln Val Ser Leu Trp Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

Asp Ile Glu Leu Thr Gln Ser Pro Ala Ser Leu Ser Val Ala Thr Gly
    690                 695                 700

Glu Lys Val Thr Ile Arg Cys Met Thr Ser Thr Asp Ile Asp Asp Asp
705                 710                 715                 720

Met Asn Trp Tyr Gln Gln Lys Pro Gly Glu Pro Lys Phe Leu Ile
                725                 730                 735

Ser Glu Gly Asn Thr Leu Arg Pro Gly Val Pro Ser Arg Phe Ser Ser
            740                 745                 750

Ser Gly Thr Gly Thr Asp Phe Val Phe Thr Ile Glu Asn Thr Leu Ser
        755                 760                 765

Glu Asp Val Gly Asp Tyr Tyr Cys Leu Gln Ser Trp Asn Val Pro Leu
    770                 775                 780
```

```
Thr Phe Gly Asp Gly Thr Lys Leu Glu Ile Lys Ser Ala Ser Thr
785                 790                 795                 800

Lys Gly Pro Ser Val Phe Pro Leu Ala Pro Ser Ser Lys Ser Thr Ser
            805                 810                 815

Gly Gly Thr Ala Ala Leu Gly Cys Leu Val Lys Asp Tyr Phe Pro Glu
            820                 825                 830

Pro Val Thr Val Ser Trp Asn Ser Gly Ala Leu Thr Ser Gly Val His
            835                 840                 845

Thr Phe Pro Ala Val Leu Gln Ser Ser Gly Leu Tyr Ser Leu Ser Ser
            850                 855                 860

Val Val Thr Val Pro Ser Ser Ser Leu Gly Thr Gln Thr Tyr Ile Cys
865                 870                 875                 880

Asn Val Asn His Lys Pro Ser Asn Thr Lys Val Asp Lys Lys Val Glu
                885                 890                 895

Pro Lys Ser Cys Asp Ile Gln Met Thr Gln Ser Pro Ala Ser Leu Ser
            900                 905                 910

Ala Ser Leu Gly Glu Thr Val Ser Ile Glu Cys Leu Ala Ser Glu Gly
            915                 920                 925

Ile Ser Asn Asp Leu Ala Trp Tyr Gln Gln Lys Ser Gly Lys Ser Pro
930                 935                 940

Gln Leu Leu Ile Tyr Ala Thr Ser Arg Leu Gln Asp Gly Val Pro Ser
945                 950                 955                 960

Arg Phe Ser Gly Ser Gly Ser Gly Thr Arg Tyr Ser Leu Lys Ile Ser
            965                 970                 975

Gly Met Gln Pro Glu Asp Glu Ala Asp Tyr Phe Cys Gln Gln Ser Tyr
            980                 985                 990

Lys Tyr Pro Trp Thr Phe Gly Cys Gly Thr Lys Leu Glu Leu Lys Arg
            995                 1000                1005

Thr Val Ala Ala Pro Ser Val Phe Ile Phe Pro Pro Ser Asp Arg Lys
    1010                1015                1020

Leu Lys Ser Gly Thr Ala Ser Val Val Cys Leu Leu Asn Asn Phe Tyr
    1025                1030                1035                1040

Pro Arg Glu Ala Lys Val Gln Trp Lys Val Asp Asn Ala Leu Gln Ser
                1045                1050                1055

Gly Asn Ser Gln Glu Ser Val Thr Glu Gln Asp Ser Lys Asp Ser Thr
            1060                1065                1070

Tyr Ser Leu Ser Ser Thr Leu Thr Leu Ser Lys Ala Asp Tyr Glu Lys
            1075                1080                1085

His Lys Val Tyr Ala Cys Glu Val Thr His Gln Gly Leu Ser Ser Pro
    1090                1095                1100

Val Thr Lys Ser Phe Asn Arg Gly Glu Cys Asp Ile Gln Met Thr Gln
1105                1110                1115                1120

Ser Pro Ala Ser Leu Ser Ala Ser Leu Gly Glu Thr Val Ser Ile Glu
            1125                1130                1135

Cys Leu Ala Ser Glu Gly Ile Ser Asn Asp Leu Ala Trp Tyr Gln Gln
            1140                1145                1150

Lys Ser Gly Lys Ser Pro Gln Leu Leu Ile Tyr Ala Thr Ser Arg Leu
            1155                1160                1165

Gln Asp Gly Val Pro Ser Arg Phe Ser Gly Ser Gly Ser Gly Thr Arg
            1170                1175                1180

Tyr Ser Leu Lys Ile Ser Gly Met Gln Pro Glu Asp Glu Ala Asp Tyr
1185                1190                1195                1200

Phe Cys Gln Gln Ser Tyr Lys Tyr Pro Trp Thr Phe Gly Cys Gly Thr
```

-continued

```
               1205                1210                1215

Lys Leu Glu Leu Lys Arg Thr Val Ala Ala Pro Ser Val Phe Ile Phe
               1220                1225                1230

Pro Pro Ser Asp Arg Lys Leu Lys Ser Gly Thr Ala Ser Val Val Cys
               1235                1240                1245

Leu Leu Asn Asn Phe Tyr Pro Arg Glu Ala Lys Val Gln Trp Lys Val
               1250                1255                1260

Asp Asn Ala Leu Gln Ser Gly Asn Ser Gln Glu Ser Val Thr Glu Gln
1265               1270                1275                1280

Asp Ser Lys Asp Ser Thr Tyr Ser Leu Ser Ser Thr Leu Thr Leu Ser
               1285                1290                1295

Lys Ala Asp Tyr Glu Lys His Lys Val Tyr Ala Cys Glu Val Thr His
               1300                1305                1310

Gln Gly Leu Ser Ser Pro Val Thr Lys Ser Phe Asn Arg Gly Glu Cys
               1315                1320                1325

Glu Val Gln Leu Ala Glu Ser Gly Gly Gly Leu Val Gln Pro Gly Arg
               1330                1335                1340

Ser Met Lys Leu Ser Cys Ala Ala Ser Gly Phe Thr Phe Ser Asn Phe
1345               1350                1355                1360

Pro Met Ala Trp Val Arg Gln Ala Pro Thr Lys Cys Leu Glu Trp Val
               1365                1370                1375

Ala Thr Ile Ser Thr Ser Gly Gly Ser Thr Tyr Tyr Arg Asp Ser Val
               1380                1385                1390

Lys Gly Arg Phe Thr Ile Ser Arg Asp Asn Ala Lys Ser Thr Leu Tyr
               1395                1400                1405

Leu Gln Met Asn Ser Leu Arg Ser Glu Asp Thr Ala Thr Tyr Tyr Cys
               1410                1415                1420

Thr Arg Thr Leu Tyr Ile Leu Arg Val Phe Tyr Phe Asp Tyr Trp Gly
1425               1430                1435                1440

Gln Gly Val Met Val Thr Val Ser Ser Ala Ser Thr Lys Gly Pro Ser
               1445                1450                1455

Val Phe Pro Leu Ala Pro Ser Ser Lys Ser Thr Ser Gly Gly Thr Ala
               1460                1465                1470

Ala Leu Gly Cys Leu Val Glu Asp Tyr Phe Pro Glu Pro Val Thr Val
               1475                1480                1485

Ser Trp Asn Ser Gly Ala Leu Thr Ser Gly Val His Thr Phe Pro Ala
               1490                1495                1500

Val Leu Gln Ser Ser Gly Leu Tyr Ser Leu Ser Ser Val Val Thr Val
1505               1510                1515                1520

Pro Ser Ser Ser Leu Gly Thr Gln Thr Tyr Ile Cys Asn Val Asn His
               1525                1530                1535

Lys Pro Ser Asn Thr Lys Val Asp Glu Lys Val Glu Pro Lys Ser Cys
               1540                1545                1550

Asp Lys Thr His Thr Cys Pro Pro Cys Pro Ala Pro Glu Ala Ala Gly
               1555                1560                1565

Gly Pro Ser Val Phe Leu Phe Pro Pro Lys Pro Lys Asp Thr Leu Met
               1570                1575                1580

Ile Ser Arg Thr Pro Glu Val Thr Cys Val Val Val Asp Val Ser His
1585               1590                1595                1600

Glu Asp Pro Glu Val Lys Phe Asn Trp Tyr Val Asp Gly Val Glu Val
               1605                1610                1615

His Asn Ala Lys Thr Lys Pro Arg Glu Glu Gln Tyr Asn Ser Thr Tyr
               1620                1625                1630
```

```
Arg Val Val Ser Val Leu Thr Val Leu His Gln Asp Trp Leu Asn Gly
            1635                1640                1645

Lys Glu Tyr Lys Cys Lys Val Ser Asn Lys Ala Leu Gly Ala Pro Ile
    1650                1655                1660

Glu Lys Thr Ile Ser Lys Ala Lys Gly Gln Pro Arg Glu Pro Gln Val
1665                1670                1675                1680

Cys Thr Leu Pro Pro Ser Arg Asp Glu Leu Thr Lys Asn Gln Val Ser
                1685                1690                1695

Leu Ser Cys Ala Val Lys Gly Phe Tyr Pro Ser Asp Ile Ala Val Glu
            1700                1705                1710

Trp Glu Ser Asn Gly Gln Pro Glu Asn Asn Tyr Lys Thr Thr Pro Pro
        1715                1720                1725

Val Leu Asp Ser Asp Gly Ser Phe Phe Leu Val Ser Lys Leu Thr Val
    1730                1735                1740

Asp Lys Ser Arg Trp Gln Gln Gly Asn Val Phe Ser Cys Ser Val Met
1745                1750                1755                1760

His Glu Ala Leu His Asn Arg Phe Thr Gln Lys Ser Leu Ser Leu Ser
                1765                1770                1775

Pro Gly Lys

<210> SEQ ID NO 234
<211> LENGTH: 1766
<212> TYPE: PRT
<213> ORGANISM: Artificial Sequence
<220> FEATURE:
<223> OTHER INFORMATION: BsAB EGFRvIII-MCSP

<400> SEQUENCE: 234

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205
```

-continued

Val Thr His Gln Gly Leu Ser Ser Pro Val Thr Lys Ser Phe Asn Arg
210                 215                 220

Gly Glu Cys Gly Gly Gly Ser Gly Gly Gly Ser Gly Gly Gly
225                 230                 235                 240

Gly Ser Gln Val Gln Leu Gln Glu Ser Gly Pro Gly Leu Val Lys Pro
                245                 250                 255

Ser Gln Thr Leu Ser Leu Thr Cys Thr Val Ser Gly Ser Ile Thr
                260                 265                 270

Ser Gly Tyr Tyr Trp Asn Trp Ile Arg Gln His Pro Gly Lys Gly Leu
            275                 280                 285

Glu Trp Ile Gly Tyr Ile Thr Phe Asp Gly Ser Asn Asn Tyr Asn Pro
290                 295                 300

Ser Leu Lys Ser Arg Val Thr Ile Ser Arg Asp Thr Ser Lys Asn Gln
305                 310                 315                 320

Phe Ser Leu Lys Leu Ser Ser Val Thr Ala Ala Asp Thr Ala Val Tyr
                325                 330                 335

Tyr Cys Ala Asp Phe Asp Tyr Trp Gly Gln Gly Thr Leu Val Thr Val
                340                 345                 350

Ser Ser Ala Ser Thr Lys Gly Pro Ser Val Phe Pro Leu Ala Pro Ser
            355                 360                 365

Ser Lys Ser Thr Ser Gly Gly Thr Ala Ala Leu Gly Cys Leu Val Glu
370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
            420                 425                 430

Gln Thr Tyr Ile Cys Asn Val Asn His Lys Pro Ser Asn Thr Lys Val
                435                 440                 445

Asp Glu Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
            515                 520                 525

Arg Glu Glu Gln Tyr Asn Ser Thr Tyr Arg Val Val Ser Val Leu Thr
530                 535                 540

Val Leu His Gln Asp Trp Leu Asn Gly Lys Glu Tyr Lys Cys Lys Val
545                 550                 555                 560

Ser Asn Lys Ala Leu Gly Ala Pro Ile Glu Lys Thr Ile Ser Lys Ala
                565                 570                 575

Lys Gly Gln Pro Arg Glu Pro Gln Val Tyr Thr Leu Pro Pro Cys Arg
            580                 585                 590

Asp Glu Leu Thr Lys Asn Gln Val Ser Leu Trp Cys Leu Val Lys Gly
            595                 600                 605

Phe Tyr Pro Ser Asp Ile Ala Val Glu Trp Glu Ser Asn Gly Gln Pro
610                 615                 620

Glu Asn Asn Tyr Lys Thr Thr Pro Pro Val Leu Asp Ser Asp Gly Ser

```
                625                630                635                640
        Phe Phe Leu Tyr Ser Lys Leu Thr Val Asp Lys Ser Arg Trp Gln Gln
                        645                650                655
        Gly Asn Val Phe Ser Cys Ser Val Met His Glu Ala Leu His Asn His
                        660                665                670
        Tyr Thr Gln Lys Ser Leu Ser Leu Ser Pro Gly Lys Asp Ile Gln Met
                        675                680                685
        Thr Gln Ser Pro Ser Ser Leu Ser Ala Ser Val Gly Asp Arg Val Thr
                690                695                700
        Ile Thr Cys Arg Ala Ser Gln Gly Ile Arg Asn Tyr Leu Asn Trp Tyr
        705                710                715                720
        Gln Gln Lys Pro Gly Lys Ala Pro Lys Leu Leu Ile Tyr Tyr Thr Ser
                        725                730                735
        Ser Leu His Ser Gly Val Pro Ser Arg Phe Ser Gly Ser Gly Ser Gly
                        740                745                750
        Thr Asp Tyr Thr Leu Thr Ile Ser Ser Leu Gln Pro Glu Asp Phe Ala
                        755                760                765
        Thr Tyr Tyr Cys Gln Gln Tyr Ser Ala Leu Pro Trp Thr Phe Gly Gln
                        770                775                780
        Gly Thr Lys Val Glu Ile Lys Arg Thr Val Ala Ala Pro Ser Val Phe
        785                790                795                800
        Ile Phe Pro Pro Ser Asp Arg Lys Leu Lys Ser Gly Thr Ala Ser Val
                        805                810                815
        Val Cys Leu Leu Asn Asn Phe Tyr Pro Arg Glu Ala Lys Val Gln Trp
                        820                825                830
        Lys Val Asp Asn Ala Leu Gln Ser Gly Asn Ser Gln Glu Ser Val Thr
                        835                840                845
        Glu Gln Asp Ser Lys Asp Ser Thr Tyr Ser Leu Ser Ser Thr Leu Thr
                        850                855                860
        Leu Ser Lys Ala Asp Tyr Glu Lys His Lys Val Tyr Ala Cys Glu Val
        865                870                875                880
        Thr His Gln Gly Leu Ser Ser Pro Val Thr Lys Ser Phe Asn Arg Gly
                        885                890                895
        Glu Cys Asp Ile Gln Met Thr Gln Ser Pro Ser Ser Leu Ser Ala Ser
                        900                905                910
        Val Gly Asp Arg Val Thr Ile Thr Cys Arg Ala Ser Gln Gly Ile Arg
                        915                920                925
        Asn Tyr Leu Asn Trp Tyr Gln Gln Lys Pro Gly Lys Ala Pro Lys Leu
        930                935                940
        Leu Ile Tyr Tyr Thr Ser Ser Leu His Ser Gly Val Pro Ser Arg Phe
        945                950                955                960
        Ser Gly Ser Gly Ser Gly Thr Asp Tyr Thr Leu Thr Ile Ser Ser Leu
                        965                970                975
        Gln Pro Glu Asp Phe Ala Thr Tyr Tyr Cys Gln Gln Tyr Ser Ala Leu
                        980                985                990
        Pro Trp Thr Phe Gly Gln Gly Thr Lys Val Glu Ile Lys Arg Thr Val
                        995                1000               1005
        Ala Ala Pro Ser Val Phe Ile Phe Pro Pro Ser Asp Arg Lys Leu Lys
                        1010               1015               1020
        Ser Gly Thr Ala Ser Val Val Cys Leu Leu Asn Asn Phe Tyr Pro Arg
        1025               1030               1035               1040
        Glu Ala Lys Val Gln Trp Lys Val Asp Asn Ala Leu Gln Ser Gly Asn
                        1045               1050               1055
```

-continued

Ser Gln Glu Ser Val Thr Glu Gln Asp Ser Lys Asp Ser Thr Tyr Ser
                1060                1065                1070

Leu Ser Ser Thr Leu Thr Leu Ser Lys Ala Asp Tyr Glu Lys His Lys
            1075                1080                1085

Val Tyr Ala Cys Glu Val Thr His Gln Gly Leu Ser Ser Pro Val Thr
        1090                1095                1100

Lys Ser Phe Asn Arg Gly Glu Cys Asp Ile Glu Leu Thr Gln Ser Pro
1105                1110                1115                1120

Ala Ser Leu Ser Val Ala Thr Gly Glu Lys Val Thr Ile Arg Cys Met
                1125                1130                1135

Thr Ser Thr Asp Ile Asp Asp Asp Met Asn Trp Tyr Gln Gln Lys Pro
            1140                1145                1150

Gly Glu Pro Pro Lys Phe Leu Ile Ser Glu Gly Asn Thr Leu Arg Pro
        1155                1160                1165

Gly Val Pro Ser Arg Phe Ser Ser Ser Gly Thr Gly Thr Asp Phe Val
    1170                1175                1180

Phe Thr Ile Glu Asn Thr Leu Ser Glu Asp Val Gly Asp Tyr Tyr Cys
1185                1190                1195                1200

Leu Gln Ser Trp Asn Val Pro Leu Thr Phe Gly Asp Gly Thr Lys Leu
                1205                1210                1215

Glu Ile Lys Ser Ser Ala Ser Thr Lys Gly Pro Ser Val Phe Pro Leu
            1220                1225                1230

Ala Pro Ser Ser Lys Ser Thr Ser Gly Gly Thr Ala Ala Leu Gly Cys
        1235                1240                1245

Leu Val Lys Asp Tyr Phe Pro Glu Pro Val Thr Val Ser Trp Asn Ser
    1250                1255                1260

Gly Ala Leu Thr Ser Gly Val His Thr Phe Pro Ala Val Leu Gln Ser
1265                1270                1275                1280

Ser Gly Leu Tyr Ser Leu Ser Ser Val Val Thr Val Pro Ser Ser Ser
                1285                1290                1295

Leu Gly Thr Gln Thr Tyr Ile Cys Asn Val Asn His Lys Pro Ser Asn
            1300                1305                1310

Thr Lys Val Asp Lys Lys Val Glu Pro Lys Ser Cys Gln Val Gln Leu
        1315                1320                1325

Gln Glu Ser Gly Pro Gly Leu Val Lys Pro Ser Gln Thr Leu Ser Leu
    1330                1335                1340

Thr Cys Thr Val Ser Gly Gly Ser Ile Thr Ser Gly Tyr Tyr Trp Asn
1345                1350                1355                1360

Trp Ile Arg Gln His Pro Gly Lys Gly Leu Glu Trp Ile Gly Tyr Ile
                1365                1370                1375

Thr Phe Asp Gly Ser Asn Asn Tyr Asn Pro Ser Leu Lys Ser Arg Val
            1380                1385                1390

Thr Ile Ser Arg Asp Thr Ser Lys Asn Gln Phe Ser Leu Lys Leu Ser
        1395                1400                1405

Ser Val Thr Ala Ala Asp Thr Ala Val Tyr Tyr Cys Ala Asp Phe Asp
    1410                1415                1420

Tyr Trp Gly Gln Gly Thr Leu Val Thr Val Ser Ser Ala Ser Thr Lys
1425                1430                1435                1440

Gly Pro Ser Val Phe Pro Leu Ala Pro Ser Ser Lys Ser Thr Ser Gly
                1445                1450                1455

Gly Thr Ala Ala Leu Gly Cys Leu Val Glu Asp Tyr Phe Pro Glu Pro
            1460                1465                1470

```
Val Thr Val Ser Trp Asn Ser Gly Ala Leu Thr Ser Gly Val His Thr
            1475                1480                1485

Phe Pro Ala Val Leu Gln Ser Ser Gly Leu Tyr Ser Leu Ser Ser Val
        1490                1495                1500

Val Thr Val Pro Ser Ser Ser Leu Gly Thr Gln Thr Tyr Ile Cys Asn
1505                1510                1515                1520

Val Asn His Lys Pro Ser Asn Thr Lys Val Asp Glu Lys Val Glu Pro
            1525                1530                1535

Lys Ser Cys Asp Lys Thr His Thr Cys Pro Pro Cys Pro Ala Pro Glu
        1540                1545                1550

Ala Ala Gly Gly Pro Ser Val Phe Leu Phe Pro Pro Lys Pro Lys Asp
    1555                1560                1565

Thr Leu Met Ile Ser Arg Thr Pro Glu Val Thr Cys Val Val Val Asp
1570                1575                1580

Val Ser His Glu Asp Pro Glu Val Lys Phe Asn Trp Tyr Val Asp Gly
1585                1590                1595                1600

Val Glu Val His Asn Ala Lys Thr Lys Pro Arg Glu Glu Gln Tyr Asn
            1605                1610                1615

Ser Thr Tyr Arg Val Val Ser Val Leu Thr Val Leu His Gln Asp Trp
        1620                1625                1630

Leu Asn Gly Lys Glu Tyr Lys Cys Lys Val Ser Asn Lys Ala Leu Gly
    1635                1640                1645

Ala Pro Ile Glu Lys Thr Ile Ser Lys Ala Lys Gly Gln Pro Arg Glu
        1650                1655                1660

Pro Gln Val Cys Thr Leu Pro Pro Ser Arg Asp Glu Leu Thr Lys Asn
1665                1670                1675                1680

Gln Val Ser Leu Ser Cys Ala Val Lys Gly Phe Tyr Pro Ser Asp Ile
            1685                1690                1695

Ala Val Glu Trp Glu Ser Asn Gly Gln Pro Glu Asn Asn Tyr Lys Thr
        1700                1705                1710

Thr Pro Pro Val Leu Asp Ser Asp Gly Ser Phe Phe Leu Val Ser Lys
    1715                1720                1725

Leu Thr Val Asp Lys Ser Arg Trp Gln Gln Gly Asn Val Phe Ser Cys
1730                1735                1740

Ser Val Met His Glu Ala Leu His Asn Arg Phe Thr Gln Lys Ser Leu
1745                1750                1755                1760

Ser Leu Ser Pro Gly Lys
            1765

<210> SEQ ID NO 235
<211> LENGTH: 1773
<212> TYPE: PRT
<213> ORGANISM: Artificial Sequence
<220> FEATURE:
<223> OTHER INFORMATION: BsAB EGFRvIII-MSLN

<400> SEQUENCE: 235

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60
```

```
Lys Gly Arg Phe Thr Ile Ser Arg Glu Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Gly Gly Gly Gly Ser Gly Gly Gly Ser Gln Val Gln
225                 230                 235                 240

Leu Val Gln Ser Gly Ala Glu Val Lys Lys Pro Gly Ala Ser Val Lys
                245                 250                 255

Val Ser Cys Lys Ala Ser Gly Tyr Ser Phe Thr Gly Tyr Thr Met Asn
            260                 265                 270

Trp Val Arg Gln Ala Pro Gly Gln Gly Leu Glu Trp Met Gly Leu Ile
        275                 280                 285

Thr Pro Tyr Asn Gly Ala Ser Ser Tyr Asn Gln Lys Phe Arg Gly Lys
    290                 295                 300

Ala Thr Met Thr Val Asp Thr Ser Thr Ser Thr Val Tyr Met Glu Leu
305                 310                 315                 320

Ser Ser Leu Arg Ser Glu Asp Thr Ala Val Tyr Tyr Cys Ala Arg Gly
                325                 330                 335

Gly Tyr Asp Gly Arg Gly Phe Asp Tyr Trp Gly Gln Gly Thr Leu Val
            340                 345                 350

Thr Val Ser Ser Ala Ser Thr Lys Gly Pro Ser Val Phe Pro Leu Ala
        355                 360                 365

Pro Ser Ser Lys Ser Thr Ser Gly Gly Thr Ala Ala Leu Gly Cys Leu
    370                 375                 380

Val Glu Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Thr Val Pro Ser Ser Ser Leu
            420                 425                 430

Gly Thr Gln Thr Tyr Ile Cys Asn Val Asn His Lys Pro Ser Asn Thr
        435                 440                 445

Lys Val Asp Glu Lys Val Glu Pro Lys Ser Cys Asp Lys Thr His Thr
    450                 455                 460

Cys Pro Pro Cys Pro Ala Pro Glu Ala Ala Gly Gly Pro Ser Val Phe
465                 470                 475                 480

Leu Phe Pro Pro Lys Pro Lys Asp Thr Leu Met Ile Ser Arg Thr Pro
```

-continued

```
                485                 490                 495
Glu Val Thr Cys Val Val Val Asp Val Ser His Glu Asp Pro Glu Val
                500                 505                 510
Lys Phe Asn Trp Tyr Val Asp Gly Val Glu Val His Asn Ala Lys Thr
            515                 520                 525
Lys Pro Arg Glu Glu Gln Tyr Asn Ser Thr Tyr Arg Val Val Ser Val
        530                 535                 540
Leu Thr Val Leu His Gln Asp Trp Leu Asn Gly Lys Glu Tyr Lys Cys
545                 550                 555                 560
Lys Val Ser Asn Lys Ala Leu Gly Ala Pro Ile Glu Lys Thr Ile Ser
                565                 570                 575
Lys Ala Lys Gly Gln Pro Arg Glu Pro Gln Val Tyr Thr Leu Pro Pro
            580                 585                 590
Cys Arg Asp Glu Leu Thr Lys Asn Gln Val Ser Leu Trp Cys Leu Val
        595                 600                 605
Lys Gly Phe Tyr Pro Ser Asp Ile Ala Val Glu Trp Glu Ser Asn Gly
    610                 615                 620
Gln Pro Glu Asn Asn Tyr Lys Thr Thr Pro Pro Val Leu Asp Ser Asp
625                 630                 635                 640
Gly Ser Phe Phe Leu Tyr Ser Lys Leu Thr Val Asp Lys Ser Arg Trp
                645                 650                 655
Gln Gln Gly Asn Val Phe Ser Cys Ser Val Met His Glu Ala Leu His
            660                 665                 670
Asn His Tyr Thr Gln Lys Ser Leu Ser Leu Ser Pro Gly Lys Asp Ile
        675                 680                 685
Glu Leu Thr Gln Ser Pro Ala Ser Leu Ser Val Ala Thr Gly Glu Lys
    690                 695                 700
Val Thr Ile Arg Cys Met Thr Ser Thr Asp Ile Asp Asp Asp Met Asn
705                 710                 715                 720
Trp Tyr Gln Gln Lys Pro Gly Glu Pro Pro Lys Phe Leu Ile Ser Glu
                725                 730                 735
Gly Asn Thr Leu Arg Pro Gly Val Pro Ser Arg Phe Ser Ser Ser Gly
            740                 745                 750
Thr Gly Thr Asp Phe Val Phe Thr Ile Glu Asn Thr Leu Ser Glu Asp
        755                 760                 765
Val Gly Asp Tyr Tyr Cys Leu Gln Ser Trp Asn Val Pro Leu Thr Phe
    770                 775                 780
Gly Asp Gly Thr Lys Leu Glu Ile Lys Ser Ser Ala Ser Thr Lys Gly
785                 790                 795                 800
Pro Ser Val Phe Pro Leu Ala Pro Ser Ser Lys Ser Thr Ser Gly Gly
                805                 810                 815
Thr Ala Ala Leu Gly Cys Leu Val Lys Asp Tyr Phe Pro Glu Pro Val
            820                 825                 830
Thr Val Ser Trp Asn Ser Gly Ala Leu Thr Ser Gly Val His Thr Phe
        835                 840                 845
Pro Ala Val Leu Gln Ser Ser Gly Leu Tyr Ser Leu Ser Ser Val Val
    850                 855                 860
Thr Val Pro Ser Ser Ser Leu Gly Thr Gln Thr Tyr Ile Cys Asn Val
865                 870                 875                 880
Asn His Lys Pro Ser Asn Thr Lys Val Asp Lys Lys Val Glu Pro Lys
                885                 890                 895
Ser Cys Asp Ile Gln Met Thr Gln Ser Pro Ser Ser Leu Ser Ala Ser
            900                 905                 910
```

Val Gly Asp Arg Val Thr Ile Thr Cys Ser Ala Ser Ser Val Ser
            915                 920                 925

Tyr Met His Trp Tyr Gln Gln Lys Ser Gly Lys Ala Pro Lys Leu Leu
            930                 935                 940

Ile Tyr Asp Thr Ser Lys Leu Ala Ser Gly Val Pro Ser Arg Phe Ser
945                 950                 955                 960

Gly Ser Gly Ser Gly Thr Asp Phe Thr Leu Thr Ile Ser Ser Leu Gln
            965                 970                 975

Pro Glu Asp Phe Ala Thr Tyr Tyr Cys Gln Gln Trp Ser Lys His Pro
            980                 985                 990

Leu Thr Phe Gly Gln Gly Thr Lys Leu Glu Ile Lys Arg Thr Val Ala
            995                 1000                1005

Ala Pro Ser Val Phe Ile Phe Pro Pro Ser Asp Arg Lys Leu Lys Ser
            1010                1015                1020

Gly Thr Ala Ser Val Val Cys Leu Leu Asn Asn Phe Tyr Pro Arg Glu
1025                1030                1035                1040

Ala Lys Val Gln Trp Lys Val Asp Asn Ala Leu Gln Ser Gly Asn Ser
            1045                1050                1055

Gln Glu Ser Val Thr Glu Gln Asp Ser Lys Asp Ser Thr Tyr Ser Leu
            1060                1065                1070

Ser Ser Thr Leu Thr Leu Ser Lys Ala Asp Tyr Glu Lys His Lys Val
            1075                1080                1085

Tyr Ala Cys Glu Val Thr His Gln Gly Leu Ser Ser Pro Val Thr Lys
            1090                1095                1100

Ser Phe Asn Arg Gly Glu Cys Asp Ile Gln Met Thr Gln Ser Pro Ser
1105                1110                1115                1120

Ser Leu Ser Ala Ser Val Gly Asp Arg Val Thr Ile Thr Cys Ser Ala
            1125                1130                1135

Ser Ser Ser Val Ser Tyr Met His Trp Tyr Gln Gln Lys Ser Gly Lys
            1140                1145                1150

Ala Pro Lys Leu Leu Ile Tyr Asp Thr Ser Lys Leu Ala Ser Gly Val
            1155                1160                1165

Pro Ser Arg Phe Ser Gly Ser Gly Ser Gly Thr Asp Phe Thr Leu Thr
            1170                1175                1180

Ile Ser Ser Leu Gln Pro Glu Asp Phe Ala Thr Tyr Tyr Cys Gln Gln
1185                1190                1195                1200

Trp Ser Lys His Pro Leu Thr Phe Gly Gln Gly Thr Lys Leu Glu Ile
            1205                1210                1215

Lys Arg Thr Val Ala Ala Pro Ser Val Phe Ile Phe Pro Pro Ser Asp
            1220                1225                1230

Arg Lys Leu Lys Ser Gly Thr Ala Ser Val Val Cys Leu Leu Asn Asn
            1235                1240                1245

Phe Tyr Pro Arg Glu Ala Lys Val Gln Trp Lys Val Asp Asn Ala Leu
            1250                1255                1260

Gln Ser Gly Asn Ser Gln Glu Ser Val Thr Glu Gln Asp Ser Lys Asp
1265                1270                1275                1280

Ser Thr Tyr Ser Leu Ser Ser Thr Leu Thr Leu Ser Lys Ala Asp Tyr
            1285                1290                1295

Glu Lys His Lys Val Tyr Ala Cys Glu Val Thr His Gln Gly Leu Ser
            1300                1305                1310

Ser Pro Val Thr Lys Ser Phe Asn Arg Gly Glu Cys Gln Val Gln Leu
            1315                1320                1325

```
Val Gln Ser Gly Ala Glu Val Lys Lys Pro Gly Ala Ser Val Lys Val
             1330                1335                1340

Ser Cys Lys Ala Ser Gly Tyr Ser Phe Thr Gly Tyr Thr Met Asn Trp
1345                1350                1355                1360

Val Arg Gln Ala Pro Gly Gln Gly Leu Glu Trp Met Gly Leu Ile Thr
                1365                1370                1375

Pro Tyr Asn Gly Ala Ser Ser Tyr Asn Gln Lys Phe Arg Gly Lys Ala
            1380                1385                1390

Thr Met Thr Val Asp Thr Ser Thr Ser Thr Val Tyr Met Glu Leu Ser
        1395                1400                1405

Ser Leu Arg Ser Glu Asp Thr Ala Val Tyr Tyr Cys Ala Arg Gly Gly
    1410                1415                1420

Tyr Asp Gly Arg Gly Phe Asp Tyr Trp Gly Gln Gly Thr Leu Val Thr
1425                1430                1435                1440

Val Ser Ser Ala Ser Thr Lys Gly Pro Ser Val Phe Pro Leu Ala Pro
                1445                1450                1455

Ser Ser Lys Ser Thr Ser Gly Gly Thr Ala Ala Leu Gly Cys Leu Val
            1460                1465                1470

Glu Asp Tyr Phe Pro Glu Pro Val Thr Val Ser Trp Asn Ser Gly Ala
        1475                1480                1485

Leu Thr Ser Gly Val His Thr Phe Pro Ala Val Leu Gln Ser Ser Gly
    1490                1495                1500

Leu Tyr Ser Leu Ser Ser Val Val Thr Val Pro Ser Ser Ser Leu Gly
1505                1510                1515                1520

Thr Gln Thr Tyr Ile Cys Asn Val Asn His Lys Pro Ser Asn Thr Lys
                1525                1530                1535

Val Asp Glu Lys Val Glu Pro Lys Ser Cys Asp Lys Thr His Thr Cys
            1540                1545                1550

Pro Pro Cys Pro Ala Pro Glu Ala Ala Gly Gly Pro Ser Val Phe Leu
        1555                1560                1565

Phe Pro Pro Lys Pro Lys Asp Thr Leu Met Ile Ser Arg Thr Pro Glu
    1570                1575                1580

Val Thr Cys Val Val Val Asp Val Ser His Glu Asp Pro Glu Val Lys
1585                1590                1595                1600

Phe Asn Trp Tyr Val Asp Gly Val Glu Val His Asn Ala Lys Thr Lys
                1605                1610                1615

Pro Arg Glu Glu Gln Tyr Asn Ser Thr Tyr Arg Val Val Ser Val Leu
            1620                1625                1630

Thr Val Leu His Gln Asp Trp Leu Asn Gly Lys Glu Tyr Lys Cys Lys
        1635                1640                1645

Val Ser Asn Lys Ala Leu Gly Ala Pro Ile Glu Lys Thr Ile Ser Lys
    1650                1655                1660

Ala Lys Gly Gln Pro Arg Glu Pro Gln Val Cys Thr Leu Pro Pro Ser
1665                1670                1675                1680

Arg Asp Glu Leu Thr Lys Asn Gln Val Ser Leu Ser Cys Ala Val Lys
                1685                1690                1695

Gly Phe Tyr Pro Ser Asp Ile Ala Val Glu Trp Glu Ser Asn Gly Gln
            1700                1705                1710

Pro Glu Asn Asn Tyr Lys Thr Thr Pro Pro Val Leu Asp Ser Asp Gly
        1715                1720                1725

Ser Phe Phe Leu Val Ser Lys Leu Thr Val Asp Lys Ser Arg Trp Gln
    1730                1735                1740

Gln Gly Asn Val Phe Ser Cys Ser Val Met His Glu Ala Leu His Asn
```

<210> SEQ ID NO 236
<211> LENGTH: 6966
<212> TYPE: DNA
<213> ORGANISM: Homo sapiens
<220> FEATURE:
<223> OTHER INFORMATION: MSCP
<220> FEATURE:
<221> NAME/KEY: CDS
<222> LOCATION: 1..6966
<223> OTHER INFORMATION: /transl_table=1

<400> SEQUENCE: 236

```
atg cag agc ggc ccg cgc ccg ccg ctg ccg gcg ccg ggc ctg gcg ctg      48
Met Gln Ser Gly Pro Arg Pro Pro Leu Pro Ala Pro Gly Leu Ala Leu
1               5                   10                  15 gcg ctg acc ctg acc atg ctg gcg cgc ctg gcg agc gcg gcg agc ttt      96
Ala Leu Thr Leu Thr Met Leu Ala Arg Leu Ala Ser Ala Ala Ser Phe
                20                  25                  30 ttt ggc gaa aac cat ctg gaa gtg ccg gtg gcg acc gcg ctg acc gat     144
Phe Gly Glu Asn His Leu Glu Val Pro Val Ala Thr Ala Leu Thr Asp
            35                  40                  45 att gat ctg cag ctg cag ttt agc acc agc cag ccg gaa gcg ctg ctg     192
Ile Asp Leu Gln Leu Gln Phe Ser Thr Ser Gln Pro Glu Ala Leu Leu
        50                  55                  60 ctg ctg gcg gcg ggc ccg gcg gat cat ctg ctg ctg cag ctg tat agc     240
Leu Leu Ala Ala Gly Pro Ala Asp His Leu Leu Leu Gln Leu Tyr Ser
65                  70                  75                  80 ggc cgc ctg cag gtg cgc ctg gtg ctg ggc cag gaa gaa ctg cgc ctg     288
Gly Arg Leu Gln Val Arg Leu Val Leu Gly Gln Glu Glu Leu Arg Leu
                85                  90                  95 cag acc ccg gcg gaa acc ctg ctg agc gat agc att ccg cat acc gtg     336
Gln Thr Pro Ala Glu Thr Leu Leu Ser Asp Ser Ile Pro His Thr Val
                100                 105                 110 gtg ctg acc gtg gtg gaa ggc tgg gcg acc ctg agc gtg gat ggc ttt     384
Val Leu Thr Val Val Glu Gly Trp Ala Thr Leu Ser Val Asp Gly Phe
            115                 120                 125 ctg aac gcg agc agc gcg gtg ccg ggc gcg ccg ctg gaa gtg ccg tat     432
Leu Asn Ala Ser Ser Ala Val Pro Gly Ala Pro Leu Glu Val Pro Tyr
        130                 135                 140 ggc ctg ttt gtg ggc ggc acc ggc acc ctg ggc ctg ccg tat ctg cgc     480
Gly Leu Phe Val Gly Gly Thr Gly Thr Leu Gly Leu Pro Tyr Leu Arg
145                 150                 155                 160 ggc acc agc cgc ccg ctg cgc ggc tgc ctg cat gcg gcg acc ctg aac     528
Gly Thr Ser Arg Pro Leu Arg Gly Cys Leu His Ala Ala Thr Leu Asn
                165                 170                 175 ggc cgc agc ctg ctg cgc ccg ctg acc ccg gat gtg cat gaa ggc tgc     576
Gly Arg Ser Leu Leu Arg Pro Leu Thr Pro Asp Val His Glu Gly Cys
                180                 185                 190 gcg gaa gaa ttt agc gcg agc gat gat gtg gcg ctg ggc ttt agc ggc     624
Ala Glu Glu Phe Ser Ala Ser Asp Asp Val Ala Leu Gly Phe Ser Gly
            195                 200                 205 ccg cat agc ctg gcg gcg ttt ccg gcg tgg ggc acc cag gat gaa ggc     672
Pro His Ser Leu Ala Ala Phe Pro Ala Trp Gly Thr Gln Asp Glu Gly
        210                 215                 220 acc ctg gaa ttt acc ctg acc acc cag agc cgc cag gcg ccg ctg gcg     720
Thr Leu Glu Phe Thr Leu Thr Thr Gln Ser Arg Gln Ala Pro Leu Ala
225                 230                 235                 240
```

(page header, continued from previous:)

```
                His Tyr Thr Gln Lys Ser Leu Ser Leu Ser Pro Gly Lys
                                1765                1770
```

|  |  |
|---|---|
| ttt cag gcg ggc ggc cgc cgc ggc gat ttt att tat gtg gat att ttt<br>Phe Gln Ala Gly Gly Arg Arg Gly Asp Phe Ile Tyr Val Asp Ile Phe<br>245 250 255 | 768 |
| gaa ggc cat ctg cgc gcg gtg gtg gaa aaa ggc cag ggc acc gtg ctg<br>Glu Gly His Leu Arg Ala Val Val Glu Lys Gly Gln Gly Thr Val Leu<br>260 265 270 | 816 |
| ctg cat aac agc gtg ccg gtg gcg gat ggc cag ccg cat gaa gtg agc<br>Leu His Asn Ser Val Pro Val Ala Asp Gly Gln Pro His Glu Val Ser<br>275 280 285 | 864 |
| gtg cat att aac gcg cat cgc ctg gaa att agc gtg gat cag tat ccg<br>Val His Ile Asn Ala His Arg Leu Glu Ile Ser Val Asp Gln Tyr Pro<br>290 295 300 | 912 |
| acc cat acc agc aac cgc ggc gtg ctg agc tat ctg gaa ccg cgc ggc<br>Thr His Thr Ser Asn Arg Gly Val Leu Ser Tyr Leu Glu Pro Arg Gly<br>305 310 315 320 | 960 |
| agc ctg ctg ctg ggc ggc ctg gat gcg gaa gcg agc cgc cat ctg cag<br>Ser Leu Leu Leu Gly Gly Leu Asp Ala Glu Ala Ser Arg His Leu Gln<br>325 330 335 | 1008 |
| gaa cat cgc ctg ggc ctg acc ccg gaa gcg acc aac gcg agc ctg ctg<br>Glu His Arg Leu Gly Leu Thr Pro Glu Ala Thr Asn Ala Ser Leu Leu<br>340 345 350 | 1056 |
| ggc tgc atg gaa gat ctg agc gtg aac ggc cag cgc cgc ggc ctg cgc<br>Gly Cys Met Glu Asp Leu Ser Val Asn Gly Gln Arg Arg Gly Leu Arg<br>355 360 365 | 1104 |
| gaa gcg ctg ctg acc cgc aac atg gcg gcg ggc tgc cgc ctg gaa gaa<br>Glu Ala Leu Leu Thr Arg Asn Met Ala Ala Gly Cys Arg Leu Glu Glu<br>370 375 380 | 1152 |
| gaa gaa tat gaa gat gat gcg tat ggc cat tat gaa gcg ttt agc acc<br>Glu Glu Tyr Glu Asp Asp Ala Tyr Gly His Tyr Glu Ala Phe Ser Thr<br>385 390 395 400 | 1200 |
| ctg gcg ccg gaa gcg tgg ccg gcg atg gaa ctg ccg gaa ccg tgc gtg<br>Leu Ala Pro Glu Ala Trp Pro Ala Met Glu Leu Pro Glu Pro Cys Val<br>405 410 415 | 1248 |
| ccg gaa ccg ggc ctg ccg ccg gtg ttt gcg aac ttt acc cag ctg ctg<br>Pro Glu Pro Gly Leu Pro Pro Val Phe Ala Asn Phe Thr Gln Leu Leu<br>420 425 430 | 1296 |
| acc att agc ccg ctg gtg gtg gcg gaa ggc ggc acc gcg tgg ctg gaa<br>Thr Ile Ser Pro Leu Val Val Ala Glu Gly Gly Thr Ala Trp Leu Glu<br>435 440 445 | 1344 |
| tgg cgc cat gtg cag ccg acc ctg gat ctg atg gaa gcg gaa ctg cgc<br>Trp Arg His Val Gln Pro Thr Leu Asp Leu Met Glu Ala Glu Leu Arg<br>450 455 460 | 1392 |
| aaa agc cag gtg ctg ttt agc gtg acc cgc ggc gcg cgc cat ggc gaa<br>Lys Ser Gln Val Leu Phe Ser Val Thr Arg Gly Ala Arg His Gly Glu<br>465 470 475 480 | 1440 |
| ctg gaa ctg gat att ccg ggc gcg cag gcg cgc aaa atg ttt acc ctg<br>Leu Glu Leu Asp Ile Pro Gly Ala Gln Ala Arg Lys Met Phe Thr Leu<br>485 490 495 | 1488 |
| ctg gat gtg gtg aac cgc aaa gcg cgc ttt att cat gat ggc agc gaa<br>Leu Asp Val Val Asn Arg Lys Ala Arg Phe Ile His Asp Gly Ser Glu<br>500 505 510 | 1536 |
| gat acc agc gat cag ctg gtg ctg gaa gtg agc gtg acc gcg cgc gtg<br>Asp Thr Ser Asp Gln Leu Val Leu Glu Val Ser Val Thr Ala Arg Val<br>515 520 525 | 1584 |
| ccg atg ccg agc tgc ctg cgc cgc ggc cag acc tat ctg ctg ccg att<br>Pro Met Pro Ser Cys Leu Arg Arg Gly Gln Thr Tyr Leu Leu Pro Ile<br>530 535 540 | 1632 |
| cag gtg aac ccg gtg aac gat ccg ccg cat att att ttt ccg cat ggc<br>Gln Val Asn Pro Val Asn Asp Pro Pro His Ile Ile Phe Pro His Gly<br>545 550 555 560 | 1680 |

```
agc ctg atg gtg att ctg gaa cat acc cag aaa ccg ctg ggc ccg gaa    1728
Ser Leu Met Val Ile Leu Glu His Thr Gln Lys Pro Leu Gly Pro Glu
            565                 570                 575 gtg ttt cag gcg tat gat ccg gat agc gcg tgc gaa ggc ctg acc ttt    1776
Val Phe Gln Ala Tyr Asp Pro Asp Ser Ala Cys Glu Gly Leu Thr Phe
580                 585                 590 cag gtg ctg ggc acc agc agc ggc ctg ccg gtg gaa cgc cgc gat cag    1824
Gln Val Leu Gly Thr Ser Ser Gly Leu Pro Val Glu Arg Arg Asp Gln
        595                 600                 605 ccg ggc gaa ccg gcg acc gaa ttt agc tgc cgc gaa ctg gaa gcg ggc    1872
Pro Gly Glu Pro Ala Thr Glu Phe Ser Cys Arg Glu Leu Glu Ala Gly
610                 615                 620 agc ctg gtg tat gtg cat cgc ggc ggc ccg gcg cag gat ctg acc ttt    1920
Ser Leu Val Tyr Val His Arg Gly Gly Pro Ala Gln Asp Leu Thr Phe
625                 630                 635                 640 cgc gtg agc gat ggc ctg cag gcg agc ccg ccg gcg acc ctg aaa gtg    1968
Arg Val Ser Asp Gly Leu Gln Ala Ser Pro Pro Ala Thr Leu Lys Val
                645                 650                 655 gtg gcg att cgc ccg gcg att cag att cat cgc agc acc ggc ctg cgc    2016
Val Ala Ile Arg Pro Ala Ile Gln Ile His Arg Ser Thr Gly Leu Arg
            660                 665                 670 ctg gcg cag ggc agc gcg atg ccg att ctg ccg gcg aac ctg agc gtg    2064
Leu Ala Gln Gly Ser Ala Met Pro Ile Leu Pro Ala Asn Leu Ser Val
        675                 680                 685 gaa acc aac gcg gtg ggc cag gat gtg agc gtg ctg ttt cgc gtg acc    2112
Glu Thr Asn Ala Val Gly Gln Asp Val Ser Val Leu Phe Arg Val Thr
690                 695                 700 ggc gcg ctg cag ttt ggc gaa ctg cag aaa cag ggc gcg ggc ggc gtg    2160
Gly Ala Leu Gln Phe Gly Glu Leu Gln Lys Gln Gly Ala Gly Gly Val
705                 710                 715                 720 gaa ggc gcg gaa tgg tgg gcg acc cag gcg ttt cat cag cgc gat gtg    2208
Glu Gly Ala Glu Trp Trp Ala Thr Gln Ala Phe His Gln Arg Asp Val
                725                 730                 735 gaa cag ggc cgc gtg cgc tat ctg agc acc gat ccg cag cat cat gcg    2256
Glu Gln Gly Arg Val Arg Tyr Leu Ser Thr Asp Pro Gln His His Ala
            740                 745                 750 tat gat acc gtg gaa aac ctg gcg ctg gaa gtg cag gtg ggc cag gaa    2304
Tyr Asp Thr Val Glu Asn Leu Ala Leu Glu Val Gln Val Gly Gln Glu
        755                 760                 765 att ctg agc aac ctg agc ttt ccg gtg acc att cag cgc gcg acc gtg    2352
Ile Leu Ser Asn Leu Ser Phe Pro Val Thr Ile Gln Arg Ala Thr Val
770                 775                 780 tgg atg ctg cgc ctg gaa ccg ctg cat acc cag aac acc cag cag gaa    2400
Trp Met Leu Arg Leu Glu Pro Leu His Thr Gln Asn Thr Gln Gln Glu
785                 790                 795                 800 acc ctg acc acc gcg cat ctg gaa gcg acc ctg gaa gaa gcg ggc ccg    2448
Thr Leu Thr Thr Ala His Leu Glu Ala Thr Leu Glu Glu Ala Gly Pro
                805                 810                 815 agc ccg ccg acc ttt cat tat gaa gtg gtg cag gcg ccg cgc aaa ggc    2496
Ser Pro Pro Thr Phe His Tyr Glu Val Val Gln Ala Pro Arg Lys Gly
            820                 825                 830 aac ctg cag ctg cag ggc acc cgc ctg agc gat ggc cag ggc ttt acc    2544
Asn Leu Gln Leu Gln Gly Thr Arg Leu Ser Asp Gly Gln Gly Phe Thr
        835                 840                 845 cag gat gat att cag gcg ggc cgc gtg acc tat ggc gcg acc gcg cgc    2592
Gln Asp Asp Ile Gln Ala Gly Arg Val Thr Tyr Gly Ala Thr Ala Arg
850                 855                 860 gcg agc gaa gcg gtg gaa gat acc ttt cgc ttt cgc gtg acc gcg ccg    2640
Ala Ser Glu Ala Val Glu Asp Thr Phe Arg Phe Arg Val Thr Ala Pro
```

```
              865                 870                 875                 880
ccg tat ttt agc ccg ctg tat acc ttt ccg att cat att ggc ggc gat    2688
Pro Tyr Phe Ser Pro Leu Tyr Thr Phe Pro Ile His Ile Gly Gly Asp
                    885                 890                 895 ccg gat gcg ccg gtg ctg acc aac gtg ctg ctg gtg gtg ccg gaa ggc    2736
Pro Asp Ala Pro Val Leu Thr Asn Val Leu Leu Val Val Pro Glu Gly
                900                 905                 910 ggc gaa ggc gtg ctg agc gcg gat cat ctg ttt gtg aaa agc ctg aac    2784
Gly Glu Gly Val Leu Ser Ala Asp His Leu Phe Val Lys Ser Leu Asn
            915                 920                 925 agc gcg agc tat ctg tat gaa gtg atg gaa cgc ccg cgc cat ggc cgc    2832
Ser Ala Ser Tyr Leu Tyr Glu Val Met Glu Arg Pro Arg His Gly Arg
        930                 935                 940 ctg gcg tgg cgc ggc acc cag gat aaa acc acc atg gtg acc agc ttt    2880
Leu Ala Trp Arg Gly Thr Gln Asp Lys Thr Thr Met Val Thr Ser Phe
945                 950                 955                 960 acc aac gaa gat ctg ctg cgc ggc cgc ctg gtg tat cag cat gat gat    2928
Thr Asn Glu Asp Leu Leu Arg Gly Arg Leu Val Tyr Gln His Asp Asp
                965                 970                 975 agc gaa acc acc gaa gat gat att ccg ttt gtg gcg acc cgc cag ggc    2976
Ser Glu Thr Thr Glu Asp Asp Ile Pro Phe Val Ala Thr Arg Gln Gly
            980                 985                 990 gaa agc agc ggc gat atg gcg tgg gaa gaa gtg cgc ggc gtg ttt cgc    3024
Glu Ser Ser Gly Asp Met Ala Trp Glu Glu Val Arg Gly Val Phe Arg
        995                 1000                1005 gtg gcg att cag ccg gtg aac gat cat gcg ccg gtg cag acc att agc    3072
Val Ala Ile Gln Pro Val Asn Asp His Ala Pro Val Gln Thr Ile Ser
    1010                1015                1020 cgc att ttt cat gtg gcg cgc ggc ggc cgc cgc ctg ctg acc acc gat    3120
Arg Ile Phe His Val Ala Arg Gly Gly Arg Arg Leu Leu Thr Thr Asp
1025                1030                1035                1040 gat gtg gcg ttt agc gat gcg gat agc ggc ttt gcg gat gcg cag ctg    3168
Asp Val Ala Phe Ser Asp Ala Asp Ser Gly Phe Ala Asp Ala Gln Leu
                1045                1050                1055 gtg ctg acc cgc aaa gat ctg ctg ttt ggc agc att gtg gcg gtg gat    3216
Val Leu Thr Arg Lys Asp Leu Leu Phe Gly Ser Ile Val Ala Val Asp
            1060                1065                1070 gaa ccg acc cgc ccg att tat cgc ttt acc cag gaa gat ctg cgc aaa    3264
Glu Pro Thr Arg Pro Ile Tyr Arg Phe Thr Gln Glu Asp Leu Arg Lys
        1075                1080                1085 cgc cgc gtg ctg ttt gtg cat agc ggc gcg gat cgc ggc tgg att cag    3312
Arg Arg Val Leu Phe Val His Ser Gly Ala Asp Arg Gly Trp Ile Gln
    1090                1095                1100 ctg cag gtg agc gat ggc cag cat cag gcg acc gcg ctg ctg gaa gtg    3360
Leu Gln Val Ser Asp Gly Gln His Gln Ala Thr Ala Leu Leu Glu Val
1105                1110                1115                1120 cag gcg agc gaa ccg tat ctg cgc gtg gcg aac ggc agc agc ctg gtg    3408
Gln Ala Ser Glu Pro Tyr Leu Arg Val Ala Asn Gly Ser Ser Leu Val
                1125                1130                1135 gtg ccg cag ggc ggc cag ggc acc att gat acc gcg gtg ctg cat ctg    3456
Val Pro Gln Gly Gly Gln Gly Thr Ile Asp Thr Ala Val Leu His Leu
            1140                1145                1150 gat acc aac ctg gat att cgc agc ggc gat gaa gtg cat tat cat gtg    3504
Asp Thr Asn Leu Asp Ile Arg Ser Gly Asp Glu Val His Tyr His Val
        1155                1160                1165 acc gcg ggc ccg cgc tgg ggc cag ctg gtg cgc gcg ggc cag ccg gcg    3552
Thr Ala Gly Pro Arg Trp Gly Gln Leu Val Arg Ala Gly Gln Pro Ala
    1170                1175                1180 acc gcg ttt agc cag cag gat ctg ctg gat ggc gcg gtg ctg tat agc    3600
```

-continued

| | | | | | | | | | | | | | | |
|---|---|---|---|---|---|---|---|---|---|---|---|---|---|---|
| Thr | Ala | Phe | Ser | Gln | Gln | Asp | Leu | Leu | Asp | Gly | Ala | Val | Leu | Tyr | Ser |
| 1185 | | | | 1190 | | | | | 1195 | | | | | 1200 | |

```
cat aac ggc agc ctg agc ccg cgc gat acc atg gcg ttt agc gtg gaa    3648
His Asn Gly Ser Leu Ser Pro Arg Asp Thr Met Ala Phe Ser Val Glu
            1205                1210                1215 gcg ggc ccg gtg cat acc gat gcg acc ctg cag gtg acc att gcg ctg    3696
Ala Gly Pro Val His Thr Asp Ala Thr Leu Gln Val Thr Ile Ala Leu
            1220                1225                1230 gaa ggc ccg ctg gcg ccg ctg aaa ctg gtg cgc cat aaa aaa att tat    3744
Glu Gly Pro Leu Ala Pro Leu Lys Leu Val Arg His Lys Lys Ile Tyr
            1235                1240                1245 gtg ttt cag ggc gaa gcg gcg gaa att cgc cgc gat cag ctg gaa gcg    3792
Val Phe Gln Gly Glu Ala Ala Glu Ile Arg Arg Asp Gln Leu Glu Ala
            1250                1255                1260 gcg cag gaa gcg gtg ccg ccg gcg gat att gtg ttt agc gtg aaa agc    3840
Ala Gln Glu Ala Val Pro Pro Ala Asp Ile Val Phe Ser Val Lys Ser
1265                1270                1275                1280 ccg ccg agc gcg ggc tat ctg gtg atg gtg agc cgc ggc gcg ctg gcg    3888
Pro Pro Ser Ala Gly Tyr Leu Val Met Val Ser Arg Gly Ala Leu Ala
                1285                1290                1295 gat gaa ccg ccg agc ctg gat ccg gtg cag agc ttt agc cag gaa gcg    3936
Asp Glu Pro Pro Ser Leu Asp Pro Val Gln Ser Phe Ser Gln Glu Ala
            1300                1305                1310 gtg gat acc ggc cgc gtg ctg tat ctg cat agc cgc ccg gaa gcg tgg    3984
Val Asp Thr Gly Arg Val Leu Tyr Leu His Ser Arg Pro Glu Ala Trp
            1315                1320                1325 agc gat gcg ttt agc ctg gat gtg gcg agc ggc ctg ggc gcg ccg ctg    4032
Ser Asp Ala Phe Ser Leu Asp Val Ala Ser Gly Leu Gly Ala Pro Leu
            1330                1335                1340 gaa ggc gtg ctg gtg gaa ctg gaa gtg ctg ccg gcg gcg att ccg ctg    4080
Glu Gly Val Leu Val Glu Leu Glu Val Leu Pro Ala Ala Ile Pro Leu
1345                1350                1355                1360 gaa gcg cag aac ttt agc gtg ccg gaa ggc ggc agc ctg acc ctg gcg    4128
Glu Ala Gln Asn Phe Ser Val Pro Glu Gly Gly Ser Leu Thr Leu Ala
                1365                1370                1375 ccg ccg ctg ctg cgc gtg agc ggc ccg tat ttt ccg acc ctg ctg ggc    4176
Pro Pro Leu Leu Arg Val Ser Gly Pro Tyr Phe Pro Thr Leu Leu Gly
            1380                1385                1390 ctg agc ctg cag gtg ctg gaa ccg ccg cag cat ggc gcg ctg cag aaa    4224
Leu Ser Leu Gln Val Leu Glu Pro Pro Gln His Gly Ala Leu Gln Lys
            1395                1400                1405 gaa gat ggc ccg cag gcg cgc acc ctg agc gcg ttt agc tgg cgc atg    4272
Glu Asp Gly Pro Gln Ala Arg Thr Leu Ser Ala Phe Ser Trp Arg Met
1410                1415                1420 gtg gaa gaa cag ctg att cgc tat gtg cat gat ggc agc gaa acc ctg    4320
Val Glu Glu Gln Leu Ile Arg Tyr Val His Asp Gly Ser Glu Thr Leu
1425                1430                1435                1440 acc gat agc ttt gtg ctg atg gcg aac gcg agc gaa atg gat cgc cag    4368
Thr Asp Ser Phe Val Leu Met Ala Asn Ala Ser Glu Met Asp Arg Gln
            1445                1450                1455 agc cat ccg gtg gcg ttt acc gtg acc gtg ctg ccg gtg aac gat cag    4416
Ser His Pro Val Ala Phe Thr Val Thr Val Leu Pro Val Asn Asp Gln
            1460                1465                1470 ccg ccg att ctg acc acc aac acc ggc ctg cag atg tgg gaa ggc gcg    4464
Pro Pro Ile Leu Thr Thr Asn Thr Gly Leu Gln Met Trp Glu Gly Ala
            1475                1480                1485 acc gcg ccg att ccg gcg gaa gcg ctg cgc agc acc gat ggc gat agc    4512
Thr Ala Pro Ile Pro Ala Glu Ala Leu Arg Ser Thr Asp Gly Asp Ser
            1490                1495                1500
```

-continued

| | |
|---|---|
| ggc agc gaa gat ctg gtg tat acc att gaa cag ccg agc aac ggc cgc<br>Gly Ser Glu Asp Leu Val Tyr Thr Ile Glu Gln Pro Ser Asn Gly Arg<br>1505                    1510                    1515                    1520 | 4560 |
| gtg gtg ctg cgc ggc gcg ccg ggc acc gaa gtg cgc agc ttt acc cag<br>Val Val Leu Arg Gly Ala Pro Gly Thr Glu Val Arg Ser Phe Thr Gln<br>                    1525                    1530                    1535 | 4608 |
| gcg cag ctg gat ggc ggc ctg gtg ctg ttt agc cat cgc ggc acc ctg<br>Ala Gln Leu Asp Gly Gly Leu Val Leu Phe Ser His Arg Gly Thr Leu<br>                  1540                    1545                    1550 | 4656 |
| gat ggc ggc ttt cgc ttt cgc ctg agc gat ggc gaa cat acc agc ccg<br>Asp Gly Gly Phe Arg Phe Arg Leu Ser Asp Gly Glu His Thr Ser Pro<br>1555                    1560                    1565 | 4704 |
| ggc cat ttt ttt cgc gtg acc gcg cag aaa cag gtg ctg ctg agc ctg<br>Gly His Phe Phe Arg Val Thr Ala Gln Lys Gln Val Leu Leu Ser Leu<br>                  1570                    1575                    1580 | 4752 |
| aaa ggc agc cag acc ctg acc gtg tgc ccg ggc agc gtg cag ccg ctg<br>Lys Gly Ser Gln Thr Leu Thr Val Cys Pro Gly Ser Val Gln Pro Leu<br>1585                    1590                    1595                    1600 | 4800 |
| agc agc cag acc ctg cgc gcg agc agc agc gcg ggc acc gat ccg cag<br>Ser Ser Gln Thr Leu Arg Ala Ser Ser Ser Ala Gly Thr Asp Pro Gln<br>                  1605                    1610                    1615 | 4848 |
| ctg ctg ctg tat cgc gtg gtg cgc ggc ccg cag ctg ggc cgc ctg ttt<br>Leu Leu Leu Tyr Arg Val Val Arg Gly Pro Gln Leu Gly Arg Leu Phe<br>1620                    1625                    1630 | 4896 |
| cat gcg cag cag gat agc acc ggc gaa gcg ctg gtg aac ttt acc cag<br>His Ala Gln Gln Asp Ser Thr Gly Glu Ala Leu Val Asn Phe Thr Gln<br>                  1635                    1640                    1645 | 4944 |
| gcg gaa gtg tat gcg ggc aac att ctg tat gaa cat gaa atg ccg ccg<br>Ala Glu Val Tyr Ala Gly Asn Ile Leu Tyr Glu His Glu Met Pro Pro<br>1650                    1655                    1660 | 4992 |
| gaa ccg ttt tgg gaa gcg cat gat acc ctg gaa ctg cag ctg agc agc<br>Glu Pro Phe Trp Glu Ala His Asp Thr Leu Glu Leu Gln Leu Ser Ser<br>1665                    1670                    1675                    1680 | 5040 |
| ccg ccg gcg cgc gat gtg gcg gcg acc ctg gcg gtg gcg gtg agc ttt<br>Pro Pro Ala Arg Asp Val Ala Ala Thr Leu Ala Val Ala Val Ser Phe<br>                  1685                    1690                    1695 | 5088 |
| gaa gcg gcg tgc ccg cag cgc ccg agc cat ctg tgg aaa aac aaa ggc<br>Glu Ala Ala Cys Pro Gln Arg Pro Ser His Leu Trp Lys Asn Lys Gly<br>1700                    1705                    1710 | 5136 |
| ctg tgg gtg ccg gaa ggc cag cgc gcg cgc att acc gtg gcg gcg ctg<br>Leu Trp Val Pro Glu Gly Gln Arg Ala Arg Ile Thr Val Ala Ala Leu<br>                  1715                    1720                    1725 | 5184 |
| gat gcg agc aac ctg ctg gcg agc gtg ccg agc ccg cag cgc agc gaa<br>Asp Ala Ser Asn Leu Leu Ala Ser Val Pro Ser Pro Gln Arg Ser Glu<br>1730                    1735                    1740 | 5232 |
| cat gat gtg ctg ttt cag gtg acc cag ttt ccg agc cgc ggc cag ctg<br>His Asp Val Leu Phe Gln Val Thr Gln Phe Pro Ser Arg Gly Gln Leu<br>1745                    1750                    1755                    1760 | 5280 |
| ctg gtg agc gaa gaa ccg ctg cat gcg ggc cag ccg cat ttt ctg cag<br>Leu Val Ser Glu Glu Pro Leu His Ala Gly Gln Pro His Phe Leu Gln<br>                  1765                    1770                    1775 | 5328 |
| agc cag ctg gcg gcg ggc cag ctg gtg tat gcg cat ggc ggc ggc ggc<br>Ser Gln Leu Ala Ala Gly Gln Leu Val Tyr Ala His Gly Gly Gly Gly<br>                  1780                    1785                    1790 | 5376 |
| acc cag cag gat ggc ttt cat ttt cgc gcg cat ctg cag ggc ccg gcg<br>Thr Gln Gln Asp Gly Phe His Phe Arg Ala His Leu Gln Gly Pro Ala<br>                  1795                    1800                    1805 | 5424 |
| ggc gcg agc gtg gcg ggc ccg cag acc agc gaa gcg ttt gcg att acc<br>Gly Ala Ser Val Ala Gly Pro Gln Thr Ser Glu Ala Phe Ala Ile Thr<br>1810                    1815                    1820 | 5472 |

| | |
|---|---:|
| gtg cgc gat gtg aac gaa cgc ccg ccg cag ccg cag gcg agc gtg ccg<br>Val Arg Asp Val Asn Glu Arg Pro Pro Gln Pro Gln Ala Ser Val Pro<br>1825                        1830                        1835                      1840 | 5520 |
| ctg cgc ctg acc cgc ggc agc cgc gcg ccg att agc cgc gcg cag ctg<br>Leu Arg Leu Thr Arg Gly Ser Arg Ala Pro Ile Ser Arg Ala Gln Leu<br>                      1845                        1850                      1855 | 5568 |
| agc gtg gtg gat ccg gat agc gcg ccg ggc gaa att gaa tat gaa gtg<br>Ser Val Val Asp Pro Asp Ser Ala Pro Gly Glu Ile Glu Tyr Glu Val<br>                1860                        1865                      1870 | 5616 |
| cag cgc gcg ccg cat aac ggc ttt ctg agc ctg gtg ggc ggc ctg<br>Gln Arg Ala Pro His Asn Gly Phe Leu Ser Leu Val Gly Gly Leu<br>1875                        1880                        1885 | 5664 |
| ggc ccg gtg acc cgc ttt acc cag gcg gat gtg gat agc ggc cgc ctg<br>Gly Pro Val Thr Arg Phe Thr Gln Ala Asp Val Asp Ser Gly Arg Leu<br>                      1890                        1895                      1900 | 5712 |
| gcg ttt gtg gcg aac ggc agc agc gtg gcg ggc att ttt cag ctg agc<br>Ala Phe Val Ala Asn Gly Ser Ser Val Ala Gly Ile Phe Gln Leu Ser<br>1905                        1910                        1915                      1920 | 5760 |
| atg agc gat ggc gcg agc ccg ccg ctg ccg atg agc ctg gcg gtg gat<br>Met Ser Asp Gly Ala Ser Pro Pro Leu Pro Met Ser Leu Ala Val Asp<br>                      1925                        1930                      1935 | 5808 |
| att ctg ccg agc gcg att gaa gtg cag ctg cgc gcg ccg ctg gaa gtg<br>Ile Leu Pro Ser Ala Ile Glu Val Gln Leu Arg Ala Pro Leu Glu Val<br>                      1940                        1945                      1950 | 5856 |
| ccg cag gcg ctg ggc cgc agc agc ctg agc cag cag cag ctg cgc gtg<br>Pro Gln Ala Leu Gly Arg Ser Ser Leu Ser Gln Gln Gln Leu Arg Val<br>                      1955                        1960                      1965 | 5904 |
| gtg agc gat cgc gaa gaa ccg gaa gcg gcg tat cgc ctg att cag ggc<br>Val Ser Asp Arg Glu Glu Pro Glu Ala Ala Tyr Arg Leu Ile Gln Gly<br>                      1970                        1975                      1980 | 5952 |
| ccg cag tat ggc cat ctg ctg gtg ggc ggc cgc ccg acc agc gcg ttt<br>Pro Gln Tyr Gly His Leu Leu Val Gly Gly Arg Pro Thr Ser Ala Phe<br>1985                        1990                        1995                      2000 | 6000 |
| agc cag ttt cag att gat cag ggc gaa gtg gtg ttt gcg ttt acc aac<br>Ser Gln Phe Gln Ile Asp Gln Gly Glu Val Val Phe Ala Phe Thr Asn<br>                      2005                        2010                      2015 | 6048 |
| ttt agc agc agc cat gat cat ttt cgc gtg ctg gcg ctg gcg cgc ggc<br>Phe Ser Ser Ser His Asp His Phe Arg Val Leu Ala Leu Ala Arg Gly<br>                      2020                        2025                      2030 | 6096 |
| gtg aac gcg agc gcg gtg gtg aac gtg acc gtg cgc gcg ctg ctg cat<br>Val Asn Ala Ser Ala Val Val Asn Val Thr Val Arg Ala Leu Leu His<br>                      2035                        2040                      2045 | 6144 |
| gtg tgg gcg ggc ggc ccg tgg ccg cag ggc gcg acc ctg cgc ctg gat<br>Val Trp Ala Gly Gly Pro Trp Pro Gln Gly Ala Thr Leu Arg Leu Asp<br>                      2050                        2055                      2060 | 6192 |
| ccg acc gtg ctg gat gcg ggc gaa ctg gcg aac cgc acc ggc agc gtg<br>Pro Thr Val Leu Asp Ala Gly Glu Leu Ala Asn Arg Thr Gly Ser Val<br>2065                        2070                        2075                      2080 | 6240 |
| ccg cgc ttt cgc ctg ctg gaa ggc ccg cgc cat ggc cgc gtg gtg cgc<br>Pro Arg Phe Arg Leu Leu Glu Gly Pro Arg His Gly Arg Val Val Arg<br>                      2085                        2090                      2095 | 6288 |
| gtg ccg cgc gcg cgc acc gaa ccg ggc ggc agc cag ctg gtg gaa cag<br>Val Pro Arg Ala Arg Thr Glu Pro Gly Gly Ser Gln Leu Val Glu Gln<br>                      2100                        2105                      2110 | 6336 |
| ttt acc cag cag gat ctg gaa gat ggc cgc ctg ggc ctg gaa gtg ggc<br>Phe Thr Gln Gln Asp Leu Glu Asp Gly Arg Leu Gly Leu Glu Val Gly<br>                      2115                        2120                      2125 | 6384 |
| cgc ccg gaa ggc cgc gcg ccg ggc ccg gcg ggc gat agc ctg acc ctg<br>Arg Pro Glu Gly Arg Ala Pro Gly Pro Ala Gly Asp Ser Leu Thr Leu | 6432 |

```
               2130                2135                2140
gaa ctg tgg gcg cag ggc gtg ccg ccg gcg gtg gcg agc ctg gat ttt     6480
Glu Leu Trp Ala Gln Gly Val Pro Pro Ala Val Ala Ser Leu Asp Phe
2145                2150                2155                2160 gcg acc gaa ccg tat aac gcg gcg cgc ccg tat agc gtg gcg ctg ctg     6528
Ala Thr Glu Pro Tyr Asn Ala Ala Arg Pro Tyr Ser Val Ala Leu Leu
                2165                2170                2175 agc gtg ccg gaa gcg gcg cgc acc gaa gcg ggc aaa ccg gaa agc agc     6576
Ser Val Pro Glu Ala Ala Arg Thr Glu Ala Gly Lys Pro Glu Ser Ser
            2180                2185                2190 acc ccg acc ggc gaa ccg ggc ccg atg gcg agc agc ccg gaa ccg gcg     6624
Thr Pro Thr Gly Glu Pro Gly Pro Met Ala Ser Ser Pro Glu Pro Ala
        2195                2200                2205 gtg gcg aaa ggc ggc ttt ctg agc ttt ctg gaa gcg aac atg ttt agc     6672
Val Ala Lys Gly Gly Phe Leu Ser Phe Leu Glu Ala Asn Met Phe Ser
    2210                2215                2220 gtg att att ccg atg tgc ctg gtg ctg ctg ctg gcg ctg att ctg         6720
Val Ile Ile Pro Met Cys Leu Val Leu Leu Leu Ala Leu Ile Leu
2225                2230                2235                2240 ccg ctg ctg ttt tat ctg cgc aaa cgc aac aaa acc ggc aaa cat gat     6768
Pro Leu Leu Phe Tyr Leu Arg Lys Arg Asn Lys Thr Gly Lys His Asp
                2245                2250                2255 gtg cag gtg ctg acc gcg aaa ccg cgc aac ggc ctg gcg ggc gat acc     6816
Val Gln Val Leu Thr Ala Lys Pro Arg Asn Gly Leu Ala Gly Asp Thr
            2260                2265                2270 gaa acc ttt cgc aaa gtg gaa ccg ggc cag gcg att ccg ctg acc gcg     6864
Glu Thr Phe Arg Lys Val Glu Pro Gly Gln Ala Ile Pro Leu Thr Ala
        2275                2280                2285 gtg ccg ggc cag ggc ccg ccg ccg ggc ggc cag ccg gat ccg gaa ctg     6912
Val Pro Gly Gln Gly Pro Pro Pro Gly Gly Gln Pro Asp Pro Glu Leu
    2290                2295                2300 ctg cag ttt tgc cgc acc ccg aac ccg gcg ctg aaa aac ggc cag tat     6960
Leu Gln Phe Cys Arg Thr Pro Asn Pro Ala Leu Lys Asn Gly Gln Tyr
2305                2310                2315                2320 tgg gtg                                                              6966
Trp Val <210> SEQ ID NO 237
<211> LENGTH: 2322
<212> TYPE: PRT
<213> ORGANISM: Homo sapiens
<220> FEATURE:
<223> OTHER INFORMATION: [CDS]:1..6966 from SEQ ID NO 236

<400> SEQUENCE: 237

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110
```

-continued

```
Val Leu Thr Val Val Glu Gly Trp Ala Thr Leu Ser Val Asp Gly Phe
            115                 120                 125
Leu Asn Ala Ser Ser Ala Val Pro Gly Ala Pro Leu Glu Val Pro Tyr
        130                 135                 140
Gly Leu Phe Val Gly Gly Thr Gly Thr Leu Gly Leu Pro Tyr Leu Arg
145                 150                 155                 160
Gly Thr Ser Arg Pro Leu Arg Gly Cys Leu His Ala Ala Thr Leu Asn
                165                 170                 175
Gly Arg Ser Leu Leu Arg Pro Leu Thr Pro Asp Val His Glu Gly Cys
                180                 185                 190
Ala Glu Glu Phe Ser Ala Ser Asp Asp Val Ala Leu Gly Phe Ser Gly
            195                 200                 205
Pro His Ser Leu Ala Ala Phe Pro Ala Trp Gly Thr Gln Asp Glu Gly
        210                 215                 220
Thr Leu Glu Phe Thr Leu Thr Thr Gln Ser Arg Gln Ala Pro Leu Ala
225                 230                 235                 240
Phe Gln Ala Gly Gly Arg Arg Gly Asp Phe Ile Tyr Val Asp Ile Phe
                245                 250                 255
Glu Gly His Leu Arg Ala Val Val Glu Lys Gly Gln Gly Thr Val Leu
            260                 265                 270
Leu His Asn Ser Val Pro Val Ala Asp Gly Gln Pro His Glu Val Ser
        275                 280                 285
Val His Ile Asn Ala His Arg Leu Glu Ile Ser Val Asp Gln Tyr Pro
290                 295                 300
Thr His Thr Ser Asn Arg Gly Val Leu Ser Tyr Leu Glu Pro Arg Gly
305                 310                 315                 320
Ser Leu Leu Leu Gly Gly Leu Asp Ala Glu Ala Ser Arg His Leu Gln
                325                 330                 335
Glu His Arg Leu Gly Leu Thr Pro Glu Ala Thr Asn Ala Ser Leu Leu
            340                 345                 350
Gly Cys Met Glu Asp Leu Ser Val Asn Gly Gln Arg Arg Gly Leu Arg
        355                 360                 365
Glu Ala Leu Leu Thr Arg Asn Met Ala Ala Gly Cys Arg Leu Glu Glu
    370                 375                 380
Glu Glu Tyr Glu Asp Asp Ala Tyr Gly His Tyr Glu Ala Phe Ser Thr
385                 390                 395                 400
Leu Ala Pro Glu Ala Trp Pro Ala Met Glu Leu Pro Glu Pro Cys Val
                405                 410                 415
Pro Glu Pro Gly Leu Pro Pro Val Phe Ala Asn Phe Thr Gln Leu Leu
            420                 425                 430
Thr Ile Ser Pro Leu Val Val Ala Glu Gly Gly Thr Ala Trp Leu Glu
        435                 440                 445
Trp Arg His Val Gln Pro Thr Leu Asp Leu Met Glu Ala Glu Leu Arg
    450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
            500                 505                 510
Asp Thr Ser Asp Gln Leu Val Leu Glu Val Ser Val Thr Ala Arg Val
        515                 520                 525
```

-continued

Pro Met Pro Ser Cys Leu Arg Arg Gly Gln Thr Tyr Leu Leu Pro Ile
530                     535                         540

Gln Val Asn Pro Val Asn Asp Pro Pro His Ile Ile Phe Pro His Gly
545                     550                 555                 560

Ser Leu Met Val Ile Leu Glu His Thr Gln Lys Pro Leu Gly Pro Glu
            565                     570                 575

Val Phe Gln Ala Tyr Asp Pro Asp Ser Ala Cys Glu Gly Leu Thr Phe
        580                 585                     590

Gln Val Leu Gly Thr Ser Gly Leu Pro Val Glu Arg Arg Asp Gln
        595                 600                 605

Pro Gly Glu Pro Ala Thr Glu Phe Ser Cys Arg Glu Leu Glu Ala Gly
610                     615                     620

Ser Leu Val Tyr Val His Arg Gly Pro Ala Gln Asp Leu Thr Phe
625                     630                 635                 640

Arg Val Ser Asp Gly Leu Gln Ala Ser Pro Ala Thr Leu Lys Val
                645                 650                 655

Val Ala Ile Arg Pro Ala Ile Gln Ile His Arg Ser Thr Gly Leu Arg
                660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
690                     695                 700

Gly Ala Leu Gln Phe Gly Glu Leu Gln Lys Gln Gly Ala Gly Gly Val
705                 710                 715                     720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
            755                 760                 765

Ile Leu Ser Asn Leu Ser Phe Pro Val Thr Ile Gln Arg Ala Thr Val
770                     775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
            805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
850                     855                 860

Ala Ser Glu Ala Val Glu Asp Thr Phe Arg Phe Arg Val Thr Ala Pro
865                     870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
930                     935                 940

Leu Ala Trp Arg Gly Thr Gln Asp Lys Thr Thr Met Val Thr Ser Phe

```
                945                 950                 955                 960
Thr Asn Glu Asp Leu Leu Arg Gly Arg Leu Val Tyr Gln His Asp Asp
                    965                 970                 975
Ser Glu Thr Thr Glu Asp Asp Ile Pro Phe Val Ala Thr Arg Gln Gly
            980                 985                 990
Glu Ser Ser Gly Asp Met Ala Trp Glu Val Arg Gly Val Phe Arg
        995                 1000                1005
Val Ala Ile Gln Pro Val Asn Asp His Ala Pro Val Gln Thr Ile Ser
    1010                1015                1020
Arg Ile Phe His Val Ala Arg Gly Gly Arg Leu Leu Thr Thr Asp
1025                1030                1035                1040
Asp Val Ala Phe Ser Asp Ala Asp Ser Gly Phe Ala Asp Ala Gln Leu
                1045                1050                1055
Val Leu Thr Arg Lys Asp Leu Leu Phe Gly Ser Ile Val Ala Val Asp
                1060                1065                1070
Glu Pro Thr Arg Pro Ile Tyr Arg Phe Thr Gln Glu Asp Leu Arg Lys
            1075                1080                1085
Arg Arg Val Leu Phe Val His Ser Gly Ala Asp Arg Gly Trp Ile Gln
    1090                1095                1100
Leu Gln Val Ser Asp Gly Gln His Gln Ala Thr Ala Leu Leu Glu Val
1105                1110                1115                1120
Gln Ala Ser Glu Pro Tyr Leu Arg Val Ala Asn Gly Ser Ser Leu Val
                1125                1130                1135
Val Pro Gln Gly Gly Gln Gly Thr Ile Asp Thr Ala Val Leu His Leu
                1140                1145                1150
Asp Thr Asn Leu Asp Ile Arg Ser Gly Asp Glu Val His Tyr His Val
            1155                1160                1165
Thr Ala Gly Pro Arg Trp Gly Gln Leu Val Arg Ala Gly Gln Pro Ala
    1170                1175                1180
Thr Ala Phe Ser Gln Gln Asp Leu Leu Asp Gly Ala Val Leu Tyr Ser
1185                1190                1195                1200
His Asn Gly Ser Leu Ser Pro Arg Asp Thr Met Ala Phe Ser Val Glu
                1205                1210                1215
Ala Gly Pro Val His Thr Asp Ala Thr Leu Gln Val Thr Ile Ala Leu
                1220                1225                1230
Glu Gly Pro Leu Ala Pro Leu Lys Leu Val Arg His Lys Lys Ile Tyr
            1235                1240                1245
Val Phe Gln Gly Glu Ala Ala Glu Ile Arg Arg Asp Gln Leu Glu Ala
    1250                1255                1260
Ala Gln Glu Ala Val Pro Pro Ala Asp Ile Val Phe Ser Val Lys Ser
1265                1270                1275                1280
Pro Pro Ser Ala Gly Tyr Leu Val Met Val Ser Arg Gly Ala Leu Ala
                1285                1290                1295
Asp Glu Pro Pro Ser Leu Asp Pro Val Gln Ser Phe Ser Gln Glu Ala
            1300                1305                1310
Val Asp Thr Gly Arg Val Leu Tyr Leu His Ser Arg Pro Glu Ala Trp
    1315                1320                1325
Ser Asp Ala Phe Ser Leu Asp Val Ala Ser Gly Leu Gly Ala Pro Leu
1330                1335                1340
Glu Gly Val Leu Val Glu Leu Glu Val Leu Pro Ala Ala Ile Pro Leu
1345                1350                1355                1360
Glu Ala Gln Asn Phe Ser Val Pro Glu Gly Gly Ser Leu Thr Leu Ala
                1365                1370                1375
```

```
Pro Pro Leu Leu Arg Val Ser Gly Pro Tyr Phe Pro Thr Leu Leu Gly
            1380                1385                1390

Leu Ser Leu Gln Val Leu Glu Pro Pro Gln His Gly Ala Leu Gln Lys
        1395                1400                1405

Glu Asp Gly Pro Gln Ala Arg Thr Leu Ser Ala Phe Ser Trp Arg Met
    1410                1415                1420

Val Glu Glu Gln Leu Ile Arg Tyr Val His Asp Gly Ser Glu Thr Leu
1425                1430                1435                1440

Thr Asp Ser Phe Val Leu Met Ala Asn Ala Ser Glu Met Asp Arg Gln
            1445                1450                1455

Ser His Pro Val Ala Phe Thr Val Thr Val Leu Pro Val Asn Asp Gln
        1460                1465                1470

Pro Pro Ile Leu Thr Thr Asn Thr Gly Leu Gln Met Trp Glu Gly Ala
    1475                1480                1485

Thr Ala Pro Ile Pro Ala Glu Ala Leu Arg Ser Thr Asp Gly Asp Ser
1490                1495                1500

Gly Ser Glu Asp Leu Val Tyr Thr Ile Glu Gln Pro Ser Asn Gly Arg
1505                1510                1515                1520

Val Val Leu Arg Gly Ala Pro Gly Thr Glu Val Arg Ser Phe Thr Gln
            1525                1530                1535

Ala Gln Leu Asp Gly Gly Leu Val Leu Phe Ser His Arg Gly Thr Leu
        1540                1545                1550

Asp Gly Gly Phe Arg Phe Arg Leu Ser Asp Gly Glu His Thr Ser Pro
    1555                1560                1565

Gly His Phe Phe Arg Val Thr Ala Gln Lys Gln Val Leu Leu Ser Leu
1570                1575                1580

Lys Gly Ser Gln Thr Leu Thr Val Cys Pro Gly Ser Val Gln Pro Leu
1585                1590                1595                1600

Ser Ser Gln Thr Leu Arg Ala Ser Ser Ala Gly Thr Asp Pro Gln
            1605                1610                1615

Leu Leu Leu Tyr Arg Val Val Arg Gly Pro Gln Leu Gly Arg Leu Phe
        1620                1625                1630

His Ala Gln Gln Asp Ser Thr Gly Glu Ala Leu Val Asn Phe Thr Gln
    1635                1640                1645

Ala Glu Val Tyr Ala Gly Asn Ile Leu Tyr Glu His Glu Met Pro Pro
1650                1655                1660

Glu Pro Phe Trp Glu Ala His Asp Thr Leu Glu Leu Gln Leu Ser Ser
1665                1670                1675                1680

Pro Pro Ala Arg Asp Val Ala Ala Thr Leu Ala Val Ala Val Ser Phe
            1685                1690                1695

Glu Ala Ala Cys Pro Gln Arg Pro Ser His Leu Trp Lys Asn Lys Gly
        1700                1705                1710

Leu Trp Val Pro Glu Gly Gln Arg Ala Arg Ile Thr Val Ala Ala Leu
    1715                1720                1725

Asp Ala Ser Asn Leu Leu Ala Ser Val Pro Ser Pro Gln Arg Ser Glu
1730                1735                1740

His Asp Val Leu Phe Gln Val Thr Gln Phe Pro Ser Arg Gly Gln Leu
1745                1750                1755                1760

Leu Val Ser Glu Glu Pro Leu His Ala Gly Gln Pro His Phe Leu Gln
            1765                1770                1775

Ser Gln Leu Ala Ala Gly Gln Leu Val Tyr Ala His Gly Gly Gly Gly
        1780                1785                1790
```

-continued

Thr Gln Gln Asp Gly Phe His Phe Arg Ala His Leu Gln Gly Pro Ala
            1795                1800                1805

Gly Ala Ser Val Ala Gly Pro Gln Thr Ser Glu Ala Phe Ala Ile Thr
        1810                1815                1820

Val Arg Asp Val Asn Glu Arg Pro Gln Pro Gln Ala Ser Val Pro
1825                1830                1835                1840

Leu Arg Leu Thr Arg Gly Ser Arg Ala Pro Ile Ser Arg Ala Gln Leu
            1845                1850                1855

Ser Val Val Asp Pro Asp Ser Ala Pro Gly Glu Ile Glu Tyr Glu Val
            1860                1865                1870

Gln Arg Ala Pro His Asn Gly Phe Leu Ser Leu Val Gly Gly Gly Leu
            1875                1880                1885

Gly Pro Val Thr Arg Phe Thr Gln Ala Asp Val Asp Ser Gly Arg Leu
        1890                1895                1900

Ala Phe Val Ala Asn Gly Ser Ser Val Ala Gly Ile Phe Gln Leu Ser
1905                1910                1915                1920

Met Ser Asp Gly Ala Ser Pro Pro Leu Pro Met Ser Leu Ala Val Asp
            1925                1930                1935

Ile Leu Pro Ser Ala Ile Glu Val Gln Leu Arg Ala Pro Leu Glu Val
            1940                1945                1950

Pro Gln Ala Leu Gly Arg Ser Ser Leu Ser Gln Gln Leu Arg Val
        1955                1960                1965

Val Ser Asp Arg Glu Glu Pro Glu Ala Ala Tyr Arg Leu Ile Gln Gly
        1970                1975                1980

Pro Gln Tyr Gly His Leu Leu Val Gly Gly Arg Pro Thr Ser Ala Phe
1985                1990                1995                2000

Ser Gln Phe Gln Ile Asp Gln Gly Glu Val Val Phe Ala Phe Thr Asn
            2005                2010                2015

Phe Ser Ser Ser His Asp His Phe Arg Val Leu Ala Leu Ala Arg Gly
            2020                2025                2030

Val Asn Ala Ser Ala Val Val Asn Val Thr Val Arg Ala Leu Leu His
            2035                2040                2045

Val Trp Ala Gly Gly Pro Trp Pro Gln Gly Ala Thr Leu Arg Leu Asp
            2050                2055                2060

Pro Thr Val Leu Asp Ala Gly Glu Leu Ala Asn Arg Thr Gly Ser Val
2065                2070                2075                2080

Pro Arg Phe Arg Leu Leu Glu Gly Pro Arg His Gly Arg Val Val Arg
            2085                2090                2095

Val Pro Arg Ala Arg Thr Glu Pro Gly Gly Ser Gln Leu Val Glu Gln
        2100                2105                2110

Phe Thr Gln Gln Asp Leu Glu Asp Gly Arg Leu Gly Leu Glu Val Gly
            2115                2120                2125

Arg Pro Glu Gly Arg Ala Pro Gly Pro Ala Gly Asp Ser Leu Thr Leu
            2130                2135                2140

Glu Leu Trp Ala Gln Gly Val Pro Pro Ala Val Ala Ser Leu Asp Phe
2145                2150                2155                2160

Ala Thr Glu Pro Tyr Asn Ala Ala Arg Pro Tyr Ser Val Ala Leu Leu
            2165                2170                2175

Ser Val Pro Glu Ala Ala Arg Thr Glu Ala Gly Lys Pro Glu Ser Ser
            2180                2185                2190

Thr Pro Thr Gly Glu Pro Gly Pro Met Ala Ser Ser Pro Glu Pro Ala
            2195                2200                2205

Val Ala Lys Gly Gly Phe Leu Ser Phe Leu Glu Ala Asn Met Phe Ser

```
                 2210              2215            2220
Val Ile Ile Pro Met Cys Leu Val Leu Leu Leu Ala Leu Ile Leu
2225                2230                2235                2240

Pro Leu Leu Phe Tyr Leu Arg Lys Arg Asn Lys Thr Gly Lys His Asp
                    2245                2250                2255

Val Gln Val Leu Thr Ala Lys Pro Arg Asn Gly Leu Ala Gly Asp Thr
                2260                2265                2270

Glu Thr Phe Arg Lys Val Glu Pro Gly Gln Ala Ile Pro Leu Thr Ala
            2275                2280                2285

Val Pro Gly Gln Gly Pro Pro Gly Gln Pro Asp Pro Glu Leu
        2290                2295                2300

Leu Gln Phe Cys Arg Thr Pro Asn Pro Ala Leu Lys Asn Gly Gln Tyr
2305                2310                2315                2320

Trp Val

<210> SEQ ID NO 238
<211> LENGTH: 981
<212> TYPE: DNA
<213> ORGANISM: Mus musculus
<220> FEATURE:
<223> OTHER INFORMATION: FAS
<220> FEATURE:
<221> NAME/KEY: CDS
<222> LOCATION: 1..981
<223> OTHER INFORMATION: /transl_table=1

<400> SEQUENCE: 238 atg ctg tgg att tgg gcg gtg ctg ccg ctg gtg ctg gcg ggc agc cag      48
Met Leu Trp Ile Trp Ala Val Leu Pro Leu Val Leu Ala Gly Ser Gln
1               5                   10                  15 ctg cgc gtg cat acc cag ggc acc aac agc att agc gaa agc ctg aaa      96
Leu Arg Val His Thr Gln Gly Thr Asn Ser Ile Ser Glu Ser Leu Lys
                20                  25                  30 ctg cgc cgc cgc gtg cgc gaa acc gat aaa aac tgc agc gaa ggc ctg     144
Leu Arg Arg Arg Val Arg Glu Thr Asp Lys Asn Cys Ser Glu Gly Leu
            35                  40                  45 tat cag ggc ggc ccg ttt tgc tgc cag ccg tgc cag ccg ggc aaa aaa     192
Tyr Gln Gly Gly Pro Phe Cys Cys Gln Pro Cys Gln Pro Gly Lys Lys
    50                  55                  60 aaa gtg gaa gat tgc aaa atg aac ggc ggc acc ccg acc tgc gcg ccg     240
Lys Val Glu Asp Cys Lys Met Asn Gly Gly Thr Pro Thr Cys Ala Pro
65                  70                  75                  80 tgc acc gaa ggc aaa gaa tat atg gat aaa aac cat tat gcg gat aaa     288
Cys Thr Glu Gly Lys Glu Tyr Met Asp Lys Asn His Tyr Ala Asp Lys
                85                  90                  95 tgc cgc cgc tgc acc ctg tgc gat gaa gaa cat ggc ctg gaa gtg gaa     336
Cys Arg Arg Cys Thr Leu Cys Asp Glu Glu His Gly Leu Glu Val Glu
            100                 105                 110 acc aac tgc acc ctg acc cag aac acc aaa tgc aaa tgc aaa ccg gat     384
Thr Asn Cys Thr Leu Thr Gln Asn Thr Lys Cys Lys Cys Lys Pro Asp
        115                 120                 125 ttt tat tgc gat agc ccg ggc tgc gaa cat tgc gtg cgc tgc gcg agc     432
Phe Tyr Cys Asp Ser Pro Gly Cys Glu His Cys Val Arg Cys Ala Ser
    130                 135                 140 tgc gaa cat ggc acc ctg gaa ccg tgc acc gcg acc agc aac acc aac     480
Cys Glu His Gly Thr Leu Glu Pro Cys Thr Ala Thr Ser Asn Thr Asn
145                 150                 155                 160 tgc cgc aaa cag agc ccg cgc aac cgc ctg tgg ctg ctg acc att ctg     528
Cys Arg Lys Gln Ser Pro Arg Asn Arg Leu Trp Leu Leu Thr Ile Leu
                165                 170                 175
```

```
gtg ctg ctg att ccg ctg gtg ttt att tat cgc aaa tat cgc aaa cgc       576
Val Leu Leu Ile Pro Leu Val Phe Ile Tyr Arg Lys Tyr Arg Lys Arg
            180                 185                 190 aaa tgc tgg aaa cgc cgc cag gat gat ccg gaa agc cgc acc agc agc       624
Lys Cys Trp Lys Arg Arg Gln Asp Asp Pro Glu Ser Arg Thr Ser Ser
        195                 200                 205 cgc gaa acc att ccg atg aac gcg agc aac ctg agc ctg agc aaa tat       672
Arg Glu Thr Ile Pro Met Asn Ala Ser Asn Leu Ser Leu Ser Lys Tyr
    210                 215                 220 att ccg cgc att gcg gaa gat atg acc att cag gaa gcg aaa aaa ttt       720
Ile Pro Arg Ile Ala Glu Asp Met Thr Ile Gln Glu Ala Lys Lys Phe
225                 230                 235                 240 gcg cgc gaa aac aac att aaa gaa ggc aaa att gat gaa att atg cat       768
Ala Arg Glu Asn Asn Ile Lys Glu Gly Lys Ile Asp Glu Ile Met His
                245                 250                 255 gat agc att cag gat acc gcg gaa cag aaa gtg cag ctg ctg ctg tgc       816
Asp Ser Ile Gln Asp Thr Ala Glu Gln Lys Val Gln Leu Leu Leu Cys
            260                 265                 270 tgg tat cag agc cat ggc aaa agc gat gcg tat cag gat ctg att aaa       864
Trp Tyr Gln Ser His Gly Lys Ser Asp Ala Tyr Gln Asp Leu Ile Lys
        275                 280                 285 ggc ctg aaa aaa gcg gaa tgc cgc cgc acc ctg gat aaa ttt cag gat       912
Gly Leu Lys Lys Ala Glu Cys Arg Arg Thr Leu Asp Lys Phe Gln Asp
    290                 295                 300 atg gtg cag aaa gat ctg ggc aaa agc acc ccg gat acc ggc aac gaa       960
Met Val Gln Lys Asp Leu Gly Lys Ser Thr Pro Asp Thr Gly Asn Glu
305                 310                 315                 320 aac gaa ggc cag tgc ctg gaa                                           981
Asn Glu Gly Gln Cys Leu Glu
                325

<210> SEQ ID NO 239
<211> LENGTH: 327
<212> TYPE: PRT
<213> ORGANISM: Mus musculus
<220> FEATURE:
<223> OTHER INFORMATION: [CDS]:1..981 from SEQ ID NO 238

<400> SEQUENCE: 239

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
```

```
145                 150                 155                 160
Cys Arg Lys Gln Ser Pro Arg Asn Arg Leu Trp Leu Thr Ile Leu
                165                 170                 175

Val Leu Leu Ile Pro Leu Val Phe Ile Tyr Arg Lys Tyr Arg Lys
                180                 185                 190

Lys Cys Trp Lys Arg Arg Gln Asp Asp Pro Glu Ser Arg Thr Ser Ser
                195                 200                 205

Arg Glu Thr Ile Pro Met Asn Ala Ser Asn Leu Ser Leu Ser Lys Tyr
        210                 215                 220

Ile Pro Arg Ile Ala Glu Asp Met Thr Ile Gln Glu Ala Lys Lys Phe
225                 230                 235                 240

Ala Arg Glu Asn Asn Ile Lys Glu Gly Lys Ile Asp Glu Ile Met His
                245                 250                 255

Asp Ser Ile Gln Asp Thr Ala Glu Gln Lys Val Gln Leu Leu Leu Cys
                260                 265                 270

Trp Tyr Gln Ser His Gly Lys Ser Asp Ala Tyr Gln Asp Leu Ile Lys
                275                 280                 285

Gly Leu Lys Lys Ala Glu Cys Arg Arg Thr Leu Asp Lys Phe Gln Asp
        290                 295                 300

Met Val Gln Lys Asp Leu Gly Lys Ser Thr Pro Asp Thr Gly Asn Glu
305                 310                 315                 320

Asn Glu Gly Gln Cys Leu Glu
                325

<210> SEQ ID NO 240
<211> LENGTH: 1005
<212> TYPE: DNA
<213> ORGANISM: Homo sapiens
<220> FEATURE:
<223> OTHER INFORMATION: FAS
<220> FEATURE:
<221> NAME/KEY: CDS
<222> LOCATION: 1..1005
<223> OTHER INFORMATION: /transl_table=1

<400> SEQUENCE: 240 atg ctg ggc att tgg acc ctg ctg ccg ctg gtg ctg acc agc gtg gcg     48
Met Leu Gly Ile Trp Thr Leu Leu Pro Leu Val Leu Thr Ser Val Ala
1               5                   10                  15 cgc ctg agc agc aaa agc gtg aac gcg cag gtg acc gat att aac agc     96
Arg Leu Ser Ser Lys Ser Val Asn Ala Gln Val Thr Asp Ile Asn Ser
                20                  25                  30 aaa ggc ctg gaa ctg cgc aaa acc gtg acc acc gtg gaa acc cag aac    144
Lys Gly Leu Glu Leu Arg Lys Thr Val Thr Thr Val Glu Thr Gln Asn
            35                  40                  45 ctg gaa ggc ctg cat cat gat ggc cag ttt tgc cat aaa ccg tgc ccg    192
Leu Glu Gly Leu His His Asp Gly Gln Phe Cys His Lys Pro Cys Pro
        50                  55                  60 ccg ggc gaa cgc aaa gcg cgc gat tgc acc gtg aac ggc gat gaa ccg    240
Pro Gly Glu Arg Lys Ala Arg Asp Cys Thr Val Asn Gly Asp Glu Pro
65                  70                  75                  80 gat tgc gtg ccg tgc cag gaa ggc aaa gaa tat acc gat aaa gcg cat    288
Asp Cys Val Pro Cys Gln Glu Gly Lys Glu Tyr Thr Asp Lys Ala His
                85                  90                  95 ttt agc agc aaa tgc cgc cgc tgc cgc ctg tgc gat gaa ggc cat ggc    336
Phe Ser Ser Lys Cys Arg Arg Cys Arg Leu Cys Asp Glu Gly His Gly
                100                 105                 110 ctg gaa gtg gaa att aac tgc acc cgc acc cag aac acc aaa tgc cgc    384
Leu Glu Val Glu Ile Asn Cys Thr Arg Thr Gln Asn Thr Lys Cys Arg
```

```
tgc aaa ccg aac ttt ttt tgc aac agc acc gtg tgc gaa cat tgc gat      432
Cys Lys Pro Asn Phe Phe Cys Asn Ser Thr Val Cys Glu His Cys Asp
        130                 135                 140 ccg tgc acc aaa tgc gaa cat ggc att att aaa gaa tgc acc ctg acc      480
Pro Cys Thr Lys Cys Glu His Gly Ile Ile Lys Glu Cys Thr Leu Thr
145                 150                 155                 160 agc aac acc aaa tgc aaa gaa gaa ggc agc cgc agc aac ctg ggc tgg      528
Ser Asn Thr Lys Cys Lys Glu Glu Gly Ser Arg Ser Asn Leu Gly Trp
                165                 170                 175 ctg tgc ctg ctg ctg ctg ccg att ccg ctg att gtg tgg gtg aaa cgc      576
Leu Cys Leu Leu Leu Leu Pro Ile Pro Leu Ile Val Trp Val Lys Arg
            180                 185                 190 aaa gaa gtg cag aaa acc tgc cgc aaa cat cgc aaa gaa aac cag ggc      624
Lys Glu Val Gln Lys Thr Cys Arg Lys His Arg Lys Glu Asn Gln Gly
        195                 200                 205 agc cat gaa agc ccg acc ctg aac ccg gaa acc gtg gcg att aac ctg      672
Ser His Glu Ser Pro Thr Leu Asn Pro Glu Thr Val Ala Ile Asn Leu
    210                 215                 220 agc gat gtg gat ctg agc aaa tat att acc acc att gcg ggc gtg atg      720
Ser Asp Val Asp Leu Ser Lys Tyr Ile Thr Thr Ile Ala Gly Val Met
225                 230                 235                 240 acc ctg agc cag gtg aaa ggc ttt gtg cgc aaa aac ggc gtg aac gaa      768
Thr Leu Ser Gln Val Lys Gly Phe Val Arg Lys Asn Gly Val Asn Glu
                245                 250                 255 gcg aaa att gat gaa att aaa aac gat aac gtg cag gat acc gcg gaa      816
Ala Lys Ile Asp Glu Ile Lys Asn Asp Asn Val Gln Asp Thr Ala Glu
            260                 265                 270 cag aaa gtg cag ctg ctg cgc aac tgg cat cag ctg cat ggc aaa aaa      864
Gln Lys Val Gln Leu Leu Arg Asn Trp His Gln Leu His Gly Lys Lys
        275                 280                 285 gaa gcg tat gat acc ctg att aaa gat ctg aaa aaa gcg aac ctg tgc      912
Glu Ala Tyr Asp Thr Leu Ile Lys Asp Leu Lys Lys Ala Asn Leu Cys
    290                 295                 300 acc ctg gcg gaa aaa att cag acc att att ctg aaa gat att acc agc      960
Thr Leu Ala Glu Lys Ile Gln Thr Ile Ile Leu Lys Asp Ile Thr Ser
305                 310                 315                 320 gat agc gaa aac agc aac ttt cgc aac gaa att cag agc ctg gtg            1005
Asp Ser Glu Asn Ser Asn Phe Arg Asn Glu Ile Gln Ser Leu Val
                325                 330                 335
```

<210> SEQ ID NO 241
<211> LENGTH: 335
<212> TYPE: PRT
<213> ORGANISM: Homo sapiens
<220> FEATURE:
<223> OTHER INFORMATION: [CDS]:1..1005 from SEQ ID NO 240

<400> SEQUENCE: 241

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80
```

```
Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 242
<211> LENGTH: 837
<212> TYPE: DNA
<213> ORGANISM: Mus <mouse, genus>
<220> FEATURE:
<223> OTHER INFORMATION: FASL
<220> FEATURE:
<221> NAME/KEY: CDS
<222> LOCATION: 1..837
<223> OTHER INFORMATION: /transl_table=1

<400> SEQUENCE: 242 atg cag cag ccg atg aac tat ccg tgc ccg cag att ttt tgg gtg gat    48
Met Gln Gln Pro Met Asn Tyr Pro Cys Pro Gln Ile Phe Trp Val Asp
1               5                   10                  15 agc agc gcg acc agc agc tgg gcg ccg ccg ggc agc gtg ttt ccg tgc    96
Ser Ser Ala Thr Ser Ser Trp Ala Pro Pro Gly Ser Val Phe Pro Cys
            20                  25                  30 ccg agc tgc ggc ccg cgc ggc ccg gat cag cgc cgc ccg ccg ccg       144
Pro Ser Cys Gly Pro Arg Gly Pro Asp Gln Arg Arg Pro Pro Pro
        35                  40                  45 ccg ccg ccg gtg agc ccg ctg ccg ccg agc cag ccg ctg ccg ctg       192
Pro Pro Pro Val Ser Pro Leu Pro Pro Ser Gln Pro Leu Pro Leu
50                  55                  60 ccg ccg ctg acc ccg ctg aaa aaa aaa gat cat aac acc aac ctg tgg   240
```

```
Pro Pro Leu Thr Pro Leu Lys Lys Lys Asp His Asn Thr Asn Leu Trp
 65                  70                  75                  80 ctg ccg gtg gtg ttt ttt atg gtg ctg gtg gcg ctg gtg ggc atg ggc    288
Leu Pro Val Val Phe Phe Met Val Leu Val Ala Leu Val Gly Met Gly
                     85                  90                  95 ctg ggc atg tat cag ctg ttt cat ctg cag aaa gaa ctg gcg gaa ctg    336
Leu Gly Met Tyr Gln Leu Phe His Leu Gln Lys Glu Leu Ala Glu Leu
                100                 105                 110 cgc gaa ttt acc aac cag agc ctg aaa gtg agc agc ttt gaa aaa cag    384
Arg Glu Phe Thr Asn Gln Ser Leu Lys Val Ser Ser Phe Glu Lys Gln
            115                 120                 125 att gcg aac ccg agc acc ccg agc gaa aaa aaa gaa ccg cgc agc gtg    432
Ile Ala Asn Pro Ser Thr Pro Ser Glu Lys Lys Glu Pro Arg Ser Val
        130                 135                 140 gcg cat ctg acc ggc aac ccg cat agc cgc agc att ccg ctg gaa tgg    480
Ala His Leu Thr Gly Asn Pro His Ser Arg Ser Ile Pro Leu Glu Trp
145                 150                 155                 160 gaa gat acc tat ggc acc gcg ctg att agc ggc gtg aaa tat aaa aaa    528
Glu Asp Thr Tyr Gly Thr Ala Leu Ile Ser Gly Val Lys Tyr Lys Lys
                    165                 170                 175 ggc ggc ctg gtg att aac gaa acc ggc ctg tat ttt gtg tat agc aaa    576
Gly Gly Leu Val Ile Asn Glu Thr Gly Leu Tyr Phe Val Tyr Ser Lys
                180                 185                 190 gtg tat ttt cgc ggc cag agc tgc aac aac cag ccg ctg aac cat aaa    624
Val Tyr Phe Arg Gly Gln Ser Cys Asn Asn Gln Pro Leu Asn His Lys
            195                 200                 205 gtg tat atg cgc aac agc aaa tat ccg gaa gat ctg gtg ctg atg gaa    672
Val Tyr Met Arg Asn Ser Lys Tyr Pro Glu Asp Leu Val Leu Met Glu
        210                 215                 220 gaa aaa cgc ctg aac tat tgc acc acc ggc cag att tgg gcg cat agc    720
Glu Lys Arg Leu Asn Tyr Cys Thr Thr Gly Gln Ile Trp Ala His Ser
225                 230                 235                 240 agc tat ctg ggc gcg gtg ttt aac ctg acc agc gcg gat cat ctg tat    768
Ser Tyr Leu Gly Ala Val Phe Asn Leu Thr Ser Ala Asp His Leu Tyr
                    245                 250                 255 gtg aac att agc cag ctg agc ctg att aac ttt gaa gaa agc aaa acc    816
Val Asn Ile Ser Gln Leu Ser Leu Ile Asn Phe Glu Glu Ser Lys Thr
                260                 265                 270 ttt ttt ggc ctg tat aaa ctg                                        837
Phe Phe Gly Leu Tyr Lys Leu
            275

<210> SEQ ID NO 243
<211> LENGTH: 279
<212> TYPE: PRT
<213> ORGANISM: Mus <mouse, genus>
<220> FEATURE:
<223> OTHER INFORMATION: [CDS]:1..837 from SEQ ID NO 242

<400> SEQUENCE: 243

Met Gln Gln Pro Met Asn Tyr Pro Cys Pro Gln Ile Phe Trp Val Asp
1               5                   10                  15

Ser Ser Ala Thr Ser Ser Trp Ala Pro Pro Gly Ser Val Phe Pro Cys
            20                  25                  30

Pro Ser Cys Gly Pro Arg Gly Pro Asp Gln Arg Arg Pro Pro Pro Pro
        35                  40                  45

Pro Pro Pro Val Ser Pro Leu Pro Pro Ser Gln Pro Leu Pro Leu
    50                  55                  60

Pro Pro Leu Thr Pro Leu Lys Lys Lys Asp His Asn Thr Asn Leu Trp
65                  70                  75                  80
```

```
Leu Pro Val Val Phe Phe Met Val Leu Val Ala Leu Val Gly Met Gly
                85                  90                  95

Leu Gly Met Tyr Gln Leu Phe His Leu Gln Lys Glu Leu Ala Glu Leu
            100                 105                 110

Arg Glu Phe Thr Asn Gln Ser Leu Lys Val Ser Ser Phe Glu Lys Gln
            115                 120                 125

Ile Ala Asn Pro Ser Thr Pro Ser Glu Lys Lys Glu Pro Arg Ser Val
130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
                165                 170                 175

Gly Gly Leu Val Ile Asn Glu Thr Gly Leu Tyr Phe Val Tyr Ser Lys
            180                 185                 190

Val Tyr Phe Arg Gly Gln Ser Cys Asn Asn Gln Pro Leu Asn His Lys
        195                 200                 205

Val Tyr Met Arg Asn Ser Lys Tyr Pro Glu Asp Leu Val Leu Met Glu
    210                 215                 220

Glu Lys Arg Leu Asn Tyr Cys Thr Thr Gly Gln Ile Trp Ala His Ser
225                 230                 235                 240

Ser Tyr Leu Gly Ala Val Phe Asn Leu Thr Ser Ala Asp His Leu Tyr
                245                 250                 255

Val Asn Ile Ser Gln Leu Ser Leu Ile Asn Phe Glu Glu Ser Lys Thr
            260                 265                 270

Phe Phe Gly Leu Tyr Lys Leu
            275

<210> SEQ ID NO 244
<211> LENGTH: 843
<212> TYPE: DNA
<213> ORGANISM: Homo sapiens
<220> FEATURE:
<223> OTHER INFORMATION: FASL
<220> FEATURE:
<221> NAME/KEY: CDS
<222> LOCATION: 1..843
<223> OTHER INFORMATION: /transl_table=1

<400> SEQUENCE: 244 atg cag cag ccg ttt aac tat ccg tat ccg cag att tat tgg gtg gat      48
Met Gln Gln Pro Phe Asn Tyr Pro Tyr Pro Gln Ile Tyr Trp Val Asp
1               5                   10                  15 agc agc gcg agc agc ccg tgg gcg ccg ccg ggc acc gtg ctg ccg tgc      96
Ser Ser Ala Ser Ser Pro Trp Ala Pro Pro Gly Thr Val Leu Pro Cys
            20                  25                  30 ccg acc agc gtg ccg cgc cgc ccg ggc cag cgc cgc ccg ccg ccg         144
Pro Thr Ser Val Pro Arg Arg Pro Gly Gln Arg Arg Pro Pro Pro
            35                  40                  45 ccg ccg ccg ccg ccg ctg ccg ccg ccg ccg ccg ccg ccg ctg ccg         192
Pro Pro Pro Pro Pro Leu Pro Pro Pro Pro Pro Pro Pro Leu Pro
50                  55                  60 ccg ctg ccg ctg ccg ccg ctg aaa aaa cgc ggc aac cat agc acc ggc     240
Pro Leu Pro Leu Pro Pro Leu Lys Lys Arg Gly Asn His Ser Thr Gly
65                  70                  75                  80 ctg tgc ctg ctg gtg atg ttt ttt atg gtg ctg gtg gcg ctg gtg ggc     288
Leu Cys Leu Leu Val Met Phe Phe Met Val Leu Val Ala Leu Val Gly
                85                  90                  95 ctg ggc ctg ggc atg ttt cag ctg ttt cat ctg cag aaa gaa ctg gcg     336
Leu Gly Leu Gly Met Phe Gln Leu Phe His Leu Gln Lys Glu Leu Ala
```

```
gaa ctg cgc gaa agc acc agc cag atg cat acc gcg agc agc ctg gaa      384
Glu Leu Arg Glu Ser Thr Ser Gln Met His Thr Ala Ser Ser Leu Glu
        115                 120                 125 aaa cag att ggc cat ccg agc ccg ccg ccg gaa aaa aaa gaa ctg cgc      432
Lys Gln Ile Gly His Pro Ser Pro Pro Pro Glu Lys Lys Glu Leu Arg
130                 135                 140 aaa gtg gcg cat ctg acc ggc aaa agc aac agc cgc agc atg ccg ctg      480
Lys Val Ala His Leu Thr Gly Lys Ser Asn Ser Arg Ser Met Pro Leu
145                 150                 155                 160 gaa tgg gaa gat acc tat ggc att gtg ctg ctg agc ggc gtg aaa tat      528
Glu Trp Glu Asp Thr Tyr Gly Ile Val Leu Leu Ser Gly Val Lys Tyr
                165                 170                 175 aaa aaa ggc ggc ctg gtg att aac gaa acc ggc ctg tat ttt gtg tat      576
Lys Lys Gly Gly Leu Val Ile Asn Glu Thr Gly Leu Tyr Phe Val Tyr
            180                 185                 190 agc aaa gtg tat ttt cgc ggc cag agc tgc aac aac ctg ccg ctg agc      624
Ser Lys Val Tyr Phe Arg Gly Gln Ser Cys Asn Asn Leu Pro Leu Ser
        195                 200                 205 cat aaa gtg tat atg cgc aac agc aaa tat ccg cag gat ctg gtg atg      672
His Lys Val Tyr Met Arg Asn Ser Lys Tyr Pro Gln Asp Leu Val Met
210                 215                 220 atg gaa ggc aaa atg atg agc tat tgc acc acc ggc cag atg tgg gcg      720
Met Glu Gly Lys Met Met Ser Tyr Cys Thr Thr Gly Gln Met Trp Ala
225                 230                 235                 240 cgc agc agc tat ctg ggc gcg gtg ttt aac ctg acc agc gcg gat cat      768
Arg Ser Ser Tyr Leu Gly Ala Val Phe Asn Leu Thr Ser Ala Asp His
                245                 250                 255 ctg tat gtg aac gtg agc gaa ctg agc ctg gtg aac ttt gaa gaa agc      816
Leu Tyr Val Asn Val Ser Glu Leu Ser Leu Val Asn Phe Glu Glu Ser
            260                 265                 270 cag acc ttt ttt ggc ctg tat aaa ctg                                  843
Gln Thr Phe Phe Gly Leu Tyr Lys Leu
        275                 280

<210> SEQ ID NO 245
<211> LENGTH: 281
<212> TYPE: PRT
<213> ORGANISM: Homo sapiens
<220> FEATURE:
<223> OTHER INFORMATION: [CDS]:1..843 from SEQ ID NO 244

<400> SEQUENCE: 245

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
```

-continued

```
             115                 120                 125
Lys Gln Ile Gly His Pro Ser Pro Pro Glu Lys Lys Glu Leu Arg
     130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                 165                 170                 175
Lys Lys Gly Gly Leu Val Ile Asn Glu Thr Gly Leu Tyr Phe Val Tyr
             180                 185                 190
Ser Lys Val Tyr Phe Arg Gly Gln Ser Cys Asn Asn Leu Pro Leu Ser
         195                 200                 205
His Lys Val Tyr Met Arg Asn Ser Lys Tyr Pro Gln Asp Leu Val Met
     210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                 245                 250                 255
Leu Tyr Val Asn Val Ser Glu Leu Ser Leu Val Asn Phe Glu Glu Ser
             260                 265                 270
Gln Thr Phe Phe Gly Leu Tyr Lys Leu
         275                 280
```

```
<210> SEQ ID NO 246
<211> LENGTH: 1233
<212> TYPE: DNA
<213> ORGANISM: Artificial Sequence
<220> FEATURE:
<223> OTHER INFORMATION: E3del
<220> FEATURE:
<221> NAME/KEY: CDS
<222> LOCATION: 1..1233
<223> OTHER INFORMATION: /transl_table=1

<400> SEQUENCE: 246 atg cga ccc tcc ggg acg gcc ggg gca gcg ctc ctg gcg ctg ctg gct    48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa ggt aat tat    96
Ala Leu Cys Pro Ala Ser Arg Ala Leu Glu Glu Lys Lys Gly Asn Tyr
                20                  25                  30 gtg gtg aca gat cac ggc tcg tgc gtc cga gcc tgt ggg gcc gac agc   144
Val Val Thr Asp His Gly Ser Cys Val Arg Ala Cys Gly Ala Asp Ser
            35                  40                  45 tat gag atg gag gaa gac ggc gtc cgc aag tgt aag aag tgc gaa ggg   192
Tyr Glu Met Glu Glu Asp Gly Val Arg Lys Cys Lys Lys Cys Glu Gly
        50                  55                  60 cct tgc cgc aaa gtg tgt aac gga ata ggt att ggt gaa ttt aaa gac   240
Pro Cys Arg Lys Val Cys Asn Gly Ile Gly Ile Gly Glu Phe Lys Asp
65                  70                  75                  80 tca ctc tcc ata aat gct acg aat att aaa cac ttc aaa aac tgc acc   288
Ser Leu Ser Ile Asn Ala Thr Asn Ile Lys His Phe Lys Asn Cys Thr
                85                  90                  95 tcc atc agt ggc gat ctc cac atc ctg ccg gtg gca ttt agg ggt gac   336
Ser Ile Ser Gly Asp Leu His Ile Leu Pro Val Ala Phe Arg Gly Asp
            100                 105                 110 tcc ttc aca cat act cct cct ctg gat cca cag gaa ctg gat att ctg   384
Ser Phe Thr His Thr Pro Pro Leu Asp Pro Gln Glu Leu Asp Ile Leu
        115                 120                 125 aaa acc gta aag gaa atc aca ggg ttt ttg ctg att cag gct tgg cct   432
Lys Thr Val Lys Glu Ile Thr Gly Phe Leu Leu Ile Gln Ala Trp Pro
```

```
                Lys Thr Val Lys Glu Ile Thr Gly Phe Leu Leu Ile Gln Ala Trp Pro
                    130                 135                 140 gaa aac agg acg gac ctc cat gcc ttt gag aac cta gaa atc ata cgc          480
Glu Asn Arg Thr Asp Leu His Ala Phe Glu Asn Leu Glu Ile Ile Arg
145                 150                 155                 160 ggc agg acc aag caa cat ggt cag ttt tct ctt gca gtc gtc agc ctg          528
Gly Arg Thr Lys Gln His Gly Gln Phe Ser Leu Ala Val Val Ser Leu
                165                 170                 175 aac ata aca tcc ttg gga tta cgc tcc ctc aag gag ata agt gat gga          576
Asn Ile Thr Ser Leu Gly Leu Arg Ser Leu Lys Glu Ile Ser Asp Gly
            180                 185                 190 gat gtg ata att tca gga aac aaa aat ttg tgc tat gca aat aca ata          624
Asp Val Ile Ile Ser Gly Asn Lys Asn Leu Cys Tyr Ala Asn Thr Ile
        195                 200                 205 aac tgg aaa aaa ctg ttt ggg acc tcc ggt cag aaa acc aaa att ata          672
Asn Trp Lys Lys Leu Phe Gly Thr Ser Gly Gln Lys Thr Lys Ile Ile
    210                 215                 220 agc aac aga ggt gaa aac agc tgc aag gcc aca ggc cag gtc tgc cat          720
Ser Asn Arg Gly Glu Asn Ser Cys Lys Ala Thr Gly Gln Val Cys His
225                 230                 235                 240 gcc ttg tgc tcc ccc gag ggc tgc tgg ggc ccg gag ccc agg gac tgc          768
Ala Leu Cys Ser Pro Glu Gly Cys Trp Gly Pro Glu Pro Arg Asp Cys
                245                 250                 255 gtc tct tgc cgg aat gtc agc cga ggc agg gaa tgc gtg gac aag tgc          816
Val Ser Cys Arg Asn Val Ser Arg Gly Arg Glu Cys Val Asp Lys Cys
            260                 265                 270 aac ctt ctg gag ggt gag cca agg gag ttt gtg gag aac tct gag tgc          864
Asn Leu Leu Glu Gly Glu Pro Arg Glu Phe Val Glu Asn Ser Glu Cys
        275                 280                 285 ata cag tgc cac cca gag tgc ctg cct cag gcc atg aac atc acc tgc          912
Ile Gln Cys His Pro Glu Cys Leu Pro Gln Ala Met Asn Ile Thr Cys
    290                 295                 300 aca gga cgg gga cca gac aac tgt atc cag tgt gcc cac tac att gac          960
Thr Gly Arg Gly Pro Asp Asn Cys Ile Gln Cys Ala His Tyr Ile Asp
305                 310                 315                 320 ggc ccc cac tgc gtc aag acc tgc ccg gca gga gtc atg gga gaa aac         1008
Gly Pro His Cys Val Lys Thr Cys Pro Ala Gly Val Met Gly Glu Asn
                325                 330                 335 aac acc ctg gtc tgg aag tac gca gac gcc ggc cat gtg tgc cac ctg         1056
Asn Thr Leu Val Trp Lys Tyr Ala Asp Ala Gly His Val Cys His Leu
            340                 345                 350 tgc cat cca aac tgc acc tac gga tgc act ggg cca ggt ctt gaa ggc         1104
Cys His Pro Asn Cys Thr Tyr Gly Cys Thr Gly Pro Gly Leu Glu Gly
        355                 360                 365 tgt cca acg aat ggg cct aag atc ccg tcc atc gcc act ggg atg gtg         1152
Cys Pro Thr Asn Gly Pro Lys Ile Pro Ser Ile Ala Thr Gly Met Val
    370                 375                 380 ggg gcc ctc ctc ttg ctg ctg gtg gtg gcc ctg ggg atc ggc ctc ttc         1200
Gly Ala Leu Leu Leu Leu Leu Val Val Ala Leu Gly Ile Gly Leu Phe
385                 390                 395                 400 atg cga agg cgc cac atc gtt cgg aag cgc tga                             1233
Met Arg Arg Arg His Ile Val Arg Lys Arg
                405                 410

<210> SEQ ID NO 247
<211> LENGTH: 410
<212> TYPE: PRT
<213> ORGANISM: Artificial Sequence
<220> FEATURE:
<223> OTHER INFORMATION: [CDS]:1..1233 from SEQ ID NO 246
```

<400> SEQUENCE: 247

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg
                405                 410
```

<210> SEQ ID NO 248
<211> LENGTH: 1410
<212> TYPE: DNA
<213> ORGANISM: Artificial Sequence
<220> FEATURE:
<223> OTHER INFORMATION: CAREpCam
<220> FEATURE:
<221> NAME/KEY: CDS
<222> LOCATION: 1..1410
<223> OTHER INFORMATION: /transl_table=1

<400> SEQUENCE: 248

```
atg gac atc aga ctg agc ctg gcc ttc ctg gtg ctg ttc atc aag ggc      48
Met Asp Ile Arg Leu Ser Leu Ala Phe Leu Val Leu Phe Ile Lys Gly
1               5                   10                  15 gtg cag tgc gag gtg cag ctg gcc gaa tct ggc ggc gga ctg gtg cag      96
Val Gln Cys Glu Val Gln Leu Ala Glu Ser Gly Gly Gly Leu Val Gln
            20                  25                  30 ccc ggc aga tcc atg aag ctg agc tgc gct gcc agc ggc ttc acc ttc     144
Pro Gly Arg Ser Met Lys Leu Ser Cys Ala Ala Ser Gly Phe Thr Phe
        35                  40                  45 agc aac ttc ccc atg gcc tgg gtg cgc cag gcc ccc acc aag tgt ctg     192
Ser Asn Phe Pro Met Ala Trp Val Arg Gln Ala Pro Thr Lys Cys Leu
    50                  55                  60 gaa tgg gtg gcc acc atc agc acc agc ggc ggc agc acc tac tac cgg     240
Glu Trp Val Ala Thr Ile Ser Thr Ser Gly Gly Ser Thr Tyr Tyr Arg
65                  70                  75                  80 gac agc gtg aag ggc cgg ttc acc atc agc cgg gac aac gcc aag agc     288
Asp Ser Val Lys Gly Arg Phe Thr Ile Ser Arg Asp Asn Ala Lys Ser
                85                  90                  95 acc ctg tac ctg cag atg aac agc ctg cgg agc gag gac acc gcc acc     336
Thr Leu Tyr Leu Gln Met Asn Ser Leu Arg Ser Glu Asp Thr Ala Thr
            100                 105                 110 tac tac tgc acc cgg acc ctg tac atc ctg cgg gtg ttc tac ttc gac     384
Tyr Tyr Cys Thr Arg Thr Leu Tyr Ile Leu Arg Val Phe Tyr Phe Asp
        115                 120                 125 tac tgg ggc cag ggc gtg atg gtg aca gtg tct agc ggc gga ggc ggc     432
Tyr Trp Gly Gln Gly Val Met Val Thr Val Ser Ser Gly Gly Gly Gly
    130                 135                 140 agc gga ggt gga gga agt ggc ggc gga gga tcc gac atc cag atg acc     480
Ser Gly Gly Gly Gly Ser Gly Gly Gly Gly Ser Asp Ile Gln Met Thr
145                 150                 155                 160 cag tct ccc gcc agc ctg agc gcc tct ctg ggc gag aca gtg tcc atc     528
Gln Ser Pro Ala Ser Leu Ser Ala Ser Leu Gly Glu Thr Val Ser Ile
                165                 170                 175 gag tgc ctg gcc agc gag ggc atc agc aac gac ctg gcc tgg tat cag     576
Glu Cys Leu Ala Ser Glu Gly Ile Ser Asn Asp Leu Ala Trp Tyr Gln
            180                 185                 190 cag aag tcc ggc aag agc ccc cag ctg ctg atc tac gcc acc agc aga     624
Gln Lys Ser Gly Lys Ser Pro Gln Leu Leu Ile Tyr Ala Thr Ser Arg
        195                 200                 205 ctg cag gac ggc gtg ccc agc aga ttc agc ggc agc ggc tcc ggc acc     672
Leu Gln Asp Gly Val Pro Ser Arg Phe Ser Gly Ser Gly Ser Gly Thr
    210                 215                 220 cgg tac agc ctg aag atc agc ggc atg cag ccc gag gac gag gcc gac     720
Arg Tyr Ser Leu Lys Ile Ser Gly Met Gln Pro Glu Asp Glu Ala Asp
225                 230                 235                 240 tac ttc tgc cag cag agc tac aag tac ccc tgg acc ttc ggc tgc ggc     768
Tyr Phe Cys Gln Gln Ser Tyr Lys Tyr Pro Trp Thr Phe Gly Cys Gly
                245                 250                 255
```

|  |  |
|---|---|
| aca aag ctg gaa ctg aag ggc gga ggg ggc tct ggg gga ggc gga tct<br>Thr Lys Leu Glu Leu Lys Gly Gly Gly Gly Ser Gly Gly Gly Gly Ser<br>260                          265                      270 | 816 |
| ctc gag gaa cag aag ctg atc agc gaa gag gac ctg act act acc aag<br>Leu Glu Glu Gln Lys Leu Ile Ser Glu Glu Asp Leu Thr Thr Thr Lys<br>      275                      280                      285 | 864 |
| cca gtg ctg cga act ccc tca cct gtg cac cct acc ggg aca tct cag<br>Pro Val Leu Arg Thr Pro Ser Pro Val His Pro Thr Gly Thr Ser Gln<br>290                          295                      300 | 912 |
| ccc cag aga cca gaa gat tgt cgg ccc cgt ggc tca gtg aag ggg acc<br>Pro Gln Arg Pro Glu Asp Cys Arg Pro Arg Gly Ser Val Lys Gly Thr<br>305                        310                      315                  320 | 960 |
| gga ttg gac ttc gcc tgt gat att tac atc tgg gca ccc ttg gcc gga<br>Gly Leu Asp Phe Ala Cys Asp Ile Tyr Ile Trp Ala Pro Leu Ala Gly<br>                            325                      330                      335 | 1008 |
| atc tgc gtg gcc ctt ctg ctg tcc ttg atc atc act ctc atc tgc tac<br>Ile Cys Val Ala Leu Leu Leu Ser Leu Ile Ile Thr Leu Ile Cys Tyr<br>                340                      345                      350 | 1056 |
| cac agg agc cga aga gca aaa ttc agc agg agt gca gag act gct gcc<br>His Arg Ser Arg Arg Ala Lys Phe Ser Arg Ser Ala Glu Thr Ala Ala<br>355                          360                      365 | 1104 |
| aac ctg cag gac ccc aac cag ctc tac aat gag ctc aat cta ggg cga<br>Asn Leu Gln Asp Pro Asn Gln Leu Tyr Asn Glu Leu Asn Leu Gly Arg<br>370                        375                      380 | 1152 |
| aga gag gaa tat gac gtc ttg gag aag aag cgg gct cgg gat cca gag<br>Arg Glu Glu Tyr Asp Val Leu Glu Lys Lys Arg Ala Arg Asp Pro Glu<br>385                        390                      395                  400 | 1200 |
| atg gga ggc aaa cag cag agg agg agg aac ccc cag gaa ggc gta tac<br>Met Gly Gly Lys Gln Gln Arg Arg Arg Asn Pro Gln Glu Gly Val Tyr<br>                            405                      410                      415 | 1248 |
| aat gca ctg cag aaa gac aag atg gca gaa gcc tac agt gag atc ggc<br>Asn Ala Leu Gln Lys Asp Lys Met Ala Glu Ala Tyr Ser Glu Ile Gly<br>                420                      425                      430 | 1296 |
| aca aaa ggc gag agg cgg aga ggc aag ggg cac gat ggc ctt tac cag<br>Thr Lys Gly Glu Arg Arg Arg Gly Lys Gly His Asp Gly Leu Tyr Gln<br>                            435                      440                      445 | 1344 |
| ggt ctc agc act gcc acc aag gac acc tat gat gcc ctg cat atg cag<br>Gly Leu Ser Thr Ala Thr Lys Asp Thr Tyr Asp Ala Leu His Met Gln<br>450                        455                      460 | 1392 |
| acc ctg gcc cct cgc taa<br>Thr Leu Ala Pro Arg<br>465 | 1410 |

<210> SEQ ID NO 249
<211> LENGTH: 469
<212> TYPE: PRT
<213> ORGANISM: Artificial Sequence
<220> FEATURE:
<223> OTHER INFORMATION: [CDS]:1..1410 from SEQ ID NO 248

<400> SEQUENCE: 249

Met Asp Ile Arg Leu Ser Leu Ala Phe Leu Val Leu Phe Ile Lys Gly
1                 5                    10                  15

Val Gln Cys Glu Val Gln Leu Ala Glu Ser Gly Gly Gly Leu Val Gln
                20                      25                      30

Pro Gly Arg Ser Met Lys Leu Ser Cys Ala Ala Ser Gly Phe Thr Phe
                        35                      40                      45

Ser Asn Phe Pro Met Ala Trp Val Arg Gln Ala Pro Thr Lys Cys Leu
        50                      55                      60

Glu Trp Val Ala Thr Ile Ser Thr Ser Gly Gly Ser Thr Tyr Tyr Arg

-continued

```
                65                  70                  75                  80
Asp Ser Val Lys Gly Arg Phe Thr Ile Ser Arg Asp Asn Ala Lys Ser
                    85                  90                  95
Thr Leu Tyr Leu Gln Met Asn Ser Leu Arg Ser Glu Asp Thr Ala Thr
                    100                 105                 110
Tyr Tyr Cys Thr Arg Thr Leu Tyr Ile Leu Arg Val Phe Tyr Phe Asp
                    115                 120                 125
Tyr Trp Gly Gln Gly Val Met Val Thr Val Ser Ser Gly Gly Gly Gly
                    130                 135                 140
Ser Gly Gly Gly Gly Ser Gly Gly Gly Ser Asp Ile Gln Met Thr
145                 150                 155                 160
Gln Ser Pro Ala Ser Leu Ser Ala Ser Leu Gly Glu Thr Val Ser Ile
                    165                 170                 175
Glu Cys Leu Ala Ser Glu Gly Ile Ser Asn Asp Leu Ala Trp Tyr Gln
                    180                 185                 190
Gln Lys Ser Gly Lys Ser Pro Gln Leu Leu Ile Tyr Ala Thr Ser Arg
                    195                 200                 205
Leu Gln Asp Gly Val Pro Ser Arg Phe Ser Gly Ser Gly Ser Gly Thr
210                 215                 220
Arg Tyr Ser Leu Lys Ile Ser Gly Met Gln Pro Glu Asp Glu Ala Asp
225                 230                 235                 240
Tyr Phe Cys Gln Gln Ser Tyr Lys Tyr Pro Trp Thr Phe Gly Cys Gly
                    245                 250                 255
Thr Lys Leu Glu Leu Lys Gly Gly Gly Ser Gly Gly Gly Gly Ser
                    260                 265                 270
Leu Glu Glu Gln Lys Leu Ile Ser Glu Glu Asp Leu Thr Thr Thr Lys
                    275                 280                 285
Pro Val Leu Arg Thr Pro Ser Pro Val His Pro Thr Gly Thr Ser Gln
                    290                 295                 300
Pro Gln Arg Pro Glu Asp Cys Arg Pro Arg Gly Ser Val Lys Gly Thr
305                 310                 315                 320
Gly Leu Asp Phe Ala Cys Asp Ile Tyr Ile Trp Ala Pro Leu Ala Gly
                    325                 330                 335
Ile Cys Val Ala Leu Leu Leu Ser Leu Ile Ile Thr Leu Ile Cys Tyr
                    340                 345                 350
His Arg Ser Arg Arg Ala Lys Phe Ser Arg Ser Ala Glu Thr Ala Ala
                    355                 360                 365
Asn Leu Gln Asp Pro Asn Gln Leu Tyr Asn Glu Leu Asn Leu Gly Arg
                    370                 375                 380
Arg Glu Glu Tyr Asp Val Leu Glu Lys Lys Arg Ala Arg Asp Pro Glu
385                 390                 395                 400
Met Gly Gly Lys Gln Gln Arg Arg Asn Pro Gln Glu Gly Val Tyr
                    405                 410                 415
Asn Ala Leu Gln Lys Asp Lys Met Ala Glu Ala Tyr Ser Glu Ile Gly
                    420                 425                 430
Thr Lys Gly Glu Arg Arg Arg Gly Lys Gly His Asp Gly Leu Tyr Gln
                    435                 440                 445
Gly Leu Ser Thr Ala Thr Lys Asp Thr Tyr Asp Ala Leu His Met Gln
                    450                 455                 460
Thr Leu Ala Pro Arg
465
```